(12) United States Patent
Al-Ali et al.

(10) Patent No.: US 11,701,043 B2
(45) Date of Patent: Jul. 18, 2023

(54) BLOOD PRESSURE MONITOR ATTACHMENT ASSEMBLY

(71) Applicant: Masimo Corporation, Irvine, CA (US)

(72) Inventors: Ammar Al-Ali, San Juan Capistrano, CA (US); Valery G. Telfort, Irvine, CA (US); Evan Thomas Fullerton, Costa Mesa, CA (US); Steven Egge, Laguna Hills, CA (US)

(73) Assignee: Masimo Corporation, Irvine, CA (US)

( * ) Notice: Subject to any disclaimer, the term of this patent is extended or adjusted under 35 U.S.C. 154(b) by 425 days.

(21) Appl. No.: 16/850,928

(22) Filed: Apr. 16, 2020

(65) Prior Publication Data

US 2020/0329984 A1 Oct. 22, 2020

Related U.S. Application Data

(60) Provisional application No. 62/888,271, filed on Aug. 16, 2019, provisional application No. 62/923,157, (Continued)

(51) Int. Cl.
*A61B 5/282* (2021.01)
*A61B 5/0205* (2006.01)
(Continued)

(52) U.S. Cl.
CPC ............ *A61B 5/282* (2021.01); *A61B 5/0006* (2013.01); *A61B 5/022* (2013.01); *A61B 5/0235* (2013.01);
(Continued)

(58) Field of Classification Search
None
See application file for complete search history.

(56) References Cited

U.S. PATENT DOCUMENTS

| 2,985,172 A | 5/1961 | Jones |
|---|---|---|
| 3,434,651 A | 3/1969 | Stec |

(Continued)

FOREIGN PATENT DOCUMENTS

| CN | 106205591 | 12/2016 |
|---|---|---|
| EP | 3 366 211 | 8/2018 |

(Continued)

OTHER PUBLICATIONS

US 2022/0192529 A1, 06/2022, Al-Ali et al. (withdrawn)
(Continued)

*Primary Examiner* — Ankit D Tejani
(74) *Attorney, Agent, or Firm* — Knobbe, Martens, Olson & Bear, LLP

(57) ABSTRACT

A blood pressure monitor configured to removably mount to a cuff in a substantially symmetrical position with respect to a width of the cuff can include a housing defining an interior, a first port, and a second port. The first port can: secure to a first prong of the cuff when the cuff is mounted in a first orientation; receive and secure to a second prong of the cuff when the cuff is mounted in a second orientation; and enable fluid communication between the interior and at least one of a first fluid passage within the first prong and a second fluid passage within the second prong. The second port can: secure to the second prong of the cuff when the cuff is mounted in the first orientation; and receive and secure to the first prong of the cuff when the cuff is mounted in the second orientation.

32 Claims, 122 Drawing Sheets

Related U.S. Application Data filed on Oct. 18, 2019, provisional application No. 62/835,386, filed on Apr. 17, 2019, provisional application No. 62/837,195, filed on Apr. 23, 2019.

(51) Int. Cl.

| | | |
|---|---|---|
| *A61B 5/021* | (2006.01) | |
| *A61B 5/022* | (2006.01) | |
| *A61B 5/0235* | (2006.01) | |
| *A61B 5/11* | (2006.01) | |
| *A61B 5/1455* | (2006.01) | |
| *A61B 5/00* | (2006.01) | |
| *A61B 5/259* | (2021.01) | |
| *A61B 5/30* | (2021.01) | |
| *A61B 5/339* | (2021.01) | |
| *A61B 5/332* | (2021.01) | |
| *F04B 45/04* | (2006.01) | |
| *F04B 53/00* | (2006.01) | |
| *A61B 5/025* | (2006.01) | |
| *A61B 5/01* | (2006.01) | |
| *A61B 5/024* | (2006.01) | |

(52) U.S. Cl.
CPC ...... *A61B 5/02055* (2013.01); *A61B 5/02108* (2013.01); *A61B 5/02141* (2013.01); *A61B 5/02208* (2013.01); *A61B 5/02225* (2013.01); *A61B 5/02233* (2013.01); *A61B 5/1117* (2013.01); *A61B 5/1455* (2013.01); *A61B 5/259* (2021.01); *A61B 5/303* (2021.01); *A61B 5/332* (2021.01); *A61B 5/339* (2021.01); *A61B 5/681* (2013.01); *A61B 5/6824* (2013.01); *A61B 5/6831* (2013.01); *A61B 5/6835* (2013.01); *A61B 5/7217* (2013.01); *F04B 45/043* (2013.01); *F04B 53/001* (2013.01); *A61B 5/01* (2013.01); *A61B 5/025* (2013.01); *A61B 5/02438* (2013.01); *A61B 5/14551* (2013.01); *A61B 5/7475* (2013.01); *A61B 2560/0214* (2013.01); *A61B 2560/0252* (2013.01); *A61B 2560/0443* (2013.01); *A61B 2560/0456* (2013.01); *A61B 2562/0204* (2013.01); *A61B 2562/0219* (2013.01); *A61B 2562/0271* (2013.01); *A61B 2562/0295* (2013.01); *A61B 2562/08* (2013.01); *A61B 2562/164* (2013.01); *A61B 2562/22* (2013.01); *A61B 2562/222* (2013.01); *A61B 2562/225* (2013.01); *A61B 2562/227* (2013.01)

(56) References Cited

U.S. PATENT DOCUMENTS

| | | |
|---|---|---|
| 4,353,372 A | 10/1982 | Ayer |
| D278,363 S | 4/1985 | Schenkel et al. |
| D295,383 S | 4/1988 | Anderson et al. |
| D297,460 S | 8/1988 | Inoue et al. |
| D298,931 S | 12/1988 | Sekiguchi |
| 4,824,402 A | 4/1989 | Sorimachi |
| 4,832,039 A | 5/1989 | Perry et al. |
| D306,011 S | 2/1990 | Komatsu |
| 4,960,128 A | 10/1990 | Gordon et al. |
| 4,960,388 A | 10/1990 | Frantz et al. |
| 4,964,408 A | 10/1990 | Hink et al. |
| 5,027,823 A | 7/1991 | Sanaka |
| D320,001 S | 9/1991 | Hirabayashi |
| D324,570 S | 3/1992 | Arioka et al. |
| D334,973 S | 4/1993 | Valentine et al. |
| 5,285,791 A | 2/1994 | Smith |
| D346,798 S | 5/1994 | Nagele |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| D360,035 S | 7/1995 | Miller et al. |
| 5,431,170 A | 7/1995 | Mathews |
| 5,436,499 A | 7/1995 | Namavar et al. |
| D361,751 S | 8/1995 | Geis |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| D372,787 S | 8/1996 | Dozier et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| D385,283 S | 10/1997 | Snyder et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| D404,357 S | 1/1999 | Foster et al. |
| 5,890,929 A | 4/1999 | Mills et al. |
| 5,919,134 A | 7/1999 | Diab |
| D417,189 S | 11/1999 | Amero, Jr. et al. |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| D428,387 S | 7/2000 | Malloy et al. |
| D429,337 S | 8/2000 | Sanfilippo |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,330,151 B1 | 12/2001 | Bates, III |
| 6,334,065 B1 | 12/2001 | Al-Ali et al. |
| 6,338,657 B1 | 1/2002 | Harper et al. |
| 6,360,114 B1 | 3/2002 | Diab et al. |
| D456,358 S | 4/2002 | Niklander et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| D462,864 S | 9/2002 | Myszka et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| D471,444 S | 3/2003 | Kim et al. |

(56) References Cited

U.S. PATENT DOCUMENTS

| | | |
|---|---|---|
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| D480,811 S | 10/2003 | Horhota et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| D486,785 S | 2/2004 | Shindo |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,735,379 B2 | 5/2004 | Salmon et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D525,362 S | 7/2006 | Nielsen et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| D531,580 S | 11/2006 | Nishio et al. |
| 7,133,710 B2 | 11/2006 | Acosta et al. |
| 7,142,901 B2 | 11/2006 | Kiani et al. |
| D535,877 S | 1/2007 | Tanninen et al. |
| D543,149 S | 5/2007 | Huang et al. |
| 7,225,006 B2 | 5/2007 | Al-Ali et al. |
| RE39,672 E | 6/2007 | Shehada et al. |
| D547,863 S | 7/2007 | Heinsch |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| D557,814 S | 12/2007 | Glenn et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| D571,478 S | 6/2008 | Horacek |
| D571,720 S | 6/2008 | Yang |
| 7,395,158 B2 | 7/2008 | Monfre et al. |
| 7,415,297 B2 | 8/2008 | Al-Ali et al. |
| D576,546 S | 9/2008 | Yang |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| D601,258 S | 9/2009 | Bell et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| D616,993 S | 6/2010 | Muis et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,904,133 B2 | 3/2011 | Gehman et al. |
| 7,909,772 B2 | 3/2011 | Popov et al. |
| D636,726 S | 4/2011 | Hiramura |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| D663,421 S | 7/2012 | Steiner et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| D666,305 S | 8/2012 | Benarieh et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,290,574 B2 | 10/2012 | Field et al. |
| 8,315,683 B2 | 11/2012 | Al-Ali et al. |
| 8,315,687 B2 | 11/2012 | Cross et al. |
| RE43,860 E | 12/2012 | Parker |
| D671,888 S | 12/2012 | Dyson et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| D675,739 S | 2/2013 | McCormack |
| 8,374,665 B2 | 2/2013 | Lamego |
| D677,632 S | 3/2013 | Riddle et al. |
| 8,388,353 B2 | 3/2013 | Kiani et al. |

(56) References Cited

U.S. PATENT DOCUMENTS

| | | |
|---|---|---|
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,562,802 B1 | 10/2013 | Beaudet et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| D696,631 S | 12/2013 | Price et al. |
| 8,630,691 B2 | 1/2014 | Lamego et al. |
| 8,639,319 B2 | 1/2014 | Hugh et al. |
| 8,641,631 B2 | 2/2014 | Sierra et al. |
| 8,652,060 B2 | 2/2014 | Al-Ali |
| 8,663,106 B2 | 3/2014 | Stivoric et al. |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| D705,738 S | 5/2014 | Schmidt et al. |
| 8,715,206 B2 | 5/2014 | Telfort et al. |
| 8,716,629 B2 | 5/2014 | Klewer et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| D709,439 S | 7/2014 | Ferber et al. |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| D712,827 S | 9/2014 | Maeda et al. |
| D712,839 S | 9/2014 | Lee et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| D719,658 S | 12/2014 | McDougall et al. |
| 8,911,377 B2 | 12/2014 | Al-Ali |
| D724,222 S | 3/2015 | Chung et al. |
| 8,989,831 B2 | 3/2015 | Al-Ali et al. |
| 8,998,809 B2 | 4/2015 | Kiani |
| D728,468 S | 5/2015 | Ferber et al. |
| 9,066,666 B2 | 6/2015 | Kiani |
| 9,066,680 B1 | 6/2015 | Al-Ali et al. |
| 9,095,316 B2 | 8/2015 | Welch et al. |
| 9,104,373 B2 | 8/2015 | Lechman et al. |
| 9,106,038 B2 | 8/2015 | Telfort et al. |
| 9,107,625 B2 | 8/2015 | Telfort et al. |
| 9,119,568 B2 | 9/2015 | Yin et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| D744,428 S | 12/2015 | Rodriguez et al. |
| D745,167 S | 12/2015 | Canas et al. |
| 9,211,095 B1 | 12/2015 | Al-Ali |
| 9,218,454 B2 | 12/2015 | Kiani et al. |
| D746,777 S | 1/2016 | Lavén et al. |
| D748,058 S | 1/2016 | Corona |
| 9,245,668 B1 | 1/2016 | Vo et al. |
| 9,267,572 B2 | 2/2016 | Barker et al. |
| D752,229 S | 3/2016 | Chen et al. |
| D752,740 S | 3/2016 | Price et al. |
| 9,277,880 B2 | 3/2016 | Poeze et al. |
| D753,065 S | 4/2016 | Corona |
| 9,307,928 B1 | 4/2016 | Al-Ali et al. |
| 9,323,894 B2 | 4/2016 | Kiani |
| D755,392 S | 5/2016 | Hwang et al. |
| D755,393 S | 5/2016 | Amsler |
| D755,974 S | 5/2016 | Chen et al. |
| 9,326,712 B1 | 5/2016 | Kiani |
| D759,828 S | 6/2016 | Riedle |
| 9,386,923 B2 | 7/2016 | Winter et al. |
| 9,392,945 B2 | 7/2016 | Al-Ali et al. |
| 9,408,542 B1 | 8/2016 | Kinast et al. |
| D767,485 S | 9/2016 | To et al. |
| D767,487 S | 9/2016 | Huang |
| 9,436,645 B2 | 9/2016 | Al-Ali et al. |
| 9,445,759 B1 | 9/2016 | Lamego et al. |
| 9,459,089 B2 | 10/2016 | Ganton et al. |
| 9,474,474 B2 | 10/2016 | Lamego et al. |
| D770,386 S | 11/2016 | Corona |
| 9,480,435 B2 | 11/2016 | Olsen |
| 9,510,755 B2 | 12/2016 | Fong et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| D782,683 S | 3/2017 | Singh et al. |
| 9,610,060 B2 | 4/2017 | Jaeschke et al. |
| 9,622,692 B2 | 4/2017 | Lamego et al. |
| D788,312 S | 5/2017 | Al-Ali et al. |
| 9,649,054 B2 | 5/2017 | Lamego et al. |
| D789,154 S | 6/2017 | Walker |
| 9,680,333 B1 | 6/2017 | Brooks et al. |
| 9,697,928 B2 | 7/2017 | Al-Ali et al. |
| D794,803 S | 8/2017 | Thom |
| D795,184 S | 8/2017 | Jung et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,833,171 B2 | 12/2017 | Yin et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| D807,501 S | 1/2018 | Reba Switala |
| 9,861,298 B2 | 1/2018 | Eckerbom et al. |
| 9,861,305 B1 | 1/2018 | Weber et al. |
| 9,877,650 B2 | 1/2018 | Muhsin et al. |
| D810,944 S | 2/2018 | Goolkasian |
| 9,891,079 B2 | 2/2018 | Dalvi |
| 9,907,473 B2 | 3/2018 | Tran |
| 9,924,897 B1 | 3/2018 | Abdul-Hafiz |
| D815,743 S | 4/2018 | Liao et al. |
| 9,936,917 B2 | 4/2018 | Poeze et al. |
| D818,129 S | 5/2018 | Heine et al. |
| 9,955,937 B2 | 5/2018 | Telfort |
| 9,955,939 B2 | 5/2018 | Sezan et al. |
| 9,965,946 B2 | 5/2018 | Al-Ali et al. |

(56) References Cited

U.S. PATENT DOCUMENTS

| | | |
|---|---|---|
| 9,968,772 B2 | 5/2018 | Kockx et al. |
| 9,985,384 B1 | 5/2018 | Johnson et al. |
| D820,790 S | 6/2018 | Rief |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,062,958 B2 | 8/2018 | Ganton et al. |
| D831,842 S | 10/2018 | Katsumata et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| D836,201 S | 12/2018 | Lee et al. |
| 10,143,383 B2 | 12/2018 | Tseng et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| D839,194 S | 1/2019 | Wardenburg |
| 10,183,142 B2 | 1/2019 | Garcia Molina et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,213,153 B2 | 2/2019 | Atallah et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| D847,372 S | 4/2019 | Crawford et al. |
| 10,258,267 B2 | 4/2019 | Ballam et al. |
| 10,279,247 B2 | 5/2019 | Kiani |
| 10,292,664 B2 | 5/2019 | Al-Ali |
| 10,299,720 B2 | 5/2019 | Brown et al. |
| D850,385 S | 6/2019 | Gregori |
| D851,261 S | 6/2019 | Ricks |
| 10,327,337 B2 | 6/2019 | Schmidt et al. |
| 10,327,713 B2 | 6/2019 | Barker et al. |
| 10,332,630 B2 | 6/2019 | Al-Ali |
| D855,203 S | 7/2019 | Katsumata et al. |
| D857,205 S | 8/2019 | Lemons et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| D868,133 S | 11/2019 | Disciullo et al. |
| 10,463,340 B2 | 11/2019 | Telfort et al. |
| 10,471,159 B1 | 11/2019 | Lapotko et al. |
| 10,478,589 B2 | 11/2019 | Cronin et al. |
| D868,974 S | 12/2019 | Albert et al. |
| D868,993 S | 12/2019 | Isozaki et al. |
| 10,499,825 B2 | 12/2019 | Solosko et al. |
| 10,505,311 B2 | 12/2019 | Al-Ali et al. |
| 10,524,672 B2 | 1/2020 | Baek et al. |
| 10,524,738 B2 | 1/2020 | Olsen |
| 10,531,813 B2 | 1/2020 | O'Neill et al. |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| D879,305 S | 3/2020 | Gummireddy et al. |
| 10,575,780 B2 | 3/2020 | Van Den Ende et al. |
| 10,595,726 B2 | 3/2020 | Cronin et al. |
| 10,603,429 B2 | 3/2020 | Dantsker |
| 10,608,817 B2 | 3/2020 | Haider et al. |
| D880,477 S | 4/2020 | Forrest et al. |
| D882,800 S | 4/2020 | Lee |
| 10,617,302 B2 | 4/2020 | Al-Ali et al. |
| 10,617,335 B2 | 4/2020 | Al-Ali et al. |
| 10,624,580 B2 | 4/2020 | DeGroot et al. |
| 10,637,181 B2 | 4/2020 | Al-Ali et al. |
| D884,165 S | 5/2020 | deBock et al. |
| D885,586 S | 5/2020 | Lopez Pimienta et al. |
| 10,642,960 B2 | 5/2020 | Goguen |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,751 B2 | 6/2020 | Kaskoun et al. |
| 10,667,764 B2 | 6/2020 | Ahmed et al. |
| D890,708 S | 7/2020 | Forrest et al. |
| 10,721,785 B2 | 7/2020 | Al-Ali |
| D892,057 S | 8/2020 | Zhang |
| D892,745 S | 8/2020 | Vlacich et al. |
| D894,131 S | 8/2020 | Biere |
| 10,736,518 B2 | 8/2020 | Al-Ali et al. |
| 10,750,984 B2 | 8/2020 | Pauley et al. |
| D895,122 S | 9/2020 | Benedikter et al. |
| D897,098 S | 9/2020 | Al-Ali |
| 10,758,164 B2 | 9/2020 | Derkx et al. |
| 10,779,098 B2 | 9/2020 | Iswanto et al. |
| 10,799,128 B2 | 10/2020 | Paulussen et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,842,464 B2 | 11/2020 | Lambert et al. |
| D904,640 S | 12/2020 | Ruhland et al. |
| D905,253 S | 12/2020 | Hubelbank |
| D905,268 S | 12/2020 | Katsumata et al. |
| D905,270 S | 12/2020 | Katsumata et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| D908,894 S | 1/2021 | Eslava et al. |
| D911,289 S | 2/2021 | Itoh et al. |
| 10,918,281 B2 | 2/2021 | Al-Ali et al. |
| D914,887 S | 3/2021 | Allen et al. |
| D914,896 S | 3/2021 | Hoshino et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,985,578 B1 | 4/2021 | Ardaman et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| D919,101 S | 5/2021 | Jung et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D924,157 S | 7/2021 | Kaplan et al. |
| D925,597 S | 7/2021 | Chandran et al. |
| D926,323 S | 7/2021 | Dascoli et al. |
| D927,699 S | 8/2021 | Al-Ali et al. |
| 11,076,777 B2 | 8/2021 | Lee et al. |
| D931,468 S | 9/2021 | Huang et al. |
| 11,114,188 B2 | 9/2021 | Poeze et al. |
| D932,634 S | 10/2021 | Kawakami et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |

(56) References Cited

U.S. PATENT DOCUMENTS

| | | |
|---|---|---|
| 11,191,484 B2 | 12/2021 | Kiani et al. |
| D940,327 S | 1/2022 | Lee et al. |
| D940,881 S | 1/2022 | Hadley et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,266,349 B2 | 3/2022 | Mizuno et al. |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0107714 A1 | 5/2005 | Matsumura et al. |
| 2005/0113704 A1 | 5/2005 | Lawson et al. |
| 2005/0234317 A1 | 10/2005 | Kiani |
| 2006/0059364 A1 | 3/2006 | Fontijn |
| 2006/0073719 A1 | 4/2006 | Kiani |
| 2006/0084880 A1 | 4/2006 | Such et al. |
| 2006/0189871 A1 | 8/2006 | Al-Ali et al. |
| 2007/0073116 A1 | 3/2007 | Kiani et al. |
| 2007/0167694 A1 | 7/2007 | Causevic et al. |
| 2007/0167850 A1 | 7/2007 | Russell et al. |
| 2007/0180140 A1 | 8/2007 | Welch et al. |
| 2007/0239230 A1 | 10/2007 | Giftakis et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2008/0281168 A1 | 11/2008 | Gibson et al. |
| 2008/0288026 A1 | 11/2008 | Cross et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0182216 A1 | 7/2009 | Roushey, III et al. |
| 2009/0204100 A1 | 8/2009 | Van Pieterson et al. |
| 2009/0247984 A1 | 10/2009 | Lamego et al. |
| 2009/0275813 A1 | 11/2009 | Davis |
| 2010/0004518 A1 | 1/2010 | Vo et al. |
| 2010/0030040 A1 | 2/2010 | Poeze et al. |
| 2010/0076315 A1 | 3/2010 | Erkamp et al. |
| 2010/0099964 A1 | 4/2010 | O'Reilly et al. |
| 2010/0106076 A1 | 4/2010 | Nisato et al. |
| 2010/0234718 A1 | 9/2010 | Sampath et al. |
| 2010/0249542 A1 | 9/2010 | Thijs et al. |
| 2010/0270257 A1 | 10/2010 | Wachman et al. |
| 2010/0298723 A1 | 11/2010 | Zhen |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125040 A1 | 5/2011 | Crawford et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2011/0237924 A1 | 9/2011 | McGusty et al. |
| 2012/0123231 A1 | 5/2012 | O'Reilly |
| 2012/0130204 A1 | 5/2012 | Basta et al. |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0271081 A1 | 10/2013 | Wang |
| 2013/0296672 A1 | 11/2013 | O'Neil et al. |
| 2013/0345921 A1 | 12/2013 | Al-Ali et al. |
| 2014/0128688 A1 | 5/2014 | Wu et al. |
| 2014/0148062 A1 | 5/2014 | Mott et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0243612 A1 | 8/2014 | Li et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2014/0326614 A1 | 11/2014 | Guthrie et al. |
| 2015/0005600 A1 | 1/2015 | Blank et al. |
| 2015/0011907 A1 | 1/2015 | Purdon et al. |
| 2015/0025400 A1 | 1/2015 | Nishioka et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0106121 A1 | 4/2015 | Muhsin et al. |
| 2015/0269825 A1 | 9/2015 | Tran |
| 2015/0313499 A1 | 11/2015 | Sohn |
| 2016/0007861 A1 | 1/2016 | Tseng et al. |
| 2016/0196388 A1 | 7/2016 | Lamego |
| 2016/0199576 A1 | 7/2016 | Savage |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0045170 A1* | 2/2017 | Lewis ............... A61M 39/10 |
| 2017/0055851 A1 | 3/2017 | Al-Ali |
| 2017/0055896 A1 | 3/2017 | Al-Ali |
| 2017/0173632 A1 | 6/2017 | Al-Ali |
| 2017/0251974 A1 | 9/2017 | Shreim et al. |
| 2017/0273695 A1* | 9/2017 | Ganske ............... A61B 5/021 |
| 2017/0296124 A1 | 10/2017 | Creemers et al. |
| 2017/0311891 A1 | 11/2017 | Kiani et al. |
| 2017/0347893 A1* | 12/2017 | Osoegawa ......... A61B 5/02233 |
| 2017/0360329 A1 | 12/2017 | Derkx et al. |
| 2018/0049656 A1 | 2/2018 | Paulussen et al. |
| 2018/0103874 A1 | 4/2018 | Lee et al. |
| 2018/0125444 A1 | 5/2018 | Kahlman et al. |
| 2018/0146867 A1 | 5/2018 | Torihama et al. |
| 2018/0168458 A1 | 6/2018 | Pekander et al. |
| 2018/0184926 A1 | 7/2018 | Doi et al. |
| 2018/0221646 A1 | 8/2018 | Silverton |
| 2018/0235567 A1 | 8/2018 | Bezemer et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0289340 A1 | 10/2018 | Trindade Rodrigues et al. |
| 2018/0296161 A1 | 10/2018 | Shreim et al. |

(56) References Cited

U.S. PATENT DOCUMENTS

| | | |
|---|---|---|
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317779 A1 | 11/2018 | Gregg et al. |
| 2018/0317826 A1 | 11/2018 | Muhsin et al. |
| 2018/0333053 A1 | 11/2018 | Verkruijsse et al. |
| 2018/0360373 A1 | 12/2018 | Aarts et al. |
| 2018/0364109 A1 | 12/2018 | Bongers et al. |
| 2019/0015023 A1 | 1/2019 | Monfre |
| 2019/0117070 A1 | 4/2019 | Muhsin et al. |
| 2019/0133488 A1 | 5/2019 | Meftah et al. |
| 2019/0142280 A1 | 5/2019 | Bongers et al. |
| 2019/0200941 A1 | 7/2019 | Chandran et al. |
| 2019/0239787 A1 | 8/2019 | Pauley et al. |
| 2019/0261923 A1 | 8/2019 | Talgorn et al. |
| 2019/0282180 A1 | 9/2019 | Babaeizadeh |
| 2019/0298195 A1 | 10/2019 | De Groot et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0035366 A1 | 1/2020 | Gummireddy et al. |
| 2020/0060869 A1 | 2/2020 | Telfort et al. |
| 2020/0069281 A1 | 3/2020 | Chan et al. |
| 2020/0085310 A1 | 3/2020 | Zahner et al. |
| 2020/0086133 A1 | 3/2020 | Wang et al. |
| 2020/0102777 A1 | 4/2020 | Yun et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0163647 A1 | 5/2020 | Hakkens et al. |
| 2020/0178932 A1 | 6/2020 | Te Velde et al. |
| 2020/0196877 A1 | 6/2020 | Vo et al. |
| 2020/0249688 A1 | 8/2020 | Caussy et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0275847 A1 | 9/2020 | Woehrle et al. |
| 2020/0288983 A1 | 9/2020 | Telfort et al. |
| 2020/0289087 A1 | 9/2020 | Beckers et al. |
| 2020/0305792 A1 | 10/2020 | Visweswara et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2020/0345252 A1 | 11/2020 | Huijbregts et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0298623 A1 | 9/2021 | Syed et al. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |

FOREIGN PATENT DOCUMENTS

| | | |
|---|---|---|
| EP | 3 384 827 | 10/2018 |
| EP | 3 430 980 | 1/2019 |
| EP | 3 488 776 | 5/2019 |
| EP | 3 560 551 | 10/2019 |
| EP | 3 566 644 | 11/2019 |
| EP | 3 578 096 | 12/2019 |
| EP | 3 594 963 | 1/2020 |
| EP | 3 598 950 | 1/2020 |
| EP | 3 622 880 | 3/2020 |
| EP | 3 626 159 | 3/2020 |
| EP | 3 653 121 | 5/2020 |
| EP | 3 711 668 | 9/2020 |
| EP | 3 725 232 | 10/2020 |
| EP | 3 062 701 | 1/2021 |
| JP | D2009-13568 | 6/2010 |
| JP | D1671743 | 10/2020 |
| JP | D1671824 | 11/2020 |
| KR | 2008-0042328 | 5/2008 |
| WO | WO 2010/020945 | 2/2010 |
| WO | WO 2013/076656 | 5/2013 |
| WO | WO 2013/124750 | 8/2013 |
| WO | WO 2015/049108 | 4/2015 |
| WO | WO 2017/093150 | 6/2017 |
| WO | WO 2017/140525 | 8/2017 |
| WO | WO 2019/005801 | 1/2019 |
| WO | WO 2020/002133 | 1/2020 |
| WO | WO 2020/002290 | 1/2020 |
| WO | WO 2020/002461 | 1/2020 |
| WO | WO 2020/078842 | 4/2020 |
| WO | WO 2020/078962 | 4/2020 |
| WO | WO 2020/120527 | 6/2020 |
| WO | WO 2020/144075 | 7/2020 |
| WO | WO 2020/214826 | 10/2020 |
| WO | WO 2020/216694 | 10/2020 |

OTHER PUBLICATIONS

Cake Board 7.5Δ Round—Golden. Online, published date unknown. Retrieved on Apr. 5, 2021 from https://banglaneed.com/product/cake-board-7 -5-round-golden/, 1 page.

Innovative Solutions in Resuscitation Therapy, "HeartStart Pads for Emergency and General Use", Online, published date 2013. Retrieved on Apr. 6, 2021 from https://www.wessex-medical.com/wp-contenl/uploads/2019/03/Philips-Defib-Pads.pdf.

Plastic Yogurt Container with Peel off Lid. Online, published date unknown. Retrieved on Apr. 6, 2021 from https://www.istockphoto.com/vector/plastic-yogurt-container-with-peel-off-lid-realistic-vector-mockup-yoghurt-gm 1179621404-330158057, 1 page.

International Preliminary Report on Patentability and Written Opinion received in PCT Application No. PCT/US2020/028542 dated Oct. 28, 2021 in 19 pages.

Invitation to Pay Additional Fees received in PCT Application No. PCT/US2020/028542 dated Jul. 9, 2020 in 17 pages.

Mindray, Date: Not Available, [online], [site visited Jun. 8, 2022]. Available from internet, https://www.cablesandsensors.com/products/mindray-datascope-compatible-reusable-temperature-probe-040-000057-00.

Pacmed, Date: Not Available, [online], [site visited Jun. 8, 2022]. Available from internet, http://www.pacmedcables.com/Datascope-Direct-Connect-Adult-Temperature-Sensor-p/ncda5172.htm.

(56) References Cited

OTHER PUBLICATIONS

International Search Report and Written Opinion received in PCT Application No. PCT/US2020/028542 dated Sep. 7, 2020 in 19 pages.
"Electrode Patch, Electrode Pads Patch Soft Electrode Pads with 2", Bobosale, retrieved on Nov. 25, 2021 from https://bobosale.online/index.php?main_page=product_info&products_id = 124693 in 1 page.
"Minimal Rounded Coasters Mockup", GraphicPear, retrieved on Nov. 25, 2021 from https://www.graphicpear.com/minimal-rounded-coasters-mockup/ in 2 pages.
"Round Coaster Mock-Up—Medium Size", EnvatoElements, retrieved on Nov. 25, 2021 from https://elements.envato.com/round-coaster-mock-up-medium-size-PFFH4M6 in 1 page.
Blood Pressure Device, U.S. Appl. No. 29/702,168, U.S. Pat. No. D. 919,094.
Blood Pressure Monitor, U.S. Appl. No. 29/775,244, U.S. Pat. No. D. 933,233.
Holder for a Blood Pressure Device, U.S. Appl. No. 29/702,174, U.S. Pat. No. D. 921,202.
Blood Pressure Monitor, U.S. Appl. No. 29/734,321, U.S. Pat. No. D. 933,232.
Blood Pressure Monitor, U.S. Appl. No. 29/789,291, U.S. Pat. No. D. 965,789.
Blood Pressure Monitor, U.S. Appl. No. 29/866,091.

\* cited by examiner

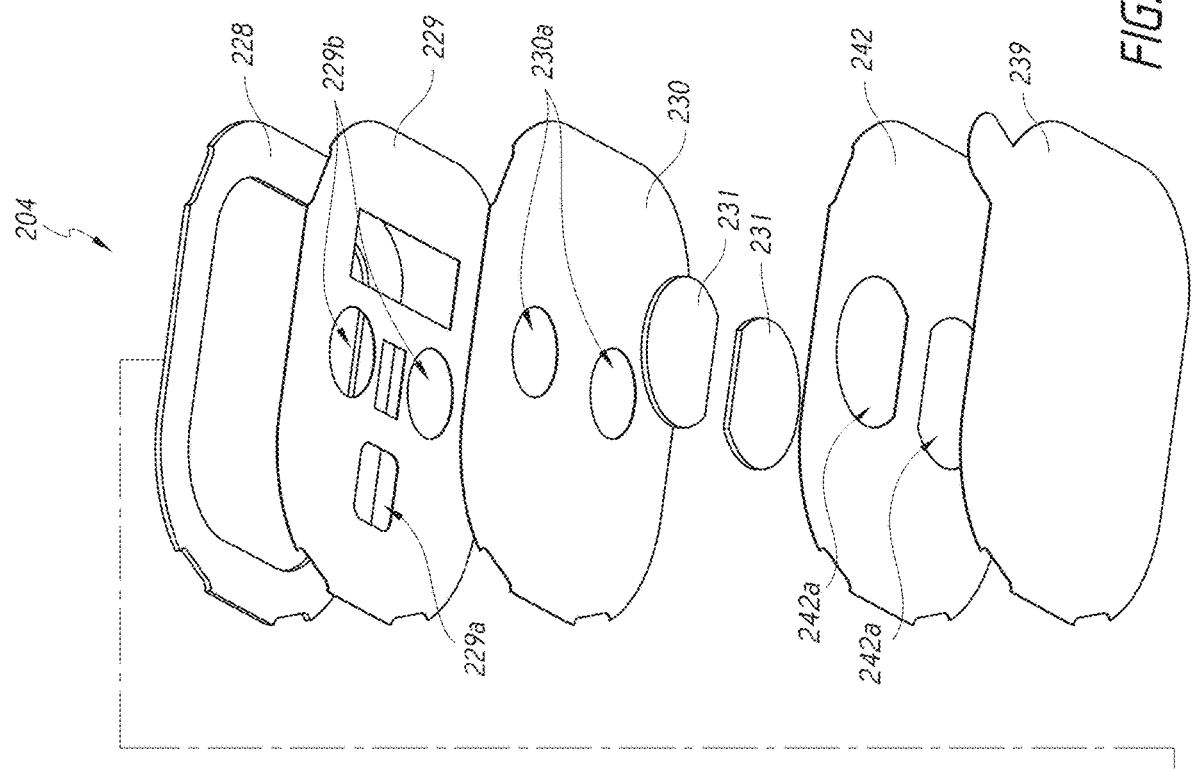
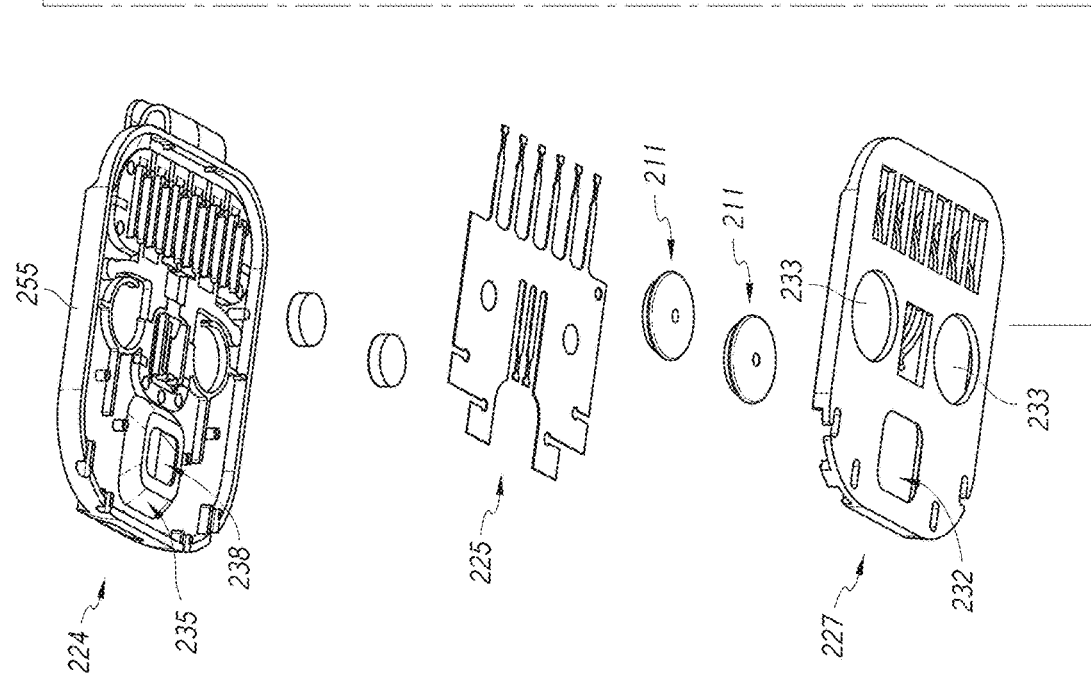
FIG. 2G

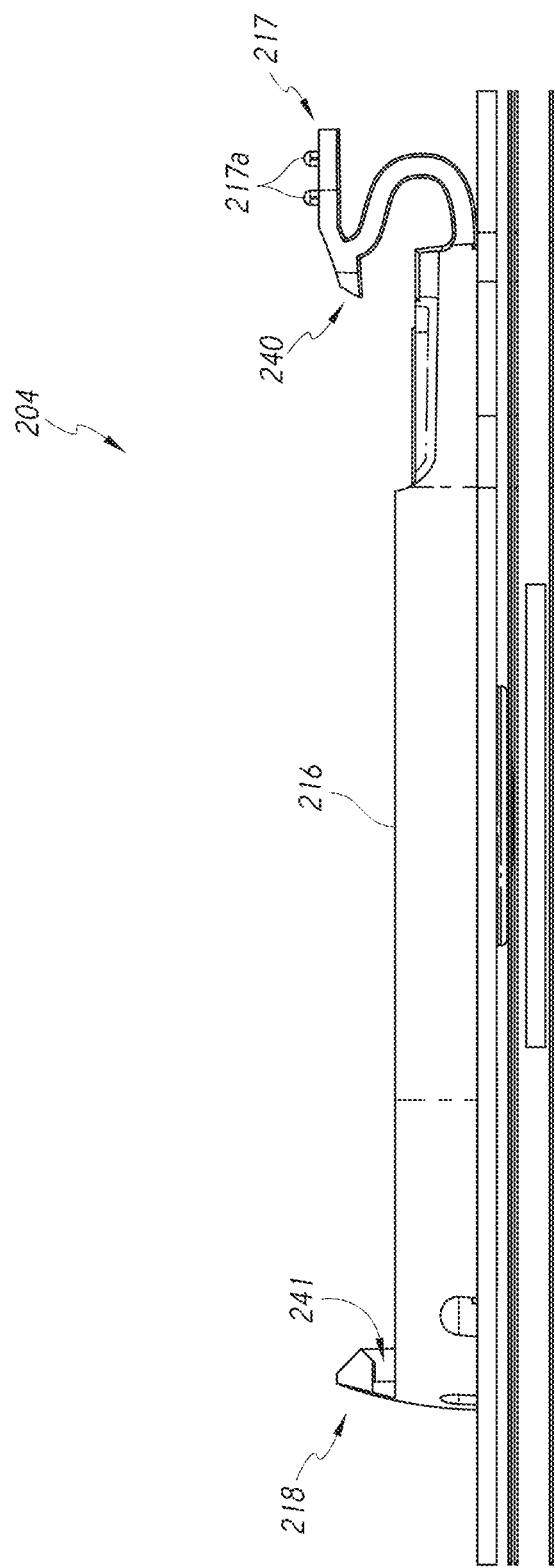

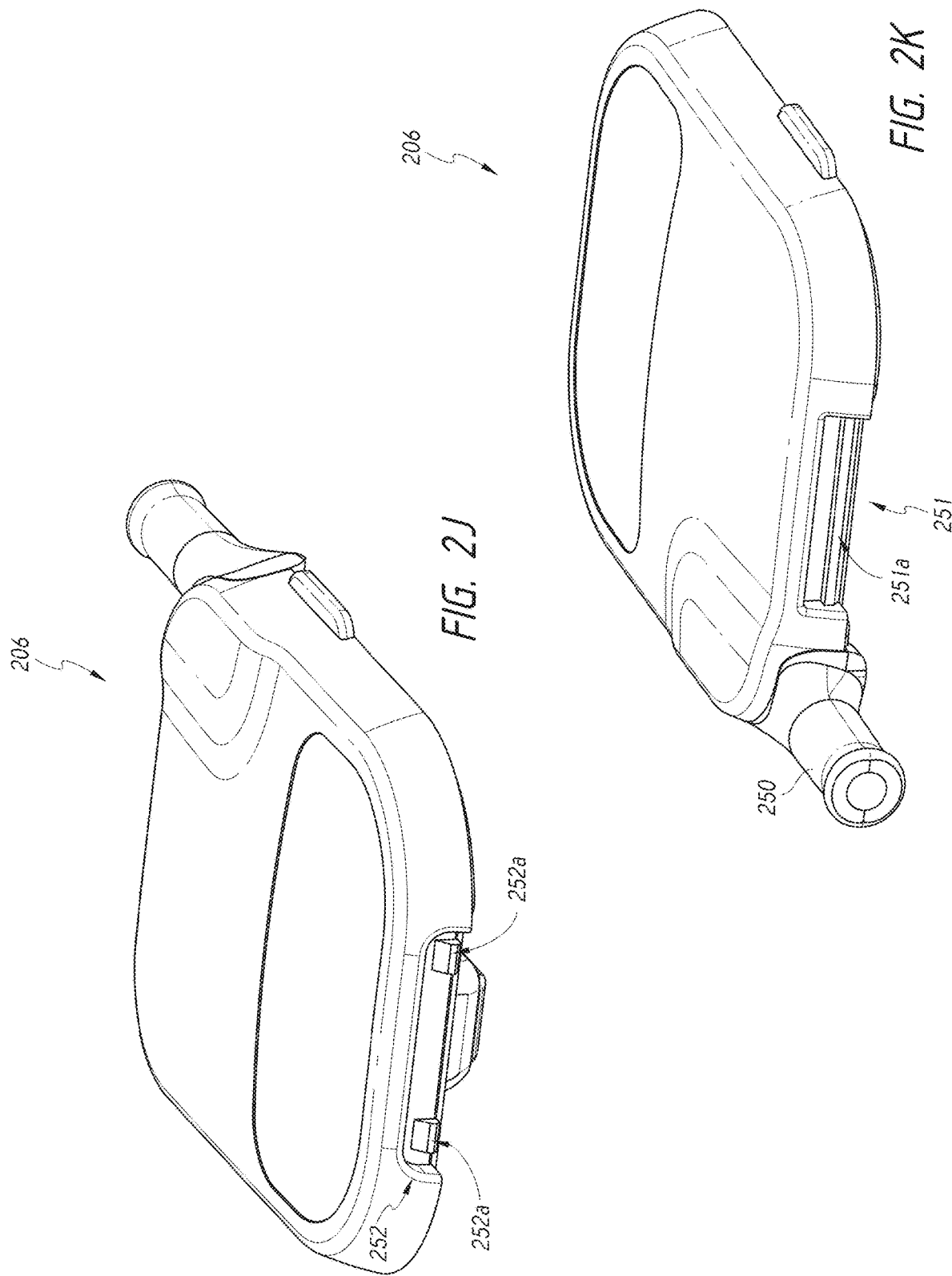

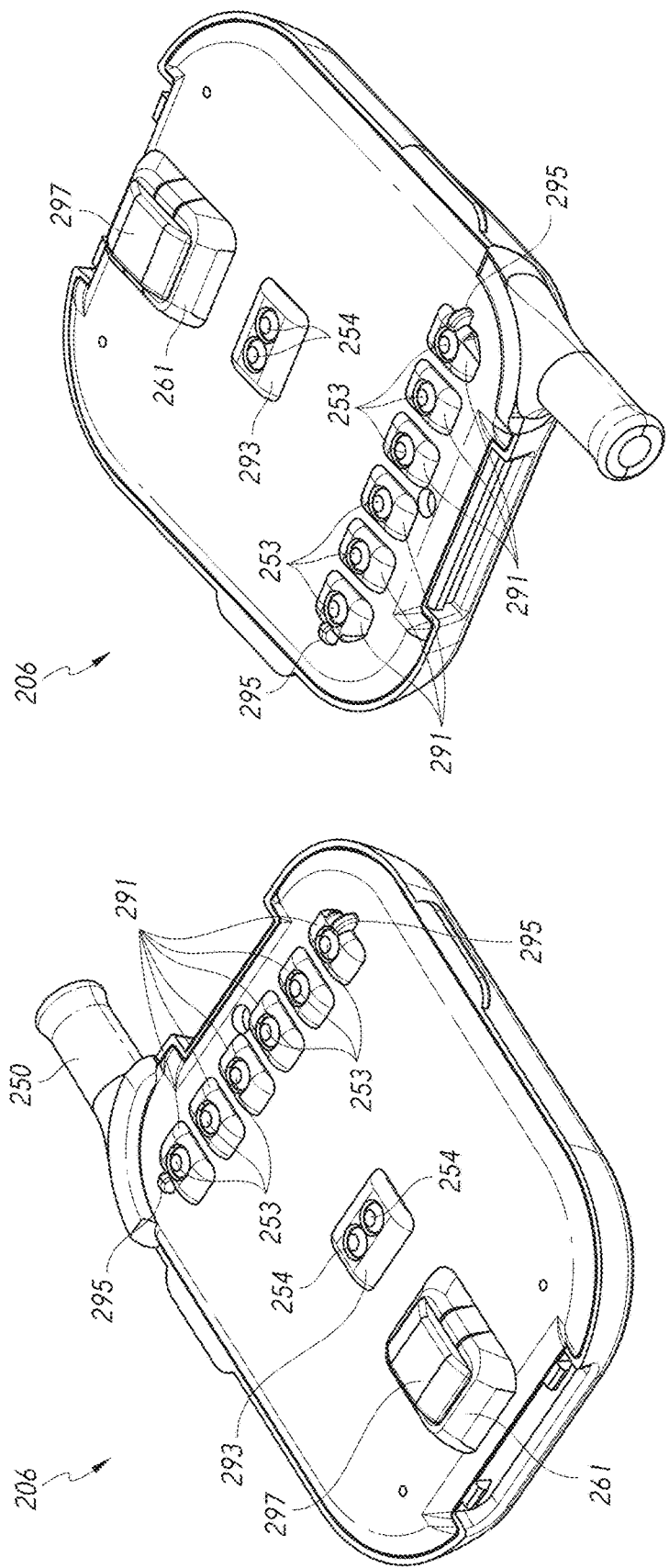
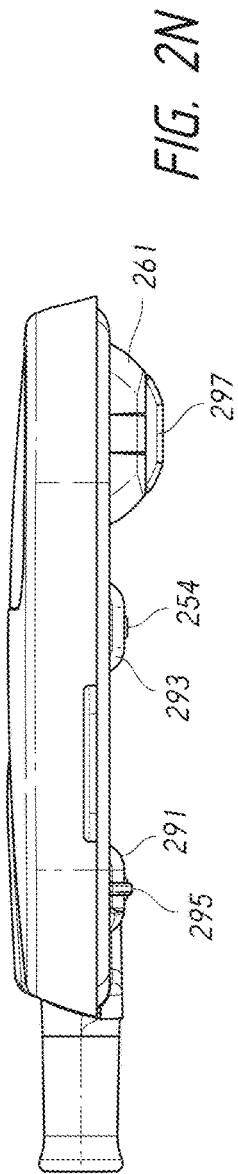
FIG. 2M
FIG. 2N
FIG. 2L

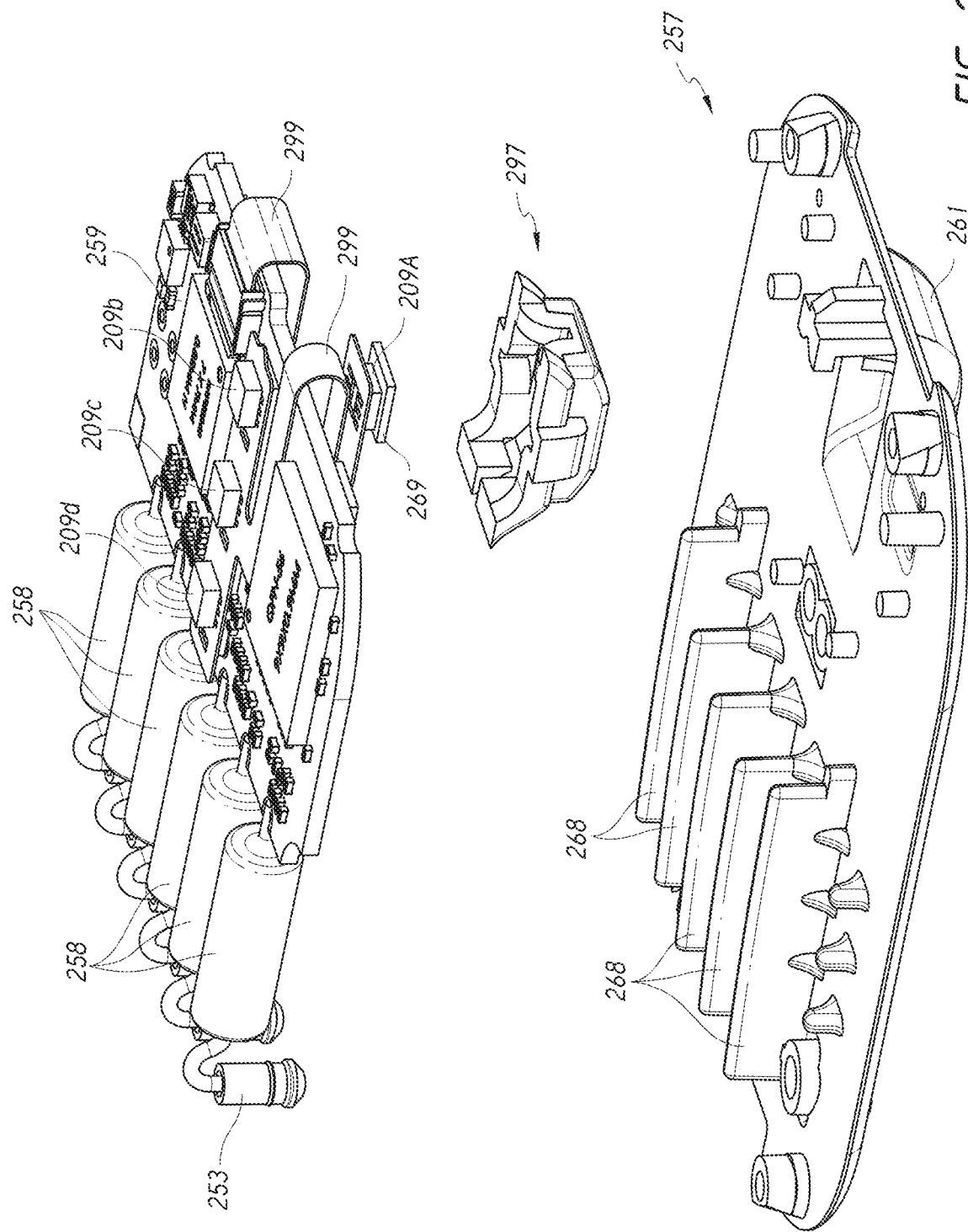

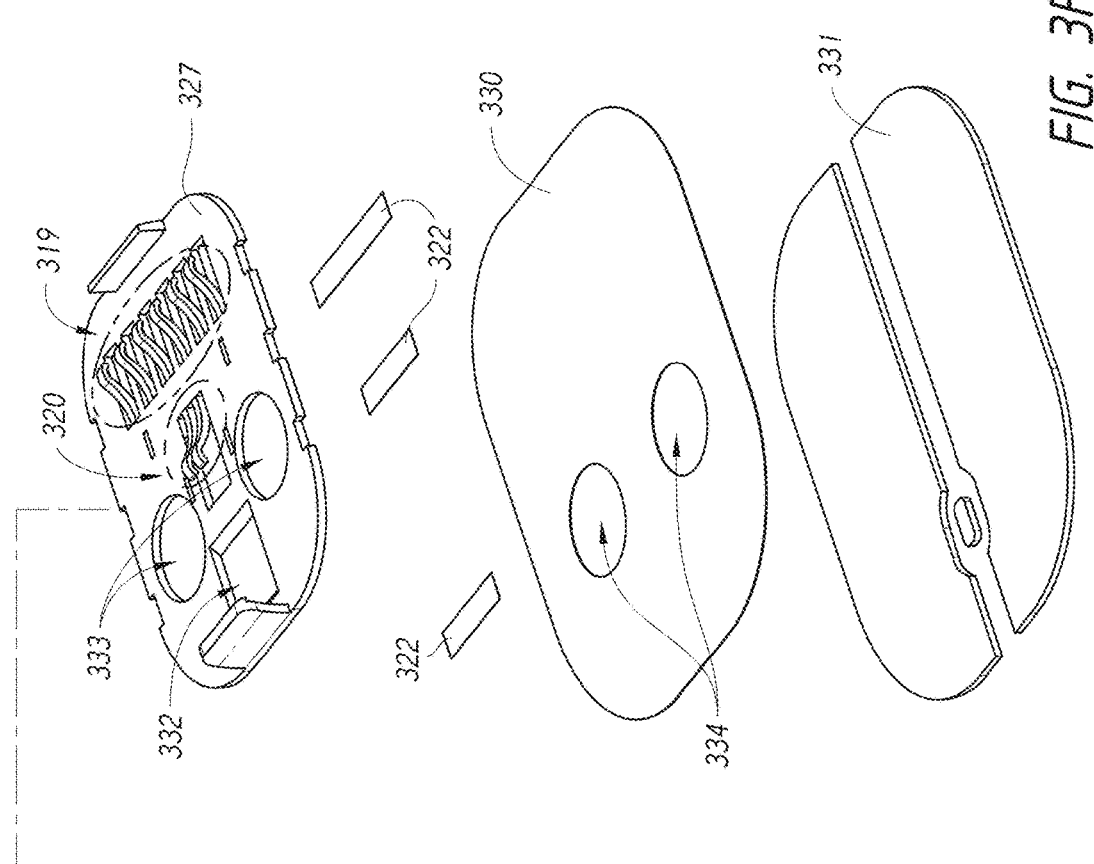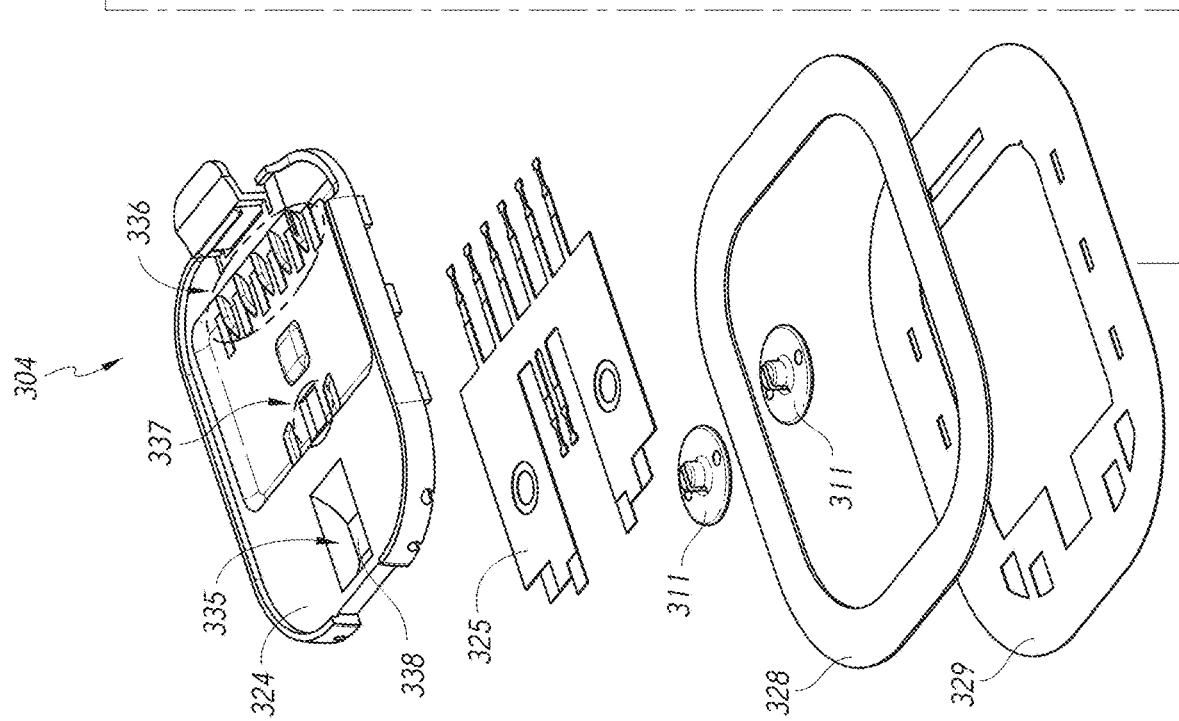
FIG. 3F

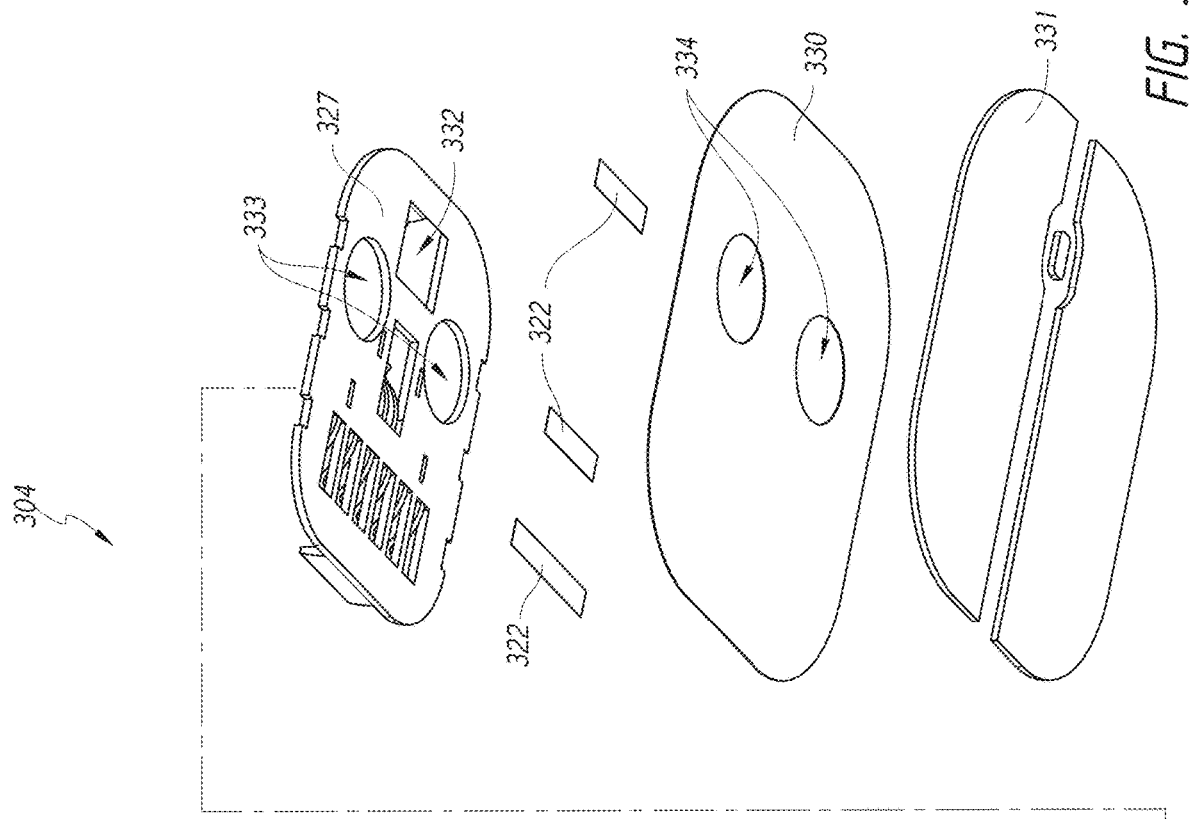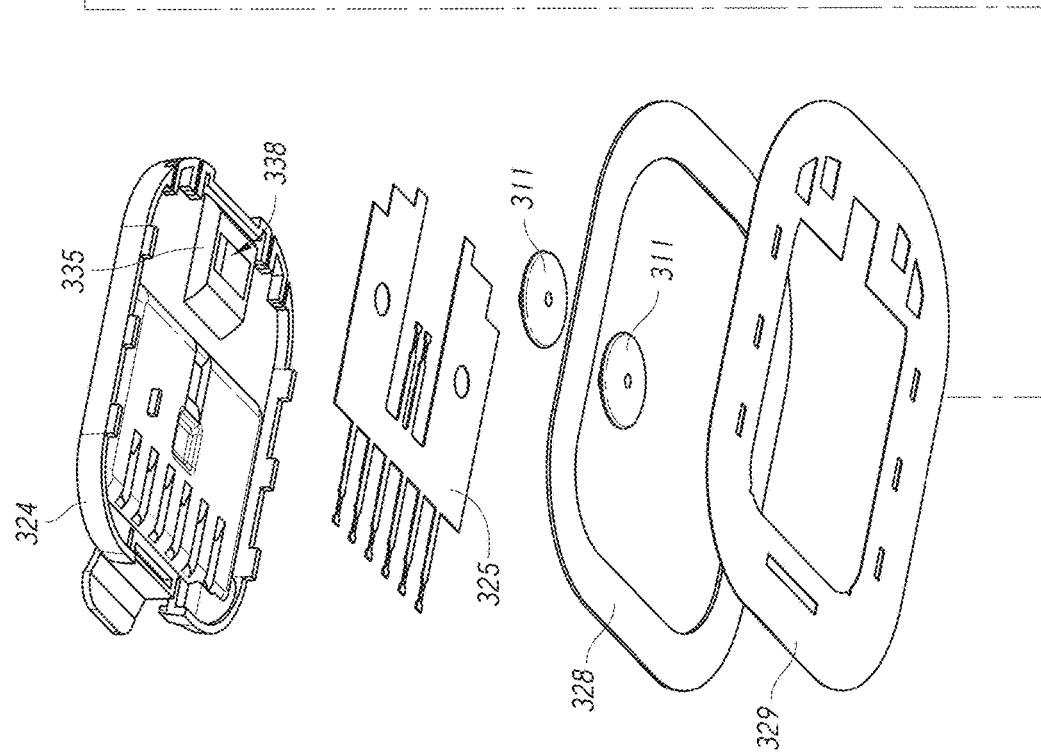
FIG. 3G

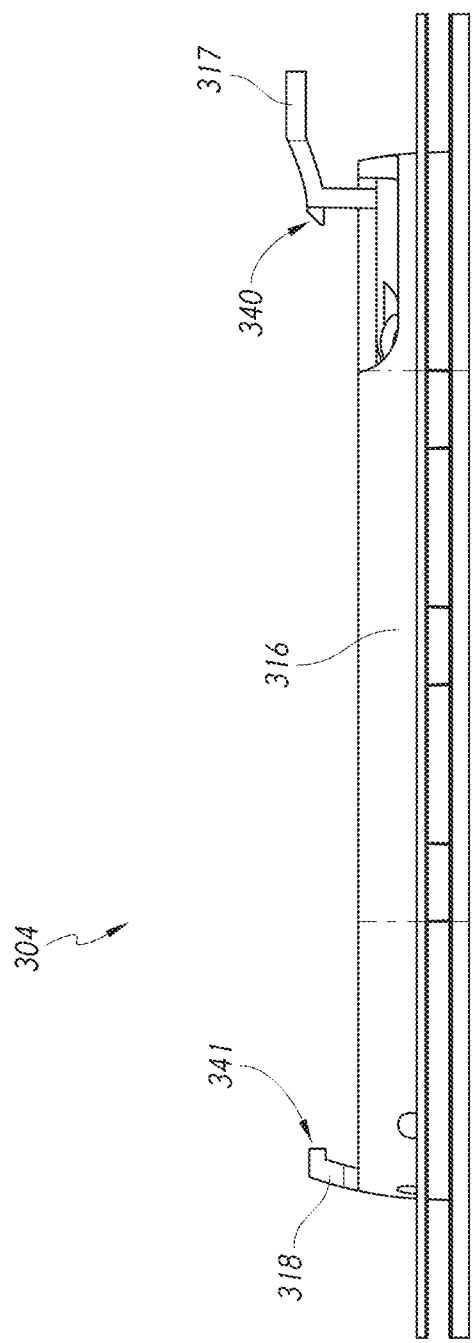

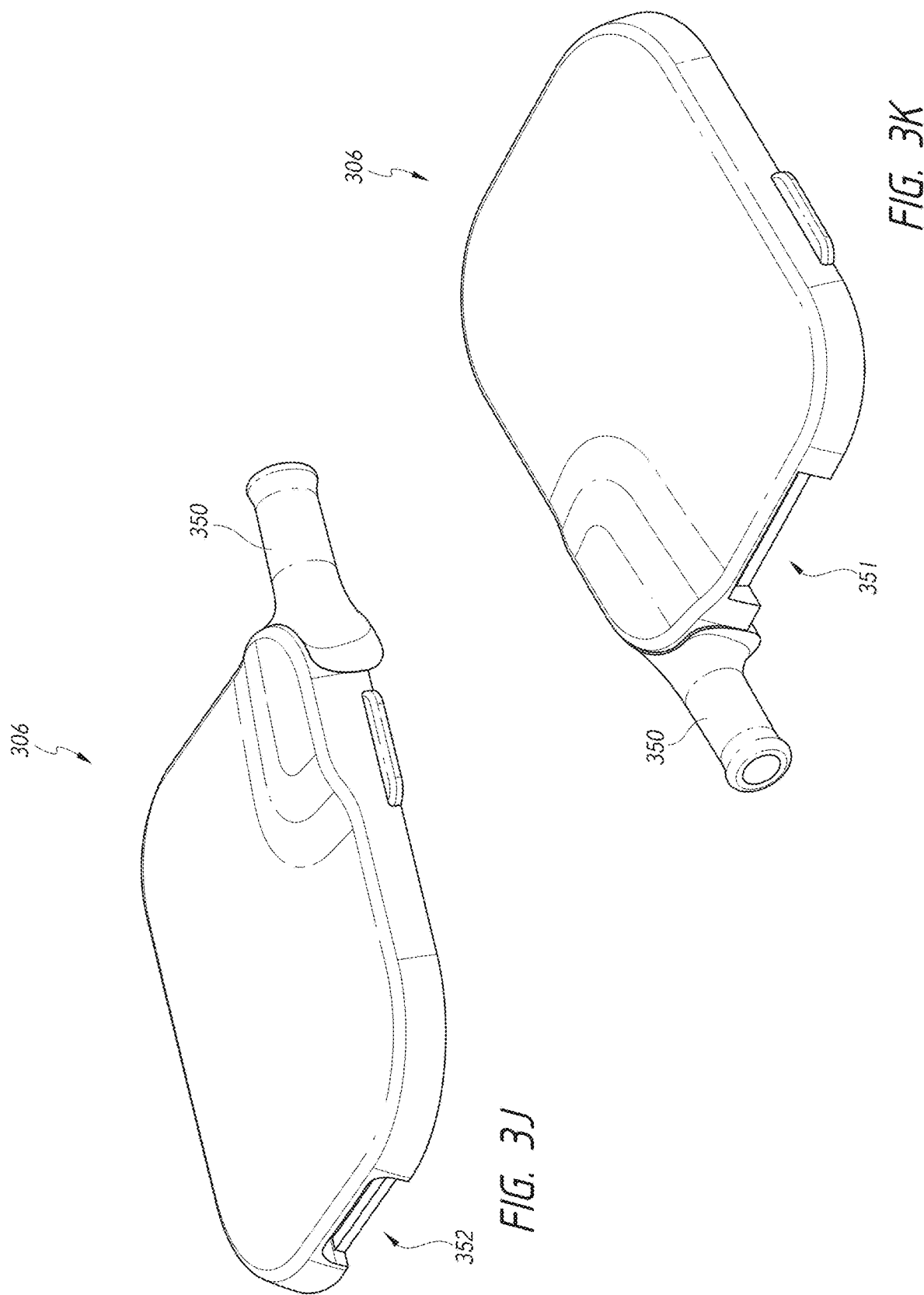

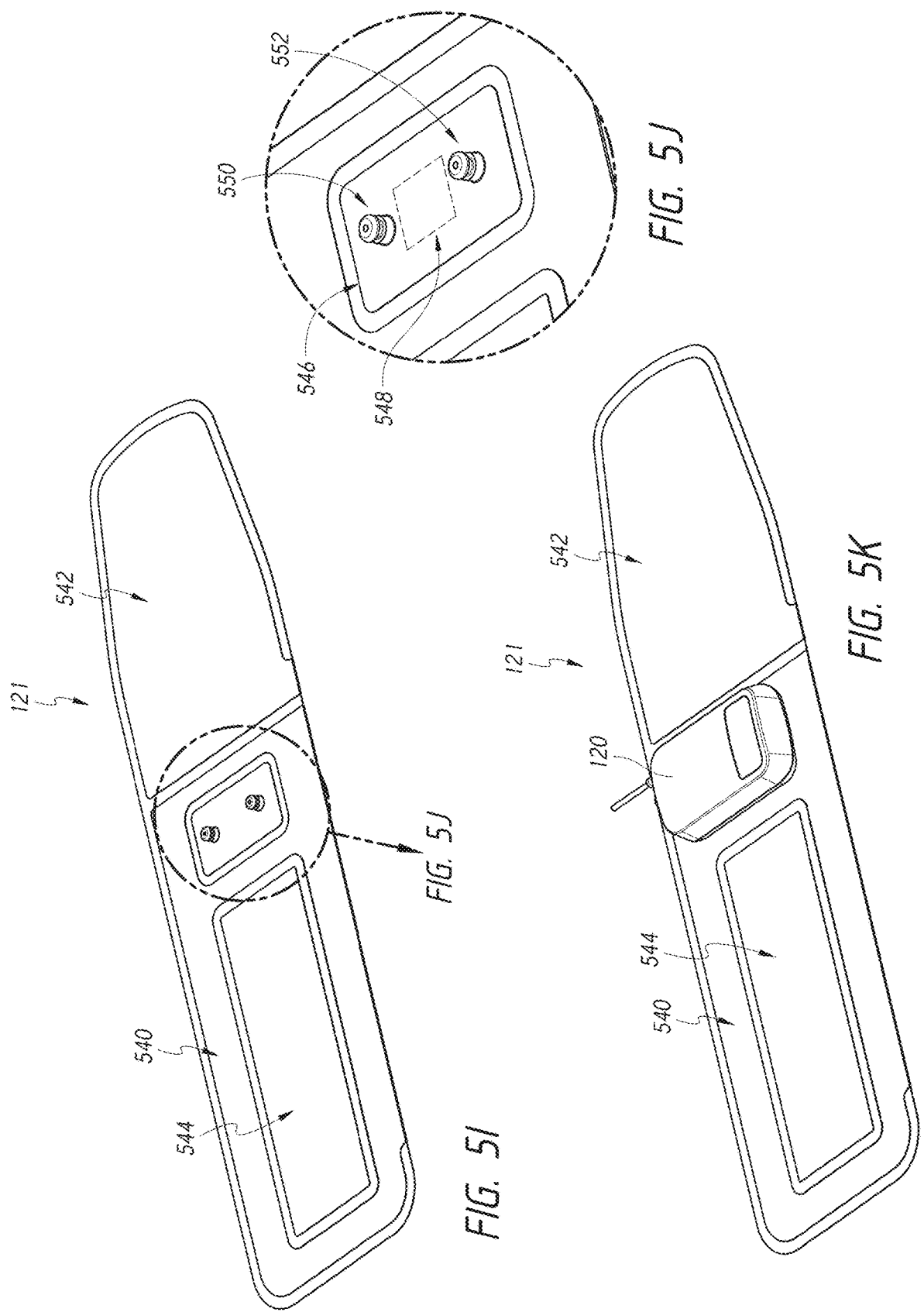

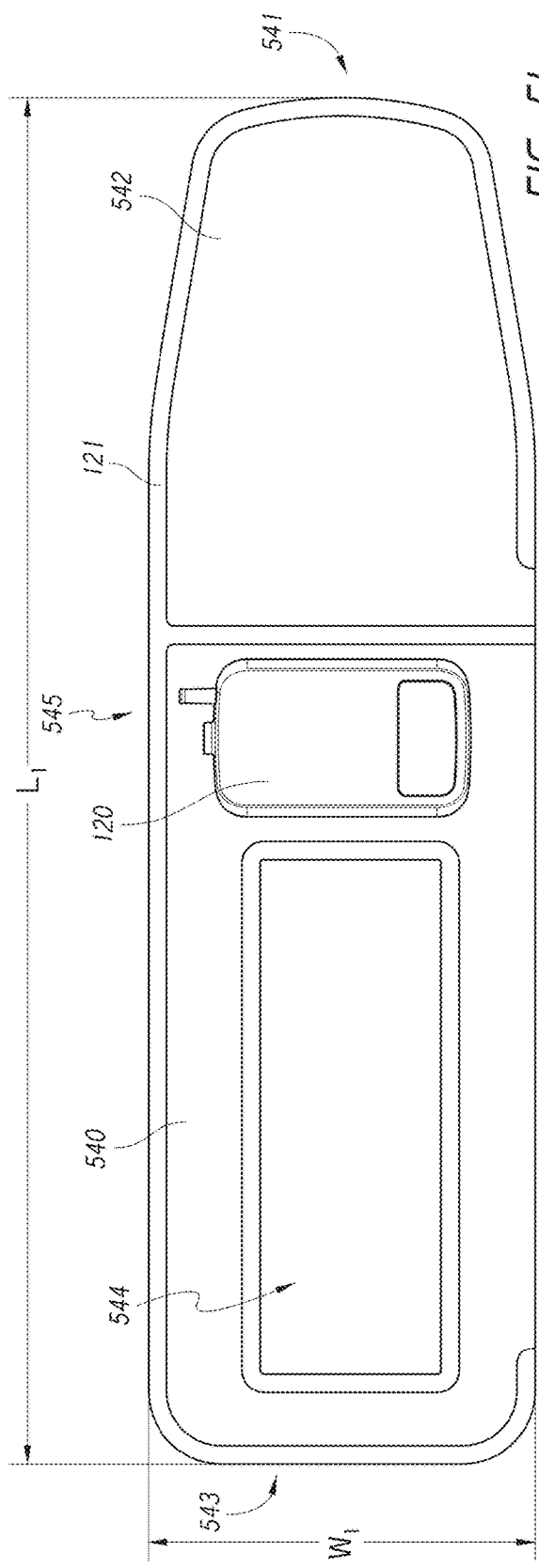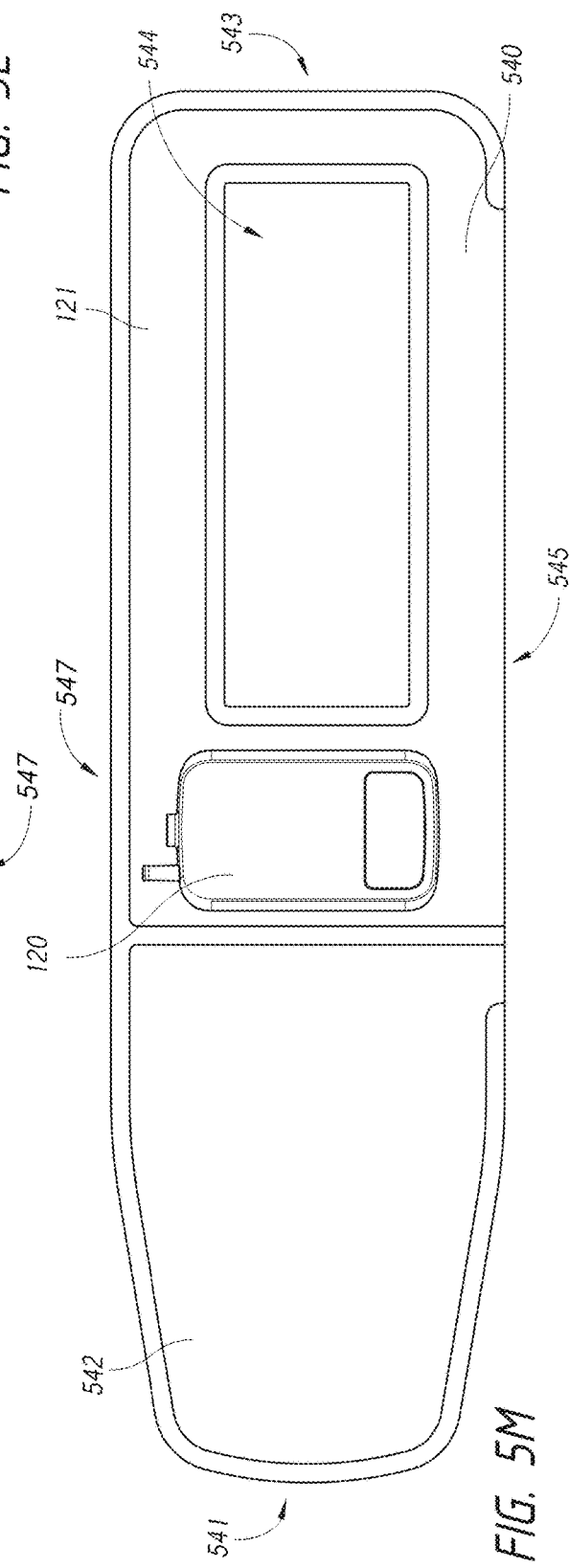

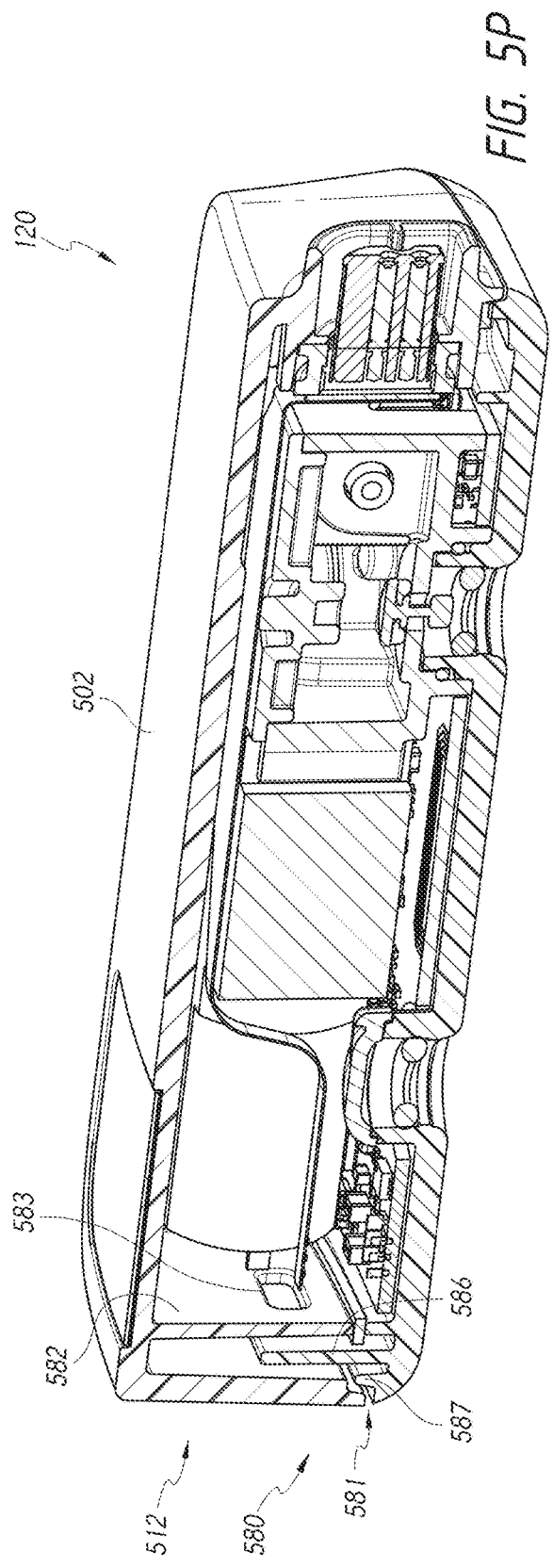
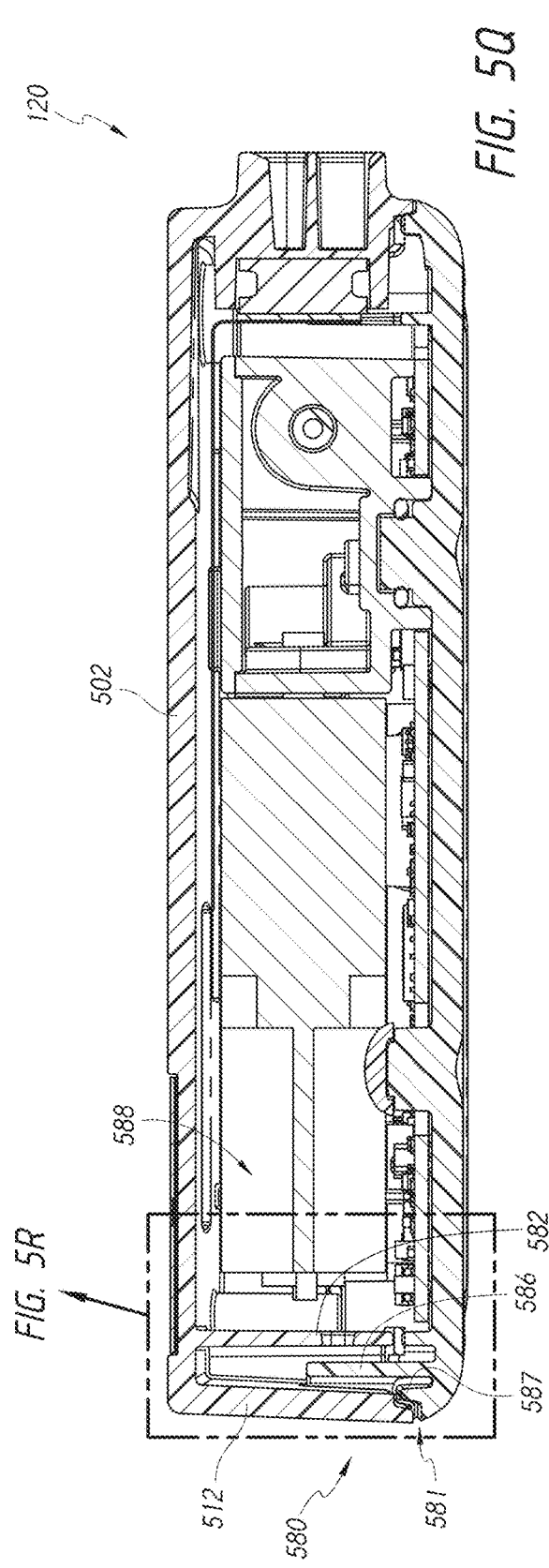

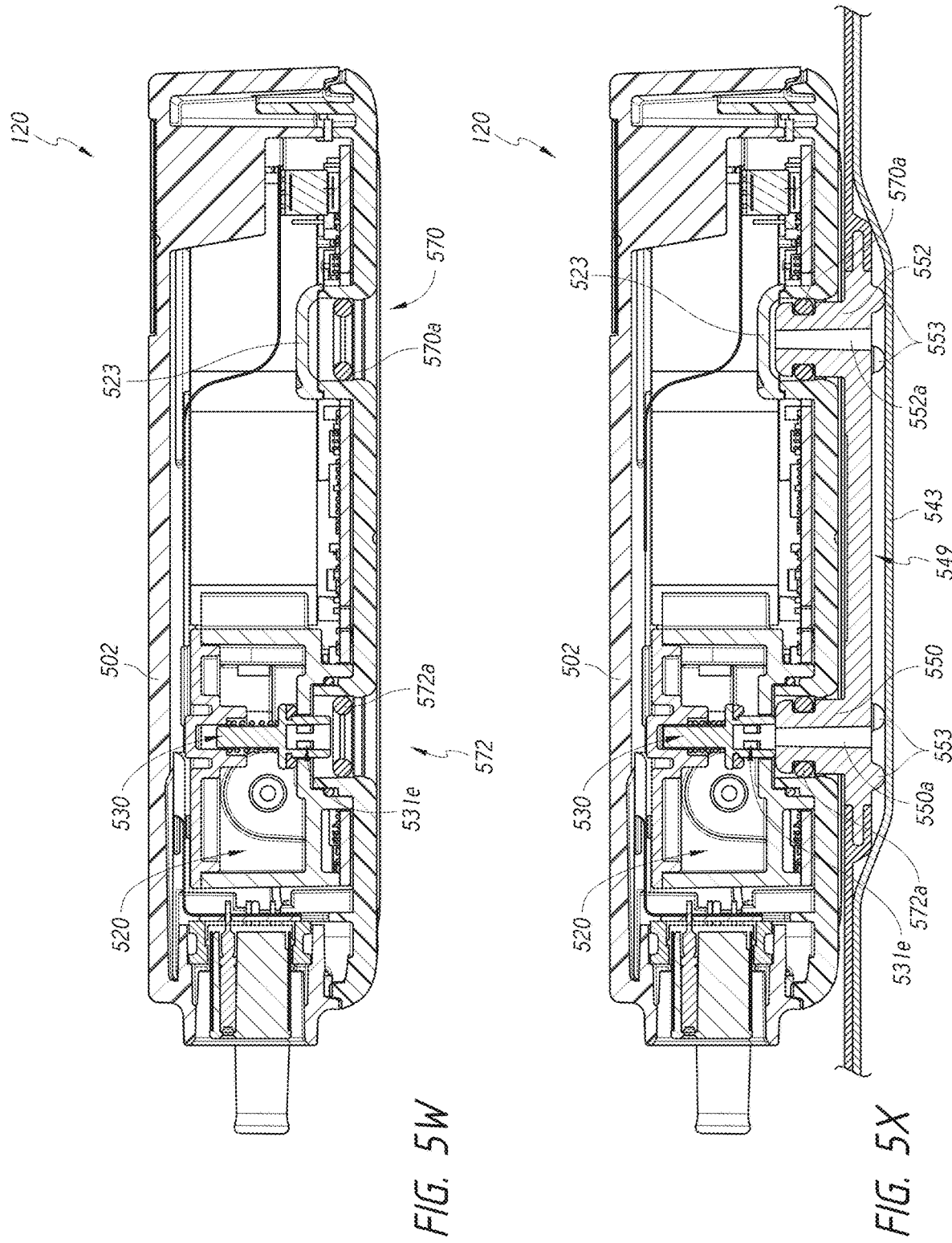

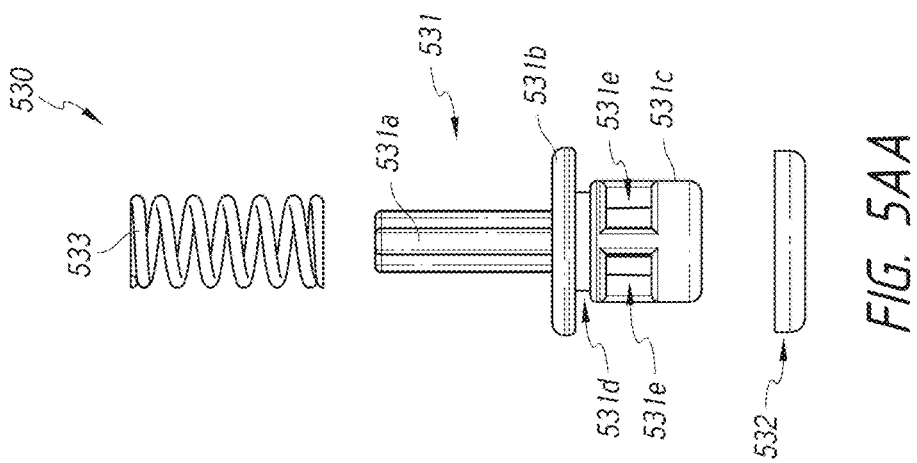
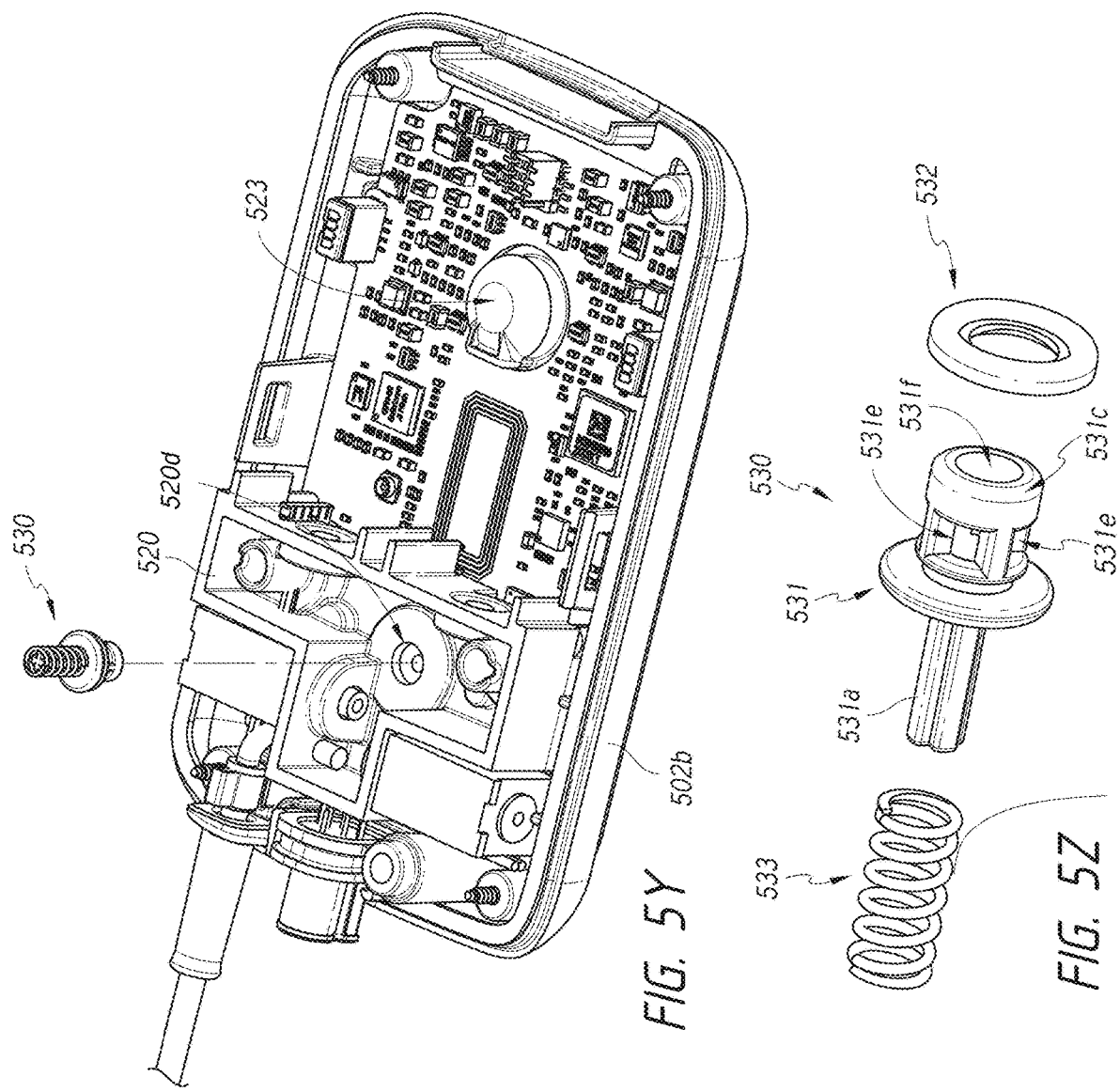

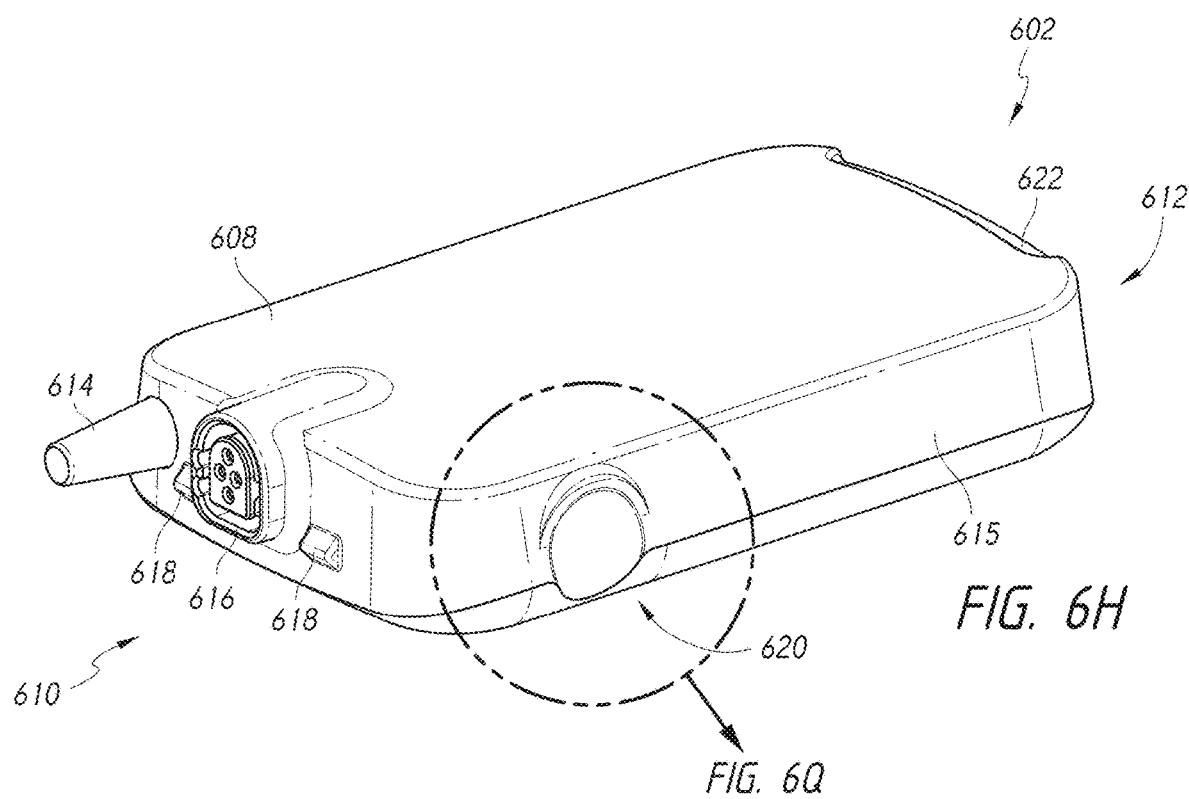
FIG. 6H
FIG. 6Q
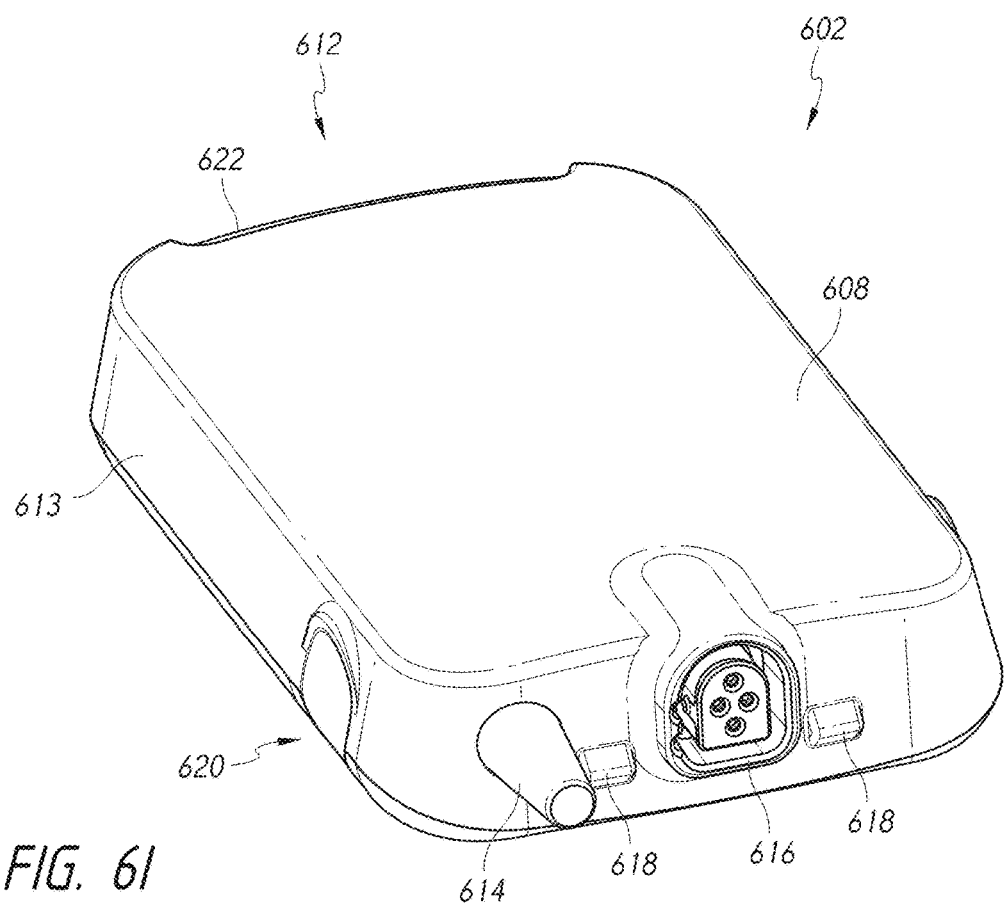
FIG. 6I

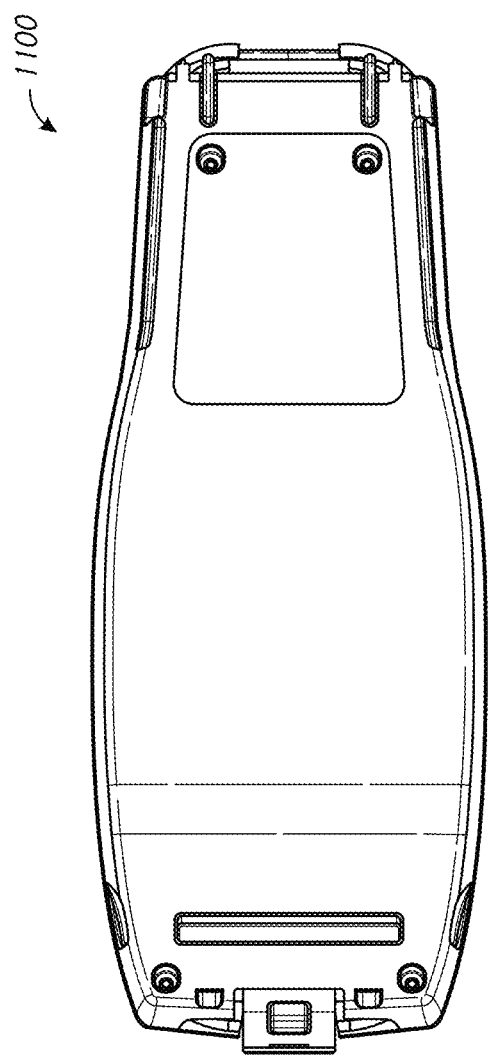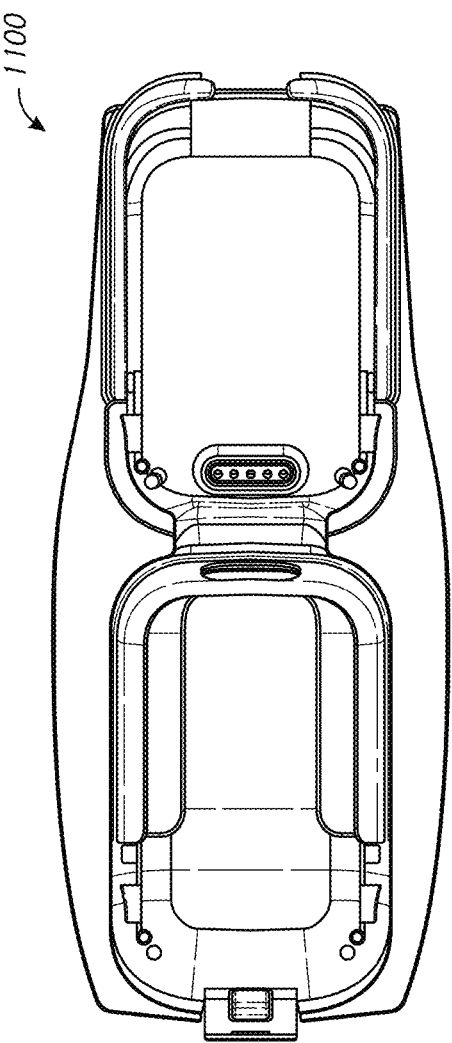

Lowpass Filters

Bandstop Filter

BLOOD PRESSURE MONITOR ATTACHMENT ASSEMBLY

INCORPORATION BY REFERENCE TO ANY PRIORITY APPLICATIONS

The present application claims priority to U.S. Provisional Application No. 62/923,157, filed Oct. 18, 2019, U.S. Provisional Application No. 62/888,271, filed Aug. 16, 2019, U.S. Provisional Application No. 62/837,195, filed Apr. 23, 2019, and U.S. Provisional Application No. 62/835,386, filed Apr. 17, 2019. All of the above-listed applications and any and all other applications for which a foreign or domestic priority claim is identified in the Application Data Sheet as filed with the present application, are hereby incorporated by reference under 37 CFR 1.57.

BACKGROUND

Field

The present disclosure generally relates to systems, methods, and devices for monitoring a patient's physiological information.

Description of the Related Art

Hospitals, nursing homes, and other patient care facilities typically utilize a number of sensors, devices, and/or monitors to collect or analyze a patient's physiological parameters such as blood oxygen saturation level, respiratory rate, pulse rate, blood pressure, and the like. Such devices can include, for example, acoustic sensors, electroencephalogram (EEG) sensors, electrocardiogram (ECG) devices, blood pressure monitors, pulse oximeters, among others. In medical environments, various sensors/devices (such as those just mentioned) are attached to a patient and connected to one or more patient monitoring devices using cables. Patient monitoring devices generally include sensors, processing equipment, and displays for obtaining and analyzing a medical patient's physiological parameters such as blood oxygen saturation level, respiratory rate, and the like. Clinicians, including doctors, nurses, and other medical personnel, use the physiological parameters obtained from patient monitors to diagnose illnesses and to prescribe treatments. Clinicians also use the physiological parameters to monitor patients during various clinical situations to determine whether to increase the level of medical care given to patients.

SUMMARY

An electrocardiogram (ECG) device configured to transmit at least one signal responsive to a wearer's cardiac electrical activity can comprise: a disposable portion and a reusable portion configured to mechanically and electrically mate with the disposable portion. The disposable portion can comprise: a base configured for placement on the wearer's body, wherein the base comprises at least one mechanical connector portion; a plurality of cables and corresponding external ECG electrodes, said external ECG electrodes configured to be secured to the wearer's body and output one or more signals responsive to the wearer's cardiac electrical activity; and a first plurality of electrical connectors, each of at least some of the first plurality of electrical connectors associated with one of the plurality of cables. The reusable portion can comprise: a cover comprising at least one mechanical connector portion configured to removably secure to the at least one mechanical connector portion of the base of the disposable portion; a second plurality of electrical connectors, each of the second plurality of electrical connectors configured to electrically connect with one of the first plurality of electrical connectors of the disposable portion; and an output connector port configured to transmit at least one signal responsive to said one or more signals outputted by the external ECG electrodes of the disposable portion. The disposable portion can further comprise a first internal ECG electrode positioned at least partially within the base, the first internal ECG electrode configured to output one or more signals responsive to the wearer's cardiac electrical activity, wherein one of the first plurality of electrical connectors is associated with the first internal ECG electrode. The output connector port can be further configured to transmit at least one signal responsive to said one or more signals outputted by the first internal ECG electrode of the disposable portion. Each of the plurality of cables of the disposable portion can be soldered to a respective one of the external ECG electrodes. The base can be configured to secure the disposable portion to the wearer's body. The base can be configured to secure the disposable portion to skin of the wearer's body. In some cases, when the base can secures the disposable portion to the skin of the wearer's body and the reusable portion is mechanically and electrically mated with the disposable portion, the reusable portion does not touch the skin. The disposable portion can further comprise a flexible circuit. The flexible circuit can comprise a first plurality of conductive strips configured to electrically connect to the plurality of cables and a second plurality of conductive strips, wherein the first plurality of electrical connectors of said disposable portion comprise the second plurality of conductive strips of the flexible circuit. The flexible circuit of the disposable portion can further comprise at least one additional conductive strip spaced from the first and second plurality of conductive strips. The reusable portion can further comprise at least one additional electrical connector operably positioned by the cover and configured to electrically connect with the at least one additional conductive strip of the flexible circuit of the disposable portion to enable the reusable portion to determine whether the disposable portion is an authorized product. Each of the first plurality of conductive strips of the flexible circuit can be soldered to one of the plurality of cables. The disposable portion can further comprise a first internal ECG electrode positioned at least partially within the base, the first internal ECG electrode configured to output one or more signals responsive to the wearer's cardiac electrical activity, wherein one of the first plurality of electrical connectors is associated with the first internal ECG electrode. The output connector port can be further configured to transmit at least one signal responsive to said one or more signals outputted by the first internal ECG electrode of the disposable portion. The flexible circuit can further comprise a first aperture and a first conductive ring positioned along the first aperture, the first conductive ring configured to electrically connect to a portion of the first internal ECG electrode, wherein the one of the first plurality of electrical connectors is electrically coupled to the first conductive ring. The disposable portion can further comprise a second internal ECG electrode positioned at least partially within the base and spaced from the first internal ECG electrode, the second internal ECG electrode configured to act as a ground electrode, wherein one of the first plurality of electrical connectors is associated with the second internal ECG electrode. The flexible circuit can further comprise a second aperture and a second conductive ring positioned along the second aperture, the second aperture spaced from the first aperture, the second conductive ring configured to electrically connect to a portion of the second internal ECG electrode. The base of the disposable portion can further comprise a plurality of pin supports, each of the plurality of pin supports configured to position one of the second plurality of conductive strips of the flexible circuit to electrically contact one of the second plurality of electrical connectors of the reusable portion when the reusable portion is mated with the disposable portion. Each of the plurality of pin supports can be flexible. Each of the plurality of pin supports can be not straight. Each of the plurality of pin supports can be arcuate. The plurality of pin supports can extend above a top surface of the base of the disposable portion. The at least one mechanical connector portion of the cover of the reusable portion can comprise at least one groove. The at least one mechanical connector portion of the base of the disposable portion can comprise at least one clip configured to removably secure within the at least one groove of the reusable portion. The at least one groove can comprise a first groove disposed on a first end of the cover and a second groove disposed on a second end of the cover, the second end opposite the first end. The at least one clip can comprise a first clip disposed on a first end of the base and a second clip disposed on a second end of the base, the second end opposite the first end. The reusable portion can further comprise: a circuit board, the circuit board comprising a processor and a memory; and a plurality of resistors electrically connected to and positioned between a portion of the circuit board and the second plurality of electrical connectors of the reusable portion, the plurality of resistors configured to protect the circuit board from sudden changes in voltage. Each of the plurality of resistors can be a low-resistance, high capacity resistor. The base of the disposable portion can further comprise a first opening and the reusable portion can further comprise a first temperature sensor, the first temperature sensor configured to align with the first opening of the disposable portion when the reusable portion is mated with the disposable portion, the first temperature sensor configured to measure a temperature of the wearer's body. A bottom portion of the reusable portion can comprise a second opening configured to align with the first opening of the base of the disposable portion when the reusable portion is mated with the disposable portion. The reusable portion can further comprise a housing, a portion of the housing extending through the second opening in the bottom portion of the reusable portion, and wherein the first temperature sensor can be positioned within the housing. The disposable portion can comprise a first substrate connected to the base and configured to secure to the wearer's skin, wherein the first opening of the base can be positioned between the first substrate and the housing of the reusable portion. The first substrate can comprise a thermally conductive material. The disposable portion can comprise a second substrate positioned between the first substrate and the base, wherein the housing of the reusable portion is configured to contact a portion of the second substrate when the reusable portion is mated with the disposable portion. The second substrate can comprise a polyethylene film. The reusable portion can further comprise a second temperature sensor at least one of vertically and horizontally spaced from the first temperature sensor, the second temperature sensor configured to measure an internal temperature of the reusable portion. The second temperature sensor can be not placed within the housing of the reusable portion. The reusable portion can further comprise a circuit board including a processor, wherein the processor is configured to determine a corrected body temperature of the wearer based on temperature data received from the first and second temperature sensors. The cover can comprise a top frame and a bottom frame. The reusable portion can further comprise a cable connected to the output connector port. In some variants, neither of the disposable portion or the reusable portion comprise a power source, and the reusable portion is configured to receive power from the cable when the cable is connected to an external power source. The cable can be configured to electrically connect to a patient monitor, and wherein the patient monitor comprises the external power source. In some variants, the disposable portion does not include a processor. The reusable portion can further comprise a motion sensor configured to measure an acceleration of the wearer when the reusable portion is mated with the disposable portion. The reusable portion can be configured such that, when the reusable portion is placed on a flat surface, none of the second plurality of electrical connectors contact the flat surface.

An electrocardiogram (ECG) device can comprise a disposable portion. The disposable portion can comprise: a base configured for placement on a wearer's body; a plurality of cables and corresponding external ECG electrodes, said external ECG electrodes configured to be secured to the wearer's body and further configured to detect electrical signals responsive to the wearer's cardiac activity; and a flexible circuit comprising a first plurality of conductive strips and a second plurality of conductive strips, each of the first plurality of conductive strips electrically connected to a respective one of the plurality of cables, wherein the second plurality of conductive strips are configured to transmit the electrical signals responsive to the wearer's cardiac electrical activity. In some variants, the disposable portion does not include a battery. In some variants, the disposable portion does not include a processor. The disposable portion can further comprise at least one substrate configured to allow the base to be secured to skin of the wearer's body. The at least one substrate can comprise a thermally conductive material. The disposable portion can further comprise at least one internal ECG electrode positioned at least partially within the base, the at least one internal ECG electrode electrically connected to the flexible circuit. The flexible circuit can further comprise at least one aperture and at least one conductive ring positioned along the at least one aperture and configured to electrically connect to a portion of the at least one internal ECG electrode. The at least one internal ECG electrode can comprise two internal ECG electrodes. The at least one aperture can comprise two apertures. The at least one conductive ring can comprise two conductive rings. The base can comprise a plurality of pin supports, each of the plurality of pin supports configured to support one of the second plurality of conductive strips of the flexible circuit. Each of the plurality of pin supports can be flexible. Each of the plurality of pin supports can be not straight. Each of the plurality of pin supports can be arcuate. The plurality of cables can be irremovably secured to the external ECG electrodes. Each of the plurality of cables can be irremovably secured to one of the first plurality of conductive strips of the flexible circuit. The plurality of cables can be soldered to the external ECG electrodes. The plurality of cables, the external ECG electrodes, and the flexible circuit can be integrally formed.

A blood pressure monitoring device configured to attach and supply air to a blood pressure cuff can comprise: a housing comprising an interior; a port configured to enable fluid communication between the interior of the housing and an interior of the blood pressure cuff; and an air intake configured to allow ambient air to enter the interior of the housing and further configured to inhibit liquids from entering the interior of the housing. The air intake can define a non-linear passageway for ambient air to enter the interior of the housing. The air intake can define a tortuous passageway for ambient air to enter the interior of the housing. The air intake can define a serpentine passageway for ambient air to enter the interior of the housing. The air intake can comprise a waterproof membrane configured to prevent liquids from entering the interior of the housing. The housing can further comprise a first side and a first inner wall. The air intake can comprise a first opening in the first side of the housing and a second opening in the first inner wall of the housing. The first opening can be not aligned with the second opening. The first opening and the second opening can be vertically spaced from one another. The housing can comprise a top surface and a bottom surface opposite the top surface and configured to be positioned closer to the blood pressure cuff when the blood pressure monitoring device is secured thereto. The first opening can be positioned closer to the bottom surface than the second opening. The first opening can comprise a slit having a slit width extending along a portion of a width of the first side and a slit height extending along a portion of a height of the first side. The slit width can be greater than the slit length. The first side can be a first end of the housing. The first inner wall can be configured to partition the interior of the housing into a first portion and a second portion, the first portion being positioned between the first side of the housing and the second portion of the interior. The first opening, the first portion, and the second opening can define the air intake. The housing can further comprise a second inner wall positioned within the first portion of the interior between the first opening and the second opening. The second inner wall can be configured to at least partially bifurcate the first portion of the interior. The housing can comprise a top interior surface and a bottom interior surface opposite the top interior surface. The first opening can be positioned at a first height relative to a bottom surface of the housing. The second opening can be positioned at a second height relative to the bottom surface of the housing. The second inner wall can extend from the bottom interior surface of the housing to a third height relative to the bottom surface of the housing. The third height can be greater than at least one of the first and second heights. The third height can be greater than the both of the first and second heights. The third height can be greater than the first height and less than the second height. The second opening in the second inner wall can comprise a first surface at a fourth height relative to the bottom surface of the housing and a second surface at a fifth height relative to the bottom surface of the housing, the fifth height being greater than the fourth height. The third height can be greater than the fourth height and less than the fifth height. The second opening in the second inner wall can comprise a first surface at a fourth height relative to the bottom surface of the housing and a second surface at a fifth height relative to the bottom surface of the housing, the fifth height being greater than the fourth height. The third height can be greater than both of the fourth height and the fifth height.

A blood pressure monitor configured to removably mount to a blood pressure cuff in a substantially symmetrical position with respect to a width of the blood pressure cuff, the blood pressure cuff configured to be mounted in a first orientation when worn on a right arm and a second orientation when worn on a left arm, the second orientation being the reverse of the first orientation, the blood pressure monitor configured to be in fluid communication with the blood pressure cuff regardless of whether the blood pressure cuff is mounted in the first or second orientation, said blood pressure monitor can comprise: a housing comprising an interior; a first port; and a second port. The first port can be configured to: receive and secure to a first prong of the blood pressure cuff when the blood pressure cuff is mounted in the first orientation; receive and secure to a second prong of the blood pressure cuff when the blood pressure cuff is mounted in the second orientation; and enable fluid communication between the interior of the housing and at least one of a first fluid passage within the first prong and a second fluid passage within the second prong. The second port can be configured to: receive and secure to the second prong of the blood pressure cuff when the blood pressure cuff is mounted in the first orientation; and receive and secure to the first prong of the blood pressure cuff when the blood pressure cuff is mounted in the second orientation. The first and second ports can be positioned along a bottom surface of the housing. The first and second ports can be spaced apart and aligned with one another. The first and second ports can extend from the bottom surface into the interior of the housing. The blood pressure cuff can comprise a bladder in fluid communication with the first and second fluid passages of the first and second prongs. The housing can be configured to inflate and deflate the bladder of the blood pressure cuff. The housing can be configured to inflate the bladder by moving air through the first port through one of the first and second fluid passages and can be further configured to deflate the bladder by allowing air from the bladder to flow through the first port into the interior of the housing. The blood pressure monitor can further comprise a valve positioned within the interior of the housing proximate to the first port, wherein, when the first or second prong is secured within the first port, the valve is in a first position, and wherein, when the neither of the first and second prong is secured within the first port, the valve is in a second position. When the valve is in the first position, a flow path through the first port can be open and, when the valve is in the second position, the flow path through the first port can be closed. When the first prong is received and secured within the second port, fluid communication between the interior of the housing and the first fluid passage can be inhibited. When the second prong is received and secured within the second port, fluid communication between the interior of the housing and the second fluid passage can be inhibited. The fluid communication can be inhibited by a cap secured to an end of the second port.

A blood pressure monitor configured to removably mount to a blood pressure cuff in a substantially symmetrical position with respect to a width of the blood pressure cuff, said blood pressure monitor can comprise: a housing comprising an interior; a first port; and a second port. The first port can be configured to: receive and secure to a first prong of the blood pressure cuff when the blood pressure cuff is mounted in a first orientation; receive and secure to a second prong of the blood pressure cuff when the blood pressure cuff is mounted in a second orientation; and enable fluid communication between the interior of the housing and at least one of a first fluid passage within the first prong and a second fluid passage within the second prong. The second port can be configured to: receive and secure to the second prong of the blood pressure cuff when the blood pressure cuff is mounted in the first orientation; and receive and secure to the first prong of the blood pressure cuff when the blood pressure cuff is mounted in the second orientation. The first and second ports can be positioned along a bottom surface of the housing. The first and second ports can be spaced apart and aligned with one another with respect to a width of the blood pressure monitor. The first and second ports can extend from the bottom surface into the interior of the housing. The blood pressure cuff can comprise a bladder in fluid communication with the first and second fluid passages of the first and second prongs. The housing can be configured to inflate and deflate the bladder of the blood pressure cuff. The housing can be configured to inflate the bladder by moving air through the first port through one of the first and second fluid passages and can be further configured to deflate the bladder by allowing air from the bladder to flow through the first port into the interior of the housing. The blood pressure monitor can further comprise a valve positioned within the interior of the housing proximate to the first port, wherein, when the first or second prong is secured within the first port, the valve is in a first position, and wherein, when the neither of the first and second prong is secured within the first port, the valve is in a second position. When the valve is in the first position, a flow path through the first port can be open and, when the valve is in the second position, the flow path through the first port can be closed. When the first prong is received and secured within the second port, fluid communication between the interior of the housing and the first fluid passage can be inhibited. When the second prong is received and secured within the second port, fluid communication between the interior of the housing and the second fluid passage can be inhibited. The fluid communication can be inhibited by a cap secured to an end of the second port. When the blood pressure cuff is mounted in the first orientation, the blood pressure cuff can be secured to a right arm of a user, and when the blood pressure cuff is mounted in the second orientation, the blood pressure cuff can be secured to a left arm of a user. The second orientation can be the reverse of the first orientation. The blood pressure monitor can be configured to be in fluid communication with a bladder of the blood pressure cuff via one of the first and second fluid passages regardless of whether the blood pressure cuff is mounted in the first or second orientation.

A blood pressure cuff configured to removably secure to a user in a first orientation and a second orientation and further configured to allow a blood pressure monitor to be removably mounted in a substantially symmetrical position with respect to a width of the blood pressure cuff, said blood pressure cuff can comprise: a first end, a second end opposite the first end, a first side, a second side opposite the first side, and a length extending between the first and second ends, wherein the width of the blood pressure cuff extends between the first and second sides, and wherein the width is smaller than the length; a bladder configured to inflate and deflate; a first prong configured to secure within a first port of the blood pressure monitor when the blood pressure cuff is in the first orientation and a second port of the blood pressure monitor when the blood pressure cuff is in the second orientation, the first prong comprising a first fluid passage in fluid communication with an interior of the bladder; a second prong configured to secure within the second port when the blood pressure cuff is in the first orientation and the first port when the blood pressure cuff is in the second orientation, the second prong comprising a second fluid passage in fluid communication with the interior of the bladder; wherein the first prong is positioned a first distance from the first end of the blood pressure cuff and the second prong is positioned a second distance from the first end of the blood pressure cuff, wherein the first and second distances are equal; and wherein the first prong is positioned a third distance from the first side of the blood pressure cuff and the second prong is positioned a fourth distance from the first side of the blood pressure cuff, wherein the third and fourth distances are not equal. The blood pressure cuff can further comprise a first attachment portion positioned between the first end and the first and second prongs and a second attachment portion positioned near the second end, the second attachment portion configured to secure to the first attachment portion when the blood pressure cuff is in the first and second orientations. The first and second attachment portions can be located on opposite surfaces of the blood pressure cuff. The blood pressure cuff can further comprise a near field communication (NFC) tag configured to electronically interact with an NFC reader in the blood pressure monitor to enable the blood pressure monitor to verify that the blood pressure cuff is an authorized product. The NFC tag can be positioned proximate at least one of the first and second prongs. The NFC tag can be positioned between the first and second prongs. Each of the first and second prongs can comprise a first end operatively connected to a portion of the blood pressure cuff, a second end opposite the first end, a reduced cross-section portion between the first and second ends, and a remainder cross-section portion, wherein the reduced cross-section area comprises a smaller cross-sectional area than the remainder cross-section portion, and wherein the reduced cross-section portion is configured to receive a sealing member within the first port of the blood pressure monitor. The reduced cross-section portion and the remainder cross-section portion can comprise a circular shape, and the reduced cross-section portion can comprise a smaller diameter than the remainder cross-section portion. Each of the first and second prongs can comprise an at least partially rounded end. Each of the first and second prongs can comprise an end having a flat surface and a rounded perimeter. When the blood pressure cuff is secured to the user in the first orientation, the blood pressure cuff can be secured to a right arm of the user, and when the blood pressure cuff is secured to the user in the second orientation, the blood pressure cuff can be secured to a left arm of a user. The second orientation can be the reverse of the first orientation. The blood pressure cuff can be configured to enable fluid communication between a bladder of the blood pressure cuff and an interior of the blood pressure device via one of the first and second fluid passages regardless of whether the blood pressure cuff is mounted in the first or second orientation.

An assembly for enabling a caregiver to secure a physiological monitoring device to an arm of a user can comprise: the physiological monitoring device; and a cradle configured to removably secure to the physiological monitoring device and to the user's arm. The physiological monitoring device can comprise: a first end, a second end opposite the first end, a first side, and a second side opposite the first side; a first connector port extending outwards from the first end and configured to electrically connect to a first cable; and a first locking tab moveably mounted relative to the first side, the first locking tab movable between an extended position and a retracted position. The cradle can comprise: a base, first and second sidewalls connected to the base and opposite one another, and a back wall connected to the base and the first and second sidewalls; a first opening in the back wall, the first opening configured to receive the first connector port of the physiological monitoring device; and a second opening in the first sidewall, the second opening configured to receive the first locking tab of the physiological monitoring device when the physiological monitoring device is secured to the cradle and the first locking tab is in the extended position. After the first connector port is received within the first opening in the back wall, the cradle can be configured to allow the physiological monitoring device to be pivoted about the back wall to secure the first locking tab within the second opening in the first sidewall. The cradle can further comprise a collar protruding from the back wall at least partially around the first opening, and the collar can be configured to receive and secure the first connector port of the physiological monitoring device. The cradle can comprise a first end and a second end opposite the first end, the back wall positioned at the first end of the cradle, and the collar can extend from the back wall in a direction away from the second end of the cradle. The collar can be configured to surround a portion of a perimeter of the first connector port when the physiological monitoring device is secured to the cradle. The collar can be configured to surround greater than 50% but less than 100% of the perimeter of the first connector port when the physiological monitoring device is secured to the cradle. The first locking tab of the physiological monitoring device can comprise a beveled end configured to allow the first locking tab to move passed a portion of the first sidewall and secure within the second opening. When the first locking tab moves passed the portion of the first sidewall, the first sidewall can contact the beveled end and move the first locking tab from the extended position towards the retracted position. The physiological monitoring device can comprise a top surface and a bottom surface opposite the top surface, the bottom surface facing towards the cradle when the physiological monitoring device is secured thereto. A surface of the beveled end of the first locking tab can face away from the top surface of the housing. The physiological monitoring device can further comprise a first button coupled to the first locking tab and moveable relative to the first side, wherein movement of the first button can cause the first locking tab to move between the extended and retracted positions. The first sidewall of the cradle can comprise a first recessed cutout configured to align with and provide access to the first button of the physiological monitoring device when the cradle is secured to the physiological monitoring device. The first recessed cutout can comprise a half-moon shape. The physiological monitoring device can further comprise: a second locking tab moveably mounted relative to the second side, the second locking tab movable between an extended position and a retracted position; and a second button coupled to the second locking tab and moveable relative to the second side, wherein movement of the second button causes the second locking tab to move between the extended and retracted positions. The cradle can further comprise: a third opening in the second sidewall, the third opening configured to receive the second locking tab of the physiological monitoring device when the physiological monitoring device is secured to the cradle and the second locking tab is in the extended position. After the first connector port is received within the first opening in the back wall, the cradle can be further configured to allow the physiological monitoring device to be pivoted about the back wall to secure the second locking tab within the third opening in the second sidewall. The second opening of the first sidewall can be aligned with the third opening of the second sidewall. The first sidewall of the cradle can comprise a first recessed cutout configured to align with and provide access to the first button of the physiological monitoring device when the cradle is secured to the physiological monitoring device. The second sidewall of the cradle can comprise a second recessed cutout configured to align with and provide access to the second button of the physiological monitoring device when the cradle is secured to the physiological monitoring device. The first recessed cutout of the first sidewall can be aligned with the second recessed cutout of the second sidewall. The cradle can further comprise a front wall connected to the base and the first and second sidewalls. The front wall can be opposite the back wall and can comprise a smaller height than the back wall. The cradle can further comprise one or more legs extending from the base and configured to allow securement of the cradle to the arm of the user. The cradle can further comprise an RFID tag and wherein the physiological monitoring device can further comprises an RFID reader configured to determine whether the cradle is an authorized product.

An assembly can comprise: a physiological monitoring device; and a cradle configured to removably secure to the physiological monitoring device and to a portion of a user's body. The physiological monitoring device can comprise: a first end, a second end opposite the first end, a first side, and a second side opposite the first side; a first locking tab moveably mounted relative to the first side, the first locking tab movable between an extended position and a retracted position. The cradle can comprise: a base, first and second sidewalls connected to the base and opposite one another, and a back wall connected to the base and the first and second sidewalls; a first opening in the first sidewall, the first opening configured to receive the first locking tab of the physiological monitoring device when the physiological monitoring device is secured to the cradle and the first locking tab is in the extended position. The back wall can be configured to support the first end of the physiological monitoring device and allow the physiological monitoring device to be pivoted about the back wall to secure the first locking tab within the first opening in the first sidewall.

A cradle configured to removably secure a physiological monitoring device and further configured to secure to an arm of a user can comprise a base, a first sidewall, a second sidewall, and a back wall. The physiological monitoring device can comprise a first locking tab movably mounted relative to a portion of the physiological monitoring device between an extended position and a retracted position. The first sidewall can be connected to and extending from the base. The first sidewall can comprise a first opening configured to receive the first locking tab of the physiological monitoring device when the physiological monitoring device is secured to the cradle and the first locking tab is in the extended position. The second sidewall can be connected to and extending from the base. The second sidewall can be opposite the first sidewall. The back wall can be connected to the base, the first sidewall, and the second sidewall. The back wall of the cradle can be configured to support a first end of the physiological monitoring device and allow the physiological monitoring device to be pivoted about the back wall to secure the first locking tab within the first opening in the first sidewall.

A physiological monitoring device configured to removably secure to a cradle, the cradle configured to secure to a portion of a user's body, the physiological monitoring device can comprise: a first end, a second end opposite the first end, a first side, and a second side opposite the first side; a first locking tab moveably mounted relative to the first side, the first locking tab movable between an extended position and a retracted position, wherein the first locking tab is further configured to secure within an opening of the cradle when in the extended position; and a first button coupled to the first locking tab and moveable relative to the first side, wherein movement of the first button in a first direction causes the first locking tab to move from the extended position to the retracted position, thereby allowing the first locking tab to move out of the opening of the cradle.

A charging station for providing power to a physiological monitoring device can comprise: a charging bay comprising a charging port configured to receive power from a power source; and a tray positioned within and movably mounted relative to the charging bay, wherein the tray is configured to secure the physiological monitoring device and move between a first position and a second position, wherein, in the first position, the tray is spaced away from the charging port, and wherein, in the second position, the tray is positioned proximate the charging port, thereby allowing the physiological monitoring device to electrically connect to the charging port. The physiological monitoring device can comprise an indicator configured to indicate a status of the physiological monitoring device. The indicator can be configured to indicate a charging status of the physiological monitoring device when electrically connected to the charging port of the charging station. The indicator can be configured to indicate whether the charging station is an authorized product when the physiological monitoring device is electrically connected to the charging port. The physiological monitoring device can comprise a display, the display including the indicator. The charging bay can comprise a first sidewall, a second sidewall opposite the first sidewall, a back wall connected to the first and second sidewalls, and a bottom panel connected to the first sidewall, the second sidewall, and the back wall, the charging port positioned on the bottom panel. The tray can be movably mounted to the first and second sidewalls of the charging bay. The tray can comprise a base, a first arm extending outward from and along a first side of the base, and a second arm extending outward from and along a second side of the base, the first side of the base being opposite the second side of the base, and wherein the first arm can be at least partially supported by the first sidewall and the second arm can be at least partially supported by the second sidewall. The base of the tray can comprise a back end and a front end opposite the back end. The back end of the tray can be configured to be positioned closer to the back wall of the charging station when the first and second arms are at least partially supported by the first and second sidewalls. The base of the tray can comprise an opening sized and shaped to match a size and shape of the charging port, the opening positioned closer to the front end of the tray than to the back end of the tray. The opening of the base of the tray can comprise a rounded shape. The charging port can comprise a pedestal protruding outward from the bottom panel, and, when the tray is in the second position, the opening of the tray can be positioned around the pedestal. The charging station can further comprise one or more prongs connected to the bottom panel, the one or more prongs configured to bias the tray towards the first position. The one or more prongs can be positioned at least partially within one or more openings in the bottom panel. The one or more prongs can comprise two prongs, and the two prongs can be spaced apart from one another. When the tray is in the second position, the tray can compress the one or more prongs. Each of the one or more prongs can comprise a straight portion connected to the bottom panel and a curved portion configured to contact the tray. The one or more prongs can comprise a first prong proximate the first sidewall and a second prong proximate the second sidewall. The tray can further comprise one or more legs extending from the base, the one or more legs configured to contact the one or more prongs. The one or more legs of the tray can extend from the base in a first direction and the first and second arms of the tray can extend from the base in a second direction opposite the first direction. Each of the one or more legs of the tray can comprise a perimeter wall and a hollow interior defined therein, the hollow interior configured to receive at least a portion of a respective one of the one or more prongs. Each of the first and second arms can comprise a first portion connected to the base and a second portion connected to the first portion, and the first portion can be angled with respect to the base and the second portion is angled with respect to the first portion. The first sidewall of the charging bay can comprise a first end connected to the back wall and a second end opposite the first end, and the first sidewall can comprise a first guide recess proximate the second end, the first guide recess configured to allow a first locking tab of the physiological monitoring device to slide therewithin. The first guide recess can be recessed from a surface of the first sidewall at a first depth and the first guide recess can be defined by no more than three walls. At least one of the walls defining the first guide recess can be sloped. The first sidewall of the charging bay can comprise a first stem wall extending from the second end of the first sidewall towards the second sidewall, and the first stem wall can comprise the first guide recess. The first sidewall can further comprise a first locking recess proximate the second end, the first locking recess configured to confine the first locking tab of the physiological monitoring device when the tray is in the second position. The first locking recess can be positioned closer to the bottom panel than the first guide recess. The first locking recess can be recessed from a surface of the first sidewall a first depth and the first guide recess can be recessed from the surface of the first sidewall at a second depth. The second depth can be less than the first depth. The first locking recess can be defined by four walls. The first locking recess can be spaced from the first guide recess. The second sidewall can comprise a third end connected to the back wall and a fourth end opposite the third end. The second sidewall can comprise a second guide recess proximate the fourth end. The second guide recess can be configured to allow a second locking tab of the physiological monitoring device to slide therewithin. The second guide recess can be recessed from a surface of the second sidewall at a third depth and the second guide recess can be defined by no more than three walls. At least one of the walls defining the second guide recess can be sloped. The second sidewall can comprise a second stem wall extending from the fourth end of the second sidewall towards the first sidewall, and the second stem wall can comprise the second guide recess. The second sidewall can further comprise a second locking recess proximate the fourth end, the second locking recess configured to confine the second locking tab of the physiological monitoring device. The second locking recess can be positioned closer to the bottom panel than the second guide recess. The second locking recess can be recessed from the surface of the second sidewall at a third depth and the second guide recess can be recessed from the surface at a fourth depth. The fourth depth can be less than the third depth. The second locking recess can be defined by four walls. The second locking recess can be spaced from the second guide recess. The power source can comprise a wall outlet and the charging station can further comprise a connector port configured to receive an end of a power cable configured to connect with said wall outlet. The power source can comprise a battery positioned within a portion of the charging station. The charging station can further comprise a base and a charging frame configured to removably secure to the base. The charging frame can comprise said charging bay. The battery can be positioned within the base of the charging station.

A charging station for providing power to one or more physiological monitoring devices can comprise a plurality of frames configured to be removably secured to one another. Each of the plurality of frames can comprise: one or more charging bays, each of the one or more charging bays comprising a charging port configured to receive power from a power source; and one or more trays. Each of the one or more trays can be: positioned within and movably mounted relative to a respective one of the one or more charging bays; and configured to secure a respective one of the one or more physiological monitoring devices and move between a first position and a second position, wherein, in the first position, each of the one or more trays is spaced away from the charging port of the respective one of the one or more charging bays, and wherein, in the second position, each of the one or more trays is positioned proximate the charging port, thereby allowing the respective one of the one or more physiological monitoring devices to electrically connect to the charging port.

A system for monitoring one or more vital signs of a patient and managing sensor cables in a patient environment can comprise: a first sensor configured to obtain physiological information related to a first physiological parameter, the first sensor configured to attach to a first portion of the patient; a second sensor configured to obtain physiological information related to a second physiological parameter, the second sensor configured to attach to a second portion of the patient, the second sensor configured to connect to the first sensor with a first cable; and a patient monitor configured to connect to the second sensor with a second cable, the patient monitor configured to receive the physiological information related to the first and second physiological parameters via the second cable, the patient monitor configured to attach to a third portion of the patient. The first sensor can comprise an electrocardiogram (ECG) device. The second sensor can comprise a blood pressure monitor. The ECG device can be configured to attach to a chest of the patient and the blood pressure device can be configured to attach to an arm of the patient. The second sensor can comprise a first connector port and a second connector port. The first connector port can be configured to connect to the first cable and the second connector port can be configured to connect to the second cable. The second sensor can further comprise a bypass bus configured to pass the physiological information obtained by the first sensor to the patient monitor without being processed by the second sensor. The second sensor can be configured to transmit the physiological information obtained by the second sensor to the patient monitor simultaneously with the physiological information from the first sensor. The first connector port and the second connector port can be positioned on a first side of the second sensor. The system can further comprise a third sensor which can be configured to obtain physiological information related to a third physiological parameter. The third sensor can be configured to attach to a third portion of the patient and connect to the patient monitor with a third cable. The patient monitor can comprise a first end, a second end opposite the first end, a first connector port positioned on the first end, and a second connector port positioned on the second end. The first connector port can be configured to connect to the third sensor via the third cable and the second connector port can be configured to connect to the second sensor via the second cable. The second connector port can comprise a first female connector configured to connect to the second cable and a second female connector configured to connect to a fourth sensor via a fourth cable. The fourth sensor can be an acoustic sensor. The third sensor can be an optical sensor. The second sensor can be a blood pressure monitor. The system can further comprise at least one cable management prong configured to secure to skin of the patient and a portion of one of the first cable or second cable. The at least one cable management prong can comprise: a base configured to secure to a patient skin surface; a stem extending outward from the base; and one or more arms extending outward from the stem, the one or more arms sized and shaped to receive and secure the portion of the one of the first cable or second cable. The base can comprise an adhesive. The base can further comprise a release liner disposed on the adhesive. The base can comprise a square shape. The stein can extend generally perpendicular to a plane of the base. The stem can extend from a middle portion of the base. The middle portion of the base can be spaced inward from at least two sides of the base. The stem can comprise a first height and a first width and the base can comprise a second height and a second width, wherein the first height greater than the second height and the first width being less than the second width. Each of the one or more arms can extend generally perpendicular to a side of the stem in a first direction. Each of the one or more arms can extend in a second direction different from the first direction. Each of the one or more arms can extend outward from the stem and curl at least partially around a radius of curvature. The one or more arms can curl in a direction away from the base. The one or more arms can comprise a C-shape. The one or more arms can comprise a cross-section that is at least partially circular. The patient monitor can comprise a wireless transceiver configured to transmit the physiological information received from the first and second sensors.

A system for monitoring one or more vital signs of a patient and managing sensor cables in a patient environment can comprise: a first sensor configured to obtain physiological information related to a first physiological parameter, the first sensor configured to attach to a first portion of the patient; a second sensor configured to obtain physiological information related to a second physiological parameter, the second sensor configured to attach to a second portion of the patient, the second sensor comprising a first connector port and a second connector port, the first connector port configured to connect to the first sensor via a first cable; and a patient monitor configured to connect to the second connector port of the second sensor via a second cable, the patient monitor configured to receive physiological information related to the first and second physiological parameters from the second sensor and further configured to attach to a third portion of the patient. The second sensor can further comprise a bypass bus configured to pass the physiological information from the first sensor to the patient monitor without being processed by the second sensor. The second sensor can be configured to transmit the physiological information obtained by the second sensor to the patient monitor simultaneously with the physiological information from the first sensor. The first and second connector ports of the second sensor can be positioned on a first side of the second sensor. The second sensor can comprise one or more cable securement arms configured to secure to a portion of one of the first or second cables. The first sensor can be an ECG device and the second sensor can be configured to measure physiological information related to a blood pressure of the patient.

A noninvasive blood pressure monitor can comprise: an inflatable cuff; a pressure transducer; an air pump; a plurality of air paths connecting the inflatable cuff, the pressure transducer, and the air pump; and an acoustic filter provided along at least one of the air paths. The noninvasive blood pressure monitor can include an air manifold that joins the plurality of air paths. The acoustic filter can be provided between the air pump and the air manifold. The acoustic filter can be provided between the inflatable cuff and the air manifold. The acoustic filter can be provided between the pressure transducer and the air manifold. The acoustic filter can be integrated with the air manifold. The air manifold can include an acoustic filtering cavity. The acoustic filtering cavity can include a plurality of ports that feed into the acoustic filtering cavity, wherein a dimension of the acoustic filtering cavity is at least 5 times a dimension of the plurality of ports. The acoustic filter can include a low-pass filter. The acoustic filter can include one or more stubs branching off from one of the plurality of air paths. The one or more stubs can be straight. The one or more stubs can be closed-ended. The acoustic filter can include two opposing stubs. The one or more stubs can have a folded configuration. The one or more stubs can include a plurality of sections joined together at one or more angles. The acoustic filter can include one or more box-shaped cavities. The acoustic filter can include a box-shaped cavity with a face attached to one of the plurality of air paths. The acoustic filter can include a box-shaped cavity attached to one of the plurality of air paths by a stub. The noninvasive blood pressure monitor can further include: a housing with two or more parts; and a gasket provided at a mating interface between the two or more parts. The noninvasive blood pressure monitor can further include noise-dampening material inside the housing. The acoustic filter can have a pass band that excludes a fundamental frequency produced by the air pump when operating at or above 50% of its maximum operating speed.

A noninvasive blood pressure monitor can comprise: an inflatable cuff; a pressure transducer; first and second air pumps; and a processor configured to independently control one or more operating characteristics of the first and second air pumps. The one or more operating characteristics of the first and second air pumps can include speed of the first or second air pump. The one or more operating characteristics of the first and second air pumps can include stroke length of the first or second air pump. The one or more operating characteristics of the first and second air pumps can include stroke phase of the first or second air pump. The monitor can be configured to: determine one or more characteristics of acoustic noise produced by the first and second air pumps; and independently adjust the one or more operating characteristics of the first and second air pumps based on the one or more characteristics of the acoustic noise. The monitor can be configured to determine the one or more characteristics of the acoustic noise produced by the first and second air pumps using a signal output from a microphone. The microphone can be integrated in the monitor. The monitor can be configured to determine the one or more characteristics of the acoustic noise produced by the first and second air pumps using a signal output from the pressure transducer. The monitor can be configured to determine the one or more characteristics of the acoustic noise produced by the first and second air pumps using electrical currents from the air pumps. The one or more characteristics of the acoustic noise produced by the first and second air pumps can be loudness. The one or more characteristics of the acoustic noise produced by the first and second air pumps can be beat frequency. The one or more characteristics of the acoustic noise produced by the first and second air pumps can include frequency content. The noninvasive blood pressure monitor can further be configured to adjust the one or more operating characteristics of the first and second air pumps based on the one or more characteristics of the acoustic noise so as to reduce an acoustic displeasure metric. The acoustic displeasure metric can be based on the one or more characteristics of the acoustic noise produced by the first and second air pumps. The monitor can be configured to control the speed of the first or second air pump so as to set a beat frequency in the acoustic noise produced by the first and second air pumps to a desired value. The monitor can be configured to control the speed of the first or second air pump so as to achieve a desired relationship between the frequency content of the acoustic noise produced by the first air pump and the frequency content of the acoustic noise produced by the second air pump. The monitor can be configured to control the speed of the first or second air pump such that the frequency content of the acoustic noise produced by the first air pump is harmonically related to the frequency content of the acoustic noise produced by the second air pump. The monitor can be configured to control the stroke phase of the first or second air pump so as to increase destructive interference between the acoustic noise produced by the first air pump and the acoustic noise produced by the second air pump.

A noninvasive blood pressure monitor can comprise: an inflatable cuff; a pressure transducer; one or more air pumps; and a processor configured to control the one or more air pumps so as to provide a first inflation rate for the inflatable cuff during a non-measurement portion of an inflation phase and a second inflation rate during a measurement portion of the inflation phase, the first inflation rate being greater than the second inflation rate. The monitor can include first and second air pumps, and the processor can be configured to turn on both the first air pump and the second air pump during the non-measurement portion of the inflation phase. The processor can be configured to subsequently turn off the second air pump during the measurement portion of the inflation phase. The processor can be configured to control the one or more air pumps so as to transition from the first inflation rate to the second inflation rate after a plethysmographic waveform is detected in an output signal from the pressure transducer. The processor can be configured to determine the second inflation rate based at least in part on a predetermined minimum number of cardiac cycles for performing a blood pressure measurement. The predetermined minimum number of cardiac cycles can be less than or equal to 15. The processor can be configured to determine the second inflation rate based at least in part on a patient's pulse rate. The processor can be configured to determine the second inflation rate based at least in part on a maximum inflation pressure. The maximum inflation pressure can be determined based on an envelope of a plurality of plethysmographic waveforms. The processor can be configured to provide the first inflation rate until a threshold air pressure in the inflatable cuff is reached. The processor can be configured to provide the first inflation rate until a plethysmographic waveform is detected in an output of the pressure transducer. The second inflation rate can be an actively-controlled target inflation rate during the measurement portion of the inflation phase. The target inflation rate can be a set air pressure increase per cardiac cycle. The target inflation rate can be changed during the measurement portion of the inflation phase. The target inflation rate can be slowed during an identified diastolic or systolic blood pressure measurement zone of air pressures in the inflatable cuff. The diastolic or systolic blood pressure measurement zone can be identified using an envelope of a plurality of plethysmographic waveforms in an output of the pressure transducer. The diastolic or systolic blood pressure measurement zone can be identified at least partially based on an inflection point in the envelope of the plurality of plethysmographic waveforms. The monitor can be configured to end the measurement portion of the inflation phase based on an envelope of a plurality of plethysmographic waveforms in an output of the pressure transducer. The monitor can be configured to end the measurement portion of the inflation phase based at least partially on an inflection point in the envelope of the plurality of plethysmographic waveforms. The monitor can be configured to determine a blood pressure measurement and a confidence metric upon ending the measurement portion of the inflation phase. The confidence metric can include a number of plethysmographic waveforms detected during the measurement portion of the inflation phase, a smoothness of an envelope of a plurality of plethysmographic waveforms in an output of the pressure transducer, or an indication of patient motion during time periods corresponding to one or more of the plethysmographic waveforms. The noninvasive blood pressure monitor can further include at least two air pumps; and a clock or counter to measure cumulative runtime of each of the at least two air pumps. The monitor can be configured to select the at least two air pumps for operation tasks so as to reduce an imbalance in their respective cumulative runtimes.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIG. 2G illustrates an exploded, bottom perspective view of the dock of FIG. 2E.

FIG. 2H illustrates a side view of the dock of FIG. 2E.

FIG. 2I illustrates a top view of a flexible circuit of the dock of FIG. 2E.

FIGS. 2J and 2K illustrate top perspective views of a hub of the reusable portion of the ECG device shown in FIG. 2C.

FIGS. 2L-2M illustrate bottom perspective views of the hub of FIGS. 2J-2K.

FIG. 2N illustrates a side view of the hub of FIGS. 2J-2K.

FIG. 2O illustrates an exploded, top perspective view of the hub of FIGS. 2J and 2K.

FIG. 2Q illustrates an exploded view of a portion of the hub of FIGS. 2J and 2K in accordance with aspects of this disclosure.

FIG. 3F illustrates an exploded, top perspective view of the dock of FIG. 3E.

FIG. 3G illustrates an exploded, bottom perspective view of the dock of FIG. 3E.

FIG. 3H illustrates a side view of the dock of FIG. 3E.

FIG. 3I illustrates a top view of a flexible circuit of the dock of FIG. 3E.

FIGS. 3J and 3K illustrate top perspective views of a hub of the reusable portion of the ECG device shown in FIG. 3C.

FIG. 3O illustrates a perspective view of the hub and dock of the ECG device of FIG. 3A and further illustrates a method of mating the hub and dock in accordance with aspects of this disclosure.

FIG. 5I illustrates a perspective view of a blood pressure cuff.

FIG. 5J illustrates an enlarged view of a portion of the blood pressure cuff of FIG. 5I.

FIG. 5K illustrates the blood pressure cuff of FIG. 5I secured to the blood pressure monitor of FIGS. 5A-5B.

FIG. 5L illustrates the blood pressure cuff of FIG. 5I in a first orientation with the blood pressure monitor secured thereto in accordance with aspects of this disclosure.

FIG. 5M illustrates the blood pressure cuff of FIG. 5I in a second orientation with the blood pressure monitor secured thereto in accordance with aspects of this disclosure.

FIGS. 5P-5Q illustrate cross-sections of the blood pressure monitor of FIGS. 5A-5B in accordance with aspects of this disclosure.

FIGS. 5W-5X illustrate cross-section views of the blood pressure monitor of FIGS. 5A-5B in accordance with aspects of this disclosure.

FIG. 5Y illustrates another perspective view of the blood pressure monitor of FIGS. 5A-5B with portions removed in accordance with aspects of this disclosure.

FIGS. 5Z and 5AA illustrate exploded views of a valve of the blood pressure monitor.

FIG. 6F-6I illustrate perspective views of a blood pressure monitor of the assembly of FIG. 6A.

FIG. 8N illustrates another side view of the cradle of FIG. 8J.

FIG. 8O illustrates a front view of the cradle of FIG. 8J.

FIG. 8P illustrates a back view of the cradle of FIG. 8J.

FIG. 8Q illustrates an enlarged view of a portion of the patient monitor shown in FIG. 8G.

FIG. 8R illustrates an enlarged, perspective view of the view shown in FIG. 8Q with a portion of the patient monitor removed in accordance with aspects of this disclosure.

FIG. 8S illustrates an enlarged, perspective view of the view shown in FIG. 8Q with a portion of the patient monitor removed in accordance with aspects of this disclosure.

FIG. 8T illustrates a top view of the enlarged view of FIG. 8R.

FIG. 8U illustrates a perspective view of a locking tab assembly of the patient monitor in accordance with aspects of this disclosure.

FIG. 8V illustrates a bottom view of the locking tab assembly of FIG. 8U.

FIGS. 9A-9C illustrate various views of a cable management prong in accordance with aspects of this disclosure.

FIG. 10A illustrates a perspective view of a charging station in accordance with aspects of this disclosure.

FIG. 10B illustrates a top view of the charging station of FIG. 10A.

Figure 10A:
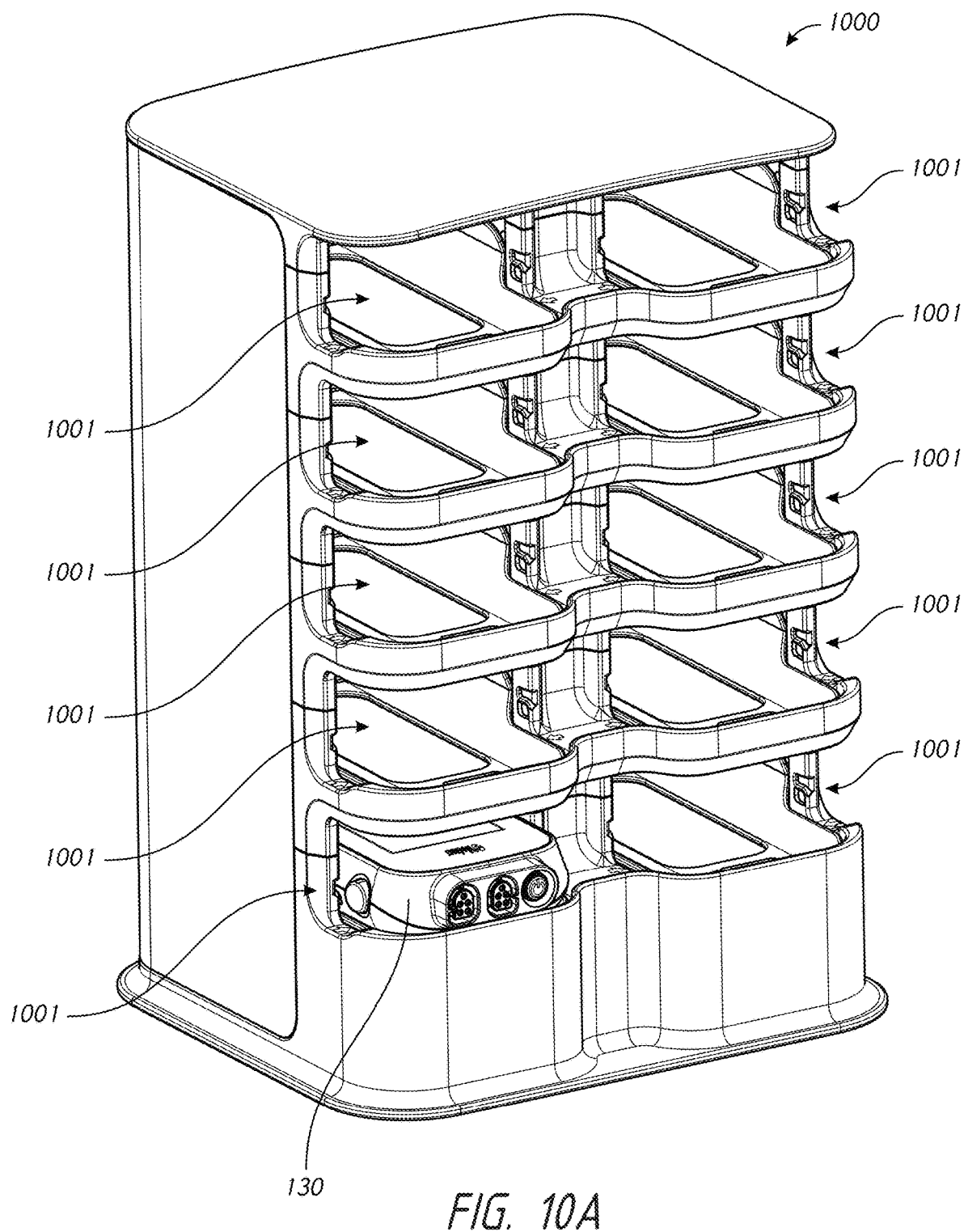
Figure 10B:
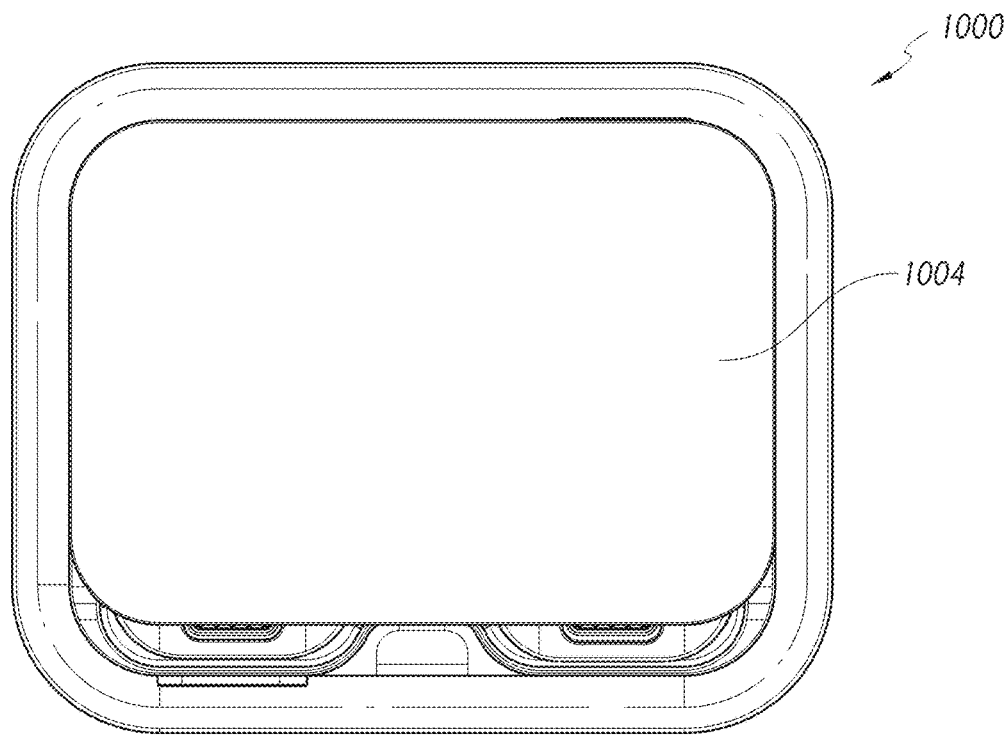
Figure 10C:
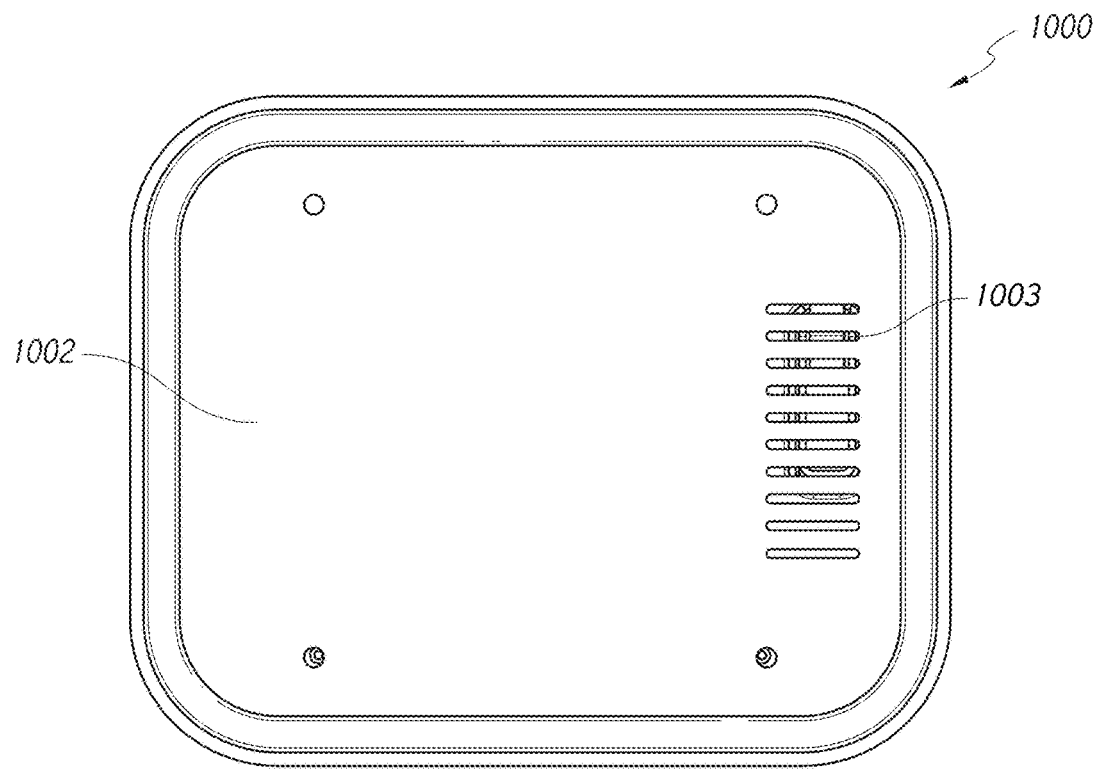

FIG. 10C illustrates a bottom view of the charging station of FIG. 10A.

Figure 10D:
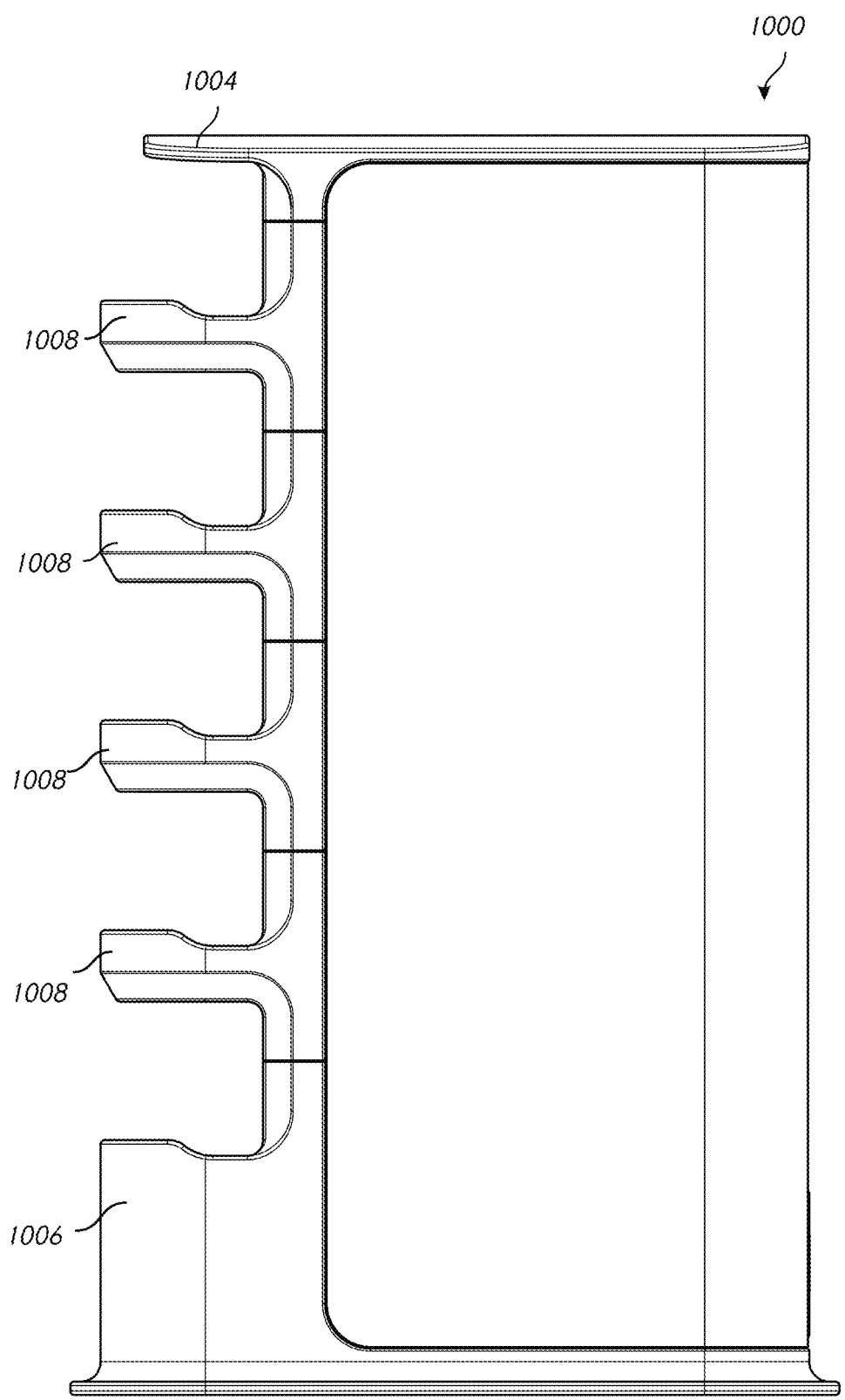

FIG. 10D illustrates a side view of the charging station of FIG. 10A.

Figure 10E:
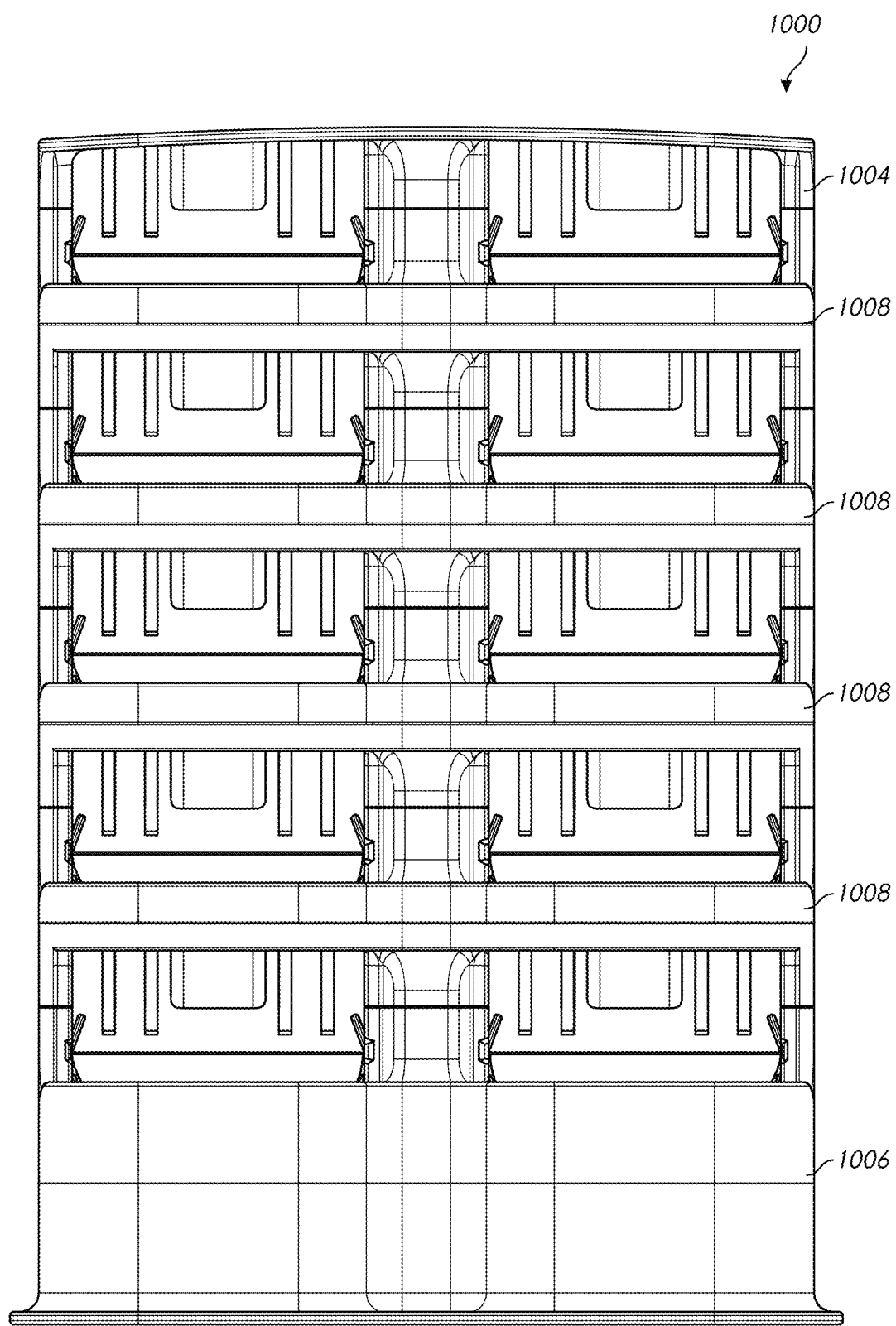

FIG. 10E illustrates a front view of the charging station of FIG. 10A.

Figure 10F:
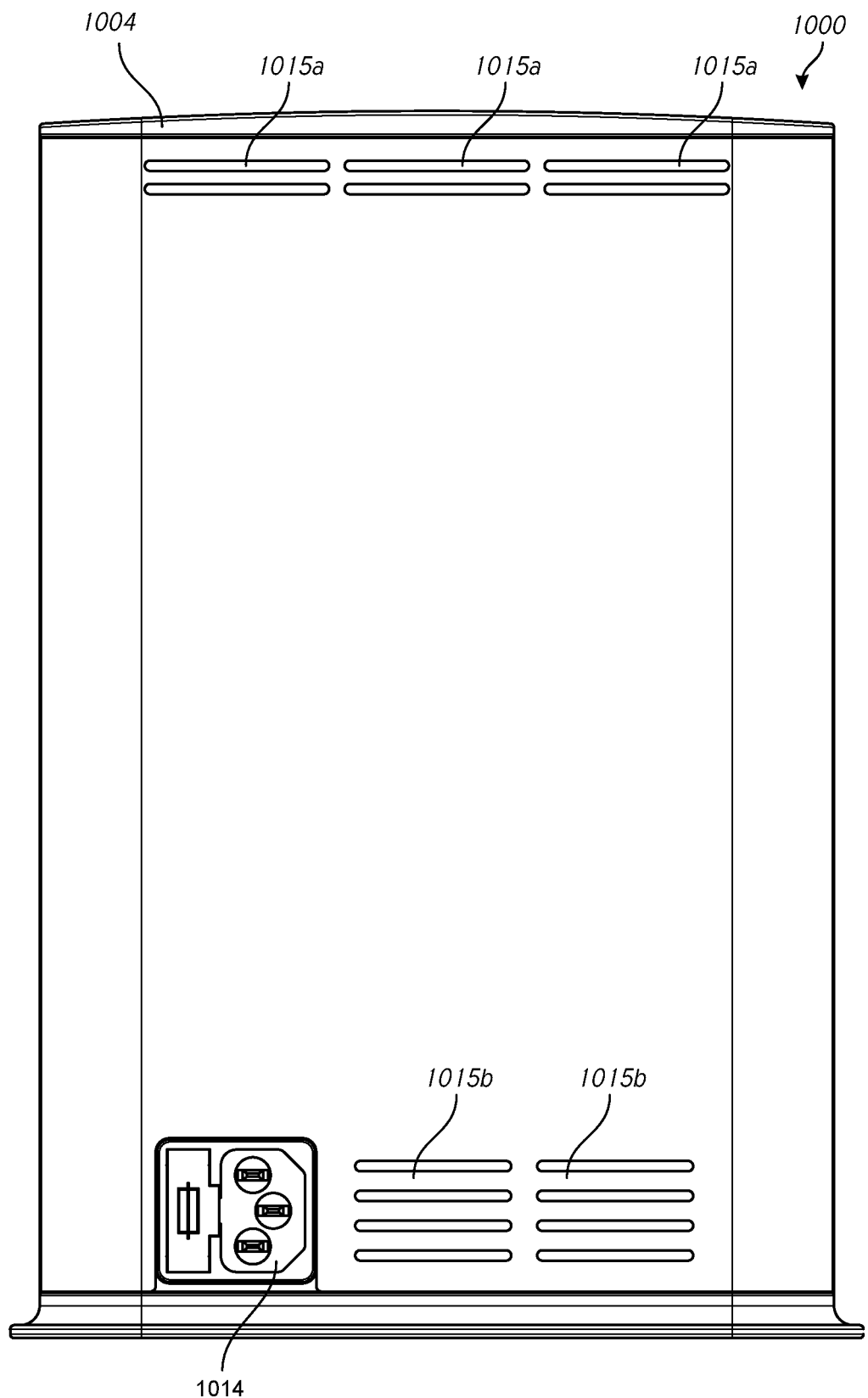

FIG. 10F illustrates a back view of the charging station of FIG. 10A.

Figure 10G:
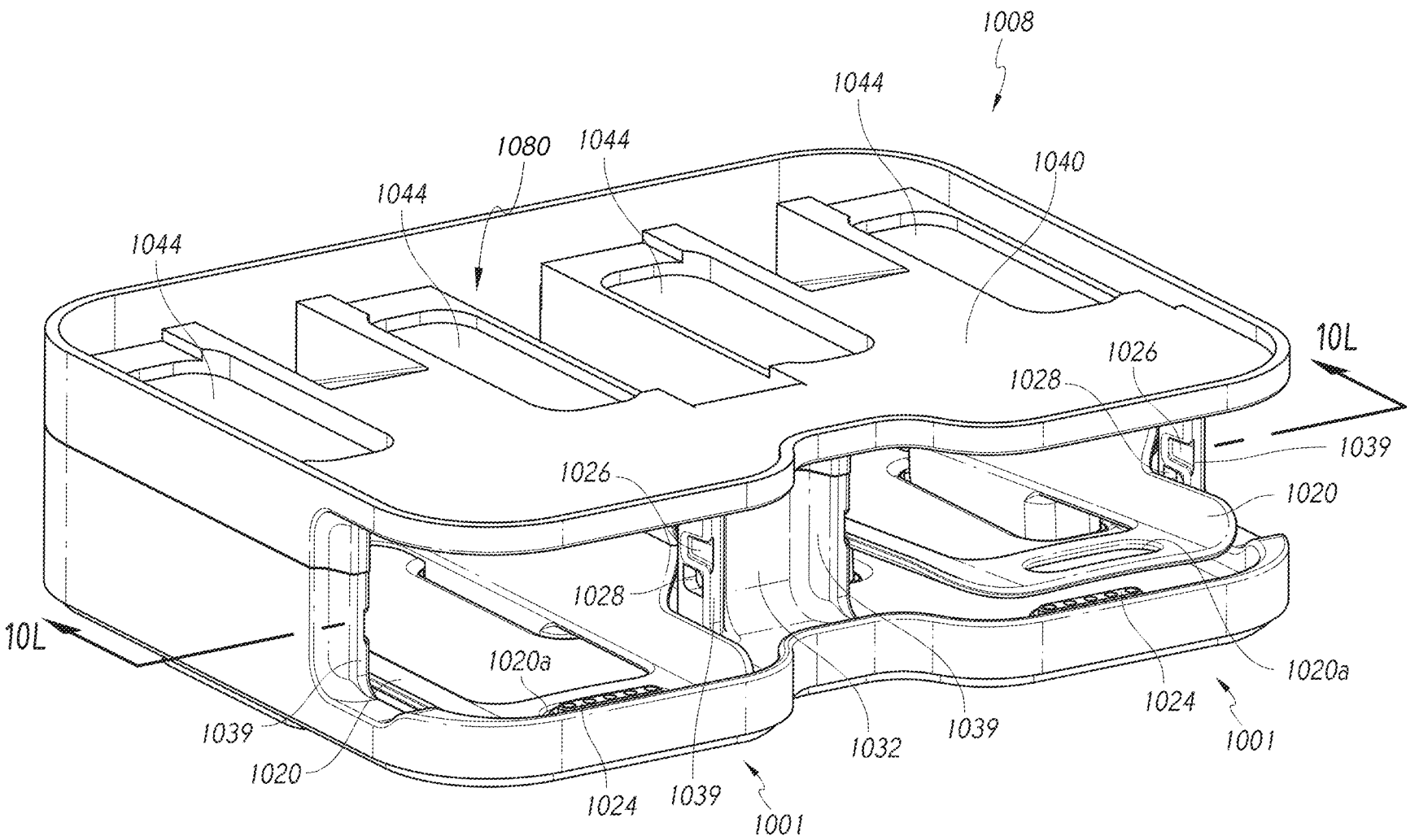

FIG. 10G illustrates a top perspective view of a frame of the charging station of FIG. 10A.

Figure 10H:

FIG. 10H illustrates another top perspective view of the frame of FIG. 10G.

Figure 10I:
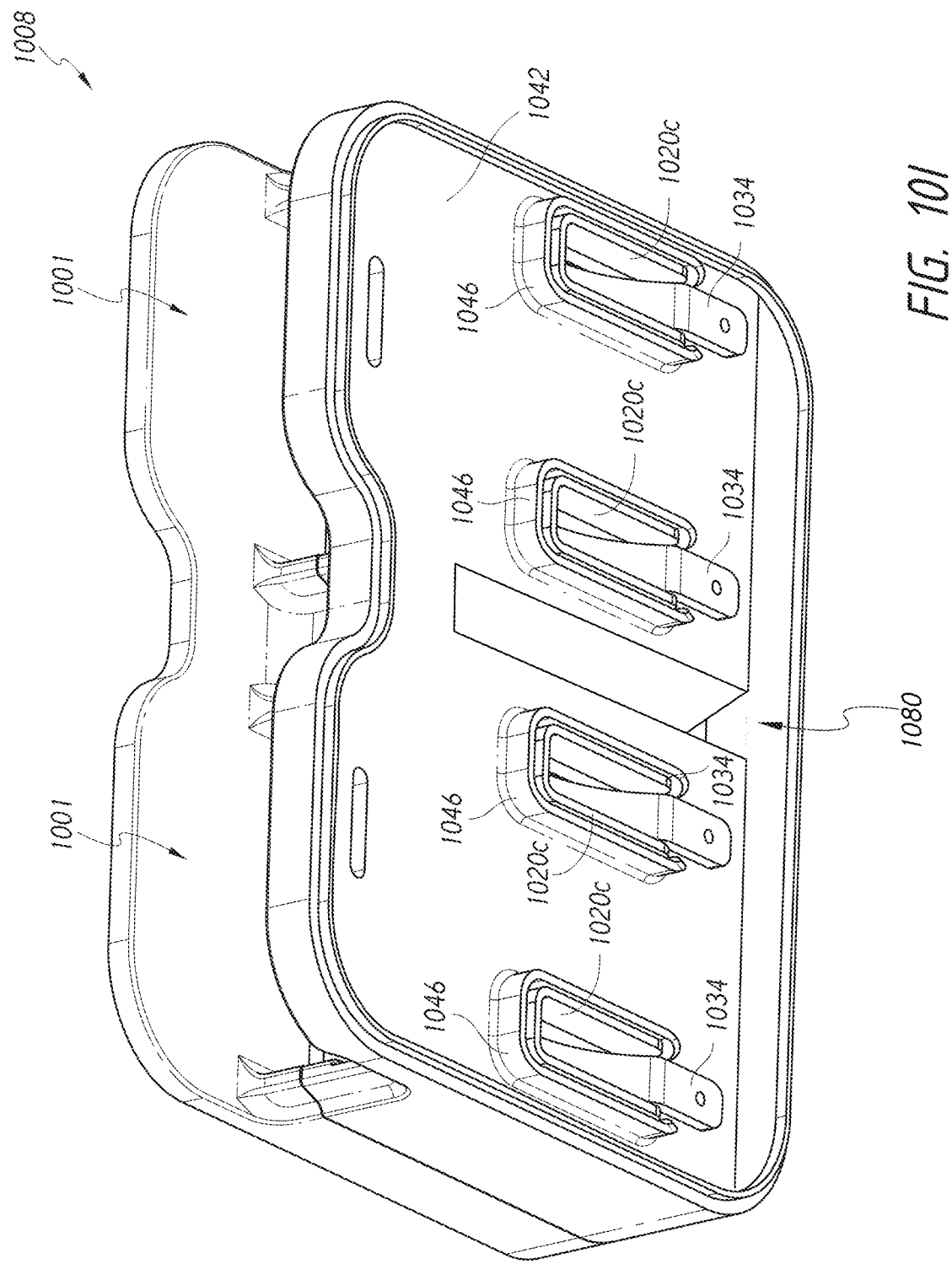

FIG. 10I illustrates a bottom perspective view of the frame of FIG. 10G.

Figure 10J:
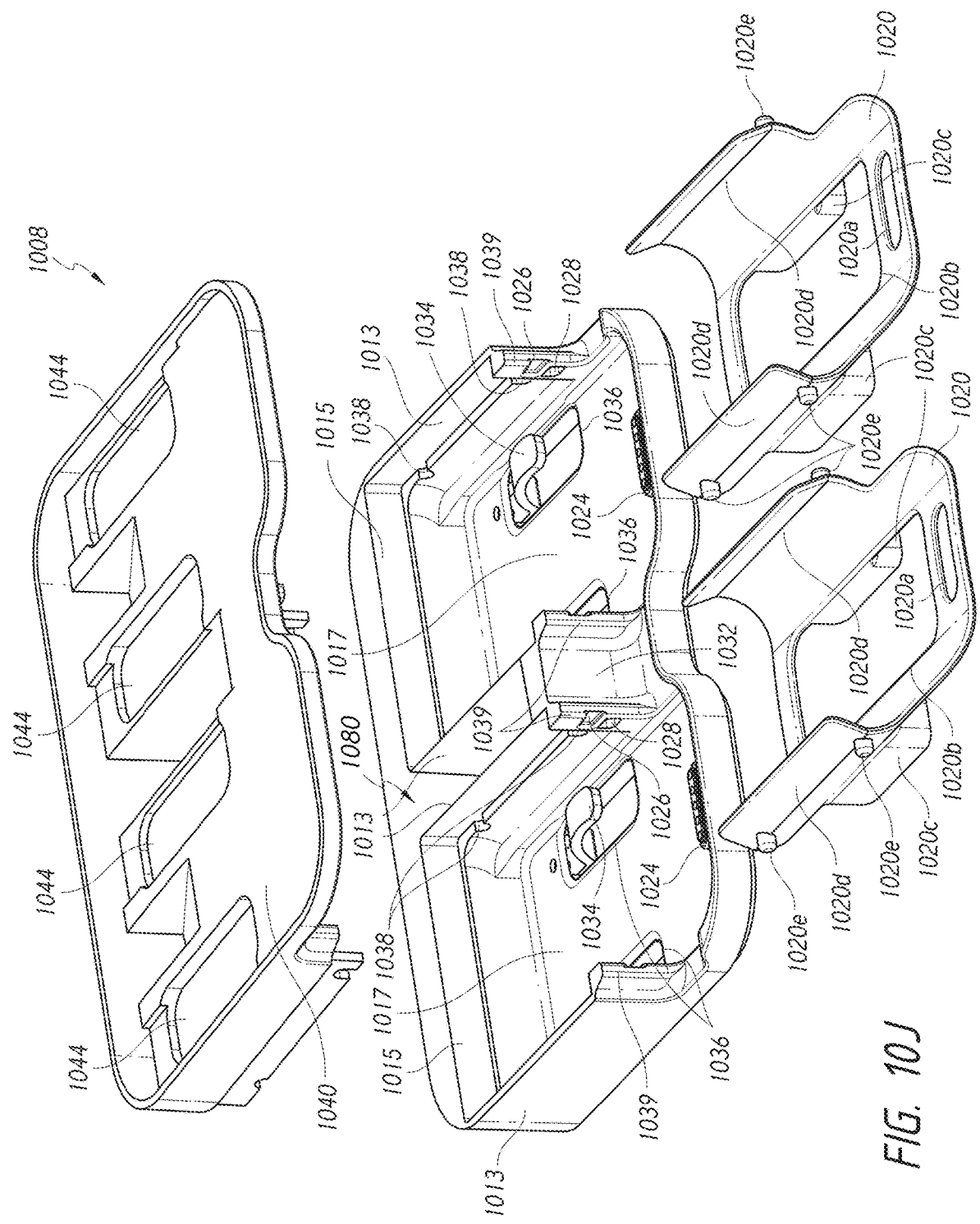

FIG. 10J illustrates an exploded view of the frame of FIG. 10G.

Figure 10K:
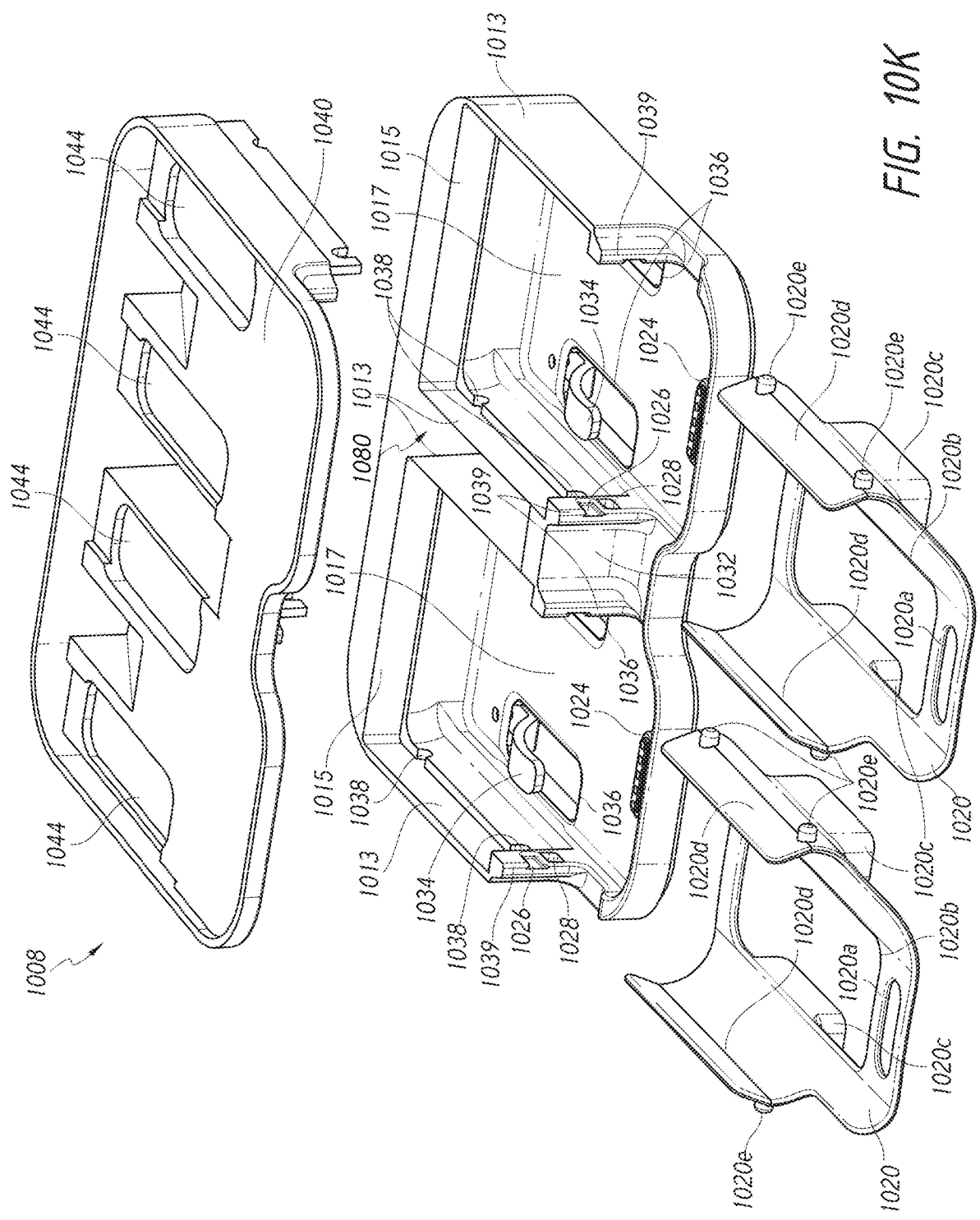

FIG. 10K illustrates another exploded view of the frame of FIG. 10G.

Figure 10L:
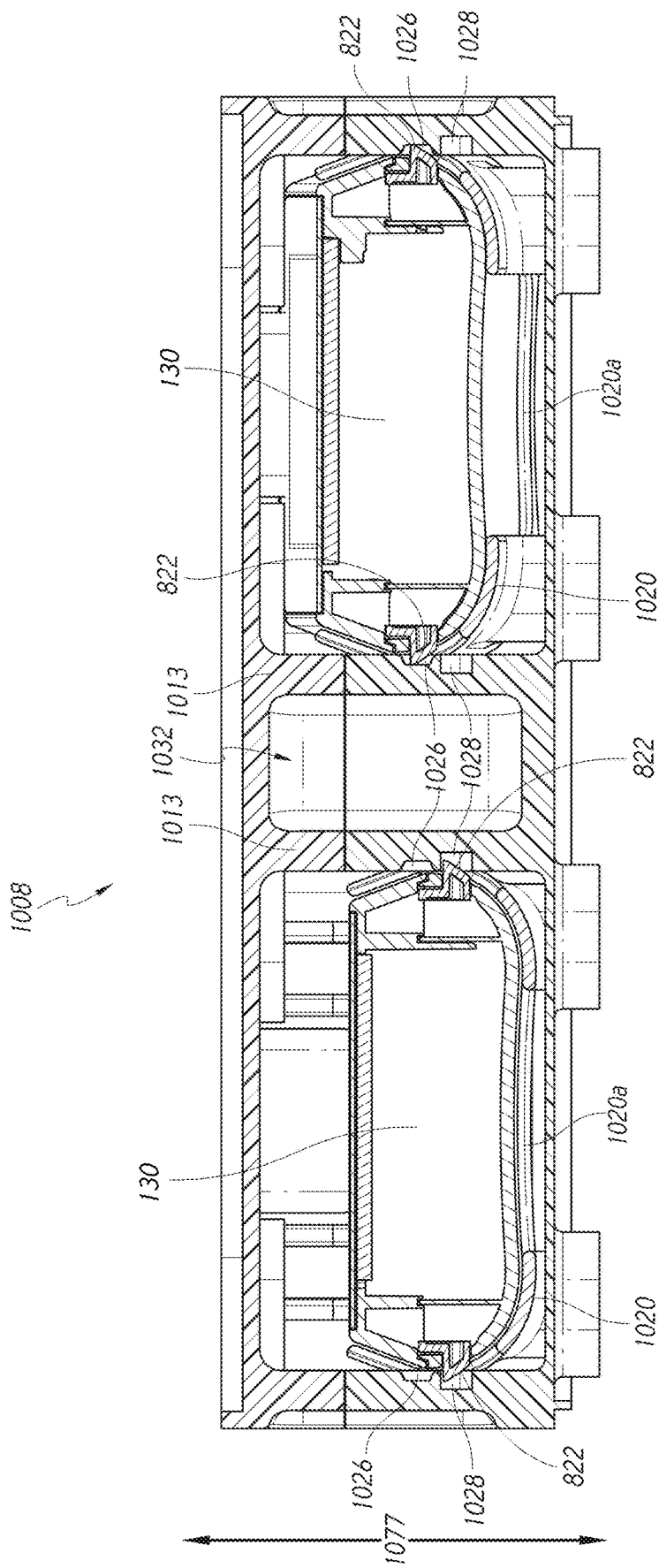

FIG. 10L illustrates a cross-section through a portion of the frame of FIG. 10G.

Figure 11A:
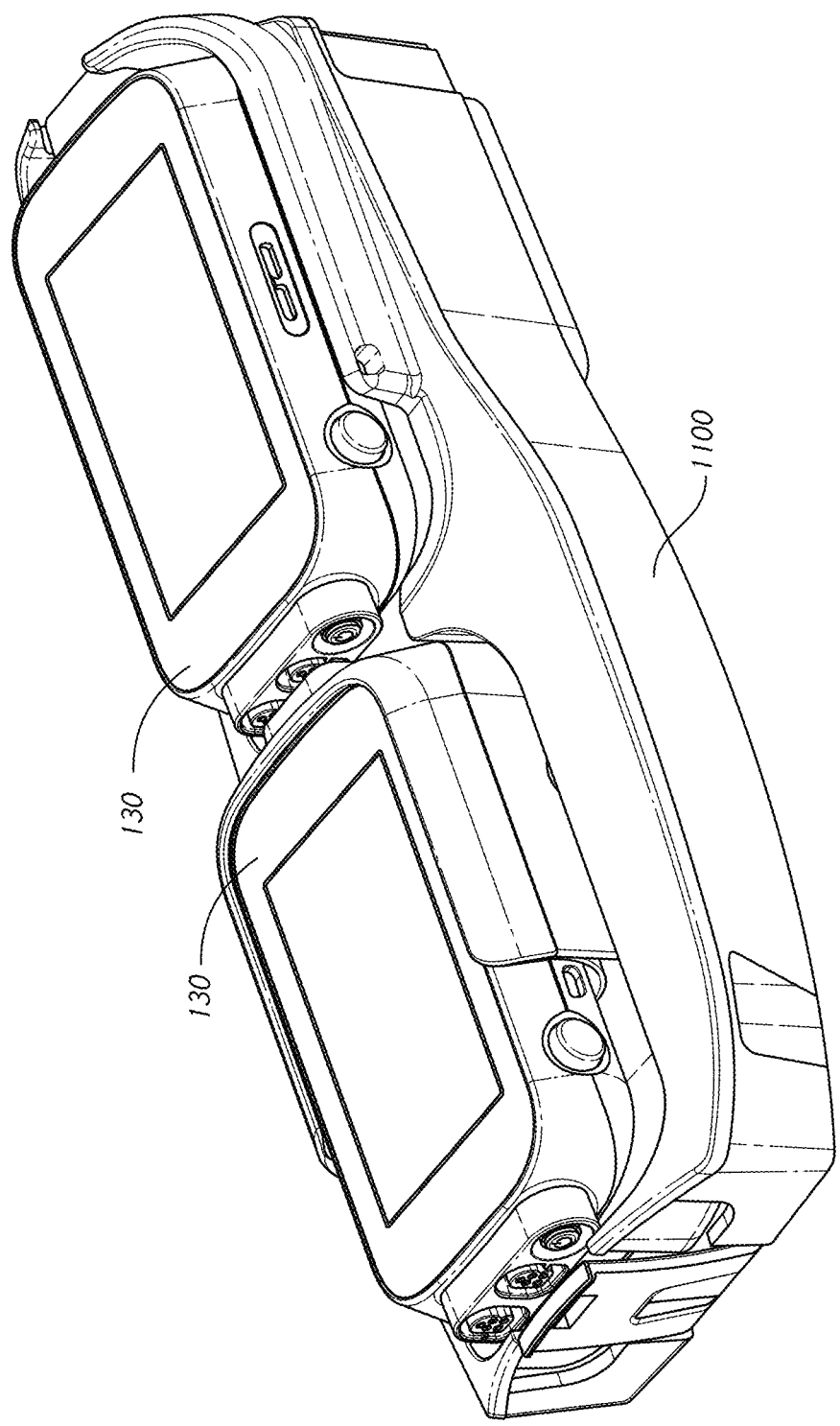
Figure 11B:
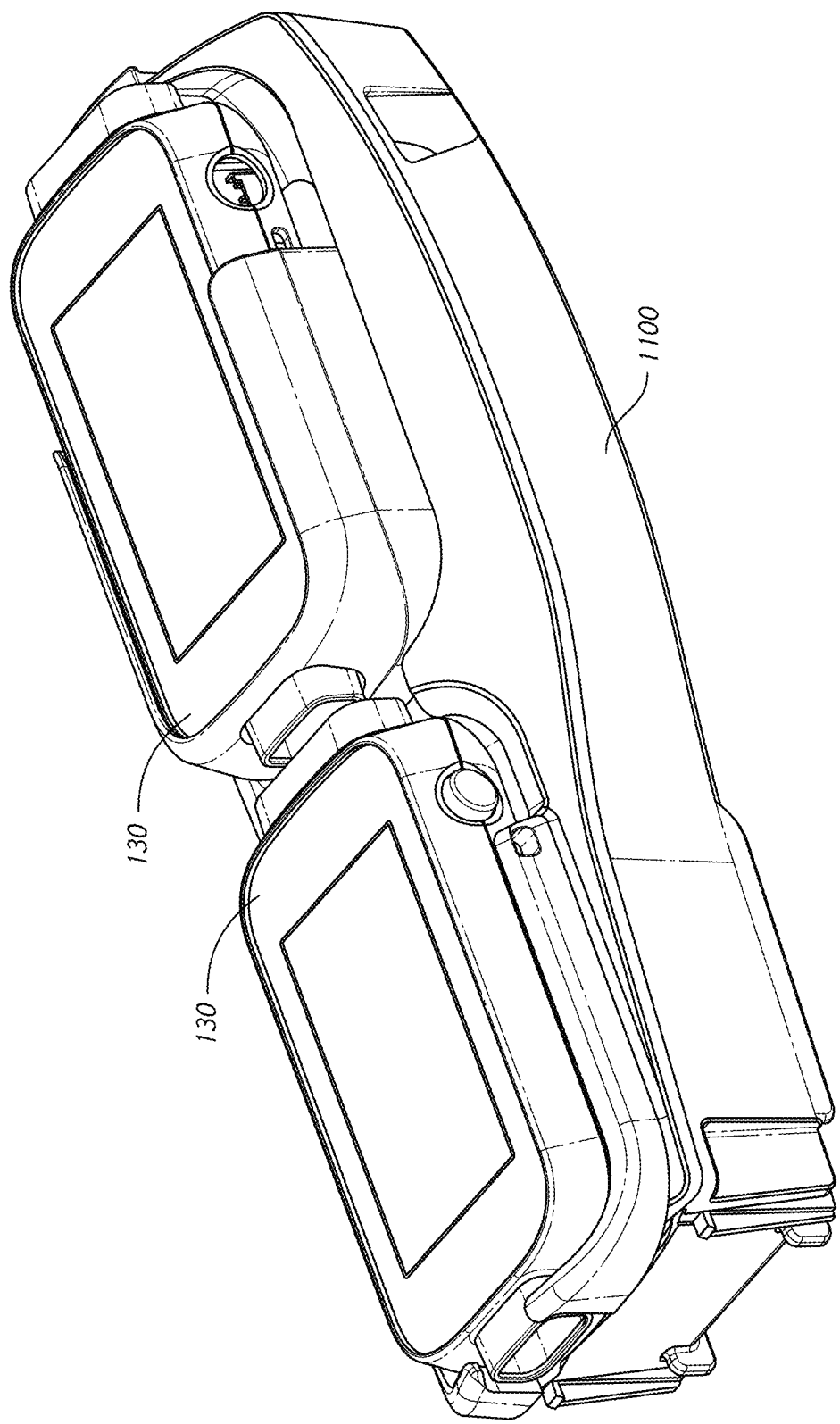

FIG. 11A-11B illustrate perspective views of a charging cradle with two patient monitors placed therein in accordance with aspects of this disclosure.

Figure 11C:
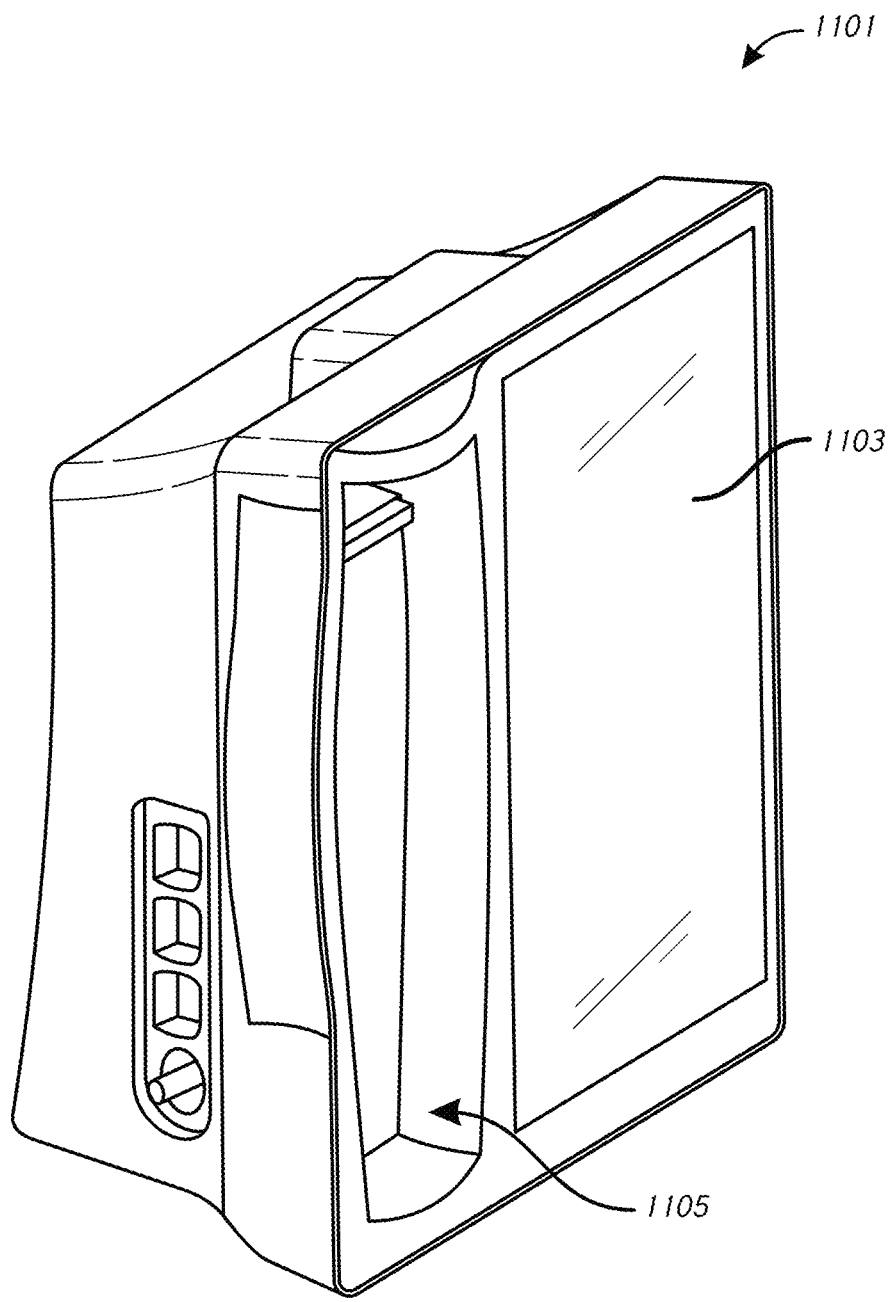

FIG. 11C illustrates a perspective view of a medical monitoring hub in accordance with aspects of this disclosure.

Figure 11D:
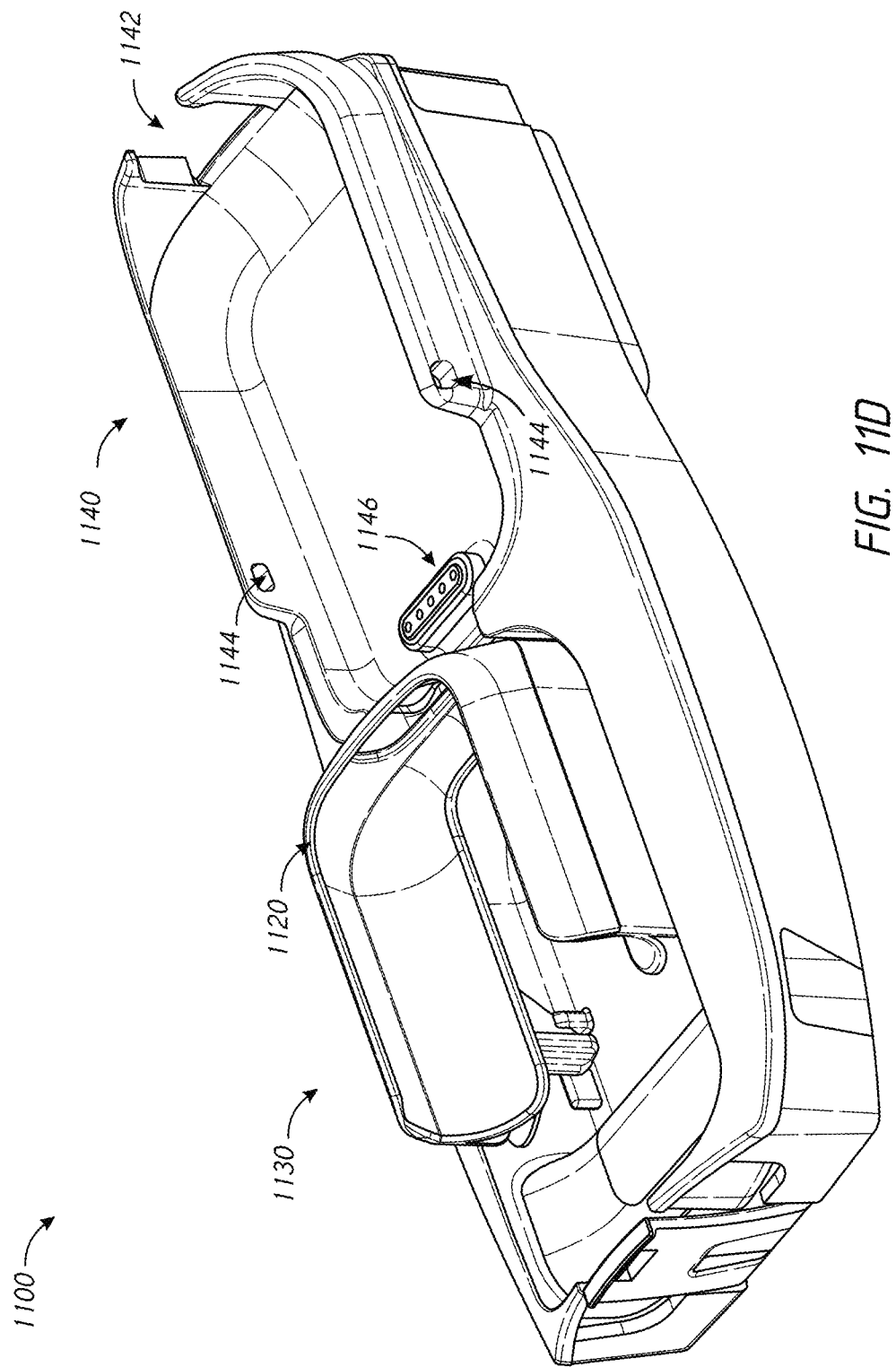
Figure 11E:
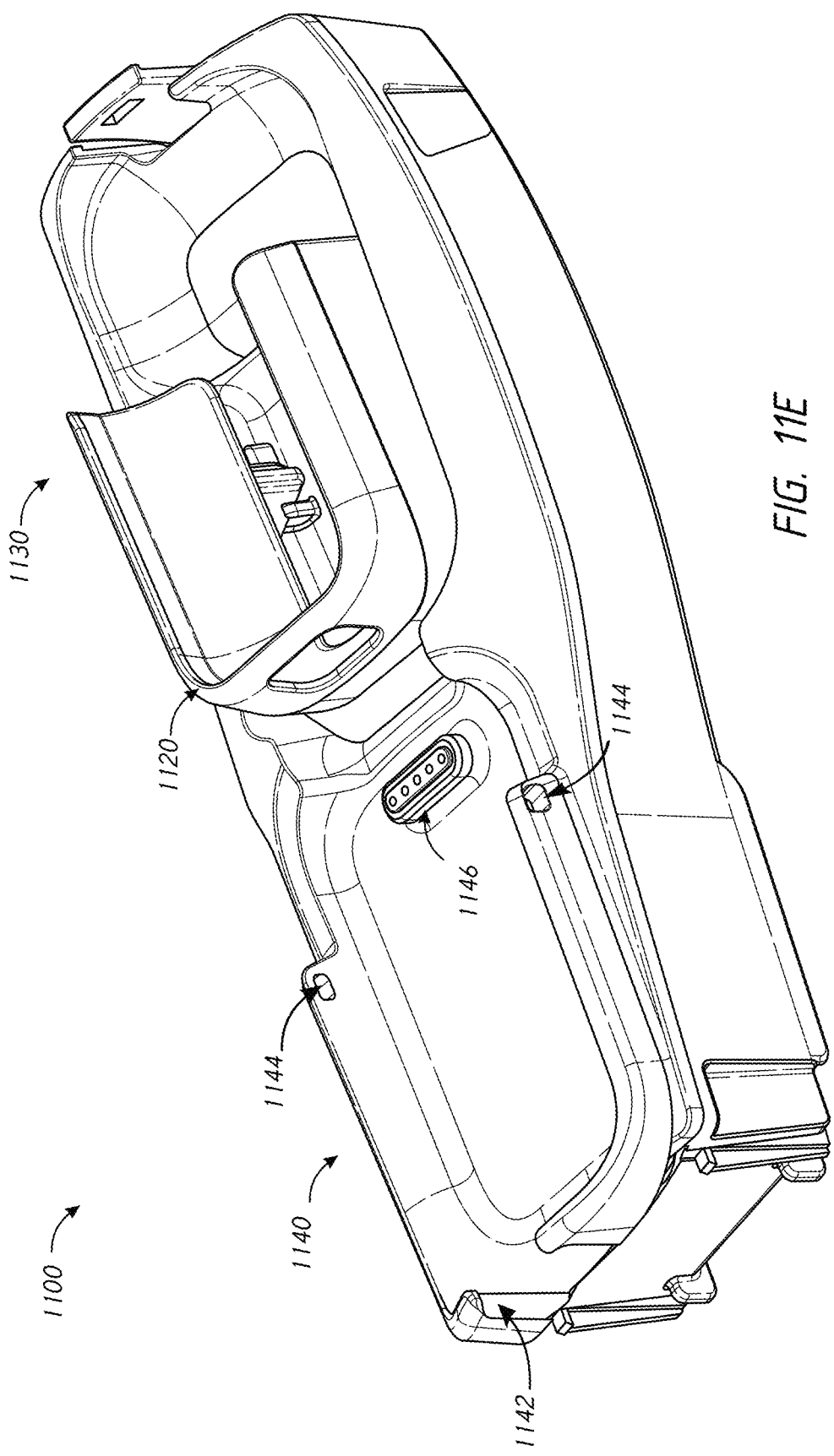

FIGS. 11D-11E illustrate perspective views of the charging cradle of FIGS. 11A-11B without the two patient monitors placed therein in accordance with aspects of this disclosure.

FIG. 11F illustrates a bottom view of the charging cradle of FIGS. 11D-11E.

FIG. 11G illustrates a top view of the charging cradle of FIGS. 11D-11E.

Figure 11H:
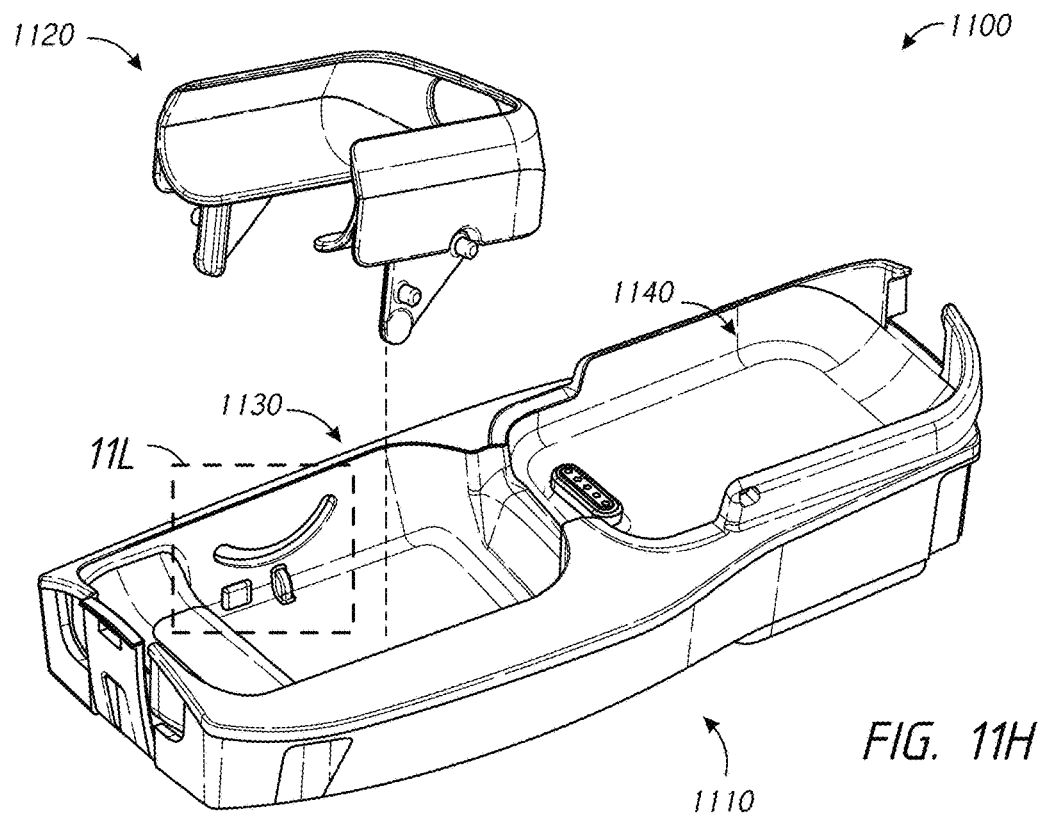

FIG. 11H illustrates an exploded perspective view of the charging cradle of FIGS. 11D-11E.

Figure 11I:
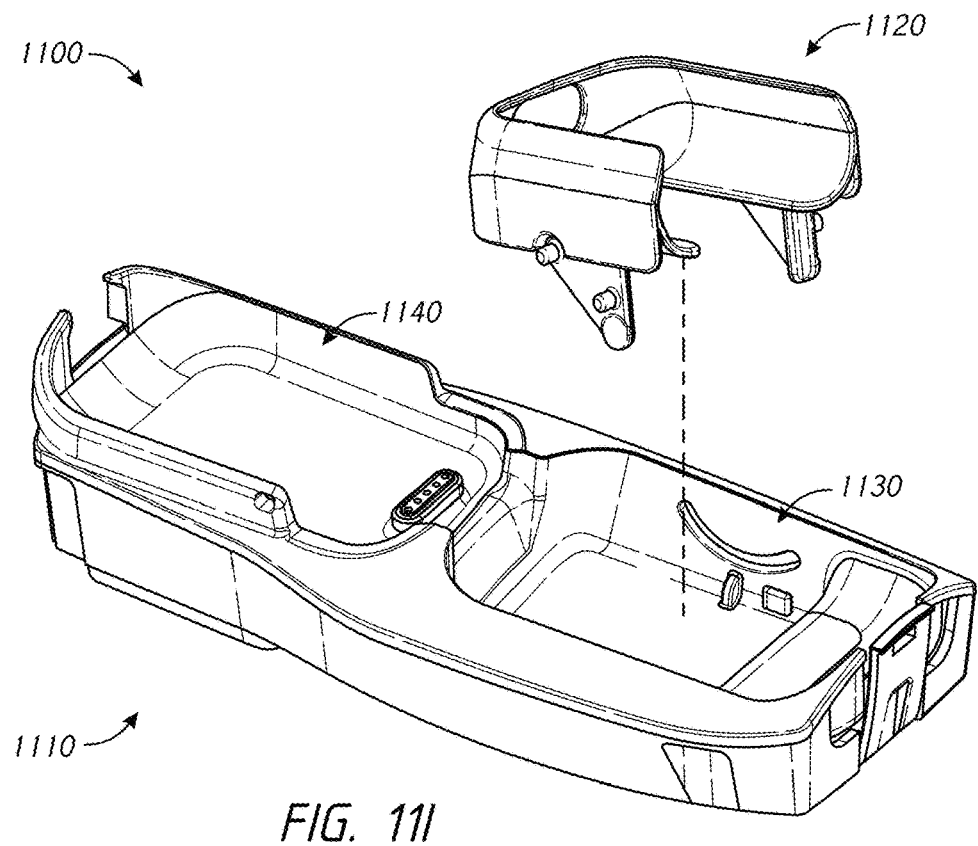

FIG. 11I illustrates another exploded perspective view of the charging cradle of FIGS. 11D-11E.

Figure 11J:
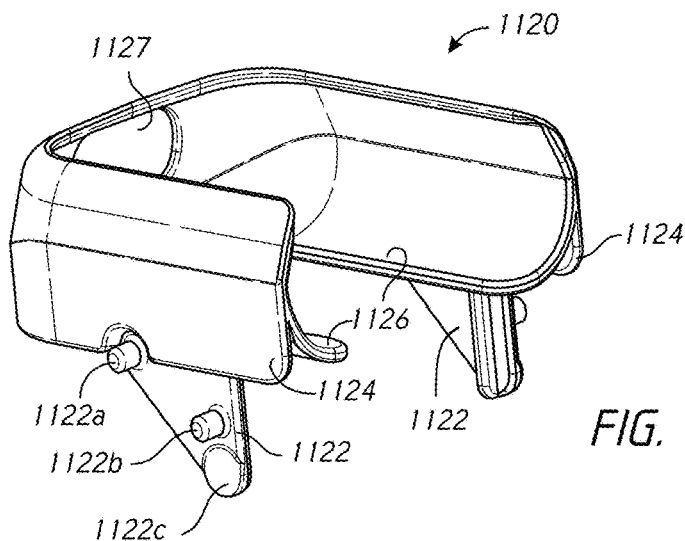

FIG. 11J illustrates a perspective view of a tray of the charging cradle of FIGS. 11D-11E.

Figure 11K:
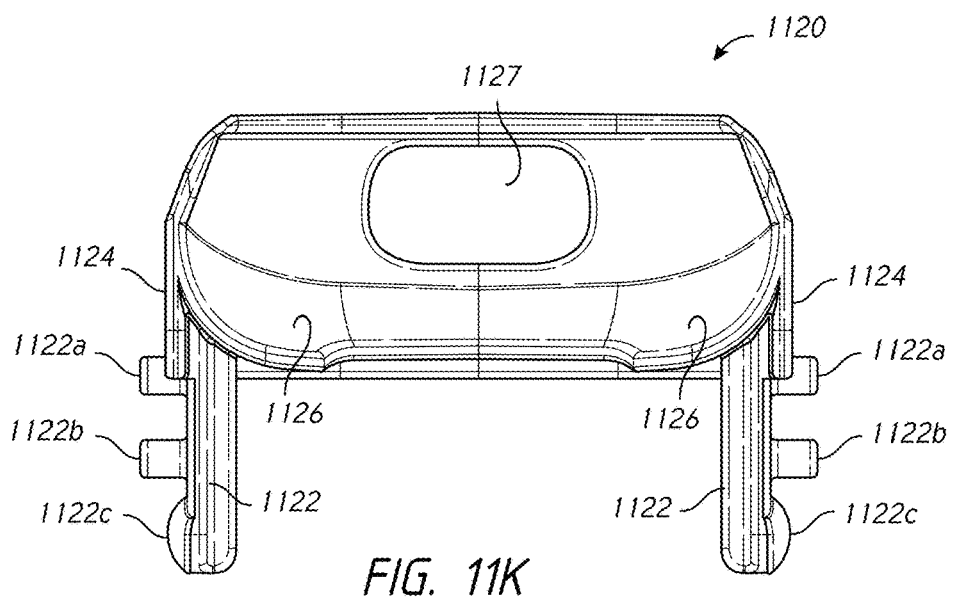

FIG. 11K illustrates a front view of the tray of FIG. 11J.

Figure 11L:
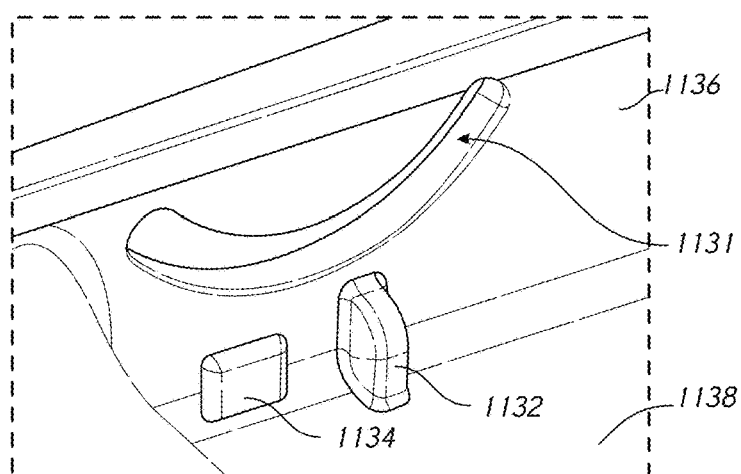

FIG. 11L illustrates an enlarged view of a portion of the charging cradle of FIG. 11H in accordance with aspects of this disclosure.

Figures 11M, 11N:
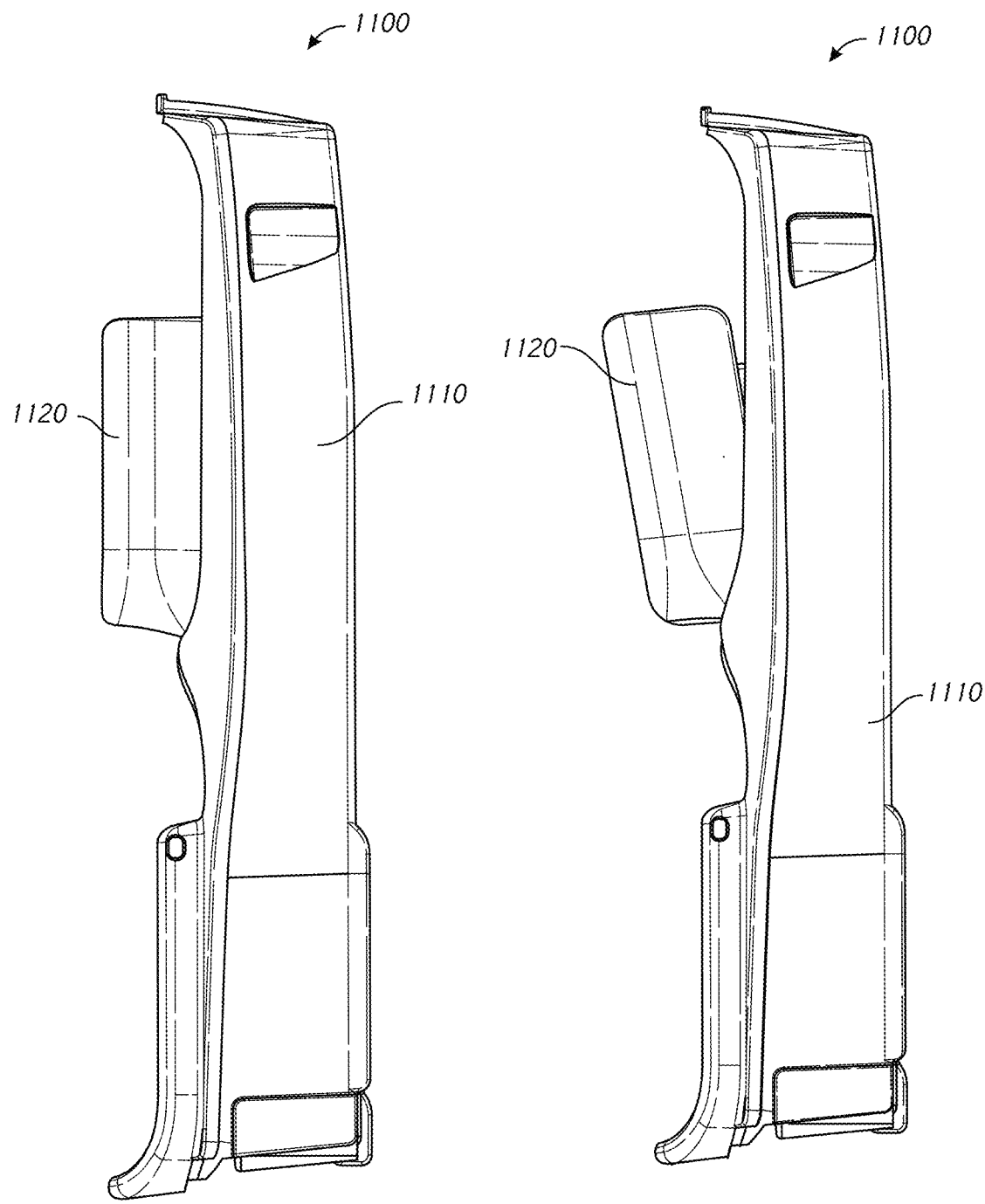

FIGS. 11M-11N illustrate side views of the charging cradle of FIGS. 11D-11E and further illustrate the rotational capabilities of the tray of the charging cradle in accordance with aspects of this disclosure.

Figure 12:
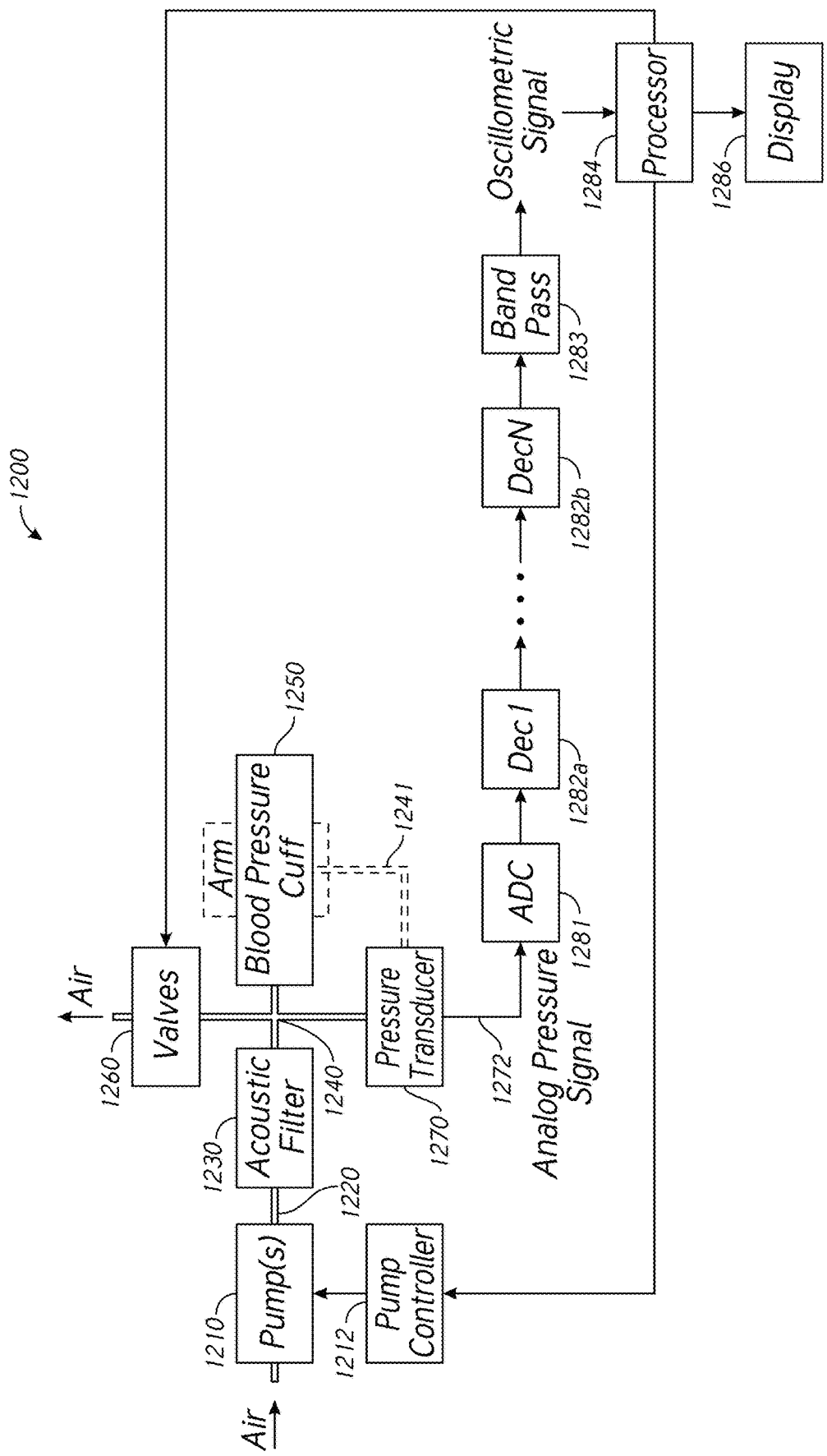

FIG. 12 is a block diagram of an example embodiment of a noninvasive blood pressure monitor.

Figure 13A:
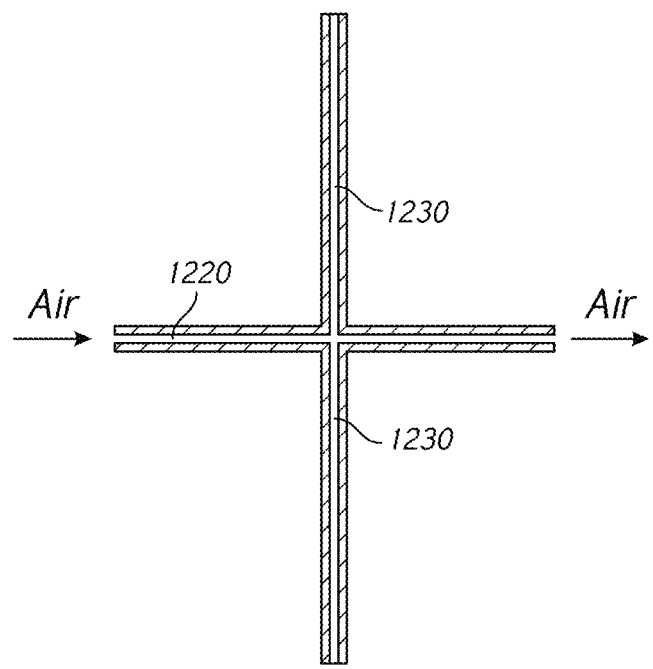

FIG. 13A illustrates an example embodiment of an acoustic filter that can be provided in a blood pressure monitor.

Figure 13B:
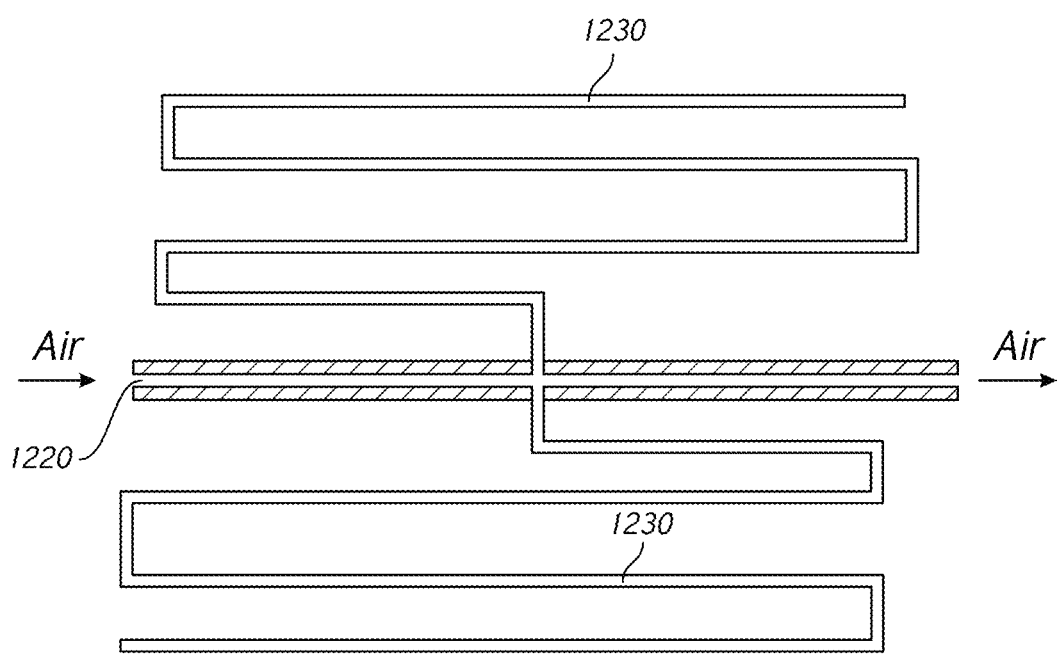

FIG. 13B illustrates another example embodiment of an acoustic filter that can be provided in a blood pressure monitor.

Figure 13C:
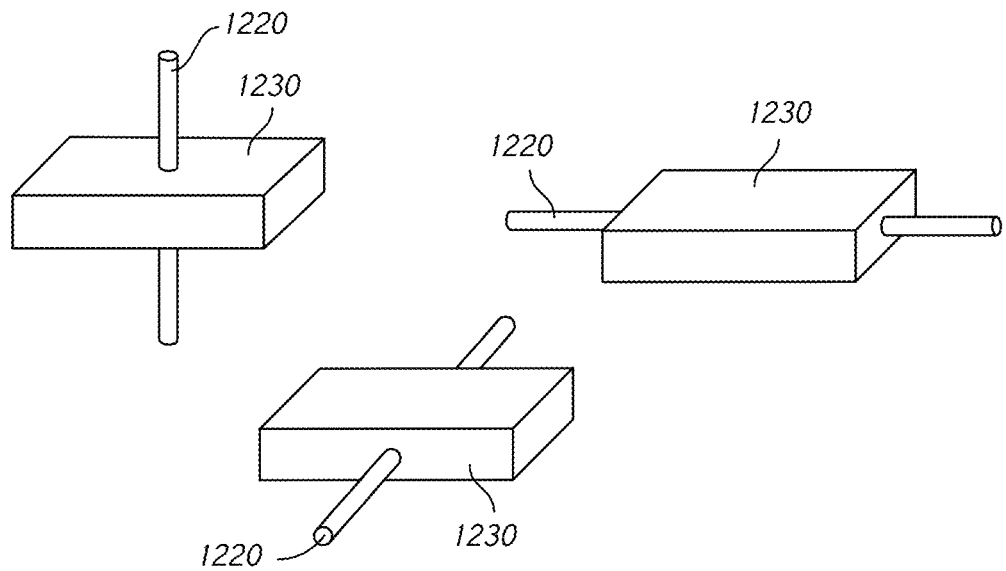

FIG. 13C illustrates additional example embodiments of acoustic filters that can be provided in a blood pressure monitor.

Figure 13D:
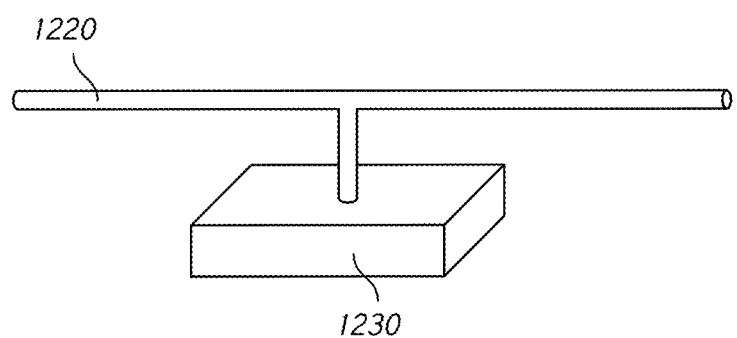

FIG. 13D illustrates yet another example embodiment of an acoustic filter that can be provided in a blood pressure monitor.

Figure 14A:
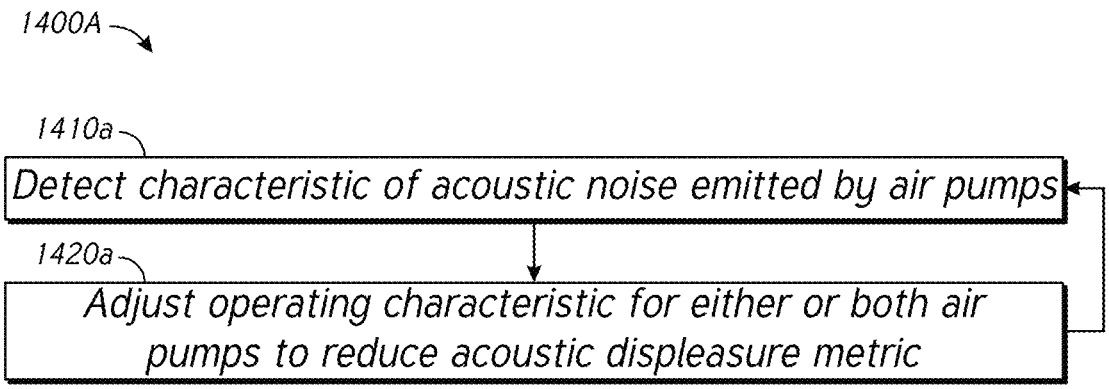

FIG. 14A is a flowchart of an example embodiment of a method for using the air pump controller to improve the audible sound emitted by a noninvasive blood pressure monitor.

Figure 14B:
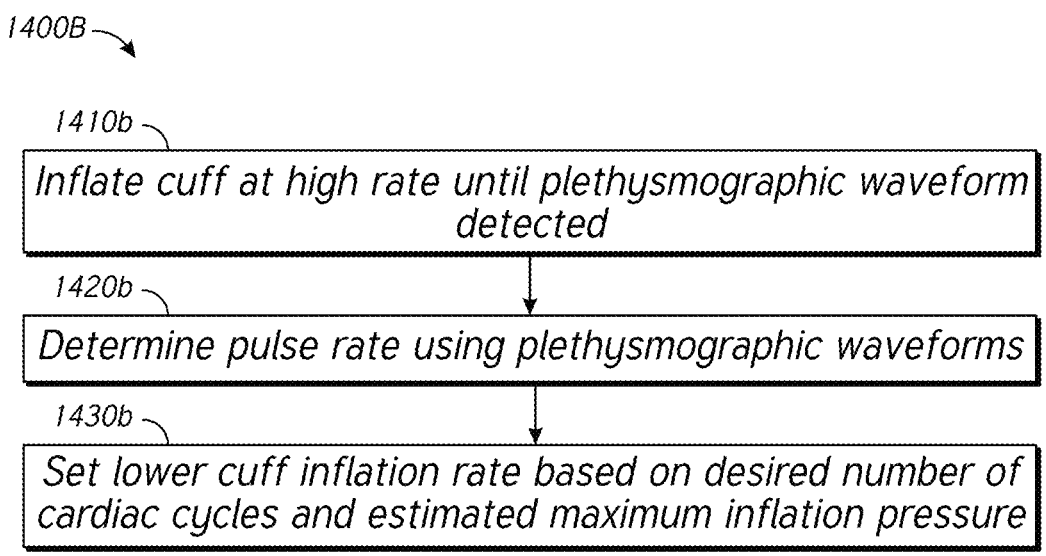

FIG. 14B is a flowchart of an example embodiment of a method for reducing the amount of time necessary for a noninvasive blood pressure monitor to perform blood pressure measurements.

Figure 14C:
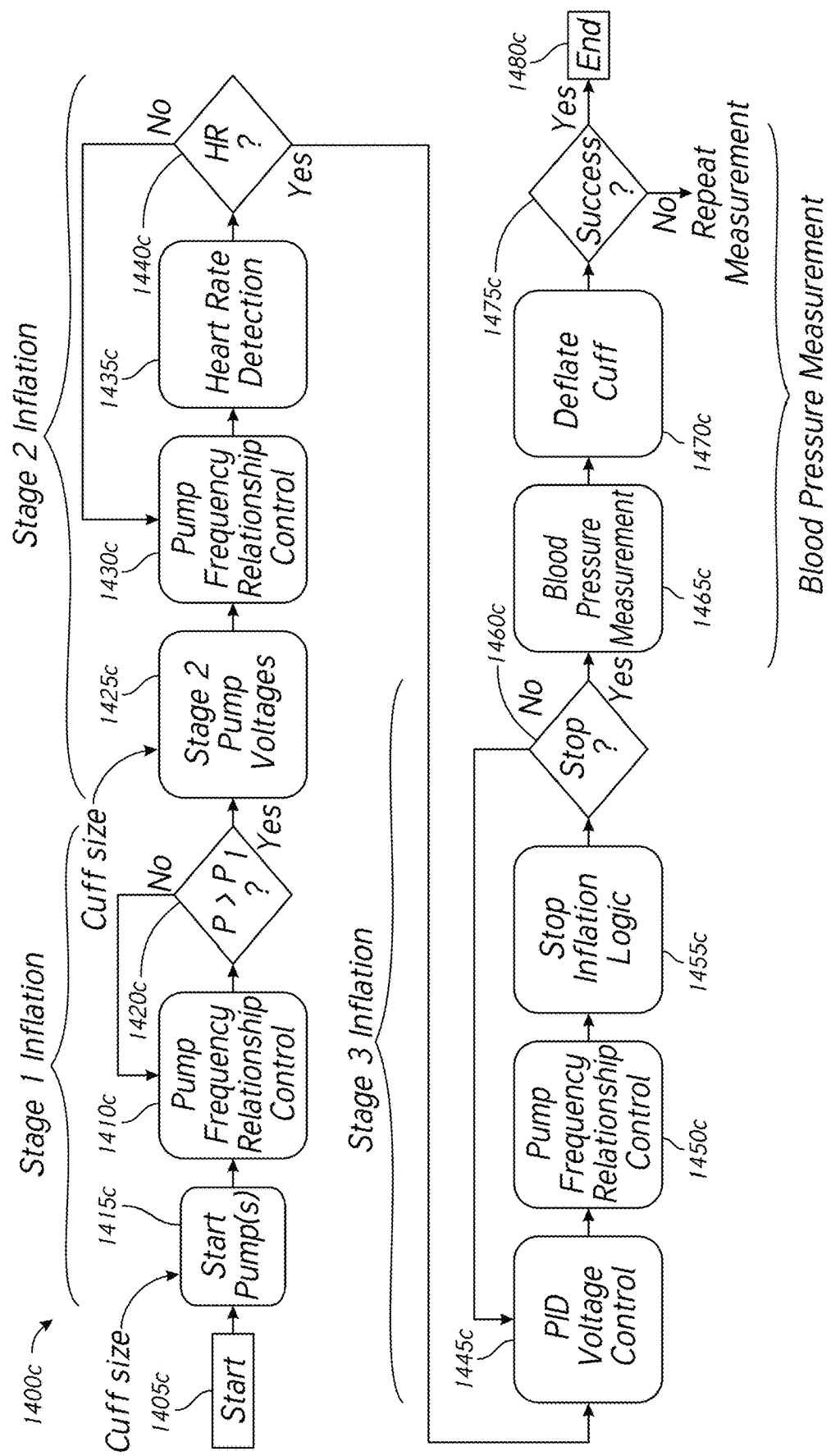

FIG. 14C illustrates an example embodiment of a method for dynamically controlling inflation of a cuff in with a blood pressure monitor.

Figure 14D:
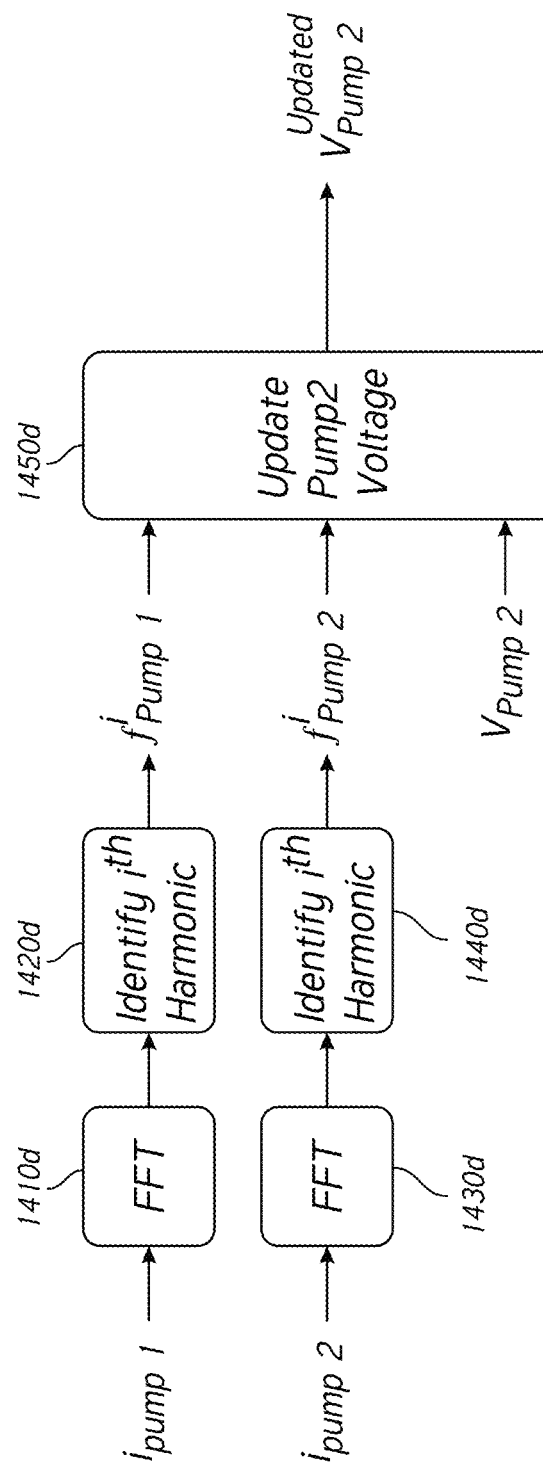

FIG. 14D illustrates an example embodiment of a method for carrying out pump frequency relationship control in a blood pressure monitor with multiple air pumps.

Figure 14E:
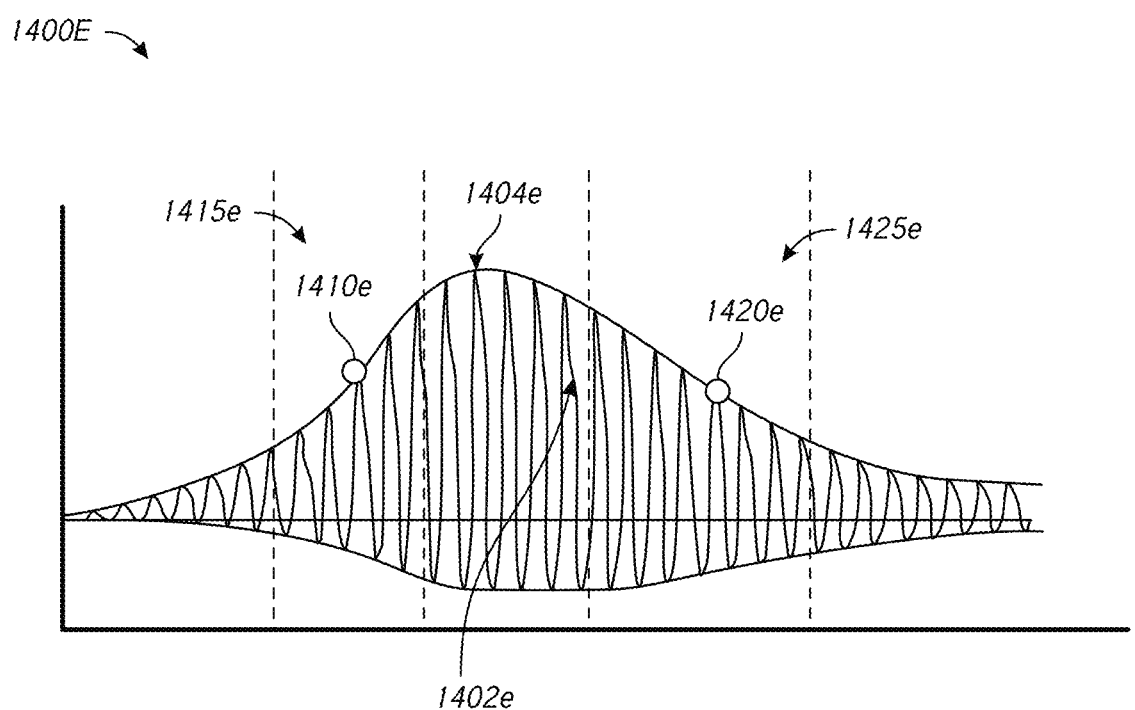

FIG. 14E illustrates how target inflation rate of a blood pressure cuff can be adjusted during a blood pressure measurement based on the envelope of an oscillometric signal produced by a blood pressure monitor.

DETAILED DESCRIPTION

The present disclosure describes various devices, systems, and methods for monitoring one or more physiological parameters of a patient.

The present disclosure will now be described with reference to the accompanying figures, wherein like numerals refer to like elements throughout. The following description is merely illustrative in nature and is in no way intended to limit the disclosure, its application, or uses. It should be understood that steps within a method may be executed in different order without altering the principles of the present disclosure. Furthermore, the devices, systems, and/or methods disclosed herein can include several novel features, no single one of which is solely responsible for its desirable attributes or which is essential to practicing the devices, systems, and/or methods disclosed herein.

Overview of Patient Monitoring Systems

This disclosure describes patient monitoring systems that can include a patient monitor (also referred to herein as "user interface monitor" and "vital signs monitor") attached to a patient and also to one or more physiological sensors. The patient monitor can collect physiological data from the various connected sensors and can process and/or display such data or information related to such data on a screen of the patient monitor. In some cases, the patient monitor includes a wireless transmitter or transceiver that can transmit such data or information to a patient monitor away from the patient. In some cases, the patient monitor can be a stand-alone unit which can present (via a screen) a significant amount of physiological information to the patient or to a caregiver. The patient monitoring system and/or the various components thereof (for example, the sensors/devices) can minimize the total amount of cables in the system. For example, one or more of the sensors/devices of the patient monitoring system can indirectly connect to the patient monitor via another one of the one or more sensors/device in the system. For example, where the system includes an ECG device, a blood pressure monitor, and a patient monitor, the ECG device can connect directly to the blood pressure monitor and indirectly to the patient monitor via a single cable directly connecting the blood pressure monitor and the patient monitor. Further, the blood pressure monitor can include bypass functionality which allows incoming data from the ECG device to be passed directly to the outgoing cable connecting the blood pressure monitor to the patient monitor (for example, without having the incoming ECG device data be processed by a processor of the blood pressure monitor). Such "indirect" cable connection between the ECG device and the patient monitor can decrease the length of cable required and can allow for improved cable management of the patient monitoring system as a whole.

Figure 1A:
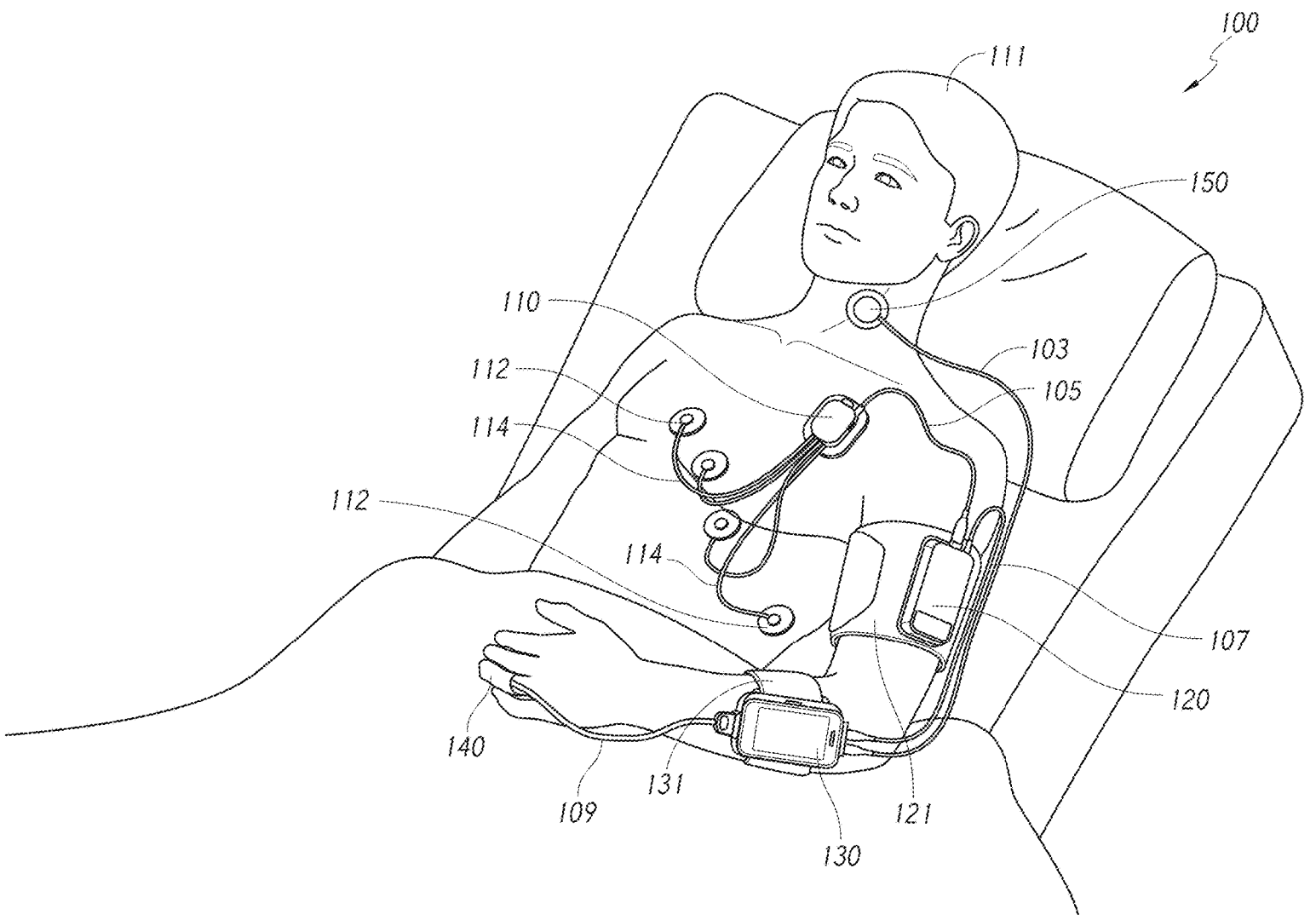
FIG. 1A illustrates a perspective view of a patient monitoring system in accordance with aspects of this disclosure.
Figure 1B:
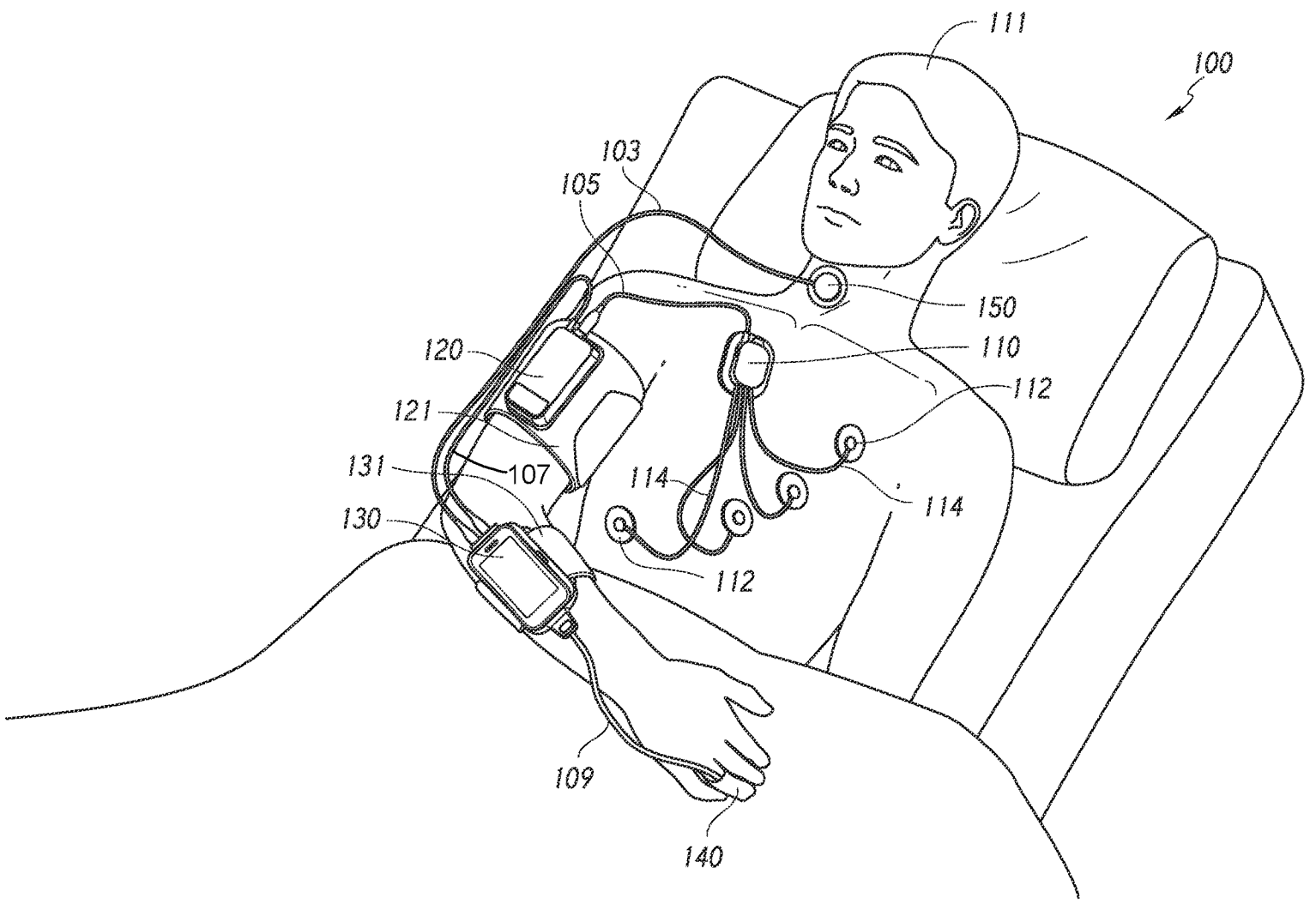
FIG. 1B illustrates another perspective view of the patient monitoring system of FIG. 1A.

FIGS. 1A-1B illustrate a patient monitoring system 100. The patient monitoring system 100 can include one or more physiological sensors attached to a patient 111. For example, the patient monitoring system 100 can include an acoustic sensor 150, an ECG device 110, a blood pressure monitor 600 (also referred to herein as "blood pressure sensor" or "blood pressure device" or "blood pressure measurement device" or "blood pressure monitoring device"), an optical sensor 140, and/or a patient monitor 130 (also referred to herein as "user interface monitor" and "vital signs monitor"). Additional sensors and/or devices other than those illustrated in FIGS. 1A-1B can also be incorporated into the system 100. Any or all of the sensors/monitors 110, 120, 130, 140, and/or 150 cables 103, 105, 107, 114, and/or blood pressure cuff 121 can be reusable, disposable, or resposable. Resposable devices can include devices that are partially disposable and partially reusable. For example, the acoustic sensor 150 can include reusable electronics but a disposable contact surface (such as an adhesive) where the sensor 150 comes in to contact with a skin of patient 111. As another example and as described in more detail below, ECG device 110 can include a reusable portion and a disposable portion.

As shown in FIGS. 1A-1B, the ECG device 110 can have multiple cables 114 connected to electrodes 112 and can be connected to the blood pressure monitor 120 via cable 105. As also shown, the blood pressure monitor 120 can be connected to the patient monitor 130 via cable 107. The system 100 can include additional sensors that can be connected to patient monitor 130. For example, the system 100 can include an acoustic sensor 150 that can be connected to the patient monitor 130 with cable 103 and/or an optical sensor 140 that can be connected to the patient monitor 130 via cable 109. The ECG device 110 can be secured to a chest of patient 111. The blood pressure monitor 120 can be secured to an arm of the patient 111 and/or a blood pressure cuff 121 that can be secured to the arm. The patient monitor 130 can be secured to a forearm of patient 111, for example, via a fastening strap 131 that can be secured to or through a portion of the patient monitor 130 and around the forearm. The acoustic sensor 150 can be secured to a neck of the patient 111. The optical sensor 140 can be secured to a finger of a patient 111, for example, an index finger of patient 111.

The electrocardiograph (ECG) device 110 of system 100 can be used to monitor electrical activity of the heart of the patient 111. The ECG device 110 can include one or more cables 114 which can be coupled to one or more external electrodes 112. The ECG device 110 can include one, two, three, four, five, six or seven or more cables 114 and/or corresponding electrodes 112. The ECG device 110 is further illustrated in FIGS. 2A-2U and is described in more detail below.

The blood pressure monitor 120 of system 100 can be utilized alongside an blood pressure cuff 121 to measure blood pressure data of the patient 111. The blood pressure cuff 121 (also referred to herein as "cuff") can be inflatable and/or deflatable. Cuff 121 can be an oscilometric cuff that is actuated electronically (e.g., via intelligent cuff inflation and/or based on a time interval) to obtain blood pressure information of patient 111. Such blood pressure data can be transferred to the patient monitor 130 via cable 107. The blood pressure monitor 120 is further illustrated in FIGS. 5A-5AA and is described in more detail below. As discussed below, the blood pressure monitor 120 can have the characteristics and/or functionality as described in more detail below with reference to FIGS. 12-14E.

The optical sensor 140 can include one or more emitters and one or more detectors for obtaining physiological information indicative of one or more blood parameters of the patient 111. These parameters can include various blood analytes such as oxygen, carbon monoxide, methemoglobin, total hemoglobin, glucose, proteins, glucose, lipids, a percentage thereof (e.g., concentration or saturation), and the like. The optical sensor 140 can also be used to obtain a photoplethysmograph, a measure of plethysmograph variability, pulse rate, a measure of blood perfusion, and the like. Information such as oxygen saturation ($SpO_2$), pulse rate, a plethysmograph waveform, perfusion index (PI), pleth variability index (PVI), methemoglobin (MetHb), carboxyhemoglobin (CoHb), total hemoglobin (tHb), glucose, can be obtained from optical sensor 140 and data related to such information can be transmitted to the patient monitor 130 via cable 109. The optical sensor 140 can be a pulse oximeter, for example.

The acoustic sensor 150 of system 100 (also referred to as an "acoustic respiratory sensor" or "respiratory sensor") can comprise an acoustic transducer, such as a piezoelectric element. The acoustic sensor 150 can connect to the patient monitor 130 via cable 103. The acoustic sensor 150 can detect respiratory and other biological sounds of a patient and provide signals reflecting these sounds to a patient monitor. The acoustic sensor 150 can be a piezoelectric sensor or the like that obtains physiological information reflective of one or more respiratory parameters of the patient 111. These parameters can include, for example, respiratory rate, inspiratory time, expiratory time, inspiration-to-expiration ratio, inspiratory flow, expiratory flow, tidal volume, minute volume, apnea duration, breath sounds, rales, rhonchi, stridor, and changes in breath sounds such as decreased volume or change in airflow. In addition, in some cases the respiratory sensor 150, or another lead of the respiratory sensor 150 (not shown), can measure other physiological sounds such as heart rate (e.g., to help with probe-off detection), heart sounds (for example, S1, S2, S3, S4, and murmurs), and changes in heart sounds such as normal to murmur or split heart sounds indicating fluid overload. In some implementations, a second acoustic respiratory sensor can be provided over the chest of the patient 111 for additional heart sound detection.

The acoustic sensor 150 can be used to generate an exciter waveform that can be detected by the optical sensor 140 at the fingertip, by an optical sensor attached to an ear of the patient, by an ECG device 110, or by another acoustic sensor. The velocity of the exciter waveform can be calculated by a processor in the patient monitor 130 and/or the blood pressure device 120. From this velocity, the processor can derive a blood pressure measurement or blood pressure estimate. The processor can output the blood pressure measurement for display. The processor can also use the blood pressure measurement to determine whether to trigger the blood pressure cuff 121.

As illustrated in FIGS. 1A-1B, patient monitoring system 100 includes various cables connecting the physiological sensors together and/or to the patient. As discussed above, the patient monitor 130 can advantageously connect to each of the various sensors 110, 120, 140, and/or 150 to gather various physiological data of the patient 111, process such data, and can conveniently display such data and/or information related to such data on a display screen for patient and/or caregiver viewing convenience. As shown, such cables can include one or more cables 114, cable 103 connected to the acoustic sensor 150, cable 105 connected to the ECG device 110, cable 107 connected to the blood pressure monitor 120, and/or cable 109 connected to the pulse oximeter 140. With all such sensors/device in the system 100 and all such cables connecting these sensors/devices, cable management can be difficult. Advantageously, system 100 and the various components thereof (sensors/devices) can be oriented, structured, and/or designed to effectively manage the various cables.

For example, while it is advantageous that data from each of the various sensors be transmitted to the patient monitor 130, such transmission can be provided indirectly through other ones of the sensors/devices of the system 100. As shown, in some instances where the system 100 includes the ECG device 110, the blood pressure monitor 120, and the patient monitor 130, instead of having the ECG device 110 connect directly to the patient monitor 130 (where such cable may have to span or cross a gap between the patient's 111 chest and the patient's arm) the ECG device 110 can connect, via cable 105, directly to the blood pressure device 120 which can be secured to an upper arm of patient 111 as shown in FIGS. 1A-1B. Further, when the ECG device 110 is attached to the chest of the patient 111 and the patient monitor 130 is attached to an arm (for example, wrist or lower arm) of the patient 111, such indirect connection can result in shorter cable lengths. Decreasing the length of cables connecting the various sensors/devices can reduce or eliminate problems associated with cabling, including, discomfort and/or annoyance for monitored patients, interference with movement of the patient and/or a caregiver's ability to interact with, engage, assess, and/or treat a patient.

FIG. 1B illustrates the system 100 as shown in FIG. 1A, but on an opposite side of the patient 111. Advantageously, connection techniques discussed above with reference to FIG. 1A are equally applicable where system 100 is secured to a right side of the patient 111. System 100 can include one or more cable management prongs (such as cable management prong 900 discussed further below with reference to FIGS. 9A-9C) which can secure to various portions of patient 111 and can also secure to portions of any of cables 103, 105, 107, and/or 109.

Figure 1C:
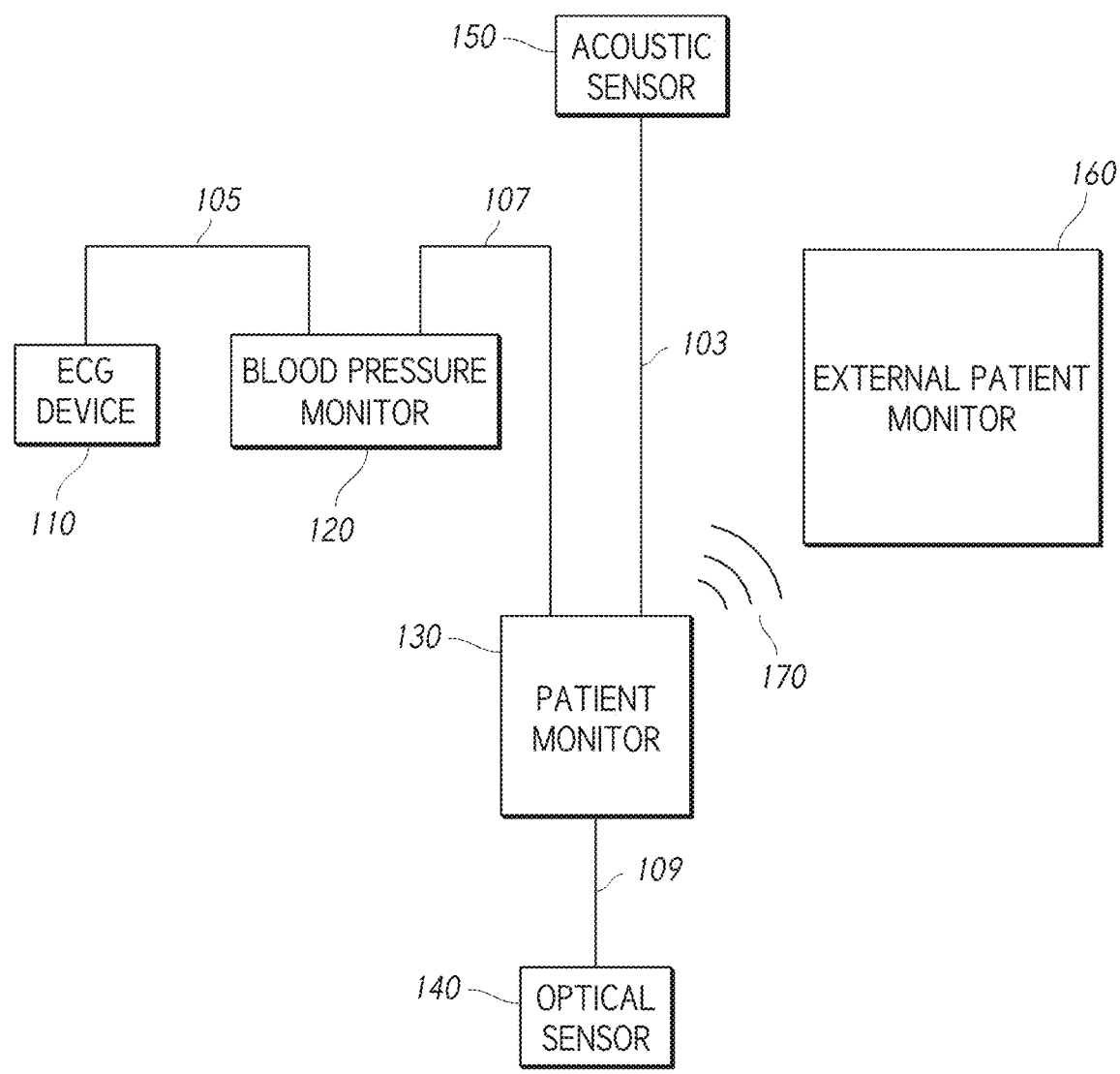
FIG. 1C illustrates a schematic diagram of the patient monitoring system of FIG. 1A in accordance with aspects of this disclosure.

FIG. 1C illustrates a schematic diagram of the system 100. FIG. 1C schematically illustrates how patient monitor 130 can obtain information from one or more physiological sensors or monitors. Patient monitor 130 can connect (via cables or wirelessly) to one or more physiological sensors to obtain various physiological information regarding a monitored patient such as is discussed above. Patient monitor 130 can be configured to store, process, transmit, transmit without processing, display, and/or display without processing the physiological information received from the one or more physiological sensors of the system 100. Patient monitor 130 is a processing device, and as such, can include the necessary components to perform the functions of a processing device. For example, patient monitor 130 can include one or more processors (such as one, two, three, or four processors which can be dedicated to processing certain physiological parameters and/or processing physiological information from certain sensors/devices), a memory device, a storage device, input/output devices, and communications connections, all connected via one or more communication bus.

As shown, patient monitoring system 100 can include the ECG device 110 and/or the blood pressure monitor 120. As also shown, the ECG device 110 and/or the blood pressure monitor 120 can connect to patient monitor 130 and transmit physiological information to patient monitor 130. Each of the ECG device 110 and/or the blood pressure monitor 120 can connect directly to the patient monitor 130 with a cable (or wirelessly). Alternatively, one or both of the ECG device 110 and the blood pressure monitor 120 can connect indirectly to the patient monitor 54. For example, the ECG device 110 can connect directly to the blood pressure monitor 120 (such as with cable 105), which then connects directly to patient monitor 130 (such as with cable 107). As discussed above, such "indirect" connection between the ECG device 110 and the patient monitor 130 can be beneficial, for example, where a number of physiological sensors/devices are attached to the patient 111 and cables are used to connect the various physiological sensors/devices to each other or the patient monitor 130. As discussed above, such "indirect" connection can reduce lengths and/or amount of cables proximate a monitored patient which can in turn reduce patient discomfort, reduce potential "snags" or cable dislodgement, and increase patient movement ability, among other things.

In some cases, the cable 103 can be configured to connect to either a connector port on the blood pressure monitor 120 or a connector port on the patient monitor 130. Additionally or alternatively, in some cases, the cable 105 can be configured to connect to either a connector port on the blood pressure monitor 120 or a connector port on the patient monitor 130. Advantageously, this can provide flexibility for the connectivity of the system 100 where the blood pressure monitor 120 is not included. Additionally, in some cases, the blood pressure monitor 120 includes one or more connector ports on an end thereof. This can additionally allow for a smaller cable length between the blood pressure monitor 120 and one or more of the ECG device 110 and/or acoustic sensor 150 when the system 100 is secured to the patient 111 in the configuration shown in FIGS. 1A-1B. Cables 103, 105, and 107 can include identical connectors on ends thereof. For example, with reference to FIGS. 2C, 5A, and 8A, connector ends 105a, 107a, and/or 103a of cables 105, 107, and/or 103 can be identical. The blood pressure monitor 120 and the patient monitor 130 can include one or more identical connector ports that are configured to electrically connect to the connectors one such ends of cables 103, 105, and 107. Advantageously, such configuration can allow the cables 103, 105, and/or 107 to electrically connect to either the blood pressure monitor 120 or the patient monitor 130, which can provide flexibility in the configuration of system 100. For example, such configuration can provide flexibility as to which of ECG device 110, blood pressure monitor 120, patient monitor 130, and/or acoustic sensor are included and/or arranged. In one non-limiting example, the ECG device 110 is secured to a chest of a monitored patient, the blood pressure monitor 120 is secured to the patient's arm (for example, the bicep and/or upper arm of the patient), the acoustic sensor 150 is secured to a neck of the patient, the optical sensor 140 is secured to a finger of the patient (for example, index finger), and the patient monitor 130 is secured to a portion of the arm of the patient (for example, the forearm of the patient).

As illustrated in FIG. 1C, the ECG device 110 can connect directly to the blood pressure monitor 120 with cable 105 and the blood pressure monitor 120 can connect directly to the patient monitor 130 with cable 107. The blood pressure monitor 120 can include bypass functionality that allows the blood pressure monitor 120 to pass physiological information received from the ECG device 110 to the patient monitor 130 without processing, storing, or otherwise altering the received information. For example, the blood pressure monitor 120 can include a bypass bus configured to transmit physiological information received from the ECG device 110 without processing the information. Additionally, the blood pressure monitor 120 can transmit physiological information that it obtains from its own measurement components along with the received information from the ECG device 110. Such transmission of the blood pressure monitor's 120 physiological information can be simultaneous or non-simultaneous with the transmission of the physiological information from the ECG device 110. Alternatively, the blood pressure monitor 120 can be configured to process or partially process the physiological information received from the ECG device 110 before transmitting to the patient monitor 130 (for example, via cable 107).

As discussed above, the patient monitoring system 100 can include sensors in addition or as an alternative to the ECG device 110 and/or blood pressure monitor 120. Such additional sensors can also be configured to connected, either directly or indirectly, to patient monitor 130. For example, patient monitoring system 100 can include the acoustic sensor 150 which can connect to patient monitor 130 via cable 103 (or wirelessly). Additionally or alternatively, patient monitoring system 100 can include the optical sensor 140, which can connect to patient monitor 130 via cable 109 (or wirelessly). While the acoustic sensor 150 and the optical sensor 140 are shown as connected to patient monitor 130 independent from the ECG device 110 and blood pressure monitor 120, one or both of the acoustic sensor 150 and the optical sensor 140 can alternatively be configured to connect to one of the ECG device 110 and the blood pressure monitor 120. For example, the acoustic sensor 150 can connect directly to the blood pressure monitor 120 and indirectly to the patient monitor 130 via cable 103. For example, system 100 can include the acoustic sensor 150, the blood pressure monitor 120 and no ECG device 110, and an end of cable 105 can connect to the blood pressure monitor 120 where the ECG device 110 could otherwise connect. Blood pressure monitor 120 can include a bypass bus configured to transmit physiological information received from the acoustic sensor 150 without processing the information. Additionally, similar to that described with respect to the ECG device 110 above, the blood pressure monitor 120 can transmit physiological information that it obtains from its own measurement components along with the received information from the acoustic sensor 150 to the patient monitor 130. Such transmission of the blood pressure monitor's 120 physiological information can be simultaneous with the transmission of the physiological information from the acoustic sensor 150. Alternatively, the blood pressure monitor 120 can be configured to process or partially process the physiological information received from the acoustic sensor 150 before transmitting to the patient monitor 130. Blood pressure monitor 120 can include a single bypass bus configured to transmit physiological information received from the ECG device 110 and/or the acoustic sensor 150 to the patient monitor 130 without processing. Alternatively, blood pressure monitor 120 can include multiple bypass buses, each of the bypass buses dedicated to one of the ECG device 110 and/or the acoustic sensor 150. Blood pressure monitor 120 can include multiple connector ports and/or connectors configured to connect to one or more cables connecting the ECG device 110 and/or the acoustic sensor 150 to the blood pressure monitor 120.

Patient monitor 130 can be configured to transmit physiological information received from one or more of the ECG device 110, blood pressure monitor 120, acoustic sensor 150, and/or the optical sensor 140 to an external patient monitor 160. The external patient monitor 160 can be, for example, a nurse's station, a clinician device, pager, cell phone, computer, multi-patient monitoring system, hospital or facility information system. An artisan will appreciate that numerous other computing systems, servers, processing nodes, display devices, printers, and the link can interact with and/or receive physiological information from the patient monitor 130.

Figure 1D:
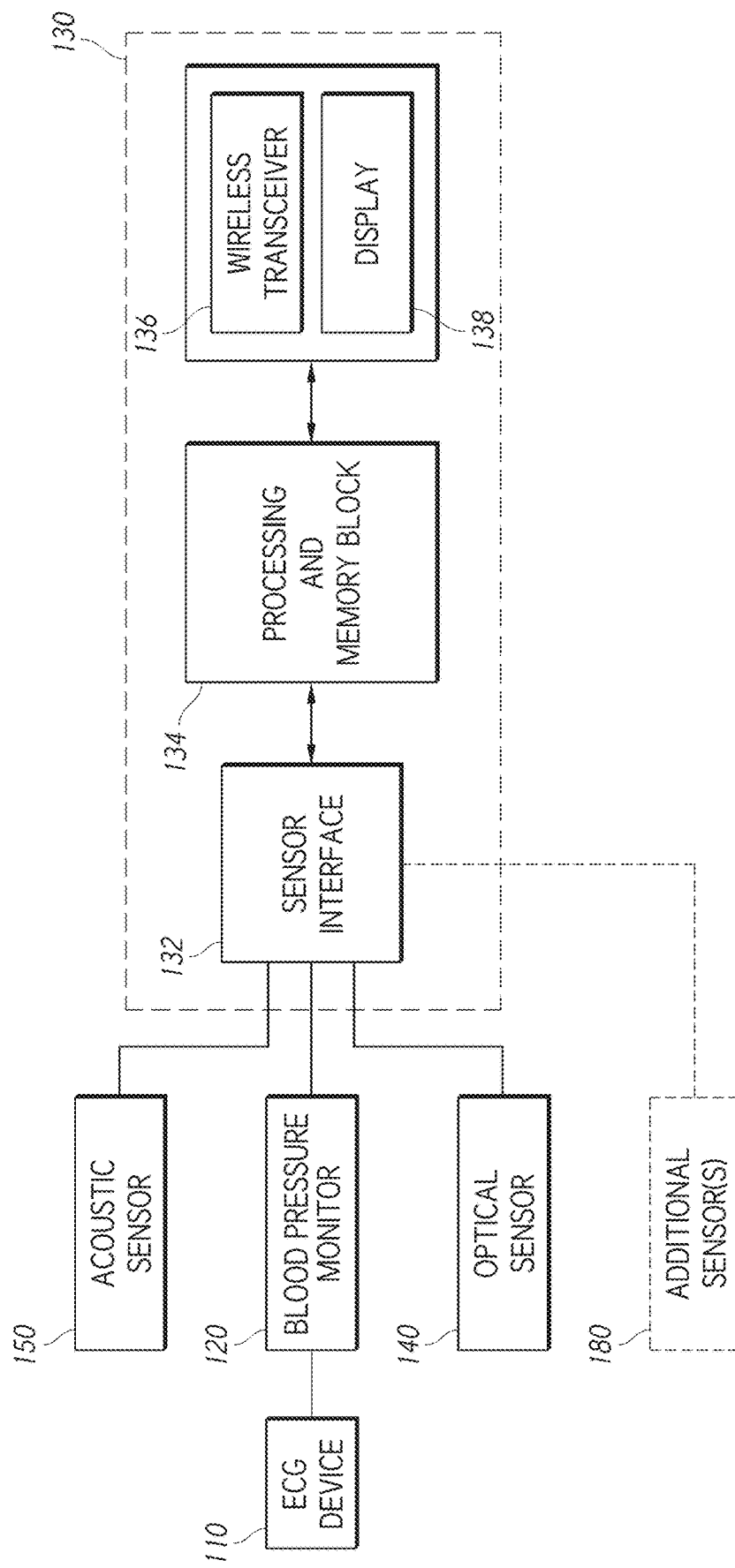
FIG. 1D illustrates another schematic diagram of the patient monitoring system of FIG. 1C in accordance with aspects of this disclosure.

FIG. 1D illustrates details of the patient monitoring system 100 and the patient monitor 130 in a schematic form. As discussed above, the patient monitoring system 130 can include one or more of ECG device 110, blood pressure monitor 120, acoustic sensor 150, and/or optical sensor 140, connected, indirectly or directly, to patient monitor 130. The patient monitoring system 130 can include one or more additional sensors 180 that can also connect indirectly or directly to patient monitor 130. ECG device 110, blood pressure monitor 120, acoustic sensor 150, optical sensor 140, and/or any additional sensors 180 can transmit physiological data to a sensor interface 132 of the patient monitor 130. The sensor interface 132 can pass the received physiological data to a processing and memory block 134. The processing and memory block 134 can include one or more processors configured to process the physiological data received from one or more of ECG device 110, blood pressure monitor 120, acoustic sensor 150, optical sensor 140, and/or any additional sensors 180 into representations of physiological parameters. The processing and memory block 134 can include a plurality of processors that are independently dedicated to processing data from different ones of the physiological sensors described above. For example, the processing and memory block 134 can include a first processor dedicated to processing data from the ECG device 110 and/or blood pressure monitor 120, a second processor dedicated to processing data from the acoustic sensor 150, and/or a third processor dedicated to processing data from the optical sensor 140. The processing and memory block 134 can include an instrument manager which may further process the received physiological parameters for display. The instrument manager may include a memory buffer to maintain this data for processing throughout a period of time. The memory buffer may include RAM, Flash, or other solid state memory, magnetic or optical disk-based memories, combinations or the same or the like. As discussed above, the patient monitor 130 can include a wireless transceiver 136. Wireless transceiver 136 can wireless transmit the physiological information received from the above-described physiological sensors and/or parameters from the one or more processors and/or the instrument manager of the processing and memory block 134. Wireless transceiver 136 can transmit received physiological data to an external device (such as external patient monitor 160) via a wireless protocol 170. The wireless protocol can be any of a variety of wireless technologies such as Wi-Fi (802.11x), Bluetooth®, ZigBee®, cellular telephony, infrared, RFID, satellite transmission, proprietary protocols, combinations of the same, and the like.

In some cases, one or more of ECG device 110, blood pressure monitor 120, acoustic sensor 150, and/or optical sensor 140 incorporated in system 100 can receive power from the patient monitor 130. In some cases, one or more of ECG device 110, blood pressure monitor 120, acoustic sensor 150, and/or optical sensor 140 incorporated in system 100 do not have an independent power source and rely upon the patient monitor 130 for power in order to operate. For example, one or more of ECG device 110, blood pressure monitor 120, acoustic sensor 150, and/or optical sensor 140 incorporated in system 100 can be configured to be in a non-operational mode unless and/or until an indirect and/or direct electrical connection is made with the patient monitor 130. As discussed further below, the patient monitor 130 can be configured to be charged from an external power source, such as charging station 1000 and/or charging cradle 1100.

Physiological Parameter Calculations

One or more of the devices discussed above can enable independent determination of certain physiological data. In some instances, the data processed from the respective devices can be used for the purposes of correlation or increasing accuracy. In some instances, the data processed from multiple devices may be aggregated to determine a particular physiological condition. Furthermore, in some instances, the independent sources of data can be used in determination of alarms.

Cardiac Parameters: Cardiac activity may be determined from ECG device 110, optical sensor 140, blood pressure monitor 120, and acoustic sensor 150. In some instances, the cardiac activity determined from the respective sensors can be used to improve accuracy of parameters related to cardiac activity. For example, the parameters can be averaged from different sources. Furthermore, deviation in the parameters can be used to determine confidence. In some instances, certain parameters derived from a particular system may be given a higher priority than if it is derived from a different system. For example, with respect to cardiac parameters, in some instances, parameters derived from the ECG device 110 may have the highest priority. Accordingly, if there is discrepancy between parameters derived from the ECG device 110 and parameters derived from the optical sensor 140, the parameters derived from the ECG device 110 may be used for further processing. In some instances, parameters derived from the ECG device 110 may have a higher weight. Furthermore, in some instances, cardiac parameters derived from the optical sensor 140 may have a higher priority than cardiac parameters derived by the blood pressure monitor 120. Additionally, in some instances, parameters derived by the blood pressure monitor 120 may have a higher priority than parameters derived by the acoustic sensor 150. Cardiac parameters can include for example, pulse rate or heart rate. Cardiac parameters can also include cardiac tone. In some instances, cardiac tone can be selected based on either parameters derived from the ECG device 110 or parameters derived from the optical sensor 140. The tone can be modulated by oxygen saturation (SpO2) values derived by optical sensor 140.

Respiratory Rate: In some instances, respiratory rate measurements may be determined from three different sources: acoustic sensor 150; optical sensor 140; and the ECG device 110 (for example, impedance). A combined respiration rate may be determined from these three different sources. As discussed above with respect to cardiac parameters, rates from independent sources can be averaged or weighted according to a priority. In some examples, the respiration rate derived from the acoustic sensor 150 has a higher priority than respiration rate derived from impedance of ECG device 110, which may in turn have a higher priority than respiration rate derived from the optical sensor 140. As discussed above, priorities can determine weight and alarm management conditions.

ECG Features: The ECG data collected can be used for ST/QT segment analysis, beat classification, and arrhythmia detection.

Temperature Features: The temperature measurements can be obtained from one or more temperature sensors in the ECG device 110 as discussed below. In some instances, a wireless sensor can be used to determine temperature. The wireless sensor is described in more detail in U.S. Pat. Pub. No. 2018/0103874, filed Oct. 12, 2017, titled "Systems and Methods for Patient Fall Detection", the disclosure of which is hereby incorporated by reference in its entirety. This wireless sensor can be disposable. The wireless sensor can also be used for detecting patient orientation and fall. In some instances, the functionality of the wireless sensor can be integrated directly in the ECG device 110 because the ECG device 110 include an accelerometer and/or gyroscope as discussed below. Therefore, in some instances, the ECG device 110 can detect temperature and patient's orientation including fall detection as described in more detail in U.S. Pat. Pub. No. 2018/0103874. When both the ECG device 110 and the wireless sensor are used, the temperature readings from the additional sensor may have a higher priority than temperature readings from the ECG device 110.

Posture/Fall Sources: In some instances, multiple devices may include an accelerometer and/or gyroscope that measures motion data. For example, the patient monitor 130, the blood pressure monitor 120, the ECG device 110, and the wireless sensor discussed above may all include an accelerometer and/or a gyroscope. The wireless sensor may connect to the patient monitor 130 via Bluetooth® or an alternative wireless communication protocol. As discussed above, the functionality of the ECG device 110 and the wireless sensor can be fused into a single device. In some instances, the wireless sensor may be used by itself when the ECG device 110 is not available or needed. As these devices are placed in different positions on the patient's body, the accelerometer and gyroscope data can be used to determine overall patient's orientation. For example, the motion data from the patient monitor 130 provides indication of the wrist motion. The motion data from the blood pressure monitor 120 provides indication of the arm motion. The motion data from the ECG device 110 and the wireless sensor can provide motion data from the patient's chest and/or back. The collective motion data can be used to determine for example if a patient is walking, exercising, lying down, or has fallen. The collective motion data can therefore provide information on a patient's posture.

Alarm Priority: In some instances, the interactions between devices can determine alarm priority. For example, when the blood pressure monitor 120 is measuring blood pressure, it can affect readings from the optical sensor 140. Accordingly, alarms corresponding to the optical sensor 140 may be suspended or muted while the blood pressure monitor 120 is measuring (inflating/deflating cuff). In some examples, the following order may be used for alarming priorities with highest priority to lowest priority: 1) Lethal Arrhythmia, 2) Apnea, 3) SpO2, 4) Cuff over pressure/time, 5) Cardiac analysis, 6) Cardiac Rate, 7) Respiration Rate, 8) MBP, and 9) temperature.

Calibration: In some instances, features from the acoustic sensor 150 can be correlated with the blood pressure monitor 120 derived features such as systolic, mean, and diastolic pressure. The correlation can be used for the purposes of calibration. Furthermore, features from the optical sensor 140 derived waveform, the ECG device 110 derived waveform can be used for determining pulse arrival time. The pulse arrival time can be used to determine pulse transit time, which can also be obtained from the acoustic sensor 150 derived waveform. Based on these pulse parameters, an indication of blood pressure can obtained, which can be calibrated periodically or over certain time periods with blood pressure measurements derived from the blood pressure monitor 120.

ECG Device

Electrocardiogram (ECG) is a widely accepted noninvasive procedure that detects the electronic impulses that travel through a patient's heart. It is often used to detect problems and/or abnormal conditions that may be related to the patient's heart. Temperature is also a widely accepted indicator of patient's health. Temperatures that are too low or too high can negatively impact a patient's metabolic rate, organ function, and/or can cause tissue damage. By collecting and monitoring ECG and temperature data of a patient, care providers can detect and/or prevent harmful conditions such as infections, cardiac arrest, stroke, and other types of conditions.

Figure 2A:
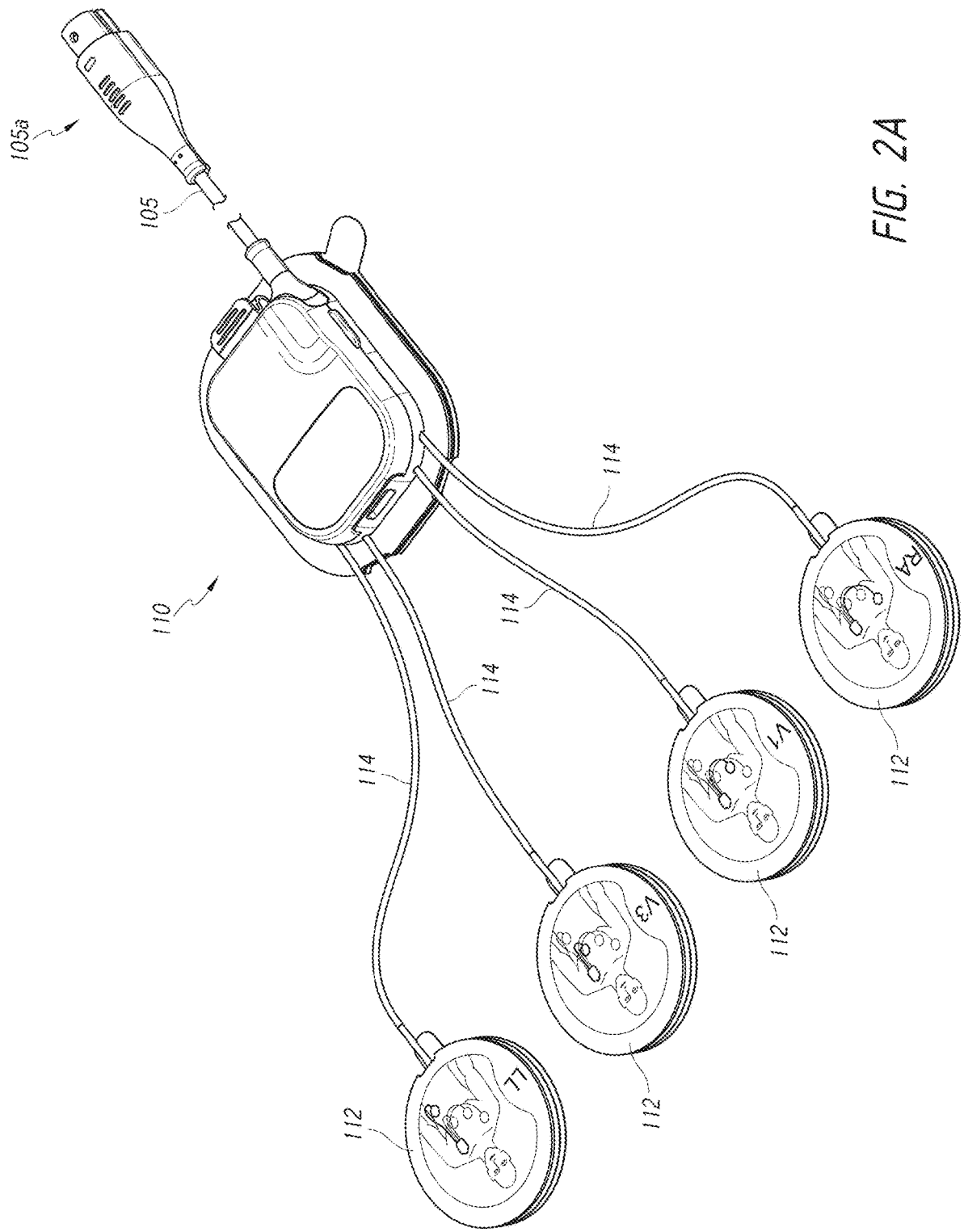
FIG. 2A illustrates a perspective view of an ECG device.

FIG. 2A illustrates an ECG device 110 (also referred to herein as "ECG sensor"). ECG device 110 can be attached to different parts of the patient 111 such as the patient's chest, back, arms, legs, neck, head, or other portions of the body of the patient. FIGS. 1A-1B illustrates ECG device 110 attached to the chest of the patient 111. With reference to FIGS. 1A-1B, 2A, and 5A, ECG device 110 can be connected to the blood pressure monitor 120 via cable 105. For example, the connector 105*a* of cable 105 can connect to the connector port 516 of the blood pressure monitor 120. In some cases, connector 105*a* is identical to connector 107*a* of cable 107. In such cases, ECG device 110 can connect directly to the patient monitor 130 via connection of connector 105*a* to a connector port of the patient monitor 130, such as connector port 832 (FIG. 8I). This can advantageously provide flexibility in the connection of the ECG device 110 when the blood pressure monitor 120 is not included in system 100, for example. In some variants, cable 105 is permanently secured to ECG device 110 at the connector port 250 (see FIGS. 2A and 2O-2P). For example, an end of cable 105 can be permanently hard-wired to a circuit board of the ECG device 110 and thus can be not removably securable like connector 105*a*.

The ECG device 110 can detect electrical signals responsive to the patient's cardiac activity and can transmit such signals, and/or physiological parameters responsive to such signals, to other patient monitoring systems and/or devices. The detected signals and/or physiological parameters can be transmitted to other patient monitoring systems and/or devices via wires or various wireless communication protocols. For example, as discussed above, the ECG device 110 can interact and/or be utilized along with devices/sensors 120, 130, 140, and/or 150.

The ECG device 110 can have the functional and/or computational capabilities to calculate physiological parameters (for example, heart rate, precise body temperature values, among others) using raw physiological data (for example, raw temperature data, raw ECG data responsive to patient cardiac activity, among others). In this regard, the ECG device 110 can transmit raw, unprocessed electrical signals or physiological data, and/or processed, calculated physiological parameters to other patient monitoring devices and/or systems, such as those discussed elsewhere herein (for example, the blood pressure monitor 120 and/or the patient monitor 130).

With reference to FIGS. 2A-2D, the ECG device 110 can include a disposable portion 203 (also referred to herein as "disposable device") and a reusable portion 205 (also referred to herein as "reusable device"). The disposable portion 203 can include a dock 204 (also referred to herein as a "base"), one or more external electrodes 112, and one or more cables 114. The one or more external electrodes 112 can be coupled to the dock 204 via the one or more cables 114. The coupling between the external electrodes 112 and the dock 204 is further described below.

The external electrodes 112 can detect electrical signals from the patient 111 responsive to the patient's cardiac activity. The electrodes 112 can be placed at various locations on the patient 111 including chest, head, arm, wrist, leg, ankle, and the like. The electrodes 112 can be coupled to one or more substrates that provide support and/or adhesion. For example, the electrodes 112 can include a substrate configured to removably secure the external electrodes 112 to the patient 111 (for example, skin of the patient) to allow for ease in repositioning the electrodes 112. The substrate can provide improved electrical conductivity between the external electrodes 112 and the patient 111. The substrate can be waterproof. The substrate can be a silicone adhesive, for example. Each of the externals electrodes 112 can include designs (such as a unique design) that can be used to provide instruction to a user or caregiver in placing and/or arranging the electrodes 112 on a patient's body, as discussed further below with reference to FIGS. 4A-4E.

Figure 2B:
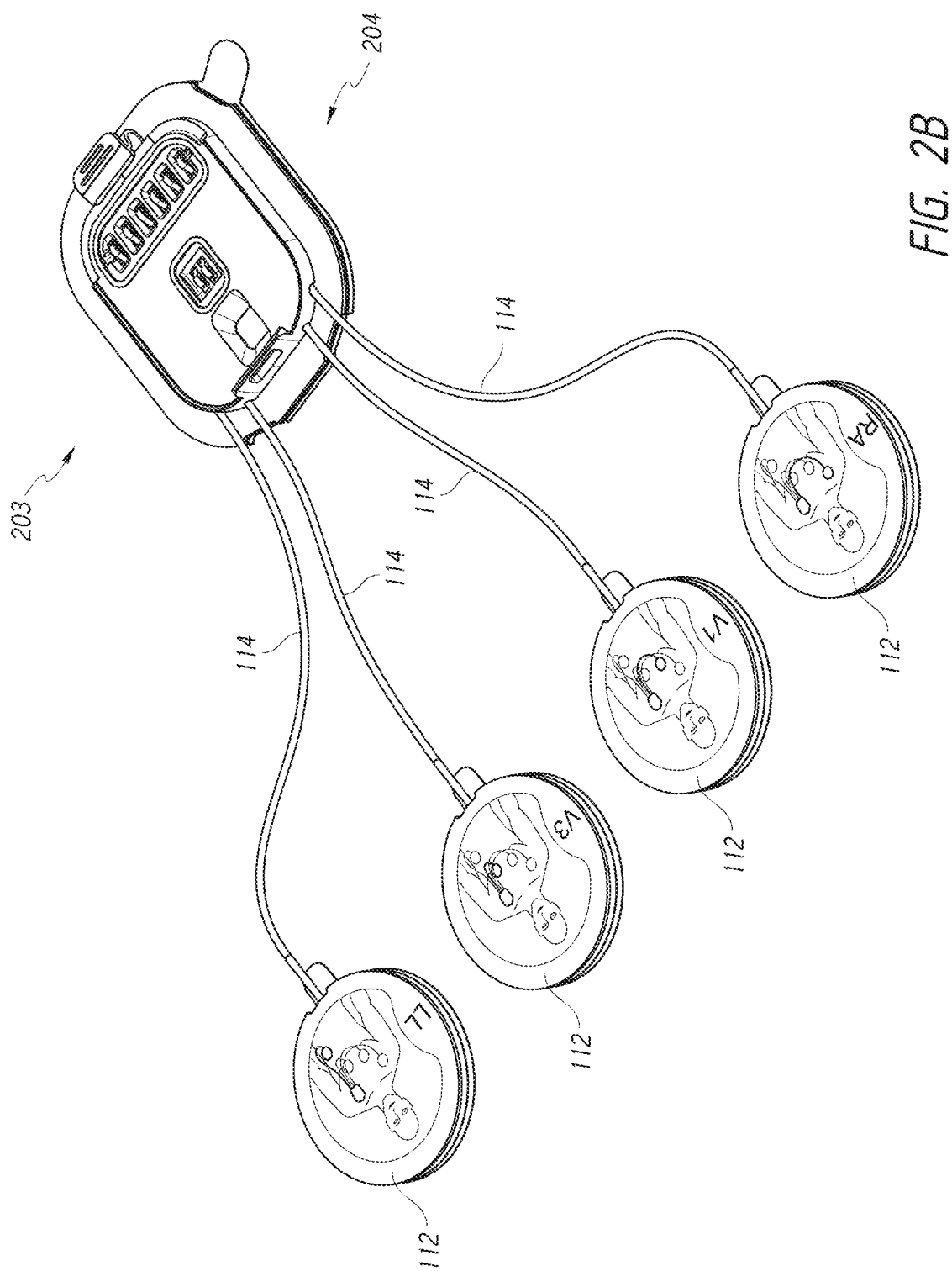
FIG. 2B illustrates a perspective view of a disposable portion of the ECG device of FIG. 2A.

The electrical signals collected by the electrodes 112 can be transmitted to the dock 204 via the cables 114. One end of the cable 114 can be coupled to the external electrode 112 while the other end of the cable 114 can be coupled to the dock 204. For example, the cables 114 can be soldered to the electrodes 112 and/or soldered to an electrical circuit of the dock 204 (such as the flexible circuit 225 as discussed below). The cables 114 can be flexible. The length of the cables 114 can be varied to provide flexibility to caregivers when placing the external electrodes 112 at various locations of the patient 111. The length of the cables 114 depicted in FIGS. 2A-2B is illustrative only is not intended to limit the scope of this disclosure.

Figure 2C:
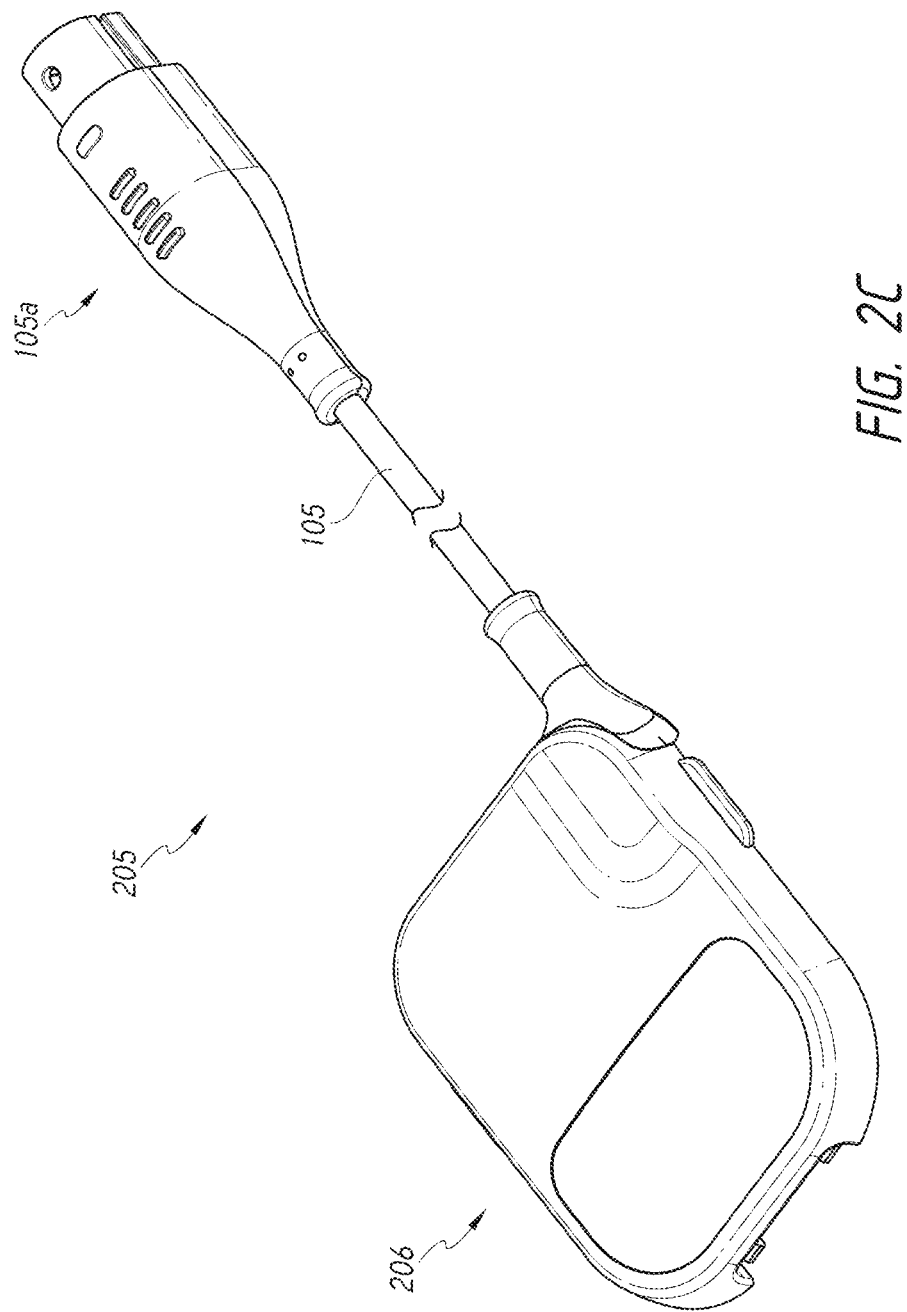
FIG. 2C illustrates a perspective view of a reusable portion of the ECG device of FIG. 2A.

FIG. 2C illustrates a perspective view of the reusable device 205. The reusable device 205 can include a hub 206 (also referred to herein as "cover"), a cable 105, and/or a connector 105a. The hub 206 can transmit electrical signals to other devices and/or systems, including multi-parameter patient monitoring systems (MPMS), via the cable 105 and the connector 105a. Additionally or alternatively, the hub 206 can wirelessly transmit electrical signals to other devices and/or systems. For example, the hub 206 can include a wireless transmitter or transceiver configured to wirelessly transmit electrical signals (for example, signals related to patient temperature and/or heart activities) using different types of wireless communication technology such as Bluetooth®, Wi-Fi, near-field communication (NFC), and the like. In some variants, the reusable device 205 does not include a cable or a connector.

The hub 206 can be of various shapes and/or sizes. For example, as shown in FIG. 2C, the hub 206 can be rectangular in shape and/or can have rounded edges and/or corners. The hub 206 can be shaped to mate with the dock 204. For example, the hub 206 can be sized and/or shaped to facilitate mechanical and/or electrical mating with the dock 204. Additional details regarding the mating of the hub 206 and the dock 204 are described further below.

Figure 2D:
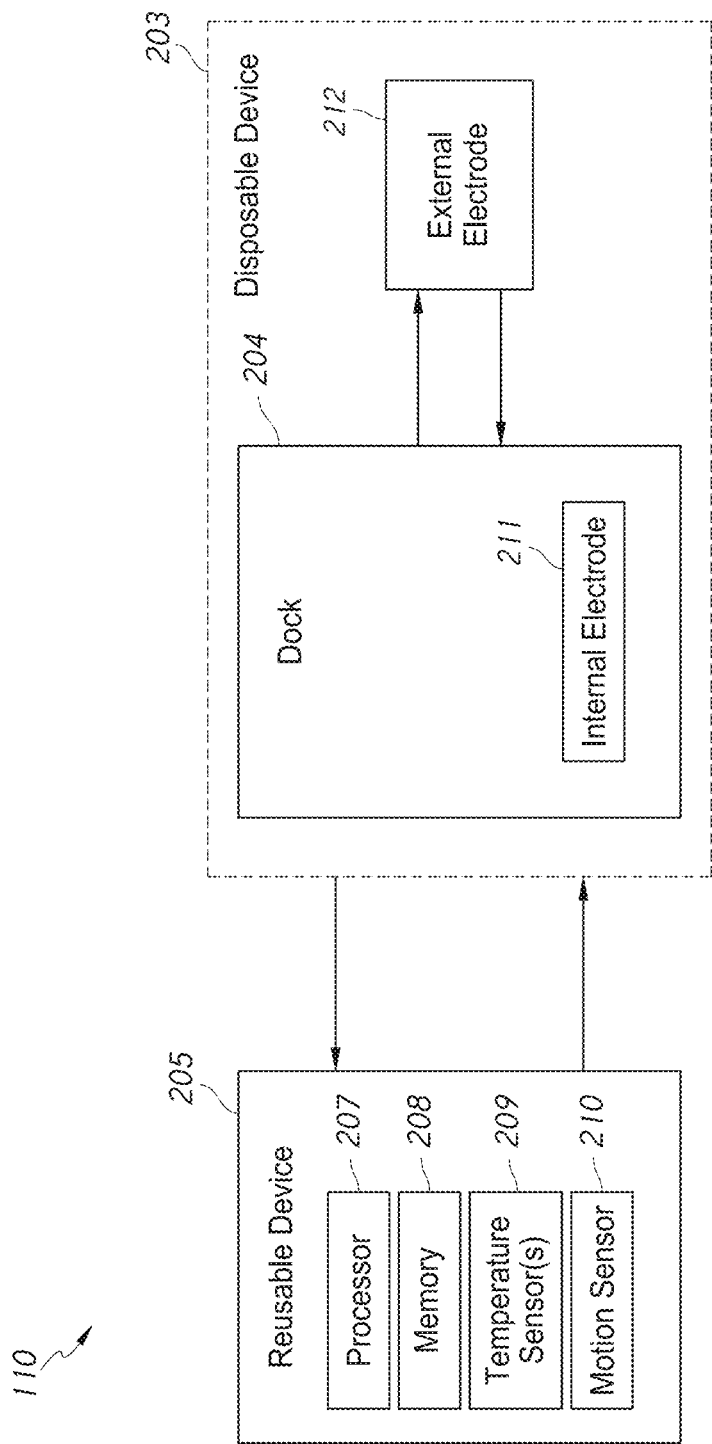
FIG. 2D illustrates a schematic diagram of the ECG device of FIG. 2A.

FIG. 2D illustrates a schematic diagram of the ECG device 110. As discussed above, the ECG device 110 can include the disposable device 203 and the reusable device 205. The disposable device 203 can include a dock 204 coupled to one or more external electrodes 112 that detect and transmit electrical signals from the patient 111 through the cables 114. The dock 204 can receive the electrical signals from the external electrodes 112 (for example, via flexible circuit 225) and transmit them to the reusable device 205. The external electrodes 112 can be placed at various locations relative to where the dock 204 is placed. For example, the dock 204 can be placed proximate, adjacent, and/or above the patient's heart and the external electrodes 112 can be placed at various locations on the patient's chest.

The external electrodes 112 can be color-coordinated and/or include graphics or visualizations that can advantageously aid a caregiver properly position and/or secure the electrodes 112 to portions of a patient's body so that accurate ECG data is collected. For example, with reference to FIGS. 2A-2B and 4D, the external electrodes 112 can include a label portion 112a that can indicate a name, number, or other identifier of a particular electrode 112, for example, with reference to another electrode or a plurality of other electrodes 112 (see "RA", "V1", "V3", "LL" in FIG. 4D). As also shown, the external electrodes 112 can include a placement indicator 112b which can indicate a proper positioning and/or placement of a particular electrode 112 with reference to another electrode 112, a plurality of other electrodes 112, and/or the dock 204 of the disposable portion 203 of the ECG device 110. For example, where the ECG device 110 includes four electrodes 112, each of the electrodes 112 can include a unique placement indicator 112b that graphically illustrates the proper placement of the particular electrode 112 with respect to each of the other electrodes 112, the cables 114, and/or the dock 204 of the disposable portion 203 on a user's body (for example, chest). As another example, where the ECG device 110 includes two electrodes 112, each of the electrodes 112 can include a unique placement indicator 112b that graphically illustrates the proper placement of the particular electrode 112 with respect to each of the other electrodes 112, the cables 114, and/or the dock 204 of the disposable portion 203 on a user's body (for example, chest). Portions of the unique placement indicators 112b can be color coordinated with actual colors of the cables 114 and/or the electrodes 112. In some variants, each unique placement indicator 112b includes a shape of the particular electrode and/or associated cable in a solid line and include shapes representing other electrodes and/or the dock in dotted line to enable differentiation. In some variants, the shapes of the particular electrode and/or the associated cable in each unique placement indicator 112b have a color that matches a color of an associated cable 114. While a body is illustrated on the electrodes 112, the design of the body is not limiting and can be sized and/or shaped in a variety of ways. Further, instead of a body, a square or other shape can be placed on the electrodes 112 and the placement indicators 112b can be shown therein.

With reference to FIGS. 2A-2B, the graphics on the electrodes 112 (as shown in the enlarged view of FIG. 4D) can be oriented in a certain orientation when coupled to the dock 204 with cables 214. For example, as shown, the unique label portion 112a, body, and/or unique placement indicator 112b for each electrode can be oriented to be "upside down" with respect to a view as shown in these figures. For example, the unique label portion 112a, body, and/or unique placement indicator 112b for each electrode can be oriented so that a lower portion of the body is closer to the dock 204 that an upper portion of the body (e.g., head) and/or so that the unique label portion 112a are "upside down" when a viewer is viewing the disposable portion 203 in a direction from the electrodes 112 towards the dock 204 (see FIG. 2B). Such orientation and/or configuration can be advantageous where the disposable portion 203 is secured to the packaging device 400 described below. For example, such orientation and/or configuration can allow a user (e.g., a caregiver) to conveniently visualize proper positioning and/or order of securing the electrodes 112 and/or the dock 204 to a patient's body when removing the electrodes 112 and/or the dock 204 from the packaging device 400 (see FIG. 4B).

The disposable device 203 can include one or more external electrodes 112. For example, the disposable device 203 can include one, two, three, four, five, six, seven, or eight or more external electrodes 112. As another example, as illustrated by FIGS. 2A-2B, the disposable device 203 can include four external electrodes 112. As another example, the disposable device 203 can include two external electrodes 112.

The dock 204 of the disposable device 203 can include one or more internal electrodes 211. For example, the dock 204 can include one, two, three, four, five, six, seven, or eight or more internal electrodes 211. For example, as illustrated in FIGS. 2F-2G, the dock 204 can include two internal electrodes 211. As another example, the dock 204 can include one internal electrode 211. In some cases, one of the internal electrodes 211 is configured to be a ground or reference electrode.

The total number of electrodes (including both external and internal electrodes) can be two, three, four, five, six, seven, eight, nine, ten, eleven, or twelve or more electrodes. For example, the disposable device 203 can include four external electrodes 112, four cables 114, and two internal electrodes 211. In another example, the disposable device 203 can include two external electrodes 112, two cables 114, and two internal electrodes 211. In another example, the disposable device 203 can include two external electrodes 112, two cables 114, and one internal electrode 211. In yet another example, the disposable device 203 can include four external electrodes 112, four cables 114, and no internal electrode 211. In yet another example, the disposable device 203 can include one external electrode 112, one cable 114, and one internal electrode 211. In another example, the disposable device 203 can include two external electrodes 112, two cables 114, and no internal electrodes 211. The number of external electrodes 112 coupled to the dock 204 of the disposable device 203 and the number of internal electrodes 211 housed within the dock 204 can be varied in various examples of disposable device 203 of the ECG device 110.

As mentioned above, FIG. 2D illustrates a schematic representation of the ECG device 110. As shown, the reusable device 205 can include a processor 207, a memory 208, one or more temperature sensors 209, and/or a motion sensor 210. The memory 208 can be a programmable read-only memory (PROM), an erasable programmable read-only memory (EPROM), an electrically erasable programmable read-only memory (EEPROM), a static random access memory (SRAM), or a dynamic random access memory (DRAM), and the like. The memory 208 can store various types of physiological data (raw and/or processed) related to the patient 111. For example, the memory 208 can store raw and/or processed physiological data related to patient temperature and electrical activity of the heart. The data related to the electrical activity of the heart can represent rhythm and/or activity of the heart. As discussed further below, the memory 208 can be utilized in combination with a memory on the disposable device 203 to enable, among other things, verification of whether the disposable device 203 is an authorized product. For example, the disposable device 203 can include a PROM, EPROM, EEPROM, SRAM, and/or DRAM that can be read by the reusable portion 205 to enable the reusable portion 205 to verify whether the disposable device 203 is an authorized product.

As discussed above, the reusable device 205 can include a motion sensor 210. The motion sensor 210 can measure static (for example, gravitational force) and/or dynamic acceleration forces (for example, forces caused by movement or vibration of the motion sensor 210). By measuring one or both of static and dynamic acceleration forces, the motion sensor 210 can be used to calculate movement or relative position of the ECG device 110. The motion sensor 210 can be an AC-response accelerometer (for example, charge mode piezoelectric accelerometer, voltage mode piezoelectric accelerometer), a DC-response accelerometer (for example, capacitive accelerometer, piezoresistive accelerometer), a microelectromechanical system (MEMS) gyroscope, a hemispherical resonator gyroscope (HRG), vibrating structure gyroscope (VSG), a dynamically tuned gyroscope (DTG), fiber optic gyroscope, and the like. The motion sensor 210 can measure acceleration forces in one-dimension, two-dimensions, or three-dimensions. With calculated position and movement data, care providers may be able to map the positions or movement vectors of the ECG device 110. Any number of motion sensors 210 can be used collect sufficient data to determine position and/or movement of the ECG device 110.

The motion sensor 210 can be and/or include a three-dimensional (3D) accelerometer. The motion sensor 210 can be and/or include an accelerometer similar or identical to those discussed in U.S. application Ser. No. 15/253,536, filed Aug. 31, 2016, titled "Patient-Worn Wireless Physiological Sensor," now U.S. Pat. No. 10,226,187, the disclosure of which is hereby incorporated by reference in its entirety. The term 3D accelerometer as used herein includes its broad meaning known to a skilled artisan. Measurements from the accelerometer can be used to determine a patient's orientation. The accelerometer can measure and output signals related to a linear acceleration of the patient with respect to gravity along three axes (for example, three, mutually orthogonal axes). For example, one axis, referred to as "roll," can correspond to the longitudinal axis of and/or extending through the patient's body (for example, along a length and/or height of the patient). Accordingly, the roll reference measurement can be used to determine whether the patient is in the prone position (for example, face down), the supine position (for example, face up), or on a side. Another reference axis of the accelerometer is referred to as "pitch." The pitch axis can correspond to the locations about the patient's hip (for example, an axis extending between and/or through the patient's hips). The pitch measurement can be used to determine whether the patient is sitting up or lying down. A third reference axis of the accelerometer is referred to as "yaw." The yaw axis can correspond to a horizontal plane in which the patient is located. When in bed, the patient can be supported by a surface structure that generally fixes the patient's orientation with respect to the yaw axis. Thus, in certain embodiments, the yaw measurement is not used to determine the patient's orientation when in a bed. The three axes that the accelerometer can measure linear acceleration with respect to can be referred to as the "X," "Y," and "Z" axes. The accelerometer can provide acceleration information along three axes, and it can provide acceleration information which is the equivalent of inertial acceleration minus local gravitational acceleration. In some embodiments, the accelerometer may be a tri-axial accelerometer, and the output of the accelerometer may include three signals, each of which represents measured acceleration along a particular axis. The output of the accelerometer can be 8-bit, 12-bit, or any other appropriate-sized output signal. The outputs of the accelerometer may be in analog or digital form. The accelerometer can be used to determine the position, orientation, and/or motion of the patient to which the ECG device 110 is attached.

The motion sensor 210 can additionally or alternatively be and/or include a gyroscope. The motion sensor 210 can be and/or include a gyroscope similar or identical to those discussed in U.S. application Ser. No. 15/253,536, filed Aug. 31, 2016, titled "Patient-Worn Wireless Physiological Sensor," now U.S. Pat. No. 10,226,187, the disclosure of which is hereby incorporated by reference in its entirety. The gyroscope can be a three-axis digital gyroscope with angle resolution of two degrees and with a sensor drift adjustment capability of one degree. The term three-axis gyroscope as used herein includes its broad meaning known to a skilled artisan. The gyroscope can provide outputs responsive to sensed angular velocity of the ECG device 110 or portions thereof (for example, the dock 204) when attached to the patient with respect to three orthogonal axes corresponding to measurements of pitch, yaw, and roll (for example, see description provided above). A skilled artisan will appreciate that numerous other gyroscopes can be used in the ECG device 110 without departing from the scope of the present disclosure. In certain embodiments, the accelerometer and gyroscope can be integrated into a single hardware component which may be referred to as an inertial measurement unit (IMU). In some embodiments, the IMU can also include an embedded processor that handles, among other things, signal sampling, buffering, sensor calibration, and sensor fusion processing of the sensed inertial data. In other embodiments, the processor can perform these functions. And in still other embodiments, the sensed inertial data are minimally processed by the components of the ECG device 110 and transmitted to an external system, such as the patient monitor 130, for further processing, thereby minimizing the complexity, power consumption, and cost of the ECG device 110, which may be or contain a disposable components as discussed elsewhere herein.

Incorporating the motion sensor 210 in the ECG device 120 can provide a number of benefits. For example, the ECG device 110 can be configured such that, when the motion sensor 210 detects motion of the patient above a threshold value, the ECG device 110 stops collecting and/or transmitting physiological data. As another example, when the motion sensor 210 detects motion of the patient above a threshold value, the ECG device 110 stops collecting, processing, and/or transmitting physiological data responsive to the patient's cardiac activity and/or temperature data of the patient. As another example, when the motion sensor 210 detects acceleration and/or angular velocity of the patient above a threshold value, the ECG device 110 stops collecting, processing, and/or transmitting physiological data responsive to the patient's cardiac activity and/or temperature data of the patient. This can advantageously reduce or prevent noise, inaccurate, and/or misrepresentative physiological data from being processed, transmitted, and/or relied upon (for example, by caregivers assessing the patient's wellness).

As discussed above, the reusable device 205 can include one or more temperature sensors 209. For example, the reusable device 205 can include one, two, three, four, five, or six or more temperature sensors 209. The temperature sensor(s) 209 can measure temperature of the patient 111 at and/or proximate to a location where the ECG device 110 is placed. The temperature sensor(s) 209 can measure temperature of the skin of the patient 111. Additionally or alternatively, the temperature sensor(s) 209 can measure ambient temperature, for example, temperatures outside the reusable device 205 and/or temperatures inside the reusable device 205 (such as at or near a circuit board of the reusable device 205). The temperature data collected from the patient 111 by the temperature sensor(s) 209 may be used to determine a core body temperature of the patient 111. The temperature sensor(s) 209 can be in electronic communication with the processor 207 and can transmit the temperature data to the processor 207. In one example, temperature sensor(s) 209 can be an infrared temperature sensor. Placement and/or arrangement of the temperature sensor(s) 209 within the reusable device 205 and/or with respect to the disposable device 203 can be varied to facilitate thermal communication between a user's skin and the temperature sensor(s) 209, as discussed further below.

The processor 207 can receive raw temperature data from the temperature sensor(s) 209. Additionally, the processor 207 can receive raw ECG data from the disposable device 203. For example, the processor 207 can receive raw ECG data from the disposable device 203 via contact between one or more electrical connectors of the reusable portion 205 and one or more electrical connectors of the disposable portion 203. As another example, the processor 207 can receive raw ECG data from the disposable device 203 via electrical contact between conductive strips 244 of the flexible circuit 225 of the disposable device 203 and conductor pins 253 of the reusable device 205. After receiving the raw ECG and temperature data, the processor 207 can perform data processing to calculate physiological parameters corresponding to temperature and/or ECG. The physiological parameters can be stored in the memory 208 or transmitted to different sensor systems, patient monitoring systems, and the like. For example, the physiological parameters can be transmitted to the blood pressure monitor 120 and/or the patient monitor 130. The data stored in the memory 208 can be stored for a predetermined length of time and transmitted to different sensor systems or patient monitoring systems or devices when the ECG device 110 is connected (via a wire or wirelessly) to such other systems or devices. Optionally, the raw temperature data and the raw ECG data can be stored in the memory 208 prior to data processing by the processor 207. The processor 207 can retrieve raw temperature and/or ECG data periodically to process and/or transmit the raw data in batches. Alternatively, the processor 207 can automatically retrieve (for example, continuously) the raw data from the memory 208 as the memory 208 receives the raw ECG and temperature data.

Figure 2E:
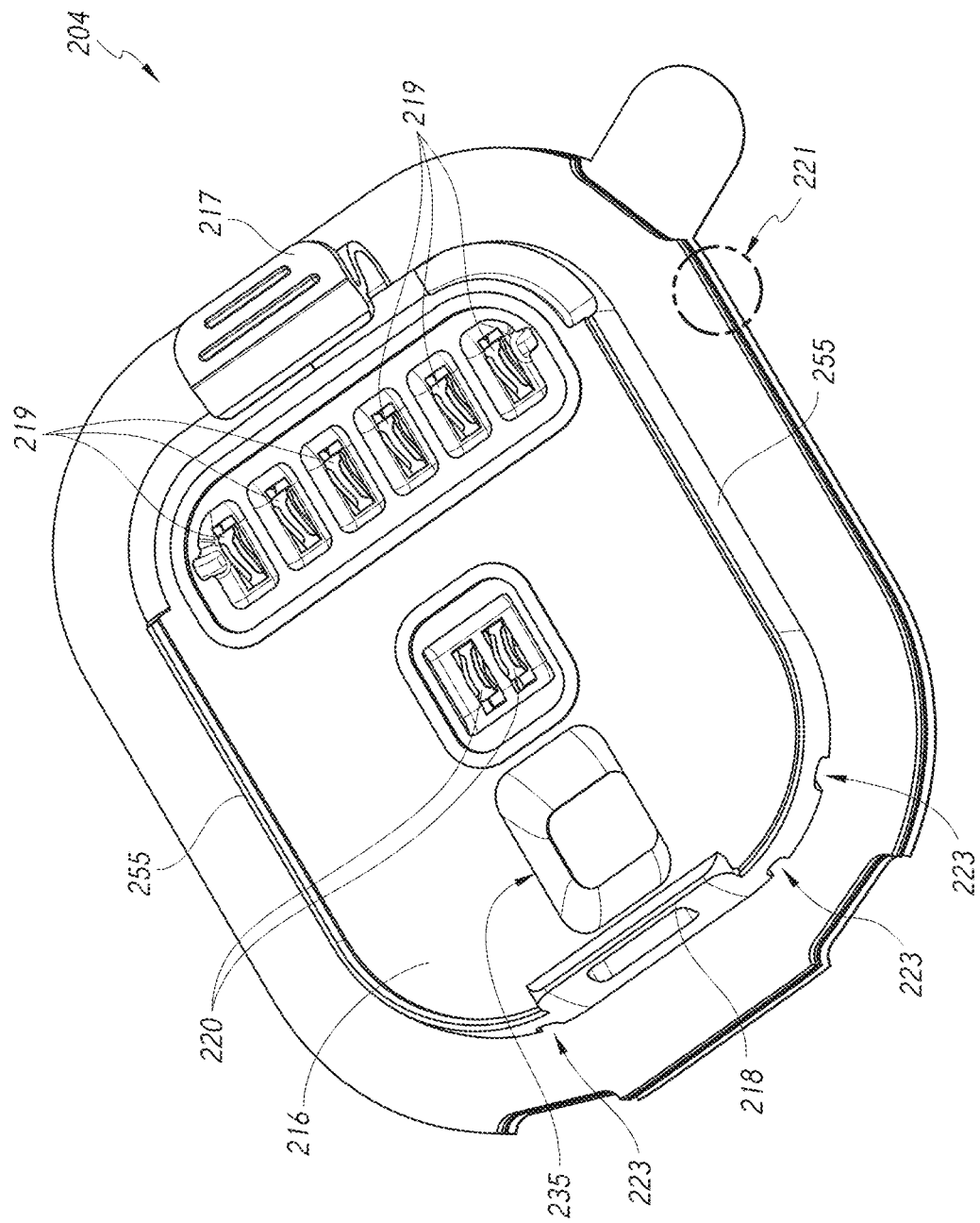
FIG. 2E illustrates a dock of the disposable portion of the ECG device shown in FIG. 2B.
Figure 2F:
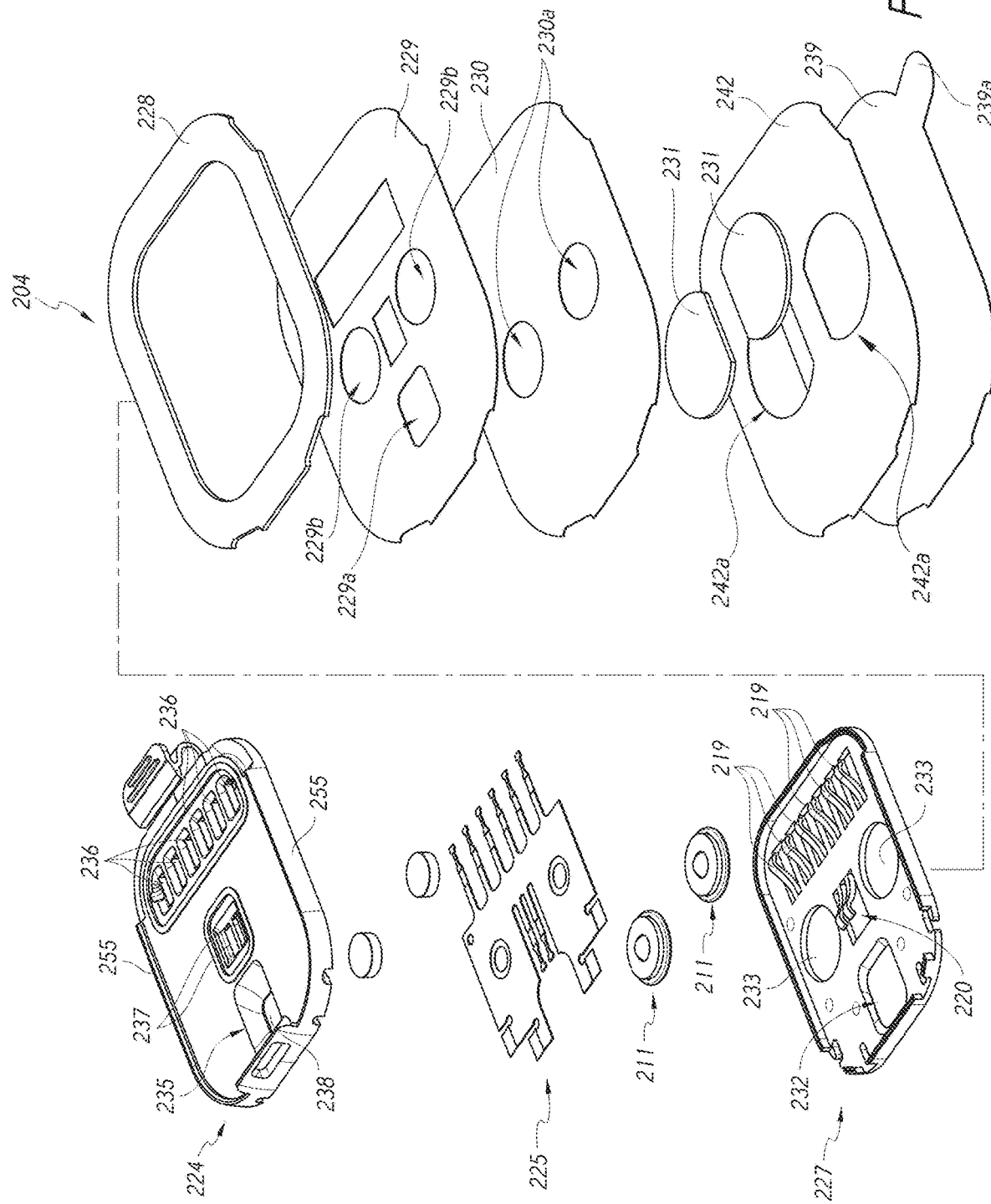
FIG. 2F illustrates an exploded, top perspective view of the dock of FIG. 2E.
Figure 21:
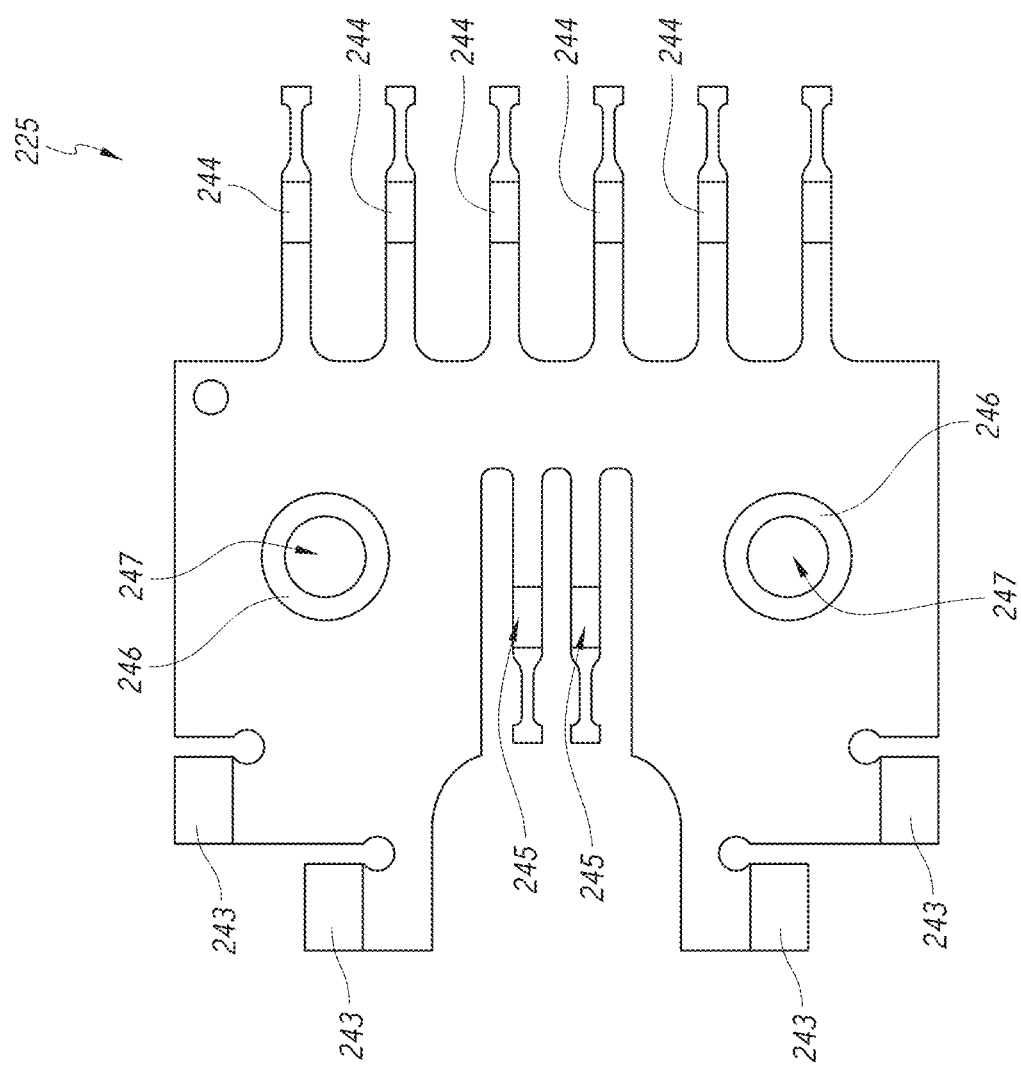
Figure 20:
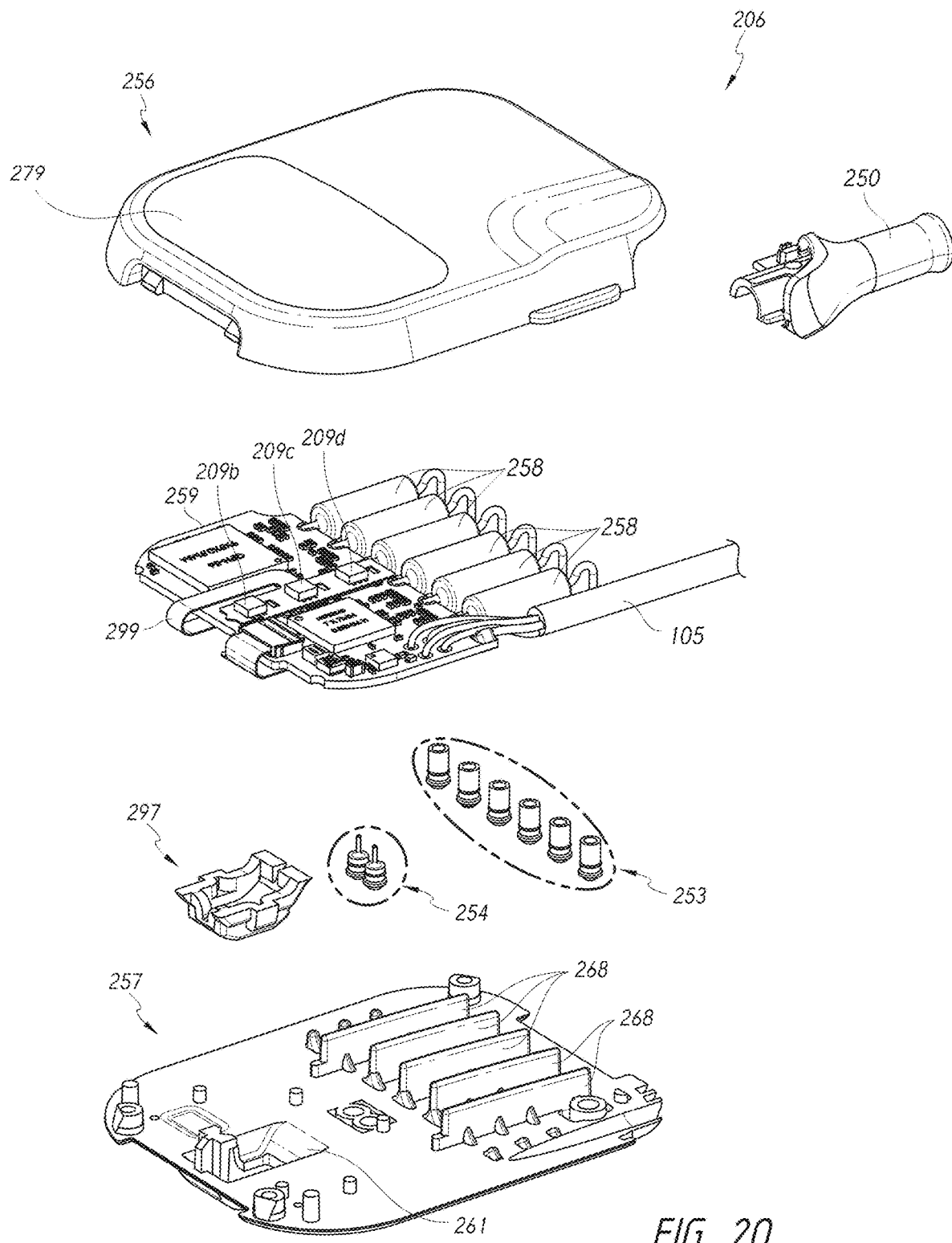

FIG. 2E illustrates a top, perspective view of the dock 204 of the disposable device 203. The dock 204 (also referred to herein as "base") can include a main body 216 and a laminate structure 221. The main body 216 can include one or more pin supports 219, one or more pin supports 220, a wall 255 extending along and/or around an exterior and/or perimeter of the main body 216, and openings 223 in the wall 255. The wall 255 can extend along and/or around a portion of the main body 216 and/or can have a height which varies along the length of the wall 255.

The dock 204 of the disposable portion 203 can include one or more mechanical connector portions configured to secure (for example, removably secure) to one or more mechanical connector portions of the hub 206 of the reusable portion 205. For example, the main body 216 can include one or both of mechanical connector portions 217 and 218. The mechanical connector portion 217 can be, for example, a clip 217 that can be configured to bend and/or flex. As discussed further below, the clip 217 can include a protrusions 240 that can extend in a direction towards the mechanical connector portion 218 (FIG. 2H). The mechanical connector portion 218 can extend outward from a portion of the main body 216. For example, the mechanical connector portion 218 can extend above a height of the wall 255. The mechanical connector portion 218 can include one or more protrusions 241 that can extend in a direction towards the mechanical connector portion 217 (FIG. 2H). The mechanical connector portions 217, 218 can assist coupling between the dock 204 and the hub 206. For example, the mechanical connector portions 217, 218 can engage corresponding mechanical connector portions of the hub 206 to hold the hub 206 in place. For example, as discussed below, the mechanical connector portions 217, 218 can removably secure within grooves 251, 252 of the hub 206. The interaction of the mechanical connector portions 217, 218 and corresponding mechanical connector portions of the hub 206 can advantageously maintain electrical communication between the dock 204 and the hub 206. The dock 204 of the disposable portion 203 can include one, two, three, or four or more mechanical connector portions and/or the hub 206 can include one, two, three, or four or more mechanical connector portions.

The mechanical connector portions 217, 218 may extend upward from outer edges of the main body 216 and/or adjacent or proximate the wall 255 as shown in FIG. 2E. The mechanical connector portions 217, 218 can be positioned opposite from each other (FIGS. 2E and 2H). In some variants, the dock 204 includes less than two mechanical connector portions or more than two mechanical connector portions. For example, in some variants, the dock 204 includes only one of mechanical connector portions 217, 218.

The pin supports 219, 220 of the dock 204 of the disposable portion 203 can support and/or operably position a plurality of electrical connectors of the disposable portion 203. For example, the pin supports 219, 220 can support and/or operably position conductive strips 245, 244 of the flexible circuit 225 of the dock 204. The dock 204 can include one, two, three, four, five, six, seven, eight, nine, or ten or more of pin supports 219 and/or 220. The pin supports 219, 220 can extend through openings or slits formed on a top surface of the main body 216. For example, as discussed below, the main body 216 can include a top frame 224 having one or more slits 236 and a bottom frame 227 which can include the one or more pin supports 219, 220. The one or more pins supports 219, 220 can extend from the bottom frame 227 and through the slits 236, 237 of the top frame 224 when the main body 216 is assembled. The slits 236, 237 formed on the top surface of the main body 216 can be rectangular or substantially rectangular in shape. The pin supports 219, 220 can be arcuate and/or can include an upward portion, an apex, and a downward portion. The upward portions of the pin supports 219, 220 can extend upward with respect to and/or beyond the top surface of the main body 216 (for example, a top surface of the top frame 224 and/or bottom frame 227) at a predetermined angle. The upper portions of the pin supports 219, 220 can terminate at the apex, from which the downward portions of the pin supports 219, 220 can extend downward towards the top surface of the main body 216 at another predetermined angle. Such configuration of the pin supports 219, 220 can allow them to function like springs when downward force is applied to the pin supports 219, 220. Optionally, the pin supports 219, 220 may not have the downward portions. The pin supports 219, 220 can be flexible and/or resilient.

The pin supports 219 can correspond and/or be associated with electrical connectors of the disposable portion 203. For example, the pin supports 219 can correspond and/or be associated with conductive strips 244 of the flexible circuit 225 (see FIGS. 2F and 2I) that carry electrical signals associated with the one or more external electrodes 112 and/or the one or more internal electrodes 211. For example, as shown in FIG. 2E, the dock 204 can have six pin supports 219 that operably position and/or support six conductive strips 244 of the flexible circuit 225 which can carry electrical signals from four external electrodes 112 (via cables 114) and two internal electrodes 211.

Similar to the pin supports 219, the pin supports 220 can correspond and/or be associated with electrical connectors of the disposable portion 203. For example, the pin supports 220 can correspond and/or be associated with conductive strips 245 of the flexible circuit 225 (see FIGS. 2F and 2I) that allow transmission of electrical signals and/or information between the dock 204 and the memory 208 of the hub 206. The flexible circuit 225 can comprise and/or be coupled to a memory (such as an PROM, EPROM, EEPROM, SRAM, and/or DRAM memory) of the disposable portion 203 configured to store information related to the disposable portion 203. The conductive strips 245 of the flexible circuit 225 can be coupled to such memory. Advantageously, the pin supports 220 can support and/or operably position the conductive strips 245 so that they contact conductor pins of the hub 206 (such as conductive pins 254), which can enable the hub 206 to determine whether the dock 204 is an authorized product.

As discussed above, the dock 204 can include one or more openings 223 in portions of the main body 216 that are configured to allow portions of the cables 114 to pass into an interior of the dock 204. For example, as discussed above, the main body 216 can include one or more openings 223 in the wall 255. The dock 204 can include one, two, three, four, five, six, seven, or eight or more openings 223. The openings 223 can be sized and/or shaped to receive portions of the cables 114 coupled to the external electrodes 112. The openings 223 can be formed on a side of the main body 216. For example, as shown in FIG. 2E, the openings 223 can be formed on a front side (or "end") of the main body 216. Alternatively, the openings 223 can be formed on different sides or portions of the main body 216. The number of the openings 223 can correspond to the number of external electrodes 112 coupled to the dock 204 and/or number of cables 114. For example, as shown in FIG. 2B, the dock 204 of the disposable device 203 can include four external electrodes 112. In this regard, the dock 204 can include four openings 223 configured to receive four cables 114 coupled to the four external electrodes 112. While FIG. 2E illustrates four openings 223, four cables 114, and four external electrodes 112, a different number of electrodes 112, openings 223 and/or cables 114 can be implemented as part of the disposable portion 203. The openings 223 can be dimensioned to create a tight fit with the cables 114. Such configuration can be advantageous in allowing the dock 204 to be water-resistant and/or waterproof. Such configuration can also help maintain integrity of connections between the cables 114 and the openings 223. For example, a tight fit between the openings 223 and portions of the cables 114 can reduce the likelihood that ends of the cables 114 connected to the flexible circuit 225 (for example, to conductive strips 243) are disconnected when opposite ends of the cables 114 are pulled, either inadvertently or intentionally.

FIGS. 2F and 2G show exploded perspective views of the dock 204 of the disposable portion 203. The dock 204 can include a top frame 224, the flexible circuit 225, one or more internal electrodes 211, a bottom frame 227, and one or more of substrates (also referred to herein as "membranes") 228, 229, 230, 231, 242, and/or 239 each of which are described further below. Advantageously, the parts illustrated in the FIGS. 2F and 2G may be laid on top of each other without folding, resulting in an increased efficiency of manufacturing process of the ECG device 110. The top and bottom frames 224, 227 can together form and/or define the main body 216, which is discussed above with reference to FIG. 2E. Further, the top frame 223 can include the wall 255 discussed above.

The top frame 224 can be coupled to the bottom frame 227 such that the top frame 224 sits on top of the bottom frame 227. The top frame 224 can include a recessed portion 235 formed from a top surface of the top frame 224. The recessed portion 235 can include an aperture 238 (see FIGS. 2F-2G) that is formed at a bottom of the recessed portion 235.

The bottom frame 227 can include an aperture 232 and one or more apertures 233. The aperture 232 of the bottom frame 227 can correspond and/or align with the recessed portion 235 of the top frame 224 such that when the top frame 224 is placed on the bottom frame 227, the aperture 232 receives the recessed portion 235 and the recessed portion 235 extends through and/or below the aperture 232. As discussed below, this can advantageously allow a portion of the reusable device 205 and the temperature sensor 209a to be positioned closer to the substrate 230, which can in turn increase thermal communication between a user's skin and the temperature sensor 209a.

As discussed above, the dock 204 can include the pin supports 219, 220. As shown in FIG. 2F, the pin supports 219, 220 can be formed on the bottom frame 227. The top frame 224 can include slits 236, 237 that can receive the pin supports 219, 220 of the bottom frame 227, respectively. When the top frame 224 is placed on the bottom frame 227, the pin supports 219, 220 can extend through and/or above the slits 236, 237 of the top frame 224.

The flexible circuit 225 can be placed and/or positioned between the top frame 224 and the bottom frame 227 (see FIGS. 2F-2G). For example, the flexible circuit 225 can be sandwiched between the top and bottom frames 224, 227 during assembly. The bottom frame 227 can operably position the flexible circuit 225 and/or portions thereof such that electrical communication between the flexible circuit 225 and a circuit board and/or flexible circuit of the reusable portion 205 is facilitated when the reusable portion 205 is secured to the disposable portion 203. For example, the pin supports 219 of the bottom frame 227 can operably position conductive strips 244 of the flexible circuit 225 so that the conductive strips 244 contact conductor pins 253 of the reusable portion 205 when the reusable and disposable portions 203, 205 are mated. Additionally or alternatively, the pin supports 220 of the bottom frame 227 can operably position conductive strips 245 of the flexible circuit 225 such that the conductive strips 245 contact conductor pins 254 of the reusable portion 205 when the reusable and disposable portions 203, 205 are mated. Such contact can advantageously allow the flexible circuit 225 to transmit information and/or physiological data from the disposable device 203 to the reusable device 205. Additional details of the flexible circuit 225 are provided below.

With reference to FIG. 2F, the internal electrodes 211 can be placed and/or positioned at least partially between the top frame 224 and the bottom frame 227. The internal electrodes 211 can be removably coupled to the flexible circuit 225. The internal electrodes 211 can be placed within the apertures 233 and the apertures 233 can be dimensioned to receive the internal electrodes 211 (and/or portions thereof).

As discussed above, the dock 204 (also referred to herein as "base") of the disposable portion 203 can include a laminate structure 221. For example, the dock 204 can include one or more of substrates 228, 229, 230, 231, 242, and/or 239. Substrate 228 can comprise foam and can be configured to surround the top and/or bottom frames 224, 227 when the dock 204 is assembled. Substrate 228 can include an opening sized and/or shaped to match a size and/or shape of a perimeter of the top and/or bottom frames 224, 227 (see FIGS. 2F-2G).

Substrate 229 can comprise an adhesive material configured to secure the substrate 228 and/or the bottom frame 227 to the substrate 230 and/or substrate 231. Substrate 229 can be, for example, a double sided adhesive layer. Substrate 229 can include one or more of openings 229a, 229b. Opening 229a can be sized and/or shaped to allow the recessed portion 235 and/or the housing 297 to contact a portion of the substrate 230 when the dock 204 is assembled and the hub 206 is mated with the dock 204. Openings 229b can be sized and/or shaped to allow the internal electrodes 211 to contact substrates 231, which are discussed further below.

Substrate 230 can be secured (for example, adhered) to substrate 229 as discussed above. As shown, substrate 230 can include apertures 230a sized and/or shaped to correspond to a size and/or shape of the internal electrodes 211. The number of apertures 230a can correspond to the number of internal electrodes 211. The apertures 230a can be dimensioned to receive the one or more internal electrodes 211. As discussed above, the opening 229a of substrate 229 can be sized and/or shaped to allow the recessed portion 235 and/or the housing 297 to contact a portion of the substrate 230 when the dock 204 is assembled and the hub 206 is mated with the dock 204. Advantageously, substrate 230 can comprise a thermally conductive material configured to provide thermal communication between the patient's skin and the housing 297. As also discussed above, the housing 297 can comprise a thermally conductive material and can house the temperature sensor 209a. Substrate 230 can comprise an electrically isolative material which can advantageously minimize or eliminate electrical interference between the patient's skin and portions of the dock 204 in areas other than the apertures 234. Substrate 230 can be, for example, a polyethylene (PE) film.

The dock 204 can include one or more substrates that provide increased electrical conductivity between the patient's skin and the internal electrodes 211. For example, the dock 204 can include one or more substrates 231, the number of which can correspond with the number of internal electrodes 211. The substrates 231 can be adhered to substrate 230 (for example, a bottom side of the substrate 230). The substrates 231 can be adhered adjacent, proximate, and/or under the apertures 230a of substrate 230 such that bottom portions of the internal electrodes 211 contact and/or secure to the substrates 231. For example, the substrates 231 can be sized and/or shaped to cover the apertures 230a when secured to the substrate 230. The substrates 231 can comprise an adhesive material. The substrates 231 can comprise an electrically conductive material. The substrates 231 can comprise, for example, hydrogel. The substrates 231 can be hydrogel patches. The substrates 231 can have a smaller area than any or all of the other substrates 228, 229, 230, 242, and/or 239.

Substrate 242 can be a bottommost layer of the dock 204 configured to contact skin of a user when the dock 204 is secured to the user. Substrate 242 can comprise a material configured to secure to skin of a user. For example, substrate 242 can comprise a material configured to allow for removable securement of the dock 204 to the user's skin. Additionally or alternatively, substrate 242 can be waterproof. Substrate 242 can comprise a silicone adhesive, for example. Substrate 242 can comprise a silicone adhesive coupled with a polyurethane layer. As shown, substrate 242 can include one or more openings 242a aligned with the one or more substrates 231. The one or more openings 242a can be sized and/or shaped to receive (for example, at least partially receive) the one or more substrates 231. Advantageously, the openings 242a are spaced from each other, and as such, can separate the substrates 231. Such separation between substrate 231 is important so that the two internal electrodes 211 (where both are included) are electrically isolated from each other and/or so that the two substrates 231 make independent electrical contact with the patient's skin. When the dock 204 is assembled and secured to the user's skin, the one or more openings 242a can be positioned with respect to the one or more substrates 231 such that the substrates 231 and portions of the substrate 242a around the one or more openings 242a contact and/or secure to the skin.

Substrate 239 can be a release liner configured to secure to one or more of the above-described substrates and further configured to be removed prior to securement of the dock 204 to a user. Substrate 239 can cover substrates 242 and/or 231. As shown in FIGS. 2F-2G, substrate 239 can include a tab 239a configured to assist in removing the substrate 239 from one or more of the above-described substrates.

FIG. 2H illustrates a side view of the dock 204 of the disposable portion 203. As discussed above, the dock 204 can include one or both of mechanical connector portions 217, 218 which can secure to mechanical connector portions of the hub 206. The mechanical connector portions 217, 218 can include protrusions 240, 241, respectively. The protrusions 240, 241 can be positioned at free (for example, cantilevered) ends of the mechanical connector portions 217, 218, such as ends opposite to ends connected to portions of dock 204 (such as the main body 216). The protrusions 240, 241 can engage protrusions 251a, 252a within grooves 251, 252 of the hub 206 (see FIGS. 2J-2K) to removably secure the hub 206 to the dock 204. When the hub 206 is mated with the dock 204, the hub 206 can be positioned at least partially between the mechanical connector portions 217, 218. The engagement between the protrusions 240, 241 and the protrusions 251a, 252a within the grooves 251, 252 can prevent movement of the hub 206 in horizontal and/or vertical directions while mated with the dock 204.

With reference to FIGS. 2H and 2J-2K, the hub 206 can include two protrusions 252a spaced from one another within the groove 252. The protrusions 252a can be tapered (FIG. 2J). The hub 206 can include a protrusion 251a which extends across a width of the groove 252. The mechanical connector portion 217 can be a clip that is flexible. The mechanical connector portion 217 can have a non-straight cross section (FIG. 2H). For example, mechanical connector portion 217 can have an S-shape. As another example, mechanical connector portion 217 can curve in multiple directions from a first end to a second end. Such configuration can advantageously allow the mechanical connector portion 217 to bend without breaking, especially where the mechanical connector portion 217 is made of a rigid plastic material. The mechanical connector portion 217 can have one or more ribs 217a on a top plate thereof, which can aid a user in moving (for example, flexing) the mechanical connector portion 217 to disconnect a portion of the hub 206 from the dock 204.

FIG. 2I illustrates a top view of the flexible circuit 225. The flexible circuit 225 can include numerous conductive surfaces and/or strips. For example, the flexible circuit 225 can include conductor strips 243, 244, 245, and/or 246. The conductor strips 243 can electrically connect to the cables 114 which cane themselves be electrically connected to the external electrodes 112. In this regard, the conductor strips 243 can receive electrical signals from the external electrodes 112 via the cables 114. The cables 114 can be soldered to the corresponding conductive strips 243. The conductor strips 246 (also referred to herein as "conductive rings") can be formed around and/or within apertures 247, as shown in FIG. 2I. The conductive rings 246 can create contact with and receive electrical signals from the internal electrodes 211. The apertures 247 can receive a top portion of the internal electrodes 211, creating contact between the conductor strips 246 and the internal electrodes 211 which allows the flexible circuit 225 to receive ECG data from the internal electrodes 211.

The conductor strips 245 can establish electrical communication between the dock 204 and the memory 208 of the reusable device 205. The conductor strips 245 of the flexible circuit 225 can be positioned adjacent to (for example, on top of) the pin supports 220. The pin supports 220 supporting the conductor strips 245 can be oriented such that when the hub 206 is mated with the dock 204, conductor pins 254 (see FIG. 2L-2M) of the hub 206 contact the conductor strips 245. The memory 208 of the reusable device 205 can be coupled to the conductor pins 254 such that contact between the conductor strips 245 and the conductor pins 254 allow electrical signals and/or information to be transmitted from the disposable device 203 to the memory 208 of the reusable device 205. Advantageously, the conductive strips 245 can be utilized to enable verification of whether the disposable portion 203 is an authorized product. For example, when the reusable portion 205 is electronically and/or mechanically mated to the disposable portion 203 such that contact is made between the conductive strips 245 and the conductor pins 254, the reusable portion 205 can determine whether the disposable portion 203 is an authorized product by analyzing information contained within a memory of the flexible circuit 225 of the disposable portion 203. As discussed above, the memory of the flexible circuit 225 can be an PROM, EPROM, EEPROM, SRAM, and/or DRAM memory configured to store information related to the disposable portion 203. Such determination can prevent damage to the reusable device 205 that may occur if an unauthorized product is secured thereto. Such determination can additionally or alternatively ensure proper functionality of the reusable device 205.

In some cases, the memory of the flexible circuit 225 is encoded with information regarding to the disposable portion 203, for example, how many external and/or internal electrodes 112, 211 are included in a particular disposable portion 203. In such cases, when the reusable portion 205 is electronically and/or mechanically mated to the disposable portion 203 such that contact is made between the conductive strips 245 and the conductor pins 254, the reusable portion 205 can determine such information and can determine a particular measurement and/or processing scenario to implement. For example, in such cases, after determining how many external and/or internal electrodes 112, 211 are included in a particular disposable portion 203, the processor 207 of the reusable portion 205 can determine that a more or less complex diagnostic and/or physiological assessment should be undertaken with respect to physiological parameters related to the patient's cardiac activity.

The conductor strips 244 can be in electronic communication with the conductor strips 243, 246 such that they can receive electrocardiogram data from the external electrodes 112 and the internal electrodes 211. The conductor strips 244 of the flexible circuit 225 can be positioned on top of the pin supports 219. The pin supports 219 supporting the conductor strips 244 can be oriented such that when the hub 206 is mated with the dock 204, conductor pins 253 (see FIG. 2L-2M) of the hub 206 can contact the conductor strips 244. The contact between the conductor strips 244 and the conductor pins 253 can allow electrical signals to be transmitted from the disposable device 203 to the processor 207 of the reusable device 205. The processor 207 of the reusable device 205 can be coupled to the conductor pins 253 to receive the electrical signals from the disposable device 203 via the conductor strips 244. The number of conductive strips 244 can correspond with the total number of conductive strips 243, 246. Each of one of the conductor strips 243 and conductor strips 246 can be associated with a different one of the conductor strips 244 of the flexible circuit 225.

FIGS. 2J-2K illustrate various perspective views of the hub 206 of the reusable portion 205. The hub 206 can include a cable outlet (also referred to herein as an "output connector port") 250, one or more mechanical connector portions, among other components discussed further below. The one or more mechanical connector portions can allow the reusable portion 205 to mate with the disposable portion 203. The one or more mechanical connector portions can be, for example, grooves 251, 252. The grooves 251, 252 can be formed on the same or different side of the hub 206. For example, as shown in FIGS. 2J and 2K, the grooves 251, 252 can be positioned opposite from each other on opposite ends of the hub 206. As discussed above, the grooves 251, 252 can interact with the protrusions 240, 241 of the mechanical connector portions 217, 218, respectively, to removably secure the dock 204 and the hub 206. The grooves 251, 252 can be dimensioned and/or shaped to engage the protrusions 240, 241, respectively. As discussed above, the grooves 251, 252 can include the protrusions 251a, 252a that can engage the protrusions 240, 241. In some variants, the mechanical connector portions 217, 218 can secure to the grooves 251, 252 in a snap-fit.

The reusable portion 205 can include one or more electrical connectors configured to connect to one or more electrical connectors of the disposable portion 203 when secured thereto. For example, with reference to FIGS. 2L-2N, the hub 206 can include one or more conductor pins 253, 254 disposed proximate to a bottom surface of the hub 206 such that when the hub 206 is coupled with the dock 204, the conductor pins 253, 254 can be in contact with the conductor strips 244, 245, respectively. The contact between the pins 253, 254 and the strips 244, 245 allows information and/or electrical signals to be transmitted from the disposable device 203 to the reusable device 205. As discussed above, the contact between the conductor strips 244 and the conductor pins 253 can allow transmission of electrical signals between the dock 204 and the processor 207 of the reusable device 205. The contact between the conductor strips 245 and the conductor pins 254 can allow transmission of information between the a memory of the dock 204 (for example, a memory of the flexible circuit 225) and the memory 208 of the reusable device 205.

The reusable portion 205 can be configured such that, when a bottom of the reusable portion 205 is placed on a flat surface, the conductor pins 253, 254 do not contact the flat surface. This can advantageously minimize the risk that the reusable portion 205 or portions thereof will "short" and/or become damaged if high voltage is introduced to the flat surface. For example, if a defibrillator is used on the patient and a bottom of the reusable portion 205 is placed on a surface of the patient, the reusable portion 205 can be configured such that the conductor pins 253, 254 are spaced away from the surface. With reference to FIGS. 2L, the hub 206, for example, a bottom frame 257 of the hub 206, can include one or more bumps 291, 293 protruding outward from a surface of the hub 206. The one or more bumps 291, 293 can include a cavity sized and/or shaped to receive a portion of the conductor pins 253, 254. The number of bumps 291, 293 can correspond with the number of conductor pins 253, 254. For example, the hub 206 can include one, two, three, four, five, six, seven, or eight or more bumps 291 and/or 293. In some variants, the hub 206 comprises a bump 293 that includes two cavities, each sized and/or shaped to receive a different one of two conductor pins 253. In some variants, a height of the bumps 291, 293 (measured from a bottom surface of the hub 206) is greater than a length of extension of the conductor pins 253, 254 through the cavities in the bumps 291, 293. This can prevent tips of the conductor pins 253, 254 from contacting a surface that the reusable portion 205 is placed upon. Additionally or alternatively, the hub 206 can include one or more stubs 295 extending outward from a bottom surface of the hub 206 (for example, a surface of the bottom frame 257 of the hub 206). For example, the hub 206 can include one, two, three, or four or more stubs 295. As another example, the hub 206 can include two stubs 295 positioned outside a plurality of bumps 291 (FIGS. 2L-2M). The one or more stubs 295 can be aligned with one another along a bottom surface of the hub 206. The one or more stubs 295 can have a height (measured from a bottom surface of the hub 206) that is greater than a length of extension of the conductor pins 253, 254 beyond the bottom surface of the hub 206. This can prevent tips of the conductor pins 253, 254 from contacting a surface that the reusable portion 205 is placed upon. Additionally or alternatively, as discussed below, the hub 206 can include a housing 297. The housing 297 can extend beyond the bottom surface of the hub 206 a distance greater than a length of extension of the conductor pins 253, 254 beyond the bottom surface of the hub 206. This can prevent tips of the conductor pins 253, 254 from contacting a surface that the reusable portion 205 is placed upon. In some cases, when a bottom of the hub 206 is placed on a surface (such as a flat surface), the one or more stubs 295 and the housing 297 contact the surface and the conductor pins 253, 254 do not contact the surface. The housing 297, stubs 295, bumps 291, 293, and/or other portions of the hub 206 can comprise a material that minimizes or prevents electrical conductivity. For example, the housing 297, stubs 295, bumps 291, 293, and/or other portions of the hub 206 can comprise boron nitride.

Figure 2P:
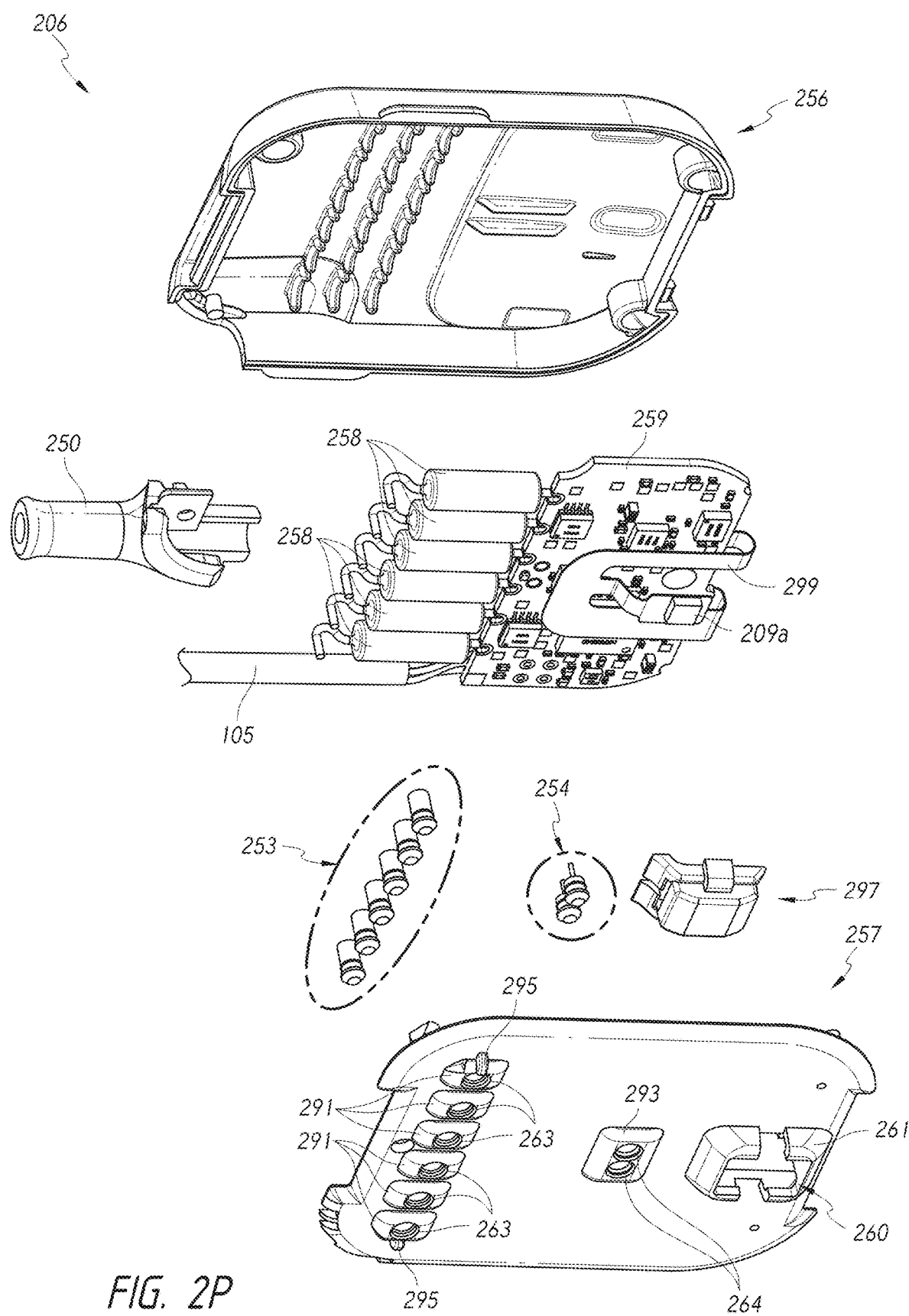
FIG. 2P illustrates an exploded, bottom perspective view of the hub of FIGS. 2J and 2K.

FIGS. 2O-2P illustrate exploded perspective views of the hub 206 of the reusable device 205. The hub 206 (also referred to herein as "cover") can include a top frame 256 and a bottom frame 257. The hub 206 can further include one or more resistors 258, a circuit board 259, the conductor pins 253, the conductor pins 254, one or more of temperature sensors 209a, 209b, 209c, 209d, a housing 297, a flexible circuit 299, and a cable outlet 250. The bumps 291 and/or 293 of the bottom frame 257 can include cavities 263 and/or cavities 264. The cavities 263, 264 can be sized and/or shaped to receive the conductor pins 253 and the conductor pins 254, respectively. The cavities 263, 264 can be dimensioned and sized such that the conductor pins 253, 254 create water-resistant seal when received by the cavities 263, 264.

The hub 206 can include a recessed portion 261. The recessed portion 261 can be, for example, formed in the bottom frame 257. The recessed portion 261 can be recessed from a top surface of the bottom frame 257 (FIG. 2O) and can extend outward (for example, below) a bottom surface of the bottom frame 257 (FIG. 2P). The recessed portion 261 can include an opening 260 formed at an end or bottom of the recessed portion 261. The recessed portion 261 can be shaped, dimensioned, and/or positioned relative to the top and/or bottom surfaces of the hub 206 such that the recessed portion 235 of the dock 204 (FIG. 2F) can receive the recessed portion 261 when the dock 204 is coupled to hub 206. As discussed further below, the recessed portion 261 can receive the housing 297 which can house temperature sensor 209a. As discussed below, the housing 297 can extend through the recessed portion 261 and at least partially through the recessed portion 235 of the dock 204 proximate to openings 258 and/or 232 such that it can contact substrate 230.

FIG. 2Q illustrates an exploded view of a portion of the assembly shown in FIGS. 2O-2P. As discussed above, the reusable portion 205 can include one or more temperature sensors 209 that can be used to measure a temperature of the patient's body (for example, via the skin) and/or an ambient temperature inside or outside the reusable portion 205. For example, the hub 206 can include a temperature sensor 209a and one or more of temperature sensors 209b, 209c, 209d. As shown, the temperature sensors 209a, 209b, 209c, 209d can be coupled to the flexible circuit 299 and the flexible circuit 299 can be coupled to the circuit board 259. Thus, temperature data from one or more of temperature sensors 209a, 209b, 209c, 209d can be transmitted to the circuit board 259. Temperature sensor 209a can be positioned adjacent and/or proximate to a different side of the circuit board 259 as the temperature sensors 209b, 209c, 209d. As shown, temperature sensor 209a can be coupled to an end portion of the flexible circuit 299. Temperature sensor 209a can be configured to be positioned closer to the patient's skin when the reusable portion 205 is mated with the disposable portion 203. As discussed above, the hub 206 can include a housing 297. Housing 297 can be configured to receive temperature sensor 209a. Temperature sensor 209a can be secured to a portion of housing 297 with a pad 269. Pad 269 can be configured to adhere temperature sensor 209a to the portion of the housing. Pad 269 can comprise a thermally conductive material.

As discussed elsewhere herein, the housing 297 can extend through portions of the bottom frame 257 and/or the dock 204 of the disposable portion 203 and contact a substrate of the dock which can contact skin of the patient. In such configuration, the housing 297 can provide thermal communication between the skin of the patient and the temperature sensor 209a housed within the housing 297. Housing 297 can comprise a material that provides thermal conductivity but minimizes or prevents electrical conductivity. This can advantageously allow the housing 297 to facilitate thermal communication between the patient's skin and the temperature sensor 209a and simultaneously minimize or eliminate damage and/or interference that may be caused from electrical interference. As an example, the housing 297 can comprise a plastic coated with and/or comprising boron nitride.

In addition to temperature sensor 209a, the reusable portion 205 can include one or more temperature sensors 209b, 209c, and 209d. The temperature sensors 209b, 209c, and 209d can be coupled to the flexible circuit 299 and be positioned away from the temperature sensor 209a. One or more of temperature sensors 209b, 209c, and 209d can be used to detect a temperature within an interior of the reusable portion 205 (for example, within an interior of the hub 206). For example, the temperature sensors 209b, 209c, and 209d can detect a temperature adjacent and/or proximate to the circuit board 259 and/or the resistors 258. In some cases, temperature data measured from temperature sensor 209a may be influenced by temperatures within the interior of the reusable portion 205. Advantageously, incorporating temperature sensor 209a along with one or more of temperature sensors 209b, 209c, and 209d can allow the processor 207 more accurately determine core body temperature of the patient. For example, the processor 207 can utilize temperature data from one or more of temperature sensors 209b, 209c, and 209d in order to adjust temperature data received from the temperature sensor 209a in order to more accurately determine a patient's body temperature. Where the hub 206 includes two or more of temperature sensors 209b, 209c, and 209d, the temperature sensors 209b, 209c, and 209d can be spaced away from each other in order to collect temperature data at various locations within the interior of the hub 206.

The circuit board 259 can include the processor 207 and the memory 208. The circuit board 259 can be operatively coupled to the external electrodes 112, the internal electrodes 211, and one or more of temperature sensors 209a, 209b, 209c, 209d in order to receive electrocardiogram data and temperature data. The hub 506 can include one or more resistors 258 coupled to the circuit board 259 and/or the conductor pins 253. The hub 506 can include one, two, three, four, five, six, seven, or eight or more resistors 258. The number of resistors 258 can correspond with the number of conductor pins 253 and/or the total number of external and internal electrodes 112, 211. The resistors 258 can be positioned between the circuit board 259 and the conductor pins 253. Advantageously, the resistors 258 can prevent or reduce the damage to the circuit board 259 (or other components of the reusable device 205) due to shorting or arcing, which may be caused when high voltage is accidentally and/or suddenly introduced via the conductor pins 253, for example, if the reusable device 205 is positioned on or proximate to a patient when a defibrillator is used. For example, the resistors 258 can be high-capacity, low-resistance resistors that allow electrical signals related to a user's cardiac electrical activity to pass therethrough but inhibit high voltage from passing to the circuit board 259 and/or other components of the reusable device 205. The resistors 258 can be soldered directly to the circuit board 259 and/or the conductive pins 253. With reference to FIGS. 2O and 2Q, the hub 206 can include one or more walls 268 configured to separate each of the one or more resistors 268. For example, the hub 206 can include a number of walls 268 that is one less than the number of resistors 258. The walls 268 can advantageously isolate portions of the resistors 258 from each other.

The reusable portion 205 can include a heat sink configured to transfer heat generated by the reusable portion 205 or portions thereof to an ambient environment outside the reusable portion 205, thereby allowing regulation of a temperature within the reusable portion 205. For example, with reference to FIG. 2O, the hub 206 of the reusable portion 205 can include a heat sink 279 positioned at or near a top surface of the hub 206. Heat sink 279 can advantageously transfer heat generated by one or more of the circuit board 259, flexible circuit 299, temperature sensor 209a, 209b, 209c, 209d, resistors 258, and/or other components, to the ambient environment outside of the hub 206. Heat sink 279 can be a metal element.

Figure 2R:
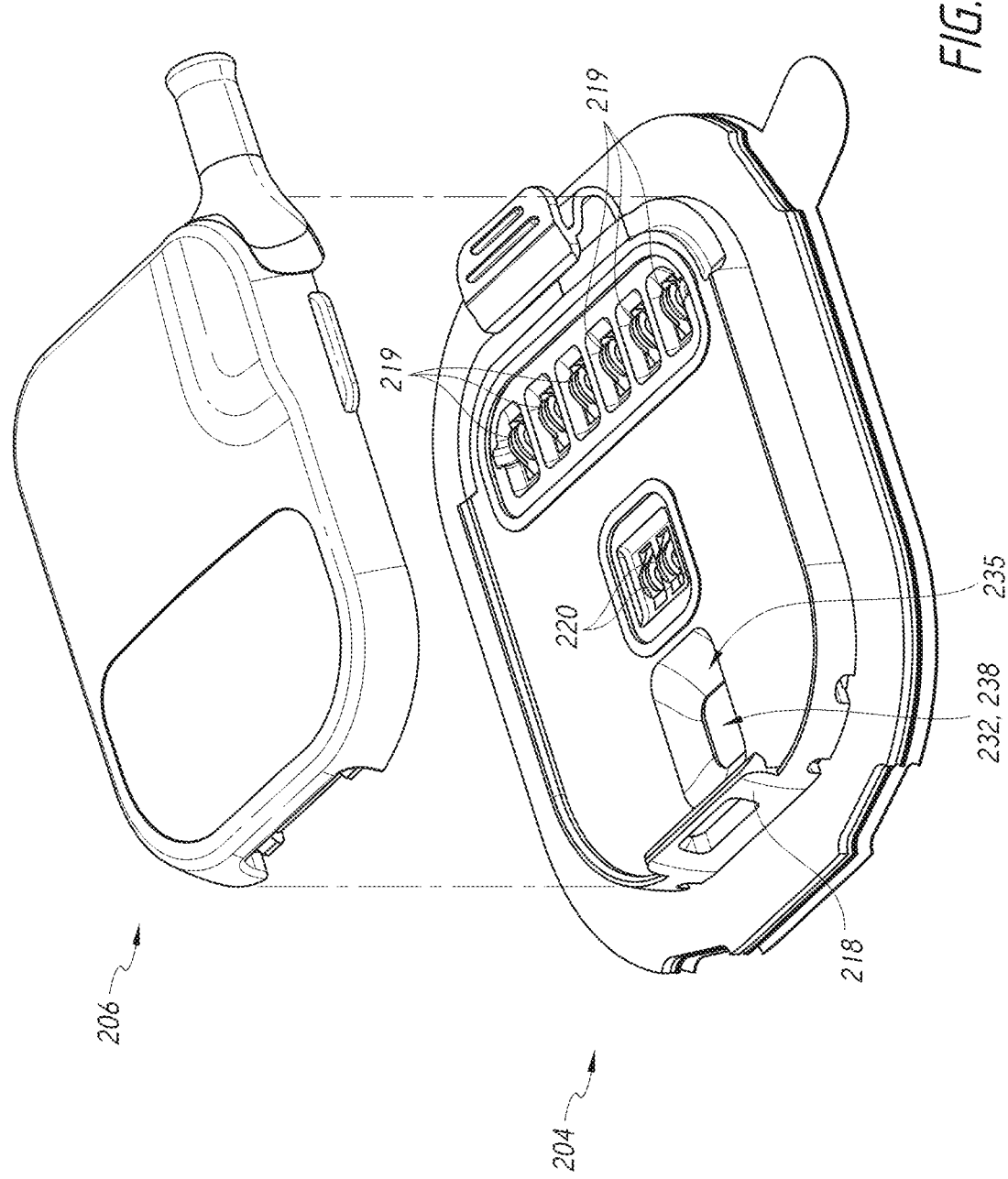
FIG. 2R illustrates a perspective view of the hub and dock of the ECG device of FIG. 2A and further illustrates a method of mating the hub and dock in accordance with aspects of this disclosure.

FIG. 2R illustrates a top, perspective view of the hub 206 and the dock 204, illustrating how the hub 206 and the dock 204 can be coupled (for example, removably coupled). The dock 204 can removably secure to the hub 206 via engagement between the mechanical connector portions 217, 218, 252, 251 as discussed above. When the dock 204 and the hub 206 are secured in such manner, the conductor pins 253, 254 (see FIG. 2L-2M) of the hub 206 can engage the pin supports 219, 220, respectively. As discussed above, the conductive strips 244, 245 of the flexible circuit 225 can be supported by the pin supports 219, 220. Accordingly, when the dock 204 and the hub 206 are secured in such manner, the conductive strips 244, 245 can contact the conductor pins 253, 254 of the hub 206. The contact between the conductive strips 244, 245 and the conductor pins 253, 254 can allow electrical signals and/or information to be transmitted from the dock 204 of the disposable device 203 to the hub 206 of the reusable device 205. Additionally, when the dock 204 and the hub 206 are secured in such manner, the housing 297 (FIGS. 2L-2M) and the recessed portion 235 can be aligned (FIG. 2R). The recessed portion 235 can be sized and/or shaped to receive the housing 297 and/or the recessed portion 261. When secured in such manner, the housing 297 can contact one of the substrates of the laminate structure 221 as discussed elsewhere herein.

Figure 2S:
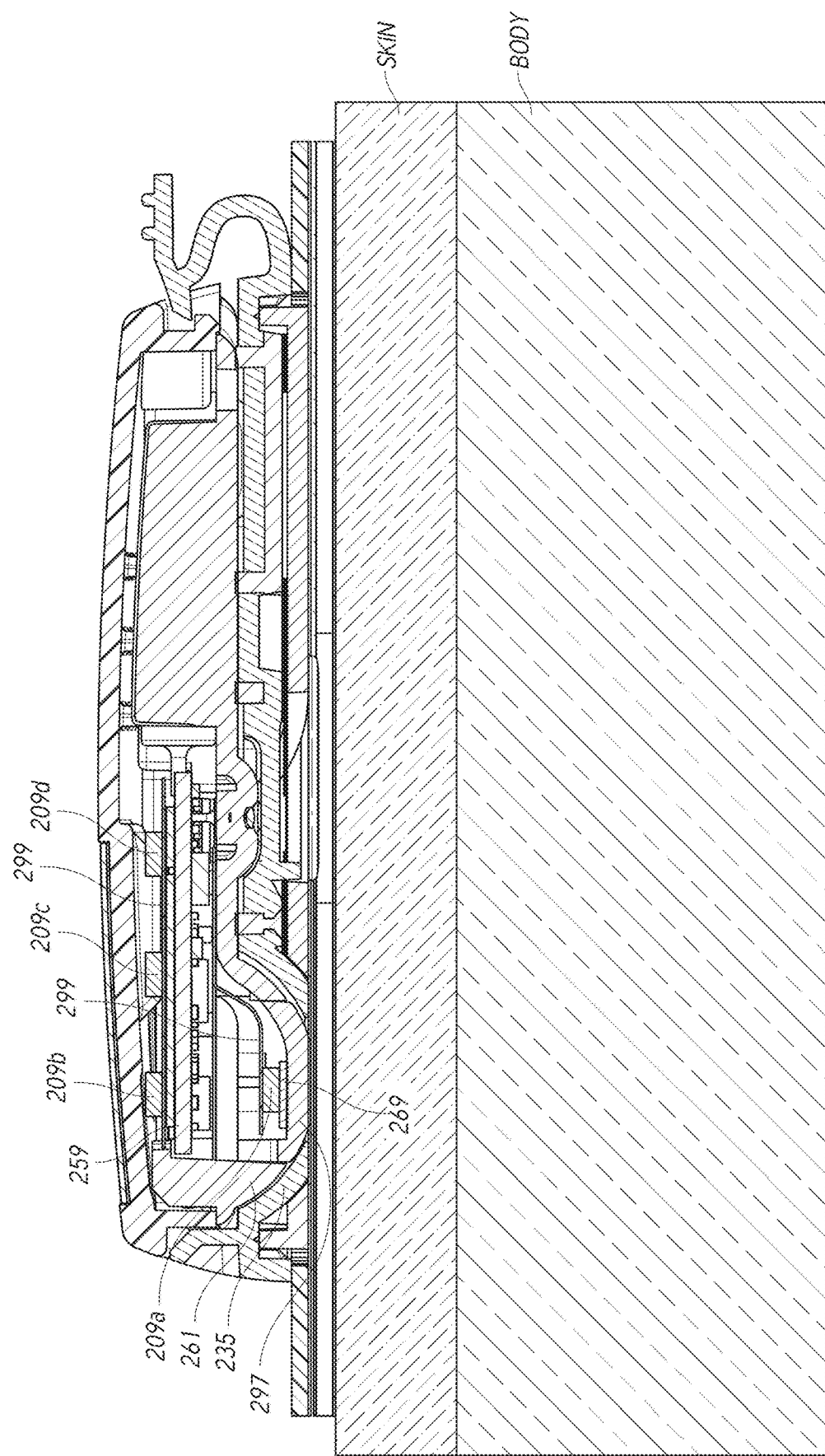
FIG. 2S illustrates a side, cross-sectional view of the ECG device of FIG. 2A on a patient, showing relative position of a temperature sensor with respect to the patient in accordance with aspects of this disclosure.

FIG. 2S illustrates a cross-sectional view of the ECG device 110 placed on a patient, showing relative positions of the temperature sensor 209a with respect to a patient's skin. FIG. 2S illustrates, among other things, the circuit board 259, flexible circuit 299, the recessed portion 261, the housing 297, the pad 269, temperature sensor 209a, and one or more of optional temperature sensors 209b, 209c, 209d. As shown, temperature sensor 209a can be secured and/or positioned above the pad 269 and a bottom of the housing 297. In this regard, the temperature sensor 209a can be in indirect contact with the patient's skin via the pad 269, housing 297, and one or more substrates of the dock 204.

Figure 2T:
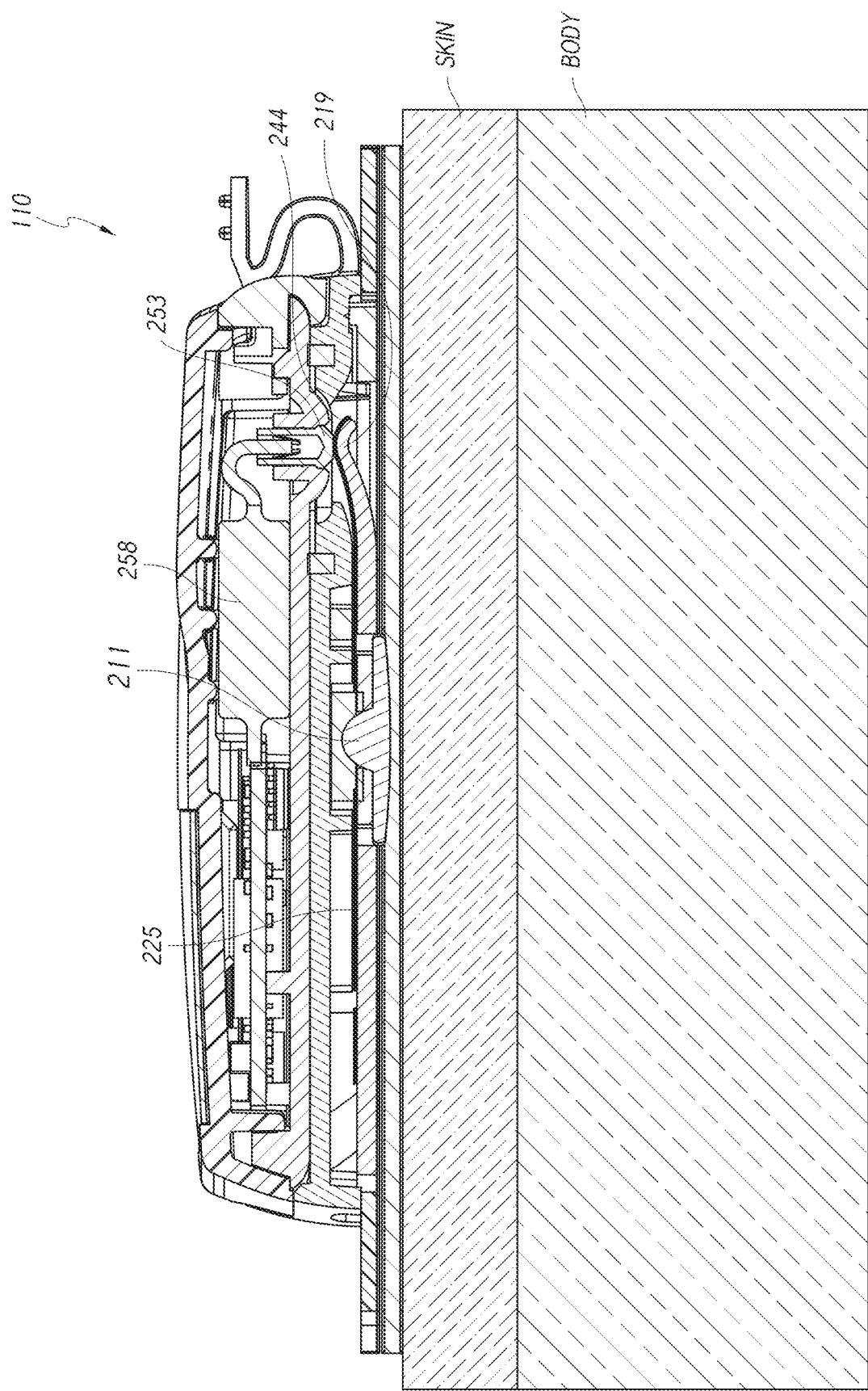
FIG. 2T illustrates a side, cross-sectional view of the ECG device of FIG. 2A on a patient, showing relative position of an internal electrode of the ECG device with respect to the patient in accordance with aspects of this disclosure.
Figure 2U:
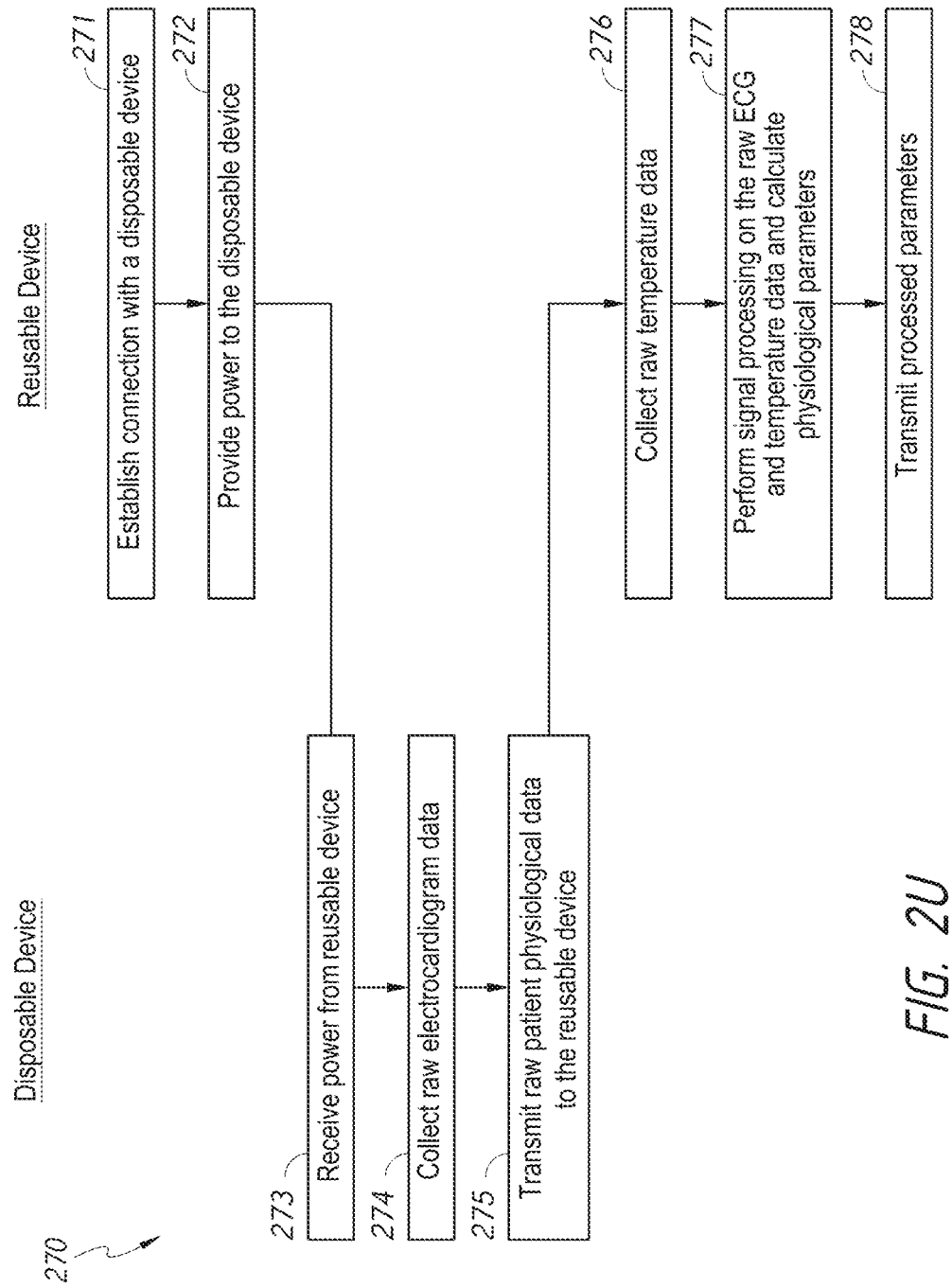
FIG. 2U illustrates a block diagram depicting a method of collecting physiological data using the ECG of FIG. 2A in accordance with aspects of this disclosure.

FIG. 2T illustrates a cross-sectional view of the ECG device 110 placed on a patient, showing relative positions of the internal electrode 211 with respect to a patient's skin. FIG. 2T illustrates, among other things, the internal electrode 211, the flexible circuit 225, conductive strips 244, pin supports 219, conductor pins 253, and resistors 258. As shown, when the reusable portion 205 and the disposable portion 203 are mated, the conductors pins 253 can contact and/or depress the pins supports 219. As also shown, the internal electrodes 211 can be in indirect contact with the skin of the patient. For example, the substrates 231 can be positioned between the internal electrodes 211 and the patient's skin. As discussed above, substrates patches 231 can facilitate transmission of electrical signals from the patient's heart to the internal electrodes 211.

FIG. 2R illustrates a block diagram representing a method 270 of determining patient physiological parameters using the ECG device 110. At step 271, the reusable device 205 establishes connection with the disposable device 203. This can occur when the reusable device is mechanically mated with the disposable device 203. The connection between the reusable device 205 and the disposable device 203 can be established via contact between the conductive pins 253, 254 and the conductive strips 244, 245 supported by pin supports 219, 220. The contact between the conductive pins 253, 254 and the conductive strips 244, 245 can occur when the hub 206 of the reusable device 205 is removably mounted on the dock 204 of the disposable device 203. At step 272, the reusable device 205 can provide power to the disposable device 203. The power provided by the reusable device 205 can power the external and internal electrodes 112, 211 to collect electrocardiogram data. In some variants, the disposable portion 203 does not comprise a power source and relies entirely on the reusable device 205 to collect electrocardiogram data.

At step 273, the disposable device 203 receives power from the reusable device 205. At step 274, the disposable device 203 uses the one or more external electrodes 112 and/or the one or more internal electrodes 211 to collect raw ECG data from the patient. At step 275, the raw ECG data collected by the external electrodes 112 and/or the internal electrodes 211 can be transmitted to the reusable device 205. The raw ECG data can be transmitted via the flexible circuit 225 as discussed above. The raw ECG data can be transmitted from the disposable device 203 to the reusable device 205 automatically or manually upon user input. The raw ECG data can be transmitted continuously or with a predetermined delay.

At step 276, the reusable device 205 can collect raw temperature data. The raw temperature data can be collected by the temperature sensor 209a. The raw temperature data can be collected simultaneously or non-simultaneously from the raw ECG data. For example, the reusable device 205 can collect the raw temperature data regardless of whether the disposable device is collecting and/or transmitting the raw ECG data. The raw temperature data can be collected from temperature sensor 209a simultaneously or non-simultaneously with temperature data collected from one or more of temperature sensors 209b, 209c, 209d. As discussed above, the processor 207 of the reusable portion 205 can determine a body temperature of the patient based on, at least, a comparison of the temperature data from temperature sensor 209a and one or more of temperature sensors 209b, 209c, 209d.

Care providers may be able to configure the ECG device 110 to determine which physiological data to be collected in different circumstances. The ECG device 110 can be configured to collect and process temperature-related physiological data in certain, predetermined situations. For example, the ECG device 110 can be configured to measure temperature of a patient when it detects ECG signals associated with irregular heart activities and/or bodily conditions. For example, the ECG device 110 can be configured to measure temperature of a patient when a variation in ECG signals over a predetermined time period exceeds a threshold value. In another example, the ECG device 110 can be configured to collect ECG data from a patient when a temperature measurement exceeds or falls below a threshold value, which can be indicative of an abnormal condition. Other types information related to different patient parameters and/or conditions can be used to trigger the ECG device 110 to collect ECG and/or temperature data.

At step 277, the reusable device 205 (for example, the processor 207) can perform signal processing on the raw ECG and temperature data to determine physiological parameters related to a patient's heart activity and temperature. At step 278, the reusable device 205 of the ECG device 110 can transmit the physiological parameters to other patient monitoring systems and/or devices via wires or various wireless communication protocols.

In some variants, the ECG device 110 is waterproof or water-resistant. For example, the reusable device 205 and/or the disposable device 203 can be configured such that, when secured to one another, they prevent water from entering into an interior thereof. This can minimize or prevent damage to the reusable device 205 and/or the disposable device 203 and/or components thereof (such as the temperature sensor 209, the internal electrodes 211, and/or the circuit board 259).

Partitioning the ECG device 110 into separable reusable and disposable portions 205, 203 provides a number of benefits over traditional ECG devices. For example, such partitioning allows a portion of the ECG device 110 (e.g., the reusable portion 205) to be reused after the device 200 after use with a given patient, and allows another portion of the device 200 (e.g., the disposable portion 203) to be disposed of after such use. By removably securing to the disposable portion 203 as discussed above, the reusable portion 205 can avoid contacting portions of the patient during use. The disposable portion 203 can secure to the patient and provide a platform by which the reusable portion 205 can attach. Such partitioning allows more expensive and/or vulnerable components, such as the circuit board 259, flexible circuit 299, temperature sensors 209a, 209b, 209c, 209d, among others, to be housed within the reusable portion 205 while less expensive and/or more durable components (such as the electrodes 112, cables 114, laminate structure 221, dock 204, among others) to be part of the disposable portion 203. Such partitioning can allow the disposable portion 203 to be secured to the patient independently of the reusable portion 205. This can be advantageous where the reusable portion 205 is connected to other physiological monitoring devices (such as the blood pressure monitor 120 and/or the patient monitor 130 via cable 105) and securement of the reusable portion 205 and the disposable portion 203 to the patient simultaneously may be more difficult (for example, because of various cables being present in the patient environment). In such circumstances, such partitioning allows a caregiver to secure the disposable portion 203 (for example, the electrodes 112 and the dock 204) to the patient, and subsequent to such securement, the caregiver can secure the reusable portion 205 to the disposable portion 203. In some variants, the reusable portion 205 weighs more than the disposable portion 203. In some variants, the disposable portion 203 does not include a processor and/or a power source (e.g., a battery). In some variants, the disposable portion 203 does not collect electrical signals responsive to the patient's cardiac activity until the reusable portion 205 is secured to the disposable portion 203.

Figure 3A:
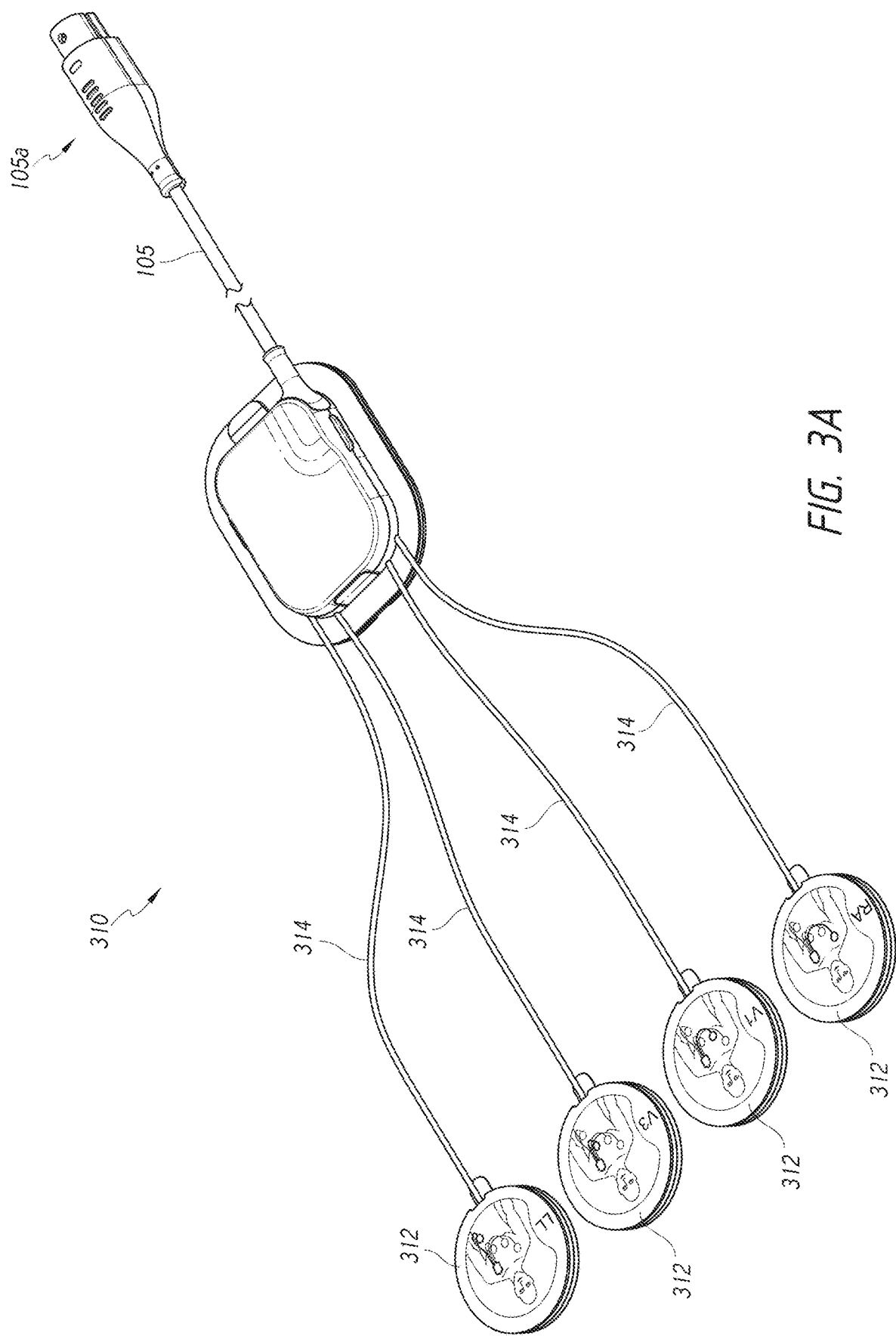
FIG. 3A illustrates a perspective view of another embodiment for an ECG device.

FIG. 3A illustrates another embodiment of an ECG device 310 (also referred to herein as "ECG sensor"). The ECG device 310 can be attached to different parts of the patient 111 such as the patient's chest, back, arms, legs, neck, head, or other portions of the body of the patient. The ECG device 310 can collect one or more types of patient physiological data and transmit the data to other monitoring systems or devices. The physiological data can be transmitted to other monitoring systems or devices via wires or various wireless communication protocols. For example, as discussed above, the ECG device 310 can interact with the various other physiological devices and/or systems, such as the blood pressure monitors discussed herein (for example, blood pressure monitor 120) and/or patient monitor 120. Accordingly, all parts of the description above with reference to ECG device 110 and FIGS. 1A-1D can be applicable to ECG device 310.

The ECG device 310 can have the functional and/or computational capabilities to calculate physiological parameters (for example, heart rate, precise body temperature values, among others) using raw physiological data (for example, raw temperature data, raw ECG data responsive to patient cardiac activity, among others). In this regard, the ECG device 310 can transmit raw, unprocessed electrical signals or physiological data, and/or processed, calculated physiological parameters to other patient monitoring devices and/or systems, such as those discussed elsewhere herein (for example, the blood pressure monitor 120 and/or the patient monitor 130).

With reference to FIGS. 3A-3D, the ECG device 310 can include a disposable portion 303 (also referred to herein as "disposable device") and a reusable portion 305 (also referred to herein as "reusable device"). The disposable portion 303 can include a dock 304 (also referred to herein as a "base"), one or more external electrodes 312, and one or more cables 314. The one or more external electrodes 312 can be coupled to the dock 304 via the one or more cables 314. The one or more external electrodes 312 and/or the cables 314 can be identical to the one or more external electrodes 112 and/or the cables 114 as discussed with respect to ECG device 110 and therefore the discussion above with reference to these component is not repeated for the sake of brevity.

Figure 3B:
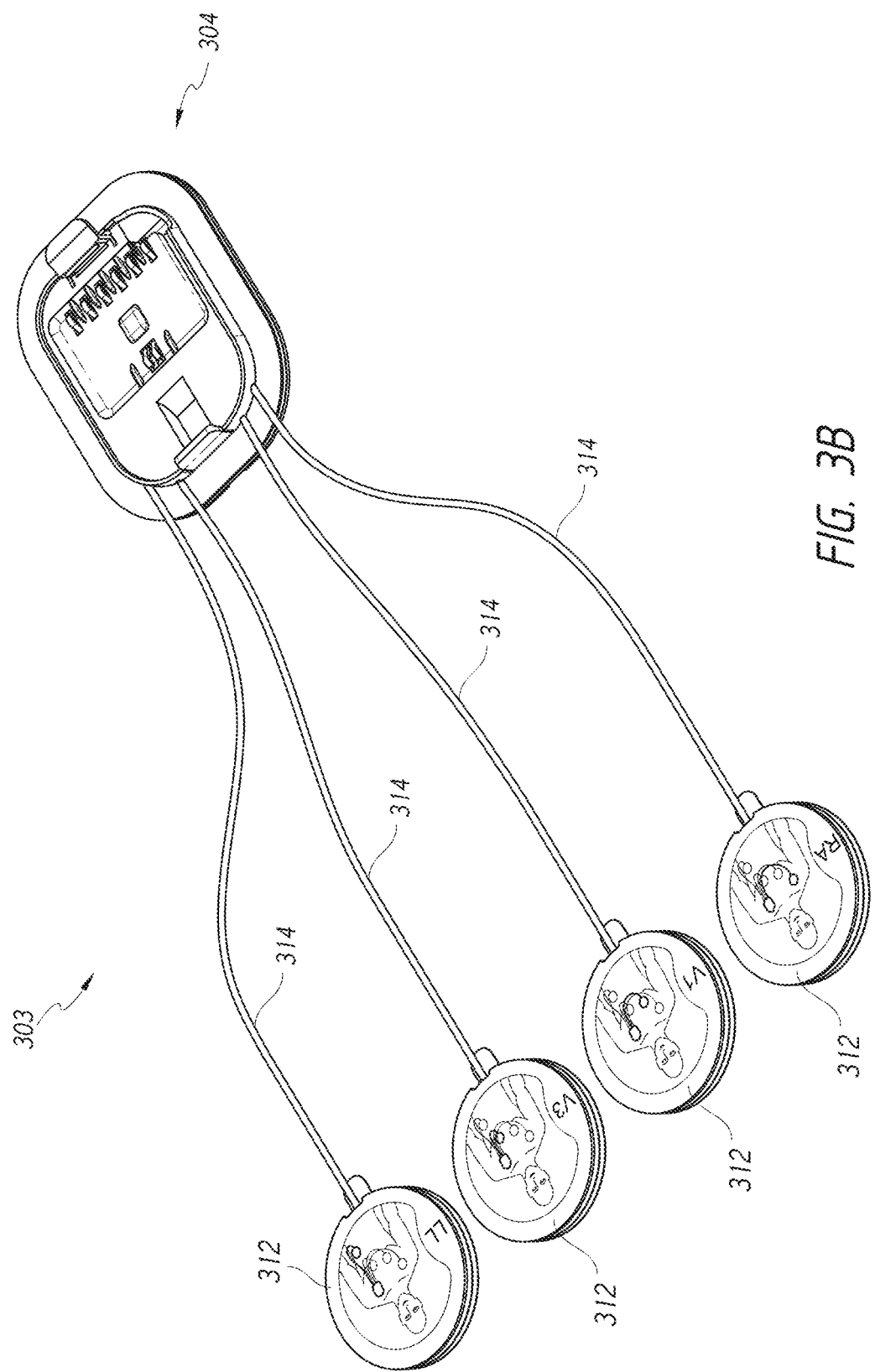
FIG. 3B illustrates a perspective view of a disposable portion of the ECG device of FIG. 3A.
Figure 3C:
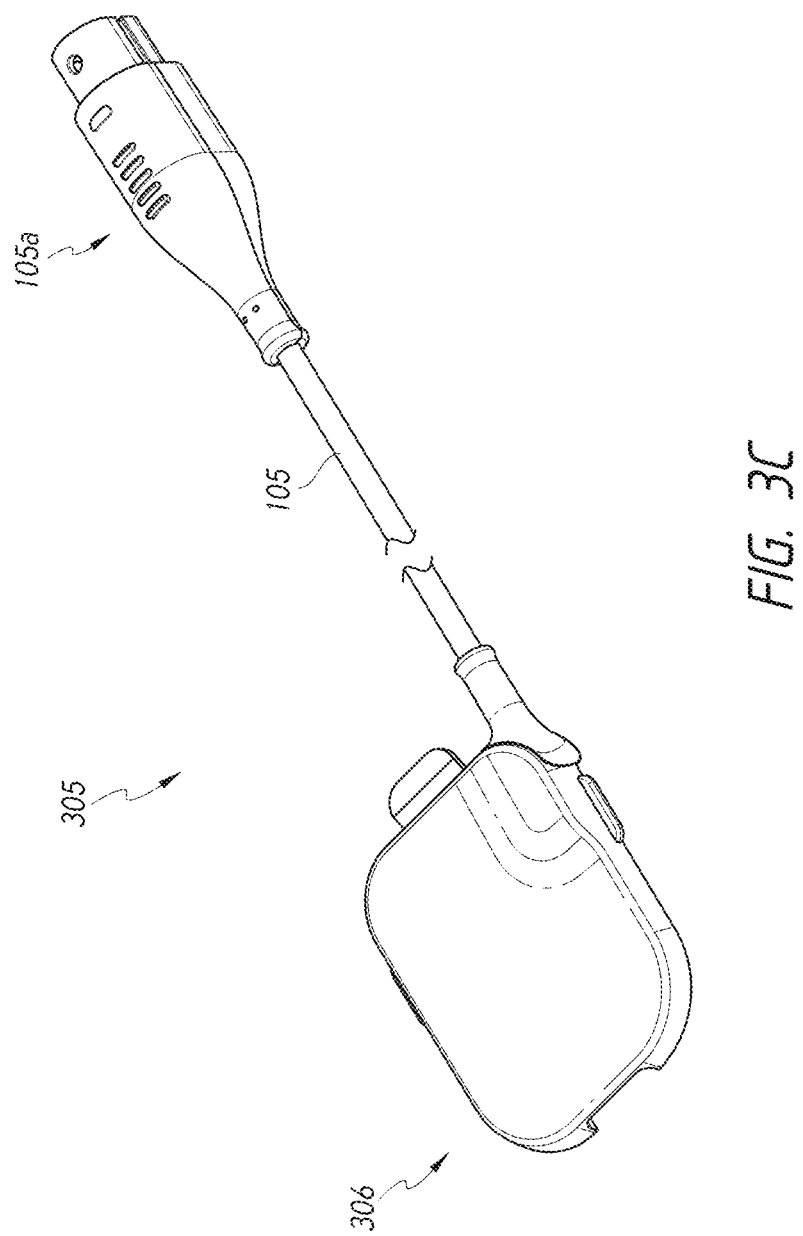
FIG. 3C illustrates a perspective view of a reusable portion of the ECG device of FIG. 3A.

FIG. 3C illustrates a perspective view of the reusable device 305. The reusable device 305 can include a hub 306 (also referred to herein as "cover"), a cable 105, and/or a connector 105a. The hub 306 can transmit electrical signals to other devices and/or systems, including multi-parameter patient monitoring systems (MPMS), via the cable 105 and the connector 105a. Additionally or alternatively, the hub 306 can wirelessly transmit electrical signals to other devices and/or systems. For example, the hub 306 can include a wireless transmitter or transceiver configured to wirelessly transmit electrical signals (for example, signals related to patient temperature and/or heart activities) using different types of wireless communication technology such as Bluetooth®, Wi-Fi, near-field communication (NFC), and the like. In some variants, the reusable device 205 does not include a cable or a connector.

The hub 306 can be of various shapes and/or sizes. For example, as shown in FIG. 3C, the hub 306 can be rectangular in shape and/or can have rounded edges and/or corners. The hub 306 can be shaped to mate with the dock 304. For example, the hub 306 can be sized and/or shaped to facilitate mechanical and/or electrical mating with the dock 304. Additional details regarding the mating of the hub 306 and the dock 304 are described further below.

Figure 3D:
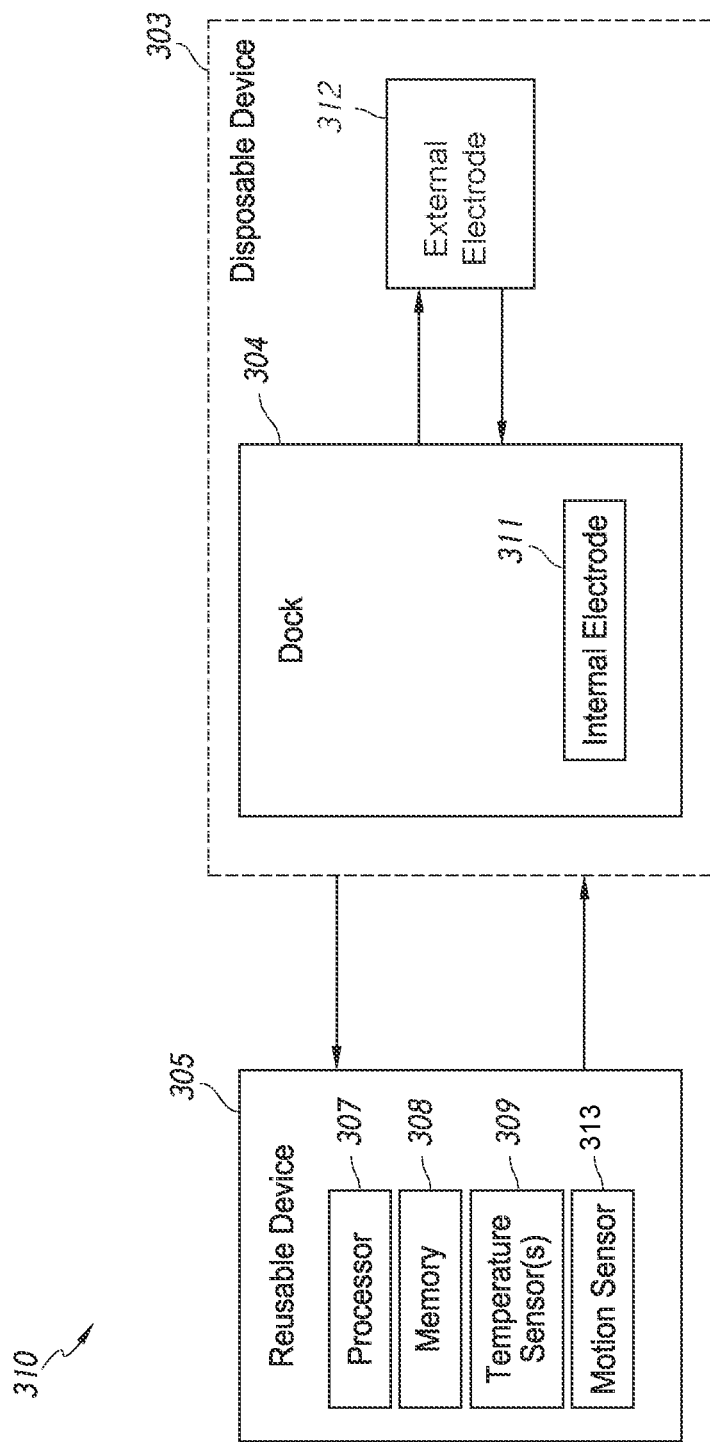
FIG. 3D illustrates a schematic diagram of the ECG device of FIG. 3A.

FIG. 3D illustrates a schematic diagram of the ECG device 310. As discussed above, the ECG device 310 can include the disposable device 303 and the reusable device 305. The disposable device 303 can include a dock 304 coupled to one or more external electrodes 312 that detect and transmit electrical signals from the patient 111 through the cables 314. The dock 304 can receive the electrical signals from the external electrodes 312 (for example, via flexible circuit 325) and transmit them to the reusable device 305. The external electrodes 312 can be placed at various locations relative to where the dock 304 is placed. For example, the dock 304 can be placed proximate, adjacent, and/or above the patient's heart and the external electrodes 312 can be placed at various locations on the patient's chest.

Similar or identical to the external electrodes 112 of ECG device 110, the externals electrodes 312 can be color-coordinated and/or include graphics or visualizations that can advantageously aid a caregiver properly position and/or secure the electrodes 312 to portions of a patient's body so that accurate ECG data is collected. Accordingly, the discussion above with reference to FIGS. 2A-2B and 4D, and ECG device 110 is equally applicable to the external electrodes 312 of ECG device 310 and is not repeated here for the sake of brevity.

The disposable device 303 can include one or more external electrodes 312. For example, the disposable device 303 can include one, two, three, four, five, six, seven, or eight or more external electrodes 312. For example, as illustrated by FIGS. 3A-3B, the disposable device 303 can include four external electrodes 312. As another example, the disposable device 303 can include two external electrodes 312.

The dock 304 of the disposable device 303 can include one or more internal electrodes 311. For example, the dock 304 can include one, two, three, four, five, six, seven, or eight or more internal electrodes 311. As another example, as illustrated in FIGS. 3F-3G, the dock 304 can include two internal electrodes 311. As another example, the dock 304 can include one internal electrode 311.

The total number of electrodes (including both external and internal electrodes) can be two, three, four, five, six, seven, eight, nine, ten, eleven, or twelve or more electrodes. For example, the disposable device 303 can include four external electrodes 312, four cables 314, and two internal electrodes 311. In another example, the disposable device 303 can include two external electrodes 312, two cables 314, and two internal electrodes 311. In another example, the disposable device 303 can include two external electrodes 312, two cables 314, and one internal electrode 311. In yet another example, the disposable device 303 can include four external electrodes 312, four cables 314, and no internal electrode 311. In yet another example, the disposable device 303 can include one external electrode 312, one cable 314, and one internal electrode 311. In another example, the disposable device 303 can include two external electrodes 312, two cables 314, and no internal electrodes 311. Various combinations of internal and external electrodes 311, 312 are possible without departing from the scope of the present disclosure. The number of external electrodes 312 coupled to the dock 304 of the disposable device 303 and the number of internal electrodes 311 housed within the dock 304 can be varied in various examples of disposable device 303 of the ECG device 310.

As illustrates in FIG. 3D, the reusable device 305 of the ECG device 310 can include a processor 307, a memory 308, a temperature sensor 309, and/or a motion sensor 313. The memory 308 can be a programmable read-only memory (PROM), an erasable programmable read-only memory (EPROM), an electrically erasable programmable read-only memory (EEPROM), a static random access memory (SRAM), or a dynamic random access memory (DRAM), and the like. The memory 308 can store various types of physiological data (raw and/or processed) related to the patient 111. For example, the memory 308 can store raw and/or processed physiological data related to patient temperature and electrical activity of the heart. The data related to the electrical activity of the heart can represent rhythm and/or activity of the heart. As discussed further below, the memory 308 can be utilized in combination with a memory on the disposable device 303 to enable, among other things, verification of whether the disposable device 303 is an authorized product. For example, the disposable device 303 can include a PROM, EPROM, EEPROM, SRAM, and/or DRAM that can be read by the reusable portion 305 to enable the reusable portion 305 to verify whether the disposable device 303 is an authorized product.

As discussed above, the reusable device 305 can include a motion sensor 313. The motion sensor 313 can be identical to the motion sensor 210 of ECG device 110. Accordingly, the discussion above with reference to motion sensor 110 of ECG device 110 is equally applicable to the motion sensor 313 of ECG device 310 and is not repeated here for the sake of brevity.

As discussed above, the reusable device 305 can include a temperature sensor 309. The temperature sensor 309 can measure temperature of the patient 111 at and/or proximate to a location where the ECG device 310 is placed. The temperature sensor 309 can measure temperature of the skin of the patient 111. Additionally or alternatively, the temperature sensor 309 can measure ambient temperature, for example, temperatures outside the reusable device 305 and/or temperatures inside the reusable device 305 (such as at or near a circuit board of the reusable device 305). The temperature data collected from the patient 111 by the temperature sensor 309 may be used to determine a core body temperature of the patient 111. The temperature sensor 309 can be in electronic communication with the processor 307 and can transmit the temperature data to the processor 307. In one example, the temperature sensor 309 can be an infrared temperature sensor. Placement and/or arrangement of the temperature sensor 309 within the reusable device 305 and/or with respect to the disposable device 303 can be varied to facilitate thermal communication between a user's skin and the temperature sensor 309, as discussed further below.

The processor 307 can receive raw temperature data from the temperature sensor(s) 309. Additionally, the processor 307 can receive raw ECG data from the disposable device 303. For example, the processor 307 can receive raw ECG data from the disposable device 303 via contact between one or more electrical connectors of the reusable portion 305 and one or more electrical connectors of the disposable portion 303. As another example, the processor 307 can receive raw ECG data from the disposable device 303 via electrical contact between conductive strips 344 of the flexible circuit 325 of the disposable device 303 and conductor pins 353 of the reusable device 305. After receiving the raw ECG and temperature data, the processor 307 can perform data processing to calculate physiological parameters corresponding to temperature and/or ECG. The physiological parameters can be stored in the memory 308 or transmitted to different sensor systems, patient monitoring systems, and the like. For example, the physiological parameters can be transmitted to the blood pressure monitor 120 and/or the patient monitor 130. The data stored in the memory 308 can be stored for a predetermined length of time and transmitted to different sensor systems or patient monitoring systems or devices when the ECG device 310 is connected (via a wire or wirelessly) to such other systems or devices. Optionally, the raw temperature data and the raw ECG data can be stored in the memory 308 prior to data processing by the processor 307. The processor 307 can retrieve raw temperature and/or ECG data periodically to process and/or transmit the raw data in batches. Alternatively, the processor 307 can automatically retrieve (for example, continuously) the raw data from the memory 308 as the memory 308 receives the raw ECG and temperature data.

Figure 3E:
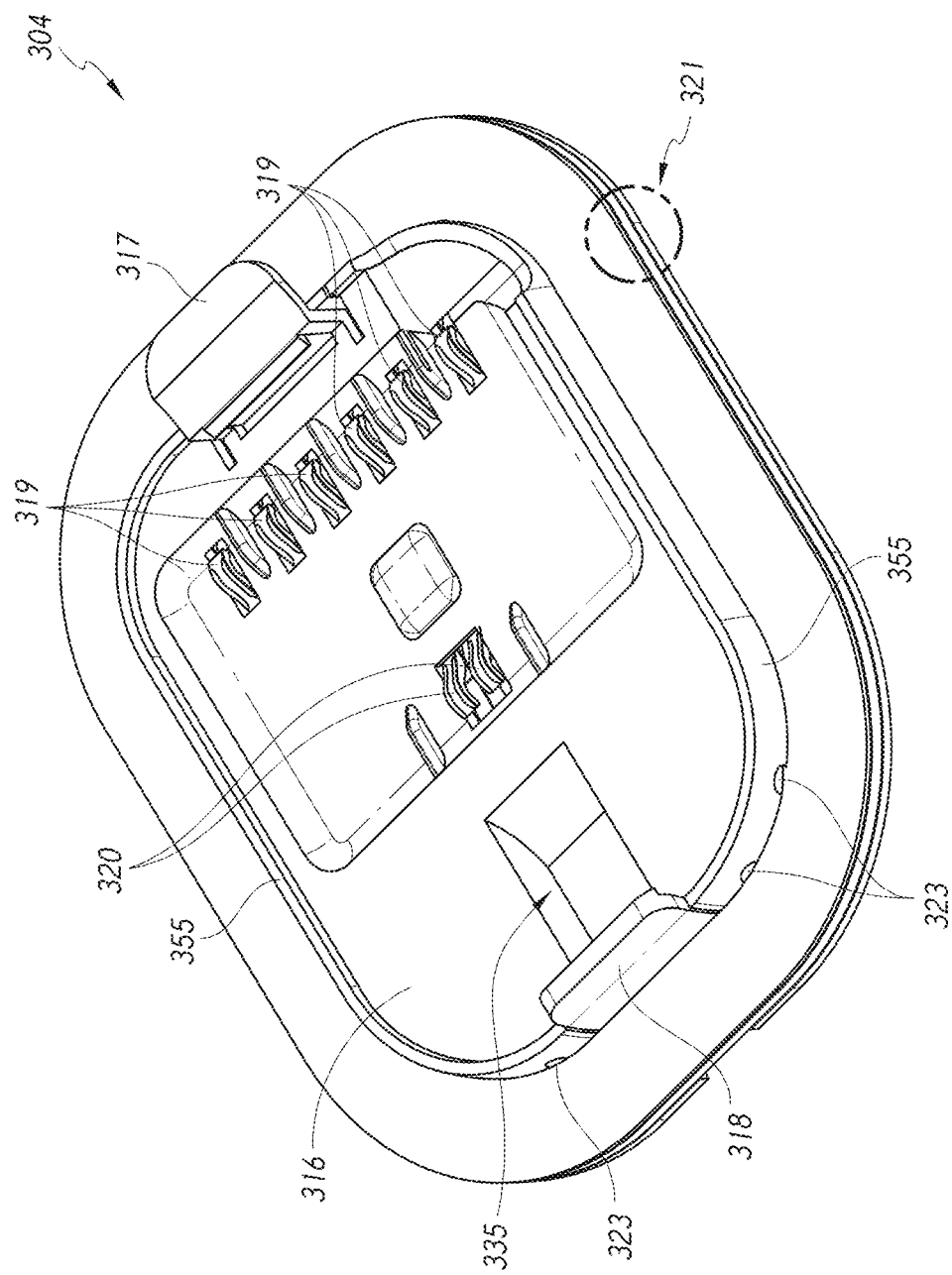
FIG. 3E illustrates a dock of the disposable portion of the ECG device shown in FIG. 3B.
Figure 31:
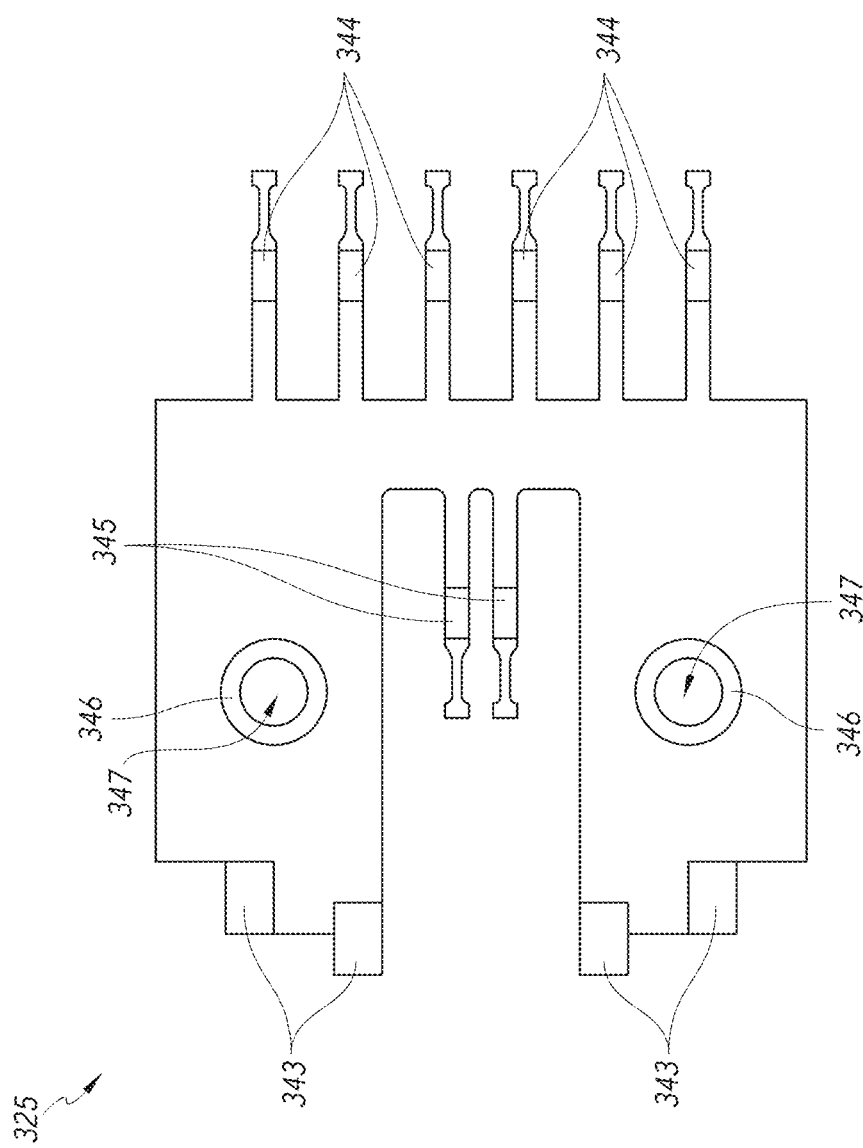

FIG. 3E illustrates a top, perspective view of the dock 304 of the disposable device 303. The dock 304 (also referred to herein as "base") can include a main body 316 and a laminate structure 321. The main body 316 can include one or more pin supports 319, one or more pin supports 320, a wall 355 extending along and/or around an exterior and/or perimeter of the main body 316, and openings 323 in the wall 355. The wall 355 can extend along and/or around a portion of the main body 316 and/or can have a height which varies along the length of the wall 355.

The dock 304 of the disposable portion 303 can include one or more mechanical connector portions configured to secure (for example, removably secure) to one or more mechanical connector portions of the hub 306 of the reusable portion 305. For example, the main body 316 can include one or both of mechanical connector portions 317 and 318. The mechanical connector portion 317 can be, for example, a clip that can be configured to bend and/or flex. As discussed further below, the clip 317 can include a protrusions 340 that can extend in a direction towards the mechanical connector portion 318 (FIG. 3H). The mechanical connector portion 318 can extend outward from a portion of the main body 316. For example, the mechanical connector portion 318 can extend above a height of the wall 355. The mechanical connector portion 318 can include one or more protrusions 341 that can extend in a direction towards the mechanical connector portion 317 (FIG. 3H). The mechanical connector portions 317, 318 can assist coupling between the dock 304 and the hub 306. For example, the mechanical connector portions 317, 318 can engage corresponding mechanical connector portions of the hub 306 to hold the hub 306 in place. For example, as discussed below, the mechanical connector portions 317, 318 can removably secure within grooves 351, 352 of the hub 306. The interaction of the mechanical connector portions 317, 318 and corresponding mechanical connector portions of the hub 306 can advantageously maintain electrical communication between the dock 304 and the hub 306. The dock 304 of the disposable portion 303 can include one, two, three, or four or more mechanical connector portions and/or the hub 306 can include one, two, three, or four or more mechanical connector portions.

The mechanical connector portions 317, 318 may extend upward from outer edges of the main body 316 and/or adjacent or proximate the wall 355 as shown in FIG. 3E. The mechanical connector portions 317, 318 can be positioned opposite from each other (FIGS. 3E and 3H). In some variants, the dock 304 includes less than two mechanical connector portions or more than two mechanical connector portions. For example, in some variants, the dock 304 includes only one of mechanical connector portions 317, 318.

The pin supports 319, 320 of the dock 304 of the disposable portion 303 can support and/or operably position a plurality of electrical connectors of the disposable portion 303. For example, the pin supports 319, 320 can support and/or operably position conductive strips 344, 345 of the flexible circuit 325 of the dock 304. The pin supports 319, 320 can extend through openings or slits formed on a top surface of the main body 316. For example, as discussed below, the main body 316 can comprise a top frame 324 having one or more slits 336 and/or opening 337 and a bottom frame 327 which can include the one or more pin supports 319, 320. The one or more pins supports 319, 320 can extend from the bottom frame 327 and through the slits 336 and opening 337 (respectively) of the top frame 324 when the main body 316 is assembled. The slits 336 and/or opening 337 formed on the top surface of the main body 316 can be rectangular or substantially rectangular in shape. The pin supports 319, 320 can be arcuate and/or can include an upward portion, an apex, and a downward portion. The upward portions of the pin supports 319, 320 can extend upward with respect to and/or beyond the top surface of the main body 316 (for example, a top surface of the top frame 324 and/or bottom frame 327) at a predetermined angle. The upper portions of the pin supports 319, 320 can terminate at the apex, from which the downward portions of the pin supports 319, 320 can extend downward towards the top surface of the main body 316 at another predetermined angle. Such configuration of the pin supports 319, 320 can allow them to function like springs when downward force is applied to the pin supports 319, 320. Optionally, the pin supports 319, 320 may not have the downward portions. The pins supports 319, 320 can be flexible and/or resilient.

The pin supports 319 can correspond and/or be associated with electrical connectors of the disposable portion 303. For example, the pin supports 319 can correspond and/or be associated with conductive strips 344 of the flexible circuit 325 (see FIGS. 3F and 3I) that carry electronic signals associated with the one or more external electrodes 312 and/or the one or more internal electrodes 311. For example, as shown in FIG. 3E, the dock 304 can have six support pins 319 that support six conductive strips 344 of the flexible circuit 325, which can carry electronic signals from four external electrodes 312 (via cables 314) and two internal electrodes 311.

Similar to the pin supports 319, the pin supports 320 can correspond and/or be associated with electrical connectors of the disposable portion 303. For example, the pin supports 320 can correspond and/or be associated with conductive strips 345 of the flexible circuit 325 (see FIGS. 3F and 3I) that allow transmission of electronic signals and/or information between the dock 304 and the memory 308 of the hub 306. The flexible circuit 325 can comprise and/or be coupled to a memory (such as an PROM, EPROM, EEPROM, SRAM, and/or DRAM memory) of the disposable portion 303 configured to store information related to the disposable portion 303. The conductive strips 345 of the flexible circuit 325 can be coupled to such memory. Advantageously, the pin supports 320 can support and/or operably position the conductive strips 345 so that they contact conductor pins of the hub 306 (such as conductive pins 354), which can enable the hub 306 to determine whether the dock 304 is an authorized product.

As discussed above, the dock 304 can include one or more openings 323 in portions of the main body 316 that are configured to allow portions of the cables 314 to pass into an interior of the dock 304. For example, as discussed above, the main body 316 can include one or more openings 323 in the wall 355. The dock 304 can include one, two, three, four, five, six, seven, or eight or more openings 323. The openings 323 can be sized and/or shaped to receive portions of the cables 314 coupled to the external electrodes 312. The openings 323 can be formed on a side of the main body 316. For example, as shown in FIG. 3E, the openings 323 can be formed on a front side (or "end") of the main body 316. Alternatively, the openings 323 can be formed on different sides or portions of the main body 316. The number of the openings 323 can correspond to the number of external electrodes 312 coupled to the dock 304 and/or number of cables 314. For example, as shown in FIG. 3B, the dock 304 of the disposable device 303 can include four external electrodes 312. In this regard, the dock 304 can include four openings 323 configured to receive four cables 314 coupled to four external electrodes 312. While FIG. 3E illustrates four openings 323, four cables 314, and four external electrodes 312, a different number of electrodes 312, openings 323 and/or cables 314 can be implemented into the disposable portion 303. The openings 323 can be dimensioned to create a tight fit with the cables 314. Such configuration can be advantageous in allowing the dock 304 to be water-resistant and/or waterproof. Additionally or alternatively, such configuration can help maintain integrity of connections between the cables 314 and the openings 323. For example, a tight fit between the openings 323 and portions of the cables 314 can reduce the likelihood that ends of the cables 314 connected to the flexible circuit 325 (for example, to conductive strips 343) are disconnected when opposite ends of the cables 314 are pulled, either inadvertently or intentionally.

FIGS. 3F and 3G show exploded perspective views of the dock 304 of the disposable portion 303. The dock 304 can include a top frame 324, the flexible circuit 325, the one or more internal electrodes 311, a substrate 328, a substrate 329, a bottom frame 327, one or more adhesives 322, a substrate 330, and a substrate 331. Advantageously, the parts illustrated in the FIGS. 3F and 3G may be laid on top of each other without folding, resulting in an increased efficiency of manufacturing process of the ECG device 310. The top and bottom frames 324, 327 can together form and/or define the main body 316, which is discussed above with reference to FIG. 3E. Further, the top frame 324 can include the wall 355 also discussed above.

The top frame 324 can be coupled to the bottom frame 327 such that the top frame 324 sits on top of the bottom frame 327. The top frame 324 can include a recessed portion 335 formed on a top surface of the top frame 324. The recessed portion 335 can include an aperture 338 (see FIGS. 3F-3G) that is formed at the bottom portion of the recessed portion 335.

The bottom frame 327 can include an aperture 332 and one or more apertures 333. The aperture 332 of the bottom frame 327 can correspond and/or align with the recessed portion 335 of the top frame 324 such that when the top frame 324 is placed on the bottom frame 327, the aperture 332 receives the recessed portion 335 and the recessed portion 335 extends through and/or below the aperture 332. As discussed below, this can advantageously allow a portion of the reusable portion 305 and the temperature sensor 309 to be positioned closer to the substrates 330 and/or 331, which can in turn increase thermal communication between a user's skin and the temperature sensor 309.

As discussed above, the dock 304 can include the pin supports 319, 320. As shown in FIG. 3F, the pin supports 319, 320 can be formed on the bottom frame 327. The top frame 324 can include slits 336 and/or opening 337 that can receive the pin supports 319, 320 of the bottom frame 327, respectively. When the top frame 324 is placed on top of the bottom frame 327, the pin supports 319, 320 can extend through and/or above the slits 336 and/or opening 337 of the top frame 324.

The flexible circuit 325 can be placed and/or positioned between the top frame 324 and the bottom frame 327 (see FIGS. 3F-3G). For example, the flexible circuit 325 can be sandwiched between the top and bottom frames 324, 327 during assembly. The bottom frame 327 can operably position the flexible circuit 325 and/or portions thereof such that electrical communication between the flexible circuit 325 and a circuit board or flexible circuit of the reusable portion 305 is facilitated when the reusable portion 305 is secured to the disposable portion 303. For example, the pin supports 319 of the bottom frame 327 can operably position conductive strips 344 of the flexible circuit 325 so that the conductive strips 344 contact conductor pins 353 of the reusable portion 305. Additionally or alternatively, the pin supports 320 of the bottom frame 327 can operably position conductive strips 345 of the flexible circuit 325 such that the conductive strips 345 contact conductor pins 354 of the reusable portion 205 when the reusable portion 205 is mated with the disposable portion 303. Such contact can allow the flexible circuit 325 to transmit information and/or physiological data between the disposable device 303 and the reusable device 305. Additional details of the flexible circuit 325 are provided below.

With reference to FIG. 3F, the internal electrodes 311 can be placed and/or positioned at least partially between the top frame 324 and the bottom frame 327. The internal electrodes 311 can be removably coupled to the flexible circuit 325. The internal electrodes 311 can be placed within the apertures 333 and the apertures 333 can be dimensioned to receive the internal electrodes 311 (and/or portions thereof).

As discussed above, the dock 304 of the disposable portion 303 can include a laminate structure 321. As also discussed, the laminate structure 321 can include one or more substrates, such as substrates 328, 329, 330, and/or 331. Substrate 328 can be, for example, a foam membrane or ring configured to surround the top and/or bottom frames 324, 327 when the dock 304 is assembled. Substrate 328 can include an opening sized and/or shaped to match a size and/or shape of a perimeter of the top and/or bottom frames 324, 327 (see FIGS. 3F-3G). Substrates 329, 330, 331 can be made of a material that that can provide thermal and/or electrical isolation or alternatively, conductivity. Substrates 328, 329, 330, 331 can be made of different materials or the same material. Substrates 329 and/or 330 can be, for example, polyethylene (PE) film.

With reference to FIGS. 3F-3G, the adhesives 322 can be affixed to a bottom surface of the bottom frame 327 to adhere the bottom frame 327 to the substrate 330. The substrate 330 can be adhered to the substrate 331. One or more apertures 334 can be formed on the substrate 330. The substrate 330 can include one, two, three, or four or more apertures 334. The number of apertures 334 can correspond to the number of internal electrodes 311. The apertures 334 can be dimensioned to receive the one or more internal electrodes 311. The substrate 330 can provide electrical isolation between the dock 304 and the patient 111, for example, in areas outside and/or around the apertures 334. The apertures 334 can allow the internal electrodes 311 to collect raw ECG data without electrical impedance or isolation provided by the substrate 330.

Substrate 331 can provide thermal and/or electrical conductivity between the dock 304 and the patient 11. Substrate 331 can be the only substrate between the internal electrodes 311 and the patient 11. The apertures 333 of the bottom frame 327 and apertures 334 of the substrate 330 can advantageously allow the internal electrodes 311 to measure electrocardiogram data from the patient 111 without any unnecessary electrical resistance and/or impedance. The substrate 331 can comprise hydrogel, for example.

FIG. 3H illustrates a side view of the dock 304 of the disposable portion 303. As discussed above, the dock 304 can include one or both of mechanical connector portions 317, 318. The mechanical connector portions 317, 318 can include protrusions 340, 341, respectively. The protrusions 340, 341 can be positioned at free (for example, cantilevered) ends of the mechanical connector portions 317, 318, such as ends opposite to ends connected to portions of dock 304 (such as the main body 316). The protrusions 340, 341 can engage the grooves 352, 351 of the hub 306 (see FIGS. 3J-3K) to removably secure the hub 306 to the dock 304. When the hub 306 is mated with the dock 304, the hub 306 can be positioned at least partially between the mechanical connector portions 317, 318. The engagement between the protrusions 340, 341 and the grooves 352, 351 can prevent movement of the hub 306 in horizontal and/or vertical directions while mated with the dock 304.

FIG. 3I illustrates a top view of the flexible circuit 325. The flexible circuit 325 can include numerous conductive surfaces and/or strips. For example, the flexible circuit 325 can include conductor strips 343, 344, 345, and/or 346. The conductor strips 343 can electrically connect to the cables 314 which can themselves be electrically connected to the external electrodes 312. In this regard, the conductor strips 343 can receive electrical signals from the external electrodes 312 via the cables 314. The cables 314 can be soldered to the corresponding conductive strips 343. The conductor strips 346 (also referred to herein as "conductive rings") can be formed around and/or within apertures 347, as shown in FIG. 3I. The conductive rings 346 can create contact with and receive electrical signals from the internal electrodes 311. The apertures 347 can receive a top portion of the internal electrodes 311, creating contact between the conductor strips 346 and the internal electrodes 311 which allows the flexible circuit 325 to receive ECG data from the internal electrodes 311.

The conductor strips 345 can establish electrical communication between the dock 304 and the memory 308 of the reusable device 305. The conductor strips 345 of the flexible circuit 325 can be positioned adjacent to (for example, on top of) the pin supports 320. The pin supports 320 supporting the conductor strips 345 can be oriented such that when the hub 306 is mated with the dock 304, conductor pins 354 (see FIG. 3L) of the hub 306 contact the conductor strips 345. The memory 308 of the reusable device 305 can be coupled to the conductor pins 354 such that contact between the conductor strips 345 and the conductor pins 354 allow electronic signals and/or information to be transmitted from the disposable device 303 to the memory 308 of the reusable device 305. Advantageously, the conductive strips 345 can be utilized to enable verification of whether the disposable portion 303 is an authorized product. For example, when the reusable portion 205 is electronically and/or mechanically mated to the disposable portion 303 such that contact is made between the conductive strips 345 and the conductor pins 354, the reusable portion 205 can determine whether the disposable portion 303 is an authorized product by analyzing information contained within a memory of the flexible circuit 325 of the disposable portion 303. As discussed above, the memory of the flexible circuit 325 can be an PROM, EPROM, EEPROM, SRAM, and/or DRAM memory configured to store information related to the disposable portion 303. Such determination can prevent damage to the reusable device 305 that may occur if an unauthorized product is secured thereto. Such determination can additionally or alternatively ensure proper functionality of the reusable device 305.

The conductor strips 344 can be in electronic communication with the conductor strips 343, 346 such that they can receive electrocardiogram data from the external electrodes 312 and the internal electrodes 311. The conductor strips 344 of the flexible circuit 325 can be positioned on top of the pin supports 319. The pin supports 319 supporting the conductor strips 344 can be oriented such that when the hub 306 is mated with the dock 304, conductor pins 353 (see FIG. 3L) of the hub 306 can contact the conductor strips 344. The contact between the conductor strips 344 and the conductor pins 353 can allow electronic signals to be transmitted from the disposable device 303 to the processor 307 of the reusable device 305. The processor 307 of the reusable device 305 can be coupled to the conductor pins 353 to receive the electronic signals from the disposable device 303 via the conductor strips 344. The number of conductive strips 344 can correspond with the total number of conductive strips 343, 346. Each of one of the conductor strips 343 and conductor strips 346 can be associated with a different one of the conductor strips 344 of the flexible circuit 325.

Figure 3L:
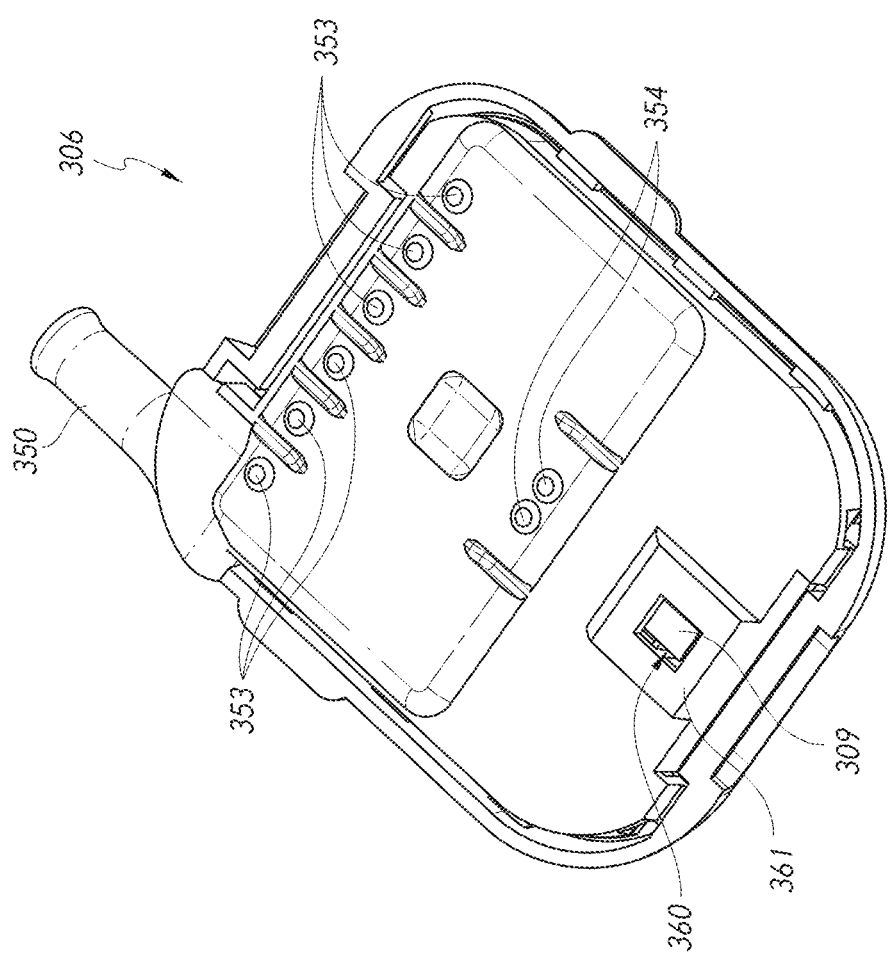
FIG. 3L illustrates a bottom perspective view of the hub of FIGS. 3J-3K.

FIGS. 3J-3L illustrate various perspective views of the hub 306 of the reusable portion 205. As shown, the hub 306 can include a cable outlet (also referred to herein as an "output connector port") 350, one or more mechanical connector portions, among other components discussed further below. The one or more mechanical connector portions can allow the reusable portion 305 to mate with the disposable portion 303. The one or more mechanical connector portions can be, for example, grooves 351, 352. The grooves 351, 352, the conductor pins 353, 354, and the temperature sensor 309. The grooves 351, 352 can be formed on the same or different side of the hub 306. For example, as shown in FIGS. 3J and 3K, the grooves 351, 352 can be positioned opposite from each other on opposite ends of the hub 306. As discussed above, the grooves 351, 352 can interact with the protrusions 340, 341 of the mechanical connector portions 317, 318, respectively, to removably secure the dock 304 and the hub 306. The grooves 351, 352 can be dimensioned and/or shaped to engage the protrusions 340, 341, respectively. For example, the mechanical connector portions 317, 318 can snap towards and/or within the grooves 351, 352 to cause the protrusions 340, 341 to engage with the grooves 351, 352.

The reusable portion 305 can include one or more electrical connectors configured to connect to one or more electrical connectors of the disposable portion 303 when secured thereto. For example, with reference to FIG. 3L, the hub 306 can include one or more conductor pins 353, 354 disposed proximate to a bottom surface of the hub 306 such that when the hub 306 is coupled with the dock 304, the conductor pins 353, 354 can be in contact with the conductor strips 344, 345, respectively. The contact between the pins 353, 354 and the strips 344, 345 allows information and/or electrical signals to be transmitted from the disposable portion 303 to the reusable portion 305. As discussed above, the contact between the conductor strips 344 and the conductor pins 353 can allow transmission of electrical signals between the dock 304 and the processor 307 of the reusable portion 305. The contact between the conductor strips 345 and the conductor pins 354 can allow transmission of information between the a memory of the dock 304 (for example, a memory of the flexible circuit 325) and the memory 308 of the reusable portion 305.

The hub 306 can include a recessed portion 361. The recessed portion 361 can be, for example, formed in the bottom frame 357. The recessed portion 361 can be recessed from a top surface of the bottom frame 357 (FIGS. 3L and 3N) and can extend outward (for example, below) a bottom surface of the bottom frame 357. The recessed portion 361 can include an opening 360 formed at an end or bottom of the recessed portion 361. The recessed portion 361 can be shaped, dimensioned, and/or positioned on the bottom surface of the hub 306 such that the recessed portion 335 of the dock 304 (FIG. 3E) can receive the recessed portion 361 when the dock 304 is coupled to hub 306. The recessed portion 361 can receive and/or house the temperature sensor 309. The temperature sensor 309 can be positioned at a predetermined distance from a bottom portion of the recessed portion 361 and/or the opening 360. As discussed below, the recessed portion 361 can extend through an opening in the dock 304 and can contact the substrate 330 and/or 331. The recessed portion 361 of the dock 304 can comprise a material that provides thermal conductivity but minimizes or prevents electrical conductivity. This can advantageously allow the recessed portion 361 to facilitate thermal communication between the patient's skin and the temperature sensor 309 and simultaneously minimize or eliminate damage and/or interference that may be caused from electrical interference. As an example, the recessed portion 361 can comprise a plastic coated with and/or comprising boron nitride.

Figure 3M:
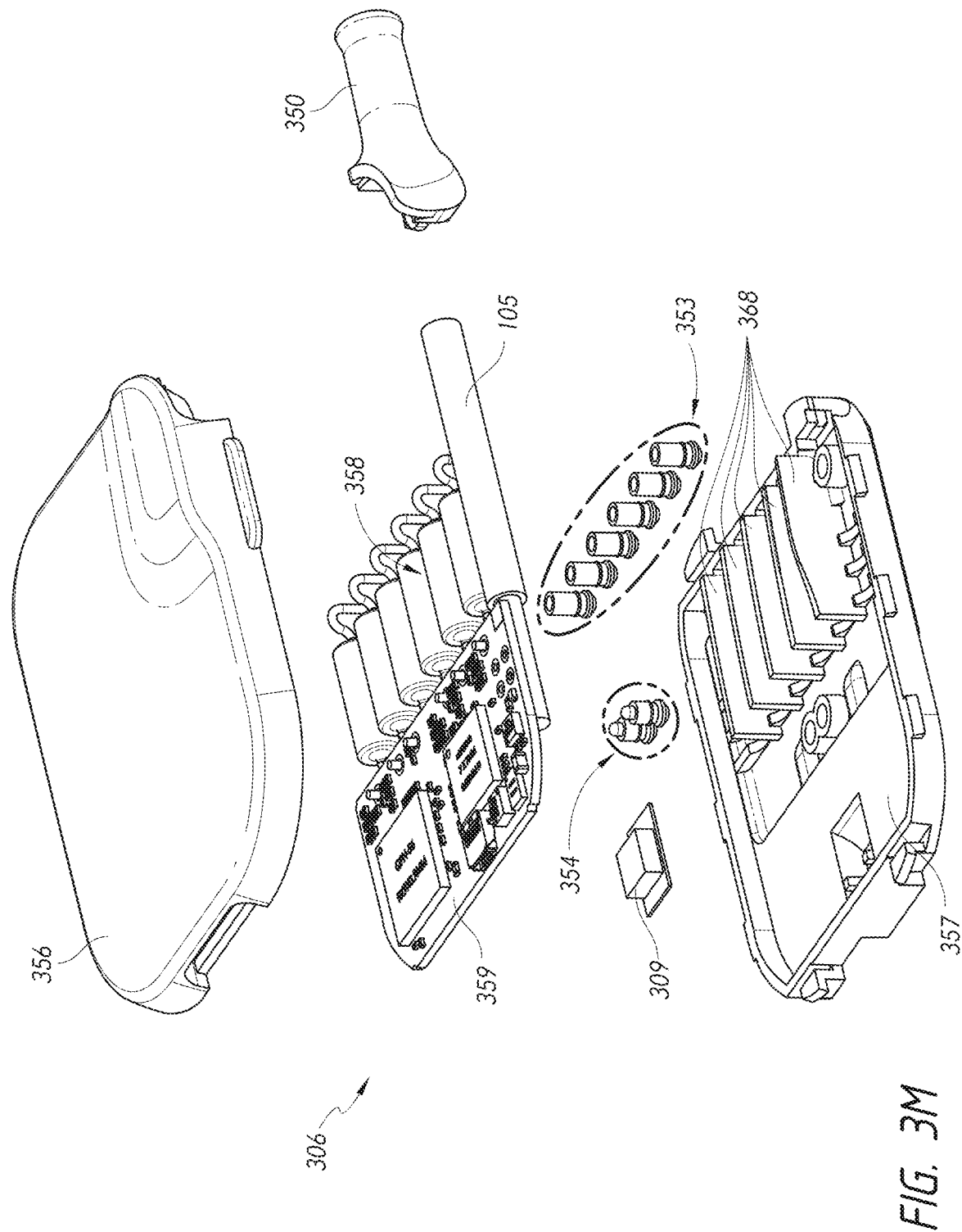
FIG. 3M illustrates an exploded, top perspective view of the hub of FIGS. 3J and 3K.
Figure 3N:
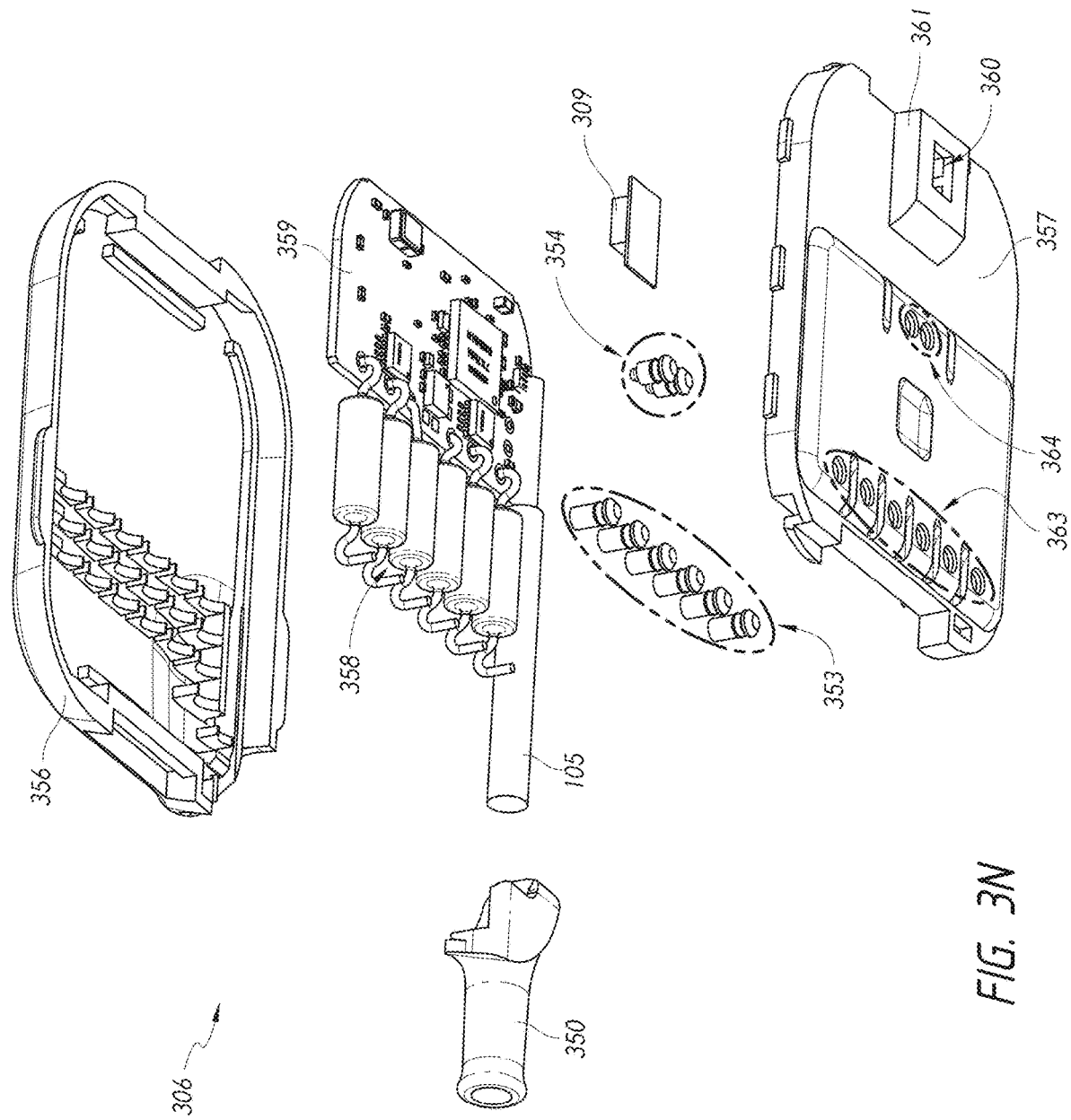
FIG. 3N illustrates an exploded, bottom perspective view of the hub of FIGS. 3J and 3K.
Figure 30:
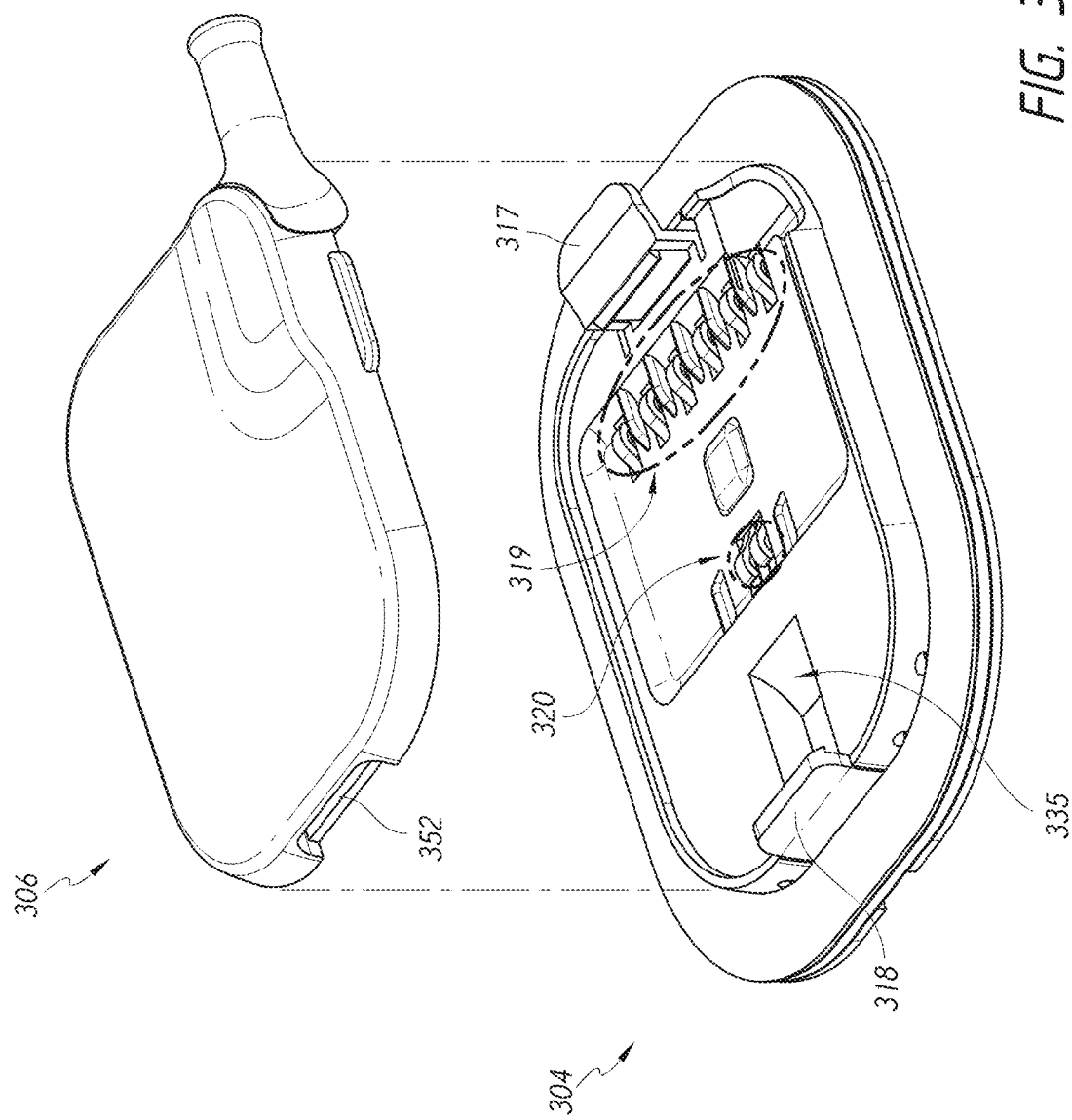

FIGS. 3M and 3N illustrate various exploded, perspective views of the hub 306 of the reusable device 305. The hub 306 (also referred to herein as "cover") can include a top frame 356 and a bottom frame 357. The hub 306 can further include one or more resistors 358, a circuit board 359, the conductor pins 353, the conductor pins 354, the temperature sensor 309, and the cable outlet 350. The bottom frame 357 can include apertures 363 and/or apertures 364 (also referred to herein as "cavities"). The apertures 363, 364 can extend through the bottom frame 357 and receive the conductor pins 353 and the conductor pins 354, respectively. The apertures 363, 364 can be dimensioned and sized such that the conductor pins 353, 354 create water-resistant seal when received by the apertures 363, 364.

The circuit board 359 can include the processor 307 and the memory 308. The circuit board 359 can be operatively coupled to the external electrodes 312, the internal electrodes 311, and the temperature sensor 309 in order to receive electrocardiogram data and temperature data. The hub 506 can include one or more resistors 358 coupled to the circuit board 359 and/or the conductor pins 353. The hub 506 can include one, two, three, four, five, six, seven, or eight or more resistors 358. The number of resistors 358 can correspond with the number of conductor pins 353 and/or the total number of external and internal electrodes 312, 311. The resistors 358 can be positioned between the circuit board 359 and the conductor pins 353. Advantageously, the resistors 358 can prevent or reduce the damage to the circuit board 359 (or other components of the reusable device 305) due to shorting or arcing, which may be caused when high voltage is accidentally and/or suddenly introduced via the conductor pins 353, for example, if the reusable device 305 is positioned on or proximate to a patient when a defibrillator is used. For example, the resistors 358 can be high-capacity, low-resistance resistors that allow electronic signals related to a user's cardiac electrical activity to pass therethrough but inhibit high voltage from passing to the circuit board 359 and/or other components of the reusable device 305. The resistors 358 can be soldered directly to the circuit board 359 and/or the conductive pins 353. As shown in FIG. 3M, the hub 306 can include one or more walls 368 configured to separate each of the one or more resistors 1358.

FIG. 3O illustrates a top, perspective view of the hub 306 and the dock 304, illustrating how the hub 306 and the dock 304 can be coupled (for example, removably coupled). The dock 304 can removably secure to the hub 306 via engagement between the mechanical connector portions 217, 218, 252, 251 as discussed above. When the dock 304 and the hub 306 are secured in such manner, the conductor pins 353, 354 (see FIG. 2L) of the hub 306 can engage the pin supports 319, 320 (see FIG. 3E), respectively. As discussed above, the conductive strips 344, 345 of the flexible circuit 325 can be supported by the pin supports 319, 320. Accordingly, when the dock 304 and the hub 306 are secured in such manner, the conductive strips 344, 345 can contact the conductor pins 353, 354 of the hub 306. The contact between the conductive strips 344, 345 and the conductor pins 353, 354 can allow electronic signals and/or information to be transmitted from the dock 304 of the disposable device 303 to the hub 306 of the reusable device 305. Additionally, when the dock 304 and the hub 306 are secured in such manner, the recessed portion 335 and the recessed portion 361 can be aligned (see FIGS. 3N-3O). The recessed portion 335 can be sized and/or shaped to receive the recessed portion 361. The aperture 360 of the recessed portion 361 (see FIG. 3N) and the aperture 338 of the recessed portion 335 (see FIG. 3F-3G) can be aligned such that the apertures 360, 338 define an open space and/or area below the temperature sensor 309. In such configuration, the recessed portion 261 can contact the substrate 334 when the reusable and disposable portions 305, 303 are mated. The apertures 338, 360 can be vertically aligned, for example.

Figure 3P:
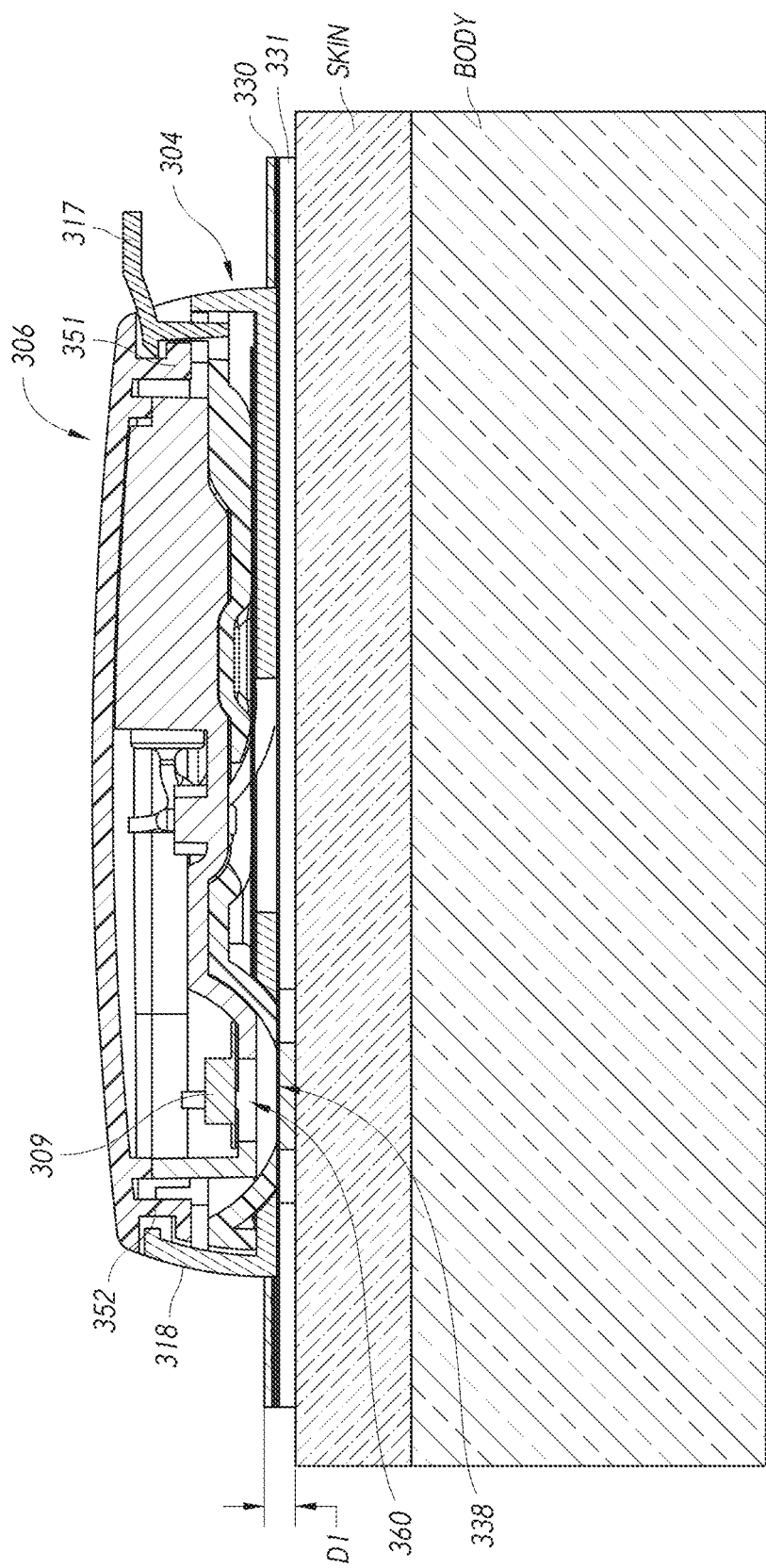
FIG. 3P illustrates a side, cross-sectional view of the ECG device of FIG. 3A on a patient, showing relative position of a temperature sensor with respect to the patient in accordance with aspects of this disclosure.
Figure 3Q:
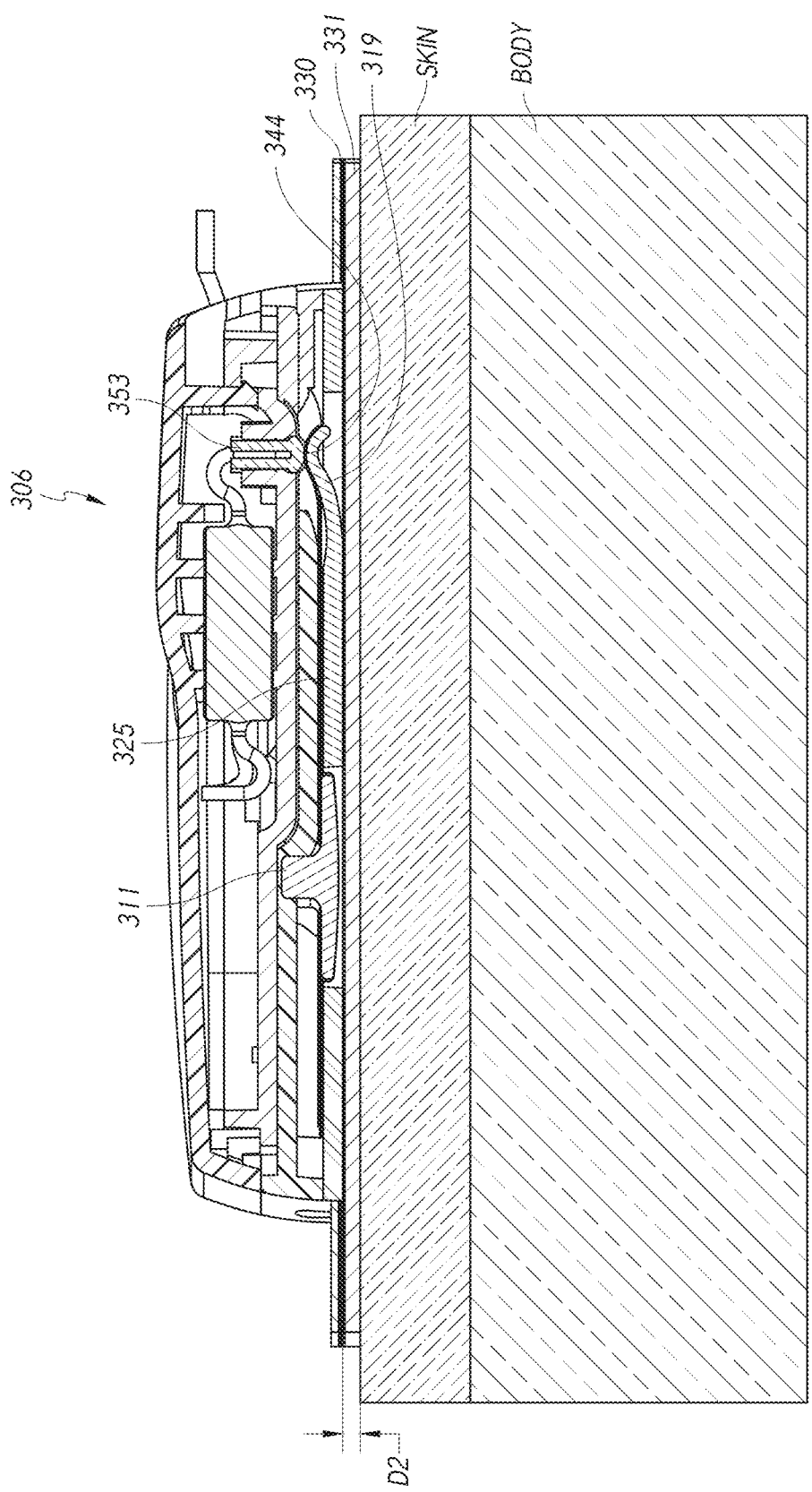
FIG. 3Q illustrates a side, cross-sectional view of the ECG device of FIG. 3A on a patient, showing relative position of an internal electrode of the ECG device with respect to the patient in accordance with aspects of this disclosure.
Figure 3R:
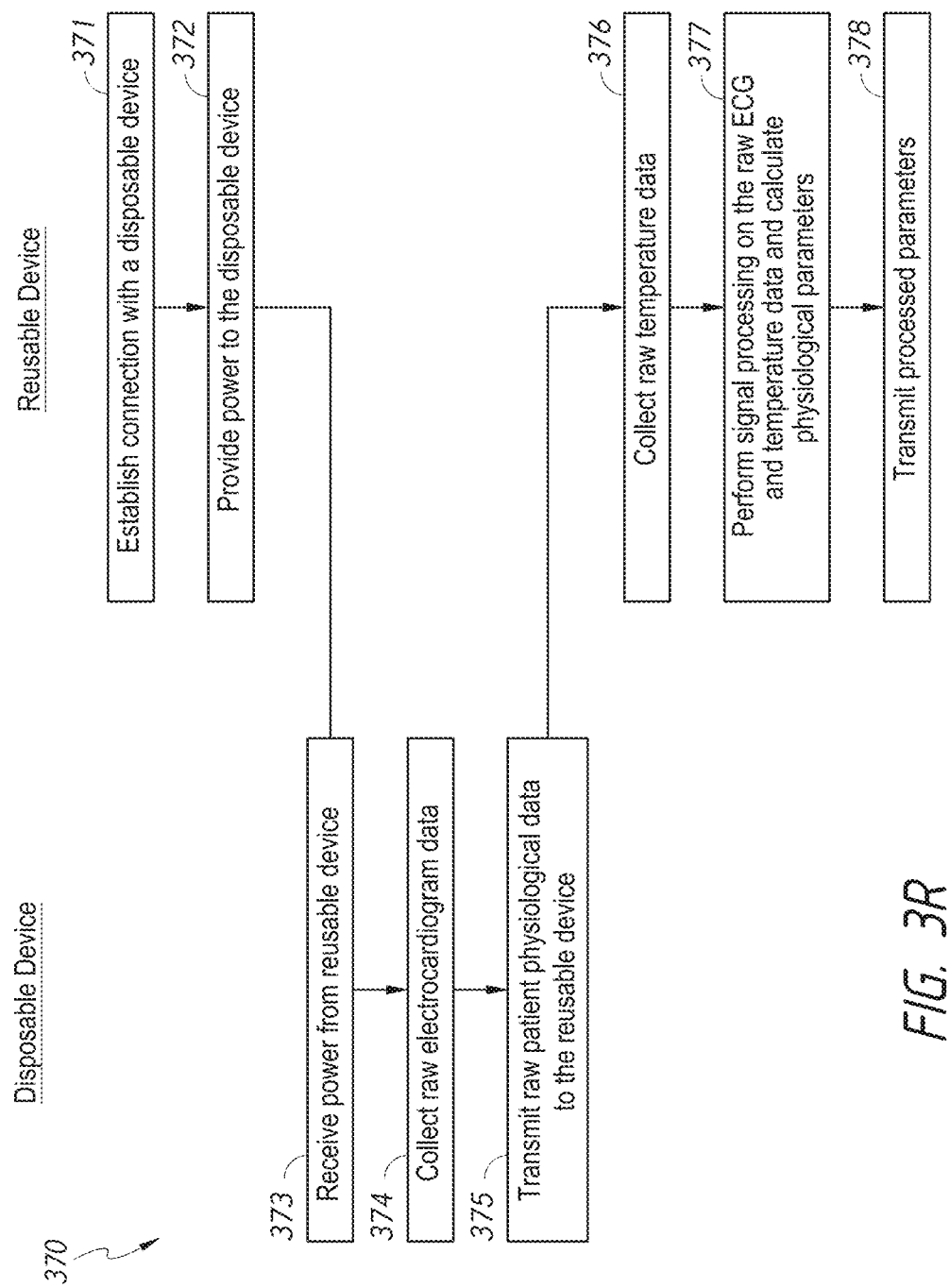
FIG. 3R illustrates a block diagram depicting a method of collecting physiological data using the ECG of FIG. 3A in accordance with aspects of this disclosure.

FIGS. 3P and 3Q illustrate cross-sectional views of the ECG device 310 placed on a patient's skin, showing relative positions of the temperature sensor 309 and an internal electrode 311, respectively, with respect to a patient's skin.

The temperature sensor 309 can be positioned a distance D1 away from an outer surface of a patient's skin. The distance D1 can be equal to the distance between the bottom-most portion of the temperature sensor 309 and a bottom surface of the substrate 331, for example. In this regard, the temperature sensor 309 may not be in direct contact with the skin of the patient. The aperture 360 of the recessed portion 361 (see FIG. 3N) and the aperture 338 of the recessed portion 335 can allow the temperature sensor 309 to collect temperature data from the patient.

With reference to FIG. 3Q, the internal electrodes 311 can be positioned a distance D2 away from the outer surface of the patient's skin. The distance D2 can be equal to the distance between the bottom-most portion of the internal electrodes 311 and the bottom surface of the substrate 331. In this regard, the internal electrodes 311 may not be in direct contact with the skin of the patient. For example, the substrate 331 can be positioned between the internal electrodes 311 and the patient's skin. Substrate 331 can comprise an electrically conductive material that facilitates transmission of electrical signals from the patient's heart to the internal electrodes 311. The laminate structure 221 can include a release liner similar or identical to release liner 239 discussed above with reference to ECG device 110 and FIGS. 2F-2G).

The distance D2 and the distance D1 can be the same or different. For example, D2 can be less than D1. In another example, D2 can be greater than D2.

FIG. 2R illustrates a block diagram representing a method 370 of determining patient physiological parameters using the ECG device 310. At step 371, the reusable device 305 establishes connection with the disposable device 303. This can occur when the reusable device is mechanically mated with the disposable device 303. The connection between the reusable device 305 and the disposable device 303 can be established via contact between the conductive pins 353, 354 and the conductive strips 344, 345 supported by pin supports 319, 320 as discussed above. The contact between the conductive pins 353, 354 and the conductive strips 344, 345 can occur when the hub 306 of the reusable device 305 is mounted on the dock 304 of the disposable device 303. At step 372, the reusable device 305 can provide power to the disposable device 303. The power provided by the reusable device 305 can power the external and internal electrodes 312, 311 to collect electrocardiogram data. In some variants, the disposable portion 303 does not comprise a power source and relies entirely on the reusable device 305 to collect electrocardiogram data.

At step 373, the disposable device 303 receives power from the reusable device 305. At step 374, the disposable device 303 uses the one or more external electrodes 312 and/or the one or more internal electrodes 311 to collect raw ECG data from the patient. At step 375, the raw ECG data collected by the external electrodes 312 and/or the internal electrodes 311 can be transmitted to the reusable device 305. The raw ECG data can be transmitted via the flexible circuit 325 as discussed above. The raw ECG data can be transmitted from the disposable device 303 to the reusable device 305 automatically or manually upon user input. The raw ECG data can be transmitted continuously or with a predetermined delay.

At step 376, the reusable device 305 can collect raw temperature data. The raw temperature data can be collected by the temperature sensor 309. The raw temperature data can be collected simultaneously or non-simultaneously from the raw ECG data. For example, the reusable device 305 can collect the raw temperature data regardless of whether the disposable device is collecting and/or transmitting the raw ECG data.

Care providers may be able to configure the ECG device 310 to determine which physiological data to be collected in different circumstances. The ECG device 310 can be configured to collect and process temperature-related physiological data in certain, predetermined situations. For example, the ECG device 310 can be configured to measure temperature of a patient when it detects ECG signals associated with irregular heart activities and/or bodily conditions. For example, the ECG device 310 can be configured to measure temperature of a patient when a variation in ECG signals over a predetermined time period exceeds a threshold value. In another example, the ECG device 310 can be configured to collect ECG data from a patient when a temperature measurement exceeds or falls below a threshold value, which can be indicative of an abnormal condition. Other types information related to different patient parameters and/or conditions can be used to trigger the ECG device 310 to collect ECG and/or temperature data.

At step 377, the reusable device 305 (for example, the processor 307) can perform signal processing on the raw ECG and temperature data to determine physiological parameters related to a patient's heart activity and temperature. At step 378, the reusable device 305 of the ECG device 310 can transmit the physiological parameters to other patient monitoring systems and/or devices via wires or various wireless communication protocols.

In some variants, the ECG device 310 is waterproof or water-resistant. For example, the reusable device 305 and/or the disposable device 303 can be configured such that, when secured to one another, they prevent water from entering into an interior thereof. This can minimize or prevent damage to the reusable device 305 and/or the disposable device 303 and/or components thereof (such as the temperature sensor 309, the internal electrodes 311, and/or the circuit board 359).

In some variants, other portions of the ECG device 310 comprise a material that provides thermal conductivity but minimize or prevent electrical conductivity, such as boron nitride. For example, portions of the dock 304 and/or the hub 306 can be made with plastic coated with boron nitride. In some variants, portions of the ECG device 310 (for example, the dock 304 and/or the hub 306) comprise materials that provide temperature isolation. For example, the dock 304 and the hub 306 can be manufactured using coated fiberglass.

ECG Packaging

Figure 4A:
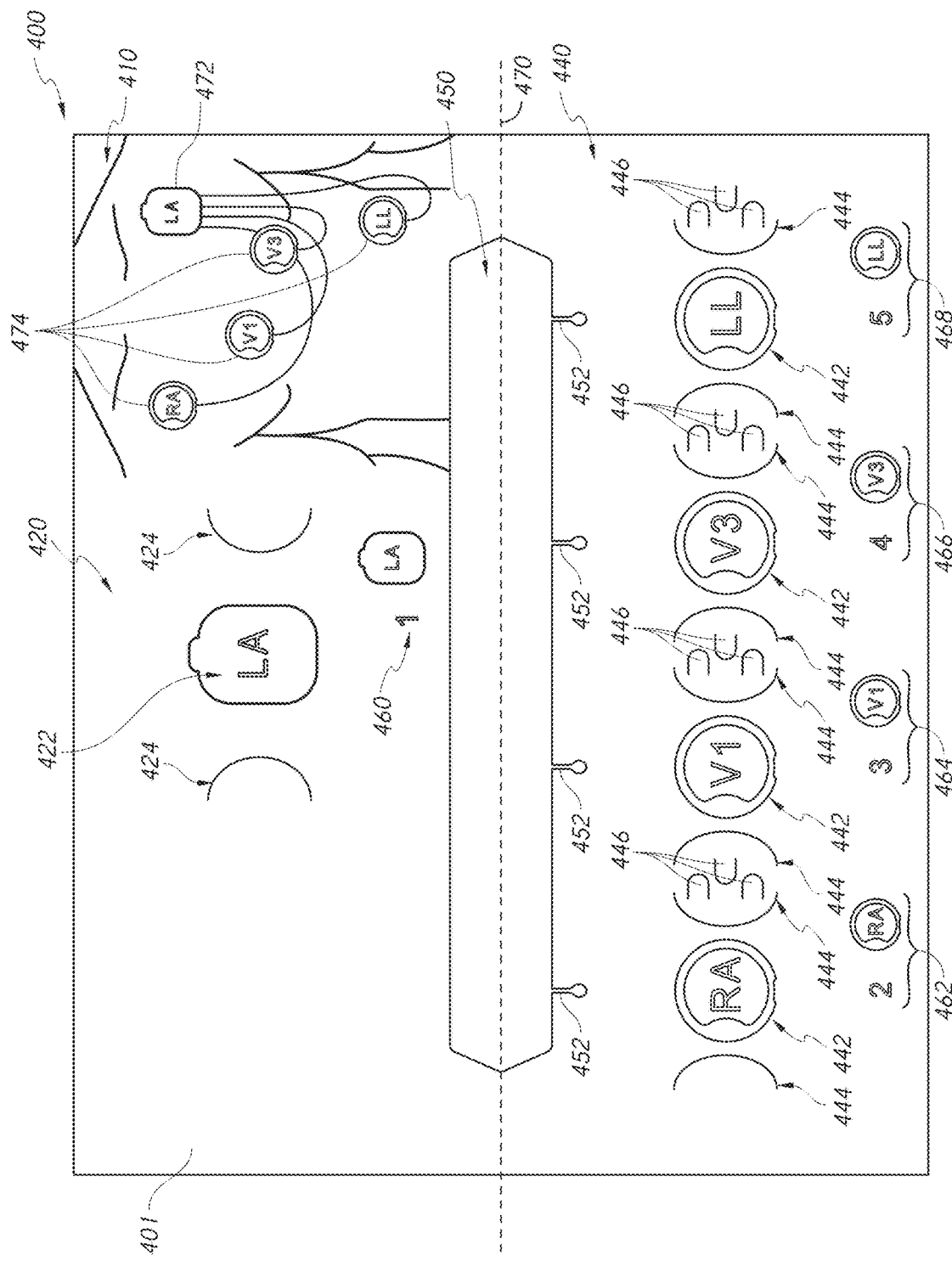
FIGS. 4A-4C illustrates various views of an ECG packaging device in accordance with aspects of this disclosure.
Figure 4B:
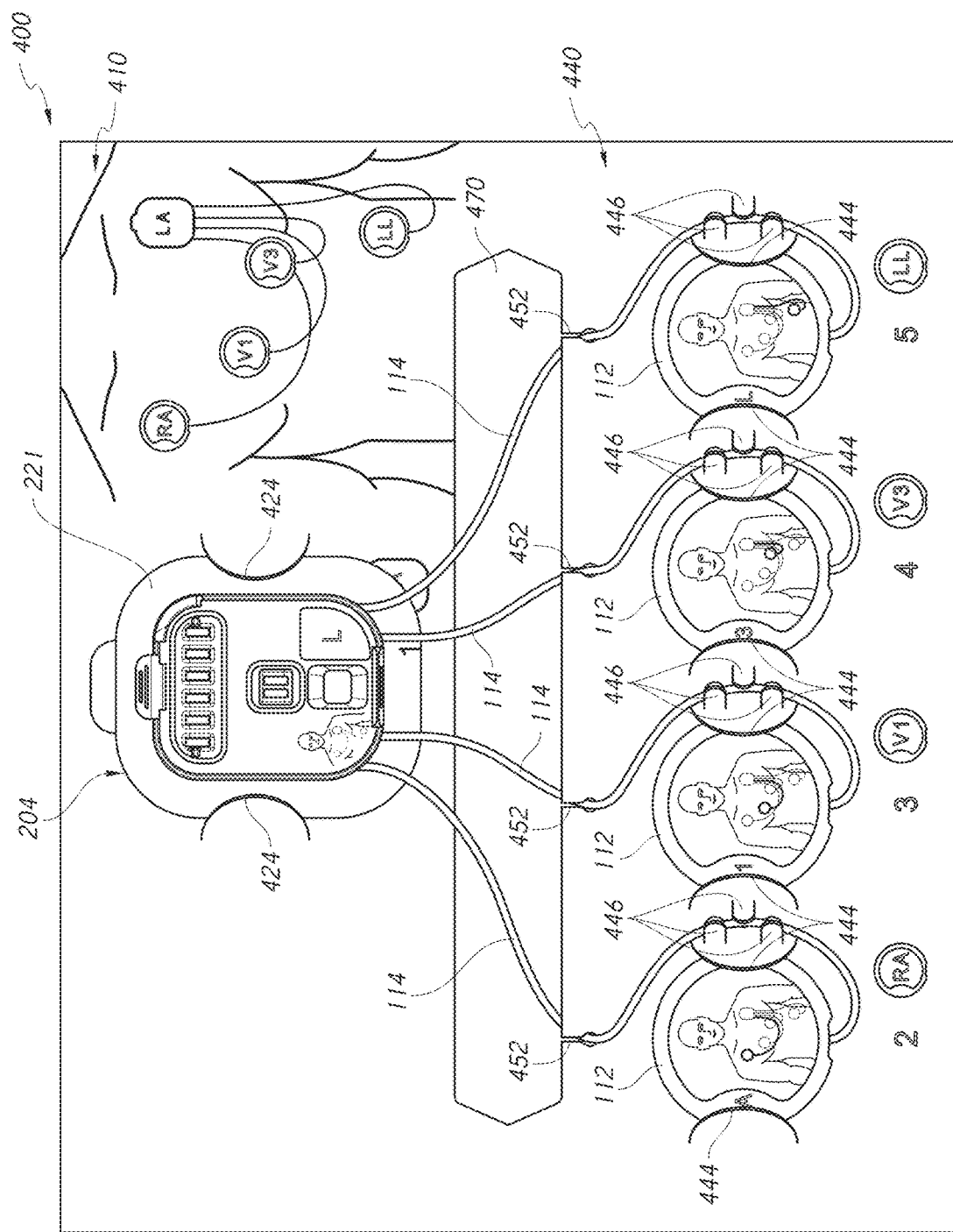
Figure 4C:
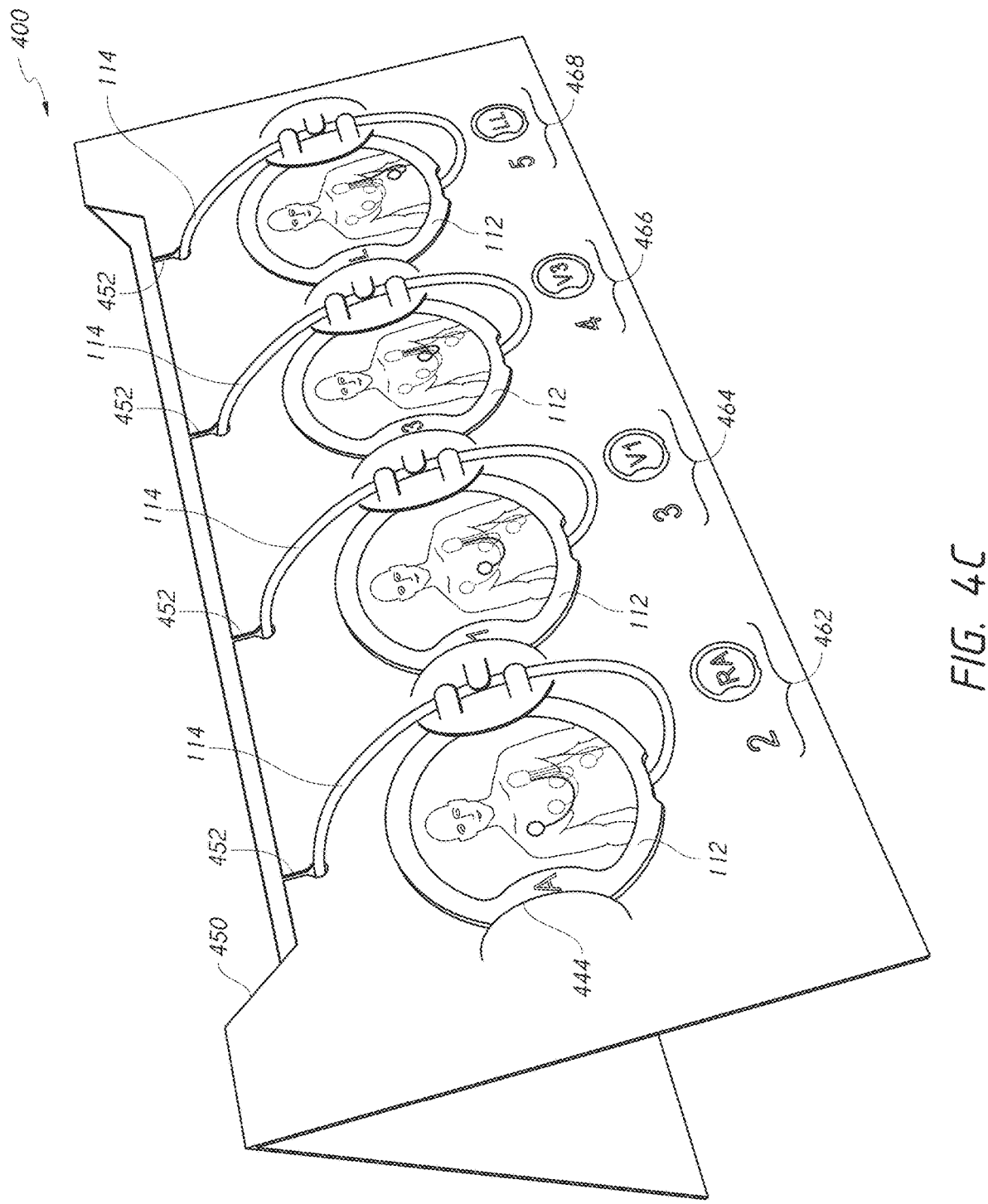

FIGS. 4A-4C illustrate views of a packaging device 400 (also referred to herein as an "ECG packaging device") that can be used to secure and/or package portions of the ECG device 110. For example, the packaging device 400 can be used to secure and/or package the disposable portion 203 of the ECG device 110. While FIGS. 4A-4C illustrate the ECG device 110 or portions thereof, it is to be understood that the ECG device 310 or portions thereof (for example, the disposable portion 303) can be secured and/or can interact with the packaging device 400 in a similar or identical manner. Accordingly, the discussion that follows below with reference to disposable device 203 of ECG device 110 is equally applicable to the disposable device 303 of ECG device 310.

With reference to FIG. 4A, the packaging device 400 can include a body placement indicator portion 410 and one or more disposable device securement portions, for example, a dock securement portion 420 and/or an electrode securement portion 440. The packaging device 400 can include an opening 450 extending along an interior of a portion of the packaging device 400 that can allow flexing and/or bending of the device 400, for example, as shown in FIG. 4C. The opening 450 can extend along a centerline axis 470 of the device 400 as shown. In such configuration, when the device 400 is bent as shown in FIG. 4C, the device 400 can be split in half and can stand upright and/or partially upright. As shown, one half can include the body placement indicator portion 410 and/or the dock securement portion 420, and the other half can include the electrode securement portion 440.

The dock securement portion 420 can be configured to secure (for example, removably secure) the dock 204 of the disposable device 203. The dock securement portion 420 can include a placement indicator 422 and one or more prongs 424, for example, one, two, three, four, five, or six or more prongs 424. As an example, the dock securement portion 420 can include two prongs 424 positioned opposite one another about the placement indicator 422 (FIG. 4A). The one or more prongs 424 can be formed from and/or integral with other portions of the device 400. The one or more prongs 424 can be bendable and/or resilient. The one or more prongs 424 can be configured to bend away from a surface 401 of the device 400 such that portions of the dock 204 can be secured between the prongs 424 and the surface 401 of the device 400. For example, with reference to FIG. 4B, the one or more prongs 424 can be configured to bend a distance away from the surface 401 an amount that is equal to or greater than a thickness of the laminate structure 221 of the dock 204 which can include one or more substrates as discussed above.

Figure 4D:
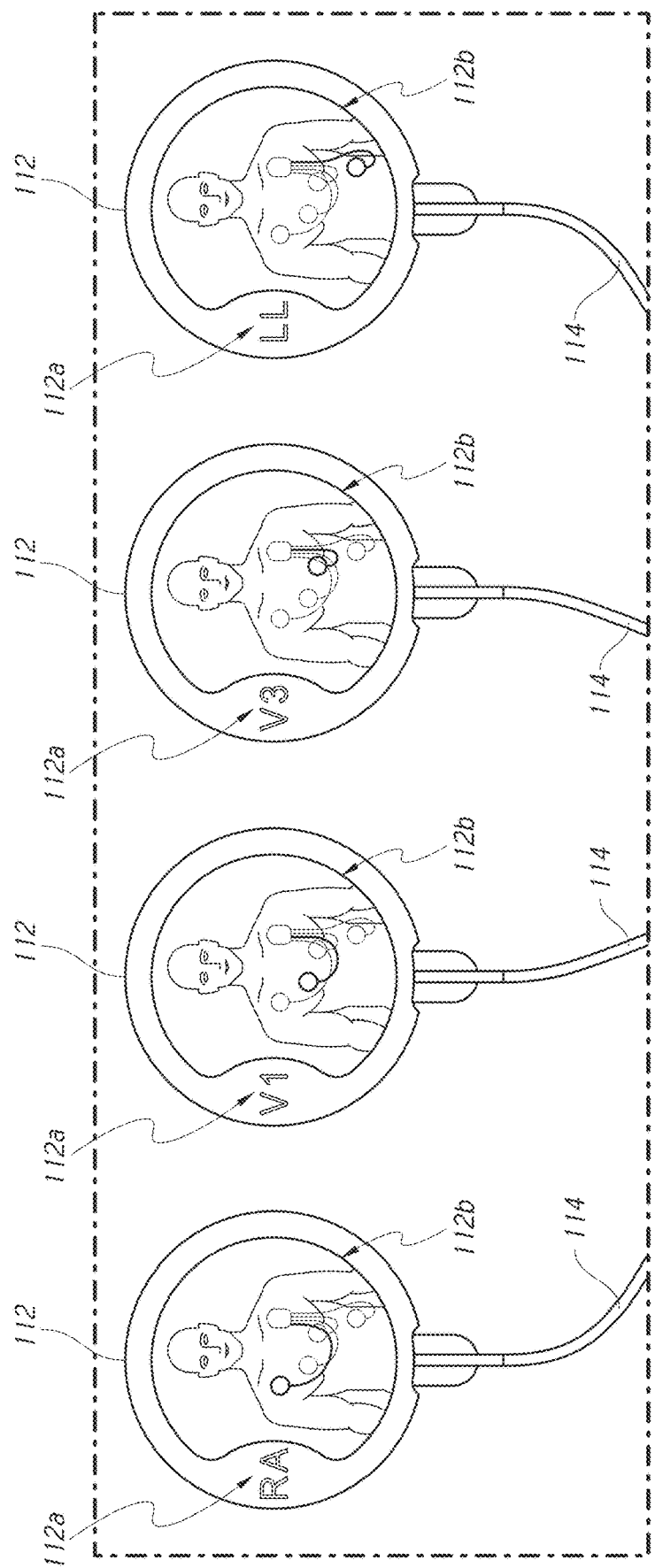
FIG. 4D illustrates various views of electrodes in accordance with aspects of this disclosure.

The electrode securement portion 440 can be configured to secure (for example, removably secure) the one or more electrodes 112 of the disposable portion 203 of the ECG device 110. The electrode securement portion 440 can include one or more placement indicators 442 configured to indicate a placement of the one or more electrodes 112. Each of the one or more placement indicators 442 can include a unique graphic and/or label that indicates placement of a particular one of the one or more electrodes 112 (FIG. 4A). For example, each of the one or more placement indicators 442 can include a graphic and/or label that corresponds to a graphic and/or label on each of the electrodes 112 as illustrated in FIG. 4D and as discussed above.

The electrode securement portion 440 can include one or more prongs 444, for example, one, two, three, four, five, or six, seven, or eight or more prongs 444. The electrode securement portion 440 can include one or more pairs of prongs 444, for example, one, two, three, four, five, or six or more pairs of prongs 444. The one or more prongs 444 can be formed from and/or integral with other portions of the device 400. The one or more prongs 444 can be bendable and/or resilient. The one or more prongs 444 can be configured to bend away from the surface 401 of the device 400 such that portions of the electrodes 112 can be secured between the prongs 444 and the surface 401 of the device 400. For example, with reference to FIG. 4B, the one or more prongs 444 can be configured to bend a distance away from the surface 401 that is dimensioned to fit thicknesses of the electrodes 112 (for example a thickness of the laminate structure 221 of the electrodes 112). The number of prongs 444 can correspond with the number of electrodes 112 of the disposable portion 203 of the ECG device 110. For example, the electrode securement portion 440 can include a pair of prongs 444 for each electrode 112 of the disposable device 203 so that each electrode 112 is secured by two prongs 444. Each prong 444 in a pair can be positioned opposite one another about the placement indicator 422 (FIG. 4A).

The packaging device 400 can include one or more features that can retain and/or secure portions of the cables 114 of the disposable portion 203 of the ECG device 110. For example, the device 400 can include one or more cable securement prongs 446 that can be configured to bend away from the surface 401 of the device 400 such that portions of the cables 114 can be received and/or secured at least partially between the prongs 446 and the surface 401 of the device 400. For example, with reference to FIG. 4B, the one or more prongs 446 can be configured to bend a distance away from the surface 401 an amount that is equal to or greater than a dimension (for example, diameters) of the cables 114. The one or more prongs 446 can be formed from and/or integral with other portions of the device 400. The one or more prongs 446 can be bendable and/or resilient. The one or more prongs 446 can be positioned in the electrode securement portion 440. For example, the one or more prongs 446 can be positioned proximate and/or between the one or more prongs 444. Such configuration can advantageously allow portions of the cable 114 to secure within the one or more prongs 446 when the one or more electrodes 112 are secured by the one or more prongs 444 (see FIG. 4A-4C). The device 400 can include one, two, three, four, five, six, seven, eight, nine, ten, eleven, or twelve or more cable securement prongs 446 or groups of cable securement prongs 446. For example, the device 400 can include a group of prongs 446 for each number of electrodes 112. For example, the device 400 can include two, three, or four prongs 446 per each number of electrodes 112. In some variants, one or more of the prongs 446 within each group are oriented opposite a nearby prong 446 in order to reduce or prevent portions of the cables 114 from being inadvertently removed (see FIG. 4A-4C).

In addition or as an alternative to the one or more cable securement prongs 446, the device 400 can include one or more notches 452 that are sized and/or shaped to receive and/or secure portions of the cables 114. For example, the device 400 can include one, two, three, or four or more notches 452. The number of notches 452 can correspond with the number of cables 114 and/or electrodes 112. The notches 452 can be positioned adjacent to the opening 450, as shown in FIGS. 4A-4B. The notches 452 can include a channel and an aperture positioned at an end of the channel. The channel can have a sized and/or shape that is smaller than a cross-section of the cables 114 and the aperture can have a cross-section that is sized and/or shaped to match the cross-section of the cables 114. Such configuration can allow portions of the cables 114 to be held at least partially within the apertures without moving out of the notches 452 via the channels. Portions of the device 400 adjacent the channels of the notches 452 can be bent or flexed to allow portions of the cables 114 to be positioned within and/or through the apertures of the notches 452.

The device 400 can include a body placement indicator portion 410 that can include a visual representation of a body and one or more body placement indicators that can indicate an a suggested placement of each of the one or more electrodes 112 and/or the dock 204 on the body. For example, with reference to FIG. 4A, the body placement indicator portion 410 can include one or more electrode body placement indicators 474 that can correspond with a different and unique one of the electrodes 112 and the placement indicators 442. Additionally or alternatively, the body placement indicator portion 410 can include a dock body placement indicator 472 that can correspond with the placement indicator 422. The one or more electrode body placement indicators 474 and dock body placement indicator 472 can advantageously help to quickly instruct a caregiver on an appropriate placement of the dock 204 and the electrodes 112 on a patient's body. Additionally, the device 400 can include placement order indicators 460, 462, 464, 466, 468 which can indicate an order in which each of the components of the disposable portion 203 should be placed and/or secured to a patient.

Figure 4E:
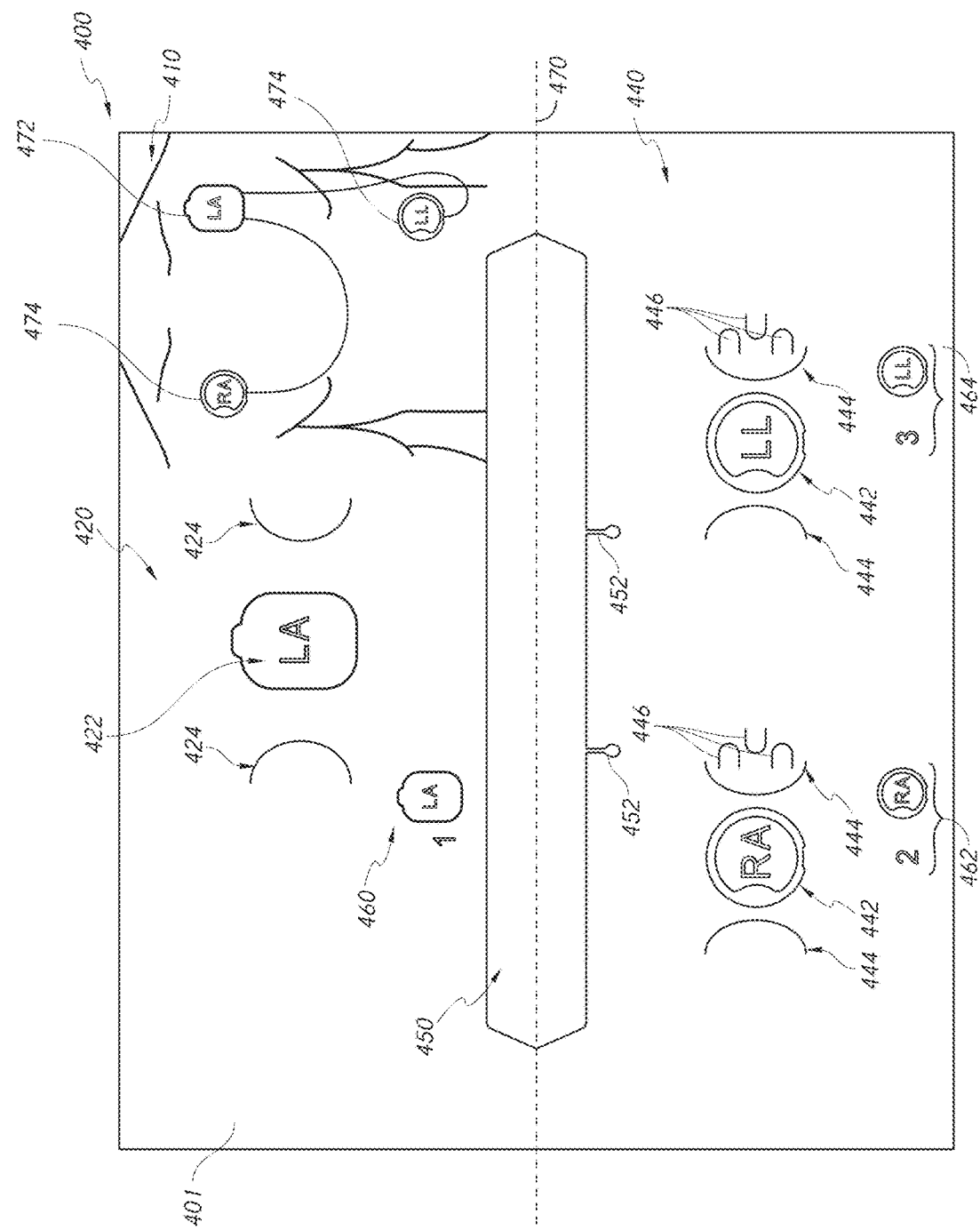
FIG. 4E illustrates an alternative configuration of the ECG packaging device of FIG. 4A in accordance with aspects of this disclosure.

While FIGS. 4A-4D illustrate packaging device 400 being configured to secure a disposable portion 203 including four electrodes 112 and four cables 114, the packaging device 400 can be configured differently in order to secure an alternative number of electrodes 112 and cables 114. For example, as shown by FIG. 4E, packaging device 400 can be configured to secure a disposable portion 203 having two electrodes 112 and two cables 114. For example, the device 400 can include two placement indicators 442, two pairs of prongs 444, one or more prongs 446 or groups of prongs 446 for each cable 114, two notches 452, two electrode body placement indicators 474, a dock body placement indicator 472, and one or more of the placement order indicators 460, 462, 464.

Blood Pressure Monitor

Figure 5A:
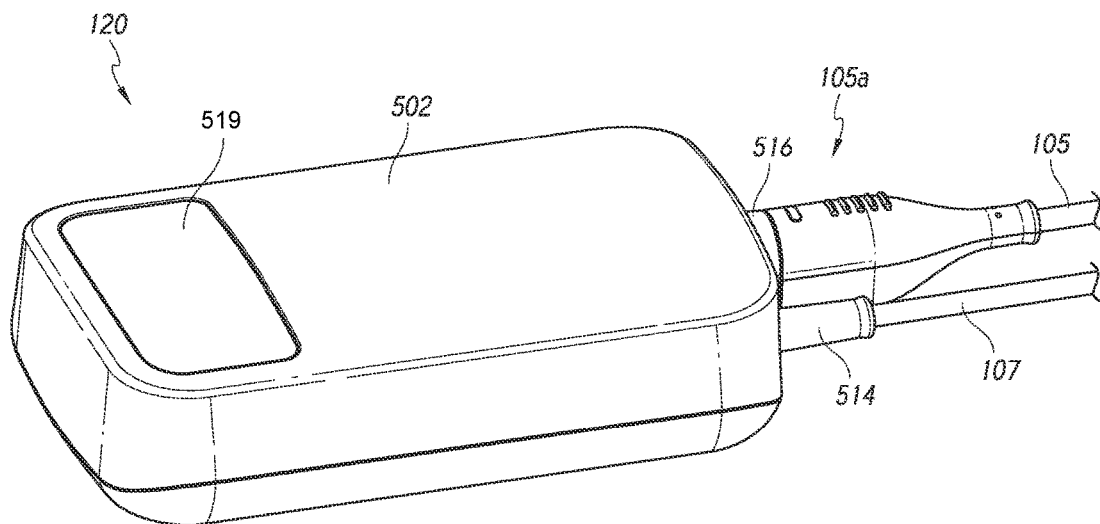
FIG. 5A-5B illustrate perspective views of a blood pressure monitor.

FIGS. 5A-5AA illustrate various views and aspects of the blood pressure monitor 120 (also referred to herein as "blood pressure device" and "blood pressure monitoring device"). While the device 120 is referred to as a "blood pressure monitor" or "blood pressure device" herein, device 120 can measure and/or monitor other parameters in addition or as an alternative to blood pressure. For example, blood pressure device 120 can measure and/or monitor the concentration or partial pressure of carbon dioxide ($CO_2$) in exhaled air of the patient. As another example, as mentioned above the blood pressure monitor 120 can include an accelerometer and/or gyroscope to measure motion data. Blood pressure device 120 can be, for example, a noninvasive blood pressure device and can have the characteristics and/or functionality as described in more detail below with reference to FIGS. 12-14E.

FIGS. 5A-5H illustrate various views of the blood pressure monitor 120. Blood pressure monitor 120 can include a housing 502. As shown in FIGS. 1A-1B, 5C-5D, and 5F, and as further discussed below, blood pressure monitor 120 can be configured to secure to an arm of patient 111, for example, by securing to a blood pressure cuff 121. Blood pressure cuff 121 can wrap around and/or otherwise secure to an arm of patient 111, and blood pressure monitor 120 can secure to the blood pressure cuff 121, for example, via securement between one or more ports of the blood pressure monitor 120 and one or more prongs of the blood pressure cuff 121 as discussed further below. As also discussed further below, blood pressure monitor 120 can be configured to connect to cuff 121 and inflate and/or deflate the cuff 121. As also discussed further below, blood pressure monitor 120 can provide air to the cuff 121 to inflate the cuff 121 to a pressure level high enough to occlude a major artery. When air is slowly released from the cuff 121, blood pressure can be estimated by blood pressure monitor 120 as described in more detail below with reference to FIGS. 12-14E.

With reference to FIGS. 1A-1B and 5A, blood pressure monitor 120 can connect to one or more physiological sensors and/or monitors, such as ECG device 110 and/or patient monitor 130, each of which are discussed in more detail elsewhere herein. For example, a cable 105 and connector 105a can connect to a connector port 516 (see FIGS. 1A-1B and 5A) of the blood pressure monitor 120 and also connect to ECG device 110 (see FIGS. 1A-1B and 2A). Additionally or alternatively, cable 107 can connect to a connector port 514 (see FIGS. 1A-1B and 5A) of the blood pressure monitor 120 and can also connect to patient monitor 130 (see FIGS. 1A-1B and FIG. 8A). For example, cable 107 and connector 107a can connect to a female connector port 832 of patient monitor 130 (see FIGS. 8A and 8I). In some variants, cable 107 is permanently secured to the blood pressure monitor 120 at the connector port 514. For example, an end of cable 107 can be permanently hard-wired to a circuit board of blood pressure monitor 120 and thus can be not removably securable like connector 105a and/or 107a. As discussed previously, blood pressure monitor 120 can include a bypass bus that can pass physiological data received from the ECG device 110 to the patient monitor 130 without processing such data. For example, the bypass bus of blood pressure monitor 120 can pass physiological data received via cable 105 and connector 105a by connector port 516 to connector port 514, through cable 107 and connector 107a, and to patient monitor 130 via connector port 433 without processing such data.

Figure 5B:
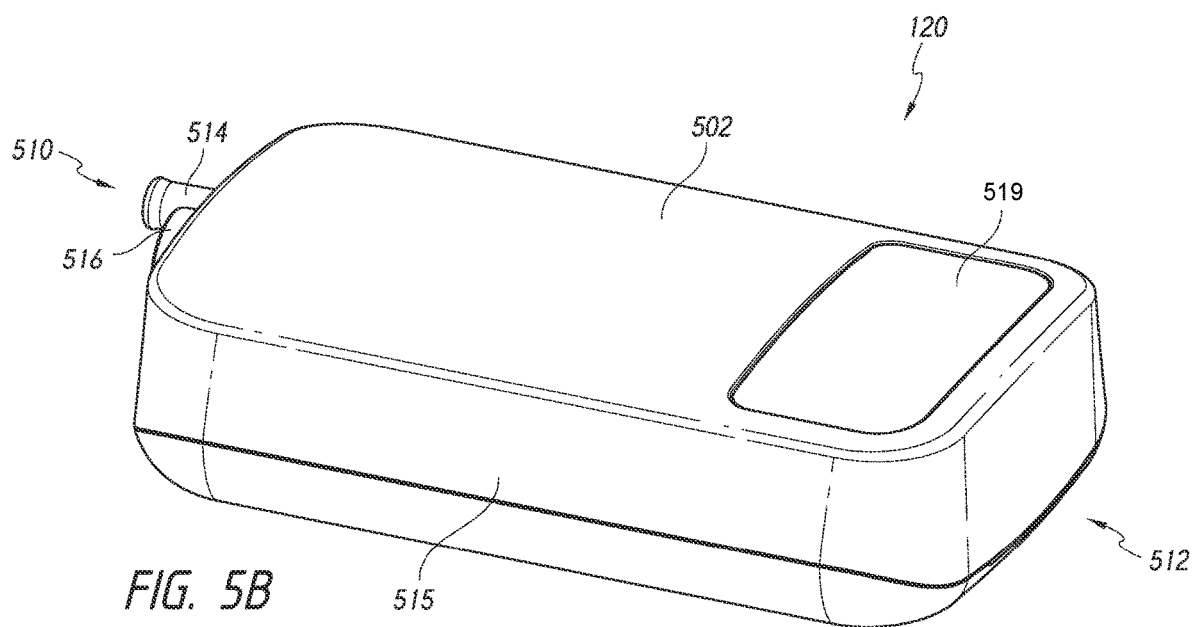
Figure 5C:
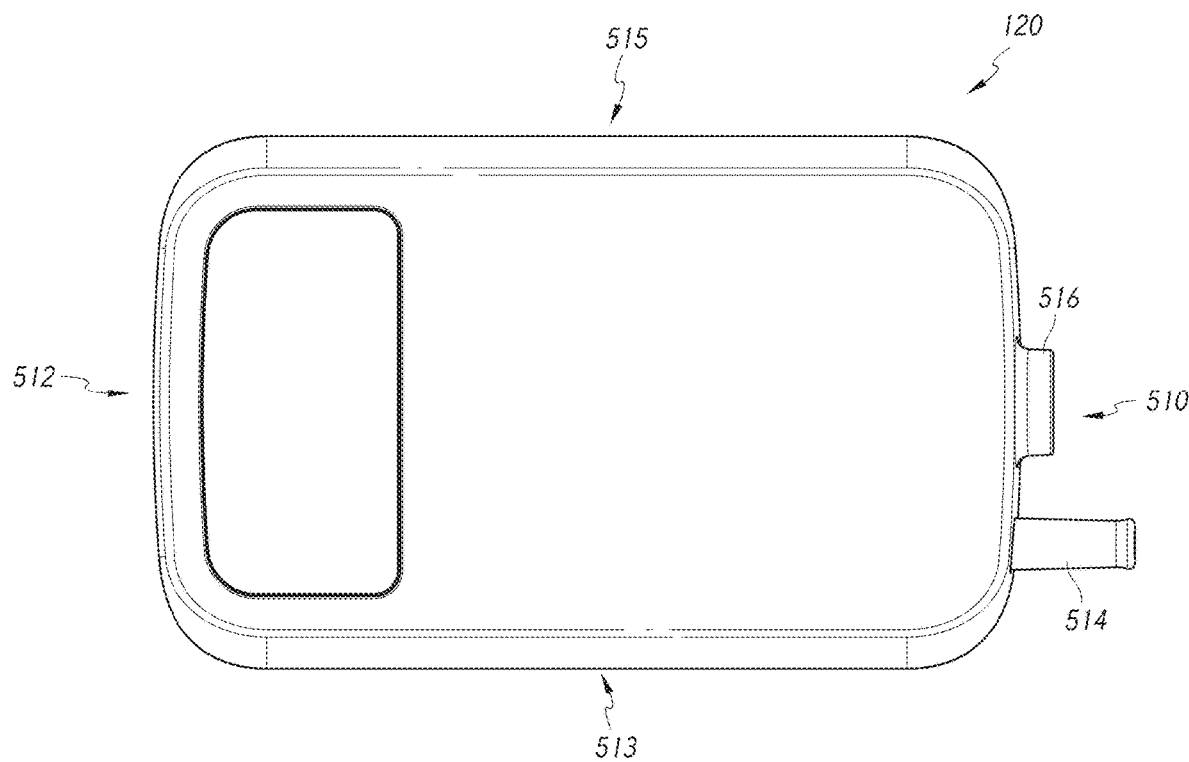
FIG. 5C illustrates a top view of the blood pressure monitor of FIGS. 5A-5B.
Figure 5D:
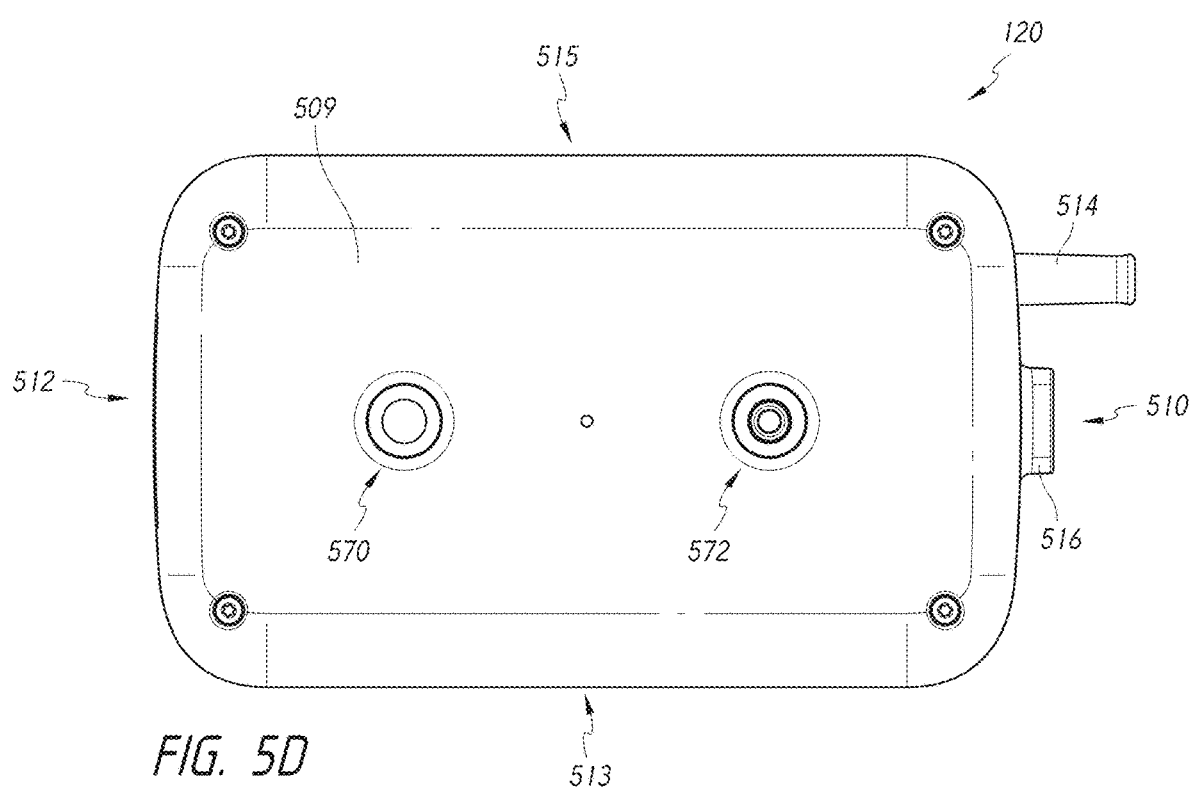
FIG. 5D illustrates a bottom view of the blood pressure monitor of FIGS. 5A-5B.
Figure 5E:
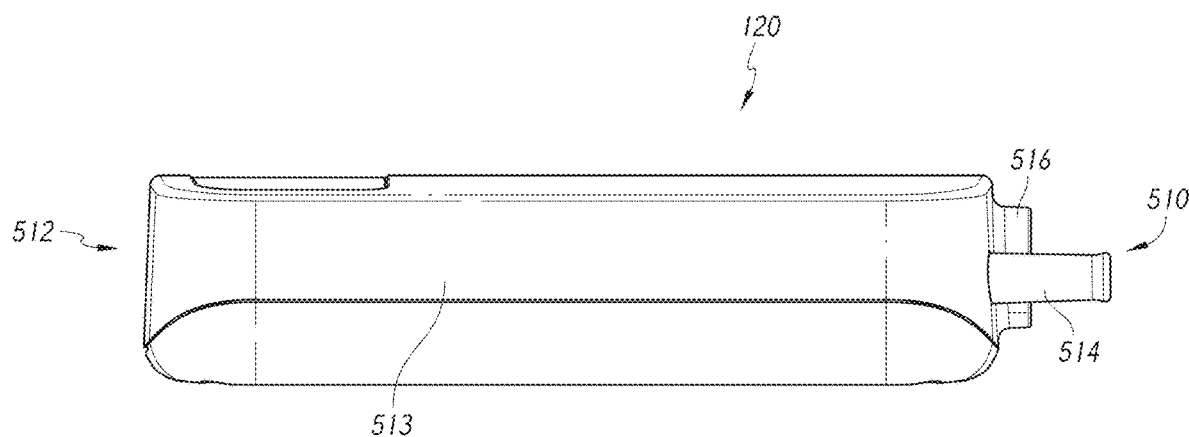
FIG. 5E illustrates a side view of the blood pressure monitor of FIGS. 5A-5B.
Figure 5F:
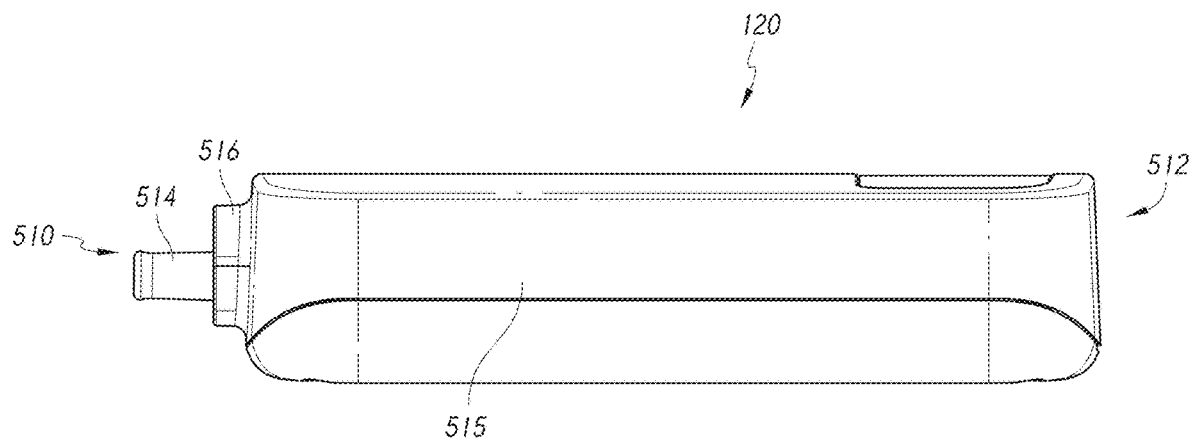
FIG. 5F illustrates another side view of the blood pressure monitor of FIGS. 5A-5B.
Figure 5G:
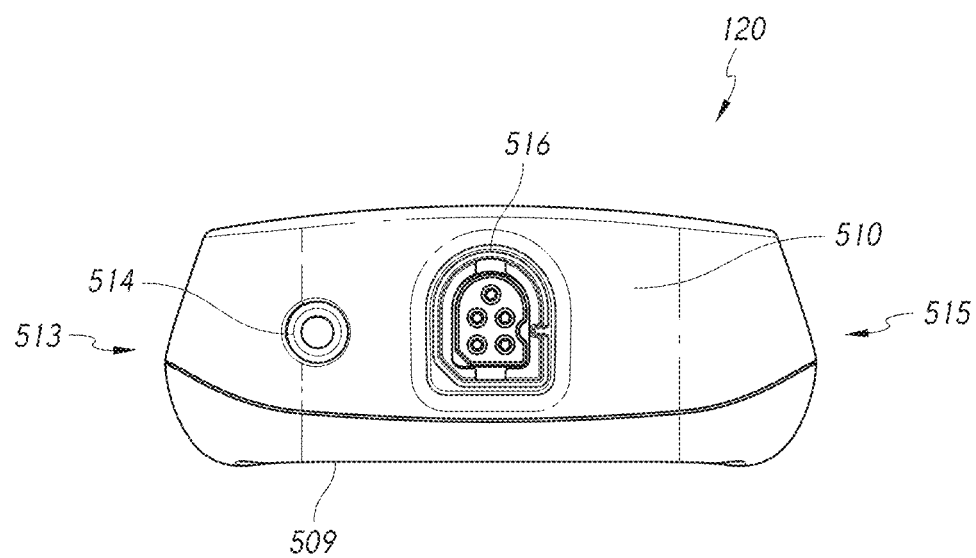
FIG. 5G illustrates a front view of the blood pressure monitor of FIGS. 5A-5B.

Blood pressure monitor 120 can include various electronic components to allow the blood pressure monitor 120 to carry out its physiological measurement and/or monitoring functionality, while the cuff 121 (FIG. 5I) can include little or no electronic components and/or functionality. For example, in some cases, the only electronic components in the cuff 121 are those that relate to and/or provide near field communication (NFC) with the blood pressure monitor 120, which is described further below. In some cases, the blood pressure monitor 120 and/or the cuff 121 can be configured such that the blood pressure monitor 120 does not contact the patient when the cuff 121 and the blood pressure monitor 120 are secured to the patient. Such configuration can allow the blood pressure monitor 120 to be "reusable" and the cuff 121 to be "disposable." In some variants, the blood pressure monitor 120 includes a label portion 519, for example, on a top surface of the blood pressure monitor 120 (FIGS. 5A-5B).

As discussed in more detail below, the blood pressure monitor 120 and the cuff 121 can include various features which allow for removable securement. Such removable securement can advantageously allow the cuff 121 to remain attached to the patient 111 while the blood pressure monitor 120 is removed from the patient 111 and/or cuff 121. This can be especially helpful where it is desirable to temporarily remove the housing 502 for inspection or repair. This can also allow a caregiver to clean the cuff 121 and/or regions of the patient 111 proximate the cuff 121 without risking damage to the blood pressure monitor 120 (or various components thereof).

FIGS. 5B-5H illustrate various views of the blood pressure monitor 120. As shown, the blood pressure monitor 120 (and/or the housing 502) can include a first end 510, a second end 512 opposite the first end 510, a first side 513, and a second side 515 opposite the first side 513. While the present disclosure refers to "end" or "side", such terminology is not intended to be limiting, but rather, is employed for mere convenience in differentiating certain features of the blood pressure monitor 120. Accordingly, while the term "end" is used for the first and second ends 510, 512, it is to be understood that such ends 510, 512 can also represent "sides" of the blood pressure monitor 120.

The connector port 516 can extend from the first end 510, and as discussed above, can connect to a connector and/or cable such as connector 105a and cable 105. Connector port 516 can protrude outward from a portion of the first end 510. The connector port 516 can be have a width and/or height that is less than a width and/or height of the first end 510. The first end 510 can additionally or alternatively include a connector port 514 which can be spaced from the connector port 516 along the first end 510. As also discussed above, connector port 514 can connect to a cable 107. As also discussed above, an end of cable 107 can be irremovably secured to blood pressure monitor 120 via connector port 514. For example, an end of the cable 107 can be hard-wired to a circuit board of blood pressure monitor 120. Connector port 514 can protrude outward from the first end 510. Connector port 514 can protrude outward from the first end 510 a distance greater than the connector port 516 (see FIGS. 5C-5D). Connector port 514 can have a circular cross-section, a conical cross-section, and/or a combination of the same or different shaped cross-sections or shapes. Connector port 514 can have a cross-section that tapers (or decreases) from a first end of the connector port 514 that connects to the first end 510 to a second end of the connector port 514 that is opposite from the first end of the connector port 514. Connector port 514 can have an increased cross-section at the second end of the connector port 514 (see FIGS. 5C-5D). Connector port 516 can be positioned in a middle of the first end 510. Connector port 514 can be positioned on either side of connector port 516 along the first end 510. As discussed further below, the blood pressure monitor 120 can include one or more ports that can provide fluid communication between an interior of the housing 502 and a bladder of the cuff 121. For example, the blood pressure monitor 120 can include one or both of ports 570, 572 (FIG. 5D), each of which are described in more detail below.

FIGS. 5I-5M illustrate various views of the cuff 121, with and without the blood pressure monitor 120 attached. As shown, the cuff 121 can include a first portion 540 and a second portion 542. The second portion 542 can have tapered or partially tapered edges, as shown. The cuff 121 can have a width $W_1$ and a length $L_1$ (see FIG. 5L). The width $W_1$ can extend between sides 545 and 547. The length $L_1$ can extend between ends 541 and 543. The width $W_1$ can be less than length $L_1$. The first portion 540 can include an attachment portion 544 configured to secure to an attachment portion of the second portion 542, which can be on an opposite surface of the cuff 121 as the attachment portion 544. For example, the attachment portion 544 can comprise a hook-and-loop fastener that can removably secure to a hook-and loop-fastener of an attachment portion of the second portion 542. The first portion 540 of the cuff 121 can include a bladder layer (also referred to herein as "bladder"), such as bladder layer 543 (see FIG. 5X) that can be configured to contact the patient when the cuff 121 is secured to the patient. The bladder 543 can be configured to inflate and deflate, as further discussed elsewhere herein. The cuff 121 can include, for example, in the first portion 540, a securement portion which can facilitate removable securement of the blood pressure monitor 120. For example, the cuff 121 can include one or more prongs that can secure to portions of the blood pressure monitor 120. For example, the cuff 121 can include one or both of prongs 550, 552 that can be configured to be received and/or secure within one or more ports of the blood pressure monitor 120 (such as ports 570, 572). The prongs 550, 552 can be spaced apart from one another. The prongs 550, 552 can be spaced equally from an end 541 and/or end 543 of the cuff 121. The prong 550 can be spaced a first distance from a first side 545 of the cuff 121 and the prong 552 can be spaced a second distance from a second side 547 of the cuff 121, and such described first and second distances can be equal. The prong 550 can be spaced a first distance from a first side 545 of the cuff 121 and the prong 552 can be spaced a second distance from the first side 545 of the cuff 121, and such described first and second distances can be not equal. The prong 550 can be spaced a first distance from a second side 547 of the cuff 121 and the prong 552 can be spaced a second distance from the second side 547 of the cuff 121, and such described first and second distances can be equal. The width $W_1$ of the cuff 121, spacing and/or positioning of the prongs 550, 552, and/or a width and/or length of the blood pressure monitor 120 can be configured such that, when the blood pressure monitor 120 is secured to the cuff 121 (for example, via securement of the prongs 550, 552 within ports 570, 572 of the blood pressure monitor 120), the blood pressure monitor 120 is positioned within the width $W_1$ of the cuff 121 (for example, ends of the blood pressure monitor 120 at or spaced inwards from sides 545, 547) (see FIGS. 5L-5M).

Advantageously, the spacing and/or positioning of the prongs 550, 552 with respect to each other and/or ends 541, 543, and/or sides 545, 547 can be configured so that the device 120 is symmetrically positioned with respect to the width $W_1$ of the cuff 121 regardless of whether the device 120 and/or the cuff 121 is secured in an first orientation (for example, FIG. 5L) or a second orientation (for example, FIG. 5M), for example, on an arm of patient 111. Such first and second orientations can be the reverse or opposite of each other (see FIGS. 5L-5M). The spacing and/or positioning of the prongs 550, 552 with respect to each other and/or ends 541, 543, and/or sides 545, 547 can be configured so that the device 120 is symmetrically positioned with respect to the width $W_1$ of the cuff 121 regardless of whether the prong 550 is secured to the port 570 or the port 572 and/or regardless of whether the prong 552 is secured to the port 570 or the port 572. This can advantageously allow the cuff 121 and the device 120 be symmetrically positioned when secured to either a right arm or a left arm of a patient 111 as illustrated in FIGS. 1A-1B. Additionally, the incorporation of both of prongs 550, 552 can provide increased stability when secured to the ports 570, 572 of the device 120. As described further below, the prongs 550, 552 can include fluid passages that are in fluid communication with the bladder 543 of the cuff 121.

Figure 5H:
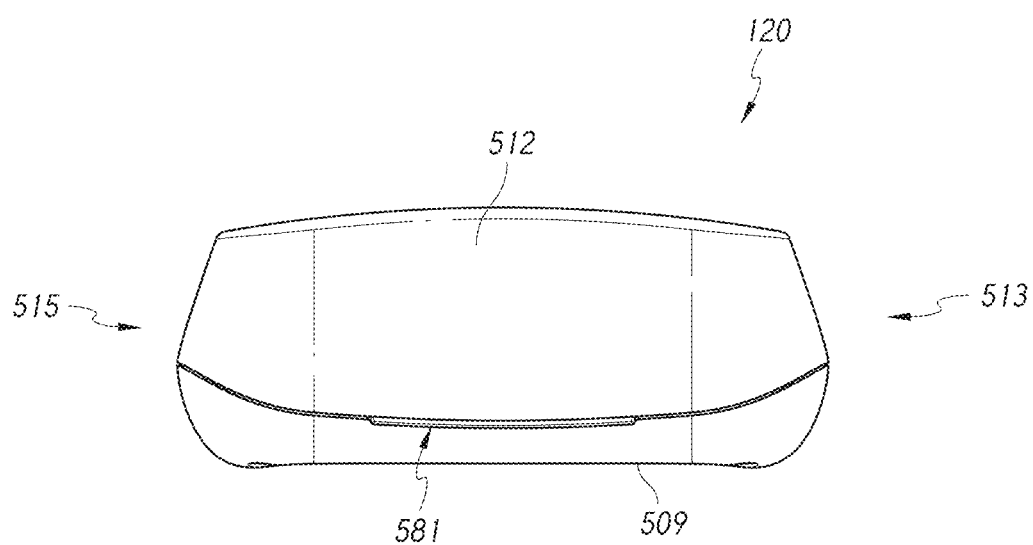
FIG. 5H illustrates a back view of the blood pressure monitor of FIGS. 5A-5B.
Figures 5N, 5O:
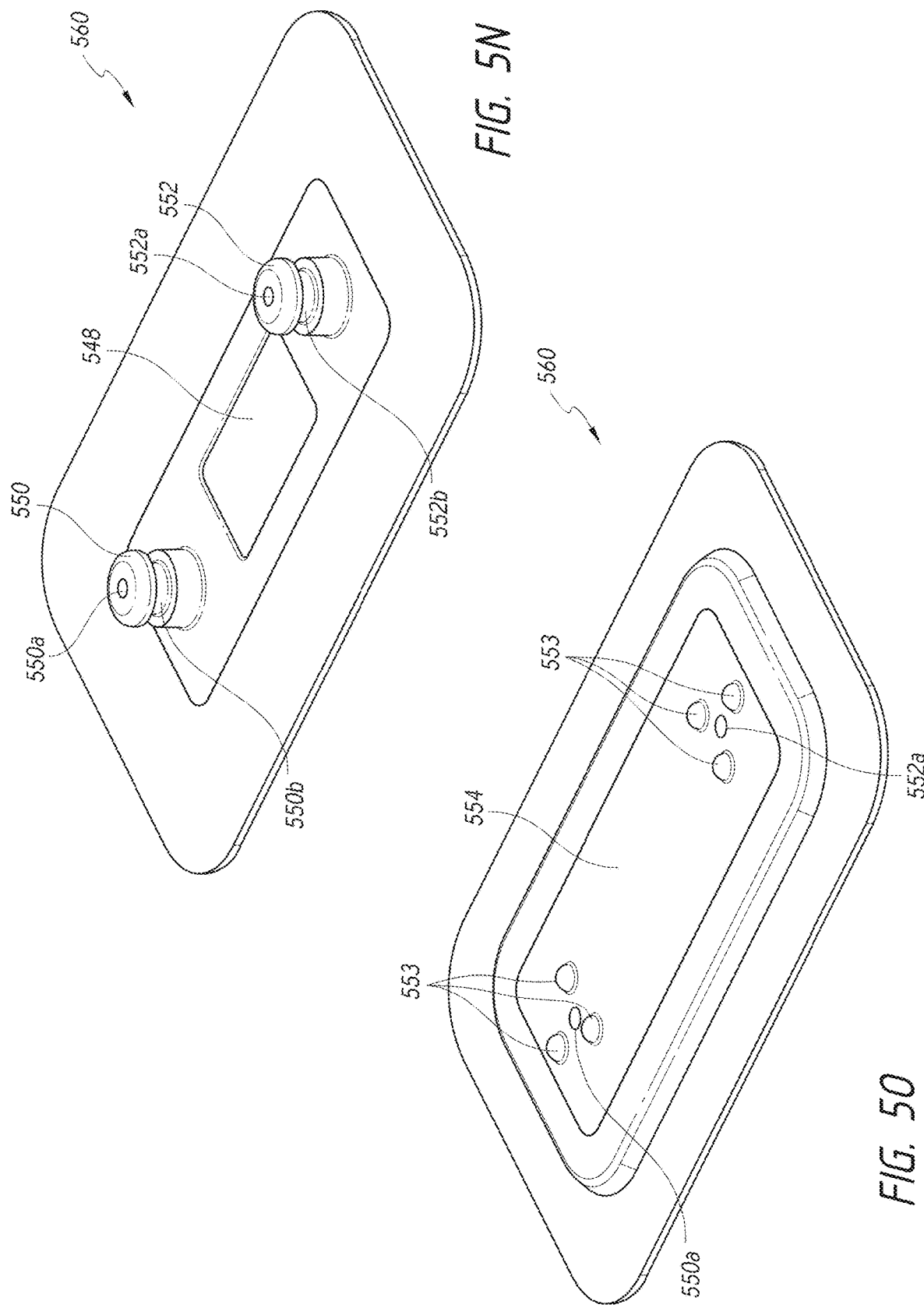
FIGS. 5N-5O illustrate perspective views of a portion of the blood pressure cuff of FIG. 5I in accordance with aspects of this disclosure.

FIGS. 5N-5O illustrate an optional support body 560 that can be secured to other portions of the cuff 121 during assembly. Where the cuff 121 includes such support body 560, the support body 560 can include the prongs 550, 552. The prongs 550, 552 can include fluid passages 550a, 552a which can extend through a length of the prongs 550, 552 and a base 554 of the support body 560 (see FIG. 5O). The support body 560 can include one or more bumps 553 extending from a bottom surface of the base 554 of the support body 560. The one or more bumps 553 can be positioned around the fluid passages 550a, 552a as shown in FIG. 5O. For example, the support body 560 can include one, two, three, or four or more bumps 553 extending from a bottom surface of the base 554 of the support body 560. The one or more bumps 553 can be spaced apart from one another relative to the fluid passages 550a, 552. Such bumps 553 can advantageously help ensure that bladder 543 does not cover the fluid passages 550a, 552a (see FIG. 5X) when the blood pressure monitor 120 is in use with the cuff 121. For example, the one or more bumps 553 can space a surface of the bladder 543 from the fluid passages 550a, 552a and provide a gap between ends of the fluid passages 550a, 552a at a surface of body 554. The support body 560 can be welded to portions of the cuff 121 such that only the prongs 550, 552 are visible, as shown in FIG. 5I-5J.

The blood pressure monitor 120 and cuff 121 can include near field communication (NFC) structure and/or functionality that can enable the blood pressure monitor 120 to, among other things: confirm that the cuff 121 is an authorized product; transfer information and/or data to the cuff 121 for storage; determine the size of a particular cuff 121 to which the blood pressure monitor 120 is attached; and/or determine a lifespan of the cuff 121. For example, in some cases, after the blood pressure monitor 120 detects a size of the cuff 121 to which it is attached via the NFC (such as that described below), the blood pressure monitor 120 determines a particular inflation rate and/or profile that is unique to that particular cuff 121. For example, such particular inflation rate and/or profile can be different for smaller cuffs 121 (for example, for young children or neonatal patients) than for larger cuffs 121 (for example, for adults). The blood pressure monitor 120 can include an NFC reader that transmits a radio frequency and the cuff 121 can include an NFC tag (for example, in the form of a sticker or label) which can be attached to a portion of the cuff 121 or within an interior portion of the cuff 121. For example, the blood pressure monitor 120 can include an RFID reader that transmits a radio frequency and the cuff 121 can include an RFID tag (for example, in the form of a sticker or label) which can be attached to a portion of the cuff 121 or within an interior portion of the cuff 121. The RFID tag can be placed on an outer surface of the cuff 121, for example, proximate to the prongs 550, 552. Alternatively, the RFID tag can be positioned within an interior portion of the cuff 121. For example, where the cuff 121 includes the support body 560, an RFID tag can be positioned within a recessed portion 548 of the support body 560 (see FIGS. 5J and 5N). The recessed portion 548 can be positioned proximate the prongs 550, 552, for example, between the prongs 550, 552. With reference to FIG. 5J, the cuff 121 can include a placement indicator 546 that can be configured to indicate a proper placement of the blood pressure monitor 120 on the cuff 121. The placement indicator 546 can have a sized and/or shaped that matches a size and/or shape of the blood pressure monitor 120 (such as a perimeter of the blood pressure monitor 120).

The blood pressure monitor 120 (for example, the housing 502) can include one or more air intakes which can enable fluid communication with ambient air outside the housing 502. As discussed elsewhere herein, the blood pressure monitor 120 can also include one or more air pumps 522 which can create suction to draw ambient air into and/or through such air intake(s) of housing 502. Such air intake(s) can be located and/or positioned in a variety of locations on the housing 502, for example, sides, ends, and/or top or bottom surfaces of housing 502. Housing 502 can include one, two, three, four, five, or six or more air intakes. For example, housing 502 can include an air intake located along one of sides 513, 515 and/or ends 510, 512.

Figure 5R:
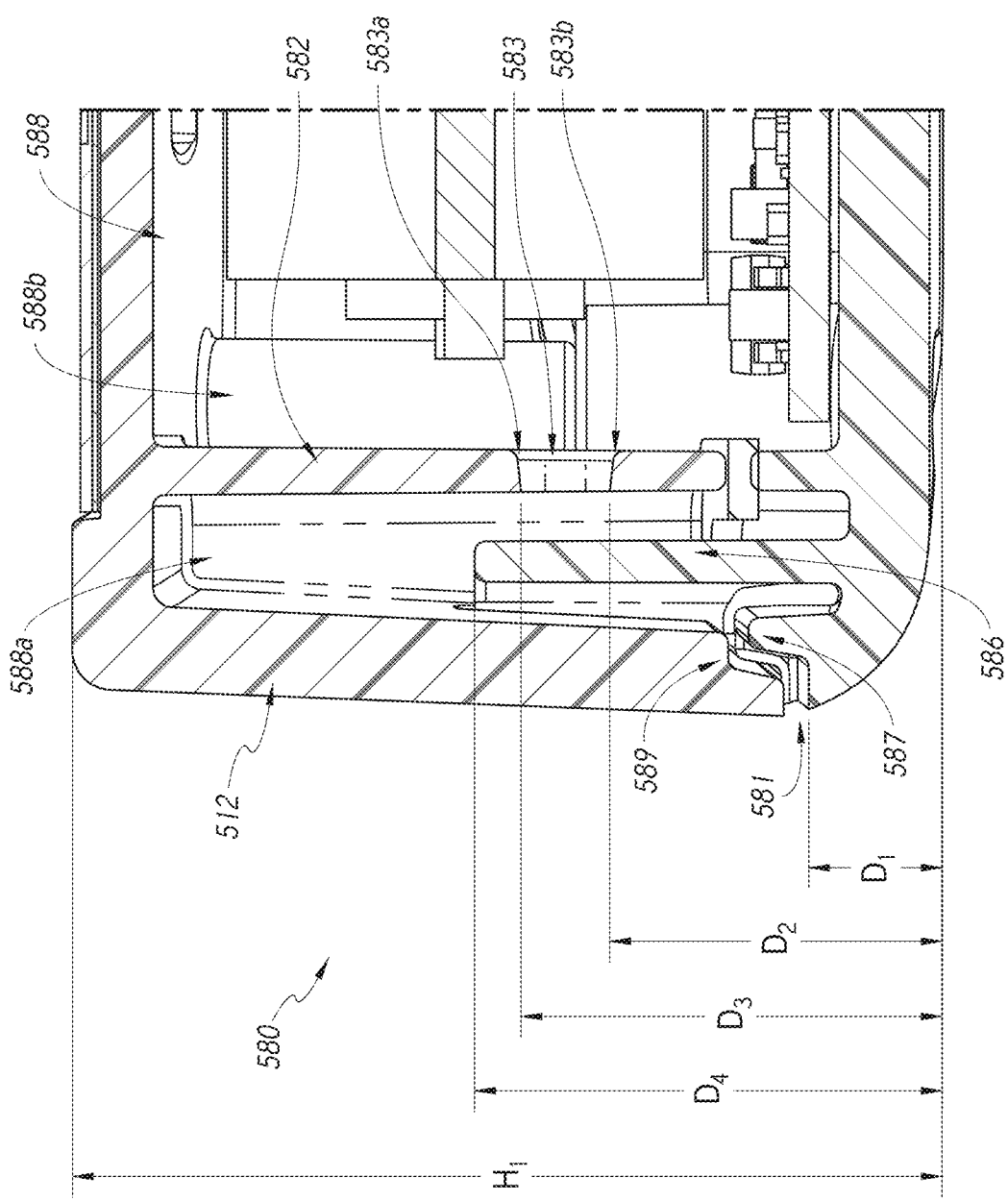
FIG. 5R illustrates an enlarged view of a portion of the cross-section view shown in FIG. 5Q.

FIGS. 5P-5Q illustrate cross-sections through the blood pressure monitor 120. FIGS. 5P-5R further illustrate an air intake 580 of the blood pressure monitor 120. The air intake 580 can be configured such that air flowing into and/or out of an interior 588 of the blood pressure monitor 120 travels in a non-straight path. As discussed below, this can advantageously inhibit liquids from entering into the interior 588, which could cause damage to internal components of the blood pressure monitor 120.

The housing 502 can include an opening 581 in a portion of the first end 512 of the housing 502. With reference to FIG. 5H, the opening 581 can comprise a slit having a width that is greater than a height. The opening 581 can extend along a portion of the first end 512 of the housing 502. The housing 502 can include an inner wall 582 spaced away from the first end 512 (or the exterior wall defined by the first end 512). With reference to FIGS. 5Q-5R, the inner wall 582 can partition (for example, "divide") the interior 588 of the housing 502 into a first portion 588a and a second portion 588b. As shown, the first portion 588a can be closer to the wall defined by the first end 512 and/or the opening 581. The first portion 588a can be in fluid communication with ambient outside the housing 502 via opening 581. The inner wall 582 can include an opening 583. The opening 583 can provide fluid communication between the first and second portions 588a, 588b. The opening 583 can comprise a square, rectangular, or circular shape, among others. The opening 583 can comprise a square or rectangular shape with rounded corners (see FIG. 5P).

As shown in FIG. 5R, the opening 581 can be positioned a distance $D_1$ from a bottom of the housing 502. A top portion 583a of the opening 583 can be positioned a distance $D_3$ away from the bottom of the housing 502 and a bottom portion 583b of the opening 583 can be positioned a distance $D_2$ from the bottom of the housing 502. As also shown, the housing 502 can have a height $H_1$.

The air intake 580 can be defined (or "formed") by the opening 581. Where the housing 502 includes the inner wall 582, the air intake 580 can be defined (or "formed") by the opening 581 and the opening 583. Further, the positioning of the openings 581, 583 relative to the bottom of the housing 502 can be selected such that a flow path for air entering or exiting the interior 588 (for example, second portion 588b) is not-straight. For example, the opening 581 and opening 583 can be not aligned with each other. As another example, the distance $D_1$ can be different from (for example, less than) one or both of distances $D_2$, $D_3$ and/or different from (for example, less than) a distance from an axis extending through a center of opening 583 and the bottom of the housing 502. Such configuration can advantageously inhibit (for example, prevent) liquids from entering into the interior 588, which could cause damage to internal components of the blood pressure monitor 120. At the same time, such configuration can still allow air to flow into and out of the interior 588 (for example, second portion 588b).

With continued reference to FIGS. 5P-5R, the housing 502 can include an inner wall 586. The inner wall 586 can extend from a bottom interior surface of the housing 502. The inner wall 586 can extend upward from the bottom interior surface (for example, towards a top interior surface of the housing 502) and partially partition the first portion 588a of the interior 588. The inner wall 586 can have a tip or end that is positioned a distance $D_4$ from the bottom of the housing 502 (see FIG. 5R). The distance $D_4$ can be different from the distance $D_1$, distance $D_2$, and/or distance $D_3$. For example, the distance $D_4$ can be greater than the distance $D_1$, distance $D_2$, and/or distance $D_3$. The inner wall 586 can extend such that a tip or end of the inner wall 586 is positioned (vertically) between the top and bottom portions 583a, 583b of the opening 583. For example, the distance $D_4$ can be greater than the distance $D_2$ less than the distance $D_3$.

In some variants, the housing 502 includes a wall 587 proximate the opening 581, which can extend from a bottom surface or portion of the housing 502 towards a top surface or portion of the housing 502. A tip or end of the wall 587 can be higher (for example, vertically) than the height of the opening 581 with reference to the view illustrated in FIG. 5R. The housing 502 can include a notched portion 589 extending along a portion of the width of the opening 581 (for example, along the first end 512) that can accommodate the wall 587 such that air can flow through opening 581, over and/or around the wall 587, and into the first portion 588a of the interior 588.

The air intake 580 can be defined (or "formed") by the opening 581 in the first end 512 and the opening 583 in the inner wall 582. The air intake 580 can additionally be defined by one or both of the inner walls 582, 586, wall 587, and/or the notched portion 589. Such configurations can create an air flow path into the interior 588 that is non-linear. For example, such configurations can create an air flow path into the interior 588 that is tortuous, meandering, and/or serpentine. As discussed below, this can advantageously allow air to flow into and out of the interior 588 but inhibit or prevent liquids from entering into the interior 588 of the blood pressure monitor 120.

Figure 5S:
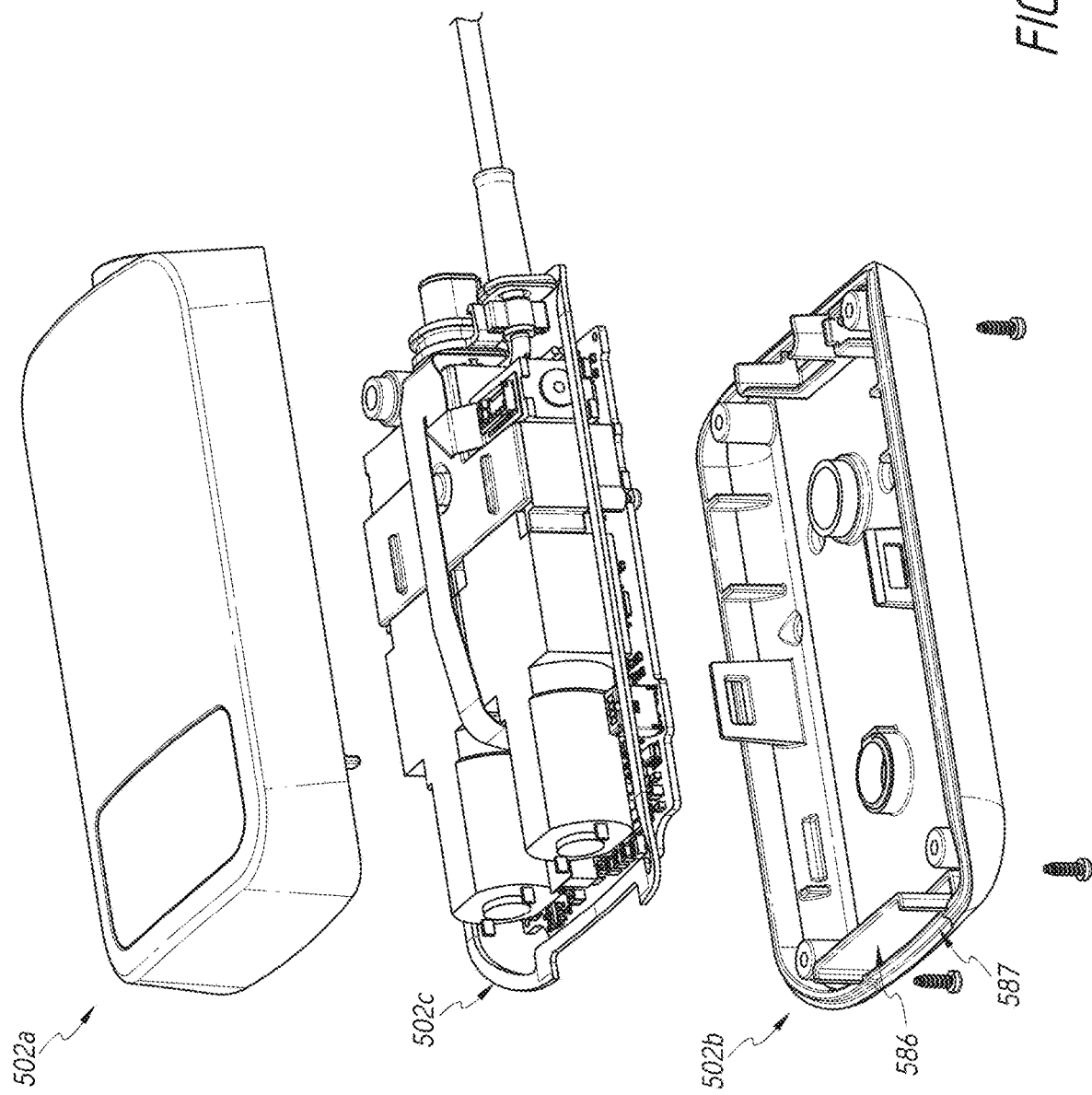
FIG. 5S-5T illustrate exploded perspective views of the blood pressure monitor of FIGS. 5A-5B in accordance with aspects of this disclosure.
Figure 5T:
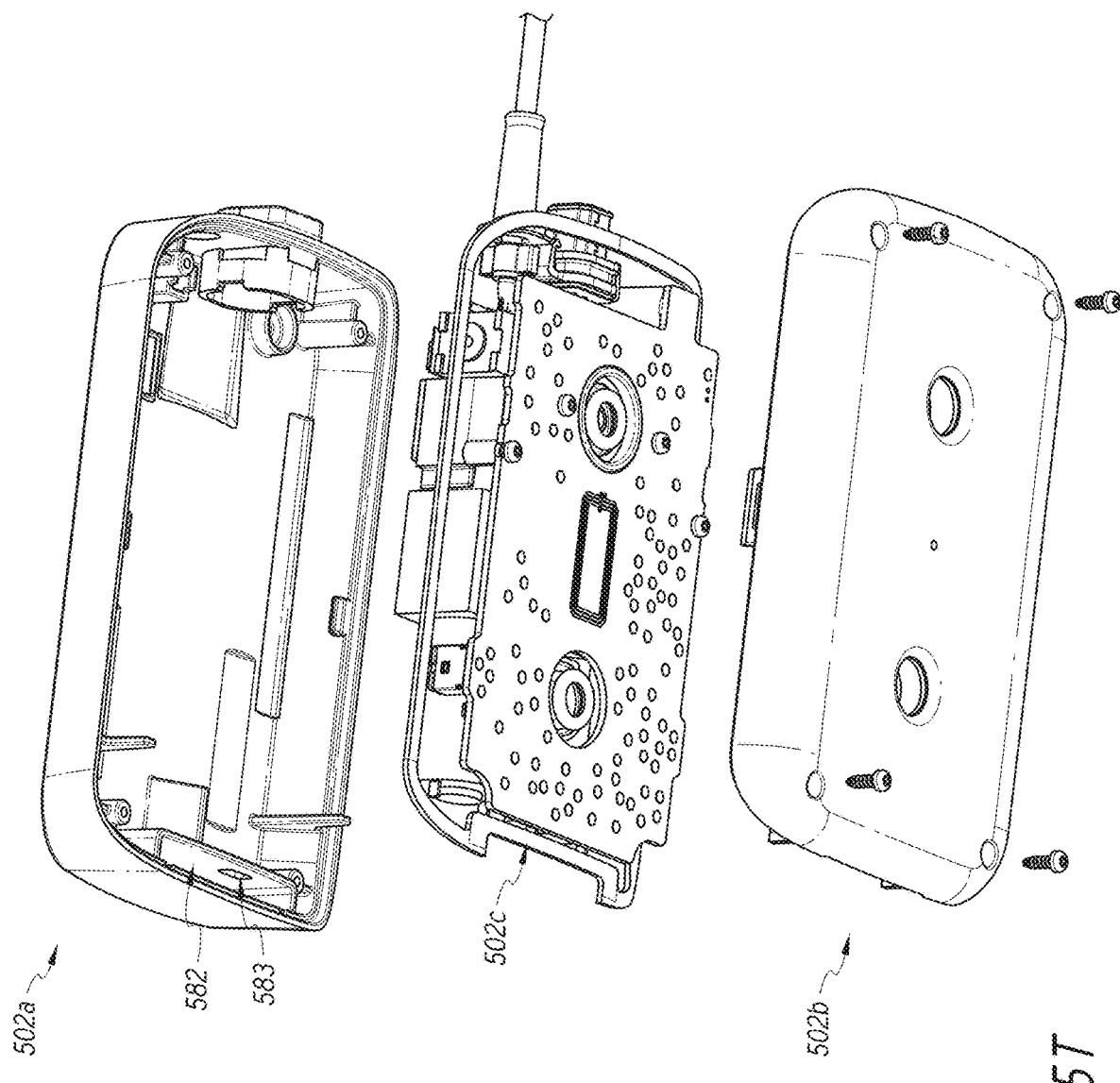

The housing 502 can be formed from more than one component. For example, with reference to FIGS. 5S-5T, the housing 502 can be formed from a top portion 502a and a bottom portion 502b. During assembly, a membrane or gasket 502c can be positioned between portions of the top and bottom portions 502a, 502b, for example to provide a seal which prevents liquid from entering an interior 588 of the housing 502. As shown, the inner wall 582 and/or the opening 583 can be formed from the top portion 502a. As also shown, the inner wall 586 and/or 587 can be formed from the bottom portion 502b. With reference to FIGS. 5R-5S, the inner wall 582 can be formed from a portion of the top portion 502a, the gasket 502c, and a portion of the bottom portion 502b so that the first interior portion 588a is sealed from the second interior portion 588b other than the opening 583 (for example, air and/or liquid cannot pass around the gasket 502c). The opening 581 can be formed by a gap between a portion of the top portion 502a and a portion of the bottom portion 502b (see FIGS. 5H and 5R). The ports 570, 572 can be formed from the bottom portion 502b (FIG. 5S-5T). For example, the ports 570, 572 can extend from a bottom interior surface of the housing 502 (for example, the bottom portion 502b) upwards toward a top interior surface of the housing 502 (for example, the top portion 502a).

Figure 5U:
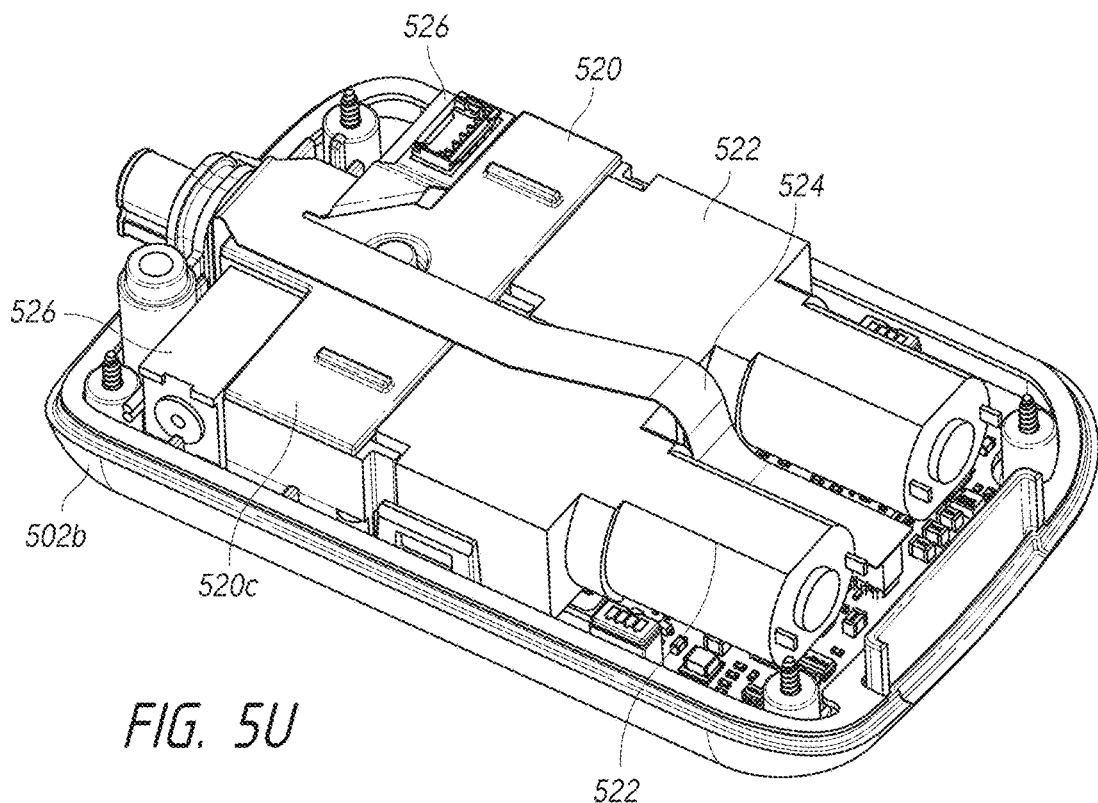
FIGS. 5U-5V illustrate perspective views of the blood pressure monitor of FIGS. 5A-5B with portions removed in accordance with aspects of this disclosure.
Figure 5V:
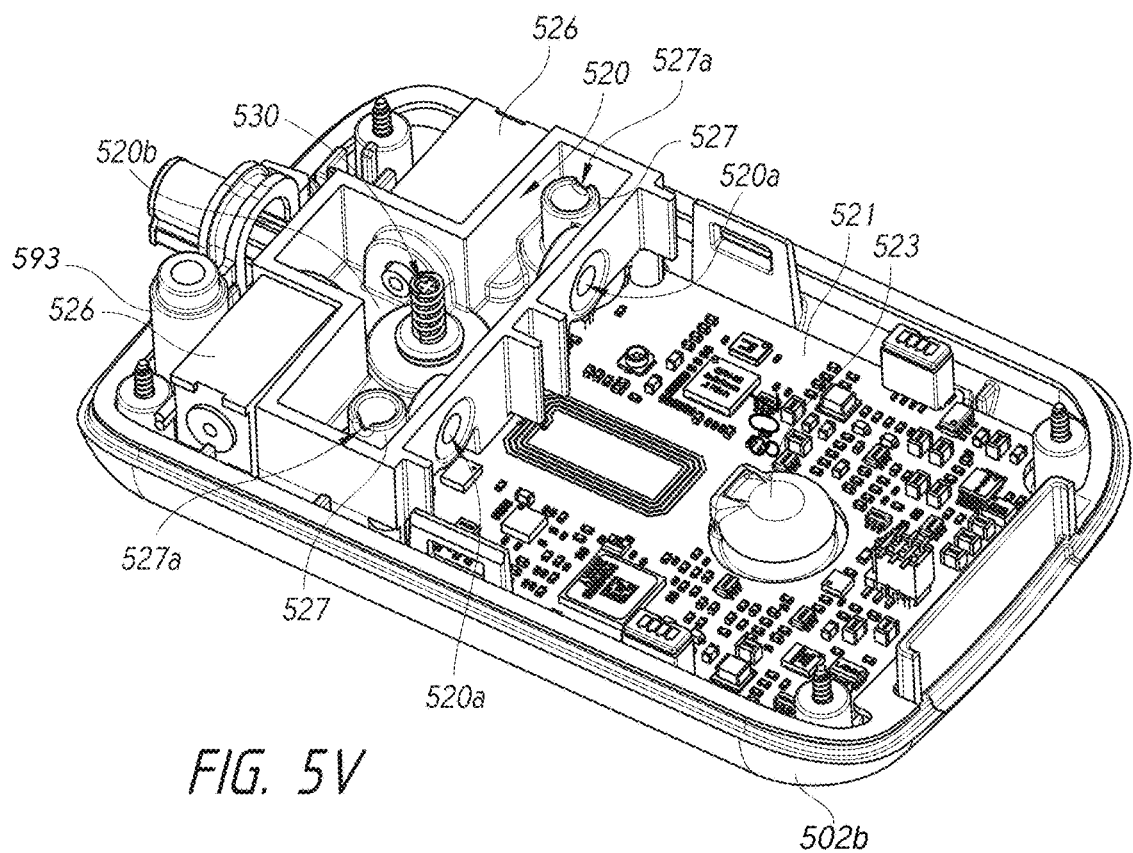

FIGS. 5U-5V illustrate the blood pressure monitor 120 with a top portion removed (for example, with the top portion 502a removed) to better illustrate internal components of the blood pressure monitor 120. FIGS. 5W-5X illustrate cross-sectional views of the blood pressure monitor 120 taken along a line through the ports 570, 572. FIG. 5V is the same as FIG. 5U except that a top portion 520c of the manifold 520 (discussed below), the pumps 522, and a flexible circuit 524 of the blood pressure monitor 120 are removed. The blood pressure monitor 120 can include one or more pumps 522, a manifold 520, one or more release valves 526, and ports 570, 572. As described further below, one or more of ports 572 can enable fluid communication between the interior 588 of the housing (for example, the manifold 520) and an interior 549 of a bladder 543 of cuff 121 when the prongs 550, 552 are receive and secured therein. As also described elsewhere herein, the prongs 550, 552 can include fluid passageways 550a, 552a that can be in fluid communication with the interior 549 of the bladder 543 of the cuff 121.

The one or more pumps 522 can create suction to draw ambient air into and/or through air intake(s) of housing 502, such as air intake 580 described above. The one or more pumps 522 can pump air into the manifold 520 (for example, via inlets 520a). Advantageously, including more than one pump into blood pressure monitor 120 can allow the device 120 (for example, the housing 502) to have a smaller height while still providing the same pumping capacity. The one or more release valves 526 can allow air to flow out of the manifold 520, for example, into an interior 588 of the housing 502.

The manifold 520 can include an opening 520d that can enable fluid communication between one of the fluid passageways 550a, 552a of one of the prongs 550, 552 and an interior of the manifold 520 when one of the prongs 550, 552 is secured within the port 572. The blood pressure monitor 120 can include a valve configured to open and/or close the opening 520d to enable or prevent such fluid communication. For example, the blood pressure monitor 120 can include a valve 530 which is positioned within the manifold 520 proximate the opening 520d. With reference to FIGS. 5Z and SAA, the valve 530 can include a body 531, a sealing ring 532, and a biasing member 533. The body 531 can include a stem 531a, a base 531b, and a head 531c. The stem 531a can be sized and/or shaped to fit within and/or through the biasing member 533. The stem 531a can comprise a cross-patterned shape or another shape. The base 531b can have a circular shape. The head 531c can have a cylindrical shape and can have one or more openings 531e and an opening 531f. For example, the head 531c can have one, two, three, or four or more openings 531e. The one or more openings 531e can be positioned around an axis extending along a length of height of the valve 530 (for example, around an axis extending along a length of the stem 531a). The opening 531f can be aligned with an axis extending along a length of the valve 531. For example, an axis extending through a center of the opening 531f can be parallel with an axis extending through the stem 531a and/or a height of the valve 530 or body 531. The opening 531f can be oriented perpendicular with respect to the openings 531e. For example, axes extending through a center of the openings 531e can be perpendicular with respect to an axis extending through a center of the opening 531f. The body 531 can include a recessed portion 531d that is sized and/or shaped to receive the sealing ring 532. As discussed further below, the valve 530 can allow air to flow through openings 531e, 531f so as to provide fluid communication between the interior of the manifold 520, the fluid passages 550a, 552a of the prongs 550, 552, and/or the interior 549 of the bladder 543 of the cuff 121.

The valve 530 can be configured to move so as to open and/or close a flow path through the opening 520a of the manifold 520. FIG. 5W illustrates a cross-section through the blood pressure monitor 120 when the valve 530 is in a first position where the valve 530 cover the opening 520d.

FIG. 5X illustrates the cross-section of FIG. 5W where the cuff 121 is secured to the blood pressure monitor 120 via securement of the prongs 550, 552 within the ports 572, 570, respectively. FIG. 5X further illustrates the valve 530 in a second position where the valve 530 does not cover or block the opening 520d. The blood pressure monitor 120 can be configured such that the valve 530 is in the second position unless and/or until one of the prongs 550, 552 is secured within the port 572. With continued reference to FIGS. 5W-5X, when one of the prongs 550, 552 are secured within the port 572, the valve 530 can be moved (for example, "pushed") from the first position (FIG. 5W) to the second position (FIG. 5X). As discussed above, the valve 530 can include one or more openings 531e and opening 531f. When the valve 530 is in the first position (FIG. 5W), the openings 531e can obstructed. For example, when the valve 530 is in the first position (FIG. 5W), fluid communication between the openings 531e and the interior of the manifold 520 can be inhibited or prevented. When the valve 530 is in the second position (FIG. 5X) the openings 531e can be in fluid communication with the interior of the manifold 520. In such second position, air can flow through the openings 531e, opening 531f, fluid passageway 550a, and into an interior 549 of a bladder 543 of the cuff 121. Further, in such second position, air can flow in an opposite direction, for example, from the interior 549 of the bladder 543 of the cuff 121, through the fluid passageway 550a, opening 531f, openings 531e, and into the interior of the manifold 520.

As discussed above, the valve 530 can include a sealing ring 532. When the valve 530 is in the first position (FIG. 5W), the sealing ring 532 can contact a surface of the manifold 520 around the opening 520d. Additionally, when the valve 530 is in the second position (FIG. 5X), the sealing ring 532 can be spaced from the surface of the manifold 520 around the opening 520a. Each of the ports 572, 570 can include a sealing ring 572a, 570a that can be received by recessed portions 550b, 552b of the prongs 550, 552 (see FIGS. 5W-5X and 5N). The recessed portions 550b, 552b of the prongs 550, 552 can comprise an annular recess around a perimeter of the prongs 550, 552.

In some cases, only one of the ports 572, 570 of the blood pressure monitor 120 is configured to enable fluid communication between an interior of the housing 502 (for example, an interior of the manifold 520) and fluid passages 550a, 552a of the prongs 550, 552 when the prongs 550, 552 are received and/or secured in the ports 572, 570. For example, with reference to FIGS. 5V-5X, the blood pressure monitor 120 can include both of ports 570 and 572 but only port 572 is configured to enable such fluid communication. The blood pressure monitor 120 can include a cap 523 (FIGS. 5V and 5Y) that is secured to an end of the port 570. In such cases, while port 570 does not enable such fluid communication, the port 570 can advantageously allow for more stability and/or more robust securement with the cuff 121. For example, regardless of whether the blood pressure monitor 120 and cuff 121 are secured in either of the two orientations shown in FIG. 5L or 5M, one of the prongs 550, 552 will be secured within port 572 to enable fluid communication between the interior 549 of the bladder 543 and the interior 588 of the housing 502. Additionally, regardless of such described orientations, the other of the two prongs 550, 552 not secured within port 572 can secure within port 570 and provide stability to the blood pressure monitor 120 on the cuff 121.

As discussed further below with reference FIGS. 12-14E, the blood pressure monitor 120 can include one or more pressure transducers that are configured to detect an air pressure in the cuff 121. The blood pressure monitor 120 can include, for example, one or two pressure transducers. The pressure transducer(s) can be coupled to and/or positioned proximate the circuit board 521. The pressure transducer(s) can be positioned adjacent and/or proximate to the manifold 520 of the blood pressure monitor 120. For example, the manifold 520 can include one or more openings in a bottom portion 520b of the manifold 520 that are positioned proximate or adjacent the pressure transducer(s). In some cases, it can be beneficial to isolate or partially isolate such openings in the manifold 520 with other portions of the manifold 520 and/or other portions of blood pressure monitor 120. For example, it can be beneficial to partially isolate such openings from inlets 520a, which can be in fluid communication with the pumps 522. The blood pressure monitor 120 can include one or more towers 527 extending around openings in the bottom portion 520b of the manifold 520 and/or extending upward from the bottom portion 520b of the manifold 520. The towers 527 can be hollow. The towers 527 can be cylindrical, for example. The towers 527 can extend from the bottom portion 520b of the manifold 520 upwards to a top portion 520c of the manifold 520 (see FIG. 5U). The towers 527 can include a notch 527a which can provide fluid communication between an interior of the towers 527 and the manifold 520. The notch 527a can be sized and/or shaped to provide an air flow path over a portion of an end of the towers 527 (for example, a top end of the towers 527) so that air can flow into the manifold 520 from the towers 527 and vice versa. Advantageously, the towers 527 can help isolate or partially isolate the openings in the bottom portion 520b and the flow path to pressure transducers from, for example, the inlets 520a of the pumps 520a which may see large fluctuations in air flow and/or pressure gradients that may interfere with the pressure transducers' ability to function and/or operate properly or efficiently.

Blood pressure monitor 120 can include one or more light emitting diode (LED) indicators that can indicate a status of the blood pressure monitor 120, for example, that the blood pressure monitor 120 is in an operational ("on") mode. The LED indicator can be coupled to a side of the circuit board 521, for example, a side that faces "up" in the orientation shown in FIG. 5V and/or faces toward a top portion 502a of the housing 502 of the monitor 120. With reference to FIG. 5V, the blood pressure monitor 120 can include a light pipe or tube 593 that surrounds and/or encircled the LED indicator. The light tube 593 can focus and/or direct light emitted from the LED indicator to a top portion of the blood pressure monitor 120, such as a top portion 502a of the housing 502 of the monitor 120. In some variants, a top portion of the blood pressure monitor 120 (for example, top portion 502a) is transparent, which can allow light from the LED indicator to be seen from outside the housing 502. The light tube 593 can be non-transparent, for example, opaque. In some variants, the housing 502 comprises an opening on a top portion thereof (such as top portion 502a) that is aligned with the light tube 593 (such as an axis of the light tube 592) which allow light from the LED indicator to pass through the top portion to be seen.

Figure 6A:
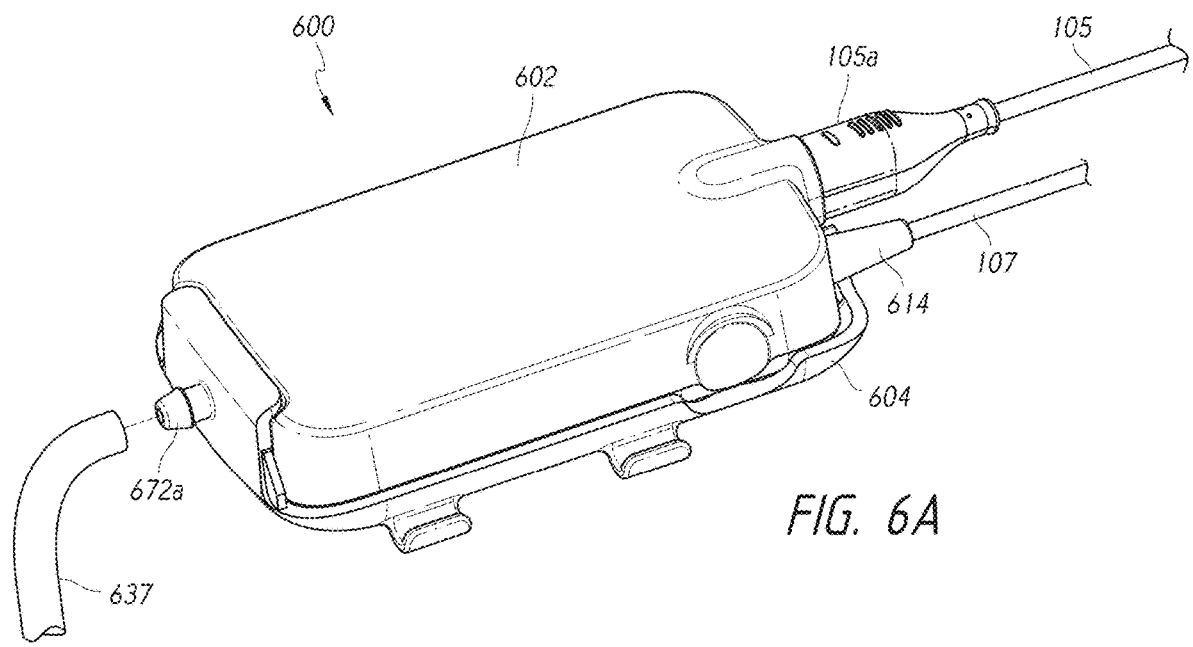
FIG. 6A illustrates a perspective view an embodiment of a blood pressure monitor assembly in accordance with aspects of this disclosure.
Figure 6B:
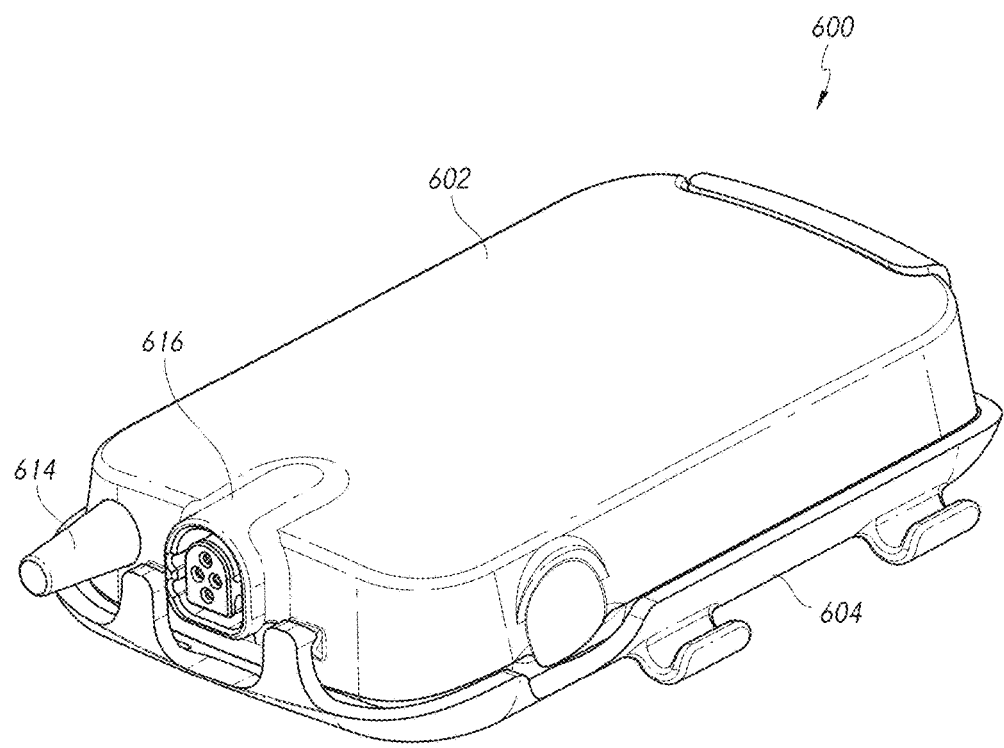
FIG. 6B illustrates another perspective view of the blood pressure monitor assembly of FIG. 6A.
Figure 6C:
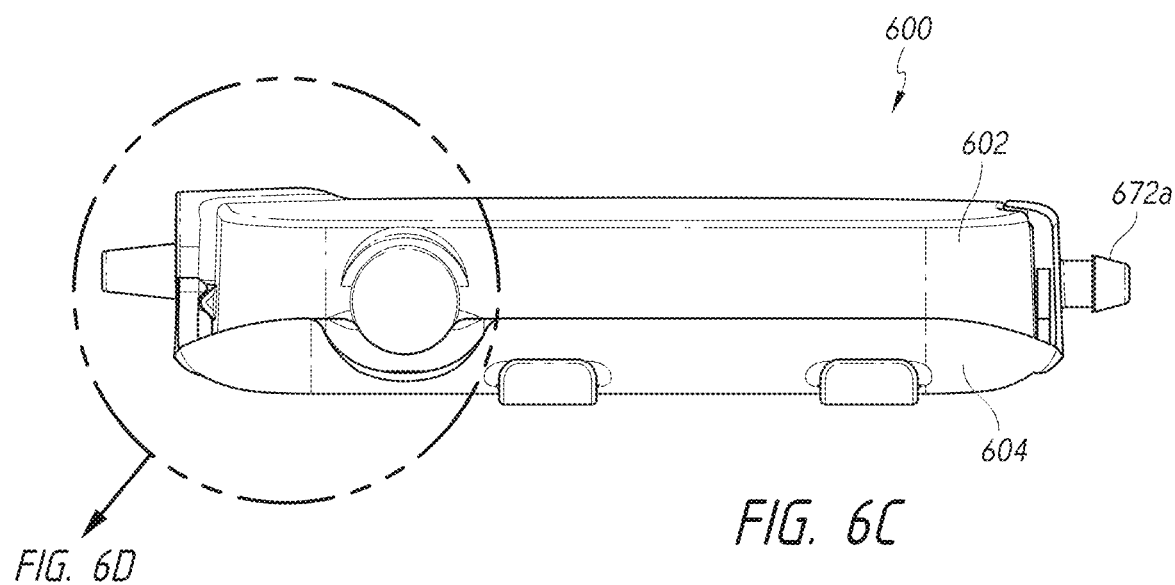
FIG. 6C illustrates a side view of the blood pressure monitor assembly of FIG. 6A.
Figure 6D:
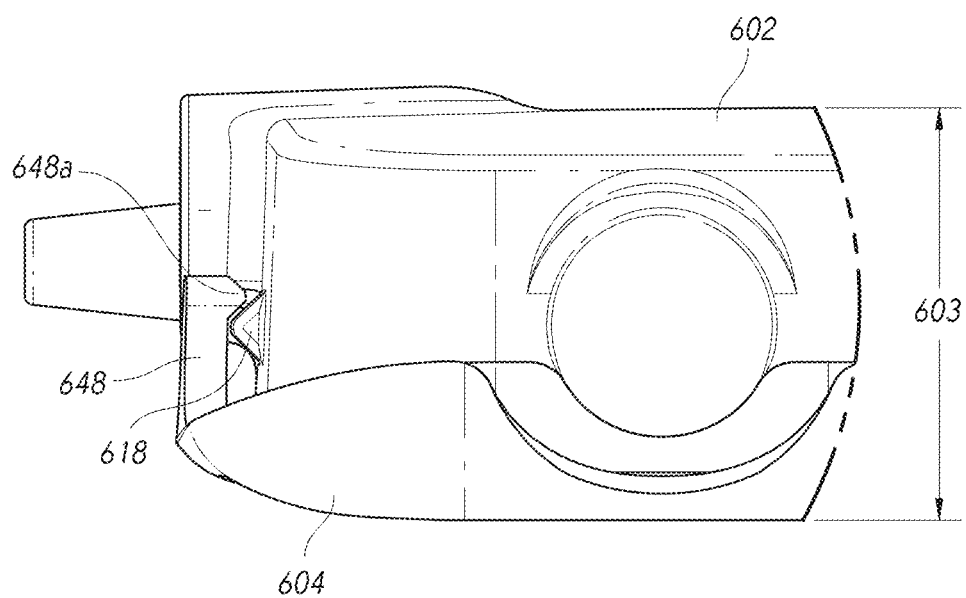
FIG. 6D illustrates an enlarged view of a portion of the blood pressure monitor assembly as shown in FIG. 6C.
Figure 6E:
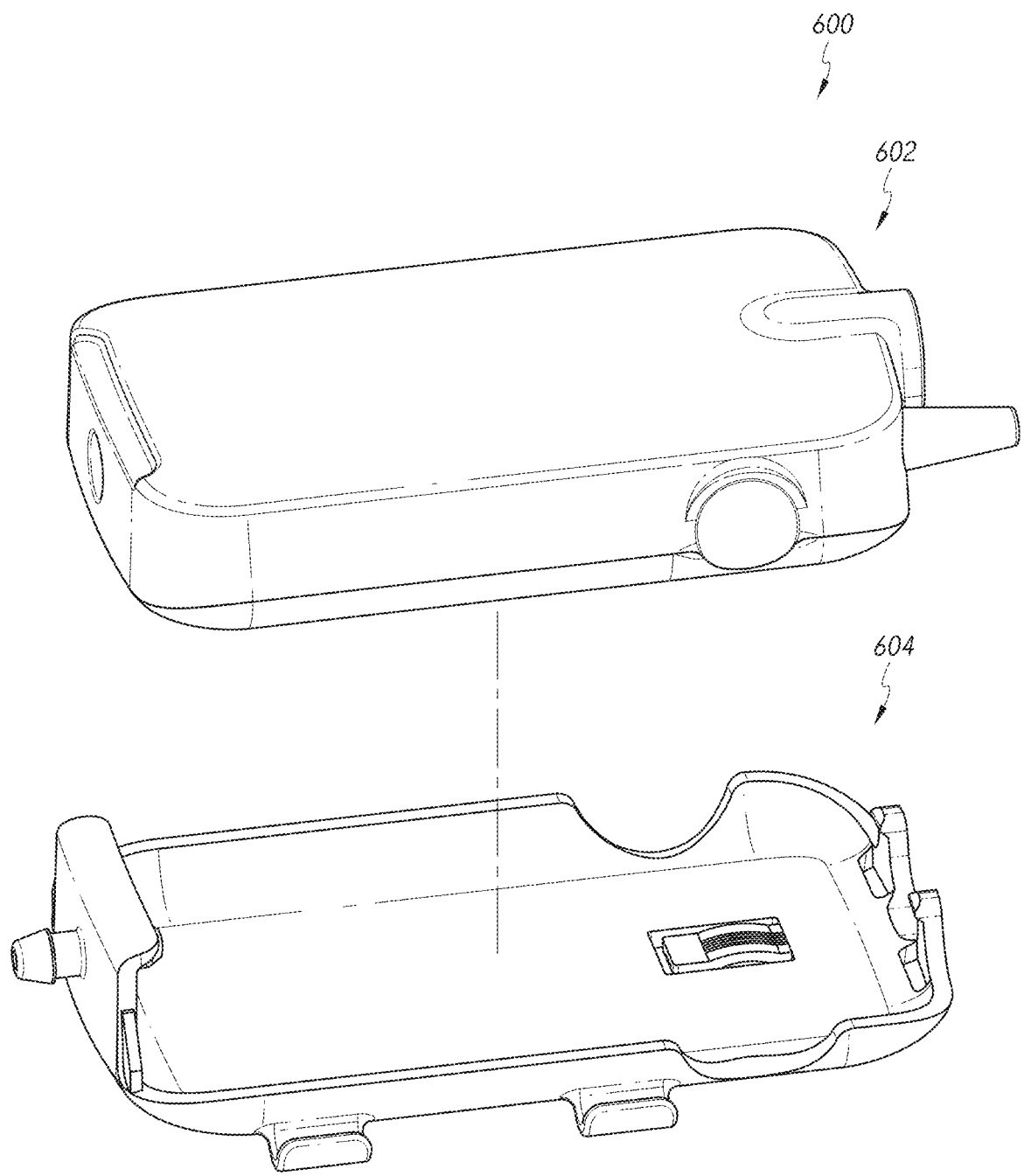
FIG. 6E illustrates an exploded view of the blood pressure monitor assembly of FIG. 6A.
Figure 6F:
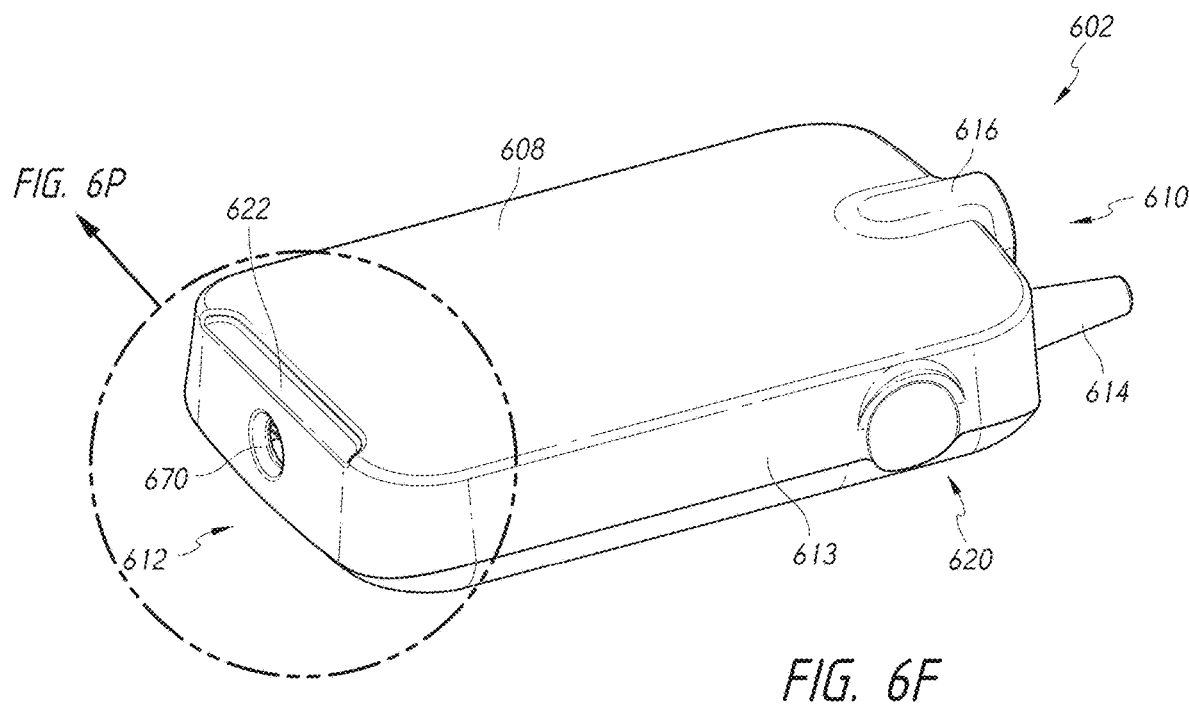
Figure 6G:
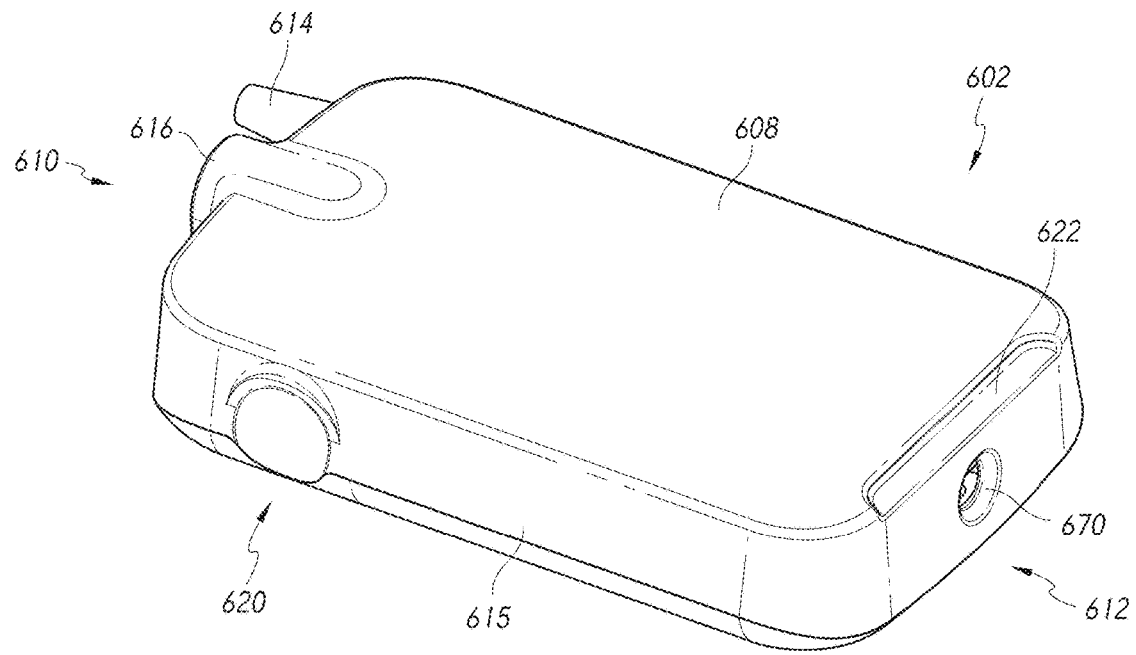
Figure 6J:
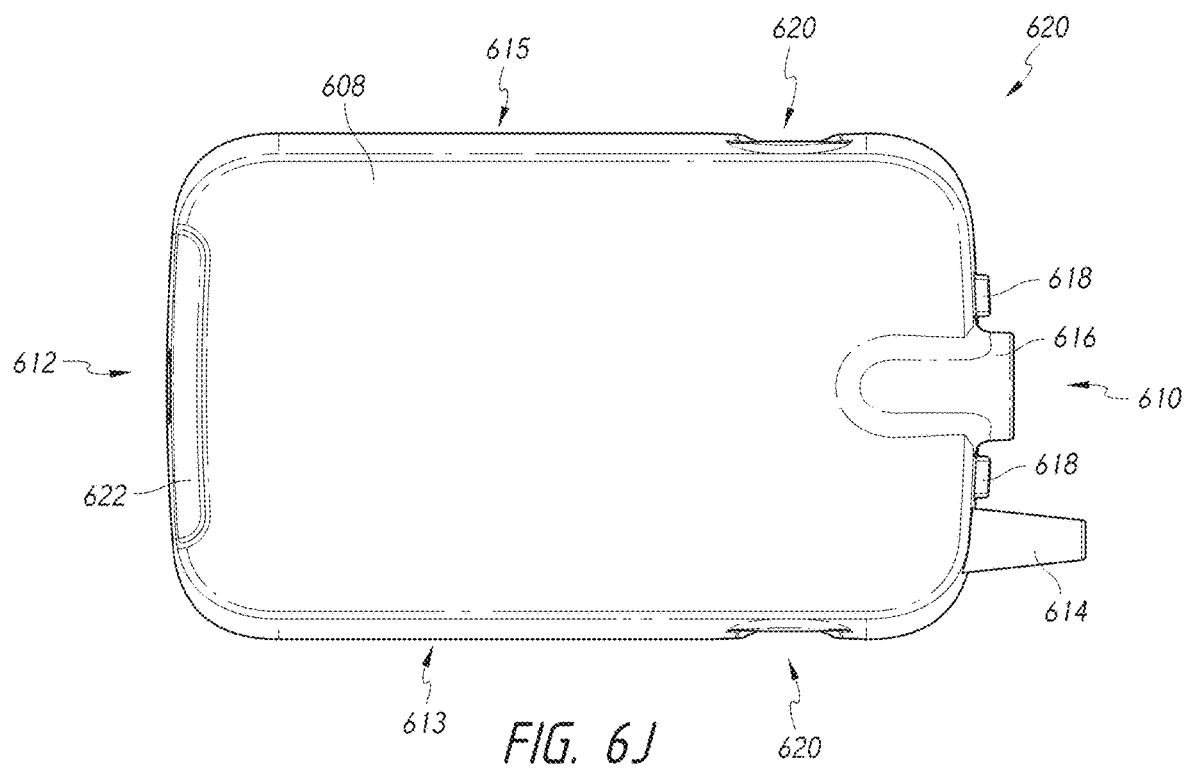
FIG. 6J illustrates a top view of the blood pressure monitor of FIGS. 6F-6I.
Figure 6K:
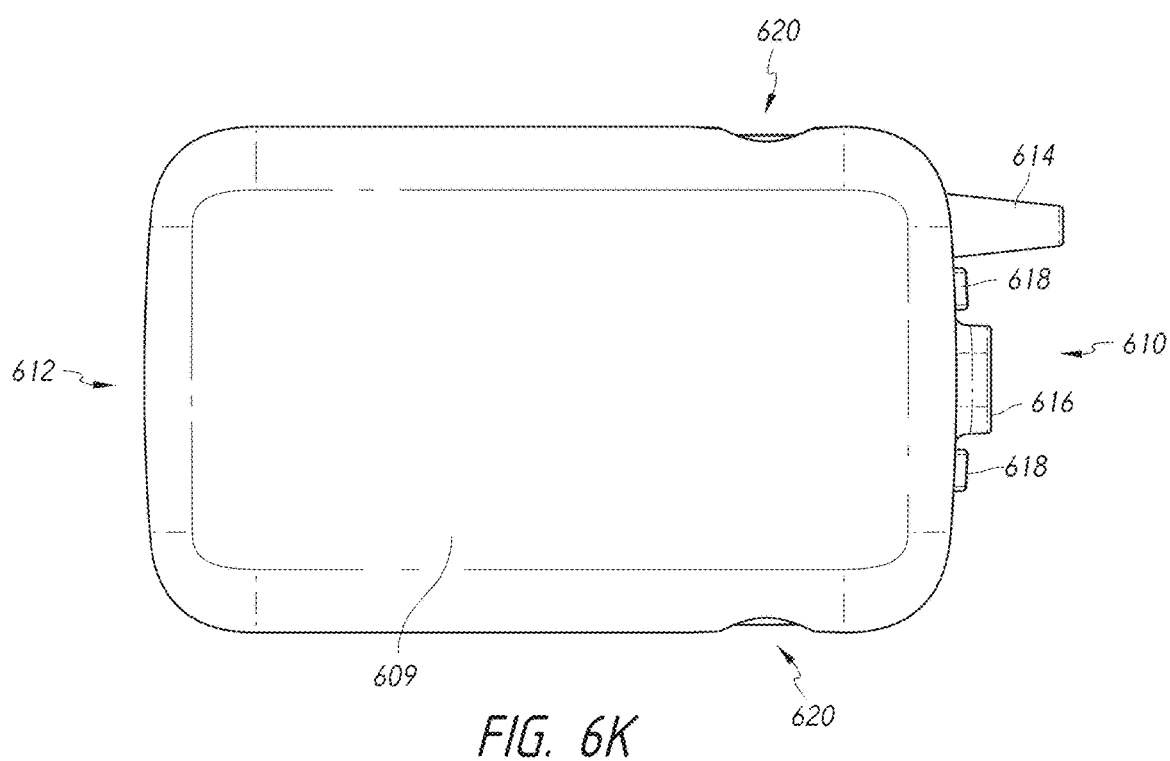
FIG. 6K illustrates a bottom view of the blood pressure monitor of FIGS. 6F-6I.
Figure 6L:
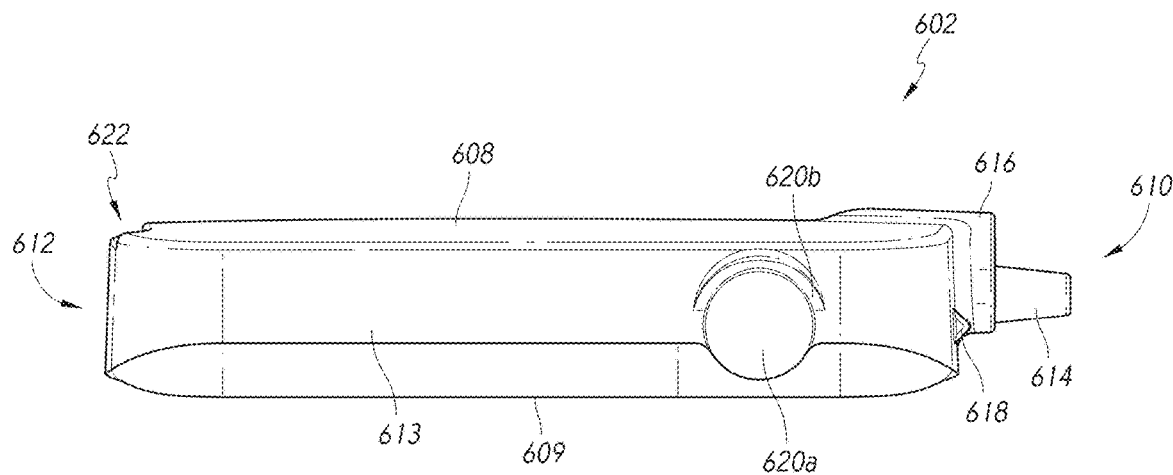
FIG. 6L illustrates a side view of the blood pressure monitor of FIGS. 6F-6I.
Figure 6M:
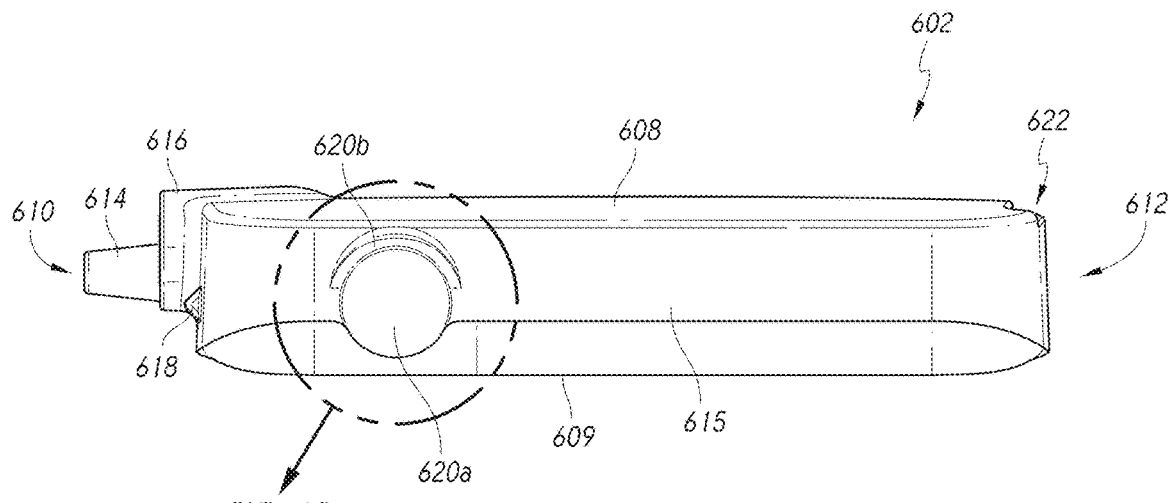
FIG. 6M illustrates another side view of the blood pressure monitor of FIGS. 6F-6I.
Figure 6N:
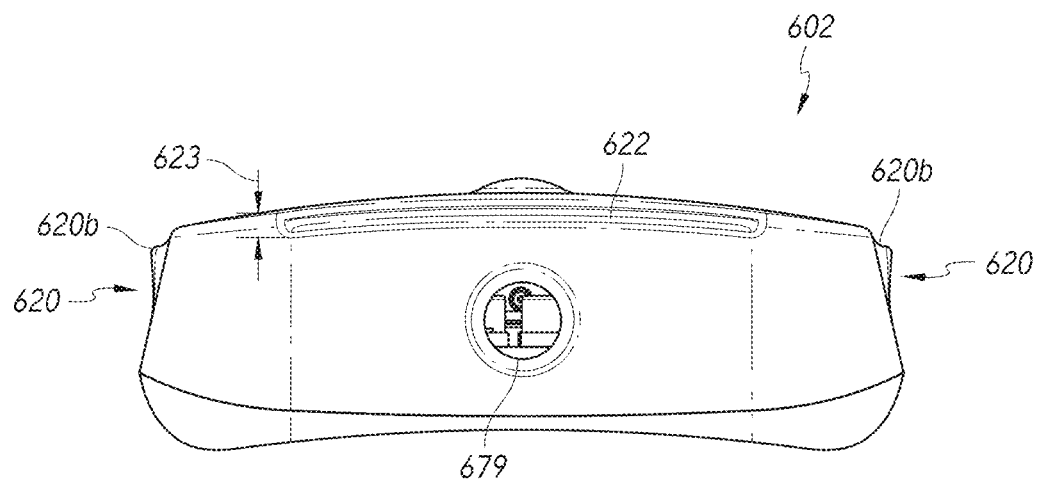
FIG. 6N illustrates a front view of the blood pressure monitor of FIGS. 6F-6I.
Figure 6O:
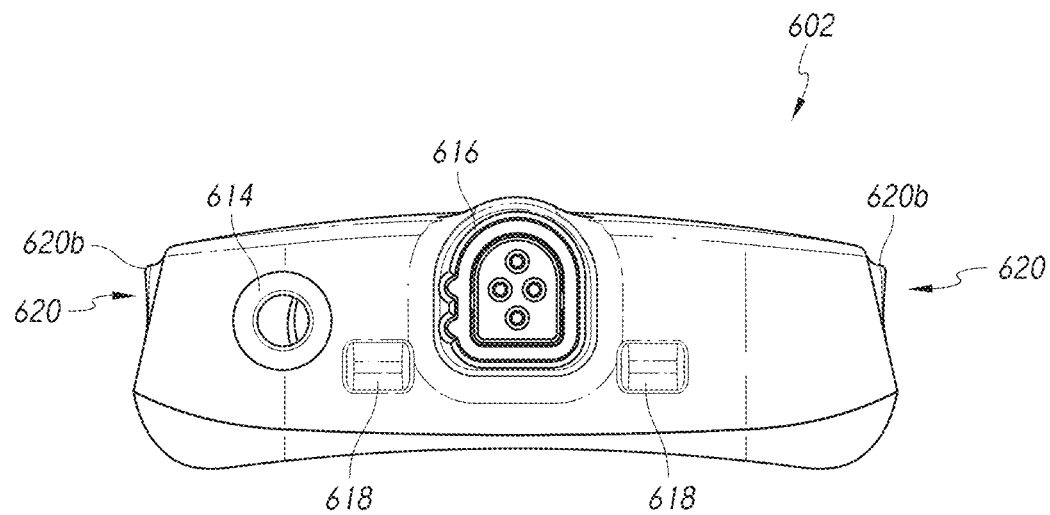
FIG. 6O illustrates a back view of the blood pressure monitor of FIGS. 6F-6I.
Figure 6P:
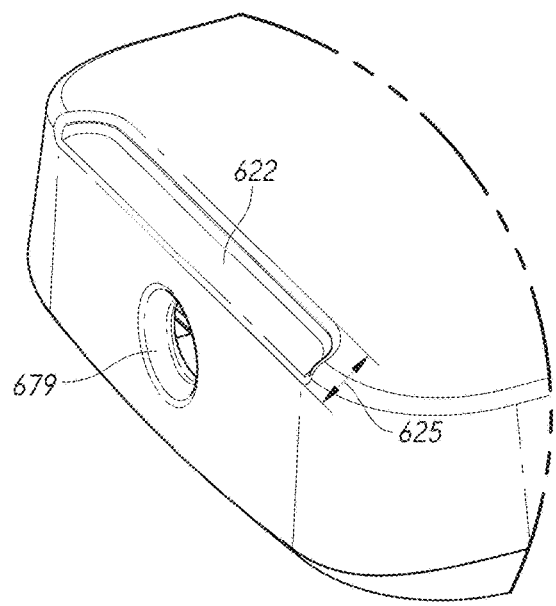
FIG. 6P illustrates an enlarged perspective view of a portion of the blood pressure monitor of FIGS. 6F-6I shown in FIG. 6F.
Figure 6Q:
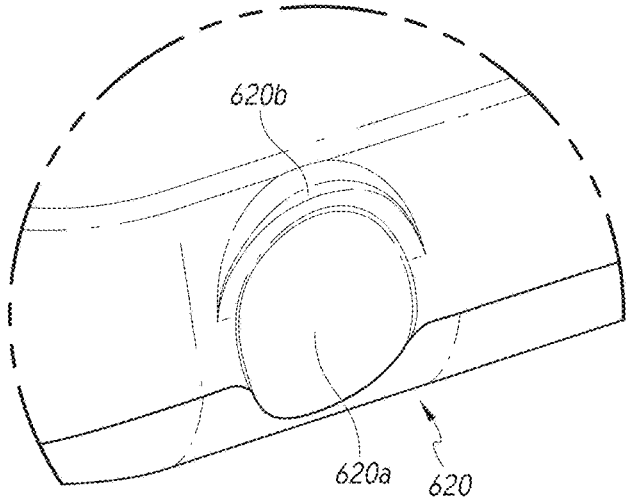
FIG. 6Q illustrates an enlarged perspective view of a portion of the blood pressure monitor of FIGS. 6F-6I as shown in FIG. 6H.
Figure 6R:
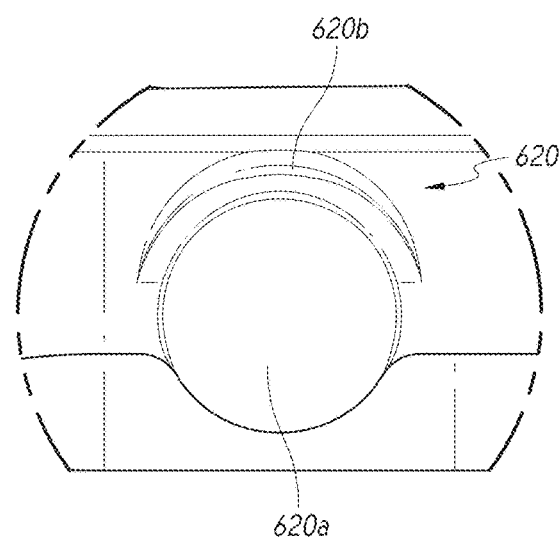
FIG. 6R illustrates an enlarged view of a portion of the housing of the blood pressure monitor of FIGS. 6F-6I as shown in FIG. 6M.
Figure 6S:
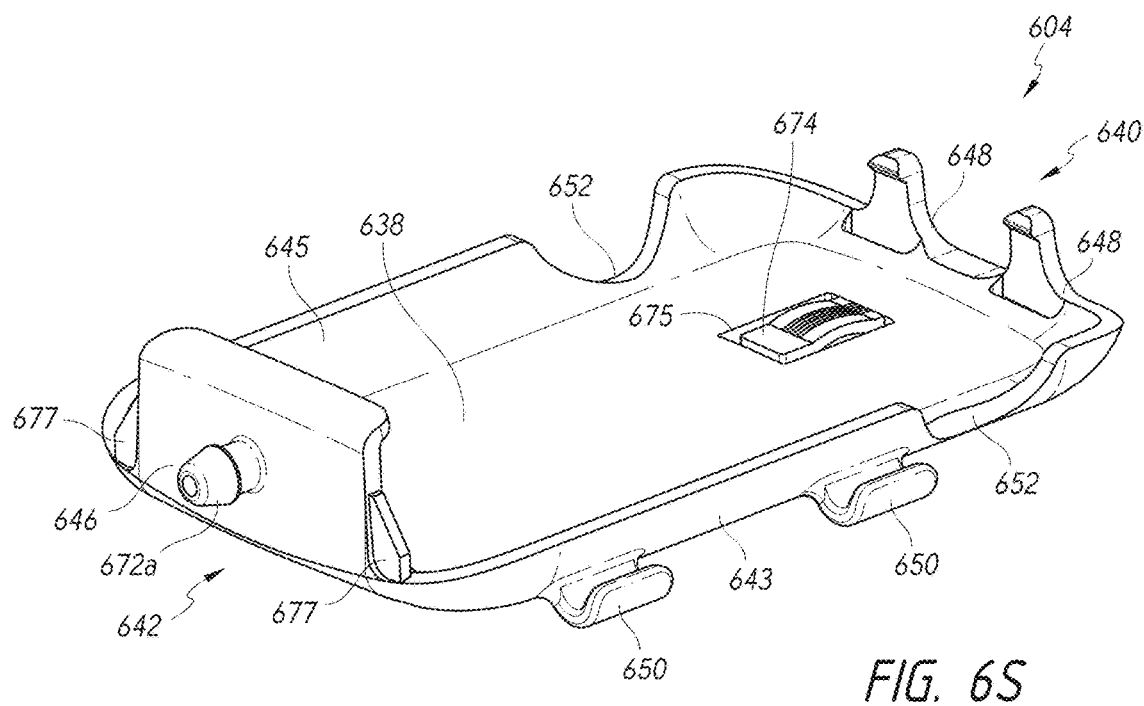
FIG. 6S-6T illustrate perspective views of a cradle of the assembly of FIG. 6A.
Figure 6T:
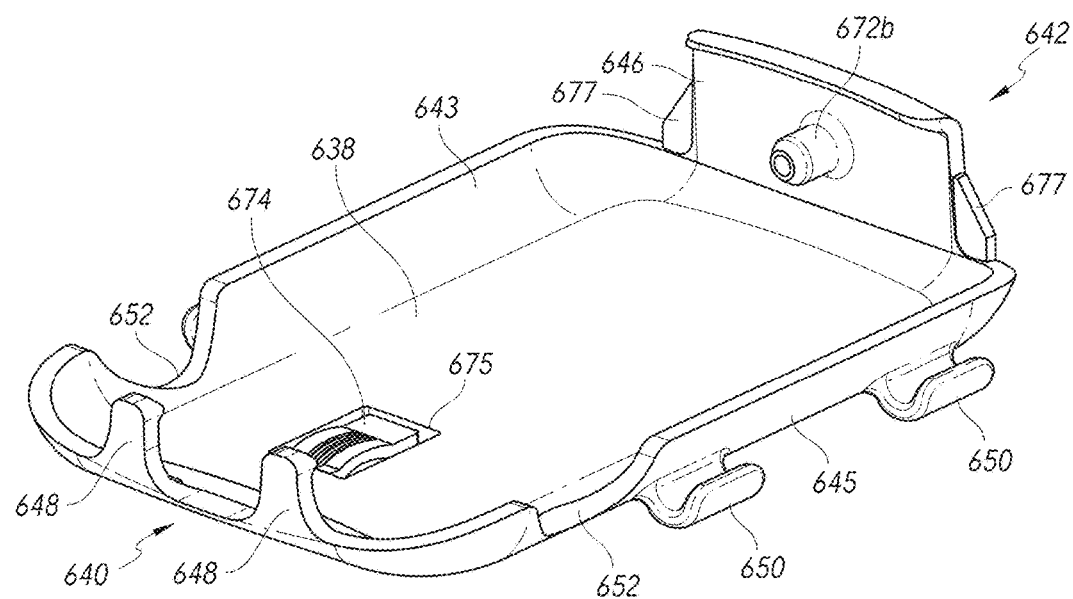
Figure 6U:
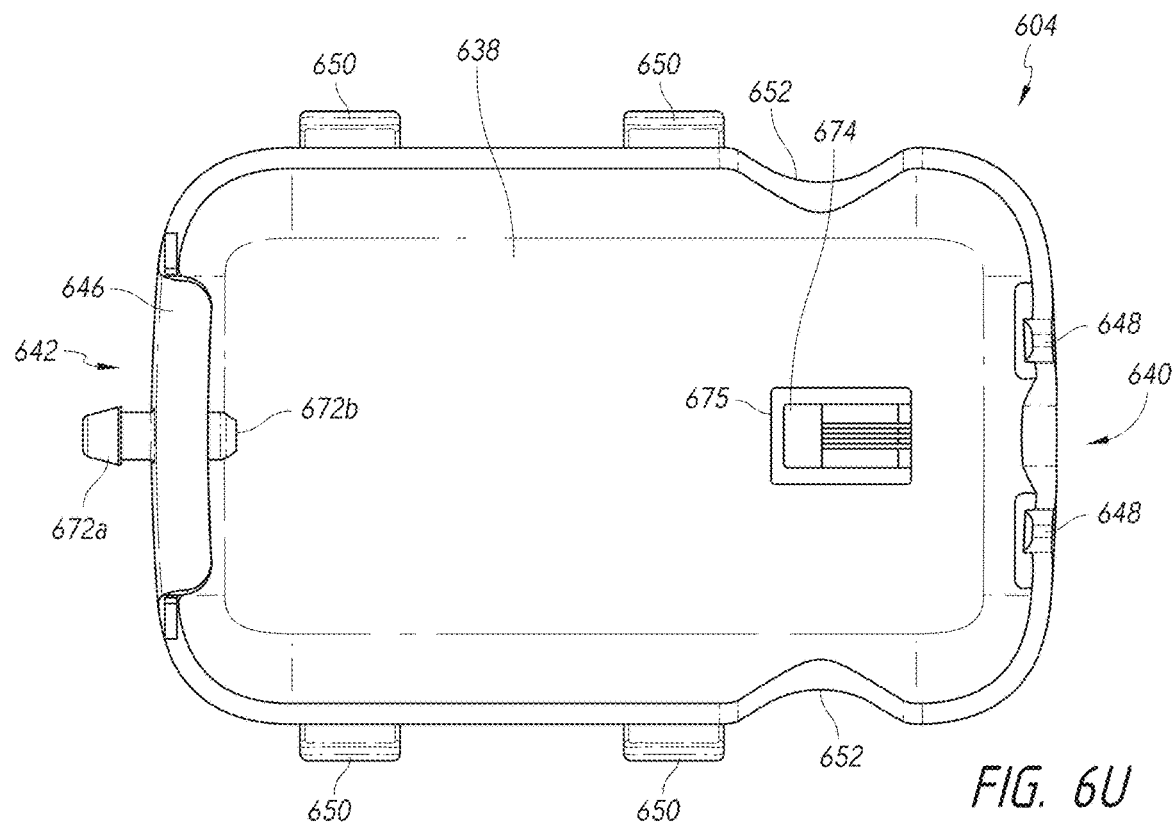
FIG. 6U illustrates a top view of the cradle of the blood pressure monitor of FIG. 6S-6T.
Figure 6V:
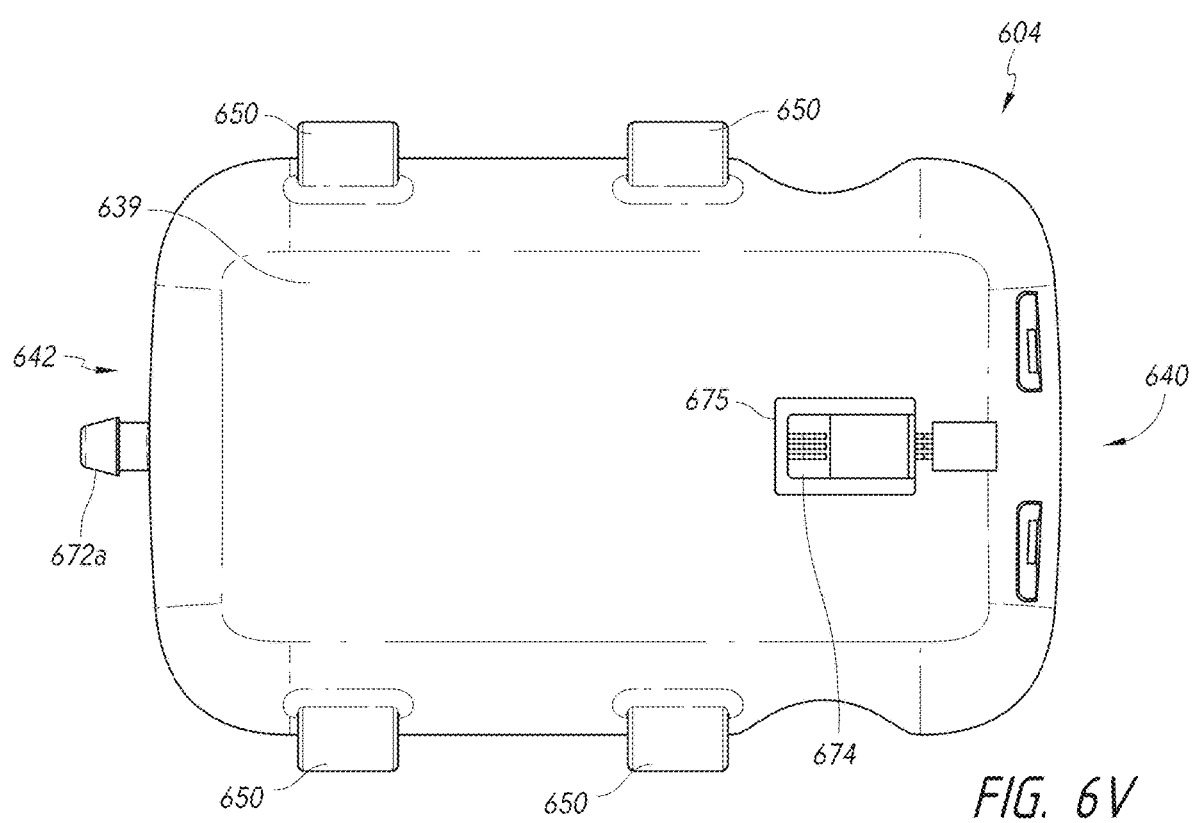
FIG. 6V illustrates a bottom view of the cradle of the blood pressure monitor of FIG. 6S-6T.
Figure 6W:
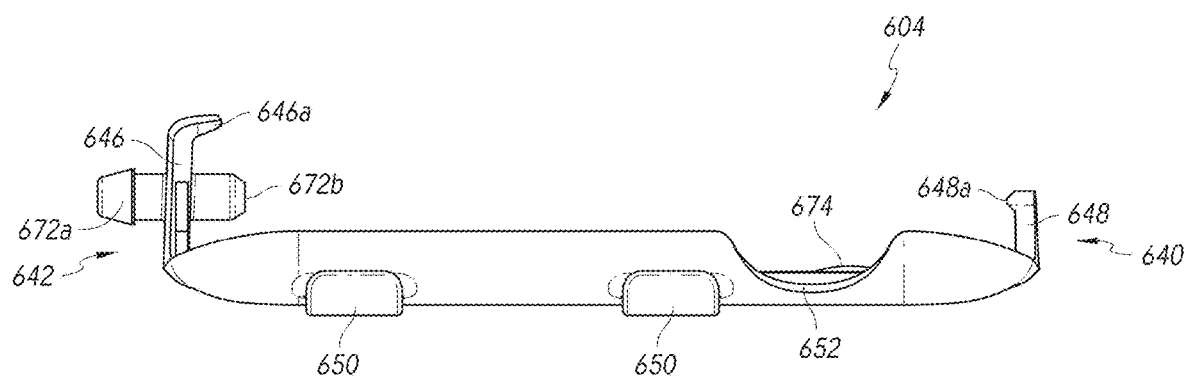
FIG. 6W illustrates a side view of the cradle of the blood pressure monitor of FIG. 6S-6T.
Figure 6X:
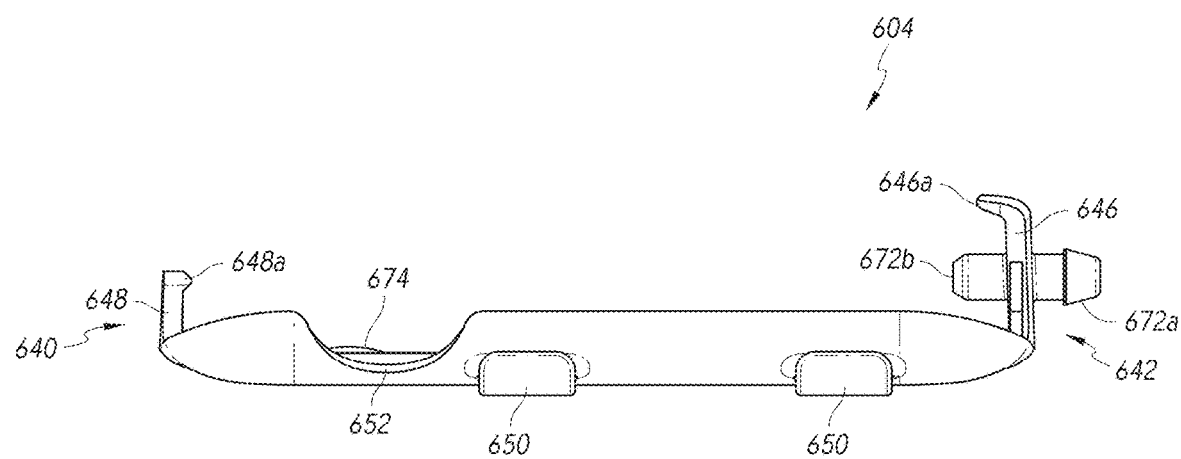
FIG. 6X illustrates another side view of the cradle of the blood pressure monitor of FIG. 6S-6T.
Figure 6Y:
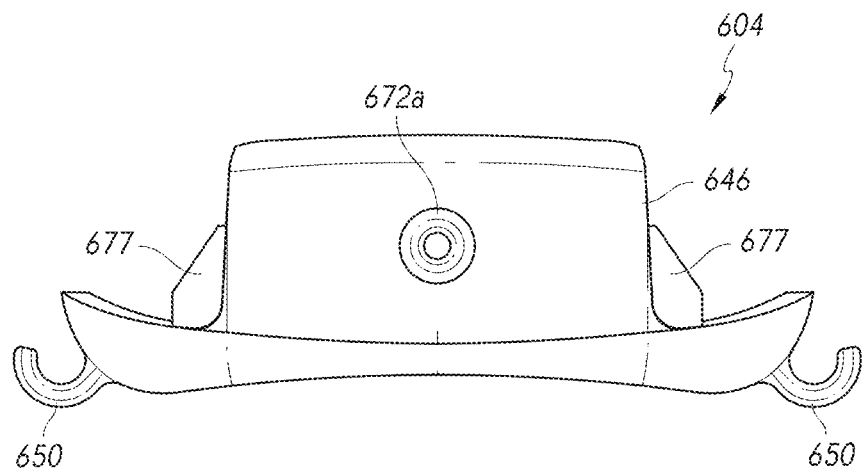
FIG. 6Y illustrates a front view of the cradle of the blood pressure monitor of FIG. 6S-6T.
Figure 6Z:
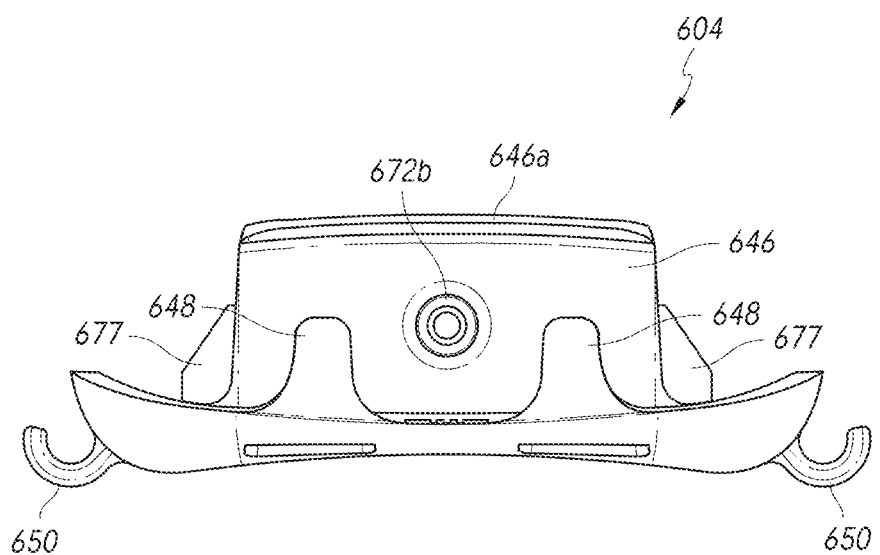
FIG. 6Z illustrates a back view of the cradle of the blood pressure monitor of FIG. 6S-6T.

FIGS. 6A-6Z illustrate various views and aspects of a blood pressure monitor assembly 600 which includes an alternative design for a blood pressure monitor 602 and also includes a cradle 604. While the device 602 is referred to herein as a "blood pressure monitor" or "blood pressure device" herein, device 602 can measure and/or monitor other parameters in addition or as an alternative to blood pressure. For example, device 602 can measure and/or monitor the concentration or partial pressure of carbon dioxide ($CO_2$) in exhaled air of the patient. Blood pressure monitor 602 can have the characteristics and/or functionality as described in more detail below with reference to FIGS. 12-14E.

With reference to FIGS. 6A-6E, blood pressure monitor assembly 600 can include a blood pressure monitor 602 and a cradle 604 configured to secure to the blood pressure monitor 602 (and vice versa). Blood pressure monitor assembly 600 can be configured to secure to an arm of patient 11. For example, blood pressure monitor assembly 600 can secure to an a blood pressure cuff (such as cuff 737 shown in FIG. 7V) that is secured to a patient's arm. The blood pressure cuff can wrap around and/or otherwise secure to an arm of patient 11, and blood pressure monitor assembly 600 can secure to the blood pressure cuff 737, for example, via securement between cradle 604 and the blood pressure cuff. For example, cradle 604 can have an adhesive or a hook-and-look fastener (for example, Velcro®) on a bottom surface thereof, which can secure to a portion of the cuff 737.

Blood pressure monitor assembly 600 can be configured to connect to a cuff 737 (see FIG. 7V) and provide air to the cuff to cause inflation and/or can allow the cuff 737 to deflate. For example, blood pressure monitor assembly 600 can include a pneumatic opening or connection point 670 (see FIG. 6F) in blood pressure device 602 (or a housing of blood pressure device 602) which can be in fluid communication with the cuff 737 via a pneumatic hose 637 (see FIG. 6A). As also discussed further below, cradle 604 can include one or more ports that can connect to and/or facilitate connection between the pneumatic hose 637 and the opening 670 in blood pressure monitor 602. For example, as discussed in more detail below, cradle 604 can include an outward port 672a that can connect to pneumatic hose 637 and an inward port 672b which connects to opening 670 in blood pressure device 602 (see FIGS. 6A and 6W-6X). The securement between outward port 672a and pneumatic hose 637 can be a snap-fit, press-fit, friction-fit, or another type of securement. Further, while FIG. 6A illustrates an end of a pneumatic hose 637 connecting to port 672a, the end of the pneumatic hose 637 can connect to port 672a via an adapter or other type of intermediary connector. Blood pressure device 602 can provide air to cuff 737 to inflate the cuff 737 to a pressure level high enough to occlude a major artery. When air is slowly released from the cuff 737, blood pressure can be estimated by the blood pressure monitor 602 as described in more detail below with reference to FIGS. 12-14E.

Blood pressure device 602 can include structure and/or functionality to cover and/or close opening 670 when the blood pressure device 602 is not in use so as to prevent debris and/or liquids from passing through opening 670 and passing into an interior of blood pressure device 602. For example, with reference to FIG. 6N, blood pressure device 602 can include a cover 679 that can cover and/or seal opening 670 when the blood pressure device 602 is not in use, and thus can prevent fluid communication between ambient air and the interior of the blood pressure device when not in use. For example, cover 679 can be a flap that can act to seal and/or close off opening 670 when the blood pressure device 602 is not connected to the cradle 604. The flap can be movable, flexible, and/or resilient. The flap can cover opening 670 unless and/or until an object pushes the flap inward at least partially into an interior of the blood pressure device 602. For example, when blood pressure device 602 is secured to cradle 604, port 672b can push the flap at least partially inward into the interior of blood pressure device 602 so that port 672b can pass at least partially into the interior of blood pressure device 602 and be in fluid communication with a conduit, manifold, pump, and/or valve within the blood pressure device 602. As another example, cover 679 can be rigid and can be electronically and/or mechanically controlled by a controller and/or processor of the blood pressure device 602. For example, cover 679 can be a rigid plate that can be moved from a position where is it not covering, or only partially covering, opening 670, to a position where it is covering and/or sealing opening 670. Cover 679 can be sized and/or shaped to match the size and/or shape opening 670. In some cases, the blood pressure device 602 can control operation (for example, movement) of the cover 679 based on interaction with cradle 604.

As discussed elsewhere herein, the blood pressure device 602 and cradle 604 can include near field communication (NFC) functional capabilities (for example, RFID) that can enable the blood pressure device 602 and cradle 604 to, among other things: confirm that the blood pressure device 602 and/or cradle 604 are authentic components; transfer data (for example, data measured and/or gathered by the blood pressure device 602 can be transferred and/or stored on the cradle 604); determine the size of a cuff to which the cradle 604 is attached; and determine a lifespan of the blood pressure device 602 and/or cradle 604. For example, as discussed below, the blood pressure device 602 can include an RFID reader that transmits a radio frequency and the cradle 604 can include an RFID tag (for example, in the form of a sticker or label) which can be attached to a portion of the cradle 604. Such NFC structure and functionality can enable the blood pressure device 602 to control operation of the cover 679 based on proximity with cradle 604. For example, when blood pressure device 602 is brought within sufficient proximity to the RFID tag of cradle 604 such that the RFID reader in the blood pressure device 602 receives a confirmatory signal from the RFID tag, blood pressure device 602 can automatically open cover 679 to reveal opening 670. For example, the range of the RFID reader and tag can be selected so that bringing the blood pressure device 602 within a certain distance of cradle 604 causes such automatic opening of cover 679. Such distance can be 1 inch, 2 inch, 3 inch, 4 inch, 5 inch, 6 inch, 7 inch, 8 inch, 9 inch, 10 inch, 11 inch, 12 inch, 1 ft, 1.5 ft, or 2 ft, or any value therebetween, or any range bounded by any combination of these values, although values outside these values or ranges can be used in some cases.

Blood pressure monitor 602 can connect to one or more physiological sensors and/or monitors, such as ECG device 110 and/or patient monitor 130, each of which are discussed in more detail elsewhere herein. For example, a cable 105 and connector 105a can connect to a connector port 616 (see FIG. 6B) of blood pressure device 602 and also connect to ECG device 110 (see FIG. 2A). Additionally or alternatively, cable 107 can connect to and/or be coupled to (for example, fixed to) to a connector port 614 (see FIG. 6A) of blood pressure device 602 and can also connect to patient monitor 130 (see FIG. 8A). For example, cable 107 and connector 107a can connect to a female connector port 832 of patient monitor 130 (see FIGS. 8A and 8I). As discussed previously, blood pressure monitor 602 can include a bypass bus that can pass physiological data received from the ECG device 110 to the patient monitor 130 without processing. For example, the bypass bus of blood pressure monitor 602 can pass physiological data received via cable 105 and connector 105a by connector port 616 to connector port 614, through cable 107 and connector 107a, and to patient monitor 130 via connector port 833.

Blood pressure monitor 602 can include various electronic components to allow the blood pressure monitor 602 to carry out its physiological measurement and/or monitoring functionality, while cradle 604 can include little or no electronic components and/or functionality. For example, blood pressure monitor 602 can include the various electronic components and/or functionality as described with reference to FIGS. 12-14E. As discussed in more detail below, blood pressure monitor 602 and cradle 604 can include various features which allow for the either or both to be removably secured to one another. Such removable securement can advantageously allow the cradle 604 to remain attached to the patient 111 and/or cuff 737 while the blood pressure monitor 602 is removed away from the patient 111 and/or cuff 737. This can be especially helpful where it is desirable to temporarily remove the blood pressure monitor 602 to charge and/or repair the blood pressure monitor 602. This can also allow a caregiver to clean the cradle 604 and/or regions of the patient 111 proximate the cradle 604 without risking damage to the blood pressure monitor 602 (or various components thereof).

FIGS. 6A-6D illustrate various view of blood pressure monitor assembly 600 where the blood pressure monitor 602 and the cradle 604 are in an assembled or secured configuration. As shown and as further discussed below, the cradle 604 can secure to the blood pressure monitor 602 (and vice versa) by securement between one or more sides or ends of the blood pressure monitor 602 and one or more sides or ends of the cradle 604. For example, a first end of the cradle 604 can secure to a first end of the blood pressure monitor 602 and/or a second end of the cradle 604 (opposite the first end of the cradle 604) can secure to a second end of the blood pressure monitor 602 (opposite the first end of the blood pressure monitor 602). The securement of the blood pressure monitor 602 by the cradle 604 can advantageously prevent movement and/or rotation of the blood pressure monitor 602 relative to the cradle 604 along an axis running through a length, width, and/or height of the blood pressure monitor 602 and/or cradle 604.

FIGS. 6F-6O illustrate various views of the blood pressure monitor 602 of blood pressure monitor assembly 600. As shown, blood pressure monitor 602 can include a first end 610, a second end 612 opposite the first end 610, a first side 613, and a second side 615 opposite the first side 613. The first end 610 can include a connector port 616, which, as discussed above, can connect to a connector and/or cable such as connector 105a and cable 105. While the present disclosure refers to "end" or "side", such terminology is not intended to be limiting, but rather, is employed for mere convenience in differentiating certain features of the blood pressure monitor 602. Accordingly, while the term "end" is used for the first and second ends 610, 612, it is to be understood that such ends 610, 612 can also represent "sides" of the blood pressure monitor 602. Connector port 616 can protrude outward from a surface of the first end 610. First end 610 can additionally or alternatively include a connector port 614 which can be spaced from the connector port 616 along a surface of the first end 610. As also discussed above, connector port 614 can connect to a cable 107. Connector port 614 can protrude outward from a surface of the first end 610. Connector port 614 can protrude outward from the first end 610 a distance greater than the connector port 616 (see FIGS. 6L-6M). Connector port 614 can have a circular cross-section, a conical cross-section, among other shapes. Connector port 614 can have a cross-section that tapers (or decreases) from a first end of the connector port 614 that connects to the first end 610 of the blood pressure monitor 602 to a second end of the connector port 614 that is opposite from the first end of the connector port 614. Connector port 616 can be positioned in a middle of the first end 610. Connector port 614 can be positioned on either side of connector port 616 along the first end 610.

As discussed above, blood pressure monitor 602 can include an opening 670 configured to connect and/or provide air to a pneumatic tube (such as hose 37). For example, blood pressure monitor 602 can have an opening 670 on a second end 612, which is opposite the first end 610 of housing. Pneumatic opening 670 can be positioned in a middle of the second end 612 or in a different location on the second end 612. Alternatively, opening 670 can be positioned on a different portion of the blood pressure monitor 602, for example one of the sides 613, 615 of blood pressure monitor 602.

Opening 670 can be sized and/or shaped to receive a portion of the cradle 604 as discussed above. For example, with reference to FIG. 6T, opening 670 can be sized and/or shaped to receive all or a portion of port 672b extending from a wall 646 of cradle 604. As further discussed below, port 672b can be rigid or non-rigid, and can have a length and/or cross-section that is sized to fit within the opening 670. Blood pressure monitor 602 can be secured or partially secured to cradle 604 via connection between the port 672b and the opening 670. For example, when the port 672b is received within opening 670, the port 672b can prevent movement of the blood pressure monitor 602 with respect to the cradle 604 along a direction that is perpendicular to an axis running through a length of port 672b and/or an axis that is parallel to a length of the blood pressure monitor 602 between the first and second ends 610, 612.

Blood pressure monitor 602 can include one or more features that help the blood pressure monitor 602 removably secure to the cradle 604. For example, housing can include one or more depressions 622 that are recessed from a surface of the blood pressure monitor 602 and are configured to engage a portion of the cradle 604. Depression 622 can be positioned on a top surface 608 of blood pressure monitor 602 (see FIGS. 6F-6G). Depression 622 can be recessed from the top surface 608 by a depth 623 (FIG. 6N) and can extend along apportion of the top surface 608. Depression 622 can be located along the top surface 608 and proximate or adjacent the second end 612. As discussed further below, depression 622 can engage with a lip 646a of a wall 646 of cradle 604 and can be sized and/or shaped to receive the lip 646a. The depth 623 of depression 622 can be equal or substantially equal to a thickness of lip 646a such that, when the lip 646a is positioned within the depression 622, a surface of the lip 646a is flush with a region of the top surface 608 of blood pressure monitor 602 that is proximate to the depression 622 (see FIG. 6C). With reference to FIGS. 6F-6G, 6J, and 6N, depression 622 can extend along a portion of a width of the blood pressure monitor 602 and can also extend along a portion of a length of the blood pressure monitor 602. For example, where the width of the blood pressure monitor 602 is the distance between sides 613 and 615 of blood pressure monitor 602 (see FIGS. 6J), depression 622 can extend along a portion of such distance, such as the entire distance, less than the entire distance, half the distance, less than half the distance, among other percentages or fractions of the distance. Additionally or alternatively, where the length of the blood pressure monitor 602 is the distance between the first end 610 and the second end 612, depression 622 can extend along such length by a distance 625 (see FIG. 6P). Distance 625 can be equal or substantially equal to a length of the lip 646a. Distance 625 can be a percentage of the length of the blood pressure monitor 602 between the first and second ends 610, 612, such as 30%, 20%, 10%, 5%, less than 50%, less than 40%, less than 30%, less than 25%, less than 20%, less than 15%, less than 10%, or less than 5%, although other percentages, values, or ranges are possible in some cases.

Additionally or alternatively, the blood pressure monitor 602 can include one or more latch arm protrusions 618 that extend outward from a surface of the blood pressure monitor 602 and are configured to engage and/or interact with one or more latch arms 648 of cradle 604. For example, as shown in at least FIGS. 6H-6K, blood pressure monitor 602 can include one or more latch arm protrusions 618 that extend or protrude outward from a surface of the first end 610 of blood pressure monitor 602. The one or more latch arm protrusions 618 can include, one, two, three, four, five, six, seven, eight, or nine or more latch arm protrusions 618. The number of latch arm protrusions 618 on the blood pressure monitor 602 can be equal to the number of latch arms 648 on the cradle 604, such that each of the latch arm protrusions 618 are configured to engage, secure, cooperate, and/or interact with a respective one of the latch arms 648 of the cradle 604. The blood pressure monitor 602 can include a first latch arm protrusion 618 that extends from a surface of the first end 610 of blood pressure monitor 602 and a second latch arm protrusion 618 that extends from the surface of the first end 610. The first and second latch arm protrusions 618 can be spaced from one another. The first and second latch arm protrusions 618 can be positioned on opposite sides of connector port 616 (where the blood pressure monitor 602 includes the connector port 616).

The one or more latch arm protrusions 618 can have a variety of shapes and/or cross-sections. For example, the one or more latch arm protrusions 618 can have a triangular shape, a square shape, a rectangle shape, a circular shape, among other shapes. As illustrated in FIGS. 6L-6M, the latch arm protrusions 618 have a triangle shape, where a tip of the triangle shape is defines the free end (not connected to the blood pressure monitor 602) of the protrusions 618. The one or more protrusions 618 can have a ramped or tapered configuration that enables them to move or slide passed a portion of the latch arms 648 while contacting the portion of the latch arms 648. The one or more latch arm protrusions 618 can have a shape or cross-section that is sized and/or shaped to correspond to a sized and/or shape of the latch arms 648 or a portion thereof. For example, where the free ends of the latch arms 648 have triangular shaped or tapering tip 648a (see FIGS. 6W-6X), the latch arm protrusions 618 can also have a triangular shaped or tapering tip. In such configurations where the shape or cross-section of the latch arm protrusions 618 correspond to the shape or cross-section of the free ends of the latch arms 648, the latch arm protrusions 618 can advantageously engage and/or secure to or with the free ends of the latch arms 648. For example, with reference to FIGS. 6C-6D, when an end of the blood pressure monitor 602 (such as first end 610 of blood pressure monitor 602) is secured to an end of cradle 604 (such as end 640 of cradle 604), the one or more protrusions 618 can contact and pass over the tips 648a of the latch arms 648, such that the tips 648a at least partially hold the protrusions 618 below (with reference to a vertical axis in the orientation shown in the FIGS. 6C-6D).

As discussed above, blood pressure monitor 602 can at least partially secure to cradle 604 via connection between the port 672b and the pneumatic opening 670. One example of securing the blood pressure monitor 602 to the cradle 604 can involve securement of the second end 612 of blood pressure monitor 602 to end 642 of the cradle 604 by placing the opening 670 over and around the port 672b. As the opening 670 is positioned over/around the port 672b, the second end 612 of blood pressure monitor 602 can move or slide towards the wall 646 of the cradle 604 at the end 642. Further, as the second end 612 of blood pressure monitor 602 moves towards the wall 646, the first end 610 of the blood pressure monitor 602 can be moved towards the end 640 of the cradle 604 such that the first end 610 contacts or approaches the one or more latch arms 648. Movement of the first end 610 of blood pressure monitor 602 towards a top surface 638 of the cradle 604 and/or towards the one or more latch arms 648 can cause the one or more latch arm protrusions 618 of the blood pressure monitor 602 to contact and pass over the tips 648a of the latch arms 648 (see FIG. 6D). Such contact between the one or more latch arm protrusions 648 and the tips 648a of the latch arms 348 can include a snap-fit, friction-fit, or press-fit. When the first end 610 of blood pressure monitor 602 is moved to contact the top surface 638 of cradle 604, the latch arm protrusions 618 can be positioned below the tips 648a of the latch arms 648, and the tips 648a can at least partially prevent movement of the latch arm protrusions 618 in a direction perpendicular to a plane of the top surface 638 of the cradle 604, for example, in a direction parallel to axis 603 as shown in FIG. 6D. If sufficient force is applied to the blood pressure monitor 602 and/or cradle 604 in such direction, the latch arm protrusions 648 can move passed (for example, above) the tips 648a of latch arms 648 so as to remove the first end 610 of blood pressure monitor 602 from the end 640 of cradle 604. Additionally, as discussed above, the cradle 604 can include a lip 646a on the wall 646 at end 642 of cradle 604 that can engage the depression 622 of the blood pressure monitor 602 and at least partially prevent movement of the blood pressure monitor 602 in a direction parallel to an extension of the wall 646 and/or perpendicular to the top surface 638.

The lip 646a and depression 622 can work alongside (or as an alternative to) the latch arms 648 and latch arm protrusions 618 and/or the opening 670 and port 672b to removably secure the blood pressure monitor 602 with the cradle 604. For example, when the opening 670 of the second end 612 of blood pressure monitor 602 is placed and/or moved over/around the port 672b, the lip 646a can slide or be received in the depression 622. Thus, the blood pressure monitor 602 and cradle 604 can include various features that enable removable securement.

The blood pressure monitor 602 and/or the cradle 604 can include one or more features that aid in the removal of the blood pressure monitor 602 from the cradle 604 (and vice versa). For example, as shown in at least FIGS. 6F-6M, blood pressure monitor 602 can include one or more grips 620 which are configured to aid in the grip or handling of the blood pressure monitor 602 (or cradle 604 if secured to the blood pressure monitor 602) and/or the removal of the blood pressure monitor 602 from the cradle 604 (and vice versa). While the figures illustrate two grips 620, the blood pressure monitor 602 can include a different number of grips 620. For example, the blood pressure monitor 602 can include one, two, three, four, five, six, seven, or eight or more grips 620. The one or more grips 620 can be located on various surfaces, ends or sides of blood pressure monitor 602. For example, the one or more grips 620 can be located on one or both of sides 613, 615 of blood pressure monitor 602. The blood pressure monitor 602 can include a first grip 620 positioned on a first side 615 and a second grip 620 positioned on a second side 613. The two grips 620 on the sides 613, 615 can be aligned with one another. Alternatively, the two grips 620 can be non-aligned. One or both of the first grip 620 and the second grip 620 can be positioned alongside 613, 615 and closer to one of the ends 610, 612 of blood pressure monitor 602. For example, the first and second grips 620 can be positioned along one of side 613, 615 and closer to the first end 610 than the second end 612. Such placement can allow removal of the first end 610 from the end 640 of cradle. For example, such placement can allow removal of the latch arm protrusions 618 from the latch arms 648 (or tips 648a of latch arms 648).

Each of the one or more grips 620 can include a recess 620a. The recess 620a can be recessed from a surface of the blood pressure monitor 602, for example, a surface of a side 613, 615 of blood pressure monitor 602. The recess 620a can be rounded or non-rounded. Recess 620a can comprise a circular or partially circular shape (for example, when viewed from the view of FIG. 4M, which shows an enlarged view of grip 620). Alternatively, recess 620a can comprise a different shape, for example a square, rectangle, triangle, pentagon, hexagon, heptagon, octagon, nonagon, decagon, among other shapes (for example, when viewed from the view of FIG. 6R, which shows an enlarged view of grip 620). A surface of recess 620a can be smooth. Alternatively, a surface of the recess 620a can be rough. The recess 620a can be sized and/or shaped to receive a portion of a finger. For example, the recess 620a can be sized and/or shaped to receive a portion of a thumb, index finger, or other finger. As another example, with reference to FIG. 6Q, the recess 620a can be shaped like a thumb or a fingernail such that sides of the recess 620a (such as the right and left sides showing in FIG. 6Q) are recessed less than a top and bottom of the recess 620a (given the orientation of FIGS. 6L-6M). Such sizing and/or shaping of the recess 620a can advantageously allow a user to better handle the blood pressure monitor 602 by positioning a portion of the user's finger within the recess 620a. Such sizing and/or shaping of the recess 620a can also advantageously allow a user to remove the blood pressure monitor 602 from the cradle 604.

Each of the one or more grips 620 can additionally or alternatively comprise a rim 620b. As shown in at least FIGS. 6L-6M and 6Q-6R, the rim 620b can extend or protrude outward from a surface of the blood pressure monitor 602. For example, rim 620b can extend outwards from a surface of side 613, side 615, and/or ends 610, 612. The rim 620b can extend outwards from a surface of the blood pressure monitor 602 proximate or adjacent the recess 620a. The rim 620b can extend outwards from a surface of the blood pressure monitor 602 and around a portion of a perimeter of the recess 620a. For example, rim 620b can extend around an entire perimeter of the recess 620a. Alternatively, rim 620b can extend around less than the entire perimeter of the recess 620a. For example, rim 620b can extend around 90%, 80%, 70%, 60%, 50%, 40%, 30%, 20%, or 10% of the perimeter of the recess 620a, although other percentages are possible. Rim 620b can extend around half or less than half the perimeter of the recess 620a. Rim 620b can extend around ⅓ or less than ⅓ the perimeter of the recess 620a. Rim 620b can extend around ¾ or less than ¾ the perimeter of the recess 620a. Rim 620b can be positioned proximate or adjacent the recess 620a and between a top or bottom of the blood pressure monitor 602. For example, blood pressure monitor 602 can include a top surface 608 (see FIG. 6J) and a bottom surface 609 (see FIG. 6K), and rim 32*b* can be positioned between recess 620*a* and the top surface 608. Alternatively or additionally, rim 620*b* can be positioned in a different location with respect to the recess 620*a* and/or top and bottom surfaces 608, 609 of blood pressure monitor 602.

Rim 620*b* can extend around a portion of the perimeter of recess 620*a* from a first end of the rim 620*b* to a second end of the rim 620*b* and rim 620*b* can have a length extending between the first and second ends. Rim 620*b* can extend outwards from a surface of the blood pressure monitor 602 a variable distance along its length. Rim 620*b* can have a constant cross-section from the first end to the second end of the rim 620*b*. Alternatively, rim 620*b* can have a variable cross-section along its length. Rim 620*b* can have a middle region positioned between the first and second ends of rim 620*b*. Rim 620*b* can have a cross-section that increases from the first end of the rim 620*b* to the middle region of the rim 620*b* and/or that decreases from the middle region to the second end of the rim 620*b*. Rim 620*b* can have a cross-section that increases from the first end to the second end or alternatively, that increases from the second end to the first end. The middle region of rim 620*b* can extend further outwards from a surface of the blood pressure monitor 602 than one or both of the first and second ends of the rim 620*b*. The middle region of the rim 620*b* can align with a center of the recess 620*a*. Rim 620*b* can have a circle shape, half-circle shape, square shape, rectangular shape, or another shape, for example, when viewed as shown in FIG. 6R which shows an enlarged view of a portion of a side 615 of blood pressure monitor 602.

As another example, blood pressure monitor 602 can include a first rim 620*b* that extends at least partially outward from side 613 and a second rim 620*b* that extends at least partially outward from side 615. The first rim 620*b* and the second rim 620*b* can align with each other, or alternatively, not align with each other. The first rim 620*b* and/or the second rim 620*b* can be positioned along sides 613, 615 and be closer to the first end 610.

Rim 620*b* can advantageously act as a gripping point to allow a user to better handle or hold the blood pressure monitor 602. Additionally, rim 620*b* can allow a user to remove the blood pressure monitor 602 from the cradle 604 when the blood pressure monitor 602 and cradle 604 are secured to one another. Rim 620*b* can act alone or alongside recess 620*a* in such manner. For example, recess 620*a* can be sized and/or shaped to receive a portion of a user's finger, and the user's finger can at least partially contact or press against a portion of rim 620*b* (such as the middle region of the rim).

FIGS. 6S-6Z illustrate various views of cradle 604 which can secure to blood pressure monitor 602 as discussed above. Cradle 604 can include a first end 640, a second end 642 opposite the first end 640, a first side 643, a second side 645 opposite the first side 643, a top interior surface 638 between the sides 643, 645, and a bottom surface 639 opposite the surface 638. The top interior surface 638 and the bottom surface 639 can together define a base of the cradle 604 which can be configured to contact and/or secure to a patient, such as patient 111 and/or a cuff 737 wrapped around an arm of a patient 111. For example, the base of the cradle 604 can include an adhesive or Velcro® configured to attach to a portion of a cuff 737. The sides 643, 645 (also referred to herein as "sidewalls") can extend outward from the base of the cradle 604 in a direction that is angled with respect to the base. For example, the sidewalls 643, 645 can extend generally perpendicularly from the base of the cradle 604.

One or both of sidewalls 643, 645 can comprise one or more recessed cutouts 652 along a portion of the sidewalls 643, 645. For example, as shown in at least FIGS. 6S-6T, sidewall 643 can include a first recessed cutout 652 and sidewall 645 can include a second recessed cutout 652. The first and second recessed cutouts on the sidewall 643, 645 can align with each other, or alternatively, not align with each other. The first and second recessed cutouts 652 can be positioned along the sidewalls 643, 645 and can be closer to the first end 640 of the cradle 604 than to the second end 642 of the cradle 604. The one or more recessed cutouts 652 in one or both of sidewalls 643, 645 can be positioned along a portion of the sidewall(s) 643, 645 that is proximate or adjacent to the one or more grips 620 of the blood pressure monitor 602, and therefore can provide access to the one or more grips 620 when the blood pressure monitor 602 and cradle 604 are secured to one another. Sidewalls 643, 645 can have a height that is equal to or less than a height of the blood pressure monitor 602. The one or more recessed cutouts 652 can be rounded and/or smooth. The one or more recessed cutouts 652 can have a half-circle shape or another shape (such as half-square, half-rectangle, half-ellipse, half-triangle, among other shapes) (see FIGS. 6W-6X).

The cradle 604 can include one or more arms that are configured to secure to a portion of a cable or tube that may connect one or more sensor or monitors in a patient environment (such as the environment illustrated in FIGS. 1A-1B). For example, as shown in FIGS. 6S-6Z, cradle 604 can include one or more arms 650 that are sized and/or shaped to receive, retain, and/or secure a portion of a cable, such as cable 105 and/or 107. For example, the cradle 604 can include one, two, three, four, five, six, seven, or eight or more arms 650. The one or more arms 650 can extend from the base defined by the bottom surface 639 and top surface 638, sidewall 643, and/or sidewall 645, for example. As another example, the cradle 604 can include two arms 650 extending from or proximate to sidewall 643 and two arms 650 extending from or proximate to sidewall 645. Respective ones of the two pairs of arms 650 in such configuration can be aligned with one another (see FIG. 6U-6V) or non-aligned.

The one or more arms 650 can extend outwards from a surface of the cradle 604 (such as a surface of the sidewalls 643, 354 in a first direction that is angled with respect to the surface. For example, the one or more arms 650 can extend generally perpendicularly with respect to a surface of the sidewalls 643, 645. Additionally, the one or more arms 650 can extend in multiple directions. For example, the one or more arms 650 can extend in a first direction that is generally perpendicular to a surface of the cradle 604 and can extend in a second direction that is angled with respect to the first direction. The one or more arms 650 can extend from the cradle 604 and can curl in a first direction (for example, up or down in the orientation as shown in FIGS. 6Y-6Z). The one or more arms 650 can extend in one or more directions so as to define an open region therein. For example, the one or more arms 650 can curl as shown in FIGS. 6Y-6Z an define an open region that has a cross-section that is shaped like a half-circle. Alternatively, the open region can have a cross-section that is shaped differently, such as half-square, half-rectangle, triangle-shaped, among other shapes. The one or more arms 650 can curl in a direction such that an open region defined therewithin faces a direction away from or opposite a direction that the bottom surface 639 of the cradle 604 faces. Alternatively, the one or more arms 650 can curl in a direction such that an open region defined therewithin faces a same direction that the bottom surface 639 of the cradle 604 faces. The open region defined by the one or more arms 650 can be sized and/or shaped to receive, retain, and/or secure a portion of a cable or tube as discussed above.

As discussed above, cradle 604 can include one or more latch arms 648 which can engage and/or secure to the latch arm protrusions 618 of the blood pressure monitor 602. The one or more latch arms 648 can extend from the first end 640 of cradle 604. Additionally or alternatively, the one or more latch arms 648 can extend from a different portion of the cradle 604 (such as one or both of sidewalls 643, 645). Cradle 604 can include a first latch arm 648 extending from a portion of the cradle 604 at the first end 640 and a second latch arm 648 extending from a portion of the cradle 604 at the first end 640. The first and second latch arms 648 can be spaced apart from one another. Where the first end 640 of the cradle 640 include two latch arms 648 and the first end 610 of blood pressure monitor 602 includes two latch arm protrusions 618, the spacing between the latch arms 648 can be the same as the spacing between the latch arm protrusions 618. Further, where the first end 640 includes two latch arms 648, the two latch arms 648 can be spaced so as to accommodate a width of the connector port 616 of the blood pressure monitor 602 (where the housing includes such connector port 616). A midpoint between the spacing of the two latch arms 648 on the first end 640 can be aligned with a midpoint of the depression 622 of a length of the depression 622 when the blood pressure monitor 602 is secured to the cradle 604. The one or more latch arms 648 can have a height or length that is less than a height of the blood pressure monitor 602 (see FIG. 6D).

The one or more latch arms 648 can have a first end that is connected to a portion of the cradle 604 and a second end opposite the first end that is free or cantilevered. As discussed above, the second, free end of the latch arms 648 can have a tip 648a (see FIGS. 6W-6X). Tip 648a can extend from the second, free end of the latch arm 648 in a direction that is non-parallel with respect a length of the latch arm 648 between the first and second ends of the latch arm 648. For example, the tip 648a can extend generally perpendicular to the second end of the latch arm 648. The tip 648a can extend from the second, free end of the latch arm 648 in a direction towards the second end 642 of cradle 604 and/or in a direction towards the wall 646 of cradle 604 (where the cradle 604 includes such wall 646). Tip 648a can be tapered or sloping, and as discussed above, can be configured to engage, contact, and/or slide passed latch arm protrusion 618.

Cradle 604 can include a wall 646 extending from a portion of the cradle 604 and proximate, adjacent, or along the second end 642 of cradle 604. For example, wall 646 can extend from the base of the cradle 604 which is defined by the top surface 638 and bottom surface 639 of cradle 604 (see FIGS. 6S-6T). Wall 646 can extend at an angle with respect to a plane of the base (such as a plane of the top and/or bottom surfaces 638, 339). For example, wall 646 can extend in a direction that is generally perpendicular to the top surface 638 of the cradle 604. Wall 646 can have a first end that is connected to a portion of cradle 604 and a second end opposite to the first end and that is free or cantilevered. Wall 646 can have a length extending between the first, connected end and the second, free end. Wall 646 can have a height that is greater than a height of the one or more latch arms 648 (see FIGS. 6W-6X). With reference to FIG. 6U, wall 646 can have a width extending along a portion of a width of the cradle 604 between the sidewalls 643, 645. The width of the wall 646 can be less than the distance between sidewalls 643, 645. Alternatively, the width of wall 646 can be equal to the distance between the sidewalls 643, 645.

As discussed above, wall 646 can include a lip 646a configured to engage, secure, and/or fit within the depression 622 of the blood pressure monitor 602. Lip 646a can extend in a direction that is non-parallel with respect to the length of the wall 646 between the first, connected end of the wall 646 and the second, cantilevered end of the wall 646. For example, the lip 646a can extend generally perpendicular to the length of the wall 646. Lip 646a can extend in a direction towards the first end 640 of the cradle 604. Where the cradle 604 includes one or more latch arms 648 on the first end 640, the lip 646a can extend in a direction towards the one or more latch arms 648. The lip 646a can be sized and/or shaped to fit within a portion of the depression 622 of blood pressure monitor 602. For example, the width, length, and/or thickness of lip 646a can be sized and/or shaped to match or substantially match the length, width, and/or depth of the depression 622. When the lip 646a is received within and/or secured to the depression 622, a top surface of the lip 646a can be flush with a region of the top surface 608 of blood pressure monitor 602 proximate or adjacent to depression 622.

As discussed above, wall 646 can include one or more ports that extend from a portion thereof. As shown in at least FIG. 6W, wall 646 can include a first port 672a that extends from a side or surface of the wall 646 and/or can include a second port 672b that extends from a side or surface of the wall 646. The first port 672a can extend from an outer surface of the wall 646 in a direction away from one or both of the first end 640 and the second end 642. The second port 672b can extend in a direction towards the first end 640 of the cradle 604. The first port 672a can have a first length and the second port 672b can have a second length that is less than, equal to, or greater than the length of the first port 672a. The first and second ports 672a, 672b can extend in opposite directions. As discussed above, the second port 672b can be sized and/or shaped to fit within the pneumatic opening 670 in blood pressure monitor 602, and can at least partially secure the blood pressure monitor 602 within the cradle 604. For example, when the port 672b is positioned within the opening 670, the port 672b can prevent or reduce the likelihood of movement of the blood pressure monitor 602 with respect to the cradle 604 in a direction that is parallel to a distance between the sidewalls 643, 645 of the cradle 604.

One or both of ports 672a, 672b can be cylindrical or non-cylindrical. One or both of ports 672a, 672b can have a cross-section that is circular, square, rectangular, or another shape. Port 672b can have a tapered or partially tapered (chamfered) tip (see FIGS. 6W-6X). such tapering or chamfer can help the free end of port 672b align with and/or be positioned within opening 670. Port 672a can have a tapered or partially tapered free end. For example, port 672a can have a first end connected to the wall 646, a second end opposite the first end, and a cross-section of the port 672a can vary along a length between the first and second ends. For example, port 672a can have a first cross-section near the wall 646 and a second cross-section near the free end. For example, port 672a can have a conically-shaped free end. Port 672a can be sized and/or shaped to secure to a tube, such as a pneumatic hose 637 as discussed above. One or both of ports 672a, 672b can be positioned along a height and/or width of wall 646. For example, one or both of ports 672a, 672b can be positioned at or proximate a middle region of the wall 646.

Port 672a can define a fluid passage and port 672b can define a fluid passage. Each of the fluid passages of the ports 672a, 672b can align with each other and also align with an opening in the wall 646. In such configuration, when a pneumatic hose/tube 637 is secured to port 672a, fluid (for example, air) can be pumped via blood pressure monitor 602 through opening 670, fluid passage defined within port 672b, an opening in the wall 646, fluid passage defined with port 672a, and the hose 37. Such pumped air can be transmitted to a blood pressure cuff 121 as discussed above.

Cradle 604 can include one or more support walls 677 proximate or adjacent to the wall 646 that can provide support to the wall 646. For example, cradle 604 can include a first support wall 677 that extends from the second end 642 of cradle 604 and connects to a first side edge of the wall 646 and a second support wall 677 that extends from the second end 642 of cradle 604 and connects to a second side edge of the wall 646.

Cradle 604 can include a mechanism that can facilitate near field communication (NFC) with the blood pressure monitor 602 as discussed above. For example, as shown in at least FIGS. 6U-6V, cradle 604 can include a prong 674 comprising an NFC tag that can communicate with a NFC reader of the blood pressure monitor 602. Such NFC can be, for example RFID, and the prong 674 can include an RFID tag configured to communicate with an RFID reader of the blood pressure monitor 602. As another example, the prong 674 can include a memory, such as an erasable programmable read-only memory (EPROM) that can contact electrical contacts on a bottom surface of blood pressure monitor 602 when blood pressure monitor 602 is secured to cradle 604. In such cases where the cradle 604 includes an NFC communication mechanism, blood pressure monitor 602 can transfer and/or collect data from the cradle 604. For example, such NFC communication can enable the blood pressure monitor 602 and/or cradle 604 to: confirm that either or both are compatible (e.g., not counterfeit); determine a lifespan (or remaining lifespan) of either component; and/or determine the size of a cuff to which the cradle 604 is attached.

As shown, prong 674 can connect to a portion of the cradle 604 (such as the base defined by the top and bottom surfaces 638, 339 of cradle 604). Prong 674 can extend from a portion of the base and extend and/or curl in a direction away from the base (such as in an upward direction given the orientation shown in FIG. 6S). Prong 674 can bias, contact, and/or press against bottom surface 609 of blood pressure monitor 602 when the blood pressure monitor 602 is secured within cradle 604. Such biasing or pressure can help the blood pressure monitor 602 better engage portions of the cradle 604 and/or help in removal of the blood pressure monitor 602 from the cradle 604. For example, prong 674 can cause the one or more latch arm protrusions 618 to contact and/or press against the latch arms 648 (or tips 648a) and/or can cause the depression 622 to contact and/or press against the lip 646a. Prong 674 can be at least partially positioned within an opening 675 in the base of the cradle 604 that extend through the top and bottom surfaces 638, 339 (see FIGS. 6U-6V).

Figure 7A:
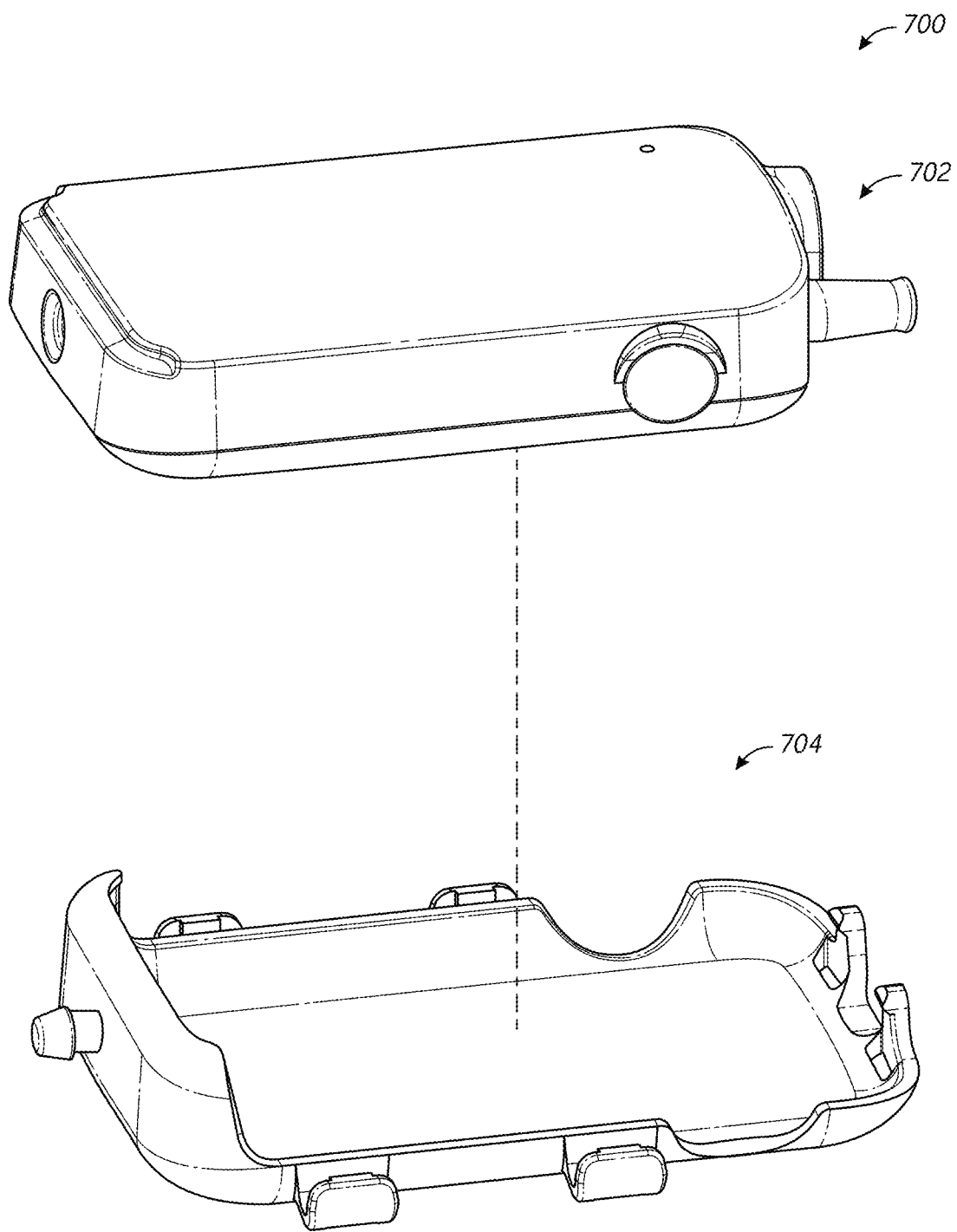
FIG. 7A illustrates an exploded view of another embodiment of a blood pressure monitor assembly in accordance with aspects of this disclosure.
Figure 7B:
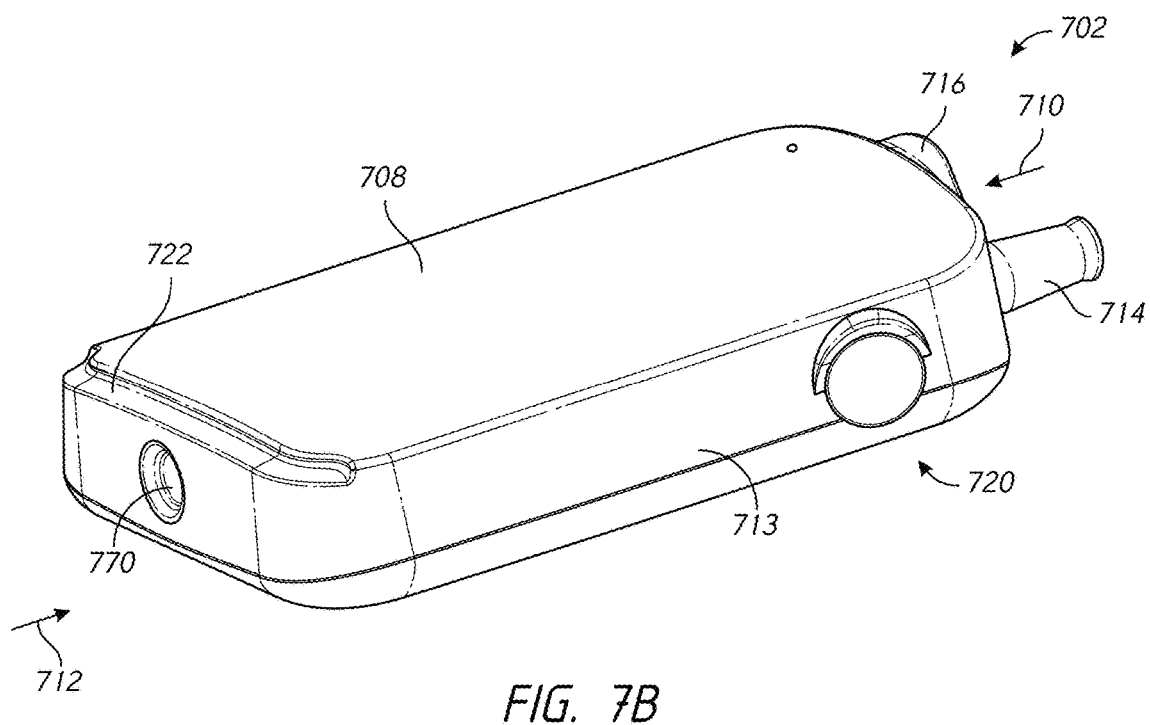
FIGS. 7B-7C illustrate perspective views of a blood pressure monitor of the assembly of FIG. 7A.
Figure 7C:
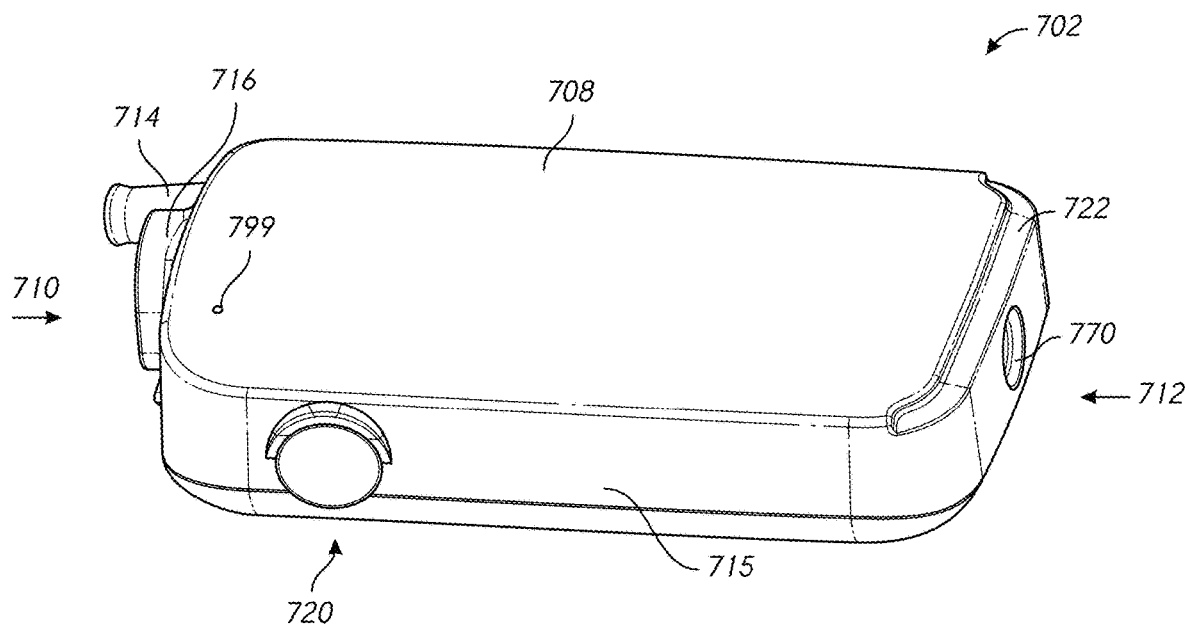
Figure 7D:
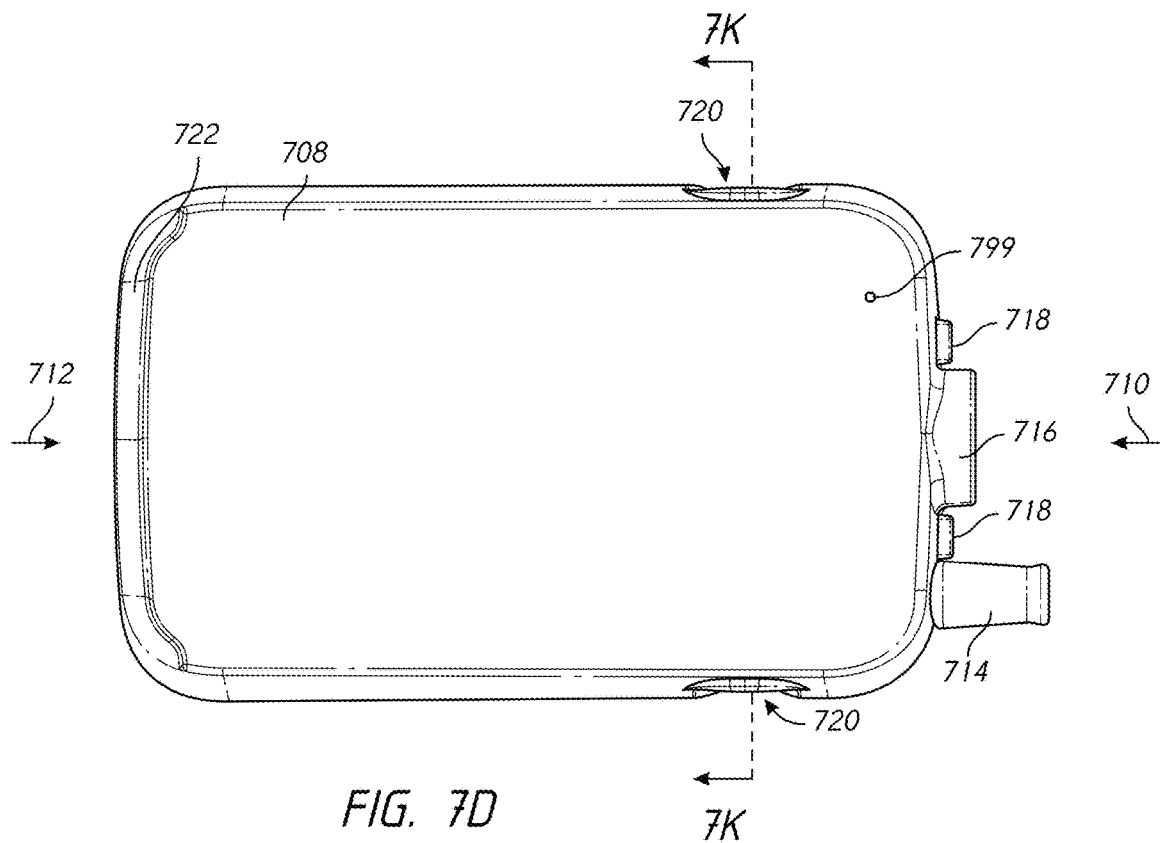
FIG. 7D illustrates a top view of the blood pressure monitor of FIG. 7B-7C.
Figure 7E:
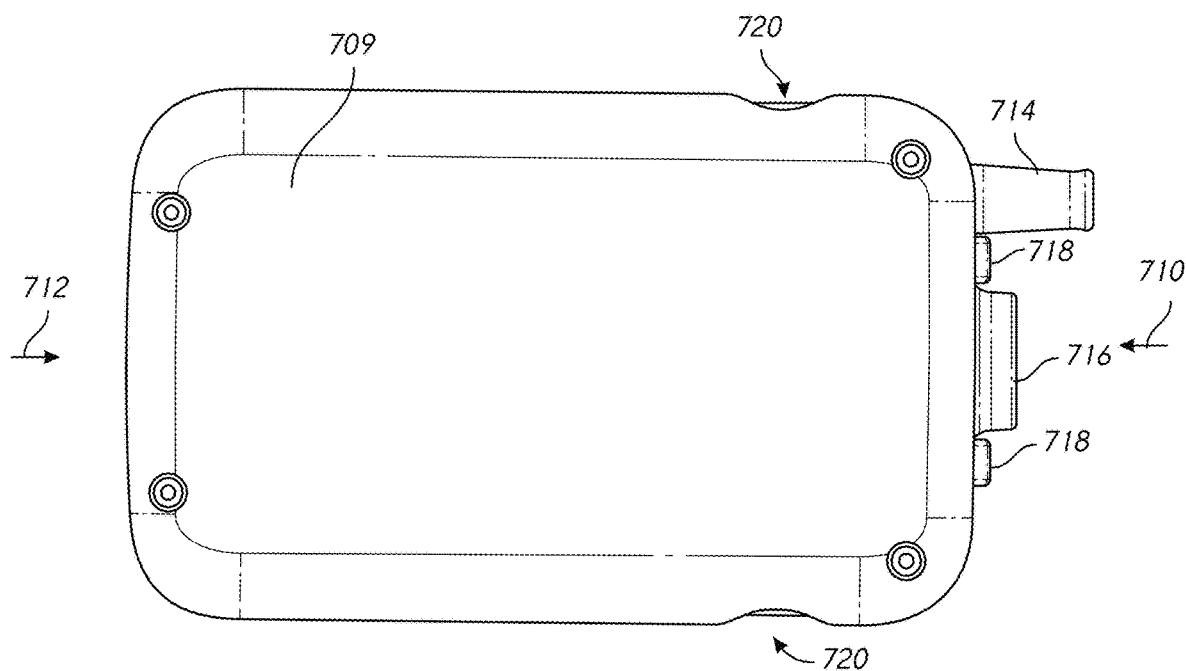
FIG. 7E illustrates a bottom view of the blood pressure monitor of FIG. 7B-7C.
Figure 7F:
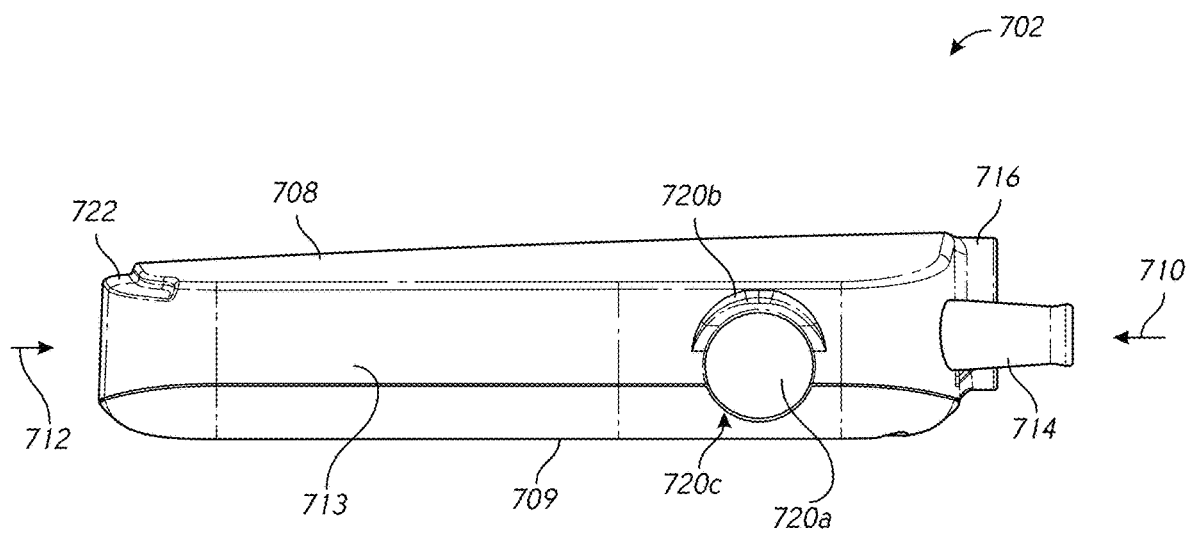
FIG. 7F illustrates a side view of the blood pressure monitor of FIG. 7B-7C.
Figure 7G:
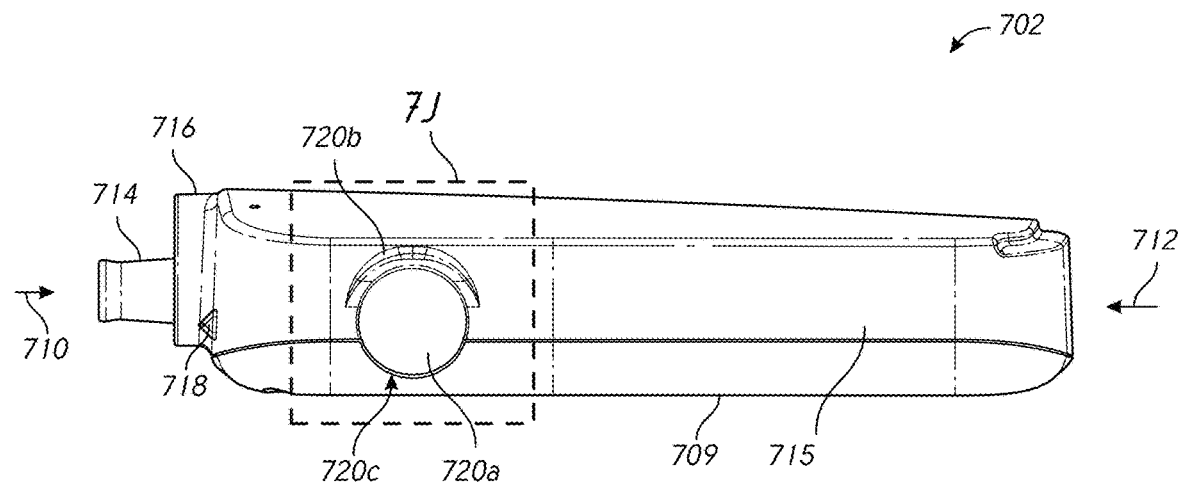
FIG. 7G illustrates another side view of the blood pressure monitor of FIG. 7B-7C.
Figure 7H:
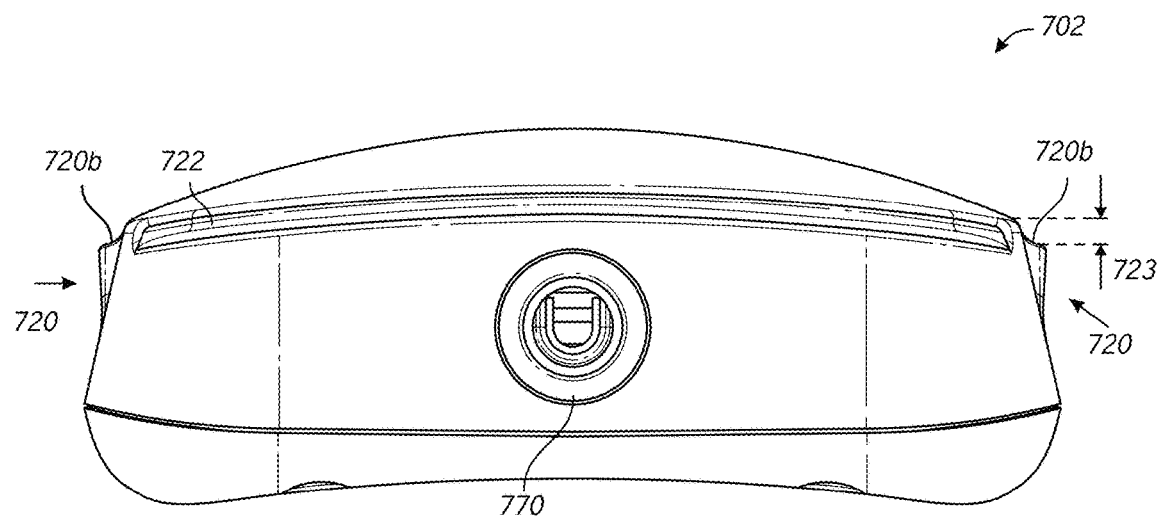
FIG. 7H illustrates a front view of the blood pressure monitor of FIG. 7B-7C.
Figure 7I:
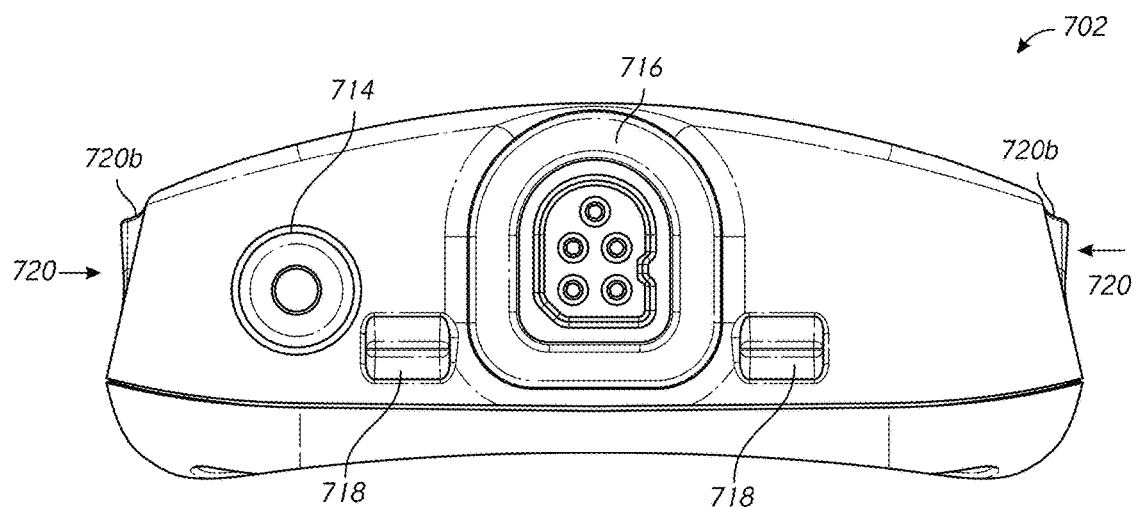
FIG. 7I illustrates a back view of the blood pressure monitor of FIG. 7B-7C.
Figure 7J:
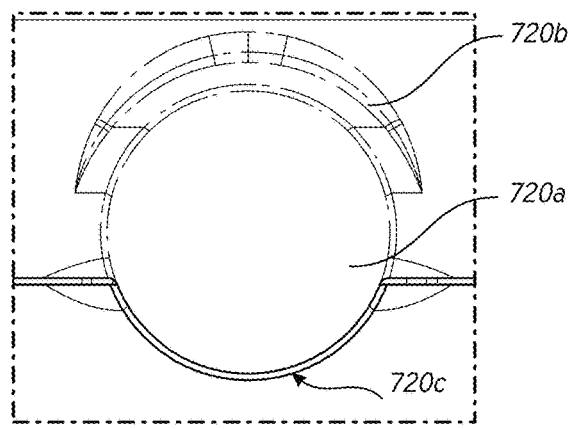
FIG. 7J illustrates an enlarged view of a portion of the view of the blood pressure monitor shown in FIG. 7G.
Figure 7K:
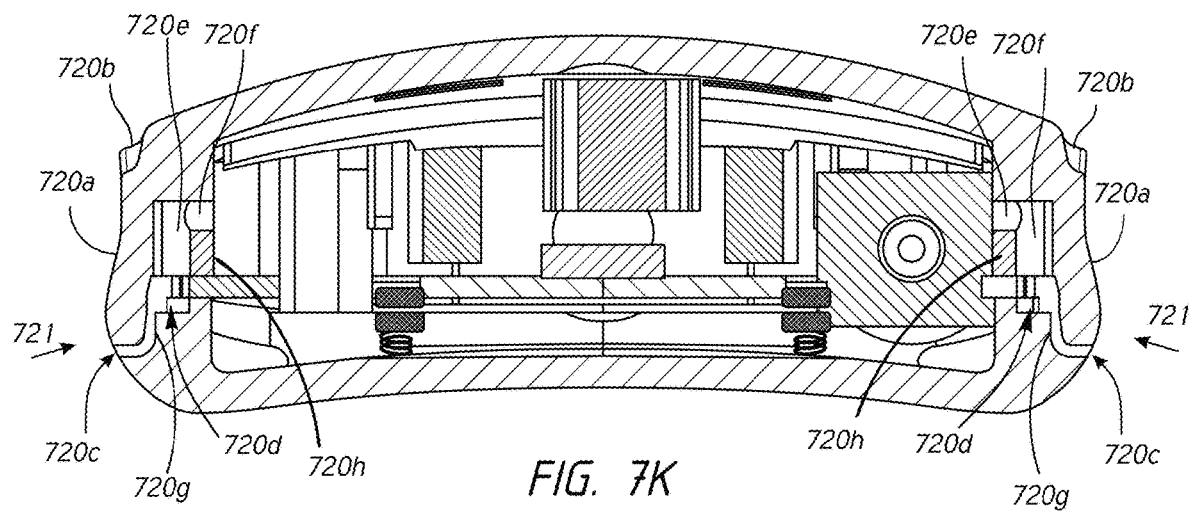
FIG. 7K illustrates a cross-section view of the blood pressure monitor of FIG. 7B-7C in accordance with aspects of this disclosure.
Figure 7L:
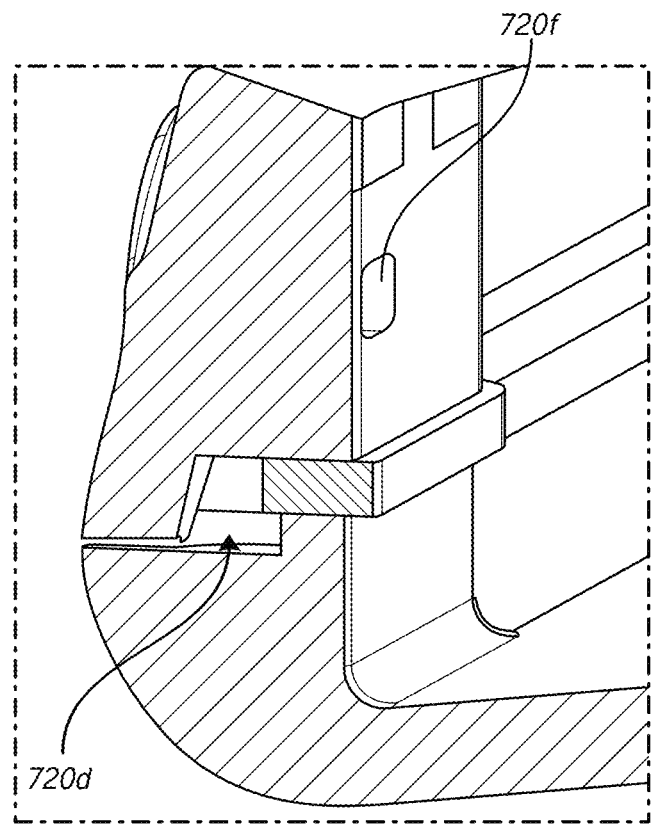
FIG. 7L illustrates an enlarged perspective view of the cross-section shown in FIG. 7K in accordance with aspects of this disclosure.
Figure 7M:
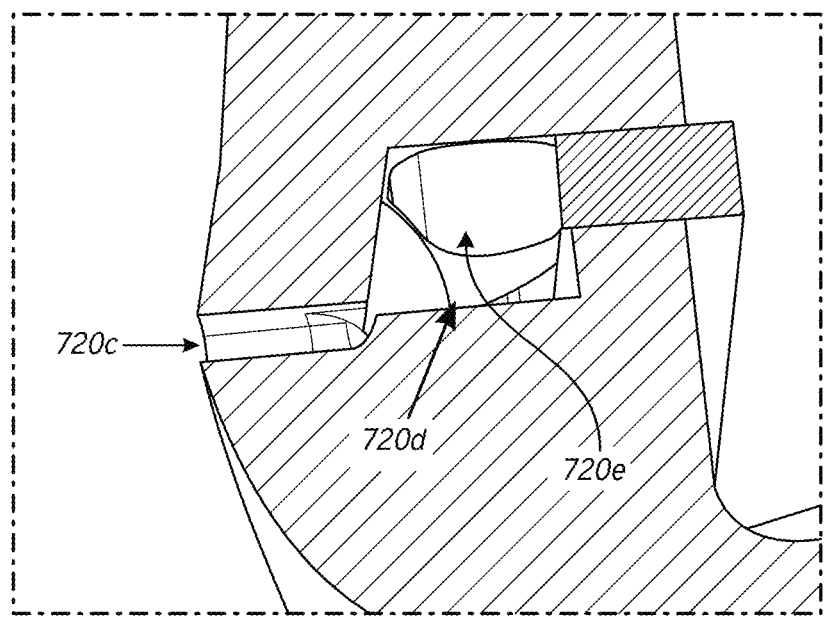
FIG. 7M illustrates another enlarged perspective view of the cross-section shown in FIG. 7K in accordance with aspects of this disclosure.
Figure 7N:
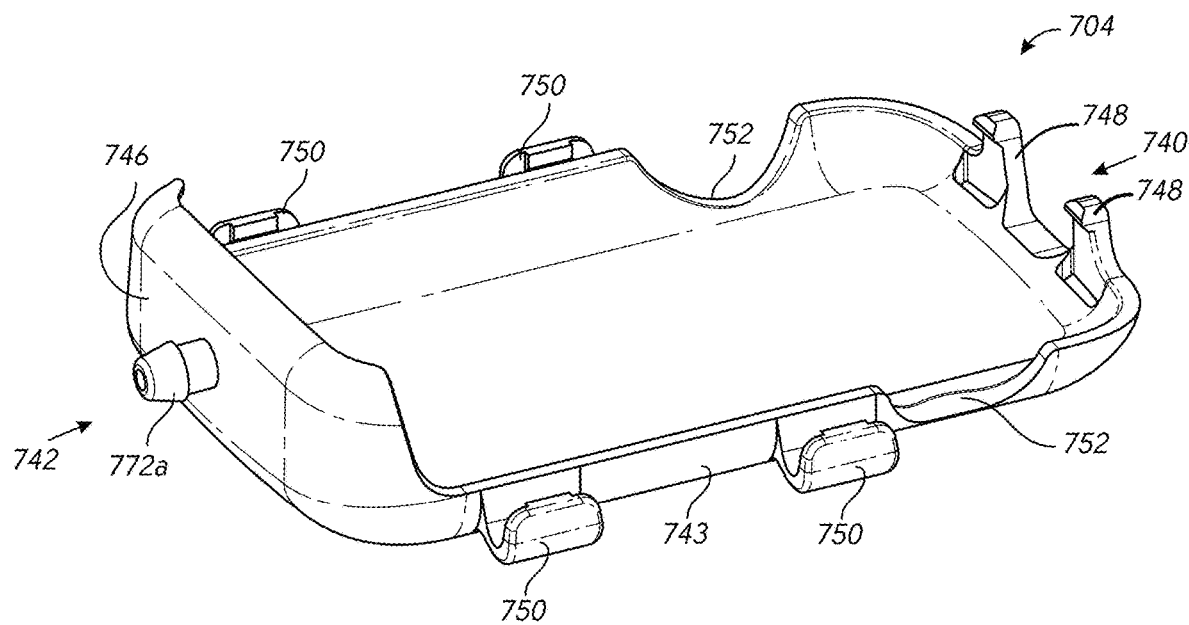
FIGS. 7N-7O illustrate perspective views of a cradle of the assembly of FIG. 7A.
Figure 7O:
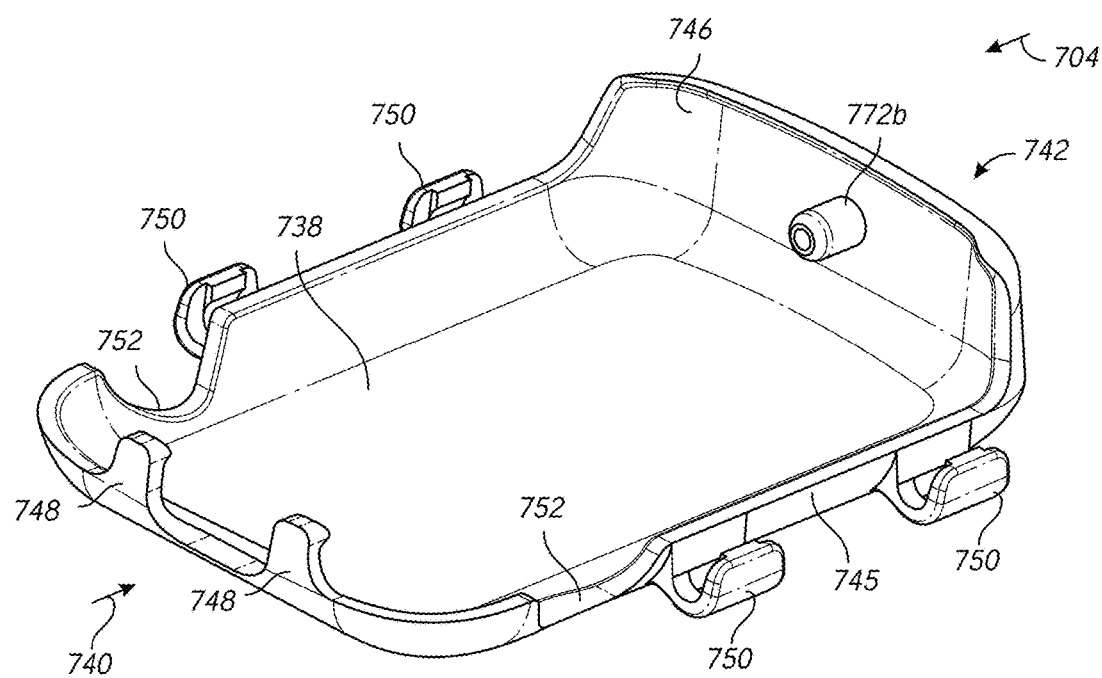
Figure 7P:
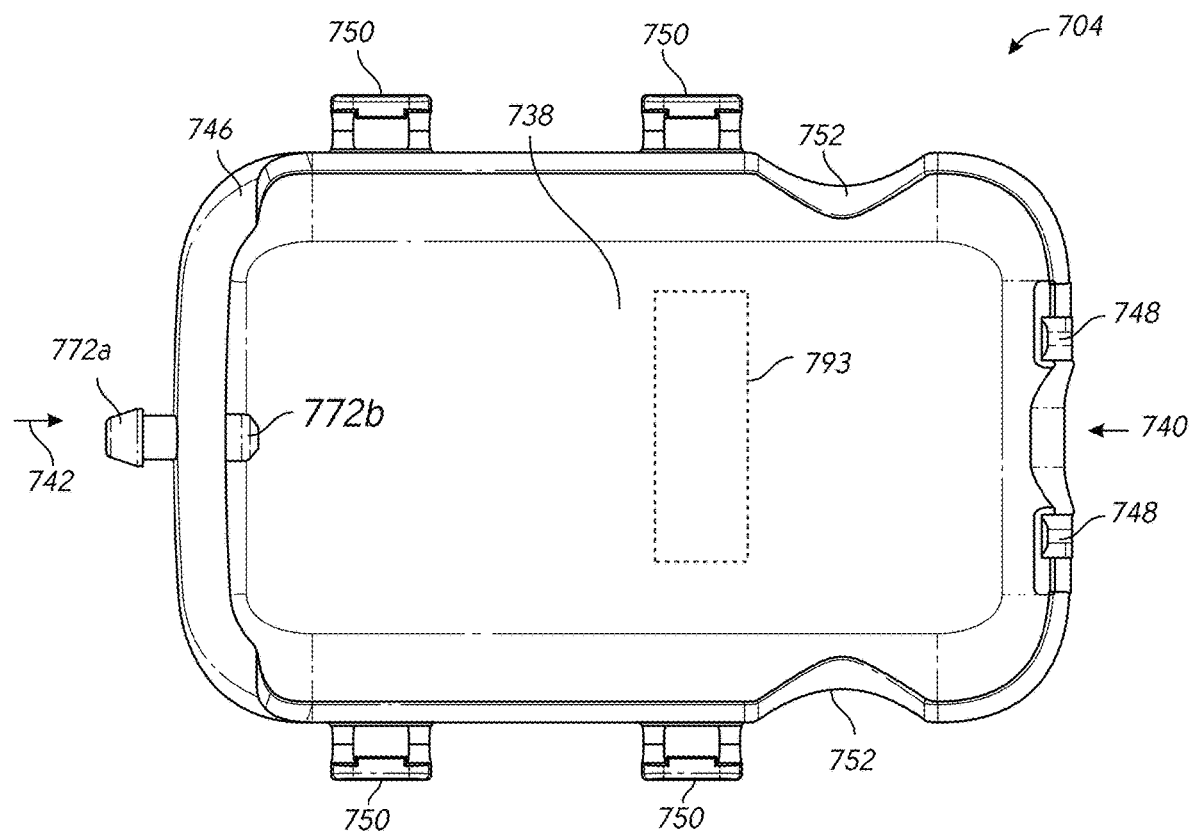
FIG. 7P illustrates a top view of the cradle of FIGS. 7N-7O.
Figure 7Q:
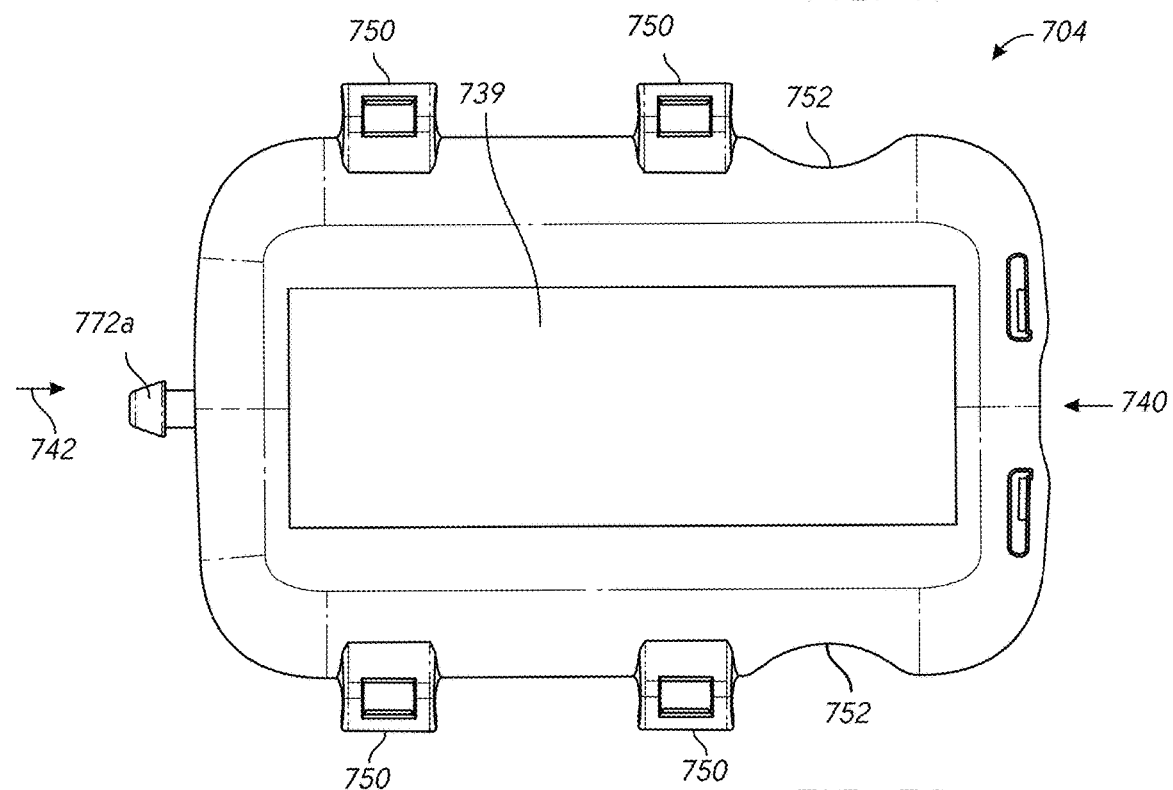
FIG. 7Q illustrates a bottom view of the cradle of FIGS. 7N-7O.
Figure 7R:
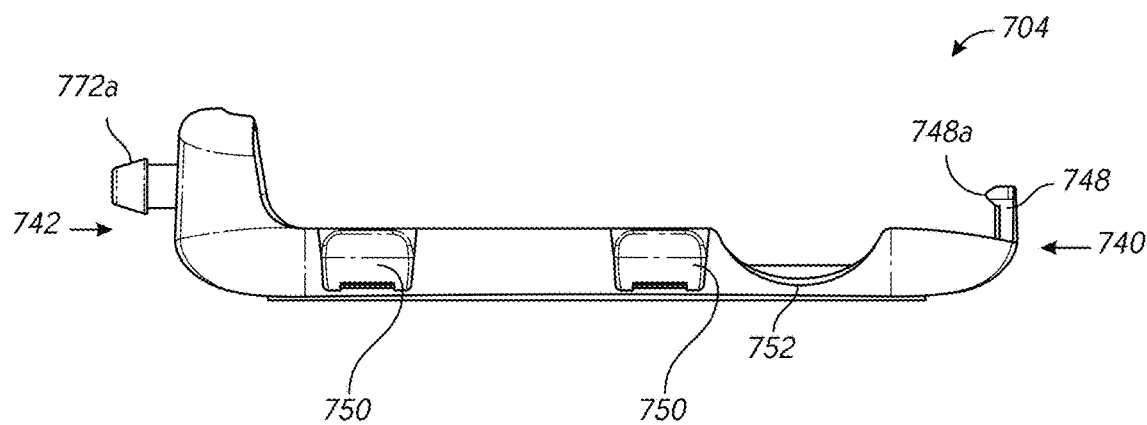
FIG. 7R illustrates a side view of the cradle of FIGS. 7N-7O.
Figure 7S:
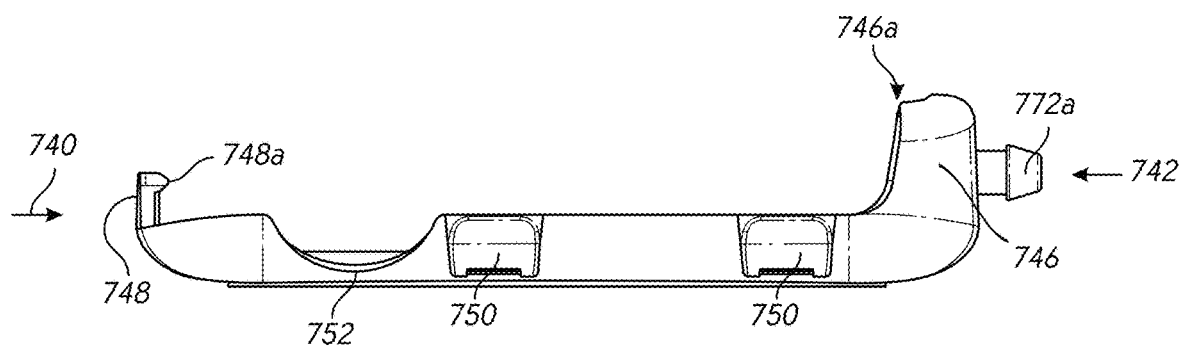
FIG. 7S illustrates another side view of the cradle of FIGS. 7N-7O.
Figure 7T:
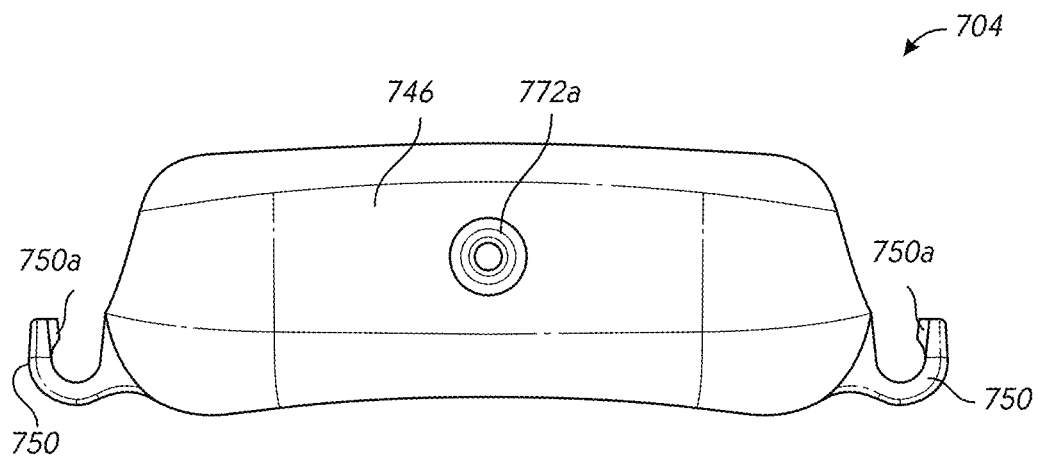
FIG. 7T illustrates a front view of the cradle of FIGS. 7N-7O.
Figure 7U:
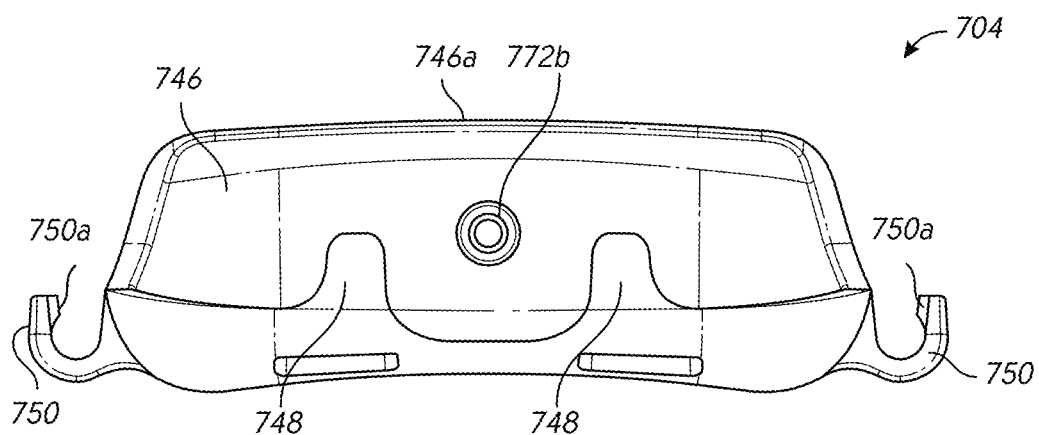
FIG. 7U illustrates a back view of the cradle of FIGS. 7N-7O.

FIGS. 7A-7U illustrate various views and aspects of an alternative design for a blood pressure monitor assembly 700 which includes an alternative design for a blood pressure monitor 702 and also includes a cradle 704. While the device 702 is referred to herein as a "blood pressure monitor" or "blood pressure device" herein, device 702 can measure and/or monitor other parameters in addition or as an alternative to blood pressure. For example, device 702 can measure and/or monitor the concentration or partial pressure of carbon dioxide ($CO_2$) in exhaled air of the patient. Blood pressure monitor 702 can have the characteristics and/or functionality as described in more detail below with reference to FIGS. 12-14E.

Figure 7V:
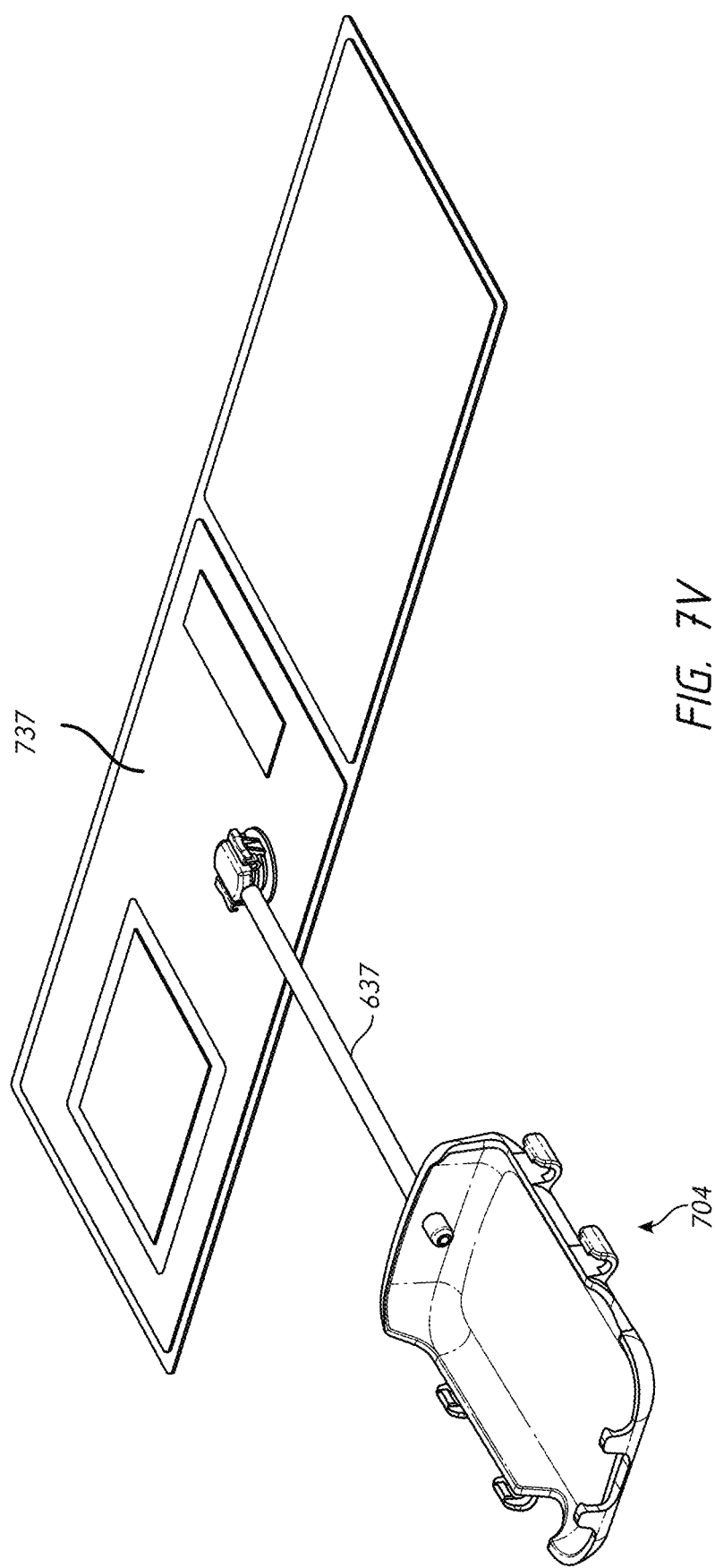
FIG. 7V illustrates the cradle of FIGS. 7N-7O connected to an example blood pressure cuff in accordance with aspects of this disclosure.

Blood pressure monitor assembly 700 can be the same in some or many respects to blood pressure monitor assembly 600 as described above. For example, blood pressure monitor 702 can be identical to blood pressure monitor 702 except for one or more of the differences discussed below. As another example, one or both of blood pressure monitor 702 and/or cradle 704 can be the same in some or many respects as the blood pressure monitor 602 and/or cradle 604 as shown and described above. Aspects or features of blood pressure monitor 702 can be combined and/or replaced with aspects or features of blood pressure monitor 602, and vice versa, without departing from the scope of this disclosure. Accordingly, numerals used in FIGS. 6A-6Z with respect to blood pressure monitor 602 and cradle 604 are similar to numerals used in FIGS. 7A-7V to denote similar features. The discussion that follows below with reference to FIGS. 7A-7V is intended to convey some additional and/or different features or aspects of blood pressure monitor 702 with respect to blood pressure monitor 602.

As shown in FIG. 7A, blood pressure monitor assembly 700 can include a blood pressure monitor 702 that can removably secure to cradle 704 in a similar or identical way in which housing 602 and cradle 604 can removably secure as described above. For example, as discussed above with reference to wall 646, lip 646a, one or more latch arms 648, tip(s) 648a, depression 622, protrusion(s) 618 of blood pressure monitor 602 or cradle 604, blood pressure monitor 702 or cradle 704 can include wall 746, lip 746a, one or more latch arms 748, tip(s) 748a, depression 722, protrusion(s) 718 which can behave in the similar or identical way in order to removably secure blood pressure monitor 702 to cradle 704.

As shown in FIG. 7B-7I, blood pressure monitor 702 can include ends 712, 710, top surface 708, bottom surface 709, sides 713, 715, connector port 714, opening 770, grip(s) 720, protrusions 718, connector port 716, each of which can be the same in some, many, or all respects as ends 612, 610, top surface 608, bottom surface 609, sides 613, 615, connector port 614, opening 670, grip(s) 620, protrusions 618, connector port 616 as shown and described above with reference to blood pressure monitor 602. While the present disclosure refers to "end" or "side", such terminology is not intended to be limiting, but rather, is employed for mere convenience in differentiating certain features of the blood pressure monitor 702. Accordingly, while the term "end" is used for the first and second ends 712, 710, it is to be understood that such ends 712, 710, can also represent "sides" of the blood pressure monitor 702.

Additionally or alternatively, as shown in FIGS. 7N-7U, cradle 704 can include ends 740, 742, sides 743, 745, ports 772a, 772b, recessed cutouts 752, top surface 738, and/or bottom surface 739, each of which can be the same in some, many, or all respects as ends 640, 642, sides 643, 645, ports 672a, 372b, recessed cutouts 652, top surface 638, and/or bottom surface 334, as shown and described elsewhere herein.

As shown in at least FIG. 7C, blood pressure monitor 702 can include a visual indicator 799 that can indicate whether the blood pressure monitor 702 is on or off, whether the blood pressure monitor 702 and the cradle 704 are not compatible with each other (for example, via NFC communication between the blood pressure monitor 702 and the cradle 704 discussed below), battery life of the blood pressure monitor 702, among other things. The indicator 799 can be an LED indicator. In some cases, LED indicator is configured to flash and/or blink to indicate one or more of the above listed scenarios.

One optional difference between the cradle 604 and the cradle 704, with reference to FIGS. 6S-6V and 7N-7Q, is that cradle 704 can have no opening 675 and/or no prong 674 like that shown with respect to cradle 604. In some cases, blood pressure monitor 702 and cradle 704 can communicate with one another via near field communication protocols, such as radio frequency protocols. For example, blood pressure monitor 702 can include a radio frequency identification reader and cradle 704 can include an NFC tag 793 (such as an RFID tag) shown in dotted lines in FIG. 7P. For example, blood pressure monitor 702 can include an RFID reader which can be positioned within an interior of blood pressure monitor 702, such as on a printed circuit board of the blood pressure monitor 702. In such scenario, cradle 604, 704 can include an RFID tag 393, in the form of a sticker or label, for example, that can transmit a signal in response to recognition of a radio frequency signal from the RFID reader in the blood pressure monitor 702. Such RFID tag 393 can be on a surface of the cradle 704, for example, on a bottom surface 739, of cradle 704. Such RFID tag 393 can be, for example, sandwiched and/or covered by a hook and loop securement patch adhered to the bottom surface 739. Alternatively, cradle 704 can include an erasable programmable read-only memory (EPROM) which can communicate (for example, transfer information or data) to the blood pressure monitor 702 via touching with an electrical contact on a surface of blood pressure monitor 702. Whether the blood pressure monitor 702 and cradle 704 include RFID or EPROM features and functionality, these components can communicate with one another to transfer information and/or data, such as the amount of lifespan of the blood pressure monitor 702 and/or the cradle 704 remaining (which can be predetermined), whether the blood pressure monitor 702 and cradle 704 are compatible (e.g., whether a counterfeit or unauthorized product is being used), among other things.

With reference to FIGS. 7B-7D and 7F-7H, blood pressure monitor 702 can include a depression 722 that is the same in some or many respects as depression 622 in blood pressure monitor 602. Depression 722 can have a depth 723 (FIG. 7H) that is equal to depth 623 as shown and described elsewhere herein with respect to blood pressure monitor 602. As can be seen in FIGS. 7B-7D and 7F-7H, depression 722 can be the same as depression 622 in every respect except the length by which the depression 722 extends along the top surface 708 of blood pressure monitor 702. For example, as shown in FIG. 7D, depression 722 can extend along a top surface 708 of blood pressure monitor 702 along an entire width of end 712 and portion(s) of the top surface 708 along one or both sides 713, 715 of blood pressure monitor 702.

With reference to FIGS. 7N-7U, cradle 704 can include a wall 746 (also referred to herein as "back wall") that can be similar to wall 646 of cradle 604 in some or many respects. For example, with reference to FIGS. 7N-7O, back wall 746 can extend upward from bottom surface 739 and/or top surface 638 and can extend along an entire width of end 742 of cradle 704. Additionally, back wall 746 can extend from bottom surface 739 and/or top surface 638 and can extend along portion(s) of sides 743, 745 of cradle 604. Similarly, back wall 746 can include a lip 746a that extends along a free end of back wall 746 in similar fashion as back wall 746.

The securement of blood pressure monitor 702 and cradle 704 can be the same in some, many, or all respects as the securement of housing 602 and cradle 704 discussed above. For example, the blood pressure monitor 702 can be secured to cradle 704 by engagement of the back wall 746 and/or lip 746a with end 712 and/or depression 722, and/or by engagement of port 772b within opening 770, and/or by engagement of the one or more latch arms 748 with protrusions 718. Similarly, blood pressure monitor 702 can include grips 720 that are similar in some, many, or all respects to grips 620 of blood pressure monitor 602 which enable a user to grip the blood pressure monitor 702 and remove the blood pressure monitor 702 from cradle 704.

With reference to FIGS. 7N-7U, cradle 704 can include arms 750 that are configured to secure to a portion of a cable or tube that may connect one or more sensor or monitors in a patient environment (such as the environment illustrated in FIGS. 1A-1B). Arm(s) 750 can be the same as arms 650 of cradle 604 in some or many respects. As shown in at least FIGS. 7N-7U, arms 750 can include a first end that connects to a portion of the cradle 704 and a second, free end. The second, free end of arms 750 can include a protrusion 750a that extend in a direction that is not parallel (for example perpendicular) with respect to the free end. In some cases, where the arms 750 curl as shown in FIGS. 7T-7U, the protrusion 750a of arms 750 can extend towards an interior of cradle 704, for example, towards sides 743, 745 (see FIGS. 7N-7O). Such protrusion 750a can help provide additional securement to a portion of a cable that is positioned in a space defined by the shape (for example, "curl") of arms 750. For example, a portion of a cable can be pushed into such space passed such protrusion 750a, and can be at least partially secured between a portion of the protrusion 750a and an inner surface of arms 750. While protrusion 750a is shown and described with respect to cradle 704, arms 650 of cradle 604 can include protrusion 750a.

As shown in FIGS. 7P-7Q, arms 750 can include an opening through a portion thereof. Such opening can help in removal of a portion of a cable from an arm 750. For example, where a portion of a cable is secured by arm 750, a user can partially insert the user's finger or another object through the opening and push on the portion of the cable so as to aid removal. While such opening is shown and described with respect to arms 750, arms 650 can also have such opening.

FIG. 7I illustrates a connector port 716, which can be the same in some or many respect to connector port 616 of blood pressure monitor 602. Connector port 716 can be identical to connector port 616 of blood pressure monitor 602 except with respect to the number and/or arrangement of female prong openings and/or slots or recesses (see FIG. 7I and FIG. 6O). Connector port 716 can connect to a cable (or a connector thereof), such as connector 105a.

Blood pressure monitor 702 can include one or more air intakes which can be in fluid communication with ambient air and can be configured to allow ambient air to flow into the interior of blood pressure monitor 702 and/or to one or more pumps within the blood pressure monitor 702, such as pumps discussed elsewhere herein. Such air intakes can also allow air to flow out from the interior of the blood pressure monitor 702 into the ambient, such as when the blood pressure monitor 702 is facilitating deflation of a connected cuff. The one or more pumps can create suction to draw ambient air into and/or through such air intake(s) of blood pressure monitor 702. Such air intake(s) can be located and/or positioned in a variety of locations on the blood pressure monitor 702, for example, sides, ends, and/or top or bottom surfaces of blood pressure monitor 702. Blood pressure monitor 702 can include one, two, three, four, five, or six or more air intakes. For example, blood pressure monitor 702 can include an air intake located along a side 713, 715 of blood pressure monitor 702.

FIGS. 7J-7M illustrate an example of an air intake 721 in blood pressure monitor 702. While these figures and the discussion below describe air intakes 721 with reference to blood pressure monitor 702, such discussion is equally applicable to blood pressure monitor 602. As shown in FIGS. 7B-7C and 7J-7M, blood pressure monitor 702 can include a grip 720 comprising a recess 720a and a rim 720b, each of which can be the same in some, many, or all respects as grip 620, recess 620a, and/or rim 620b discussed above. Thus, the discussion with reference to grip 620, recess 620a, and/or rim 620b is equally applicable to grip 720, recess 720a, and/or rim 720b. Air intake 721 can include one or more openings in an exterior portion (for example, a side of blood pressure monitor 702) and/or an interior portion (for example, an inner wall of the blood pressure monitor 702). For example, with reference to FIGS. 15F-15G, the opening in the exterior portion can be an opening in a side 713, 715 of blood pressure monitor 702, and such opening can comprise a slit 720c along a portion of the side 713, 715. Slit 720c can extend adjacent and/or along a portion of a perimeter of recess 720a. For example, slit 720c can extend adjacent and/or along less than ¾, less than ½, less than ¼, less than ⅙, or less than ⅛ of a perimeter or recess 720a, or any value therebetween, or any range bounded by any combination of these values, although values outside these values or ranges can be used in some cases. As another example, slit 720c can extend adjacent and/or along at least ⅛, at least ⅙, at least ¼, at least ½, or any value therebetween, or any range bounded by any combination of these values, although values outside these values or ranges can be used in some cases. In some cases, the slit 720c is positioned along a portion of the perimeter of the recess 720a that is opposite the rim 720b. For example, the slit 720c can be positioned closer to a bottom of blood pressure monitor 702 than recess 720a and/or rim 720b. Slit 720c can be positioned closer to a bottom surface of blood pressure monitor 702 than to a top surface of blood pressure monitor 702.

FIG. 7K illustrates a cross-section through blood pressure monitor 702 along the dotted line as shown in FIG. 7D. FIG. 7K illustrates, in part, slit 720c. As shown, air can flow through slit 720c and/or around a portion of a perimeter of recess 720a, above and/or adjacent to a wall 720g, into and/or through a first chamber 720d, into and/or through a second chamber 720e, into and/or through a chamber or opening 720f, and into an interior of blood pressure monitor 702 and/or into one or more pumps as discussed elsewhere herein. Where the slit 720c extends along a perimeter of recess 720a, wall 720g and/or chamber 720d can also extend along, adjacent to, and/or behind the recess 720a (or a portion of recess 720a) so as to collect the air flowing in and along an entire length of slit 720c. As shown, wall 720g can extend upward (for example, in a direction towards the top surface of blood pressure monitor 702) above slit 720c. As shown in FIG. 7K, blood pressure monitor 702 can include an inner wall 720h that is positioned closer to an interior of blood pressure monitor 702 than side 713, 715 and/or slit 720c. As also shown, the chamber 720f can extend through inner wall 720h.

FIGS. 7L-7M illustrate enlarged perspective views of a portion of a cross-section through blood pressure monitor 702. The cross-section as shown in FIG. 7L is oriented differently than the cross-section as shown in FIG. 7K so as to better illustrate opening 720f. With reference to FIG. 7D, the cross-section shown in FIG. 7L is spaced further to the "right" than the cross-section line "7K" shown in FIG. 7D. The cross-section shown in FIG. 7M is also spaced away from the cross-section as shown in FIG. 7K so as to better illustrate chamber 720e. As shown, chamber 720e can extend upward (for example, in a direction towards a top surface of blood pressure monitor 702) to the chamber 720f. With reference to FIGS. 7K-7L, chamber or opening 720f can extend transverse (for example, perpendicular) to chamber 720e and be open and/or adjacent to an interior of blood pressure monitor 702.

Advantageously, the structure, arrangement, and/or configuration of air intake 721 can prevent or reduce the likelihood that liquids will intrude an interior of blood pressure monitor 702 and cause damage to the electrical and/or mechanical components therein. For example, with reference to FIG. 7K, for liquids to get into an interior of blood pressure monitor 702 via slit 720c, such liquids would have to pass through slit 720c, pass upward (defying gravity) along and/or above wall 720g, in and/or through chambers 720d, 720e, and pass through chamber 720f of inner wall 720h. In a typical patient care environment, the likelihood of liquids traveling through the air intake 721 in such manner is low, especially where blood pressure monitor 702 is secured to cradle 704 on a cuff similar to that shown in FIGS. 1A-1B.

FIG. 7V illustrates how cradle 704 can connect with an exemplary blood pressure cuff 737 via a tube or hose, such as pneumatic hose 637 discussed and shown previously. As discussed previously, an end of hose 637 can be fluidly connected to an interior of cuff 737 and an end of hose 637 can secure to port 772a of cradle 704 such that, when port 772b is positioned within opening 770 of blood pressure monitor 702, blood pressure monitor 702 can be in fluid communication with the interior of cuff 737. Cuff 737 can be secured to a portion of a patient's body, such as an arm, thigh, or other portion. For example, cuff 737 can be secured to an arm of patient 111 as shown by cuff 121 in FIG. 1A-1B.

Noninvasive Blood Pressure Measurement

The human cardiovascular system is made up of the heart, blood vessels, and blood. The heart pumps blood through the blood vessels in order to transport oxygen, nutrients, etc., throughout the body.

Blood pressure is a measure of the pressure exerted by the circulating blood on the walls of the blood vessels and is typically measured in one of the large arteries. Blood pressure varies during the cardiac cycle from one heartbeat to the next. When the heart contracts, blood pressure momentarily rises and then subsequently falls until the next heartbeat. The systolic pressure is the maximum blood pressure attained during a cardiac cycle, while the diastolic pressure is the minimum blood pressure during the cardiac cycle. The mean arterial pressure (MAP) is the average blood pressure during the cardiac cycle. Blood pressure depends on a number of factors, including blood volume, cardiac output, vascular resistance, arterial stiffness, etc.

In medicine, blood pressure is a vital sign which can be used as an indicator of a patient's condition. Improved devices and techniques for measuring blood pressure can therefore help improve patient monitoring capabilities.

FIG. 12 is a block diagram of an example embodiment of the noninvasive blood pressure monitor 1200. Blood pressure monitor 1200 can include any of the features of any other blood pressure monitor (e.g., 120, 602, 702) described herein. For example, the blood pressure monitor 1200 can be a mobile device designed to strap to the arm of a patient via a cuff (e.g., 121). The blood pressure monitor 1200 can include electronics for determining blood pressure values, an interface for communicating blood pressure values to an external device, an integrated display for displaying the blood pressure values, etc. The components shown in the block diagram of FIG. 12 can be contained in, attached to, and/or supported by any of the housings of the blood pressure monitors (e.g., 120, 602, 702) described herein. Additionally, the following description provided with reference to blood pressure monitor 1200 is equally applicable to any other blood pressure monitor (e.g., 120, 602, 702) described herein.

The blood pressure monitor 1200 can include one or more air pumps 1210 (e.g., one, two, three, four, or more air pumps). The air pumps 1210 can be similar or identical to pumps 522 described herein. The air pump(s) 1210 create suction to draw air in through an air intake (e.g., 580) in the housing (e.g., 502) of the blood pressure monitor 1200. The air is then forced by the air pump(s) 1210 through an air path, such as a conduit 1220, toward an air manifold 1240 provided in the housing. One advantage associated with the use of multiple air pumps 1210 is that smaller pumps can be used to provide a similar amount of air flow as a single larger pump but can be laid out in the housing of the blood pressure monitor 1200 in a more flexible manner than a single larger pump can. The greater flexibility in the layout of multiple smaller pumps, as compared to a single larger pump, can in turn allow for a more compact design of the blood pressure monitor 1200.

The air manifold 1240 supplies air to an inflatable blood pressure cuff 1250. Air manifold 1240 can include any of the features of air manifold 520 described herein, and inflatable blood pressure cuff 1250 can include any of the features of blood pressure cuff 121 described herein. The cuff 1250 can be connected to the air manifold 1240 using, for example, an air supply port (e.g., 570), which may directly couple with a connector built into the cuff 1250 or which may couple to the cuff 1250 via a flexible hose or some other air path. The air manifold 1240 can also provide and/or connect to air paths for one or more air release valves 1260 and a pressure transducer 1270, as schematically shown in FIG. 12. The air manifold 1240 therefore can allow air flow between the pump(s) 1210, the cuff 1250, the pressure transducer 1270, and/or the release valve(s) 1260.

As described further herein, one or more acoustic filters 1230 can be provided along the air path(s) in the blood pressure monitor 1200 to attenuate selected frequencies of air pressure waves caused by operation of the air pump(s) 1210. In the illustrated embodiment, a single acoustic filter 1230 is provided along the conduit 1220 between the air pump(s) 1210 and the air manifold 1240. In some embodiments, however, the monitor 1200 can include multiple acoustic filters 1230 and the acoustic filter(s) can be provided at various different positions along the air path(s) (e.g., between the air manifold 1240 and the cuff 1250 and/or between the air manifold and the pressure transducer 1270).

The inflatable cuff 1250 of the blood pressure monitor 1200 is designed to strap around a monitoring site on the patient's body. The monitoring site may be, for example, the patient's lower arm at the wrist. Blood pressure in the radial artery can be measured at this site. In other embodiments, the inflatable cuff 1250 of the blood pressure monitor 1200 may be designed to strap around the upper arm of the patient so as to measure blood pressure at the brachial artery.

The cuff 1250 can include an internal compliant bladder whose volume expands in response to the pressure of the air supplied from the air pump(s) 1210. The air pump(s) 1210 can cause the air pressure inside the cuff 1250 to increase over time according to a desired inflation profile. For example, the air pump(s) 1210 can be controlled so as to linearly ramp up air pressure within the cuff 1250, though other inflation profiles can also be used (e.g., a stepped inflation profile or a piecewise linear inflation profile with segments having different slopes). The inflation profile of the cuff 1250 can be specified by, for example, using an air pump controller 1212 to control the speed(s) of the air pump(s) and/or to turn different air pumps 1210 on or off at selected times.

In some cases, the desired inflation profile may not be readily achievable by operation of one or more air pumps 1210 alone. In some of those cases, the air release valve(s) 1260 may be used in conjunction with the air pump(s) 1210 to achieve the desired inflation profile. For example, the monitor 1200 may implement time-overlapping operation of the air pump(s) 1210 and the air release valve(s) 1260. The resulting composite inflation profile is the summation of the inflation profile attributable solely to the air pump(s) 1210 and the lesser deflation profile attributable to the air release valve(s) 1260.

As the air pressure increases and the compliant bladder expands during the inflation phase, the cuff 1250 exerts pressure on the patient's artery at the monitoring site. Pulsatile blood pressure variations inside the artery during each cardiac cycle cause the arterial wall to expand and contract, thus changing the volume of the artery. These variations in the volume of the artery are partially transmitted via tissue and skin to the bladder in the cuff 1250 and are measurable by the pressure transducer 1270, which is connected to the cuff by an air pathway (e.g., the manifold 1240 or an optional separate bypass air pathway 1241). The pressure transducer 1270 generates an output signal indicative of the pressure associated with the expansion and contraction of the artery during each cardiac cycle. The pressure transducer 1270 can be any of a variety of pressure sensors, such as a flexible diaphragm whose deflection is measured and then output as an electrical signal.

Once the cuff 1250 has been inflated to or beyond the point of occluding the artery, the air release valve(s) 1260 can be operated so as to controllably reduce air pressure in the cuff. During the deflation phase, the air release valve(s) 1260 can be used to reduce air pressure in the cuff 1250 according to a desired deflation profile. For example, the valve(s) can be operated so as to linearly ramp down air pressure inside the cuff 1250, though other deflation profiles can also be used (e.g., a stepped deflation profile or a piecewise linear deflation profile with segments having different slopes).

In some cases, the desired deflation profile may not be readily achievable by operation of one or more air release valves 1260 alone. In some of those cases, the air pump(s) 1210 may be used in conjunction with the air release valve(s) 1260 to achieve the desired deflation profile. For example, the monitor 1200 may implement time-overlapping operation of the air release valve(s) 1260 and the air pump(s) 1210. The resulting composite deflation profile is the summation of the deflation profile attributable solely to the air release valve(s) 1260 and the lesser inflation profile attributable to the air pump(s) 1210.

This technique may be useful, for example, in embodiments of the blood pressure monitor 1200 which use a relatively inexpensive air release valve 1260 in order to reduce overall cost. Some inexpensive valves release air pressure in bursts rather than continuously. This can result in a stepped waveform deflation profile. Although a stepped deflation profile may be useful in some embodiments, if a more continuous deflation profile is desired, the air pump(s) 1210 can be operated during the deflation phase to provide an inflation profile that represents the difference between the desired composite deflation profile and the deflation profile attributable solely to the air release valve(s) 1260.

In some embodiments, a first air release valve 1260 can serve as a relatively slow bleed valve to reduce air pressure inside the cuff 1250 according to normal operation during a blood pressure measurement. Meanwhile a second air release valve 1260 can serve as a relatively fast bleed emergency release valve capable of quickly deflating the cuff 1250 if the need arises. The valve(s) 1260 can be designed to fail in the open state so that air pressure inside the cuff 1250 is released in the event of a power failure.

In order to obtain a measurement using the blood pressure monitor 1200, the cuff 1250 can be secured around the patient's arm at the measurement site. The monitor 1200 can then implement desired inflation and deflation profiles to obtain an output signal from the pressure transducer 1270 which can be processed to yield one or more blood pressure measurement values. During this process, when the air pressure inside the cuff 1250 is greater than the minimum, or diastolic blood pressure—but less than the maximum, or systolic blood pressure—inside the artery, the cuff partially collapses the arterial wall at the measurement site. The partial collapse of the arterial wall restricts blood flow through the artery. The degree of collapse—and the resulting restriction of blood flow through the artery—depends on the extent to which the air pressure in the cuff 1250 exceeds the minimum blood pressure in the artery. When the air pressure inside the cuff 1250 rises to exceed the maximum blood pressure in the artery, the artery becomes occluded and blood flow is cut off.

The patient's diastolic blood pressure measurement value is related to the pressure detected by the pressure transducer 1270 when, during the inflation phase, the cuff 1250 begins to interrupt continuous blood flow through the artery at the measurement site or, during the deflation phase, the cuff ceases to interrupt continuous flow. The patient's systolic blood pressure measurement value is related to the pressure detected by the pressure transducer 1270 when, during the inflation phase, the cuff 1250 just occludes the artery and pulsing blood flow ceases or, during the deflation phase, the artery is no longer fully occluded and blood just begins to once again flow through the artery.

The diastolic and systolic blood pressure measurement values can be determined based on the pressure transducer output signal during the inflation phase and/or the deflation phase. In some embodiments, the pressure transducer 1270 outputs an analog pressure signal 1272 which varies as a function of time in response to the air pressure in the cuff 1250 and the pressure transmitted to the transducer by the artery via the cuff 1250. The analog pressure signal can then be converted to a digital signal by an analog-to-digital converter 1281. In some embodiments, the digital pressure signal can be decimated, as shown by the decimation blocks 1282. The digital pressure signal can then be processed to obtain an oscillometric signal. The oscillometric signal includes plethysmographic waveforms which correspond to changes in the volume of the artery as it expands and contracts in response to pulsing blood.

In some embodiments, the processing of the digital pressure signal to obtain the oscillometric signal can include frequency filtering. For example, the digital pressure signal can be bandpass filtered to reject lower and higher frequency components which are not attributable to blood pressure variations, as shown by the bandpass filter block 1283. Thus, the oscillometric signal includes plethysmographic signal content that is attributable to blood pressure variations in the artery at the measurement site, but typically excludes low-frequency pressure variations that are attributable to the inflation and deflation of the cuff 1250 as well as higher-frequency pressure variations that are attributable to vibrations of the air pump(s) 1210. The frequency filtering can be carried out by, for example, a single-stage or multi-stage filter. Additional and/or different signal processing operations can also, or alternatively, be applied to the digital signal. The resulting oscillometric signal can then be analyzed by a processor to determine one or more blood pressure values. This analysis can be performed locally by a processor 1284 provided in the blood pressure monitor 1200 itself or by an external processor to which the oscillometric signal (or a predecessor signal) may be transmitted.

The processor 1284 can cause the blood pressure measurement values to be transmitted to an external device (e.g., a bedside patient monitor) and/or to be shown on a display 1286 integrated in the blood pressure monitor 1200. In addition to calculating and/or displaying blood pressure values, the processor 1284 can also be used to control the air pump(s) 1210 (via the air pump controller 1212) and the air release valve(s) 1260. The processor 1284, air pump(s) 1210, air release valve(s) 1260, display 1286, and/or other components of the blood pressure monitor 1200 can be powered by a battery provided in the housing of the monitor or by a power bus from another component.

Although not illustrated, some embodiments of the blood pressure monitor 1200 may include either an integrated microphone or a microphone input port that allows the monitor to be connected to an external microphone. The microphone can be used to provide a signal for performing auscultatory blood pressure measurements using Korotkoff sounds. The microphone can also be used to provide a signal for controlling operation of the air pump(s) 1210, as discussed further herein.

In addition, some embodiments of the noninvasive blood pressure monitor 1200 may include an accelerometer. The accelerometer can be used, for example, to detect patient motion during a blood pressure measurement. If patient motion is detected during a measurement by the accelerometer, the blood pressure values can be flagged or rejected, depending on a selected property of the detected motion (e.g., the magnitude of the motion signal). Alternatively and/or additionally, the blood pressure monitor 1200 can output a message or warning (e.g., via the display 1286 or a speaker) to the patient to hold still during the measurement. In some embodiments, the blood pressure monitor 1200 can check the accelerometer signal prior to performing a blood pressure measurement. If the accelerometer signal is indicative of patient motion, then the monitor 1200 can delay the blood pressure measurement until patient motion is no longer detected.

In addition, the accelerometer can be used to determine if the patient's arm is in a desired position during a blood pressure measurement. For example, blood pressure measurements are typically more accurate if the patient's arm is elevated near the same height as the patient's heart. For a wrist-worn blood pressure monitor 1200, this may be the case when the monitor is detected by the accelerometer to be horizontally level (within a specified range of angles). If, however, the blood pressure monitor 1200 is detected to be too vertically-oriented due to the patient's lower arm being elevated or hanging down, the blood pressure values can be flagged or rejected. Alternatively and/or additionally, the blood pressure monitor 1200 can output a message or warning (e.g., via the display 1286 or a speaker) to the patient to level his or her lower arm during the measurement.

Example Acoustic Design for Noninvasive Blood Pressure Monitor

Since the blood pressure monitor 1200 is a portable device designed to be worn by the patient, there is a greater need—as compared to other non-wearable blood pressure monitors which can readily be positioned at a greater distance from the patient—to reduce acoustic noise produced by the monitor.

The air pump(s) 1210 are typically the dominant source of acoustic noise from the blood pressure monitor 1200. In order to dampen the sound from the blood pressure monitor 1200, the air pump(s) 1210 can be provided in a noise-dampening housing. The housing can include, for example, two or more parts that join together to enclose the interior components of the blood pressure monitor 1200. One or more gaskets can be provided at the mating interface(s) between the parts of the housing. The gasket(s) can reduce acoustic noise from the blood pressure monitor 1200 by preventing the parts of the housing from vibrating against one another and by providing a seal that helps to prevent sound waves from exiting the housing. The amount of sound attenuation may be dependent on the material properties of the gasket, and more specifically the mismatch in material acoustic properties between the housing material and the gasket itself.

Acoustic noise from the blood pressure monitor 1200 can be further reduced with noise-dampening materials. Open space within the housing of the blood pressure monitor 1200 can be partially or completely filled with noise-dampening material. The noise-dampening material(s) can be provided as a single piece, multiple layers, many small pieces, and/or combinations of the same or the like. The noise-dampening material may be, for example, loosely-layered tissue-like materials, low-density foam pieces, aerogel, etc.

As already discussed, the blood pressure monitor can include air paths which join the air pump(s) 1210, the manifold 1240, the cuff 1250, the air release valve(s) 1260, and/or the pressure transducer 1270. The air pump(s) 1210 can create unwanted acoustic noise which manifests as air pressure waves which propagate to the cuff 1250, the air release valve(s) 1260, and/or the pressure transducer 1270 via the air paths that connect these components. In order to reduce the propagation of these air pressure waves between the air pump(s) 1210 and any of the other components of the monitor 1200, an acoustic filter 1230 can be provided at any point along the air path(s) (e.g., conduit 1220 or manifold 1240).

In some embodiments, one or more acoustic filters 1230 can be provided along the air path(s) between the pump(s) 1210 and the cuff 1250. This may be advantageous because the cuff 1250 may act as a speaker by amplifying air pressure waves coupled into it via the air path from the pump(s) 1210. If an acoustic filter 1230 is provided between the air pump(s) 1210 and the cuff 1250, undesirable air pressure waves can be reduced or eliminated prior to amplification by the cuff 1250, thereby reducing noise output from the cuff. One or more additional acoustic filters 1230 can also, or alternatively, be provided along the air path(s) between the air pump(s) 1210 and the pressure transducer 1270 and/or between the air pump(s) and the air release valve(s) 1260.

As just discussed, the acoustic filter 1230 shown in FIG. 12 attenuates unwanted air pressure waves that would otherwise reach the cuff 1250. This reduces irritating noise and provides for a more pleasant user experience. The acoustic filter 1230 also attenuates unwanted air pressure waves that would otherwise reach the pressure transducer 1270 and possibly corrupt its output signal. The acoustic filter 1230 can therefore attenuate variations in the output signal of the pressure transducer 1270 which would otherwise manifest as signal noise. Accordingly, the acoustic filter 1230 can not only reduce audible noise emanating from the blood pressure monitor 1200 but can also reduce signal noise and thereby improve fidelity of the measurements produced by the monitor.

In FIG. 12, the acoustic filter 1230 is illustrated as being provided along the air path between the pump(s) 1210 and the air manifold 1240. This arrangement may be advantageous because the acoustic filter 1230 is provided upstream of the manifold 1240 where air paths branch off and can therefore reduce unwanted air pressure waves at multiple components of the monitor 1200. In some embodiments, however, an acoustic filter can be provided along one or more air paths at points downstream from the air manifold 1240. For example, an acoustic filter can be provided along the air path between the air manifold 1240 and the cuff 1250, and/or along the air path between the air manifold 1240 and the pressure transducer 1270.

FIG. 13A illustrates an example embodiment of the acoustic filter 1230. The air conduit 1220 between the air pump(s) 1210 and the blood pressure cuff 1250 is shown. The illustrated embodiment of the acoustic filter 1230 is made up of opposing closed-ended stubs, or elongated cavities, which branch off of the air supply conduit 1220. These opposing stubs form a column of air that can be vibrated by air pressure waves from the air pump(s) 1210. The air pressure waves from the air pump(s) 1210 propagate through the air supply conduit 1220 until arriving at the acoustic filter 1230. The air pressure waves can then propagate down the opposing stubs of the acoustic filter 1230 and can reflect from the closed ends of the stubs. Depending upon the length of the stubs, some frequencies of the reflected waves destructively interfere with waves propagating in the air supply conduit 1220. The length of the stubs can be determined based on the acoustic output of the air pump(s) 1210 so as to effectively induce destructive wave interference for the dominant wavelength(s) to be attenuated. This type of acoustic filter can function as a low-pass filter.

FIG. 13B illustrates another example embodiment of the acoustic filter 1230. The acoustic filter 1230 shown in FIG. 13B is similar to the one shown in FIG. 13A in that it consists of opposing stubs or elongated cavities which branch off of the air supply conduit 1220. However, in the embodiment shown in FIG. 13B, the stubs of the acoustic filter 1230 have a folded or tortuous—rather than straight— configuration. As shown, a folded configuration of the acoustic filter 1230 can include multiple sections—straight or curved—joined together (e.g., at angles). The folded configuration may be advantageous in some embodiments because it is a more compact design that can efficiently use space within the housing of the blood pressure monitor 1200. This type of acoustic filter can likewise function as a low-pass filter.

FIG. 13C illustrates additional example embodiments of the acoustic filter 1230. The example acoustic filters 1230 shown in FIG. 13C are box-shaped cavities that are intersected by the air supply conduit 1220. As shown, the box-shaped cavities may be proportioned with different sizes in different dimensions. For example, the box-shaped cavities may have relatively large faces joined by relatively thin side edges. FIG. 13C shows that the air supply conduit 1220 may intersect with a box-shaped cavity at the larger faces or at the thinner side edges. Similar to the stub filters shown in FIGS. 13A and 13B, the box-shaped acoustic filters 1230 shown in FIG. 13C function by creating reflected waves which can cause destructive interference with the air pressure waves propagating down the air supply conduit 1220. These types of acoustic filters can also function as low-pass filters. The box-shaped filters may be more effective in some embodiments than the stub line filters, however, because they include a greater interaction area at the intersection with the air supply conduit 1220. Although box-shaped cavities are illustrated, other shapes of enclosed cavities are also possible and may be effective depending on the air pressure waves produced by the air pump(s) 1210.

FIG. 13D illustrates yet another example embodiment of the acoustic filter 1230. In this embodiment, the acoustic filter is a box-shaped enclosure which is not intersected by the air supply conduit 1220, but rather is joined to the air supply conduit 1220 by an open-ended stub. This embodiment can effectively function as a band-stop filter. Although a box-shaped enclosure is illustrated, other shapes are also possible.

In some embodiments, the acoustic filter(s) 1230 can be integrated with the air manifold 1240. For example, the air manifold 1240 can itself be shaped and/or sized to act as the acoustic filter 1230. In some embodiments, the air manifold 1240 can include an acoustic filtering cavity. The acoustic filtering cavity can be box-shaped such as is shown in FIG. 13C, though other cavity shapes are also possible. The cavity can include multiple air conduits or ports which join with the cavity to connect the air manifold 1240 with other components. The dimensions of the acoustic filtering cavity can be at least 2, 3, 4, 5, 10, 15, or 20 times the size of the dimensions of conduits or ports which feed into the cavity.

In some embodiments, the acoustic filters 1230 described herein can be designed such that their pass bands exclude some or all of the acoustic frequencies produced by the air pump(s) 1210 at normal operating speeds. For example, the acoustic filters 1230 described herein can be designed such that their pass bands exclude the fundamental frequency produced by the air pump(s) at or above 50%, 60%, 70%, 80%, or 90% of their maximum operating speeds.

Air manifold 520, discussed above, is an example of an acoustic filter 1230 integrated with an air manifold. Air manifold 520 includes multiple box-shaped acoustic filtering cavities joined together to create a larger acoustic filtering cavity. Various faces of the acoustic filtering cavity in air manifold 520 include ports which connect the manifold to air pumps, the cuff, release valves, and a pressure transducer. Acoustic waves which enter the air manifold 520 through any of these ports can reflect from various walls of the acoustic filtering cavity, thereby resulting in destructive interference at certain frequencies.

Example Inflation Control Techniques

In some embodiments, the air pump controller 1212 can be used for dynamically controlling one or more operating characteristics (e.g., speed, stroke length, stroke phase, etc.) of each of the air pump(s) 1210 in the noninvasive blood pressure monitor 1200. The ability to dynamically control operating characteristics of the air pump(s) 1210 can be used to achieve multiple advantages, including improving the audible sound emitted by the blood pressure monitor 1200 and reducing the amount of time necessary for the monitor to perform blood pressure measurements, as shown in FIGS. 14A-14C, respectively.

FIG. 14A is a flowchart of an example embodiment of a method 1400A for using the air pump controller 1212 to improve the audible sound emitted by the blood pressure monitor 1200. As already discussed, the blood pressure monitor 1200 can include technology, such as gaskets, acoustic filters, noise-dampening material, etc., for reducing the amount of audible noise it emits. In the case that not all of the audible noise can be eliminated, however, it may be possible to make the remaining noise more pleasant for the patient.

The example method shown in FIG. 14A is applicable to embodiments of the blood pressure monitor 1200 which include multiple air pumps 1210. By including multiple air pumps 1210, the blood pressure monitor 1200 has the ability to alter the inflation rate of the cuff 1250 by turning different air pumps on or off at different times. For example, if the blood pressure monitor 1200 includes two air pumps 1210, the inflation rate of the cuff 1250 can be doubled by turning the second air pump on at approximately the same speed as the first air pump. Or conversely, when the two air pumps are running at approximately the same speed, the inflation rate of the cuff 1250 can be halved by turning one of the air pumps off. Although similar changes in the inflation rate of the cuff 1250 could possibly be achieved by dramatically changing the operating speed of a single air pump, doing so could result in relatively large changes in the frequency of the acoustic noise emitted by the air pump (the frequency of the acoustic noise is related to the speed of the air pump), which could shift the acoustic noise into the passband of the acoustic filter 1230, require a more complicated design for the acoustic filter 1230, and/or otherwise compromise the performance of the noise-reducing technology in the blood pressure monitor 1200. Multiple-air-pump embodiments may also be advantageous in that they may provide for a larger range of inflation rates than could be achieved by adjusting the speed of a single air pump.

One potential difficulty, however, with using multiple air pumps 1210 is that different air pumps may run at slightly different speeds even when provided with identical drive signals. This may be attributable to, for example, manufacturing tolerances or uneven wear of internal moving parts over time. Since the frequency of the acoustic noise from an air pump is related to its speed, slight speed differences for the multiple air pumps 1210 can cause them to emit noise at slightly different frequencies, thus possibly resulting in perceptible beat frequencies or other acoustic effects which may be unpleasant for the user. This and other problems can be solved according to the method 1400A shown in FIG. 14A.

The method 1400A begins at block 1410a where the blood pressure monitor 1200 detects one or more characteristics of the acoustic noise emitted by the air pumps 1210, whether on an individual or collective basis. The detected acoustic noise characteristic(s) can include, for example, loudness, frequency content, relative phase of frequency components, beat frequencies, etc. Acoustic noise characteristics can be determined by using the processor 1284 to analyze the output signal from a microphone integrated in, or connected to, the monitor 1200 or to analyze the output signal from the pressure transducer 1270. The analysis can be performed using, for example, Fourier transforms or other frequency domain analysis techniques, an envelope detection algorithm, or other known signal processing techniques.

Then, at block 1420*a*, the blood pressure monitor 1200 can use the air pump controller 1212 to make one or more adjustments (e.g., via open-loop or feedback control) to one or more operating characteristics of the air pumps 1210 so as to reduce an acoustic displeasure metric. The acoustic displeasure metric can be any objective metric that is correlated with the subjective displeasure that the sound emitted by the air pumps 1210 causes for a representative group of patients. In some cases, the acoustic displeasure metric can be equal to, or based on, an acoustic noise characteristic, or a combination of multiple acoustic noise characteristics, that is/are detected in block 1410*a*. For example, the acoustic displeasure metric can be based on the loudness of the sound, the beat frequency, etc. Method 1400A can be repeated iteratively during the inflation phase of a blood pressure measurement or until the acoustic displeasure metric is reduced beyond a desired threshold.

In some embodiments, the blood pressure monitor can use the air pump controller 1212 to reduce the acoustic displeasure metric by adjusting the speed, stroke length, or stroke phase of either or both air pumps 1210. For example, the acoustic noise characteristic that is detected in block 1410*a* can be the loudness of the noise produced by the air pumps 1210. The loudness of the noise can also serve as the acoustic displeasure metric in block 1420*a*. Then at block 1420*a*, the stroke phases of the air pumps 1210 can be adjusted (e.g., toward a relative phase difference of 180 degrees) so as to increase the destructive interference between the respective sound waves they produce. By increasing the degree of destructive interference, the loudness of the acoustic noise (i.e., the acoustic displeasure metric) can be reduced.

In other embodiments, the acoustic noise characteristic that is detected in block 1410*a* can be the beat frequency produced by the air pumps 1210 operating at slightly different speeds. The acoustic displeasure metric in block 1420*a* can be, for example, inversely related to the beat frequency such that a lower beat frequency results in a higher acoustic displeasure metric and a higher beat frequency results in a lower acoustic displeasure metric. Then at block 1420*a*, the speed of one of the air pumps can be adjusted so as to change the beat frequency in a way that reduces the displeasure metric. For example, the difference in speed of one of the air pumps with respect to the other can be increased, thereby increasing separation between the respective frequency content of the acoustic noise emitted by the air pumps. This in turn will increase the beat frequency so it is more pleasant-sounding. In some embodiments, the monitor 1200 can identify a dominant frequency in the acoustic noise emitted by each of the air pumps 1210 and the air pump controller 1212 can be used to make adjustments which increase the difference between the respective dominant frequencies. The adjustments can be made by altering the drive signal to a single air pump while holding the drive signal to the other pump steady, or by altering the drive signals for both pumps. In other embodiments, the acoustic displeasure metric can be proportional to the beat frequency such that a lower beat frequency (e.g., low enough to be imperceptible to the human ear) results in a lower acoustic displeasure metric and a higher beat frequency results in a higher acoustic displeasure metric. Then at block 1420*a*, the speed of one of the air pumps can be adjusted to as to reduce the acoustic displeasure metric by, for example, driving the beat frequency toward zero.

In some embodiments, the air pump controller 1212 can be used to make adjustments which cause the frequency content of the acoustic noise emitted by one of the air pumps 1210 to have a desired relationship in comparison to the frequency content of the acoustic noise emitted by another of the air pumps. For example, the relationship can be that the dominant frequency of the acoustic noise emitted by one of the pumps be harmonically related (or have any other offset) to the dominant frequency of the acoustic noise emitted by another of the air pumps since harmonic frequencies (i.e., frequencies related by a whole number multiple) are generally considered to be pleasant to the ear. Any other desired relationship between the respective dominant frequencies of the air pumps can also be used.

FIG. 14B is a flowchart of an example embodiment of a method 1400B for reducing the amount of time necessary for the noninvasive blood pressure monitor 1200 to perform blood pressure measurements. The inflation phase for the cuff 1250 can be divided into a non-measurement portion and a measurement portion. The method 1400B begins at block 1410*b* where the blood pressure monitor 1200 inflates the cuff 1250 at a relatively high rate during the non-measurement portion of the inflation phase until a plethysmographic waveform is detected in the signal from the pressure transducer 1270. Plethysmographic waveforms are indicative of changes in arterial volume caused by instantaneous blood pressure variations during cardiac cycles from one heartbeat to the next. Plethysmographic waveforms are not present in the signal from the pressure transducer 1270 until the air pressure inside the cuff 1250 causes the cuff to squeeze the arm with sufficient force to become responsive to the pulsing of the patient's artery.

Since no clinically relevant measurements can be obtained from the output of the pressure transducer 1270 until plethysmographic waveforms begin to appear, the overall process for obtaining a blood pressure measurement can be accelerated by quickly inflating the cuff 1250 to that point during the non-measurement portion of the inflation phase. In embodiments where blood pressure measurements are taken during the inflation phase, it may be undesirable, however, to continue to inflate the cuff 1250 at the same high rate after plethysmographic waveforms have appeared in the output signal of the pressure transducer 1270. This is because the blood pressure measurements may be reliant on data from a certain predetermined minimum number of cardiac cycles, so a high cuff inflation rate may completely occlude the patient's artery before a sufficient number of cardiac cycles have occurred, thus negatively impacting the accuracy of the blood pressure measurements. Accordingly, the blood pressure monitor 1200 can reduce the inflation rate of the cuff 1250 during the measurement portion of the inflation phase (e.g., as delineated by the detected presence of plethysmographic waveforms in the output from the pressure transducer 1270) so as to allow for an adequate number of cardiac cycles before the artery is completely occluded.

At block 1420*b* of the method 1400B, the blood pressure monitor 1200 can determine the patient's pulse rate from the period or fundamental frequency of the train of plethysmographic waveforms. The pulse rate can typically be determined within 2-3 cardiac cycles. Then, at block 1430*b*, given the patient's pulse rate, the blood pressure monitor 1200 can set (e.g., lower) the cuff inflation rate so as to allow for an adequate number of cardiac cycles to occur before reaching the maximum inflation pressure. In some embodiments, the monitor may allow ≤15, or ≤12, or ≤10 cardiac cycles (inclusive of the cardiac cycles also used to determine the pulse rate) to make the blood pressure measurements prior to reaching the maximum inflation pressure. (Note: In some embodiments, the maximum inflation pressure may be determined based on the shape of the envelope of the train of plethysmographic waveforms in the oscillometric signal. This technique can make use of the fact that the envelope reaches a maximum amplitude at the mean arterial pressure. This point can be identified by detecting the envelope of the oscillometric signal and then detecting when the slope of the envelope crosses zero. Once the mean arterial pressure is estimated from the maximum value—or first-derivative zero-crossing—of the envelope of the oscillometric signal, it can be used to estimate the diastolic and systolic blood pressure values. The maximum inflation pressure can then be set to a value at least as high as the estimated systolic pressure.)

FIG. 14C illustrates an example embodiment of a method 1400C for dynamically controlling inflation of the cuff 1250 in the blood pressure monitor 1200. The method 1400C begins at the start block 1405c before subsequently entering the first of three inflation stages: stage 1 inflation, stage 2 inflation, and stage 3 inflation.

In the embodiment illustrated in FIG. 14C, stage 1 is a non-blood-pressure-measurement inflation stage. The purpose of the first inflation stage is to quickly fill dead space in the cuff 1250. As already mentioned herein, the blood pressure monitor 1200 cannot perform a measurement until plethysmographic waveforms begin appearing in the output of the pressure transducer 1270. Such plethysmographic waveforms do not begin to appear until the cuff exerts adequate pressure at the measurement site. Thus, the first inflation stage is used to quickly increase the volume of the cuff 1250 from its deflated state.

The first inflation stage begins at block 1410c where at least one of the air pumps 1210 is started. The first inflation stage is a relatively high-rate inflation stage. Thus, the starting output volume of the air pump(s) 1210 at block 1410c can be, for example, at least 60%, or at least 70%, or at least 80%, or at least 90%, or at least 95% of the maximum operating output volume available from the pumps. In some embodiments, the starting output volume of the air pump(s) 1210 can be a fixed value or it can be variable based on one or more inputs. For example, block 1410c can receive the size of the cuff 1250 as an input to determine the starting pump output volume. (The blood pressure monitor 1200 can utilize different sized cuffs 1250 depending upon the measurement site (e.g., wrist or upper arm) or the size of the patient (e.g., child, adolescent, adult, etc.)) In some embodiments, the cuff size can be stored in a near-field communication (NFC) or radio frequency (RF) tag located on or in the cuff 1250 and can be read by an NFC or RF tag reader provided in the blood pressure monitor 1200, though other techniques for receiving the cuff size as an input can also be used. For a larger sized cuff 1250, the starting output volume of air at block 1410c can be set to a higher value; for a smaller sized cuff, the starting output volume of air can be set to a lower value.

Since the first inflation stage is intended to be a relatively high-rate inflation stage, it will often be the case that multiple air pumps will be started at block 1410c. In those embodiments, the first inflation stage can optionally include block 1415c where pump frequency relationship control is performed. As described herein, even though two air pumps may be provided with identical drive signals they may have slightly different operating speeds. Since the frequency of the acoustic noise produced by each air pump 1210 is dependent on its operating speed, this offset in operating speeds can result in acoustic beat frequencies that may be unpleasant-sounding to the user. Thus, block 1415c can be implemented so as to control the respective operating speeds of the air pumps 1210 so as to achieve a desired relationship between the respective acoustic frequencies they produce.

FIG. 14D illustrates an example embodiment of a method for carrying out the pump frequency relationship control in block 1415c of FIG. 14C. In operation, a drive signal, such as a selected voltage, is applied to each of the air pumps 1210. An operating electrical current is developed in each air pump 1210 in response to the applied voltage. These operating electrical currents are generally periodic waveforms whose periodicities are indicative of the respective operating speeds of the air pumps 1210. In the illustrated embodiment, the operating electrical current signal, $i_{pump1}$, of the first air pump 1210 is input into a first Fast Fourier Transform (FFT) block 1410d, while the operating electrical current signal, $i_{pump2}$, of the second air pump 1210 is input into a second FFT block 1430d. The respective FFT blocks 1410d, 1430d can calculate the frequency content of the operating current signals from the air pumps 1210. Although FFT blocks are illustrated, any technique for determining frequency content of the operating current signals can be used.

Once the frequency content of the operating current signals has been determined by FFT blocks 1410d, 1430d, the ith harmonic of the frequency content of the operating electrical current signals can be respectively determined at blocks 1420d and 1440d. In some embodiments, blocks 1420d and 1440d output the frequency of the first harmonic, or fundamental frequency, of the operating current signals from the air pumps 1210.

The selected harmonic of each of the operating current signals is then input into block 1450d. Block 1450d can also receive as an input the current drive signal being applied to either or both air pumps 1210. In the illustrated embodiment, the current voltage, $V_{pump2}$, being applied to the second air pump 1210 is input into block 1450d. In response to these inputs, block 1450d outputs an updated voltage to be applied to either or both air pumps 1210. In the illustrated embodiment, block 1450d outputs an updated voltage to be applied to the second air pump 1210. The updated voltage can be selected so as to achieve a desired relationship between the identified harmonic from the operating electrical current of the first air pump and the identified harmonic from the operating electrical current of the second air pump. In some embodiments, the desired relationship between the identified frequencies can be that they are the same. This frequency relationship would set the operating speeds of the air pumps 1210 to be the same. In other embodiments, however, the desired frequency relationship can be a non-zero offset value (e.g., one that produces a beat frequency lower than the frequency threshold the human ear is able to perceive, or one that causes the frequencies to be harmonically related at integer multiples of one another, etc.). In some embodiments, the desired frequency relationship can be set based on input from the user. For example, the user can provide an input via a button, knob, or other input device to set the frequency offset at a value that is acoustically pleasing to the user.

The voltage update block 1450d can operate in an open loop or a closed loop control mode. In the case of an open loop control mode, the operating speed of at least one of the air pumps, e.g., the second air pump 1210, can be characterized for a range of input voltages. For example, a look-up table can include the operating speed of the second air pump 1210 for each of a range of input voltages. The voltage update block 1450d can receive the operating speed of the first air pump 1210 as an input in the form of the frequency of the ith harmonic of the operating electrical current of the first air pump. The voltage update block 1450*d* can then select and output the updated voltage, $V_{pump2}$, which results in the ith harmonic of the operating electrical current of the second air pump having the desired relationship with the ith harmonic of the operating electrical current of the first air pump. In the case of the closed loop control mode, the voltage update block 1450*d* can iteratively adjust the updated voltage, $V_{pump2}$, applied to the second air pump. The voltage update block 1450*d* can then determine the effect of that adjustment on the relationship between the respective operating frequencies of the air pumps. If the adjustment resulted in the relationship between the respective operating frequencies of the air pumps being closer to the desired relationship, then the voltage update block 1450*d* can make a subsequent adjustment to $V_{pump2}$ in the same direction. If, on the other hand, the adjustment resulted in the relationship between the respective operating frequencies of the air pumps being further from the desired relationship, then the voltage update block 1450*d* can make a subsequent adjustment to $V_{pump2}$ in the opposite direction. The magnitude of the adjustment can vary depending upon how close the desired frequency relationship is to being satisfied. An example closed loop control mode can be governed by the following equations: $Vu_{pdated\_pump2}=V_{pump2}+dV$, where $dV=\alpha*df$ if $dV_{min} \leq E*df \leq dV_{max}$, or $dV=dV_{min}$ if $\alpha*df<dV_{min}$, or $dV=dV_{max}$ if $\alpha*df>dV_{max}$; $df=f_{pump2}-f_{pump1}$ and $\alpha$=constant.

Decision block 1420*c* illustrates an example ending criterion for the first inflation stage. In the illustrated embodiment, the ending criterion for the first inflation stage is that the pressure in the cuff 1250, as measured by the pressure transducer 1270, is above a threshold pressure $P_1$. An example of the threshold pressure is 30 mmHg, though other pressure thresholds can also be used. Other ending criteria can also be used. For example, in some embodiments, the ending criterion for the first inflation stage is that a plethysmographic waveform has been detected in the output from the pressure transducer 1270.

If it is determined at decision block 1420*c* that the ending criterion for the first inflation stage has not been met, then the method 1400C can return to block 1415*c* to iteratively perform pump frequency relationship control. This can be done because the operating frequency of each of the air pumps 1210 may change in response to the increasing back pressure from the cuff 1250 as it is inflated. If, on the other hand, the ending criterion for the first inflation stage is satisfied at decision block 1420*c*, the second inflation stage begins.

The second inflation stage is a non-blood-pressure-measurement inflation stage, but it is a heart-rate-detection inflation stage. The second inflation stage begins at block 1425*c* where the drive signal(s) (e.g., input voltage(s)) for the air pump(s) 1210 is/are set. In some embodiments, the output volume of the air pump(s) 1210 at block 1425*c* can be set to a value that is lower than the output volume of air during the first inflation stage. The starting output volume of the air pump(s) 1210 during the second inflation stage can be a fixed value or it can be variable based on one or more inputs. For example, block 1430*c* can receive the size of the cuff 1250 as an input to determine the starting pump output volume for the second inflation stage. The inflation rate of the cuff 1250 can be slowed in the second inflation stage—relative to the first inflation stage—so as to facilitate detection of a heart rate from an oscillometric signal collected by the pressure transducer 1270.

The second inflation stage can then continue to block 1430*c* where pump frequency relationship control can once again be performed. This can be done as described with respect to block 1415*c*. Then, at block 1435*c*, the blood pressure monitor 1200 can analyze the output of the pressure transducer 1270 to determine whether plethysmographic waveforms are present and whether a heart rate can be detected. In some embodiments, the heart rate can be determined based on the frequency of the plethysmographic waveforms in the oscillometric signal. Subsequently, at decision block 1440*c*, if no heart rate is yet detected then the method 1400C can iteratively return to blocks 1430*c* and 1435*c*. Once plethysmographic waveforms are present in the oscillometric signal from the pressure transducer 1270 and a heart rate is detected, then decision block 1440*c* can cause the method 1400C to proceed to the third inflation stage.

The third inflation stage is a blood-pressure-measurement inflation stage. At block 1445*c*, a control loop, such as a proportional-integral-derivative (PID) controller, sets the drive signal(s) of the air pump(s) 1210 so as to achieve a target inflation rate per unit time or per cardiac cycle. In some embodiments, accuracy of the blood pressure measurement performed by the blood pressure monitor 1200 may be partially dependent upon the number cardiac cycles—and the corresponding number of plethysmographic waveforms—that are detected during the blood pressure measurement phase. The target inflation rate can be selected so as to allow for a desired number of cardiac cycles before the pressure inside the cuff 1250 reaches the patient's systolic blood pressure. The target inflation rate can be selected so as to balance speed of measurement against measurement accuracy. In some embodiments, the target inflation rate is 9 mmHg per heartbeat, or cardiac cycle, though other target inflation rates can also be used.

In some embodiments, the target inflation rate is the same for all patients. In other embodiments, however, the target inflation rate can be adjusted for each patient. For example, the target inflation rate may be adjusted based on the detected heart rate at block 1435*c* (e.g., for patients with higher heart rates, the target inflation rate can be set to a higher value per unit time; for patients with lower heart rates, the target inflation rate can be set to a lower value per unit time).

In some embodiments, the target inflation rate can be maintained steady during the entire measurement phase. In other embodiments the target inflation rate can be changed for different sections of the measurement phase, as described with respect to FIG. 14E.

FIG. 14E illustrates how target inflation rate of the blood pressure cuff 1250 can be adjusted during a blood pressure measurement based on the envelope of the oscillometric signal produced by the blood pressure monitor 1200. An oscillometric signal 1402*e* is shown in FIG. 14E. The oscillometric signal is plotted as a function of pressure in the cuff 1250. The oscillometric signal includes a train of plethysmographic waveforms—each corresponding to a cardiac cycle or heartbeat—detected by the pressure transducer 1270. The oscillometric signal has an envelope 1404*e*. The envelope 1404*e* generally begins at or near zero prior to the cuff 1250 exerting enough pressure on the measurement site to detect plethysmographic waveforms. Once the cuff 1250 does exert adequate pressure on the measurement site, plethysmographic waveforms begin to appear in the oscillometric signal 1402*e*, with the amplitudes of the plethysmographic waveforms initially increasing in response to rising pressure in the cuff 1250. When the cuff 1250 reaches the mean arterial pressure, plethysmographic waveform magnitude reaches a maximum value, causing the envelope 1404e to likewise reach a maximum value. The amplitudes of the plethysmographic waveforms then decrease in response to rising pressure in the cuff 1250. Eventually, the pressure in the cuff 1250 causes the artery at the measurement site to be occluded, causing plethysmographic waveforms to disappear or have their amplitudes drop below a threshold value.

Point 1410e in FIG. 14E is the rising inflection point of the envelope 1404e of the oscillometric signal 1402e, while point 1420e is the falling inflection point of the envelope. The dashed vertical bars on either side of the rising inflection point 1410e define a diastolic blood pressure measurement zone 1415e on the rising side of the envelope 1404e prior to reaching its peak, while the dashed vertical bars on either side of the falling inflection point 1420e define a systolic blood pressure measurement zone 1425e on the falling side of the envelope after it has already peaked. The zone between the diastolic blood pressure measurement zone 1410e and the systolic blood pressure measurement zone 1420e—which encompasses the peak of the envelope 1404e of the oscillometric signal 1402e—is the mean arterial blood pressure measurement zone.

In some embodiments, the target inflation rate of the cuff 1250 can be set to a lower value when the air pressure in the cuff 1250 is in the diastolic blood pressure measurement zone 1415e and/or in the systolic blood pressure measurement zone 1425e, as compared to a higher target inflation rate when the air pressure in the cuff is below the diastolic blood pressure measurement zone 1415e, in the mean arterial blood pressure measurement zone, and/or above the systolic blood pressure measurement zone 1425e. The lower target inflation rate while in the diastolic blood pressure measurement zone 1415e and/or the systolic blood pressure measurement zone 1425e allows for more plethysmographic waveforms to be collected in these zones. In some embodiments, this increased measurement resolution in these zones can allow for improved diastolic and/or systolic blood pressure measurements. Meanwhile, by increasing the target inflation rate when the air pressure in the cuff 1250 is outside of these measurement zones, the overall speed of the blood pressure measurement can be improved without necessarily sacrificing measurement accuracy.

In some embodiments, the blood pressure monitor 1200 includes an envelope detector to detect the envelope 1404e of the oscillometric signal 1402e from the pressure transducer 1270. The blood pressure monitor 1200 can detect when the air pressure in the cuff 1250 is in the diastolic blood pressure measurement zone 1415e, the systolic blood pressure measurement zone 1425e, or the in-between mean arterial blood pressure measurement zone based on the derivatives of the envelope 1404e. For example, while the cuff 1250 is being inflated, the left edge of the diastolic blood pressure measurement zone 1415e can be identified by the first derivative of the envelope 1404e rising above a set threshold. The rising inflection point 1410e can be identified by the first derivative of the envelope 1404e reaching a local maximum value or by the second derivative of the envelope 1404e crossing zero. The right edge of the diastolic blood pressure measurement zone 1415e can be identified by the first derivative of the envelope 1404e falling below a set threshold after the rising inflection point 1410e has already been detected. The peak of the envelope 1404e can indicate that the air pressure in the cuff 1250 is in the mean arterial pressure measurement zone. This can be identified by the first derivative of the envelope 1404e crossing zero. The left edge of the systolic blood pressure measurement zone 1425e can be identified by the first derivative of the envelope 1404e falling below a threshold after the envelop maximum has already been detected. The falling inflection point 1420e can be identified by the first derivative of the envelope 1404e reaching a local minimum value or by the second derivative of the envelope 1404e crossing zero. The right edge of the systolic blood pressure measurement zone 1425e can be identified by the first derivative of the envelope 1404e rising above a set threshold after the falling inflection point 1420e has already been detected.

Block 1445c can perform one or more cycles of the PID control loop before proceeding to block 1450c where pump frequency relationship control can once again be performed. This can be done as described with respect to block 1415c.

At block 1455c, the blood pressure monitor 1200 can execute stop inflation logic to determine whether to cease inflation of the cuff 1250. The stop inflation logic can identify the falling inflection point 1420e and/or the systolic blood pressure measurement zone 1425e of the envelope 1404e of the oscillometric signal using the above-described techniques. At decision block 1460c, the blood pressure monitor 1200 can determine whether a stop inflation criterion is satisfied. In some embodiments, the stop inflation criterion is that the air pressure in the cuff 1250 has reached the falling inflection point 1420e of the envelope 1404e of the oscillometric signal 1402e, or surpassed it by a set threshold. In some embodiments, the stop inflation criterion is that the air pressure in the cuff 1250 has reached the right edge of, or exited, the systolic blood pressure measurement zone 1425e. If the stop inflation criterion is not satisfied, then the method 1400C can repeat blocks 1445c and 1450c so as to continue tracking the target inflation rate and the desired relative pump frequency relationship. The stop inflation logic can also be repeated at block 1455c.

Once the stop inflation criterion is satisfied at decision block 1460c, the blood pressure monitor can proceed to block 1465c to calculate and output one or more blood pressure measurements (e.g., diastolic pressure, mean arterial pressure, systolic pressure, etc.). At block 1470c, the blood pressure monitor 1200 deflates the cuff 1250 using the air release valve(s) 1260.

At decision block 1475c, the blood pressure monitor 1200 can calculate a confidence metric to determine whether the blood pressure measurement was successful. In some embodiments, the confidence metric includes the number of plethysmographic waveforms detected during the measurement phase, with lower numbers of plethysmographic waveforms being indicative of a lower confidence value. In some embodiments, the confidence metric includes the smoothness of the envelope 1404e of the oscillometric signal 1402e, with a smoother envelope being indicative of a higher confidence value. In some embodiments, the confidence metric includes a measure of the amount of patient motion detected during the blood pressure measurement; a greater amount of patient motion during the measurement can be indicative of a lower confidence value. Patient motion can be calculated based on a signal from an accelerometer included in the blood pressure monitor 1200. In some embodiments, a measure of patient motion can be calculated, using the accelerometer output, for the time period corresponding to each plethysmographic waveform in the oscillometric signal 1402e. Plethysmographic waveforms captured during time periods where the patient motion rises above a set threshold can be discarded. The confidence metric can include the number or percentage of discarded plethysmographic waveforms, with lower numbers or percentages being indicative of higher confidence. Other confidence metrics can also be used.

If the blood pressure measurement is determined to have been successful based on the confidence metric (e.g., based on the confidence metric being above a set threshold), then the method 1400C proceeds to block 1480c and ends. Otherwise, the method 1400C can be repeated by starting again at block 1405c.

The methods described with respect to FIGS. 14A-14C may involve the operation of one of multiple air pumps 1210 for longer periods of time than another of the air pumps. For example, the first stage of inflation in FIG. 14C may involve operation of two air pumps, whereas slower inflation stages may only require operation of a single air pump in some circumstances. This can result in an imbalance over time in the cumulative operation time of each of the air pumps. Over months or years of use, this may cause the air pump 1210 with longer cumulative run time to exhibit greater signs of wear than another air pump with lesser cumulative run time. This can in turn increase any mismatch in operation speeds of the air pumps, causing control loops in blocks 1415c, 1430c, 1445c, and 1450c to have to provide mismatched drive signals to the air pumps in order to obtain the desired operation, which may further exacerbate differences in wear. Thus, in some embodiments, the blood pressure monitor 1200 can include a runtime counter or clock (e.g., with non-volatile memory) for each of the air pumps 1210. The runtime counter or clock for each of the air pumps 1210 can track the cumulative runtime for each air pump over the lifetime of the blood pressure monitor 1200 or over some designated period of time. The blood pressure monitor can then select individual ones of the air pumps 1210 for performing required operation tasks, such as individually inflating the cuff 1250 for some inflation stage, in a manner so as to reduce any imbalance that may develop in the respective cumulative runtimes of the air pumps. In addition, with reference to FIG. 14D, the blood pressure monitor may alternate the air pump designated as "pump 1," since pump 1 may be operated at a more constant speed, thus experiencing less overall wear than "pump 2," whose input voltage may be constantly adjusted to maintain the desired frequency relationship between the two pumps.

Patient Monitor

Figure 8A:
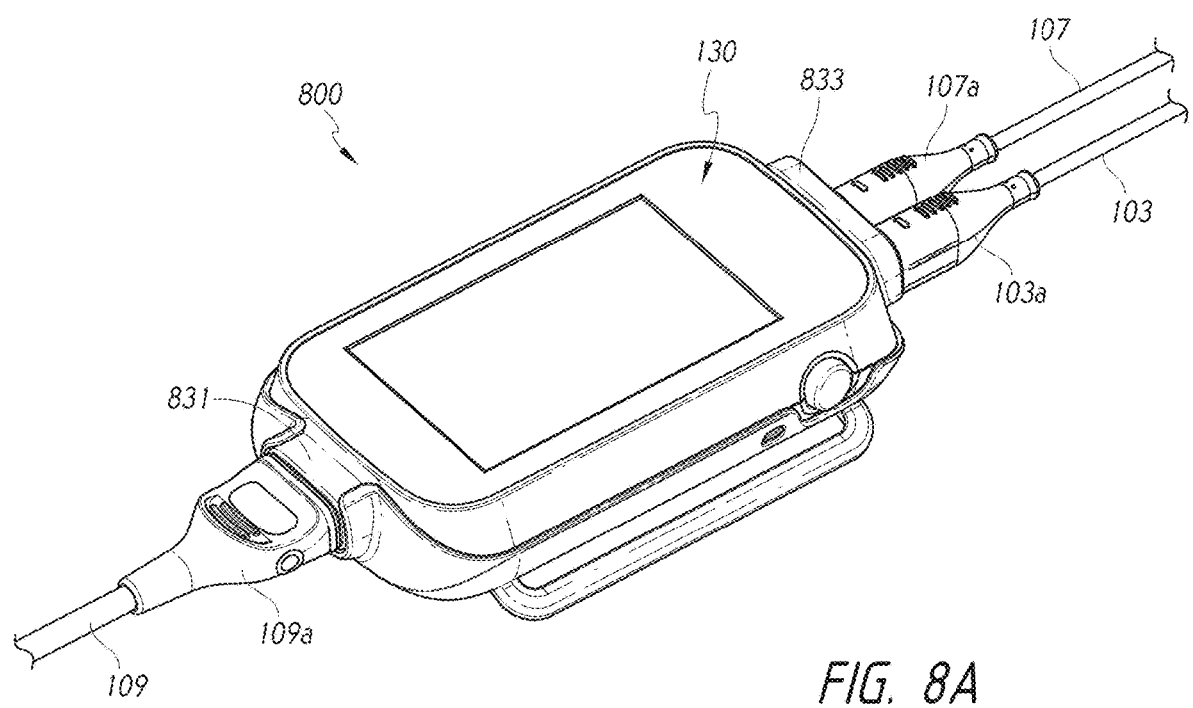
FIG. 8A illustrates a perspective view of a patient monitor assembly with connected cables in accordance with aspects of this disclosure.
Figure 8B:
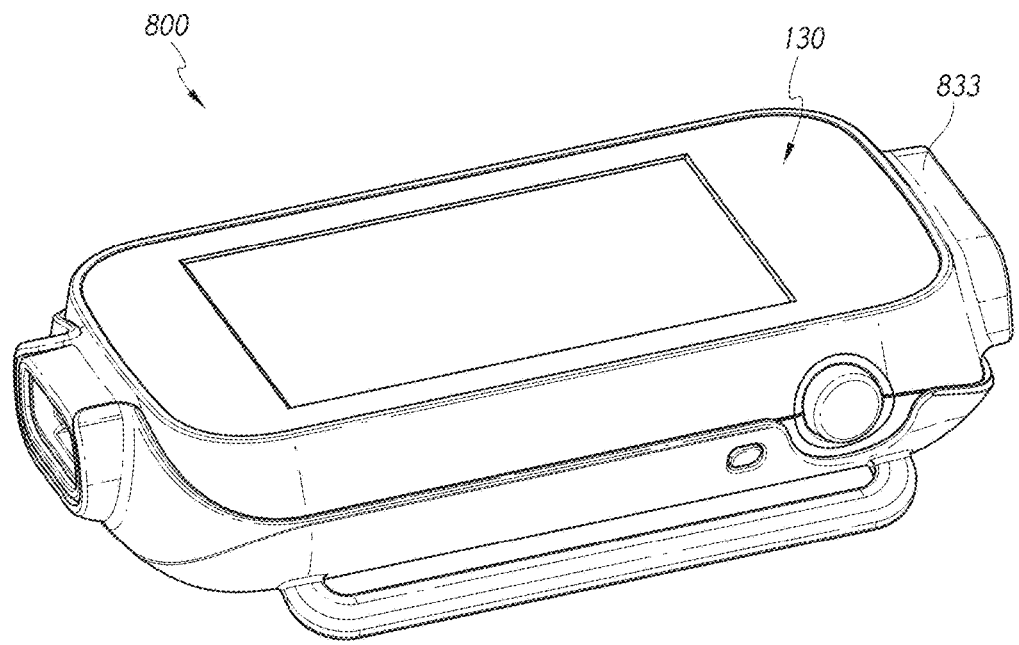
FIG. 8B illustrates another perspective view of the patient monitor assembly of FIG. 8A without cables attached.
Figure 8C:
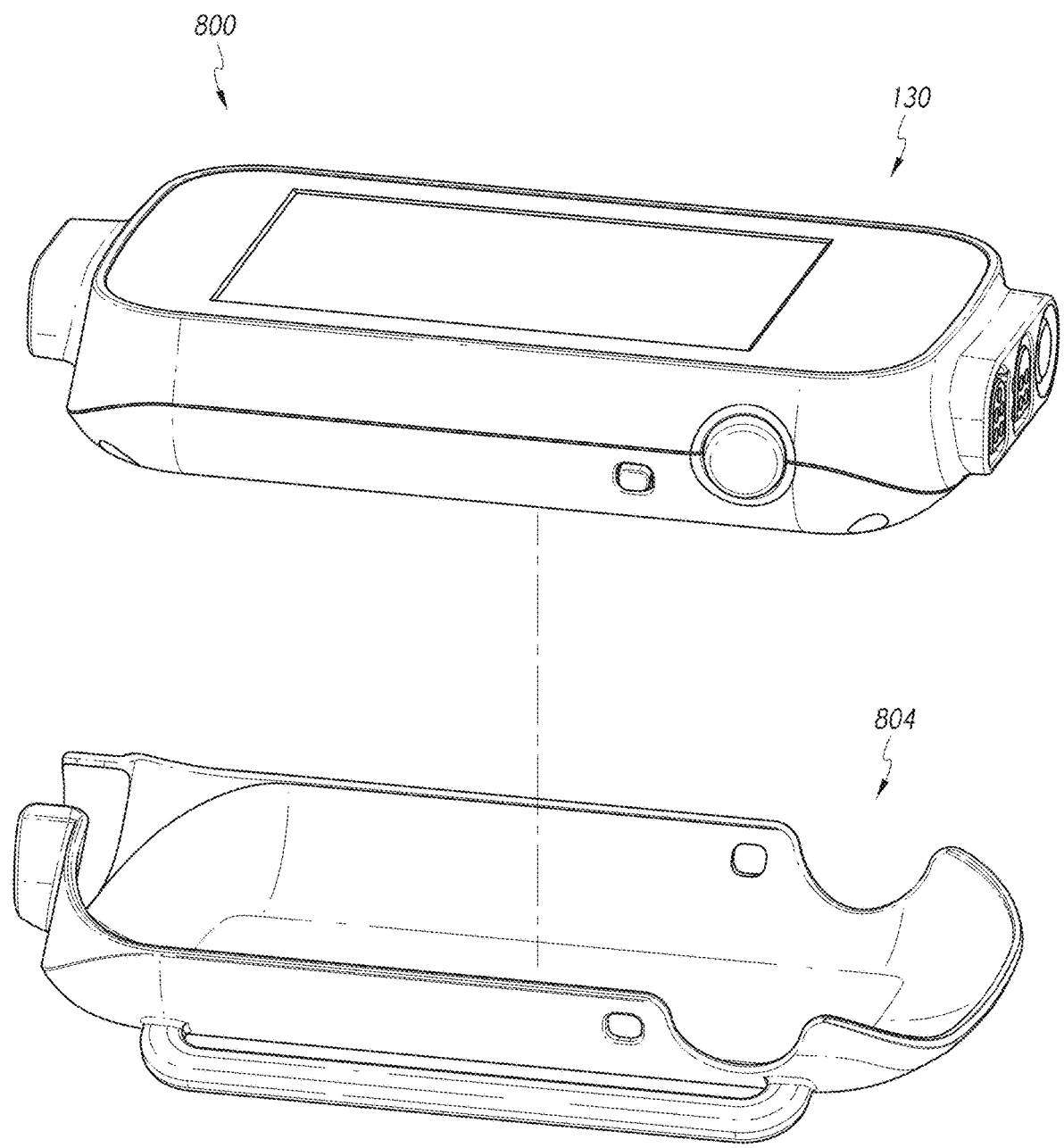
FIG. 8C illustrates an exploded view of the patient monitor assembly of FIG. 8B.
Figure 8D:
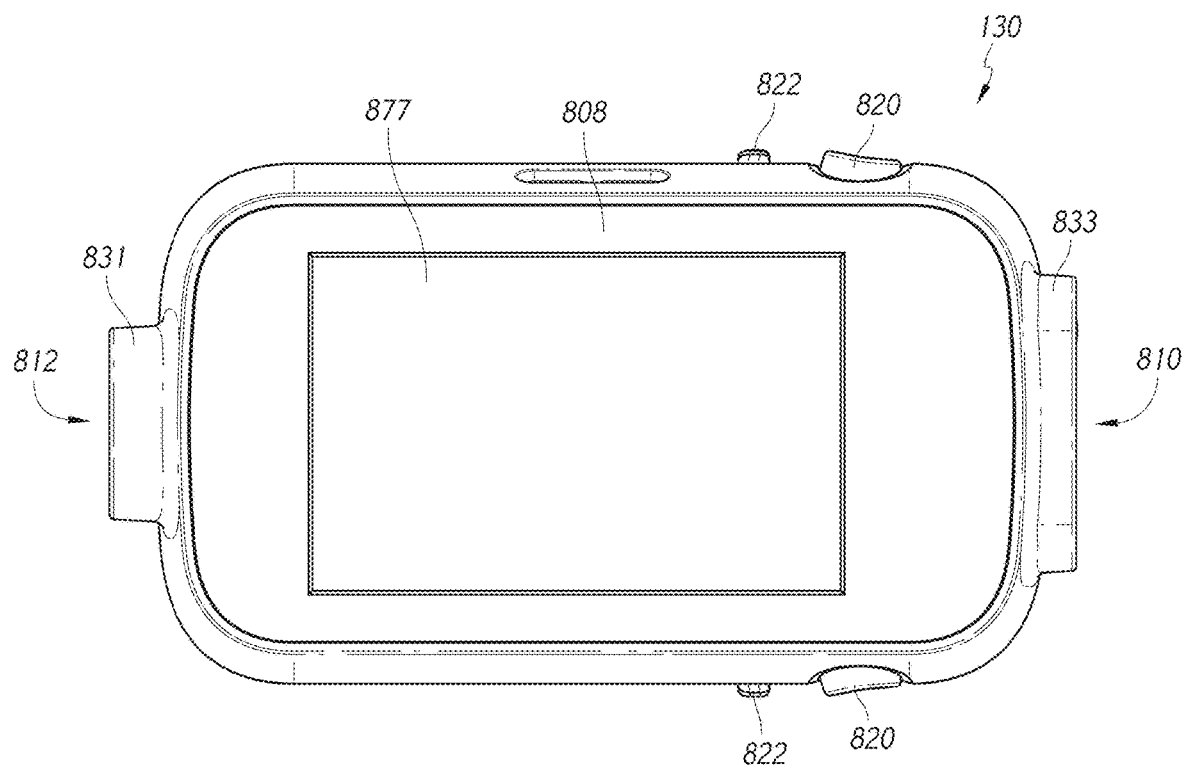
FIG. 8D illustrates a top view of a patient monitor of the assembly of FIG. 8B.
Figure 8E:
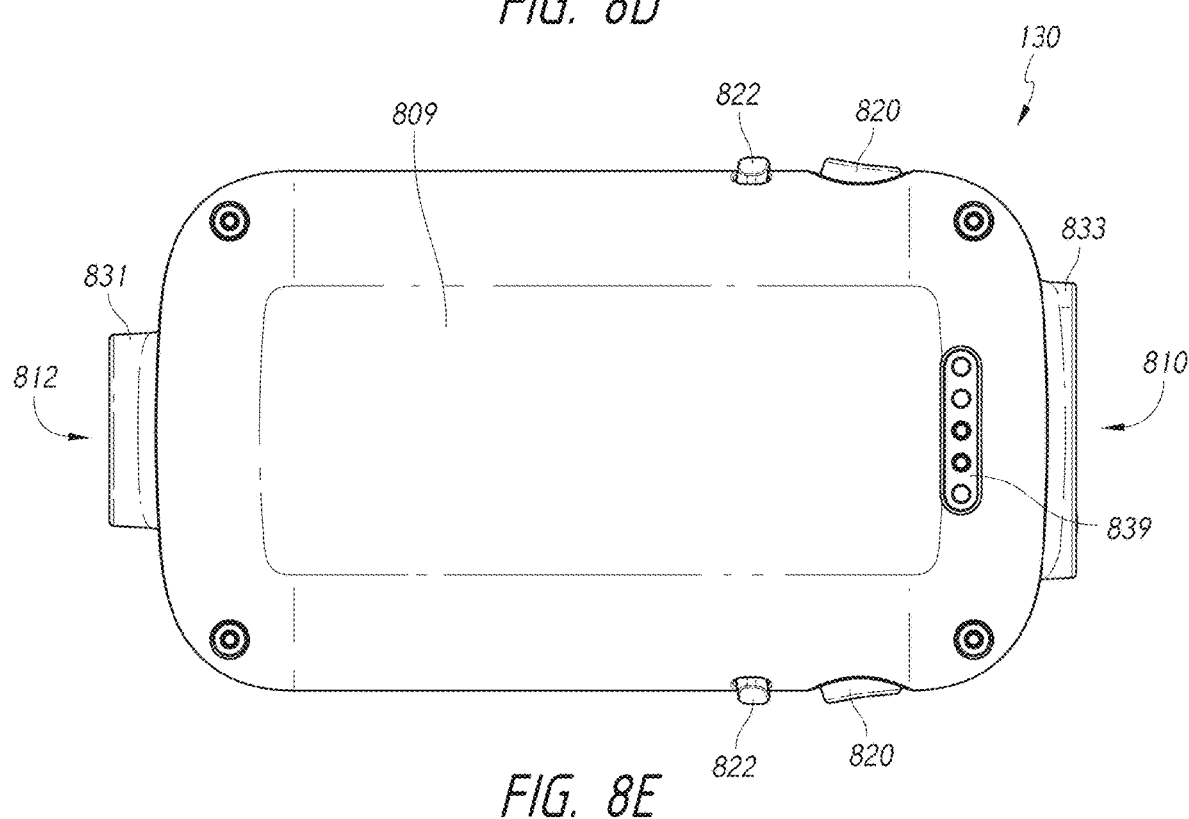
FIG. 8E illustrates a bottom view of the patient monitor of FIG. 8D.
Figure 8F:
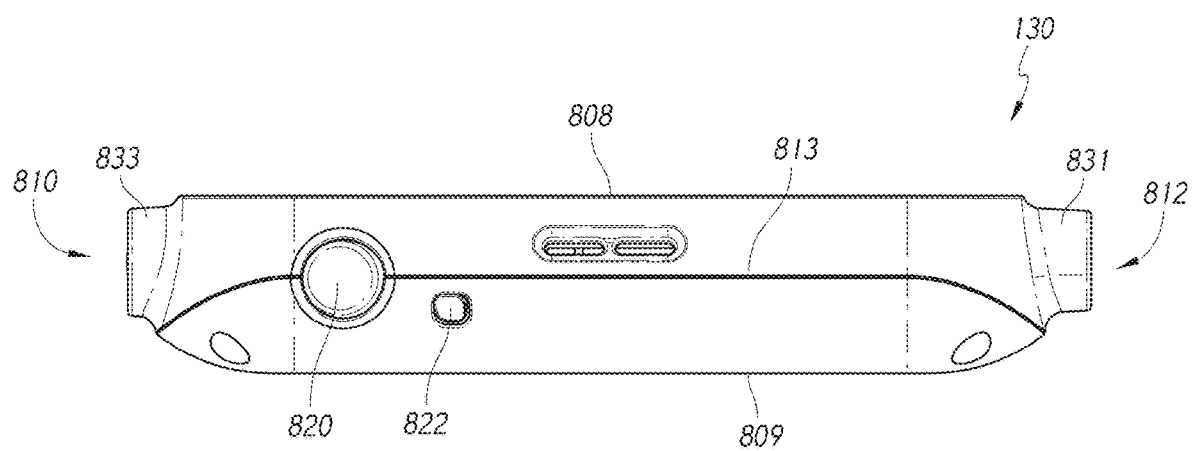
FIG. 8F illustrates a side view of the patient monitor of FIG. 8D.
Figure 8G:
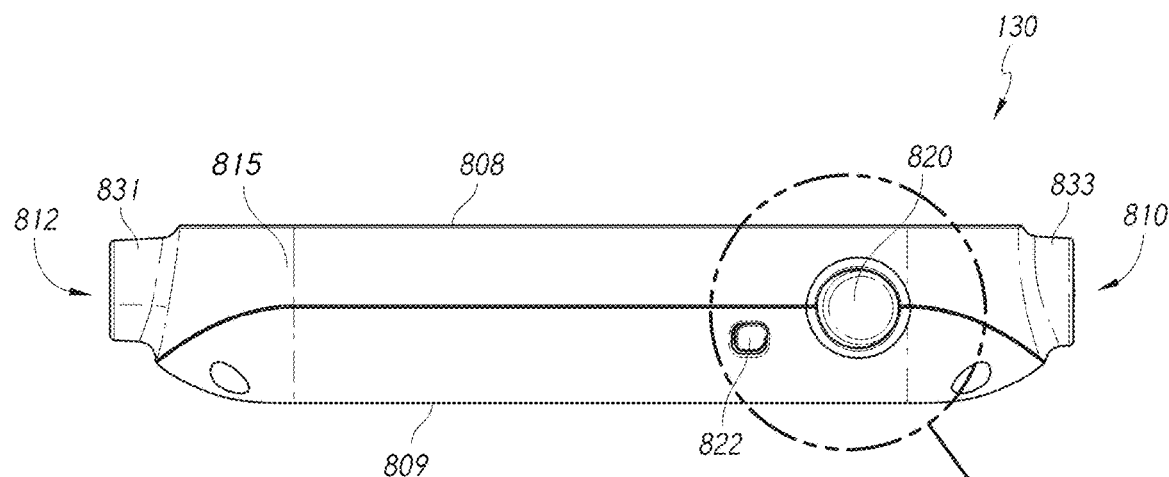
FIG. 8G illustrates another side view of the patient monitor of FIG. 8D.
Figure 8H:
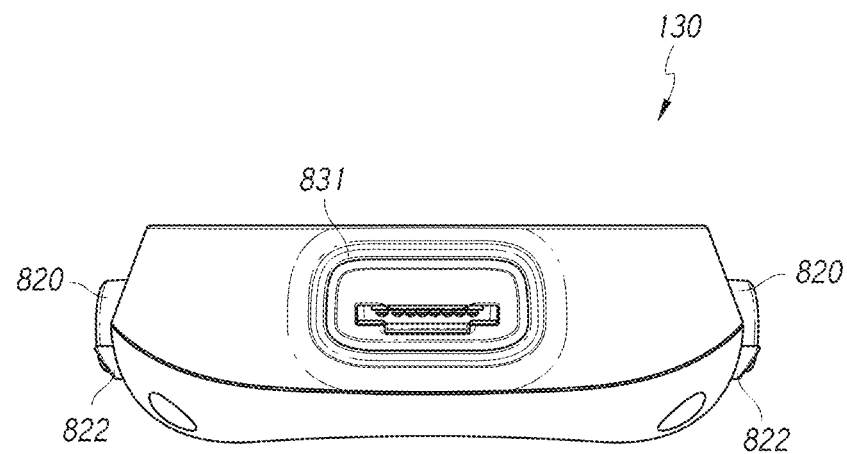
FIG. 8H illustrates a front view of the patient monitor of FIG. 8D.
Figure 8I:
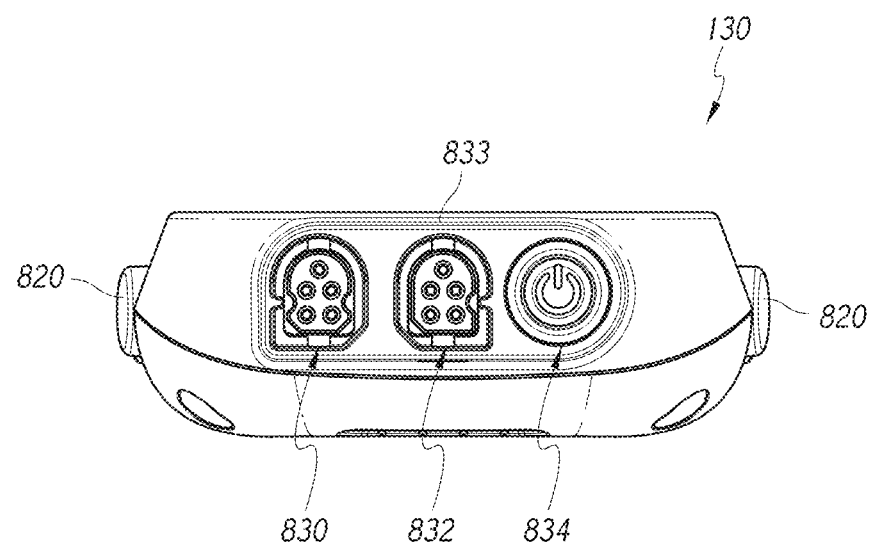
FIG. 8I illustrates a back view of the patient monitor of FIG. 8D.
Figure 8J:
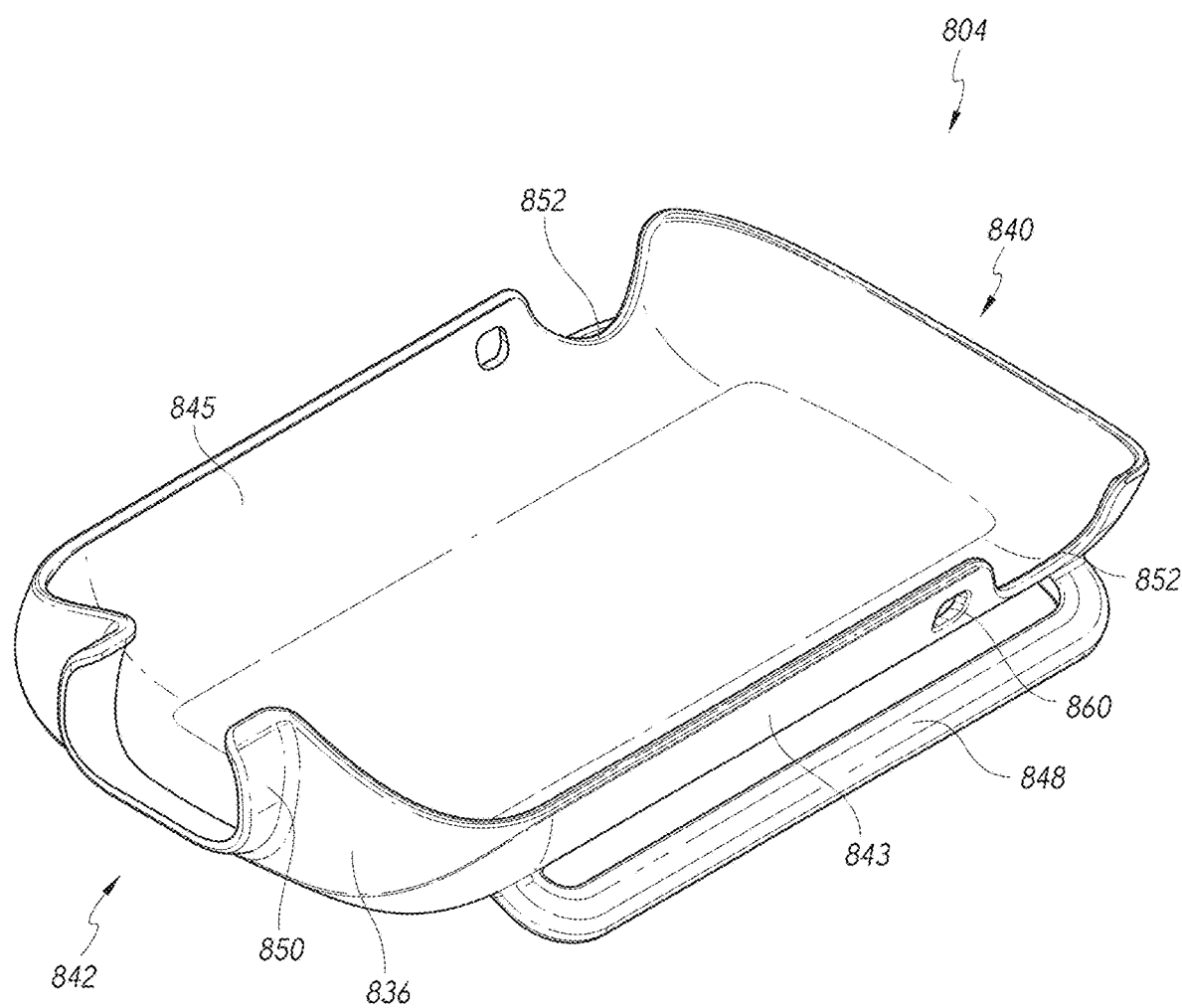
FIG. 8J illustrates a perspective view of a cradle of the assembly of FIG. 8B.
Figure 8K:
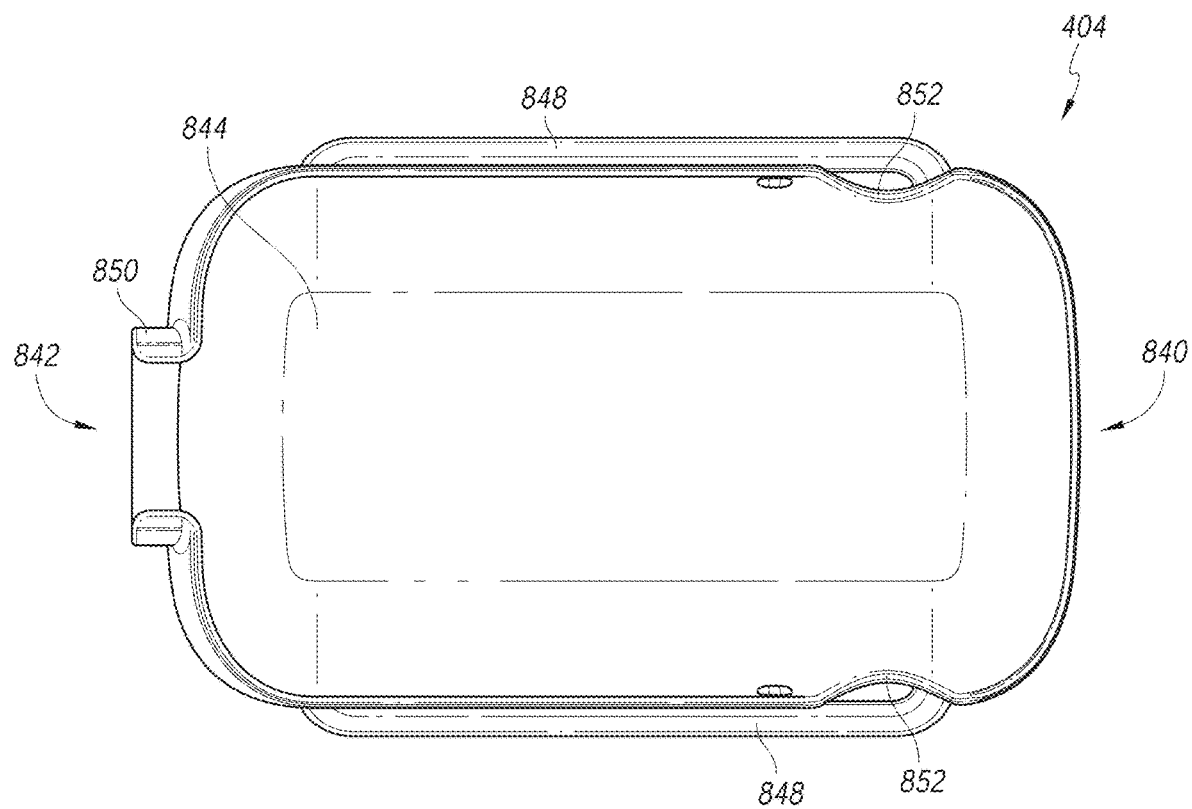
FIG. 8K illustrates a top view of the cradle of FIG. 8J.
Figure 8L:
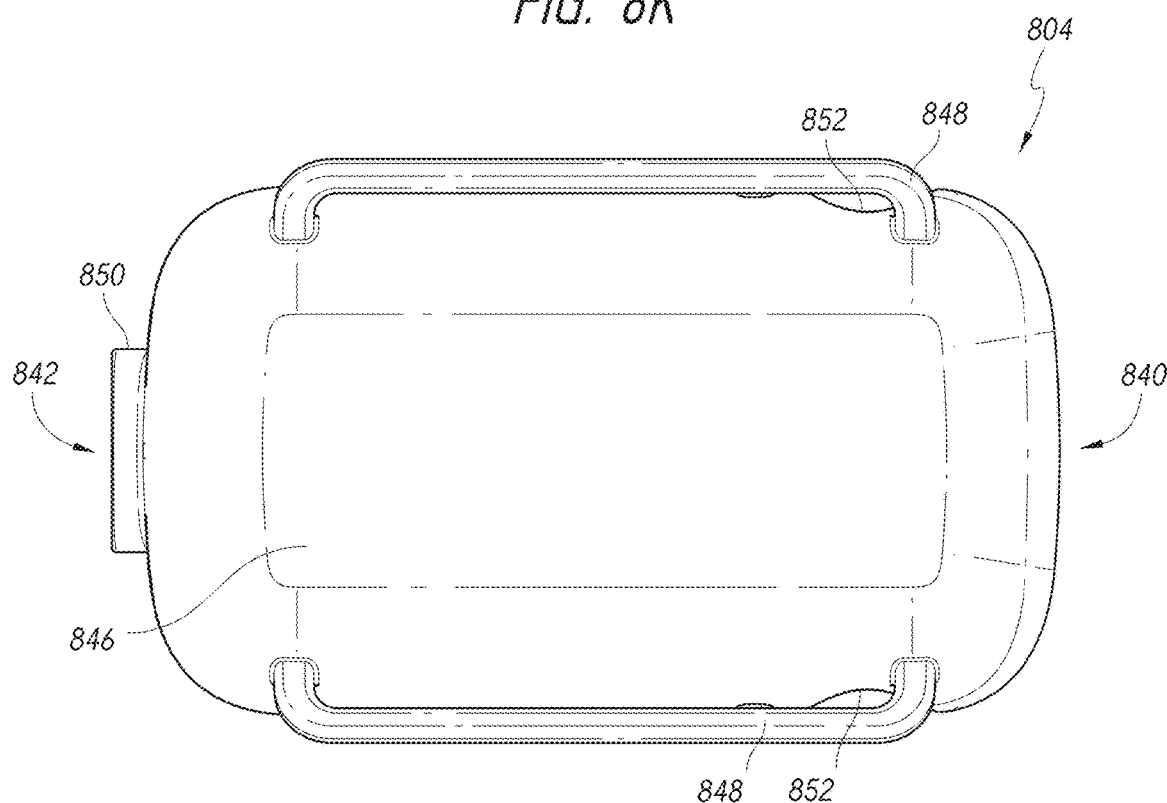
FIG. 8L illustrates a bottom view of the cradle of FIG. 8J.
Figure 8M:
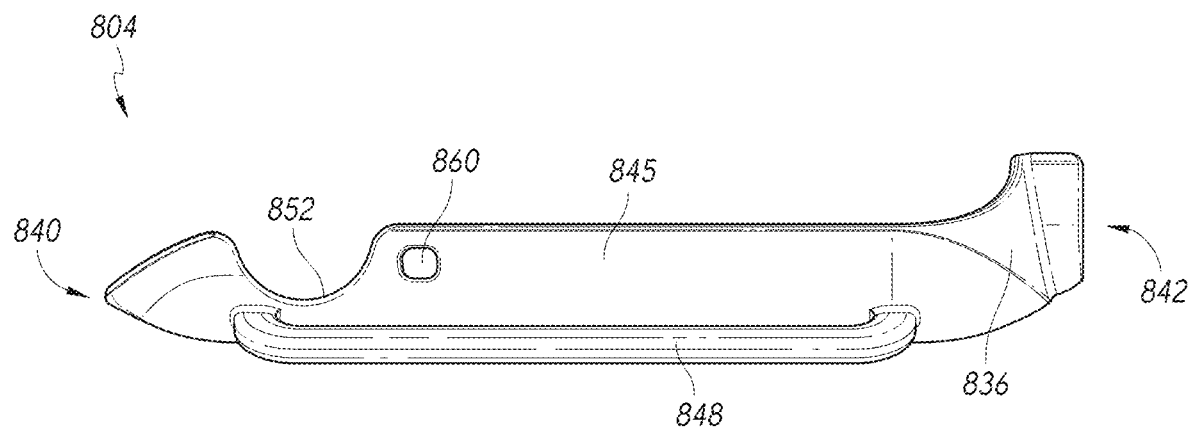
FIG. 8M illustrates a side view of the cradle of FIG. 8J.
Figure 8N:
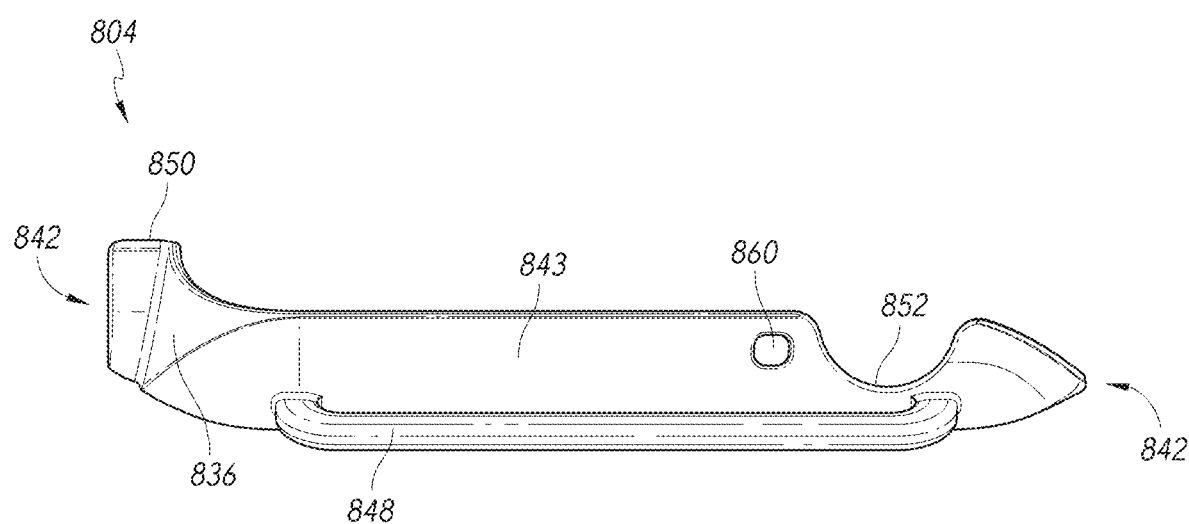
Figure 8O:
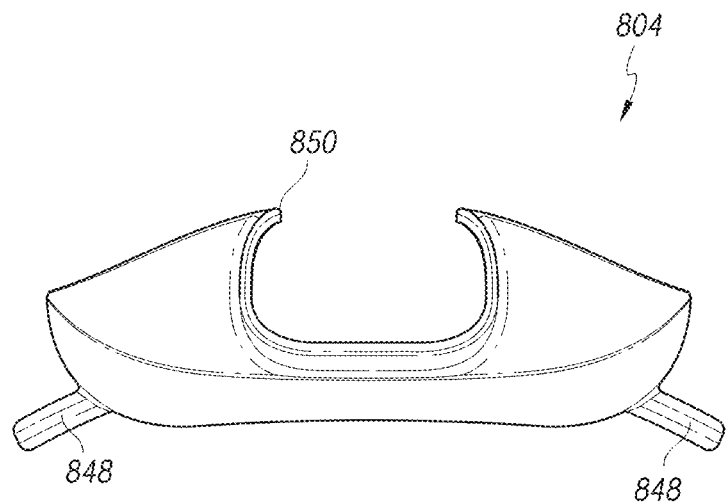
Figure 8P:
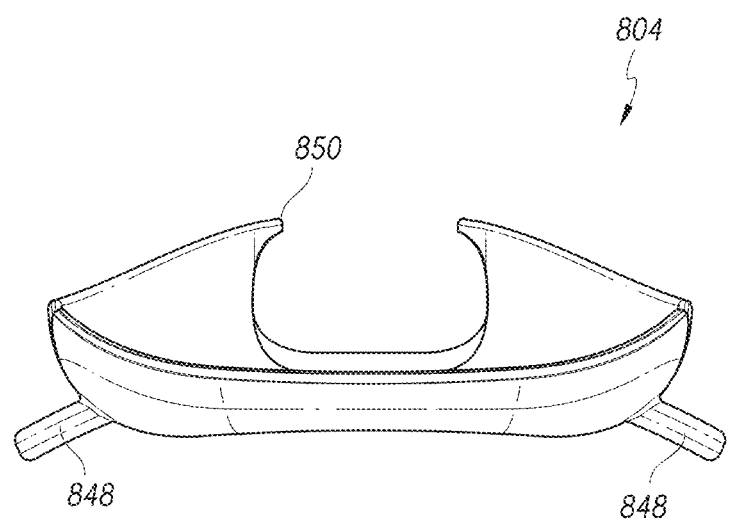
Figure 8Q:
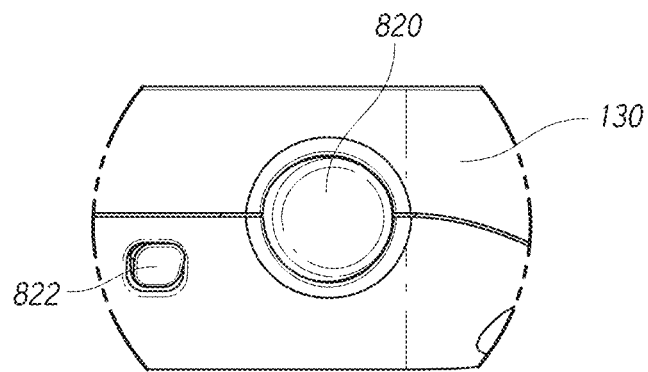
Figure 8R:
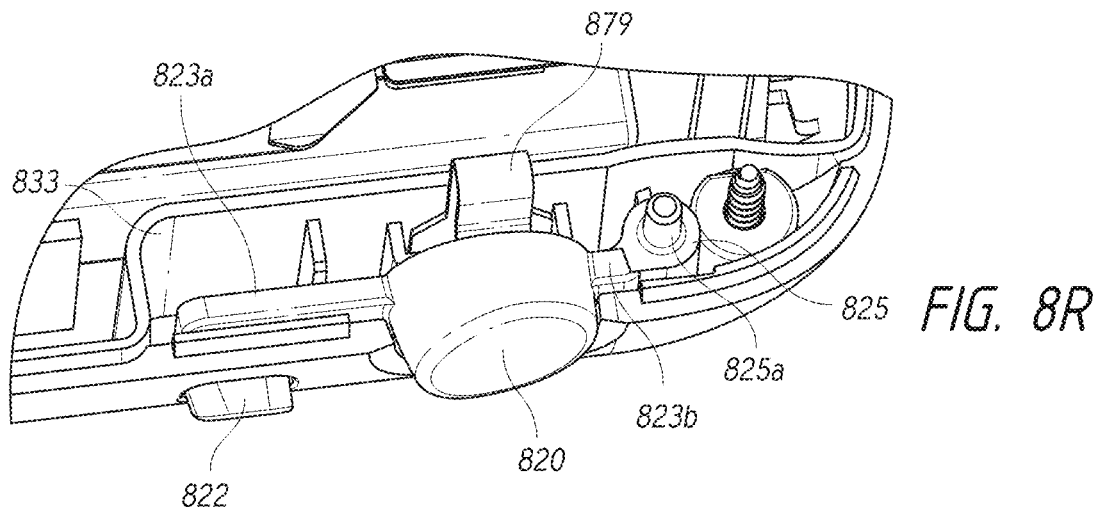
Figure 8S:
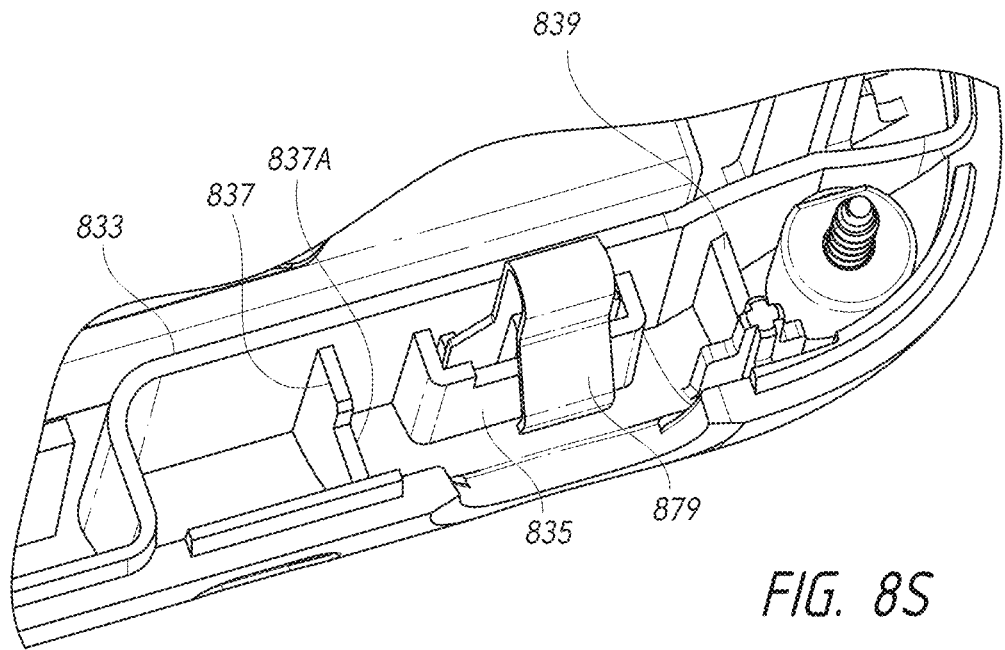
Figure 8T:
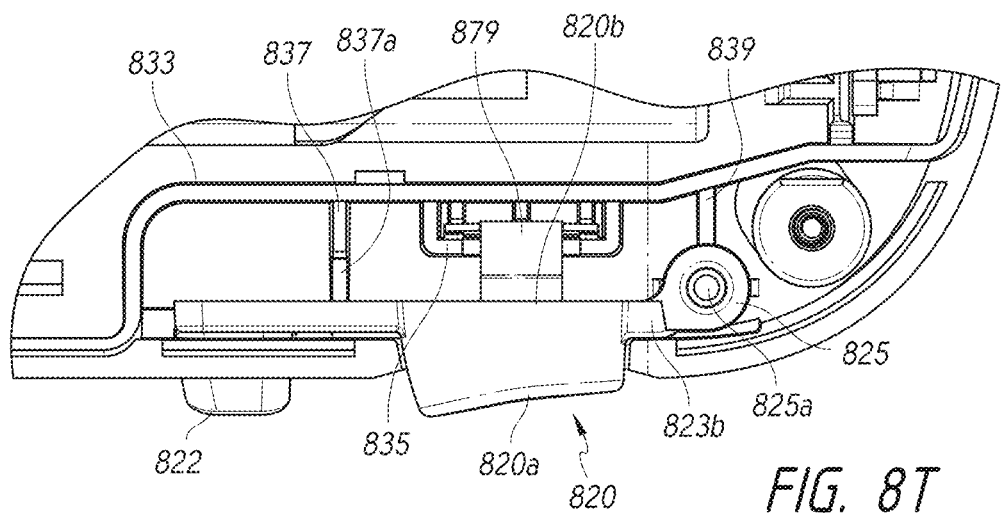
Figure 8U:
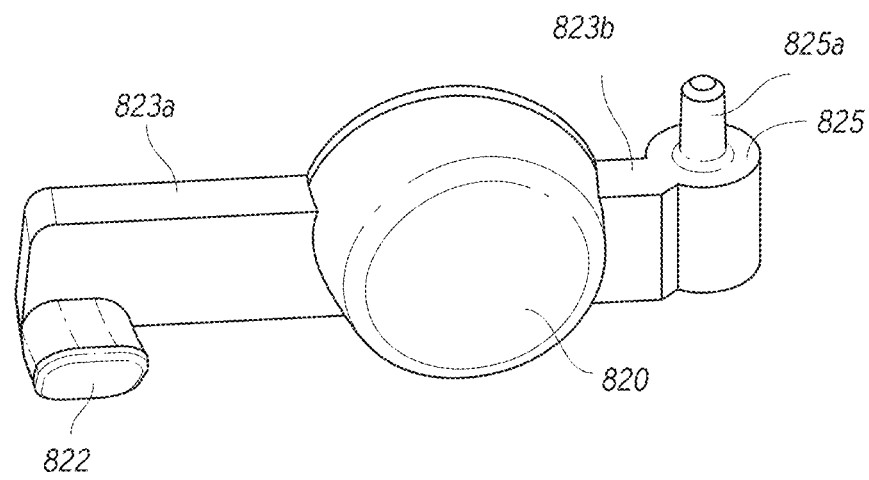
Figure 8V:
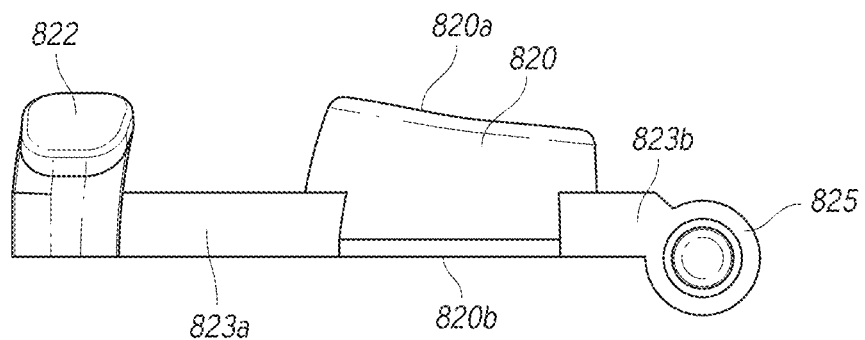

FIGS. 8A-8V illustrate various views and aspects of an assembly 800 which can include patient monitor 130 and a cradle 804. Patient monitor 130 can be a fully functional, stand-alone monitor capable of various physiological measurements. Patient monitor 130 can be small and light enough to comfortably be secured to and carried around on an arm of a patient, for example, via a fastening strap 131 (see FIG. 1A-1B).

As discussed above, patient monitor 130 can connect one or more sensors or monitors in a patient environment. For example, as illustrated in FIGS. 1A-1B, patient monitor 130 can connect to blood pressure monitor 120, acoustic sensor 150, ECG device 110, and/or optical sensor 140. Patient monitor 130 can connect to blood pressure monitor 120 via cable 107 and connector 107a. While the discussion below with reference to FIGS. 8A-8V and patient monitor 130 may reference ECG device 110 and/or blood pressure monitor 120, the discussion below is equally applicable to ECG device 310 and blood pressure monitors 600, 700. For example, patient monitor 130 can connect to and/or interact with to ECG device 310 and blood pressure monitors 600, 700 in an identical or similar way as to ECG device 110 and blood pressure monitor 120.

As shown in FIG. 8A, connector 107a of cable 107 can connect to connector port 833 on a first end or side of patient monitor 130. Patient monitor 130 can additionally or alternatively connect to another sensor, for example, acoustic sensor 150, via cable 103 and connector 103a. Connector 103a can connect to connector port 833. Connector port 833 of patient monitor 130 can have more than one connector which can allow it to connect to both of connectors 107a and 103a. For example, with reference to FIG. 8I, connector port 833 can have a first female connector port 830 and a second female connector port 832 spaced from one another and positioned within a perimeter of the connector port 833. Patient monitor 130 can additionally or alternatively have a connector and/or connector port on another end or side of the patient monitor 130. For example, as shown in at least FIGS. 8A and 8H, patient monitor 130 can have a connector port 831 that can connect to a connector 109a and cable 109. Cable 109 can connect to a physiological sensor or monitor such as optical sensor 140. As shown, connector port 833 can be located on (and/or extending from) an end of patient monitor 130 that is opposite to an end of the patient monitor 130 that connector port 831 is located on (and/or extends from). Such configuration can prevent cable clutter and entanglements, especially where the patient monitor 130 is secured to a portion of a patient's body in between multiple sensors which are also secured to the patient, for example as shown in FIGS. 1A-1B. Connector 107a, connector 103a, and/or connector 109a can be waterproof and can be easily sterilized to avoid contamination.

As discussed above, patient monitor 130 can store, process, transmit, transmit without processing, display, and/or display without processing the physiological information received from the one or more physiological sensors, such as from acoustic sensor 150, ECG device 110, blood pressure monitor 120, and/or optical sensor 140. Patient monitor 130 is a processing device, and as such, can include the necessary components to perform the functions of a processing device. For example, patient monitor 130 can include one or more processors (such as one, two, three, or four processors which can be dedicated to processing certain physiological parameters and/or processing physiological information from certain sensors/devices), a memory device, a storage device, input/output devices, and communications connections, all connected via one or more communication bus.

As discussed above, patient monitor 130 can transmit physiological information received from one or more of the acoustic sensor 150, ECG device 110, blood pressure monitor 120, and/or optical sensor 140 to an external patient monitor that is located away from the patient 111, such as external patient monitor 160. The external patient monitor 160 can be, for example, a nurse's station, a clinician device, pager, cell phone, computer, multi-patient monitoring system, hospital or facility information system. An artisan will appreciate that numerous other computing systems, servers, processing nodes, display devices, printers, and the link can interact with and/or receive physiological information from the patient monitor 130.

Patient monitor 130 can include a sensor interface (such as sensor interface 132) that is configured to receive physiological information from one or more of the acoustic sensor 150, ECG device 110, blood pressure monitor 120, and/or optical sensor 140. The sensor interface of patient monitor 130 can pass the received physiological data to a processing and memory block (such as processing and memory block 134). The processing and memory block can include one or more processors configured to process the physiological data received from one or more of the acoustic sensor 150, ECG device 110, blood pressure monitor 120, and/or optical sensor 140 into representations of physiological parameters. The processing and memory block can include a plurality of processors that are independent dedicated to processing data from different physiological sensors (such as the acoustic sensor 150, ECG device 110, blood pressure monitor 120, and/or optical sensor 140). For example, the processing and memory block can include a first processor dedicated to processing data from the acoustic sensor 150, a second processor dedicated to processing data from the blood pressure monitor 120, and/or a third processor dedicated to processing data from the optical sensor 140. The processing and memory block can include an instrument manager which may further process the received physiological parameters for display. The instrument manager may include a memory buffer to maintain this data for processing throughout a period of time. The memory buffer may include RAM, Flash, or other solid state memory, magnetic or optical disk-based memories, combinations or the same or the like. Patient monitor 130 can include a wireless transceiver (such as wireless transceiver 136). The wireless transceiver can wirelessly transmit the physiological information received from the external physiological sensors (such as the acoustic sensor 150, ECG device 110, blood pressure monitor 120, and/or optical sensor 140) and/or parameters from the one or more processors and/or the instrument manager of the processing and memory block. The wireless transceiver can transmit received physiological data to an external device via a wireless protocol. The wireless protocol can be any of a variety of wireless technologies such as Wi-Fi (802.11x), Bluetooth®, ZigBee®, cellular telephony, infrared, RFID, satellite transmission, proprietary protocols, combinations of the same, and the like.

Patient monitor 130 can display one or more physiological parameters on a screen or display thereof. Patient monitor 130 can include a display (such as display 877 as shown in FIG. 8D), control buttons (such as an on-off button 834 shown in FIG. 8I), one or more microphones and/or one or more speakers for enabling audio communication and/or messages or alerts. Display 877 of patient monitor 130 can be a touch-screen. Patient monitor 130 can include a battery configured to provide power to the electronics within the patient monitor 130. Patient monitor 130 can include a battery that is rechargeable. For example, as discussed elsewhere herein, patient monitor 130 can be configured to be charged from an external power source, such as charging station 1000 and/or charging cradle 1100.

As shown in FIGS. 8A-8C, the assembly 800 can include the patient monitor 130 and a cradle 804. As discussed in more detail below, the patient monitor 130 and the cradle can be configured to removably secure to one another. As shown in FIGS. 1A-1B, patient monitor 130 can secure to a patient 111, for example, a forearm of patient 111. For example, cradle 804 of patient monitor 130 include one or more legs 848 (also referred to herein as "strap hoops") extending from a surface of the cradle 804 which define an opening sized to allow a fastening strap (such as strap 131) to fit within and/or pass through. After passing through the one or more legs 848 of cradle 604, strap 131 can wrap around the patients arm (see FIGS. 1A-1B). In addition or as an alternative to the one or more legs 848, the cradle 604 can include a hook-and-look attachment on a bottom surface thereof that allows the cradle 604 to secure to strap 131 and thus to the patient 111 and/or can include an adhesive (for example, a silicone adhesive) that allows the cradle 804 to secure to skin of the patient 111. Advantageously, the patient monitor 130 can be removed from the cradle 604 before, during, and/or after the cradle 604 is attached to the patient 111 and/or strap 131. This can be especially helpful where it is desirable to temporarily remove the patient monitor 130 to charge and/or repair the patient monitor 130, which can house the electronics of the patient monitor 130. This can also allow a caregiver to clean the cradle 804 and/or regions of the patient 111 proximate the cradle 804 without risking damage to the patient monitor 130 (or various components thereof).

FIGS. 8D-8I illustrates various views of patient monitor 130. Patient monitor 130 can include a top surface 808, a bottom surface 809 opposite the top surface 808, a first end 810, a second end 812 opposite the first end 810, a first side 813, and a second side 815 opposite the first side 813. As discussed above, patient monitor 130 can include one or more connector ports configured to connect to one or more cables, and in turn, to one or more physiological sensors and/or monitors. For example, patient monitor 130 can include a first connector port 833 on first end 810 and/or a second connector port 831 on second end 812.

Connector port 833 can extend or protrude from a surface of the first end 810 (see, for example, FIGS. 8D-8E). Connector port 833 can have a width that is equal to or smaller than a width of the patient monitor 130 between the first and second sides 813, 815 (see FIGS. 8D-8E and 8H-8I). Connector port 833 can have a height that is equal to or smaller than a height of the patient monitor 130 between the top and bottom surfaces 808, 809 of patient monitor 130 (see FIGS. 8H-8I). Connector port 833 can include one or more connector ports configured to connect to one or more cables. For example, as shown in FIG. 8I, connector port 833 can include a first female connector port 830 and a second female connector port 832 spaced from each other and within a perimeter of the connector port 833. The size and/or shape of the female connector ports 830, 832 can correspond to a size and/or shape of a cable connector to which it connects, such as cable connectors 107a, 103a shown in FIG. 8A. Patient monitor 130 can include a control button to control various functionality. For example, patient monitor 130 can include an on-off button 834. On-off button 834 can be located within the perimeter of the connector port 833. As shown in FIG. 8I, on-off button 834 can be positioned proximate to female connector ports 430, 832. Connector port 833 can advantageously connect and obtain data from multiple physiological sensors simultaneously. For example, connector port 833 can connect and obtain data from the blood pressure monitor 120 from connector port 832, and can also connect and obtain data from an acoustic sensor 150 from connector port 830. As also discussed herein, the data obtained from blood pressure monitor 120 can include physiological data from the ECG device 110 and physiological data from blood pressure monitor 120.

Connector port 831 can extend or protrude from a surface of the second end 812 (see, for example, FIGS. 8F-8G). Connector port 831 can have a width that is equal to or smaller than a width of the patient monitor 130 between the first and second sides 813, 815 (see FIG. 8D-8G). Connector port 831 can have a height that is equal to or smaller than a height of the patient monitor 130 between the top and bottom surfaces 808, 809 of patient monitor 130 (see FIG. 8H). Connector port 831 can include one or more connectors configured to connect to one or more cables. For example, as shown in FIG. 8H, connector port 831 can include a connector within a perimeter of the connector port 833. The size and/or shape of the connector(s) with the connector port 831 can correspond to a size and/or shape of a cable connector to which it connects, such as cable connector 109*a* shown in FIG. 8A. Connector ports 833, 831 can be located on opposite ends of patient monitor 130 (for example, ends 810, 812) and can be aligned with each other or non-aligned with each other. For example, as shown in FIGS. 8A-8B, connector ports 833, 831 can be aligned about an axis running through a center of the ports 833, 831 and along a length of the patient monitor 130 between the first and second ends 810, 812. As also shown in FIGS. 8A-8B, connector port 833 can have a width that is greater than a width of connector port 831 (the width being measured about an axis up-down in the view of these figures). Connector port 831 can protrude from a surface of the second end 812 a first distance and connector port 833 can protrude from a surface of the first end 810 a second distance. The first and second distances can be equal or unequal. For example, the connector port 831 can have a length that is greater than a length of connector port 833. As discussed further below, the connector port 831 can be sized and/or shaped to secure within collar 850 of cradle 804 so as to secure the patient monitor 130 to cradle 804.

Patient monitor 130 can include one or more electrical contacts 839 which allow charging of a battery of the patient monitor 130. For example, as discussed further below, the electrical contacts 839 can mate or otherwise contact electrical contacts 1024 in charging station 1000 and/or electrical contact 1146 of charging cradle 1100.

As discussed previously, patient monitor 130 can be removably secured to cradle 804. As shown in at least FIGS. 8D-8G, patient monitor 130 can include one or more locking tabs 822 and/or one or more buttons 820. The one or more locking tabs 822 can secure to and/or within a portion of cradle 804, such as openings 860 of cradle 804. The one or more locking tabs 822 can be positioned along one or more of side 813, side 815, end 810, end 812, and/or another location of patient monitor 130. The one or more locking tabs 822 can extend and/or retract within one or more openings in the patient monitor 130 that surround the locking tabs 822 (for example, one or more openings in a housing of the patient monitor 130). The one or more locking tabs 822 can be coupled to one or more buttons 820, such that movement of the buttons 820 can cause the locking tabs 822 to move (for example, extend or retract). As an example, movement of a button 820 in a direction towards an interior of patient monitor 130 can cause a coupled locking tab 822 to retract in a direction towards the interior of the patient monitor 130. Alternatively, movement of a button 820 in a direction towards an interior of patient monitor 130 can cause a coupled locking tab 822 to extend in a direction away from the interior of the patient monitor 130. The one or more locking tabs 822 and the one or more buttons 820 can be positioned proximate and/or adjacent to one another. The one or more locking tabs 822 and/or the one or more buttons 820 can be positioned along one or both sides 813, 815 of patient monitor 130 and can be positioned closer to either end 810 or end 812. For example, the one or more locking tabs 822 and/or the one or more buttons 820 can be positioned closer to the first end 810 than to the second end 812 and/or can be positioned closer to the connector port 833 than to the connector port 831.

In some cases, patient monitor 130 and cradle 804 can communicate with one another via near field communication (NFC) protocols, such as radio frequency protocols. For example, patient monitor 130 can include an NFC reader and cradle 804 can include an NFC tag (such as an RFID tag). For example, patient monitor 130 can include an RFID reader which can be positioned within an interior of patient monitor 130, such as on a printed circuit board of the patient monitor 130. In such scenario, cradle 804 can include an RFID tag, in the form of a sticker or label, for example, that can transmit a signal in response to recognition of a radio frequency signal from the RFID reader in the patient monitor 130. Such RFID tag can be on a surface of the cradle 804, for example, on a bottom or top surface 808, 809 of cradle 804. Alternatively, cradle 804 can include an erasable programmable read-only memory (EPROM) which can communicate (for example, transfer information or data) to the patient monitor 130 via touching with electrical contacts 839 (FIG. 8E) on a surface of patient monitor 130. Whether the patient monitor 130 and cradle 804 include RFID or EPROM features and functionality, these components can communicate with one another to transfer information and/or data, such as the amount of lifespan of the patient monitor 130 and/or the cradle 804 remaining (which can be predetermined), whether the patient monitor 130 and cradle 804 are compatible (e.g., whether a counterfeit or unauthorized product is being used), among other things.

FIG. 8Q illustrates an enlarged view of a portion of the patient monitor 130 as shown in FIG. 8G. FIGS. 8R-8S illustrate a locking tab 822 and a button 820 along with other corresponding structure associated with and/or connected to patient monitor 130. As shown, locking tab 822 and button 820 can be coupled with a stem 823*a* which can extend between the locking tab 822 and the button 820. Locking tab 822, stem 823*a*, and/or button 820 can rotate about a pivot point. For example, button 820 can connect to stem 823*a* on one side of button 820 and also to a stem 823*b* on an opposite side of button 820. Stem 823*b* can connect button 820 to a pivot connector 825. Pivot connector 825 can have a cylindrical cross-section (see FIGS. 8U-8V) or other cross-section. Pivot connector 825 can have a hollow or partially hollow interior (see FIG. 8V) that is sized and/or shaped to receive and/or secure to a pivot pin 893 extending from a portion of the patient monitor 130. The pivot pin 893 can extend from a bottom portion of the patient monitor 130 underneath the pivot connector 825. For example, with reference to FIGS. 8R-8T, the pivot pin 893 can be positioned below and/or within the pivot connector 825.

When positioned around and/or secured to the pivot pin 893, the pivot connector 825 can be prevented from moving in a direction perpendicular to an axis extending through a length or height of the pivot pin 893 and/or the pivot connector 825 while also allowing the pivot connector 825 to rotate about such axis. Further, when positioned around and/or secured to the pivot pin 893, the pivot connector 825 can allow the stem 823*b*, button 820, stem 823*a*, and locking tab 822 to rotate about an axis extending through a height of the pivot connector 825.

Pivot connector 825 can include a tip 825*a* extending from a portion of the pivot connector 825 (see, for example, FIG. 8U). For example, tip 825*a* can extend from a top surface of the pivot connector 825. Tip 825*a* can be spaced inward from a perimeter of the top surface of the pivot connector 825. Tip 825*a* can have a cylindrical cross-section or other cross-section. Tip 825*a* can be sized and/or shaped to fit within an opening or hollow chamber of the patient monitor 130 that is positioned above the tip 825*a*. When tip 825*a* is secured and/or positioned within such opening or hollow chamber of patient monitor 130, interior surfaces of the opening or hollow chamber can prevent movement of the tip 825*a* in a direction perpendicular to an axis running through a height or length of tip 825*a* while also allowing the tip 825*a* to rotate within the opening or hollow chamber. Thus, engagement between the pivot connector 825 and pivot pin 893 of the patient monitor 130 underneath the pivot connector 825 alone or in combination with the engagement between the tip 825a and an opening or hollow chamber of the patient monitor 130 above the tip 825a can support the stem 823b, button 820, stem 823a, and locking tab 822 and allow such elements to rotate about an axis extending through the pivot connector 825 and/or tip 825a. Such rotation can allow the locking tab 822 and/or button 820 to extend and/or retract farther or closer from an interior of the hosing 802.

The locking tab 822, stem 823a, button 820, stem 823b, pivot connector 825, and/or tip 825a can be positioned within a portion of patient monitor 130 proximate to a perimeter of patient monitor 130. For example, with reference to FIGS. 8R-8T, patient monitor 130 can include an inner wall 833 that defines a chamber sized and shaped to allow for the movement of the locking tab 822, stem 823a, button 820, stem 823b, pivot connector 825, and/or tip 825a. Inner wall 833 can connect to a first portion of a side or end of the patient monitor 130 and a second portion of a side or end of the patient monitor 130.

With continued reference to FIGS. 8R-8T, the chamber defined by the inner wall 833 can include one or more additional walls that engage or contact portions of the stem 823a, button 820, and/or stem 823b. For example, the chamber defined by the inner wall 833 can include a wall 837 that extends generally perpendicular to a portion of the inner wall 833 and towards the stem 823a. Wall 837 can include a recessed portion 837a. Recessed portion 837a can have a smaller height than the remainder of wall 837. Recessed portion 837a of wall 837 can be positioned underneath a portion of stem 823a. The length of the recessed portion 837a can define a space or distance that the stem 823a can move within the chamber. For example, when a force is applied to button 820 in a direction towards an interior of patient monitor 130, stem 823a can move (for example, pivot) towards wall 837 and above recessed portion 837a of wall 837. Once stem 823a passes an end of recessed portion 837a, stem 823a contact the remainder of wall 837 and is prevented from moving further inwards. Thus, the recessed portion 837a of wall 837 can define the distance by which the stem 823a and/or locking tab 822 can move into the interior of patient monitor 130. Further, since stem 823a and/or locking tab 822 can be coupled to any or all of button 820 and/or stem 423, recessed portion 837a of wall 837 can define the distance by which all of these elements can move into the interior of patient monitor 130.

The chamber defined by the inner wall 833 can additionally or alternatively include a wall 835 that extends from inner wall 833. As shown in FIG. 8S-8T, wall 835 can extend from two portions of inner wall 833 at least partially towards button 820. The distance between an outwards surface of wall 835 and button 820 can define a space or distance that the button 820 can move within the chamber. For example, when a force is applied to button 820 in a direction towards an interior of patient monitor 130, stem button 820 can move (for example pivot) towards wall 835. As shown in FIGS. 8R-8T, the patient monitor 130 can include a biasing member 879 that is configured to bias the stem 823b, button 820, stem 823a, and locking tab 822 towards an extended position. The biasing member 879 can be a spring or a prong. The biasing member 879 can be positioned and/or secured within or to a portion of the patient monitor 130, for example, at least partially secured within a chamber defined between the inner wall 83 and the inner wall 835 (see FIG. 8S). The biasing member 879 can apply a force to the stem 823b, button 820, stem 823a, and/or locking tab 822 or portions thereof to bias the locking tab 882 towards a position where the locking tab 822 is further from an interior of the patient monitor 130. In some cases, when button 820 is pressed inward, the button 820 can depress the biasing member 879 such that the biasing member 879 and/or the button 820 contact the inner wall 835. Accordingly, the inner wall 835 can prevent the button 820 from moving further inwards.

Thus, the wall 835 can define a distance by which the button 820 can move into the interior of patient monitor 130. Further, since button 820 can be coupled with stem 823b, 823a, and/or locking tab 822, wall 835 can define the distance by which all of these elements can move into the interior of patient monitor 130.

As shown in at least FIGS. 8U-8V, locking tab 822 can extend outward from a surface and/or side of stem 823a. Locking tab 822 can extend outwards from a first end of stem 823a that is opposite a second end of stem 823b that connects to button 820. Locking tab 822 can have a height that is smaller than a height of stem 324b (see FIG. 8U). Locking tab 822 can have a extend from stem 823a a length such that a thickness of the stem 823a and the length of the locking tab 822 is equal or substantially equal to a portion of an end 820a of button 820 (see FIG. 8V). Locking tab 822 can have a tapered end. For example, as shown in FIGS. 8U-8V, a free/cantilevered end of locking tab 822 can be tapered such that a surface of the free end faces a direction at least partially towards a bottom surface 809 of patient monitor 130, cradle 804, and/or strap 131 (when strap 131 is secured to cradle 804 and patient monitor 130). Such tapering can advantageously allow the free end of locking tab 822 to contact, pass, and/or slide over a portion of cradle 804 proximate to opening 860 of cradle 804. For example, with reference to at least FIGS. 8M-8N and 8U, the tapered end of locking tab 822 can contact and/or pass over the portion of cradle 804 that is above opening 860 when the patient monitor 130 is placed into the cradle 804. In some cases, when patient monitor 130 is placed into cradle 804 from atop the cradle 804 (with reference to the view shown in FIGS. 8C), the tapered end of locking tab 822 can contact and slide passed the portion of cradle 804 above opening 860 and such portion of cradle 804 can press locking tab 822 inwards. Once the locking tab 822 reaches the opening 860, locking tab 822 can extend into and/or through opening 860. Such "automatic" movement to an extended position can result from the biasing of the locking tab 822 and/or button 820 that is discussed above with reference to biasing member 879. Once positioned within and/or through opening 860, locking tab 822 can prevent or reduce movement of the patient monitor 130 with respect to the cradle 804 in a direction perpendicular to the bottom and/or top surfaces 809, 808 of patient monitor 130 and/or in a direction parallel with a length of patient monitor 130 between the first and second ends 810, 812. In order to allow the patient monitor 130 to be removed from the cradle 804, the button 820 can be pressed (for example, towards an interior of the patient monitor 130), thus rotating the locking tab 822 (and/or stem 823a, 823b) about the pivot described above and inward toward an interior of the patient monitor 130. Such movement (for example, retraction) of the locking tab 822 towards the interior of patient monitor 130 can remove locking tab 822 from opening 860, which in turn allows at least a portion of patient monitor 130 to be removed from cradle 804.

Button 820 can be cylindrical or partially cylindrical, among other shapes. Button 820 can have a circular, square, rectangular, triangle, pentagon, hexagon, heptagon, octagon, nonagon, or decagon shape, among other shapes. Button 820 can have a tapered free end 820a (the end not connected to stems 823a, 823b). For example, as shown in at least FIG. 8V, a free end 820a of button 820 can be tapered such that a portion or side of the free end 820a has a longer length than another portion or side of the free end 820a. For example, a portion of the free end 820a of button 820 that is closer to the locking tab 822 and/or stem 823a can have a greater length and/or can extend further from stems 823a, 823b than a portion of the free end that is closer to the stem 823b and/or pivot connector 825. Such tapering and/or length difference can advantageously provide better gripping of button 820 by a user. For example, when a user applies a force to button 820 in a direction towards an interior of patient monitor 130, the stem 823b, button 820, stem 823a, and locking tab 822 (also referred to herein as "locking tab assembly") can rotate about pivot connector 825 and move towards the interior of patient monitor 130. As such movement/rotation occurs, a user's finger may tend to slip off the free end 820a proximate the stem 823a and/or locking tab 822. Thus, where free end 820a of button 820 is tapered as shown in FIGS. 8U-8V, such tapering can help a user better engage the button 820 in order to retract and/or extend the locking tab 822 to removably secure the patient monitor 130 and cradle 804.

Patient monitor 130 can include one, two, three, four, five, six, seven, or eight or more locking tabs 822 and/or can include one, two, three, four, five, six, seven, or eight or more buttons 820. For example, patient monitor 130 can include a first locking tab 822 positioned on a first side 813 and a second locking tab 822 positioned on a second side 815 opposite the first side 813. Additionally, patient monitor 130 can include a first button 820 positioned on first side 813 and a second button 820 positioned on second side 815. The first locking tab 822 and first button 820 can be positioned proximate and/or adjacent to one another, and/or closer to first end 810 than to second end 812 of patient monitor 130. The second locking tab 822 and second button 820 can be positioned proximate and/or adjacent to one another, and/or closer to first end 810 than to second end 812 of patient monitor 130. The first locking tab 822 can be aligned with the second tab 822 and/or the first button 820 can be aligned with the second button 820.

FIGS. 8J-8P illustrate various views of cradle 804. As discussed elsewhere herein, cradle 804 can removably secure to patient monitor 130. Cradle 804 can include a first end 840, a second end 842 opposite the first end 840, a first sidewall 845, a second sidewall 834 opposite the first sidewall 845, a top surface 844, and a bottom surface 846 opposite the top surface 844. The top surface 844 and the bottom surface 846 can together define a base of the cradle 804, from which sidewalls 454, 834, and/or walls along first and second ends 840, 842 can extend.

As discussed above, cradle 804 can include one or more legs 848 (also referred to herein as "strap hoops") configured to secure to fastening strap 131 as shown in FIGS. 1A-1B. For example, cradle 804 can include one, two, three, or four or more legs 848. Each of one or more legs 848 can extend from and connect to a first portion of cradle 804 and a second portion of cradle 804 spaced from the first portion so as to define an opening that is sized and/or shaped to receive a portion of strap 131. For example, the distance between the first and second portions of the cradle 804 from which legs 848 extend from can be selected to match a width of strap 131. As shown in at least FIGS. 8K-8L, cradle 804 can include a first leg 848 extending from or proximate to sidewall 845 and a second leg 848 extending from or proximate to sidewall 834. The first and second legs 848 can be aligned with each other or unaligned with each other.

One or both of sidewalls 843, 845 can comprise one or more recessed cutouts 852 along a portion of the sidewalls 843, 845. For example, as shown in FIGS. 8M-8N, sidewall 843 can include a first recessed cutout 852 and sidewall 845 can include a second recessed cutout 852. The first and second recessed cutouts 852 on the sidewalls 843, 845 can align with each other, or alternatively, not align with each other. The first and second recessed cutouts 852 can be positioned along the sidewalls 843, 845 and can be closer to the first end 840 of the cradle 804 than to the second end 842 of the cradle 804 (see FIGS. 8M-8N). The recessed cutouts 852 in one or both of sidewalls 843, 845 can be positioned along a portion of the sidewall(s) 843, 845 that is proximate or adjacent to the one or more locking tabs 822 and/or one or more buttons 820 of the patient monitor 130. For example, the one or more recessed cutouts 852 can be sized and/or shaped to at least partially surround button 820 when patient monitor 130 is secured to cradle 804. Such location of the one or more recessed cutouts 852 can provide access to the one or more buttons 820 when the patient monitor 130 and cradle 804 are secured to one another. Sidewalls 843, 845 can have a height that is equal to or less than a height of the patient monitor 130 (see FIG. 8B). The one or more recessed cutouts 852 can be rounded and/or smooth. The one or more recessed cutouts 852 can have a half-circle shape or another shape (such as half-square, half-rectangle, half-ellipse, half-triangle, among other shapes) (see FIGS. 8M-8N).

As shown throughout FIGS. 8J-8P cradle 804 can include a collar 850 that is sized and/or shaped to receive, surround, and/or secure to a portion of patient monitor 130. For example, collar 850 can be sized and/or shaped to receive, surround, and/or secure connector port 831 (or a portion thereof). FIG. 8J illustrates a perspective view of cradle 804 and collar 850, while FIGS. 8A-8C illustrate how collar 850 can secure to connector port 831 of housing 403. Cradle 804 can include a wall 836 (also referred to herein as "back wall") along the second end 842 that extends from the base defined by the top and bottom surfaces 844, 846 of cradle 804. Wall 836 can include an opening 836a (see FIGS. 8O-8P). Opening 836a can be positioned and/or aligned with a center of a width of the wall 836 or positioned in an alternative location. Collar 850 can extend or protrude outward from a portion of the wall 836, for example, around and/or partially around a perimeter of opening 836a. Collar 850 can extend in a direction that is non-parallel with respect to the wall 836. For example, collar 850 can extend outward from the wall 836 in a direction generally perpendicular with respect to the wall 836. Collar 850 can extend away from the wall 836 a distance or length. Collar 850 can extend in a direction away from the end 840 (see FIGS. 8M-8N). The length of the collar 850 can be equal or substantially equal to a length of connector port 831. The width of the collar 850 can be equal or substantially equal to a width of connector port 831.

Collar 850 can have a cross-section that is sized and/or shaped to match or partially match a cross-section of the connector port 831. Collar 850 can have a rounded cross-section or non-rounded cross-section. Collar 850 can have a cross-section with a perimeter that is sized and/or shaped to surround a portion of the perimeter of the cross-section of the connector port 831 when secured thereto. For example, collar 850 can have a cross-section having a perimeter that is 90%, 80%, 70%, 60%, 50%, 40%, 30%, or 20% of the perimeter of the cross-section of the connector port 831, although other percentages are possible in some cases. Collar 850 can be sized and/or shaped to surround 90%, 80%, 70%, 60%, 50%, 40%, 30%, or 20% of the perimeter of the cross-section of the connector port 831 when secured thereto.

Patient monitor 130 can be secured to cradle 804 in a variety of ways. For example, one method of securing patient monitor 130 to cradle 804 can be by first placing and/or securing connector port 831 on second end 812 of patient monitor 130 such that connector port 831 is positioned through opening 836a and/or within collar 850 on second end 842 of cradle 804. Placement and/or securement of connector port 831 into and/or through opening 829a and/or within collar 850 can be completed by insertion of connector port 831 along an axis running through a center of the opening 836a and/or collar 850 (for example, aligned with a length of cradle 804 between first and second ends 840, 842). Additionally or alternatively, connector port 831 can be inserted into and/or secured within collar 850 by placing port 831 into collar 850 along a direction that is perpendicular to the axis running through the center of collar 850. Regardless of the direction of securement of connector port 831 to collar 850, such securement can be a snap fit, friction fit, press fit, or another type of securement. After connector port 831 is secured within collar 850 (thus securing the second end 812 of patient monitor 130 to the second end 842 of cradle 804), end 810 of patient monitor 130 and end 840 of cradle 804 can be positioned proximate to and/or secured to one another. For example, end 810 of housing 804 can be moved toward top surface 844 and/or end 840 of cradle until the one of more locking tabs 822 engage with the opening 860 (which can be as described above). For example, after the connector port 831 is positioned within and/or through the opening 836a and/or collar 850, another portion of the patient monitor 130 can be rotated and/or pivoted about the wall 836 such that the one or more locking tabs 822 engage with one or more openings 860.

Such securement of the connector port 831 to the collar 850 prior to the securement of the locking tabs 822 to the openings 860 can be advantageous when the patient monitor 130 is secured to a patient in a manner such that the first end 810 of the patient monitor 130 and/or first end 840 of cradle 804 are positioned vertically above the second end 812 of the patient monitor 130 and/or second end 842 of cradle 804. For example, in such vertical orientation, connector port 831 can be advantageously vertically supported by back wall 836, opening 836a, and/or collar 850 and a portion of patient monitor 130 (such as first end 810) can be moved so that the locking tab(s) 822 snap into openings 860.

Cable Management Prongs

Figure 9A:
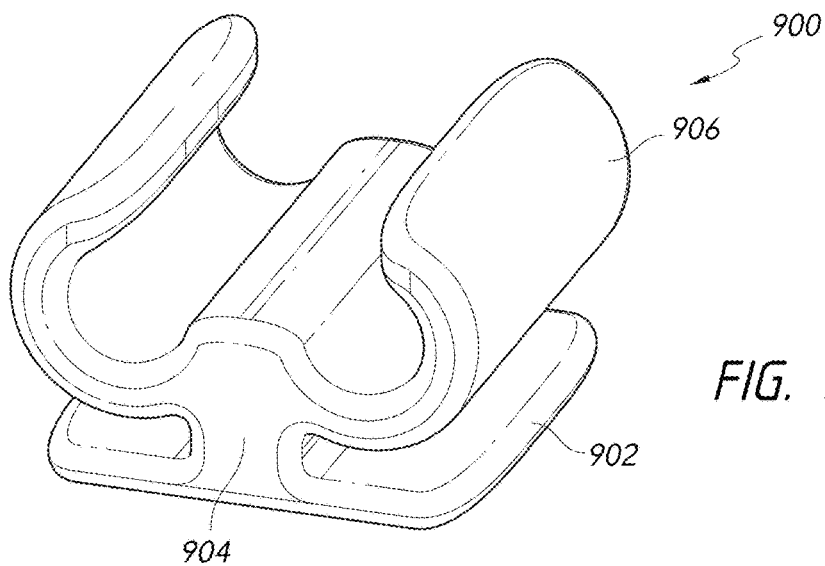
Figure 9B:
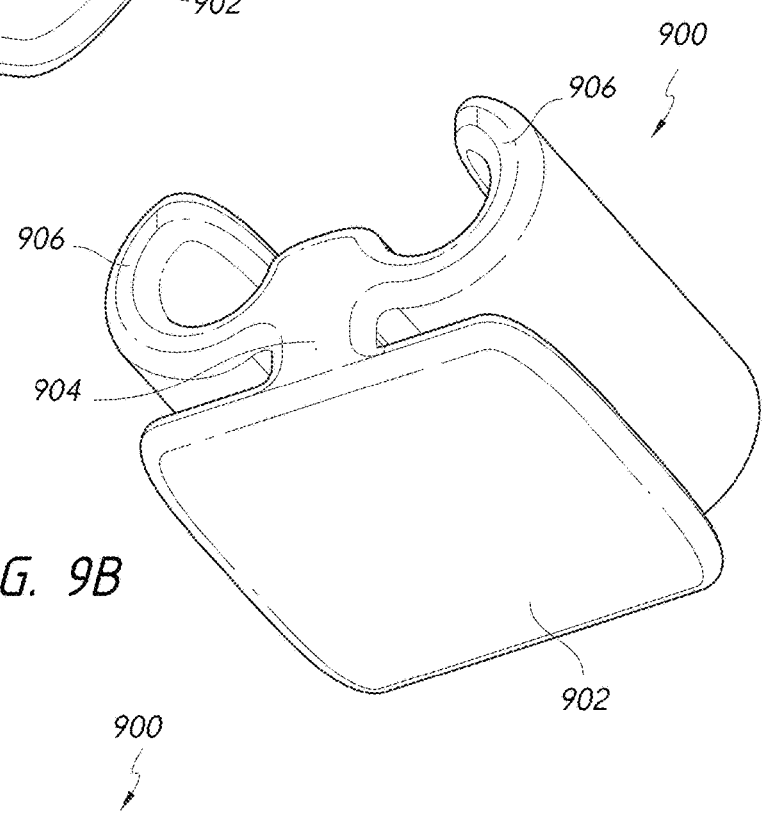
Figure 9C:
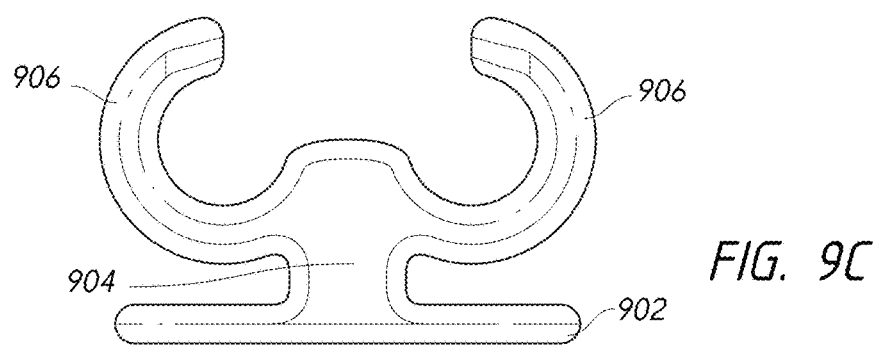

FIGS. 9A-9C illustrate various views of a cable management prong 900 (also referred to herein as "cable securement prong" "cable prong" and "prong"). One or more cable prongs 900 can be utilized alongside any or all of the sensors, monitors, cables, and/or tubes discussed herein. For example, one or more cable prongs 900 can be used within patient monitoring system 100 and can be used alongside acoustic sensor 150, ECG device 110, blood pressure monitor 120, patient monitor 130, optical sensor 140, cable 103, 105, 107, and/or 109. One or more cable prongs 900 can advantageously secure to one or more portions of cables 103, 105, 107, and/or 109. As discussed above, where patient monitoring system 100 includes multiple physiological sensors and such sensors are connected via cables, such cables can interfere with a patient's ability to move and/or a caregivers ability to interact with the patient. Such cables often dangle, intersect, tangle, and get caught on objects present or introduced nearby. This can in turn lead to dislodgement of cables from connected physiological sensors/monitors, which can, in some cases, interfere with or stop monitoring of a patient's physiological condition. The one or more cable prongs 900 can advantageously be used to manage one or more cables in a patient monitoring environment and thus prevent or reduce occurrence of the above-mentioned problems.

Cable prong 900 can include a base 902, a stem 904 extending from the base 902, and one or more arms 906 extending from the stem 904. Base 902 can be configured to secure to a portion of a patient, such as skin of the patient. Base 902 can include an adhesive bottom surface, for example, that can adhere to the patient's skin. Base 902 can have a square, rectangular, circular, triangular, pentagonal, hexagonal, heptagonal, octagonal, nonagonal, decagonal, or other shape (for example, when viewed from the view of FIG. 9B). Base 902 can include an adhesive layer configured to allow for securement of the prong 900 to skin of a patient and a release layer positioned overtop the adhesive layer that is removable. Such adhesive layer can comprise, for example, a silicone adhesive.

Stem 904 can extend outward from a surface of base 902. For example, stem 904 can extend outward from the base 902 in a direction that is non-parallel with respect to a surface of the base 902, such as perpendicular to the surface of the base 902. Stem 904 can have a thickness or width that is less than a width of the base 902 (see FIG. 9C). Stem 904 can extend from the base 902 and be spaced from sides of the base 902 (see FIG. 9C). For example, stem 904 can extend from a middle portion of base 902. Stem 904 have a length that is equal to or less than a length of the base 902, where the "length" of the stem 904 and the base 902 is in a direction perpendicular to the "width" of the base 904 (for example, the "length" can refer to "into" the page in the view of FIG. 9C).

Cable prong 900 can include one or more arms 906 that extend from a portion of the stem 904 and that are sized and/or shaped to receive, retain, surround, and/or secure a portion of a cable (such as a portion of cables 103, 105, 107, and/or 109). For example, cable prong 900 can include one, two, three, or four arms extending from stem 904. As another example, cable prong 900 can include a first arm 906 extending from a first side of stem 904 and a second arm 906 extending from a second side of stem 904 opposite the first side 904 (see FIG. 9A-9C). The one or more arms 906 can extend from the stem 904 proximate a free (top) end of the stem 904 opposite the base 904. The one or more arms 906 can extend from stem 904 in one or more directions. For example, the one or more arms 906 can extend generally perpendicular to stem 904 and can curl in a direction facing away from base 902. Alternatively, the one or more arms 906 can extend generally perpendicular to stem 904 and can curl in a direction toward base 902. The one or more arms 906 can be rounded or non-rounded. The one or more arms 906 can comprise a partially circular, partially square, or partially rectangular cross-section. The one or more arms 906 can extend outward from stem 904 and define an open region that is sized and/or shaped to receive, retain, surround, and/or secure a portion of a cable (such as a portion of cables 103, 105, 107, and/or 109). The one or more arms 906 can have a C-shape (see FIG. 9C). Alternatively, the one or more arms 906 can have an L-shape, U-shape, J-shape, among other shapes.

While FIGS. 9A-9C illustrate a cable prong 900 having two, opposing arms 906, cable prong 900 could have a single arm 906 extending from a portion of the stem 904. Moreover, cable prong 900 could have three or four arms 906, where each of the arms 906 extend from different ones of four surfaces of stem 904.

With reference to FIGS. 1A-1B, one or more cable prongs 900 can be utilized within patient monitoring system 100 to secure one or more of cables 103, 105, 107, and/or 109. For example, patient monitoring system 100 can include a first cable prong 900 which can secure to a portion of cable 109 and also secure to a portion of the skin of patient 111 between the optical sensor 140 and the patient monitor 130 (for example, on or near a wrist of patient 111). Additionally or alternatively, patient monitoring system 100 can include a second cable prong 900 which can secure to a portion of cable 107 and also secure to a portion of the skin of patient 111 between the patient monitor 130 and the blood pressure monitor 120 (for example, at or near an elbow of patient 111). Additionally or alternatively, patient monitoring system 100 can include a third cable prong 900 which can secure to a portion of cable 105 and also secure to a portion of the skin of patient 111 between the blood pressure monitor 120 and the ECG device 110 (for example, at or near an upper chest or collar bone of patient 111). Additionally or alternatively, patient monitoring system 100 can include a fourth cable prong 900 which can secure to a portion of cable 103 and also secure to a portion of the skin of patient 111 between the patient monitor 130 and the blood pressure monitor 120 (for example, at or near an elbow of patient 11). As an alternative to having two separate prongs 900 for securing cables 103 and 107, for example, at or near an elbow of patient 111, a single prong 900 can be used to secure both of cables 103 and 107. Such dual securement of cables 103 and 107 is possible with prong 900 where prong 900 has more than one wing 906 as described and shown above. Additionally or alternatively, patient monitoring system 100 can include a fifth cable prong 900 which can secure to a portion of cable 103 and also secure to a portion of the skin of patient 111 between the blood pressure monitor 120 and the acoustic sensor 150 (for example, at or near a neck or shoulder of patient 111). While the terms "first," "second,", "third," "fourth," and "fifth" have been used above, such usage is for convenience only and is not intended to convey that the presence of the "fifth," "fourth,", "third," "second," or "first" prong 900 requires the presence of any of the other numbered prongs 900 and/or requires the other prongs 900 to be positioned in the exemplary manner described above.

Charging Station

FIGS. 10A-10F illustrates various view of a charging station 1000. Charging station 1000 can include one or more charging bays that are sized and/or shaped to receive a physiological sensor, device, and/or monitor. For example, as shown in FIG. 10A, charging station 1000 can include one or more charging bays 1001, which can be sized and/or shaped to receive all or a portion of patient monitor 130. Each of the one or more charging bays 1001 can include a charging bay including electrical contacts (such as charging bay 1024 discussed further below) which can connect to electrical contacts of a physiological sensor, device, and/or monitor (such as electrical contacts 839 of patient monitor 130 as shown in FIG. 8E) in order to provide power to the same.

Charging station 1000 can include one or more frames which can include the one or more charging bays. For example, as shown in FIGS. 10D-10E, charging station 1000 can include one or more frames 1008. For example, charging station 1000 can include, one, two, three, four, five, six, seven, or eight or more frames 1008. Charging station 1000 can include a base 1006. Base 1006 can connect to and/or support the one or more frames 1008. The one or more frames 1008 can secure, connect, and/or support one another and/or can stack atop each other. Additionally, the one or more frames 1008 can secure to, connect to, and/or can stack atop base 1006. The amount of frames 1008 can be selectively customized by attaching or removing the one or more frames 1008 to or from one another.

Base 1006 can include a bottom portion which has a greater width and/or length than an upper portion of the base 1006. Such configuration can allow the bottom portion to support the upper portion of the base 1006 and/or the one or more frames 1008 that are attached to the base 1006. For example, such configuration can allow the base 1006 to resist an overturning force, rotation, and/or tendency of the charging station 1000, especially where a plurality of frames 1008 are attached to base 1006. As shown in FIG. 11C, base 1006 can have a bottom surface 1002. Bottom surface 1002 of base 1006 can have a vent 1003 including one or more openings. For example, the one or more openings of vent 1003 can have a square, rectangular, circular, triangular, pentagonal, hexagonal, heptagonal, octagonal, nonagonal, decagonal, or other shape (for example, when viewed from the view of FIG. 10C). The one or more openings of vent 1003 can have a rounded or non-rounded shape. The one or more vents 1003 can allow air to flow into an interior of the base 1006 and/or charging station 1000. Such venting can be important since a significant amount of heat can be generated by the charging station 1000 and/or from one or more devices secured therein. Charging station 1000 can include one or more vents 1015a, 1015b on a back cover or portion of the station 1000, as shown in FIG. 10F. The one or more vents 1015a, 1015b can include one or more openings comprising a variety of sizes and/or shapes. For example, the one or more openings of vent 1015a, 1015b can have a square, rectangular, circular, triangular, pentagonal, hexagonal, heptagonal, octagonal, nonagonal, decagonal, or other shape (for example, when viewed from the view of FIG. 10F). The one or more openings of vents 1015a, 1015b can have a rounded or non-rounded shape. As shown in FIG. 10F, the vents 1015a can be located adjacent or proximate a top of the charging station 1000, for example, proximate the roof 1004, and the vents 1015b can be positioned at or near a bottom of the charging station 1000.

Charging station 1000 can include and/or connect to a power source. For example, where charging station 1000 includes a base 1006, base 1006 can include a power connector port 1014 configured to receive and/or connect to a power source, for example to a wall outlet via a power cable.

As shown in FIG. 10B, charging station 1000 can include a roof 1004. Roof 1004 can be attached to one of the frame(s) 1008. For example, a frame 1008 that is intended to be a top of the charging station 1000 can include or attach to roof 1004. Roof 1004 can have a width and/or length that is less than, equal to, or greater than a width and/or length of the one or more frames 1008 and/or the base 1006.

FIGS. 10G-10H illustrate two different perspective views frame 1008. As discussed above, one or more of frames 1008 can be secured to, supported by, and/or stacked atop of another one of frames 1008. Frame 1008 can have a top portion/panel having a top surface 1040 and a bottom portion/panel having a bottom surface 1042 (see FIGS. 10G-10I). One or more of frames 1008 can be secured and/or stacked with respect to another frame 1008 such that a top surface 1040 of one frame 1008 contacts, faces, and/or secures to a bottom surface 1042 of another frame 1008. Frame 1008 can include one or more recessed portions 1044 that are recessed from top surface 1040 a given depth. For example, frame 1008 can include one, two, three, four, five, six, seven, or eight or more recessed portions 1044. Frame 1008 can additionally include one or more skirt walls 1046 protruding outward from bottom surface 1042 a given length. For example, frame 1008 can include one, two, three, four, five, six, seven, or eight or more skirt walls 1046. As another example, the frame 1008 can include two openings 1036 (see FIG. 10J), two recessed portions 1044 (see FIG. 10J), and two skirt walls 1046 (see FIG. 10I) extending from bottom surface 1042 around openings 1036 and/or below each charging bay 1001. Frame 1008 can include two charging bays 1001, for example (see FIGS. 10G-10I). The one or more skirt walls 1046 can extend outward from the bottom surface 1042 and around one or more openings 1036 in portions of the frame 1008 (see FIGS. 10I-10K). The frame 1008 can include an equal amount of recessed portions 1044 as skirt walls 1046. The one or more recessed portions 1044 can be sized and/or shaped to receive all or a portion of the length/height of the one or more skirt walls 1046 and vice versa. The depth of the one or more recessed portions 1044 can be equal to, less than, or greater than the length/height of the one or more skirt walls 1046. The one or more skirt walls 1046 can secure within the one or more recessed portions 1044 via a press fit, friction fit, snap fit, or another type of fit or securement. Thus, a first frame 1008 can secure to a second frame 1008 via interaction and/or securement between one or more recessed portions 1044 and one or more skirt walls 1046.

With reference to FIGS. 10J-10K, frame 1008 can include one or more sidewalls 1013, one or more back walls 1015, and one or more bottom or floor panels 1017. The one or more sidewalls 1013 can connect to the one or more back walls 1015. The one or more bottom or floor panels 1017 can connect to the one or more back walls 1015 and/or one or more sidewalls 1013. The one or more bottom or floor panels 1017 can extending along a plane that is perpendicular to a plane of the one or more sidewalls 1013 and/or the one or more back walls 1015. The one or more sidewalls 1013, one or more back walls 1015, and/or one or more bottom or floor panels 1017 can define the one or more charging bays 1001.

Frame 1008 can include an amount of sidewalls 1013, back walls 1015, and/or bottom panels 1017 according to the amount of charging bays 1001 included in frame 1008. For example, where frame 1008 includes a single charging bay 1001, frame 1008 can include a back wall 1015, two sidewalls 1013 connected to the back wall 1015, and a bottom panel 1017 connected to the sidewalls 1013 and/or the back wall 1015. As another example, where frame 1008 includes two charging bays 1001 as shown in the exemplary illustration of FIGS. 10G-10K, frame 1008 can include two exterior sidewalls 1013, one or more interior sidewalls 1013 (those which divide or separate the two charging bays 1001), two back panels 1015 (which can be integral or separated), and two bottom panels 1017. Where frame 1008 includes a plurality of charging bays 1001, such charging bays 1001 can be separated by a middle portion 1032 which can include one or more of the interior sidewalls 1013. As shown by the cross-section of FIG. 10L, middle portion 1032 can have a first interior sidewall 1013, a second interior sidewall 1013, and hollow section therebetween. Use of the phrase "interior sidewall" is intended to mean a sidewall 1013 of the frame 1008 that is spaced interior to an exterior perimeter of the frame 1008. Similarly, use of the phrase "exterior sidewall" is intended to mean a sidewall 1013 of frame 1008 that is positioned along and/or that at least partially defines an exterior perimeter of frame 1008.

As shown by FIGS. 10J-10K, the sidewalls 1013 of frame 1008 can include one or more stem walls 1039 extending outward and/or adjacent to a surface, corner, and/or end of the sidewalls 1013. For example, stem walls 1039 can be positioned near front ends of the sidewalls 1013 that are opposite to back ends of the sidewall 1013 adjacent to back walls 1015. The stem walls 1039 can include one or more guide recesses 1026 and/or one or more locking recesses 1028 as discussed further below.

Each of the one or more charging bays 1001 can be at least partially defined by cavities in the frame 1008 and stem walls 1039 near the front of the frame 1008. Each charging bay 1001 can be bordered by a stem wall 1039 on two front corners thereof. The term "front corners" is meant as indicating corners near the entrance of the charging bays 1001.

FIGS. 10J-10K show an exploded view of frame 1008. Frame 1008 can include one or more trays 1020 sized and/or shaped to fit within and/or secure to the one or more charging bays 1001 of frame 1008. The one or more trays 1020 can include one, two, three, four, five, or six or more trays 1020. The amount of trays 1020 can be equal to the amount of bays 1001 present in frame 1008. Tray 1020 can be sized and/or shaped to hold and/or secure a physiological sensor, device, or monitor. For example, tray 1020 can be sized and/or shape to hold and/or secure patient monitor 130. Tray 1020 can include an opening 1020a which is sized and/or shaped to accommodate charging port 1024 of the frame 1008. The charging port 1024 of frame 1008 can extend outward and/or upward from a surface of frame 1008. The charging port 1024 can comprise and/or be formed on a pedestal (see FIGS. 10J-10K). The charging port 1024 can be sized and/or shaped to pass at least partially through opening 1020a, as discussed in more detail below. The charging port 1024 can be electrically coupled to a battery or power source inside or outside the charging station 1000.

Tray 1020 can include a base portion having an opening 1020b that is larger than opening 1020a. Opening 1020b can be positioned underneath a bottom surface of patient monitor 130 (for example), when patient monitor 130 is held and/or secured by tray 1020. Opening 1020b can provide venting and airflow in and around portions of patient monitor 130 (or another type of physiological device) when held and/or secured by tray 1020.

Tray 1020 can include sidewalls 1020d (also referred to herein as "arms") extending outward and/or upwards from the base portion of tray 1020. For example, tray 1020 can include two opposing arms 1020d. Arms 1020d can extend in one or more directions and/or can curve or be angled. For example, arms 1020d can be angled and/or curved such that the arms 1020d can extend adjacent to and/or surround a portion of sides of patient monitor 130 (such as sides 813 and/or 815 of patient monitor 130). Such configuration can prevent patient monitor 130 from moving in a direction perpendicular to a plane of the base portion and/or opening 1020b of tray 1020 when secured to the tray 1020, while at the same time allowing patient monitor 130 to be inserted within tray 1020 in a direction generally parallel to such plane (for example, along an axis parallel to a length of tray 1020).

Tray 1020 can include one or more knobs 1020e extending outwards from a surface of one or more of the arms 1020d of tray 1020. For example, tray 1020 can include one, two, three, four, five, six, seven, or eight or more knobs 1020e. As another example, tray 1020 can include a pair of knobs 1020e on a first arm 1020d and a pair of knobs 1020e on a second arm 1020d opposite the first arm 1020d (see FIGS. 10J-10K). The one or more knobs 1020e can be sized and/or shaped to secure to one or more detents 1038 on frame 1008. The one or more detents 1038 can be located along inner walls of frame 1008 which define the one or more charging bays 1001. The one or more knobs 1020*e* can be configured to secure to the one or more detents 1038 via press fit, snap fit, friction fit, or another type of fit or securement. The one or more knobs 1020*e* can be configured to slide within the one or more detents 1038 from above without being secured in a press fit, snap fit, friction fit, or another type of fit or securement such that tray 1020 can easily be lifted in and out of bay 1001 by vertically moving knobs 1020*e* out of detents 1038. The knobs 1020*e* can have a circular cross-section and the detents 1038 can have a half-circle shape, although other shapes are possible. Thus, the trays 1020 can be at least partially held, received, and/or secured within the charging bays 1001 by securement between the one or more knobs 1020*e* and the one or more detents 1038. The knobs 1020*e* can be positioned in the detents 1038 such that the tray 1020 is movable between one or more positions as discussed further below.

As shown in FIGS. 10J-10K, tray 1020 can include one or more legs 1020*c* extending outward and/or downward from the base portion of tray 1020. The one or more legs 1020*c* can extend from the base portion of tray 1020 in a direction opposite to the direction that the arms 1020*d* extend from the base portion. The one or more legs 1020*c* can include, for example, two legs 1020*c*. The one or more legs 1020*c* can be sized and/or shaped to correspond with the size and/or shape of openings 1036 and/or one or more prongs 1034. When tray 1020 is placed within a charging bay 1001, a leg 1020*c* can be positioned proximate to, adjacent to, above, and/or around opening 1036 and/or a prong 1034. Frame 1008 can include one or more prongs 1034 positioned and/or extending within or through opening 1036 (see FIGS. 10I-10K). Frame 1008 can include one, two, three, four, five, six, seven, or eight or more prongs 1034. Frame 1008 can include an equal amount of prongs 1034 and openings 1036, and the number of prongs 1034 and openings 1036 can be equal to the number of legs 1020*c* in tray 1020. Prongs 1034 can help bias a tray 1020 when a physiological device (such as patient monitor 130) is not received and/or secured within the tray 1020. For example, when tray 1020 is positioned within a charging bay 1001, a top surface of a prong 1034 can contact and/or apply a force to a bottom surface of the legs 1020*c* so as to keep at least a portion of the tray 1020 in a raised position. The charging bay 1001 on the right side of frame 1008 in FIGS. 10G-10H illustrates a tray 1020 in a raised position, whereas the charging bay 1001 on the left side of frame 1008 in FIGS. 10G-10H illustrates a tray 1020 in a lowered position. In the lowered position, the opening 1020*a* of tray 1020 is positioned around the charging port 1024 of frame 1008. In the raised position, the opening 1020*a* of tray 1020 is spaced from the charging port 1024 of frame 1008. Thus, prongs 1034 can bias a portion of the tray 1020 (for example, a "front" portion of tray 1020 which is proximate to opening 1020*a*) so that it is spaced away from charging port 1024 and/or an inner surface of frame 1008. If a portion of the tray 1020 is pushed downward toward the inner surface of frame 1008 and/or towards the charging port 1024, a bottom surface of the tray 1020 (for example, legs 1020*c*) can compress the prong(s) 1034. The one or more legs 1020*c* can be defined by a perimeter wall extending from the base of the tray 1020. As shown in FIG. 10I, the perimeter wall can have an opening on an end opposite the base of the tray 1020. The perimeter wall can have a hollow interior therewithin. The hollow interior can be sized and/or shaped to receive at least a portion of the a prong 1034. When received and/or extending through the hollow interior of the leg 1020*c*, an end of prong 1034 can contact and/or apply pressure to the base of the tray 1020.

As shown in FIG. 10I-10J, prong(s) 1034 can pass through openings 1036 and/or skirt walls 1046 and secure or connect (at an end thereof) to a portion of bottom surface 1042 of frame 1008. As shown in FIGS. 10I-10K, prong(s) 1034 can have a straight portion which connects and/or secures to the bottom surface 1042 (see FIG. 10I) and a curved or flared portion which extends into an interior of charging bay 1001 and/or applies a biasing force to a portion of tray 1020 (see FIGS. 10J-10K).

As shown in FIGS. 10G-10K, stem walls 1039 positioned on sides of charging bay 1001 and/or at corners thereof can have a guide recess 1026 and/or a locking recess 1028. Guide recesses 1026 can be sized and/or shaped to receive locking tabs 822 of patient monitor 822. Guide recesses 1026 can have a height and/or width to allow the locking tabs 822 to pass therewithin when patient monitor 822 is inserted into a charging bay 1001. Guide recesses 1026 can be recessed from a surface of stem walls 1039 a depth that is equal to or greater than a length of locking tabs 822 of patient monitor 130. Guide recesses 1026 can have three inner walls defining the recess and an open front portion. Such configuration allows locking tab 822 to pass into the guide recess 1026. Locking recesses 1028 can be sized and/or shaped to receive, secure, surround, and/or confine locking tabs 822 of patient monitor 822. Locking recesses 1028 can have a height and/or width to allow the locking tabs 822 to extend therewithin when patient monitor 822 is inserted into a charging bay 1001 and the patient monitor 130 is in a lowered position (as discussed further below). Locking recesses 1028 can be recessed from a surface of stem walls 1039 a depth that is equal to or greater than a length of locking tabs 822 of patient monitor 130. Locking recesses 1028 can be recessed a depth greater than or equal to the recess depth of guide recesses 1026 (see FIG. 11L). Locking recesses 1028 can have four walls that define the recess and act to confine, secure, and/or lock the locking tabs 822.

FIG. 10L illustrates a cross-section taken along a portion of frame 1008 as shown in FIG. 10G when two patient monitors 130 are inserted into the charging bays 1001. The right hand side of FIG. 10L illustrates a patient monitor 130 in the raised position (discussed above) where the locking tabs 822 are positioned within the guide recesses 1026. The left hand side of FIG. 10L illustrates a patient monitor 130 in the lowered position where the locking tabs 822 are positioned within locking recesses 1028.

To secure a patient monitor 130 within a charging bay 1001 and/or to electrically connect the patient monitor 130 to the charging station 1000 (or frame 1008 thereof), the patient monitor 130 can be inserted into tray 1020 within a charging bay 1001. As the patient monitor 130 is inserted into tray 1020 and/or charging bay 1001, locking tabs 822 of patient monitor 130 can pass and/or slide within guide recess(es) 1026 of stem walls 1039 positioned at front corners of sides of the charging bay 1001. To electrically connect the patient monitor 130 to the frame 1008 (for example, to begin charging), a front portion of patient monitor 130 (for example, the end 810 of patient monitor 130 as shown in FIG. 8I) can be pressed by a user. Application of a force in a downward manner (for example, toward charging port 1024 of frame 1008) moves a front portion of tray 1020 toward an inner surface of frame 1008 in charging bay 1001 such that opening 1020*a* of tray 1020 slides over and/or around charging port 1024. After the charging port 1024 passes through opening 1020a, electrical contacts 839 of patient monitor 130 (see FIG. 8E) can mate (for example, connect) with electrical contracts 1024 of frame 1008. Further, as a downward force is applied to the patient monitor 130 and tray 1020, the tray 1020 compresses the one or more prongs 1034. Additionally, as such downward force is applied to the patient monitor 130 and tray 1020, the locking tabs 822 of patient monitor 130 move and/or slide from the guide recesses 1026 to the locking recesses 1028 (for example, by sliding over a wall or non-recessed portion of stem walls 1039 separating the guide recesses 1026 from the locking recesses 1028 as shown in FIG. 10L). Once the locking tabs 822 move into the locking recesses 1028, the locking recesses 1028 prevent movement of the locking tabs 822 (and thus the patient monitor 130) in a direction parallel to axis 1077 as shown in FIG. 10L which can be parallel with a height of the frame 1008 and/or patient monitor 130. When the locking tabs 822 pass from the guide recesses 1026 to the locking recesses 1028, the locking tabs 822 can snap into place. As discussed previously, the locking tabs 822 can have tapered ends. Such tapered ends of locking tabs 822 can help the locking tabs 822 slide over the walls or non-recessed portion of stem walls 1039 separating the guide recesses 1026 from the locking recesses 1028 and thereafter snap and/or extend into and/or within locking recesses 1028.

As discussed above, after the charging port 1024 passes through opening 1020a, electrical contacts 839 of patient monitor 130 (see FIG. 8E) can mate (for example, electrically connect) with charging port 1024 of frame 1008. The patient monitor 130 can include an indicator that illustrates a charging status of the patient monitor 130. For example, the patient monitor 130 can include an indicator that visually indicates when electrical contacts 839 of patient monitor 130 connect with charging port 1024 of frame 1008. For example, patient monitor 130 can include an LED indicator on a portion of end 810. As another example, on/off button 834 on end 810 of patient monitor 130 can be configured to illuminate when electrical contacts 839 of patient monitor 130 connect with charging port 1024 of frame 1008. For example, on/off button 834 can be made of a transparent or semi-transparent material and one or more LEDs can be positioned between the on/off button 834 and the interior of the patient monitor 130, and such one or more LEDs can be configured to illuminate when electrical contacts 839 of patient monitor 130 connect with charging port 1024 of frame 1008. Such indicator on patient monitor 130 can also indicate (for example, by illumination or flashing) whether the patient monitor 130 and/or the charging station 1000 (or frame thereof) are compatible, whether the patient monitor 130 has reached an end of its service life. In some variants, the charging station 1000 does not include any indicators, such as charging status indicators. For example, the charging station 1000 can have not charging status indicators and the only charging status indicator is on the patient monitor 130.

As discussed above, the charging station 1000 can include one or more vents to allow air to flow into an interior of the charging station 1000 and to allow heat to dissipate from the interior of the charging station 1000. For example, as discussed above, charging station 1000 can include one or more of vents 1003 (FIG. 10C) or vents 1015a, 1015b (FIG. 10F). In some variants, the charging station 1000 is configured to allow heat generated from an interior of the charging station 1000 to flow up to the top of the charging station 1000 and out vents 1015a. For example, one or more of the frames 1008 can include openings configured to provide a flow path for heat to pass upward through the frames 1008 toward a top of the charging station 1000 and out the vents 1015a. For example, with reference to FIG. 10I-10K, the bottom surface 1042 can have an opening 1080 that separates portions of the frame 1008 and allows hot air to pass through. The structure and configuration of the frame 1008 can incorporate an opening like opening 1080. Advantageously, heat generated by electrical components in the base 1006 of the charging station 1000 along with heat generated from the one or more patient monitors 130 secured in the charging bays 1001 of the frames 1008 can efficiently pass through openings 1080 and flow upward to a top of the charging station 1000 and out vents 1015a.

Charging Cradle

FIGS. 11A-11B illustrate various views of a charging cradle 1100 with two patient monitors 130 secured therein. As shown, one or more patient monitors 130 can be secured within portions of the charging cradle 1100. Charging cradle 1100 can itself be secured within a portion of a medical monitoring hub, such as medical monitoring hub 1101. For example, charging cradle 1100 can be sized and/or shaped to fit within a docking station 1105 of medical monitoring hub 1101. Charging cradle 1100 can transfer physiological data, for example, from a patient monitor 130, to medical monitoring hub 1101 via contact between electrical contacts on charging cradle 1100 and electrical contacts in docking station 1105. Charging cradle 1100 can itself comprise a rechargeable battery or battery pack that can be recharged, for example, when the charging cradle 1100 is secured to docking station 1105 of the hub 1101. Medical monitoring hub 1101 can include a display 1103 which can display information responsive to physiological data obtained from the charging cradle 1100 and/or patient monitor 130.

FIGS. 11D-11E and 11G illustrate charging cradle 1100 without patient monitors 130 secured therein. Charging cradle 1100 can include one or more docks configured to secure a patient monitor 130. For example, charging cradle 1100 can include two docks, each of which are sized, shaped, and configured to secure a patient monitor 130. In some cases, charging cradle 1100 can include a first dock 1140 including a charging port 1146 including electrical contacts and a second dock 1130 that does not include a charging port 1146 but rather is intended to secure a patient monitor 130 without charging. The electrical contacts of the charging port 1146 of the dock 1140 can electrically connect to electrical contacts on patient monitor 130 when the patient monitor 130 is secured to the dock 1140. For example, the electrical contacts of the charging port 1146 of the dock 1140 can electrically connect to electrical contacts 839 on patient monitor 130 when the patient monitor 130 is secured to the dock 1140 (see FIG. 8E).

Dock 1140 can include one or more openings 860 in sidewalls extending from a bottom surface of dock 1140 that are sized and/or shaped to receive locking tabs 822 of patient monitor 130. Additionally or alternatively, dock 1140 can include an opening 1142 in a end wall of the dock 1140. Opening 1142 can be sized and/or shaped to surround a portion of a perimeter of connector port 831 of patient monitor 130. Opening 1142 can be similar to opening 836a of cradle 804.

The securement between the locking tabs 822 of patient monitor 130 within the openings 1144 can be similar or identical to the securement of locking tabs 822 to openings 860 of cradle 804. Thus, the discussion above with reference to the securement of locking tabs 822 to openings 860 of cradle 804 is equally applicable to the securement between the locking tabs 822 of patient monitor 130 within the openings 1144 of dock 1140. Similarly, the securement between connector port 831 of patient monitor 130 and opening 1142 can be similar in some or many respects as the securement between connector port 831 of patient monitor 130 and opening 836a and/or collar 450. For example, connector port 831 can be inserted along a direction parallel to an axis extending through opening 1142 and/or a direction perpendicular to such direction.

As shown in FIGS. 11D-11E and 11H-11I, dock 1130 can include a tray 1120 that can be sized and/or shaped to secure and/or surround patient monitor 130. Tray 1120 can be similar in some or many respects as tray 1020 of charging frame 1008. For example, with reference to FIGS. 11J-11K, tray 1120 can include outer wall 1124 that can be U-shaped and an inner portion 1126. Inner portion 1126 can extend toward an interior of tray 1120 and can be curved, as shown. Inner portion 1126 can have a size and/or shape that corresponds to a size and/or shape of a patient monitor 130. Outer wall 1124 and/or inner portion 1126 can be shaped so as to surround the sides and/or bottom of patient monitor 130 when patient monitor 130 is placed therein. Outer wall 1124 can include an opening 1127 sized and/or shaped to receive connector port 831 of patient monitor 130. Patient monitor 130 can be secured within tray 1120 by placement of connector port 831 within and/or through opening 1127 and/or by the shape of outer wall 1124 and/or inner portion 1126.

As shown in at least FIGS. 11H-11I, charging cradle 1100 can include a base 1110 which can include dock 1130 and dock 1140. Tray 1120 can be secured within a portion or portions of dock 1130 of base 1110. For example, tray 1120 can include one or more legs 1122 (such as one, two, three, or four of more legs) that can secure to portions of dock 1130. Legs 1122 can extend from the outer wall 1124 of tray 1120 (see FIG. 11J-11K). Legs 1122 can include nubs 1122a, 1122b which protrude outward from a surface of leg 1122. For example, nubs 1122a, 1122b can extend perpendicular to a surface of leg 1122. Nubs 1122a, 1122b can be sized and/or shape to fit within slot 1131 on an interior surface of a wall 1136 of dock 1130 (see FIG. 11L). Nubs 1122a, 1122b can have a circular cross-section. Nubs 1122a, 1122b can be rounded and/or cylindrical. Such configurations can help the nubs 1122a, 1122b more easily slide within slots 1131. Slot 1131 can be recessed from an interior surface of a wall 1136 of dock 1130. Slot 1131 can extend along a portion of such surface of wall 1136 and can be curved. When nubs 1122a, 1122b of legs 1122 are positioned within slots 1130 of dock 1130 and tray 1120 is positioned within dock 1130, tray 1120 can be rotatably secured to dock 1130. For example, in such configuration, tray 1120 can be prevented from being separated from dock 1130, but can allow tray 1120 to rotate and/or swivel by movement of the nubs 1122a, 1122b within and/or along slots 1131. FIG. 11M illustrates a first position of the tray 1120 secured within dock 1130 and FIG. 11N illustrates a second position of tray 1120 secured within dock 1130. Thus, the nubs 1122a, 1122b and slots 1131 allow the tray 1120 to rotate outward from base 1110 while still being prevented from removal. Such configuration (FIG. 11N) can allow a patient monitor 130 to be more easily inserted into tray 1120 from a top position. After a patient monitor 130 is inserted into the tray 1120 as shown in FIG. 11N, the tray can be rotated back toward base 1110.

Dock 1130 of base 1110 and/or tray 1120 can include additional features to help securement therebetween. For example, with reference to FIGS. 11J-11L, leg 1122 can include a bump 1122c and the dock 1130 can include a stopper 1132 and a bump 1134. Bump 1122c can extend outward (for example, perpendicular) from a surface of leg 1122. Bump 1134 of dock 1130 can protrude outward (for example, perpendicular) from a surface of wall 1136 of dock 1130. Stopper 1132 can also extend outward (for example, perpendicular) from the same surface of the wall 1136 of dock 1130. Stopper 1132 can extend further outwards from the wall of dock 1130 than the bump 1134.

When tray 1120 is rotated and/or positioned as shown in FIG. 11M, bump 1122c can be positioned between bump 1134 and stopper 1132. Such positioning can prevent rotation of tray 1120, via sliding of nubs 1122a, 1122b within slot 1131, until a sufficient force is applied so that bump 1122c can pass over bump 1134 in dock 1130. Bump 1122c can be rounded and/or smooth, and in some cases comprises a partially spherical shape. Bump 1134 can be rounded and/or smooth, and in some cases comprises a partially square shape, for example, with rounded edges and/or sides (see FIG. 11L). Stopper 1132 can prevent tray 1120 from rotating beyond a certain position, for example, the position of tray 1120 shown in FIG. 11M.

Additional Considerations

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention.

Depending on the embodiment, certain acts, events, or functions of any of the methods described herein can be performed in a different sequence, may be added, merged, or left out altogether (e.g., not all described acts or events are necessary for the practice of the method). Moreover, in certain embodiments, acts or events may be performed concurrently, e.g., through multi-threaded processing, interrupt processing, or multiple processors, rather than sequentially.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, conventional processor, controller, microcontroller, state machine, etc. A processor can also be implemented as a combination of computing devices, e.g., a combination of a DSP and a microprocessor, a plurality of microprocessors, one or more microprocessors in conjunction with a DSP core, or any other such configuration. In addition, the term "processing" is a broad term meant to encompass several meanings including, for example, implementing program code, executing instructions, manipulating signals, filtering, performing arithmetic operations, and the like.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, a DVD, or any other form of storage medium known in the art. A storage medium is coupled to the processor such that the processor can read information from, and write information to, the storage medium. In the alternative, the storage medium may be integral to the processor. The processor and the storage medium can reside in an ASIC. The ASIC can reside in a user terminal. In the alternative, the processor and the storage medium can reside as discrete components in a user terminal.

The modules can include, but are not limited to, any of the following: software or hardware components such as software object-oriented software components, class components and task components, processes, methods, functions, attributes, procedures, subroutines, segments of program code, drivers, firmware, microcode, circuitry, data, databases, data structures, tables, arrays, or variables.

In addition, although this invention has been disclosed in the context of certain preferred embodiments, it should be understood that certain advantages, features and aspects of the systems, devices, and methods may be realized in a variety of other embodiments. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred embodiments.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or methods illustrated can be made without departing from the spirit of the disclosure. As will be recognized, certain embodiments described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

What is claimed is:

1. A blood pressure monitor configured to removably mount to a blood pressure cuff in a substantially symmetrical position with respect to a width of the blood pressure cuff, the blood pressure cuff configured to be mounted in a first orientation when worn on a right arm and a second orientation when worn on a left arm, the second orientation being the reverse of the first orientation, the blood pressure monitor configured to be in fluid communication with the blood pressure cuff regardless of whether the blood pressure cuff is mounted in the first or second orientation, said blood pressure monitor comprising:
a housing comprising an interior;
a first port configured to:
receive and secure to a first prong of the blood pressure cuff when the blood pressure cuff is mounted in the first orientation;
receive and secure to a second prong of the blood pressure cuff when the blood pressure cuff is mounted in the second orientation; and
enable fluid communication between the interior of the housing and at least one of a first fluid passage within the first prong and a second fluid passage within the second prong; and
a second port configured to:
receive and secure to the second prong of the blood pressure cuff when the blood pressure cuff is mounted in the first orientation; and
receive and secure to the first prong of the blood pressure cuff when the blood pressure cuff is mounted in the second orientation,
wherein, when the first prong is received and secured within the second port, fluid communication between the interior of the housing and the first fluid passage is inhibited.

2. The blood pressure monitor of claim 1, wherein the first and second ports are positioned along a bottom surface of the housing.

3. The blood pressure monitor of claim 2, wherein the first and second ports are spaced apart and aligned with one another.

4. The blood pressure monitor of claim 3, wherein the first and second ports extend from the bottom surface into the interior of the housing.

5. The blood pressure monitor of claim 2, wherein the blood pressure cuff comprises a bladder in fluid communication with the first and second fluid passages of the first and second prongs.

6. The blood pressure monitor of claim 5, wherein the blood pressure monitor is configured to inflate and deflate the bladder of the blood pressure cuff.

7. The blood pressure monitor of claim 6, wherein the blood pressure monitor is configured to inflate the bladder by moving air through the first port through one of the first and second fluid passages and further configured to deflate the bladder by allowing air from the bladder to flow through the first port into the interior of the housing.

8. The blood pressure monitor of claim 1, further comprising a valve positioned within the interior of the housing proximate to the first port, wherein, when the first or second prong is secured within the first port, the valve is in a first position, and wherein, when neither of the first and second prong is secured within the first port, the valve is in a second position.

9. The blood pressure monitor of claim 8, wherein, when the valve is in the first position, a flow path through the first port is open and wherein, when the valve is in the second position, the flow path through the first port is closed.

10. The blood pressure monitor of claim 1, wherein, when the second prong is received and secured within the second port, fluid communication between the interior of the housing and the second fluid passage is inhibited.

11. The blood pressure monitor of claim 1, wherein the fluid communication is inhibited by a cap secured to an end of the second port.

12. A blood pressure monitor configured to removably mount to a blood pressure cuff in a substantially symmetrical position with respect to a width of the blood pressure cuff, said blood pressure monitor comprising:
    a housing comprising an interior;
    a first port configured to:
        receive and secure to a first prong of the blood pressure cuff when the blood pressure cuff is mounted in a first orientation;
        receive and secure to a second prong of the blood pressure cuff when the blood pressure cuff is mounted in a second orientation; and
        enable fluid communication between the interior of the housing and at least one of a first fluid passage within the first prong and a second fluid passage within the second prong; and
    a second port configured to:
        receive and secure to the second prong of the blood pressure cuff when the blood pressure cuff is mounted in the first orientation; and
        receive and secure to the first prong of the blood pressure cuff when the blood pressure cuff is mounted in the second orientation;
    wherein, when the first prong is received and secured within the second port, fluid communication between the interior of the housing and the first fluid passage is inhibited.

13. The blood pressure monitor of claim 12, wherein the first and second ports are positioned along a bottom surface of the housing.

14. The blood pressure monitor of claim 13, wherein the first and second, ports are spaced apart and aligned with one another with respect to a width of the blood pressure monitor.

15. The blood pressure monitor of claim 13, wherein the first and second ports extend from the bottom surface into the interior of the housing.

16. The blood pressure monitor of claim 13, wherein the blood pressure cuff comprises a bladder in fluid communication with the first and second fluid passages of the first and second prongs.

17. The blood pressure monitor of claim 16, wherein the blood pressure monitor is configured to inflate and deflate the bladder of the blood pressure cuff.

18. The blood pressure monitor of claim 17, wherein the blood pressure monitor is configured to inflate the bladder by moving air through the first port through one of the first and second fluid passages and further configured to deflate the bladder by allowing air from the bladder to flow through the first port into the interior of the housing.

19. The blood pressure monitor of claim 12, further comprising a valve positioned within the interior of the housing proximate to the first port, wherein, when the first or second prong is secured within the first port, the valve is in a first position, and wherein, when neither of the first and second prong is secured within the first port, the valve is in a second position.

20. The blood pressure monitor of claim 19, wherein, when the valve is in the first position, a flow path through the first port is open and wherein, when the valve is in the second position, the flow path through the first port is closed.

21. The blood pressure monitor of claim 12, wherein, when the second prong is received and secured within the second port, fluid communication between the interior of the housing and the second fluid passage is inhibited.

22. The blood pressure monitor of claim 12, wherein the fluid communication is inhibited by a cap secured to an end of the second port.

23. The blood pressure monitor of claim 12, wherein, when the blood pressure cuff is mounted in the first orientation, the blood pressure cuff is secured to a right arm of a user, and wherein, when the blood pressure cuff is mounted in the second orientation, the blood pressure cuff is secured to a left arm of the user.

24. The blood pressure monitor of claim 23, wherein the second orientation is the reverse of the first orientation.

25. The blood pressure monitor of claim 23, wherein the blood pressure monitor is configured to be in fluid communication with a bladder of the blood pressure cuff via one of the first and second fluid passages regardless of whether the blood pressure cuff is mounted in the first or second orientation.

26. An assembly comprising:
    a blood pressure monitor comprising:
        a housing comprising an interior;
        a first port; and
        a second port spaced from said first port; and
    a blood pressure cuff configured to secure around a portion of a subject's body, said blood pressure cuff comprising:
        a bladder;
        a first prong comprising a first fluid passage in fluid communication with an interior defined at least partially by said bladder; and
        a second prong spaced from said first prong, said second prong comprising a second fluid passage in fluid communication with said interior defined at least partially, by said bladder;

wherein said blood pressure monitor and said blood pressure cuff are removably attachable to one another via engagement between said first and second ports and said first and second prongs; and wherein the blood pressure monitor is configured such that, when said first prong is secured within said first port and said second prong is secured within said second port:

said interior of said housing is in fluid communication with said first fluid passageway of said first port; and fluid communication between said interior of said housing and said second fluid passageway of said second port is inhibited.

27. The assembly of claim 26, wherein the blood pressure monitor is configured such that, when said second prong is secured within said first port and said first prong is secured within said second port:

said interior of said housing is in fluid communication with said second fluid passageway of said second port; and fluid communication between said interior of said housing and said first fluid passageway of said first port is inhibited.

28. The assembly of claim 26, wherein the blood pressure monitor is configured to inflate and deflate the bladder of the blood pressure cuff.

29. The assembly of claim 28, wherein the blood pressure monitor is configured to inflate the bladder by moving air through the first port through one of the first and second fluid passages and further configured to deflate the bladder by allowing air from the bladder to flow through the first port into the interior of the housing.

30. The assembly of claim 27, further comprising a valve positioned within the interior of the housing proximate to the first port, wherein, when the first or second prong is secured within the first port, the valve is in a first position, and wherein, when neither of the first and second prong is secured within the first port, the valve is in a second position.

31. The assembly of claim 30, wherein, when the valve is in the first position, a flow path through the first port is open and wherein, when the valve is in the second position, the flow path through the first port is closed.

32. The assembly of claim 26, wherein the fluid communication is inhibited by a cap secured to an end of the second port.

* * * * *